(12) United States Patent
Lee et al.

(10) Patent No.: US 9,643,946 B2
(45) Date of Patent: May 9, 2017

(54) TRICYCLIC COMPOUND AND USE THEREOF

(71) Applicant: SK CHEMICALS CO., LTD., Seongnam-si, Gyeonggi-do (KR)

(72) Inventors: Ju Young Lee, Suwon-si (KR); Jeong A Lee, Ansan-si (KR); Jaeseung Ahn, Seoul (KR); Je Ho Ryu, Seongnam-si (KR); Min-Young Han, Seongnam-si (KR); Taekyung Yoo, Uiwang-si (KR); Joon Ho Sa, Seongnam-si (KR); Jae-Sun Kim, Suwon-si (KR); Jeongmin Seo, Seongnam-si (KR)

(73) Assignee: SK CHEMICALS CO., LTD., Seongnam-si (KR)

( * ) Notice: Subject to any disclaimer, the term of this patent is extended or adjusted under 35 U.S.C. 154(b) by 0 days.

(21) Appl. No.: 14/771,049

(22) PCT Filed: Feb. 28, 2014

(86) PCT No.: PCT/KR2014/001686
§ 371 (c)(1),
(2) Date: Aug. 27, 2015

(87) PCT Pub. No.: WO2014/133361
PCT Pub. Date: Sep. 4, 2014

(65) Prior Publication Data
US 2016/0009677 A1  Jan. 14, 2016

(30) Foreign Application Priority Data

Feb. 28, 2013 (KR) .................. 10-2013-0022038
Sep. 12, 2013 (KR) .................. 10-2013-0109840

(51) Int. Cl.
| | |
|---|---|
| *C07D 307/80* | (2006.01) |
| *C07D 313/10* | (2006.01) |
| *C07D 335/02* | (2006.01) |
| *C07D 405/12* | (2006.01) |
| *C07D 239/70* | (2006.01) |
| *C07D 307/20* | (2006.01) |
| *C07C 317/18* | (2006.01) |
| *C07C 229/46* | (2006.01) |
| *C07C 59/72* | (2006.01) |
| *C07D 223/20* | (2006.01) |
| *C07D 311/80* | (2006.01) |
| *C07D 313/12* | (2006.01) |
| *C07D 407/12* | (2006.01) |
| *C07D 409/12* | (2006.01) |
| *C07D 409/14* | (2006.01) |
| *C07D 413/12* | (2006.01) |

(52) U.S. Cl.
CPC .......... *C07D 307/80* (2013.01); *C07C 59/72* (2013.01); *C07C 229/46* (2013.01); *C07C 317/18* (2013.01); *C07D 223/20* (2013.01); *C07D 239/70* (2013.01); *C07D 307/20* (2013.01); *C07D 311/80* (2013.01); *C07D 313/10* (2013.01); *C07D 313/12* (2013.01); *C07D 335/02* (2013.01); *C07D 405/12* (2013.01); *C07D 407/12* (2013.01); *C07D 409/12* (2013.01); *C07D 409/14* (2013.01); *C07D 413/12* (2013.01); *C07C 2101/02* (2013.01); *C07C 2103/26* (2013.01); *C07C 2103/32* (2013.01)

(58) Field of Classification Search
CPC ............... C07D 307/80; C07D 307/20; C07D 313/10; C07D 313/12
See application file for complete search history.

(56) References Cited

U.S. PATENT DOCUMENTS

| | | |
|---|---|---|
| 2006/0258722 A1 | 11/2006 | Yasuma et al. |
| 2012/0004166 A1 | 1/2012 | Keil et al. |
| 2014/0080891 A1 | 3/2014 | Yasuma et al. |

FOREIGN PATENT DOCUMENTS

| | | |
|---|---|---|
| EP | 1559422 A1 | 8/2005 |
| KR | 101058772 B1 | 8/2011 |
| WO | 2004/106276 A1 | 12/2004 |
| WO | 2005/051890 A1 | 6/2005 |
| WO | 2005086661 A2 | 9/2005 |
| WO | 2008/130514 A1 | 10/2008 |

OTHER PUBLICATIONS

Kane et al 'The future or pharmacotherapy for schizophrenia' World Psychiatry, 2(2), p. 81-86, 2003.*
International Searching Authority, International Search Report for PCT/KR2014/001686 dated Jun. 27, 2014.
Communication dated Jun. 20, 2016 from the European Patent Office in counterpart European application No. 14756272.2.
Bharate et al., "Progress in the discovery and development of small-molecule modulators of G-protein-coupled receptor 40 (GPR40/FFA1/FFAR1); an emerging target for type 2 diabetes," Expert Opinion on Therapeutic Patents, 2009, vol. 19, No. 2, pp. 237-264.

* cited by examiner

*Primary Examiner* — Wu-Cheng Winston Shen
*Assistant Examiner* — Christopher R Stone
(74) *Attorney, Agent, or Firm* — Sughrue Mion, PLLC

(57) ABSTRACT

The present invention relates to: a compound selected from the group consisting of a tricyclic compound having the structure of formula I, a pharmaceutically acceptable salt, an isomer, a solvate and a precursor thereof; and a use thereof. The compound effectively controls GPR40, and thus, can be effectively used for the prophylaxis or treatment of diseases associated with GPR40, for example, diabetes and many other diseases.

8 Claims, No Drawings

TRICYCLIC COMPOUND AND USE THEREOF

FIELD OF THE INVENTION

The present invention relates to a novel tricyclic compound, and a use thereof, and, more particularly to, a tricyclic compound having a structure of Formula I, and a use of the compound for preventing or treating various diseases including diabetes.

BACKGROUND OF THE INVENTION

Diabetes is a progressive debilitating disease that causes various microvascular and macrovascular complications and morbidity. Type II diabetes mellitus that is the most common type of diabetes is characterized by an increase in insulin resistance associated with inappropriate secretion of insulin after compensatory hyperinsulinemia. Free fatty acids (FFAs) are generally known to have an influence on secretion of insulin from β cells by promoting glucose-stimulated insulin secretion (GSIS), and regulate the release of insulin when G protein-coupled receptors (GPRs) expressed in the β cells respond to a change in blood sugar levels (see Nature, 2003, vol. 422, pp. 173-176). Among these, GPR40 (also known as a fatty acid receptor 1 (FFAR1)) is a membrane-bound FFA receptor that is preferentially expressed in pancreatic islets and particularly β cells to mediate heavy- and long-chain fatty acid-induced insulin secretion. It is known that compounds regulating the expression of GPR40 may be used to exhibit an incretin effect so as to promote GSIS, and may also be combined with a wide range of anti-diabetic drugs to treat diabetes, etc. Further, it is known that the compounds regulating the expression of GPR40 may be used to treat various diseases such as impaired glucose tolerance, ketosis, acidosis, diabetic neuropathy, diabetic nephropathy, diabetic retinopathy, macular edema, hyperlipidemia, genital disorders, skin diseases, arthropathia, osteopenia, arteriosclerosis, thrombotic diseases, dyspepsia, memory and learning difficulties, depression, manic depression, schizophrenia, attention-deficit hyperactivity disorder (ADHD), visual impairments, appetite dysregulation (for example, hyperorexia), obesity, hypoglycemia, hypertension, edemas, insulin resistance, labile diabetes, lipoatrophia, insulin allergies, insulinoma, lipotoxicity, pancreatic fatigue, hyperinsulinemia, cancers (for example, breast cancer), metabolic syndromes, immune diseases (for example, immunodeficiency), inflammatory diseases (for example, enteritis, arthritis, allergies), multiple sclerosis, acute renal failure, and the like, in addition to the diabetes.

There are a large number of reported compounds that have an ability to modulate a GPR40 receptor and are useful as drugs for preventing or treating diabetes. For example, WO 2004/106276 and WO 2005/051890 disclose compounds having an ability to modulate a GPR40 receptor. In recent years, WO 2008/001931, WO 2008/130514, and WO 2012/010413 disclose compounds that have an ability to modulate a GPR40 receptor and are useful as drugs for preventing or treating diabetes.

Although efforts to search for compounds modulating a GPR40 receptor have continued as described above, novel compounds having excellent efficacy are still required.

SUMMARY OF THE INVENTION

Therefore, it is an aspect of the present invention to provide a novel tricyclic compound.

It is another aspect of the present invention to provide a pharmaceutical use of the tricyclic compound.

To achieve the above goals, the present invention provides a compound selected from the group consisting of a tricyclic compound represented by the following Formula I, and a pharmaceutically acceptable salt, isomer, solvate and precursor thereof.

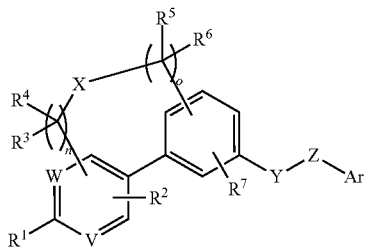

<Formula I>

In Formula I, V, W, X, Y, Z, Ar, $R^1$, $R^2$, $R^3$, $R^4$, $R^5$, $R^6$, $R^7$, n, and o are as defined in this disclosure.

According to another aspect, the present invention provides a use of a compound selected from the group consisting of the tricyclic compound of Formula I, and the pharmaceutically acceptable salt, isomer, solvate and precursor thereof, for the manufacture of a medicament for preventing or treating various diseases associated with GRP40, for example, diseases selected from the group consisting of diabetes, impaired glucose tolerance, ketosis, acidosis, diabetic neuropathy, diabetic nephropathy, diabetic retinopathy, macular edema, hyperlipidemia, genital disorders, skin diseases, arthropathia, osteopenia, arteriosclerosis, thrombotic diseases, dyspepsia, memory and learning difficulties, depression, manic depression, schizophrenia, attention-deficit hyperactivity disorder, visual impairments, appetite dysregulation, obesity, hypoglycemia, hypertension, edemas, insulin resistance, labile diabetes, lipoatrophia, insulin allergies, insulinoma, lipotoxicity, pancreatic fatigue, hyperinsulinemia, cancers, metabolic syndromes, immune diseases, inflammatory diseases, multiple sclerosis and acute renal failure.

Also, the present invention provides a pharmaceutical composition for preventing or treating various diseases associated with GRP40, which includes a compound selected from the group consisting of the tricyclic compound of Formula I, and the pharmaceutically acceptable salt, isomer, solvate and precursor thereof, and a pharmaceutically acceptable carrier.

Further, the present invention provides a method of preventing or treating various diseases associated with GRP40 in a mammal, which includes administering a compound selected from the group consisting of the tricyclic compound of Formula I, and the pharmaceutically acceptable salt, isomer, solvate and precursor thereof to the mammal.

DETAILED DESCRIPTION OF THE INVENTION

Hereinafter, the terms used in the present invention will be defined.

The term "halogen" used in the present invention encompasses fluoro, chloro, bromo, and iodo.

The term "alkyl" or "alkylene" used in the present invention encompasses a branched or linear saturated aliphatic hydrocarbon group having a specified number of carbon atoms. For example, the term "$C_{1-6}$ alkyl" refers to an alkyl group having 1 to 6 carbon atoms. Specific examples of the alkyl group include methyl (Me), ethyl (Et), propyl (for example, n-propyl, and isopropyl), butyl (for example, n-butyl, isobutyl, and t-butyl), and pentyl (for example, n-pentyl, isopentyl, and neopentyl), but are not limited thereto.

The term "alkoxy" used in the present invention refers to an —O-alkyl group. The term "$C_{1-6}$ alkoxy" includes $C_1$, $C_2$, $C_3$, $C_4$, $C_5$, and $C_6$ alkoxy groups. Specific examples of the alkoxy group include methoxy, ethoxy, propoxy (for example, n-propoxy, and isopropoxy), and t-butoxy, but are not limited thereto. Similarly, the term "alkylthio" used in the present invention includes an alkyl group having a specified number of carbon atoms, which is attached through a sulfur bridge, for example an —S-methyl group, and an —S-ethyl group.

The term "amino" used in the present invention includes a mono- or di-$C_{1-6}$ alkyl-amino group (for example, methylamino, ethylamino, propylamino, dimethylamino, and diethylamino), a mono- or di-$C_{6-14}$ aryl-amino group (for example, phenylamino, diphenylamino, 1-naphthylamino, and 2-naphthylamino), a mono- or di-$C_{7-16}$ aralkyl-amino group (for example, benzylamino, and phenethylamino), an N—$C_{1-6}$ alkyl-N—$C_{6-14}$ aryl-amino group (for example, N-methyl-N-phenylamino, and N-ethyl-N-phenylamino), and an N—$C_{1-6}$ alkyl-N—$C_{7-16}$ aralkyl-amino group (for example, N-methyl-N-benzylamino, and N-ethyl-N-benzylamino), but the present invention is not limited thereto.

The term "acyl" used in the present invention includes a formyl group, a carboxyl group, a carbamoyl group, a $C_{1-6}$ alkyl-carbonyl group, a $C_{1-6}$ alkoxy-carbonyl group, a $C_{3-8}$ cycloalkyl-carbonyl group, a $C_{6-14}$ aryl-carbonyl group, a $C_{7-16}$ aralkyl-carbonyl group, a $C_{6-14}$ aryloxy-carbonyl group, a $C_{7-16}$ aralkyloxy-carbonyl group, a mono- or di-$C_{1-6}$ alkylcarbamoyl group, a mono- or di-$C_{6-14}$ arylcarbamoyl group, a $C_{3-8}$ cycloalkyl-carbamoyl group, a $C_{7-16}$ aralkyl-carbamoyl group, a nitrogen-containing heterocyclyl-carbonyl group, a thiocarbamoyl group, and a mono- or di-$C_{1-6}$ alkyl-phosphono group, but is not limited thereto.

The phrase "substituted or unsubstituted" is used in the present invention to refer to a compound that is unsubstituted or substituted with 1 to 3 substituents selected from the following examples. For example, the substituted compound refers to a compound that may be substituted with at least one substituent selected from the group consisting of a 4- to 7-membered heterocyclyl containing 1 to 4 heteroelements selected from the group consisting of N, O, S, S(=O), and S(=O)$_2$ (which may be also substituted with 1 to 3 substituents selected from the group consisting of a halogenated $C_{1-6}$ alkyl group, a hydroxyl group, and a $C_{1-6}$ alkoxy-carbonyl group, preferably 1 to 3 substituents selected from the group consisting of pyridyl, thiazolyl, pyrrolidinyl, oxopyrrolidinyl, tetrahydropyranyl, tetrahydrothiopyranyl, 1-oxidotetrahydrothiopyranyl, 1,1-dioxidotetrahydrothiopyranyl, and oxetanyl), a $C_{3-8}$ cycloalkyl, a hydroxy, a halogenated $C_{1-6}$ alkoxy, an amino, a mono- or di-$C_{1-6}$ alkylamino, an N—$C_{1-6}$ alkyl-N—$C_{1-6}$ alkyl-carbonyl-amino, a $C_{7-16}$ aralkyloxy, a $C_{1-6}$ alkylthio, a $C_{1-6}$ alkylsulfinyl, a $C_{1-6}$ alkylsulfonyl, and a mono- or di-$C_{1-6}$ alkyl-phosphono.

The term "carbocyclyl" used in the present invention includes a radical group of any stable 3-, 4-, 5-, 6-, 7- or 8-membered monocyclic or bicyclic rings, or 7-, 8-, 9- or 10-membered bicyclic rings, which may be saturated, unsaturated, partially unsaturated, or aromatic. Examples of such a carbocyclyl include cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, and adamantyl, but are not limited thereto. Unless stated otherwise, the preferred carbocyclyl is cyclopropyl, cyclobutyl, cyclopentyl, cyclohexyl, phenyl, or naphthyl. When the "carbocyclyl" is used, the carbocyclyl includes an "aryl" group. The "aryl" group, for example, refers to a monocyclic or bicyclic aromatic hydrocarbon group including phenyl and naphthyl. The term "bicyclic carbocycle" refers to a stable 9- or 10-membered carbocyclyl group which contains two fused rings and is composed of carbon atoms. In the two fused rings, a first ring is a benzo ring fused to a second ring; and the second ring is a saturated, unsaturated, or partially unsaturated 5- or 6-membered carbon ring. The bicyclic carbocyclyl group may be attached to a pendant group through any carbon atom generating a stable structure.

Unless stated otherwise, the term "heterocyclyl" used in the present invention, for example, includes a 5- to 14-membered (monocyclic, bicyclic or tricyclic) heterocyclyl containing one or two or more (i.e., 1 to 4) heteroelements selected from the group consisting of N, O, S, S(=O), and S(=O)$_2$ as a ring-forming element in addition to the carbon atom, preferably (i) a 5- to 14-membered (preferably 5- to 10-membered) aromatic heterocyclyl, and (ii) a 5- to 10-membered non-aromatic heterocyclyl, and the like. Among these, a 5- or 6-membered aromatic heterocyclyl is preferred. Examples of the aromatic heterocyclyl may include thienyl, furyl, pyridyl, thiazolyl, oxazolyl, pyrazinyl, pyrimidinyl, pyrrolyl, imidazolyl, pyrazolyl, triazolyl, tetrazolyl, pyridazinyl, isothiazolyl, isoxazolyl, indolyl, 2-benzothiazolyl, 2-benzoxazolyl, benzimidazolyl, benzo[b]thienyl, benzo[b]furanyl, quinolyl, and isoquinolyl, but are not limited thereto. Examples of the non-aromatic heterocyclyl may include pyrrolidinyl, oxazolidinyl, imidazolinyl, pyperidinyl, pyperazinyl, morpholinyl, thiomorpholinyl, 1,1-dioxidotetrahydro-2H-thiopyranyl, and tetrahydropyranyl, but are not limited thereto.

The phrase "pharmaceutically acceptable" is used in the present invention to refer to a compound, a material, a composition, and/or a dosage form which is/are suitable for being used in contact with tissues of humans and animals without causing excessive toxicity, irritation, an allergic reaction, and/or other problems or complications within the scope of fair medical judgment, and has a balance of reasonable benefit-to-risk ratios.

The present invention provides a compound selected from the group consisting of a tricyclic compound represented by the following Formula I, and a pharmaceutically acceptable salt, isomer, solvate and precursor thereof:

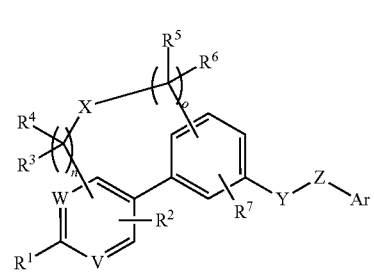

<Formula I> wherein

V and W are each independently =C(R$^{14}$)—, or =N—;

X is —CH$_2$—, —O—, —O—CH$_2$—O—, —S—, —C(=O)—, —S(=O)—, —S(=O)$_2$—, or —NR$^{15}$—;

Y is a C$_{1-6}$ alkylene;

Z is —O—, —S—, —C(=O)—, —S(=O)—, —S(=O)$_2$—, or —NR$^{15}$—;

Ar is one of the following substituents (a) to (c),

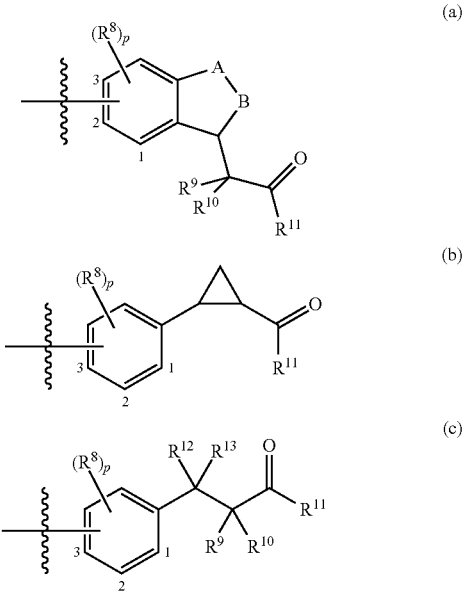

wherein A is —CH$_2$—, —CF$_2$—, —O—, —NR$^{15}$—, —S—, —S(=O)—, —S(=O)$_2$—, —C(=O)—, or —CH(OR$^{15}$)—;

B is a C$_{1-3}$ alkylene;

R$^1$ is hydrogen, a halogen, hydroxy, amino, nitro, cyano, a C$_{1-6}$ alkyl, a C$_{1-10}$ alkoxy, a C$_{1-6}$ alkylthio, acyl, a C$_{1-6}$ alkylsulfonyloxy, a C$_{3-12}$ carbocyclyl, a C$_{3-12}$ carbocyclyloxy, a C$_{3-12}$ carbocyclylsulfonyloxy, a 5- to 14-membered heterocyclyl, a 5- to 14-membered heterocyclyloxy, or a 5- to 14-membered heterocyclylsulfonyloxy;

R$^2$, R$^3$, R$^4$, R$^5$, R$^6$, and R$^7$ are each independently hydrogen, a halogen, amino, cyano, a C$_{1-6}$ alkyl, a C$_{1-6}$ alkoxy, a C$_{1-6}$ alkylthio, acyl, a C$_{3-12}$ carbocyclyl, or a 5- to 14-membered heterocyclyl;

R$^8$ is hydrogen, a halogen, hydroxy, amino, nitro, cyano, a C$_{1-6}$ alkyl, a C$_{1-6}$ alkoxy, or a C$_{1-6}$ alkylthio;

R$^9$ and R$^{10}$ are each independently hydrogen, a halogen, hydroxy, a C$_{1-6}$ alkyl, or a C$_{1-6}$ alkoxy;

R$^{11}$ is hydroxy, amino, or a C$_{1-6}$ alkoxy;

R$^{12}$ is hydrogen, a C$_{1-6}$ alkyl, a C$_{2-6}$ akenyl, a C$_{2-6}$ alkynyl, a C$_{1-6}$ alkoxy, a C$_{1-6}$ alkoxy-C$_{1-6}$ alkyl, a C$_{3-12}$ carbocyclyl, or a 5- to 14-membered heterocyclyl;

R$^{13}$ is hydrogen, or a C$_{1-6}$ alkyl;

R$^{14}$ is hydrogen, a halogen, amino, —CF$_3$, nitro, cyano, a C$_{1-6}$ alkyl, a C$_{1-6}$ alkoxy, a C$_{1-6}$ alkylthio, acyl, a C$_{3-12}$ carbocyclyl, or a 5- to 14-membered heterocyclyl;

R$^{15}$ is hydrogen, or a C$_{1-6}$ alkyl; and n, o, and p are each independently 0, 1, 2, or 3;

provided that the alkylene, the alkyl, the akenyl, the alkynyl, the alkoxy, the alkylthio, the amino, the acyl, the alkylsulfonyloxy, the carbocyclyl, the carbocyclyloxy, the carbocyclylsulfonyloxy, the heterocyclyl, the heterocyclyloxy, and the heterocyclylsulfonyloxy may each independently be substituted with at least one substituent selected from the group consisting of a 4- to 7-membered heterocyclyl (unsubstituted or substituted with 1 to 3 substituents selected from the group consisting of hydroxy, a halogenated C$_{1-6}$ alkyl, and a C$_{1-6}$ alkoxy-carbonyl), a C$_{3-8}$ cycloalkyl, hydroxy, a C$_{1-6}$ alkoxy, a halogenated C$_{1-6}$ alkoxy, amino, a mono- or di-C$_{1-6}$ alkyl-amino, an N—C$_{1-6}$ alkyl-N—C$_{1-6}$ alkyl-carbonyl-amino, a C$_{7-16}$ aralkyloxy, a C$_{1-6}$ alkylthio, a C$_{1-6}$ alkylsulfinyl, a C$_{1-6}$ alkylsulfonyl, and a mono- or di-C$_{1-6}$ alkyl-phosphono; and the heterocyclyl contains 1 to 4 heteroelements selected from the group consisting of N, O, S, S(=O), and S(=O)$_2$.

According to one preferred embodiment, in the compound of Formula I:

V and W are each independently =C(R$^{14}$)—, or =N—;

X is —CH$_2$—, —O—, —O—CH$_2$—O—, —S—, or —NR$^{15}$—;

Y is a C$_{1-3}$ alkylene;

Z is —O—, —S—, or —NR$^{15}$—, provided that Z is substituted at the 2$^{nd}$ or 3$^{rd}$ carbon atom of Ar;

Ar is one of the substituents (a) to (c);

A is —CH$_2$—, —CF$_2$—, —O—, or —NR$^{15}$—;

B is a C$_{1-2}$ alkylene;

R$^1$ is hydrogen, a halogen, hydroxy, amino, nitro, cyano, a C$_{1-6}$ alkyl, a C$_{1-10}$ alkoxy, a C$_{1-6}$ alkylthio, acyl, a C$_{1-6}$ alkylsulfonyloxy, a C$_{3-12}$ carbocyclyl, a C$_{3-12}$ carbocyclyloxy, a C$_{3-12}$ carbocyclylsulfonyloxy, a 5- to 14-membered heterocyclyl, a 5- to 14-membered heterocyclyloxy, or a 5- to 14-membered heterocyclylsulfonyloxy;

R$^2$ is hydrogen, a halogen, amino, cyano, a C$_{1-6}$ alkyl, a C$_{1-6}$ alkoxy, a C$_{1-6}$ alkylthio, a C$_{3-12}$ carbocyclyl, or a 5- to 14-membered heterocyclyl;

R$^3$, R$^4$, R$^5$, and R$^6$ are each independently hydrogen, a halogen, amino, a C$_{1-6}$ alkyl, or a C$_{1-6}$ alkoxy;

R$^7$ is hydrogen, a halogen, amino, cyano, a C$_{1-6}$ alkyl, a C$_{1-6}$ alkoxy, a C$_{1-6}$ alkylthio, a C$_{3-12}$ carbocyclyl, or a 5- to 14-membered heterocyclyl;

R$^8$ is hydrogen, a halogen, amino, a C$_{1-6}$ alkyl, or a C$_{1-6}$ alkoxy;

R$^9$ and R$^{10}$ are each independently hydrogen, a halogen, hydroxy, a C$_{1-6}$ alkyl, or a C$_{1-6}$ alkoxy;

R$^{11}$ is hydroxy, or a C$_{1-6}$ alkoxy;

R$^{12}$ is hydrogen, a C$_{1-6}$ alkyl, a C$_{2-6}$ akenyl, a C$_{2-6}$ alkynyl, a C$_{1-6}$ alkoxy, a C$_{1-6}$ alkoxy-C$_{1-6}$ alkyl, a C$_{3-12}$ carbocyclyl, or a 5- to 14-membered heterocyclyl;

R$^{13}$ is hydrogen, or a C$_{1-6}$ alkyl;

R$^{14}$ is hydrogen, a halogen, amino, —CF$_3$, a C$_{1-6}$ alkyl, a C$_{1-6}$ alkoxy, acyl, a C$_{3-12}$ carbocyclyl, or a 5- to 14-membered heterocyclyl;

R$^{15}$ is hydrogen, or a C$_{1-6}$ alkyl; and n, o, and p are each independently 0, 1, or 2;

provided that the alkylene, the alkyl, the alkynyl, the alkoxy, the alkylthio, the amino, the acyl, the alkylsulfonyloxy, the carbocyclyl, the carbocyclyloxy, the carbocyclylsulfonyloxy, the heterocyclyl, and the heterocyclyloxy may each independently substituted with at least one substituent selected from the group consisting of a 4- to 7-membered heterocyclyl (unsubstituted or substituted with 1 to 3 substituents selected from the group consisting of hydroxy, a halogenated C$_{1-6}$ alkyl, and a C$_{1-6}$ alkoxy-carbonyl), a C$_{3-8}$ cycloalkyl, hydroxy, a C$_{1-6}$ alkoxy, a halogenated C$_{1-6}$ alkoxy, amino, a mono- or di-C$_{1-6}$ alkyl-amino, an N—C$_{1-6}$ alkyl-N—C$_{1-6}$ alkyl-carbonyl-amino, a C$_{7-16}$ aralkyloxy, a C$_{1-6}$ alkylthio, a C$_{1-6}$ alkylsulfinyl, a C$_{1-6}$ alkylsulfonyl, and a mono- or di-C$_{1-6}$ alkyl-phosphono; and the heterocyclyl contains 1 to 4 heteroelements selected from the group consisting of N, O, S, S(=O), and S(=O)$_2$.

According to another preferred embodiment, in the compound of Formula I:

V and W are each independently =C(R$^{14}$)—, or =N—;
X is —CH$_2$—, —O—CH$_2$—O—, —O—, —S—, or —NR$^{15}$—;
Y is a C$_{1-3}$ alkylene;
Z is —O—, —S—, or —NR$^{15}$—, provided that Z is substituted at the 2$^{nd}$ or 3$^{rd}$ carbon atom of Ar;
Ar is one of the substituents (a) to (c);
A is —CH$_2$—, —CF$_2$—, —O—, or —NR$^{15}$—;
B is a C$_{1-2}$ alkylene;
R$^1$ is hydrogen, a halogen, hydroxy, amino, a C$_{1-6}$ alkyl, a C$_{1-10}$ alkoxy, acyl, a C$_{1-6}$ alkylsulfonyloxy, a C$_{3-12}$ carbocyclyloxy, a 5- to 14-membered heterocyclyl, or a 5- to 14-membered heterocyclyloxy;
R$^2$, R$^3$, R$^4$, R$^5$, R$^6$, R$^7$, and R$^8$ are each independently hydrogen, a halogen, amino, a C$_{1-6}$ alkyl, or a C$_{1-6}$ alkoxy;
R$^9$ and R$^{10}$ are each independently hydrogen, or a halogen;
R$^{11}$ is hydroxy, or a C$_{1-6}$ alkoxy;
R$^{12}$ is hydrogen, a C$_{1-6}$ alkyl, a C$_{2-6}$ akenyl, a C$_{2-6}$ alkynyl, a C$_{1-6}$ alkoxy, a C$_{1-6}$ alkoxy-C$_{1-6}$ alkyl, a C$_{3-12}$ carbocyclyl, or a 5- to 14-membered heterocyclyl;
R$^{13}$ is hydrogen;
R$^{14}$ is hydrogen, a halogen, amino, a C$_{1-6}$ alkyl, a C$_{1-6}$ alkoxy, or acyl;
R$^{15}$ is hydrogen, methyl, ethyl, or isopropyl; and
n, o, and p are each independently 0, 1, or 2;
provided that the alkylene, the alkyl, the alkynyl, the alkoxy, the amino, the acyl, the alkylsulfonyloxy, the carbocyclyloxy, the heterocyclyl, and the heterocyclyloxy may each independently be substituted with at least one substituent selected from the group consisting of a 4- to 7-membered heterocyclyl (unsubstituted or substituted with 1 to 3 substituents selected from the group consisting of hydroxy, a halogenated C$_{1-6}$ alkyl, and a C$_{1-6}$ alkoxy-carbonyl), a C$_{3-8}$ cycloalkyl, hydroxy, a C$_{1-6}$ alkoxy, a halogenated C$_{1-6}$ alkoxy, amino, a mono- or di-C$_{1-6}$ alkyl-amino, an N—C$_{1-6}$ alkyl-N—C$_{1-6}$ alkyl-carbonyl-amino, a C$_{7-16}$ aralkyloxy, a C$_{1-6}$ alkylthio, a C$_{1-6}$ alkylsulfinyl, a C$_{1-6}$ alkylsulfonyl, and a mono- or di-C$_{1-6}$ alkyl-phosphono; and the heterocyclyl contains 1 to 4 heteroelements selected from the group consisting of N, O, S, S(=O), and S(=O)$_2$.

According to still another preferred embodiment, in the compound of Formula I:

V and W are each independently =CH—, or =N—;
X is —CH$_2$—, —O—, —O—CH$_2$—O—, or —N(CH$_2$CH$_3$)—;
Y is methylene;
Z is —O— or —NH—, provided that Z is substituted at the 2$^{nd}$ or 3$^{rd}$ carbon atom of Ar;
Ar is one of the substituents (a) to (c);
A is —O—;
B is methylene;
R$^1$ is methylsulfonylpropoxy, ethylsulfonylpropoxy, ethoxyethoxy, morpholino, morpholinoethoxy, tetrahydrofuranyloxy,

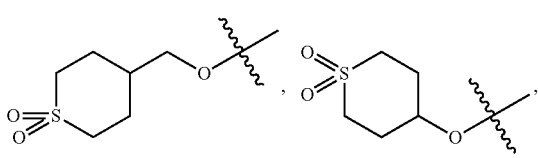

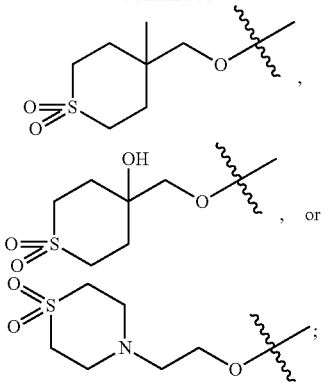

R$^2$ is hydrogen, or methyl;
R$^3$, R$^4$, R$^5$, and R$^6$ are each independently hydrogen, or methyl;
R$^7$ and R$^8$ are each independently hydrogen, or fluoro;
R$^9$ and R$^{10}$ are hydrogen;
R$^{11}$ is hydroxy;
R$^{12}$ is hydrogen, methyl, propyl, cyclopropyl, ethoxymethyl, ethynyl, —CH=CH—CH$_3$, —C≡C—CH$_3$, fluorophenyl, or methyloxazolyl;
R$^{13}$ is hydrogen;
n and o are each independently 0, 1, or 2; and
p may be 0 or 1.

Specific examples of the preferred compounds according to the present invention are as described below:

(1) 2-((3S)-6-((11-methyl-9-(3-(methylsulfonyl)propoxy)-6,7-dihydro-5H-dibenzo[a,c][7]annulen-4-yl)methoxy)-2,3-dihydrobenzofuran-3-yl)acetic acid;

(2) (1S,2S)-2-(4-((9-(3-(methylsulfonyl)propoxy)-6,7-dihydrodibenzo[b,d]oxepin-2-yl)methoxy)phenyl)cyclopropanecarboxylic acid;

(3) (1S,2S)-2-(4-(((9-(2-ethoxyethoxy)-6,7-dihydrodibenzo[b,d]oxepin-2-yl)methyl)amino)phenyl)cyclopropanecarboxylic acid;

(4) (1S,2S)-2-(4-(((9-(3-(methylsulfonyl)propoxy)-6,7-dihydrodibenzo[b,d]oxepin-2-yl)methyl)amino)phenyl)cyclopropanecarboxylic acid;

(5) (S)-2-(6-((9-(3-(methylsulfonyl)propoxy)-6,7-dihydro-5H-dibenzo[a,c][7]annulen-2-yl)methoxy)-2,3-dihydrobenzofuran-3-yl)acetic acid;

(6) (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylic acid;

(7) 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-yl)acetic acid;

(8) (1R,2R)-2-(4-(((10-methyl-8-(3-(methylsulfonyl)propoxy)-6H-benzo[c]chromen-4-yl)methyl)amino)phenyl)cyclopropanecarboxylic acid;

(9) (1S,2S)-2-(4-(((10-methyl-8-(3-(methylsulfonyl)propoxy)-6H-benzo[c]chromen-2-yl)methyl)amino)phenyl)cyclopropanecarboxylic acid;

(10) (S)-2-(6-((5-methyl-7-(3-(methylsulfonyl)propoxy)-9,10-dihydrophenanthren-1-yl)methoxy)-2,3-dihydrobenzofuran-3-yl)acetic acid;

(11) (S)-2-(6-((5-methyl-7-(3-(methylsulfonyl)propoxy)-9,10-dihydrophenanthren-3-yl)methoxy)-2,3-dihydrobenzofuran-3-yl)acetic acid;

(12) (S)-2-(6-((7-(2-ethoxyethoxy)-5-methyl-9,10-dihydrophenanthren-3-yl)methoxy)-2,3-dihydrobenzofuran-3-yl)acetic acid;

(13) 2-((3S)-6-((11-methyl-9-(3-(methylsulfonyl)propoxy)-6,7-dihydrodibenzo[b,d]oxepin-4-yl)methoxy)-2,3-dihydrobenzofuran-3-yl)acetic acid;
(14) 2-((3S)-6-((11-methyl-9-(3-(methylsulfonyl)propoxy)-6,7-dihydrodibenzo[b,d]oxepin-2-yl)methoxy)-2,3-dihydrobenzofuran-3-yl)acetic acid;
(15) (1S,2S)-2-(4-(((11-methyl-9-(3-(methylsulfonyl)propoxy)-6,7-dihydrodibenzo[b,d]oxepin-2-yl)methyl)amino)phenyl)cyclopropanecarboxylic acid;
(16) (1S,2S)-2-(4-(((8-(2-ethoxyethoxy)-10-methyl-6H-benzo[c]chromen-2-yl)methyl)amino)phenyl)cyclopropanecarboxylic acid;
(17) (S)-2-(6-((8-(2-ethoxyethoxy)-10-methyl-6H-benzo[c]chromen-2-yl)methoxy)-2,3-dihydrobenzofuran-3-yl)acetic acid;
(18) (1S,2S)-2-(4-(((9-(3-(methylsulfonyl)propoxy)-5,7-dihydrodibenzo[c,e]oxepin-2-yl)methyl)amino)phenyl)cyclopropanecarboxylic acid;
(19) (1S,2S)-2-(4-(((11-methyl-9-(3-(methylsulfonyl)propoxy)-5,7-dihydrodibenzo[c,e]oxepin-4-yl)methyl)amino)phenyl)cyclopropanecarboxylic acid;
(20) (S)-2-(6-((9-(3-(methylsulfonyl)propoxy)-5,7-dihydrodibenzo[c,e]oxepin-2-yl)methoxy)-2,3-dihydrobenzofuran-3-yl)acetic acid;
(21) (1S,2S)-2-(4-(((3-(3-(methylsulfonyl)propoxy)-6,7-dihydrodibenzo[b,d]oxepin-10-yl)methyl)amino)phenyl)cyclopropanecarboxylic acid;
(22) (1S,2S)-2-(4-(((9-(2-ethoxyethoxy)-5,7-dihydrodibenzo[c,e]oxepin-2-yl)methyl)amino)phenyl)cyclopropanecarboxylic acid;
(23) (S)-2-(6-((9-(2-ethoxyethoxy)-5,7-dihydrodibenzo[c,e]oxepin-2-yl)methoxy)-2,3-dihydrobenzofuran-3-yl)acetic acid;
(24) (1S,2S)-2-(4-((9-(3-(methylsulfonyl)propoxy)-5,7-dihydrodibenzo[c,e]oxepin-2-yl)methoxy)phenyl)cyclopropanecarboxylic acid;
(25) (1S,2S)-2-(4-((9-(3-(methylsulfonyl)propoxy)-6,7-dihydro-5H-dibenzo[a,c][7]annulen-2-yl)methoxy)phenyl)cyclopropanecarboxylic acid;
(26) (S)-2-(6-((10-methyl-8-(3-(methylsulfonyl)propoxy)-6H-benzo[c]chromen-2-yl)methoxy)-2,3-dihydrobenzofuran-3-yl)acetic acid;
(27) (S)-2-(6-((9-(2-ethoxyethoxy)-6,7-dihydro-5H-dibenzo[a,c][7]annulen-2-yl)methoxy)-2,3-dihydrobenzofuran-3-yl)acetic acid;
(28) (1S,2S)-2-(4-(((9-(2-ethoxyethoxy)-6,7-dihydro-5H-dibenzo[a,c][7]annulen-2-yl)methyl)amino)phenyl)cyclopropanecarboxylic acid;
(29) (1S,2S)-2-(4-(((11-methyl-9-(3-(methylsulfonyl)propoxy)-6,7-dihydro-5H-dibenzo[a,c][7]annulen-2-yl)methyl)amino)phenyl)cyclopropanecarboxylic acid;
(30) (1S,2S)-2-(4-((10-methyl-8-(3-(methylsulfonyl)propoxy)-6H-benzo[c]chromen-2-yl)methoxy)phenyl)cyclopropanecarboxylic acid;
(31) (1S,2S)-2-(4-((5-methyl-7-(3-(methylsulfonyl)propoxy)-9,10-dihydrophenanthren-3-yl)methoxy)phenyl)cyclopropanecarboxylic acid;
(32) (S)-2-(6-((9-(3-(methylsulfonyl)propoxy)-6,7-dihydrodibenzo[b,d]oxepin-2-yl)methoxy)-2,3-dihydrobenzofuran-3-yl)acetic acid;
(33) 2-((3S)-6-((11-methyl-9-(3-(methylsulfonyl)propoxy)-5,7-dihydrodibenzo[c,e]oxepin-2-yl)methoxy)-2,3-dihydrobenzofuran-3-yl)acetic acid;
(34) (1S,2S)-2-(4-(((11-methyl-9-(3-(methylsulfonyl)propoxy)-5,7-dihydrodibenzo[c,e]oxepin-2-yl)methyl)amino)phenyl)cyclopropanecarboxylic acid;
(35) 2-((3S)-6-((9-(2-ethoxyethoxy)-11-methyl-6,7-dihydro-5H-dibenzo[a,c][7]annulen-2-yl)methoxy)-2,3-dihydrobenzofuran-3-yl)acetic acid;
(36) 2-((3S)-6-((9-((1,1-dioxidotetrahydro-2H-thiopyran-4-yl)oxy)-11-methyl-6,7-dihydrodibenzo[b,d]oxepin-2-yl)methoxy)-2,3-dihydrobenzofuran-3-yl)acetic acid;
(37) 2-((3S)-6-((9-(2-(1,1-dioxidothiomorpholino)ethoxy)-11-methyl-6,7-dihydrodibenzo[b,d]oxepin-2-yl)methoxy)-2,3-dihydrobenzofuran-3-yl)acetic acid;
(38) 2-((3S)-6-((9-(3-(ethylsulfonyl)propoxy)-11-methyl-6,7-dihydrodibenzo[b,d]oxepin-2-yl)methoxy)-2,3-dihydrobenzofuran-3-yl)acetic acid;
(39) (1S,2S)-2-(4-((11-methyl-9-(3-(methylsulfonyl)propoxy)-6,7-dihydrodibenzo[b,d]oxepin-2-yl)methoxy)phenyl)cyclopropanecarboxylic acid;
(40) (1S,2S)-2-(2-fluoro-4-((11-methyl-9-(3-(methylsulfonyl)propoxy)-6,7-dihydrodibenzo[b,d]oxepin-2-yl)methoxy)phenyl)cyclopropanecarboxylic acid;
(41) (1S,2S)-2-(4-((9-(3-(ethylsulfonyl)propoxy)-11-methyl-6,7-dihydrodibenzo[b,d]oxepin-2-yl)methoxy)-2-fluorophenyl)cyclopropanecarboxylic acid;
(42) (S)-2-(6-((3-(3-(methylsulfonyl)propoxy)-6,7-dihydrodibenzo[b,d]oxepin-10-yl)methoxy)-2,3-dihydrobenzofuran-3-yl)acetic acid;
(43) (S)-2-(6-((6,6-dimethyl-9-(3-(methylsulfonyl)propoxy)-6,7-dihydrodibenzo[b,d]oxepin-2-yl)methoxy)-2,3-dihydrobenzofuran-3-yl)acetic acid;
(44) (S)-2-(6-((5-ethyl-9-(3-(methylsulfonyl)propoxy)-6,7-dihydro-5H-dibenzo[b,d]azepin-2-yl)methoxy)-2,3-dihydrobenzofuran-3-yl)acetic acid;
(45) (1S,2S)-2-(4-((5-ethyl-9-(3-(methylsulfonyl)propoxy)-6,7-dihydro-5H-dibenzo[b,d]azepin-2-yl)methoxy)phenyl)cyclopropanecarboxylic acid;
(46) 2-((3S)-6-((9-((4-hydroxy-1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid;
(47) 2-((3S)-6-((9-((1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid;
(48) (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)phenyl)cyclopropanecarboxylic acid;
(49) (1S,2S)-2-(4-((9-(3-(ethylsulfonyl)propoxy)-11-methyl-6,7-dihydrodibenzo[b,d]oxepin-2-yl)methoxy)phenyl)cyclopropanecarboxylic acid;
(50) (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)-2-fluorophenyl)cyclopropanecarboxylic acid;
(51) (1S,2S)-2-{2-fluoro-4-[9-(4-hydroxy-1,1-dioxido-hexahydro-thiopyran-4-ylmethoxy)-11-methyl-6,7-dihydro-5-oxa-dibenzo[a,c]cyclohepten-2-ylmethoxy]-phenyl}-cyclopropanecarboxylic acid;
(52) (1S,2S)-2-(4-(((9-((1,1-dioxidotetrahydro-2H-thiopyran-4-yl)oxy)-11-methyl-6,7-dihydrodibenzo[b,d]oxepin-2-yl)methyl)amino)-2-fluorophenyl)cyclopropanecarboxylic acid;
(53) (1S,2S)-2-(4-(((9-(3-(ethylsulfonyl)propoxy)-11-methyl-6,7-dihydrodibenzo[b,d]oxepin-2-yl)methyl)amino)-2-fluorophenyl)cyclopropanecarboxylic acid;
(54) 2-((3S)-6-((6,6,11-trimethyl-9-(3-(methylsulfonyl)propoxy)-6,7-dihydrodibenzo[b,d]oxepin-2-yl)methoxy)-2,3-dihydrobenzofuran-3-yl)acetic acid;

(55) 2-((3S)-6-((9-((1,1-dioxidotetrahydro-2H-thiopyran-4-yl)oxy)-11-methyl-6,7-dihydro-5H-dibenzo[a,c][7]annulen-2-yl)methoxy)-2,3-dihydrobenzofuran-3-yl)acetic acid;

(56) 2-((3S)-6-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)-2,3-dihydrobenzofuran-3-yl)acetic acid;

(57) 2-((3S)-6-((9-(3-(ethylsulfonyl)propoxy)-11-methyl-6,7-dihydro-5H-dibenzo[a,c][7]annulen-2-yl)methoxy)-2,3-dihydrobenzofuran-3-yl)acetic acid;

(58) (1S,2S)-2-(4-4H-methyl-9-(3-(methylsulfonyl)propoxy)-6,7-dihydro-5H-dibenzo[a,c][7]annulen-2-yl)methoxy)phenyl)cyclopropanecarboxylic acid;

(59) (1S,2S)-2-(4-((9-((1,1-dioxidotetrahydro-2H-thiopyran-4-yl)oxy)-11-methyl-6,7-dihydro-5H-dibenzo[a,c][7]annulen-2-yl)methoxy)phenyl)cyclopropanecarboxylic acid;

(60) (1S,2S)-2-(4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid;

(61) (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylic acid;

(62) (1S,2S)-2-(2-fluoro-4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid;

(63) (1S,2S)-2-(2-fluoro-4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid;

(64) (S)-2-(6-((9-((1,1-dioxidotetrahydro-2H-thiopyran-4-yl)oxy)-6,7-dihydro-5H-dibenzo[a,c][7]annulen-2-yl)methoxy)-2,3-dihydrobenzofuran-3-yl)acetic acid;

(65) (S)-2-(6-((9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;

(66) (S)-2-(6-((9-(3-(ethylsulfonyl)propoxy)-6,7-dihydro-5H-dibenzo[a,c][7]annulen-2-yl)methoxy)-2,3-dihydrobenzofuran-3-yl)acetic acid;

(67) (1S,2S)-2-(4-((9-((1,1-dioxidotetrahydro-2H-thiopyran-4-yl)oxy)-6,7-dihydro-5H-dibenzo[a,c][7]annulen-2-yl)methoxy)phenyl)cyclopropanecarboxylic acid;

(68) (1S,2S)-2-(4-((9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid;

(69) (1S,2S)-2-(4-((9-(3-(ethylsulfonyl)propoxy)-6,7-dihydro-5H-dibenzo[a,c][7]annulen-2-yl) methoxy)phenyl)cyclopropanecarboxylic acid;

(70) (1S,2S)-2-(4-(((9-((1,1-dioxidotetrahydro-2H-thiopyran-4-yl)oxy)-6,7-dihydro-5H-dibenzo[a,c][7]annulen-2-yl)methyl)amino)phenyl)cyclopropanecarboxylic acid;

(71) (1S,2S)-2-(4-(((9-((4-hydroxy-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid;

(72) (1S,2S)-2-(4-(((9-(3-(ethylsulfonyl)propoxy)-6,7-dihydro-5H-dibenzo[a,c][7]annulen-2-yl)methyl)amino)phenyl)cyclopropanecarboxylic acid;

(73) (1S,2S)-2-(4-(((9-((1,1-dioxidotetrahydro-2H-thiopyran-4-yl)oxy)-11-methyl-6,7-dihydrodibenzo[b,d]oxepin-2-yl)methyl)amino)phenyl)cyclopropanecarboxylic acid;

(74) (1S,2S)-2-(4-(((9-(3-(ethylsulfonyl)propoxy)-11-methyl-6,7-dihydro-5H-dibenzo[a,c][7]annulen-2-yl)methyl)amino)phenyl)cyclopropanecarboxylic acid;

(75) (1S,2S)-2-(4-(((9-((1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid;

(76) (1S,2S)-2-(4-(((9-((1,1-dioxidotetrahydro-2H-thiopyran-4-yl)oxy)-11-methyl-6,7-dihydro-5H-dibenzo[a,c][7]annulen-2-yl)methyl)amino)phenyl)cyclopropanecarboxylic acid;

(77) (1S,2S)-2-(4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid;

(78) (1S,2S)-2-(4-(((9-((1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid;

(79) 2-((S)-6-(((R)-6-methyl-9-(3-(methylsulfonyl)propoxy)-6,7-dihydrodibenzo[b,d]oxepin-2-yl)methoxy)-2,3-dihydrobenzofuran-3-yl)acetic acid;

(80) (S)-2-(6-((9-(3-(methylsulfonyl)propoxy)dibenzo[d,f][1,3]dioxepin-2-yl)methoxy)-2,3-dihydrobenzofuran-3-yl)acetic acid;

(81) 2-((3S)-6-((1-methyl-3-morpholino-6,7-dihydro-5H-benzo[3,4]cyclohepta[1,2-d]pyrimidin-10-yl)methoxy)-2,3-dihydrobenzofuran-3-yl)acetic acid;

(82) (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-yl)acetic acid;

(83) (S)-2-(6-(((9-((1,1-dioxidotetrahydro-2H-thiopyran-4-yl)methoxy)-6,7-dihydro-5H-dibenzo[a,c][7]annulen-2-yl)methyl)amino)-2,3-dihydrobenzofuran-3-yl)acetic acid;

(84) (S)-2-(6-((9-((1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;

(85) (S)-2-(6-((9-((1,1-dioxidotetrahydro-2H-thiopyran-4-yl)methoxy)-3-fluoro-6,7-dihydro-5H-dibenzo[a,c][7]annulen-2-yl)methoxy)-2,3-dihydrobenzofuran-3-yl)acetic acid;

(86) (1S,2S)-2-(4-(((9-((1,1-dioxidotetrahydro-2H-thiopyran-4-yl)methoxy)-3-fluoro-6,7-dihydro-5H-dibenzo[a,c][7]annulen-2-yl)methyl)amino)phenyl)cyclopropanecarboxylic acid;

(87) (1S,2S)-2-(4-(((9-(3-(ethylsulfonyl)propoxy)-11-methyl-6,7-dihydrodibenzo[b,d]oxepin-2-yl)methyl)amino)phenyl)cyclopropanecarboxylic acid;

(88) 2-((3S)-6-((9-(2-ethoxyethoxy)-11-methyl-6,7-dihydrodibenzo[b,d]oxepin-2-yl)methoxy)-2,3-dihydrobenzofuran-3-yl)acetic acid;

(89) (1S,2S)-2-(4-((1-methyl-3-morpholino-5H-benzo[3,4]cyclohepta[1,2-d]pyrimidin-10-yl)methoxy)phenyl)cyclopropanecarboxylic acid;

(90) 2-((3S)-6-((1-methyl-3-(3-(methylsulfonyl)propoxy)-6,7-dihydro-5H-benzo[3,4]cyclohepta[1,2-d]pyrimidin-10-yl)methoxy)-2,3-dihydrobenzofuran-3-yl)acetic acid;

(91) (S)-2-(6-(((9-(2-ethoxyethoxy)-6,7-dihydro-5H-dibenzo[a,c][7]annulen-2-yl)methyl)amino)-2,3-dihydrobenzofuran-3-yl)acetic acid;

(92) (S)-2-(6-(((9-(3-(ethylsulfonyl)propoxy)-6,7-dihydro-5H-dibenzo[a,c][7]annulen-2-yl)methyl)amino)-2,3-dihydrobenzofuran-3-yl)acetic acid;

(93) (S)-2-(6-((9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;

(94) (1S,2S)-2-(4-(((9-((4-methyl-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid;

(95) (S)-2-(6-((3-fluoro-9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;

(96) (S)-2-(6-((3-fluoro-9-(3-(methylsulfonyl)propoxy)-6,7-dihydro-5H-dibenzo[a,c][7]annulen-2-yl)methoxy)-2,3-dihydrobenzofuran-3-yl)acetic acid;

(97) (S)-2-(6-((9-(3-(ethylsulfonyl)propoxy)-3-fluoro-6,7-dihydro-5H-dibenzo[a,c][7]annulen-2-yl)methoxy)-2,3-dihydrobenzofuran-3-yl)acetic acid;

(98) (S)-2-(6-((9-((1,1-dioxidotetrahydro-2H-thiopyran-4-yl)oxy)-3-fluoro-6,7-dihydro-5H-dibenzo[a,c][7]annulen-2-yl)methoxy)-2,3-dihydrobenzofuran-3-yl)acetic acid;

(99) (S)-2-(6-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;

(100) (1S,2S)-2-(4-((9-((1,1-dioxidotetrahydro-2H-thiopyran-4-yl)oxy)-3-fluoro-6,7-dihydro-5H-dibenzo[a,c][7]annulen-2-yl)methoxy)phenyl)cyclopropanecarboxylic acid;

(101) (1S,2S)-2-(4-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid;

(102) (1S,2S)-2-(4-((3-fluoro-9-(3-(methylsulfonyl)propoxy)-6,7-dihydro-5H-dibenzo[a,c][7]annulen-2-yl)methoxy)phenyl)cyclopropanecarboxylic acid;

(103) (1S,2S)-2-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)cyclopropanecarboxylic acid;

(104) (1S,2S)-2-(4-(((3-fluoro-9-(3-(methylsulfonyl)propoxy)-6,7-dihydro-5H-dibenzo[a,c][7]annulen-2-yl)methyl)amino)phenyl)cyclopropanecarboxylic acid;

(105) (1S,2S)-2-(4-(((9-(3-(ethylsulfonyl)propoxy)-3-fluoro-6,7-dihydro-5H-dibenzo[a,c][7]annulen-2-yl)methyl)amino)phenyl)cyclopropanecarboxylic acid;

(106) 2-((S)-6-((3-fluoro-9-(((R)-tetrahydrofuran-3-yl)oxy)-6,7-dihydro-5H-dibenzo[a,c][7]annulen-2-yl)methoxy)-2,3-dihydrobenzofuran-3-yl)acetic acid;

(107) (S)-2-(6-((3-fluoro-9-(2-morpholinoethoxy)-6,7-dihydro-5H-dibenzo[a,c][7]annulen-2-yl) methoxy)-2,3-dihydrobenzofuran-3-yl)acetic acid;

(108) (S)-3-(4-((9-(3-(methylsulfonyl)propoxy)-6,7-dihydro-5H-dibenzo[a,c][7]annulen-2-yl)methoxy)phenyl)hex-4-ynoic acid;

(109) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoic acid;

(110) (S)-3-(4-((9-((1,1-dioxidotetrahydro-2H-thiopyran-4-yl)oxy)-6,7-dihydro-5H-dibenzo[a,c][7]annulen-2-yl)methoxy)phenyl)hex-4-ynoic acid;

(111) (S)-3-(4-((9-(3-(ethylsulfonyl)propoxy)-6,7-dihydro-5H-dibenzo[a,c][7]annulen-2-yl)methoxy)phenyl)hex-4-ynoic acid;

(112) (S)-3-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)hex-4-ynoic acid;

(113) (S)-3-(4-((9-((1,1-dioxidotetrahydro-2H-thiopyran-4-yl)methoxy)-6,7-dihydrodibenzo[b,d]oxepin-2-yl)methoxy)phenyl)hex-4-ynoic acid;

(114) (S)-3-(4-((3-((1,1-dioxidotetrahydro-2H-thiopyran-4-yl)methoxy)-6,7-dihydro-5H-benzo[3,4]cyclohepta[1,2-b]pyridin-10-yl)methoxy)phenyl)hex-4-ynoic acid;

(115) (R)-3-cyclopropyl-3-(3-((9-((1,1-dioxidotetrahydro-2H-thiopyran-4-yl)methoxy)-6,7-dihydro-5H-dibenzo[a,c][7]annulen-2-yl)methoxy)phenyl)propanoic acid;

(116) 3-cyclopropyl-3-(4-((9-((1,1-dioxidotetrahydro-2H-thiopyran-4-yl)methoxy)-6,7-dihydro-5H-dibenzo[a,c][7]annulen-2-yl)methoxy)phenyl)propanoic acid;

(117) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hexanoic acid;

(118) (R,Z)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-enoic acid;

(119) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(5-methylisoxazol-3-yl)propanoic acid;

(120) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(isoxazol-3-yl)propanoic acid;

(121) 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(3-methylisoxazol-5-yl)propanoic acid;

(122) (S)-3-(4-((3-(3-(methylsulfonyl)propoxy)-6,7-dihydro-5H-benzo[3,4]cyclohepta[1,2-b]pyridin-10-yl)methoxy)phenyl)hex-4-ynoic acid;

(123) (S)-3-(4-((3-(3-(ethylsulfonyl)propoxy)-6,7-dihydro-5H-benzo[3,4]cyclohepta[1,2-b]pyridin-10-yl)methoxy)phenyl)hex-4-ynoic acid;

(124) (S)-3-(4-((3-((1,1-dioxidotetrahydro-2H-thiopyran-4-yl)oxy)-6,7-dihydro-5H-benzo[3,4]cyclohepta[1,2-b]pyridin-10-yl)methoxy)phenyl)hex-4-ynoic acid;

(125) (S)-3-(4-((5-methyl-7-(3-(methylsulfonyl)propoxy)-9,10-dihydrophenanthren-3-yl)methoxy)phenyl)hex-4-ynoic acid;

(126) (S)-3-(4-((7-(2-ethoxyethoxy)-5-methyl-9,10-dihydrophenanthren-3-yl)methoxy)phenyl)hex-4-ynoic acid;

(127) (S)-3-(4-((5-methyl-7-(3-(methylsulfonyl)propoxy)-9,10-dihydrophenanthren-1-yl)methoxy)phenyl)hex-4-ynoic acid;

(128) (S)-3-(4-((11-methyl-9-(3-(methylsulfonyl)propoxy)-6,7-dihydro-5H-dibenzo[a,c][7]annulen-2-yl)methoxy)phenyl)hex-4-ynoic acid;

(129) (S)-3-(4-((9-(3-(methylsulfonyl)propoxy)dibenzo[d,f][1,3]dioxepin-2-yl)methoxy)phenyl)hex-4-ynoic acid;

(130) (S)-3-(4-((6,6-dimethyl-9-(3-(methylsulfonyl)propoxy)-6,7-dihydrodibenzo[b,d]oxepin-2-yl)methoxy)phenyl)hex-4-ynoic acid;

(131) (S)-3-(4-((1-methyl-3-(3-(methylsulfonyl)propoxy)-6,7-dihydro-5H-benzo[3,4]cyclohepta[1,2-d]pyrimidin-10-yl)methoxy)phenyl)hex-4-ynoic acid;

(132) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid;

(133) (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid;

(134) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-4-ethoxybutanoic acid;
(135) (S)-3-(4-(((9-(3-(methylsulfonyl)propoxy)-6,7-dihydro-5H-dibenzo[a,c][7]annulen-2-yl)methyl)amino)phenyl)hex-4-ynoic acid;
(136) (S)-3-(4-(((9-((1,1-dioxidotetrahydro-2H-thiopyran-4-yl)methoxy)-6,7-dihydro-5H-dibenzo[a,c][7]annulen-2-yl)methyl)amino)phenyl)hex-4-ynoic acid;
(137) 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(4-fluorophenyl)propanoic acid;
(138) (S)-3-(4-((11-methyl-9-(((R)-tetrahydrofuran-3-yl)oxy)-6,7-dihydro-5H-dibenzo[a,c][7]annulen-2-yl)methoxy)phenyl)hex-4-ynoic acid;
(139) (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)pent-4-ynoic acid;
(140) (S)-3-(4-((5-ethyl-9-(((R)-tetrahydrofuran-3-yl)oxy)-6,7-dihydro-5H-dibenzo[b,d]azepin-2-yl)methoxy)phenyl)hex-4-ynoic acid;
(141) sodium (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylate;
(142) sodium 2-((3S)-6-((11-methyl-9-(3-(methyl sulfonyl)propoxy)-6,7-dihydro-5H-dibenzo[a,c][7]annulen-2-yl)methoxy)-2,3-dihydrobenzofuran-3-ylacetate;
(143) sodium (1S,2S)-2-(4-((11-methyl-9-(3-(methyl sulfonyl)propoxy)-6,7-dihydrodibenzo[b,d]oxepin-2-yl)methoxy)phenyl)cyclopropanecarboxylate;
(144) sodium (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylate;
(145) sodium (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-ylacetate;
(146) sodium (S)-3-(4-((9-(3-(methyl sulfonyl)propoxy)-6,7-dihydro-5H-dibenzo[a,c][7]annulen-2-yl)methoxy)phenyl)hex-4-ynoate; and
(147) sodium (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoate.

The present invention includes a pharmaceutically acceptable salt, isomer, solvate and precursor of the compound of Formula I.

The term "pharmaceutically acceptable salt" used in the present invention refers to a derivative obtained by converting a parent compound into a salt thereof by using an acid or base. Examples of the pharmaceutically acceptable salt include an inorganic or organic acid salt containing a basic moiety, for example, an amine; an alkali or organic salt containing an acidic moiety, for example, carboxylic acid, but are not limited thereto. For example, the pharmaceutically acceptable salt includes a conventional non-toxic salt, or a quaternary ammonium salt of a parent compound, which is formed from a non-toxic inorganic or organic acid. For example, such a conventional non-toxic salt includes salts derived from inorganic acids, for example, hydrochloric acid, hydrobromic acid, sulfuric acid, sulfamic acid, phosphoric acid, and nitric acid; and salts prepared from organic acids, for example, acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, etc.

The pharmaceutically acceptable salt according to the present invention may be prepared from a parent compound containing a basic or acidic moiety by using a conventional chemical reaction. Generally, such a salt may be prepared by allowing the compound in the form of a free acid or base to react with a stoichiometric amount of a base or acid in water, an organic solvent, or a mixture thereof (generally, a non-aqueous medium such as ether, ethyl acetate, ethanol, isopropanol, or acetonitrile is preferred).

Also, the compound of Formula I may have a structure in which hydrogen atoms of carboxyl groups (—COOH) contained in the compound are replaced by alkaline metals (Li, Na, K, etc.) through an ionic bond thereto. Such an ionic salt compound may also be in the form of a pharmaceutically acceptable salt of the compound of Formula I, which is encompassed in the scope of the present invention.

Also, the compound of Formula I may include one or more unsymmetrically substituted carbon atoms, and may be isolated in an optically active or racemic form. Therefore, the compound of Formula I particularly includes all chiral, diastereomeric, racemic, and geometrically isomeric forms of the compound of Formula I. A method of preparing and isolating such an optically active form is widely known in the relevant art. For example, a mixture of stereoisomers may be isolated by isolation of a racemic form, by normal-phase chromatography, reversed-phase chromatography or chiral chromatography, by a standard technique including salt formation and recrystallization, etc., or by chiral synthesis from a chiral starting material or chiral synthesis using synthesis of a target chiral center.

Further, the compound of Formula I may be in the form of a solvate. A solvate refers to a physical aggregation of the compound according to the present invention and one or more solvent molecules (regardless of an organic or inorganic solvent). The physical aggregation includes a hydrogen bond. In a certain case, for example, when one or more solvent molecules are incorporated into a crystal lattice of a crystalline solid, it is possible to isolate a solvate. The solvent molecules may be present in the solvate in a regular arrangement and/or an irregular arrangement. The solvate may include either a stoichiometric or nonstoichiometric amount of the solvent molecules. The term "solvate" includes both a solution-phase solvate and a solvate that can be isolated. The exemplary solvate includes a hydrate, an ethanolate, a methanolate, and an isopropanolate, but is not limited thereto. A solvation method is generally known in the art.

Also, the compound of Formula I may be in the form of a precursor. Any compound that may be converted in vivo to provide a physiologically active agent (i.e., the compound of Formula I) is a prodrug which falls within the scope of the present invention. Various types of prodrugs and methods of preparing same are widely known in the art.

Compounds containing a carboxyl group may form a physiologically hydrolyzable ester which functions as a prodrug that generates the compound of Formula I by means of hydrolysis in vivo. Preferably, since in many cases, the hydrolysis generally occurs under the influence of digestive enzymes, such a prodrug is orally administered. When the ester itself is active, or the hydrolysis occurs in blood, the prodrug may be used for parenteral administration. Examples of the physiologically hydrolyzable ester of the compound of Formula I include a $C_{1-6}$ alkyl, a $C_{1-6}$ alkyl-benzyl, 4-methoxybenzyl, indanyl, phthalyl, methoxymethyl, a $C_{1-6}$ alkanoyloxy-$C_{1-6}$ alkyl (for example, acetoxymethyl, pivaloyloxymethyl, or propionyloxymethyl), a $C_{1-6}$ alkoxycarbonyloxy-$C_{1-6}$ alkyl (for example, methoxycarbonyl-oxymethyl, ethoxycarbonyloxymethyl, glycyloxymethyl, phenylglycyloxymethyl, or (5-methyl-2-oxo-1,3-dioxolen-4-yl)-methyl), and other widely known physiologically hydrolyzable esters, such as those used in penicillin and cephalosporin industries. Such an ester may be prepared by conventional techniques known in the art.

The compounds according to the present invention may be prepared by using the methods as described below or methods in the working examples, or other known methods, methods apparent to those skilled in the art, or modified methods thereof. Unless particularly stated otherwise, respective symbols of the compounds in the following schemes are as defined above.

Compounds Ia, Ia', Ib, Ib', Ic, and Ic' may be prepared by using the following Scheme 1 or 2, or a method similar to Scheme 1 or 2.

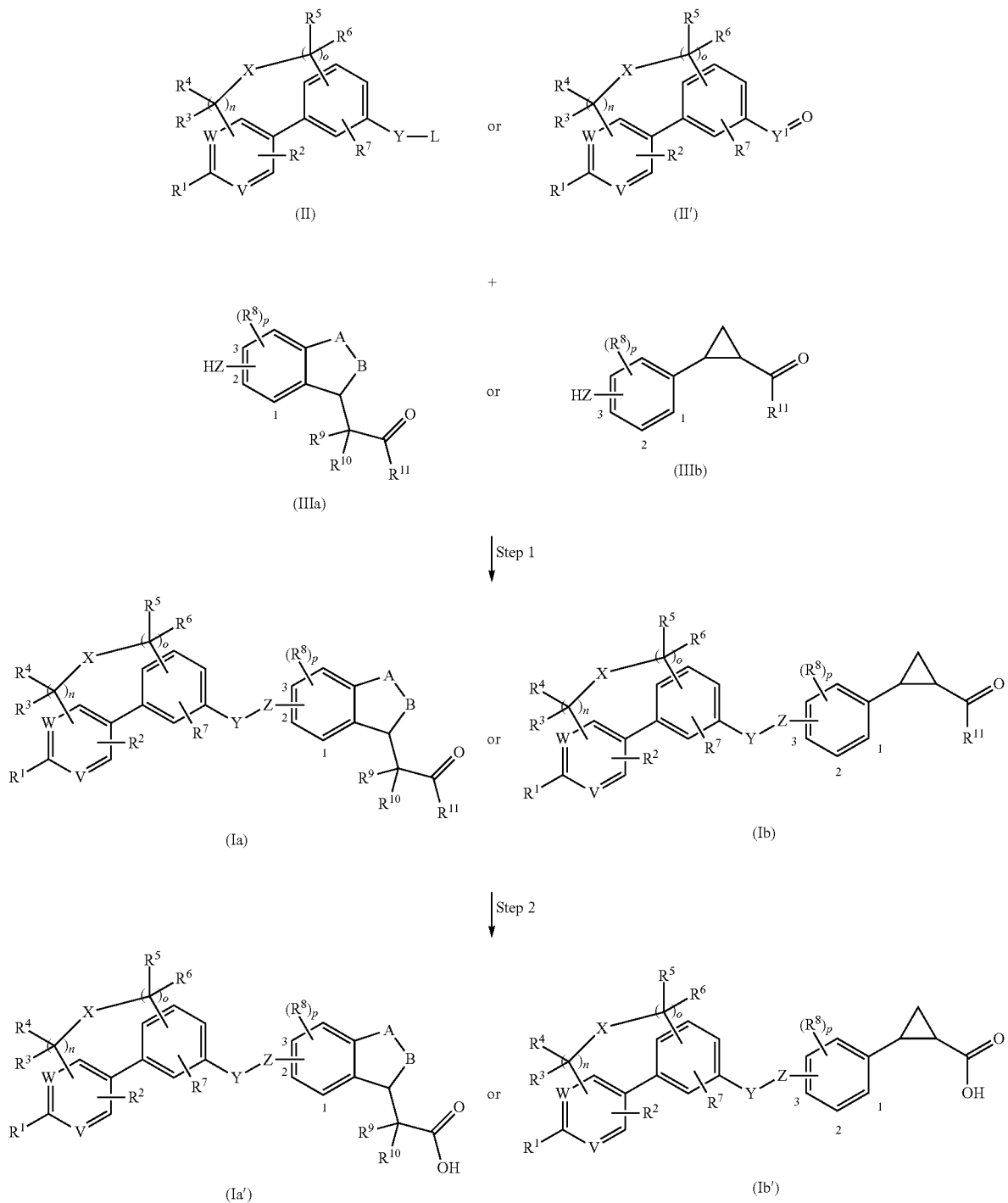

Scheme 2

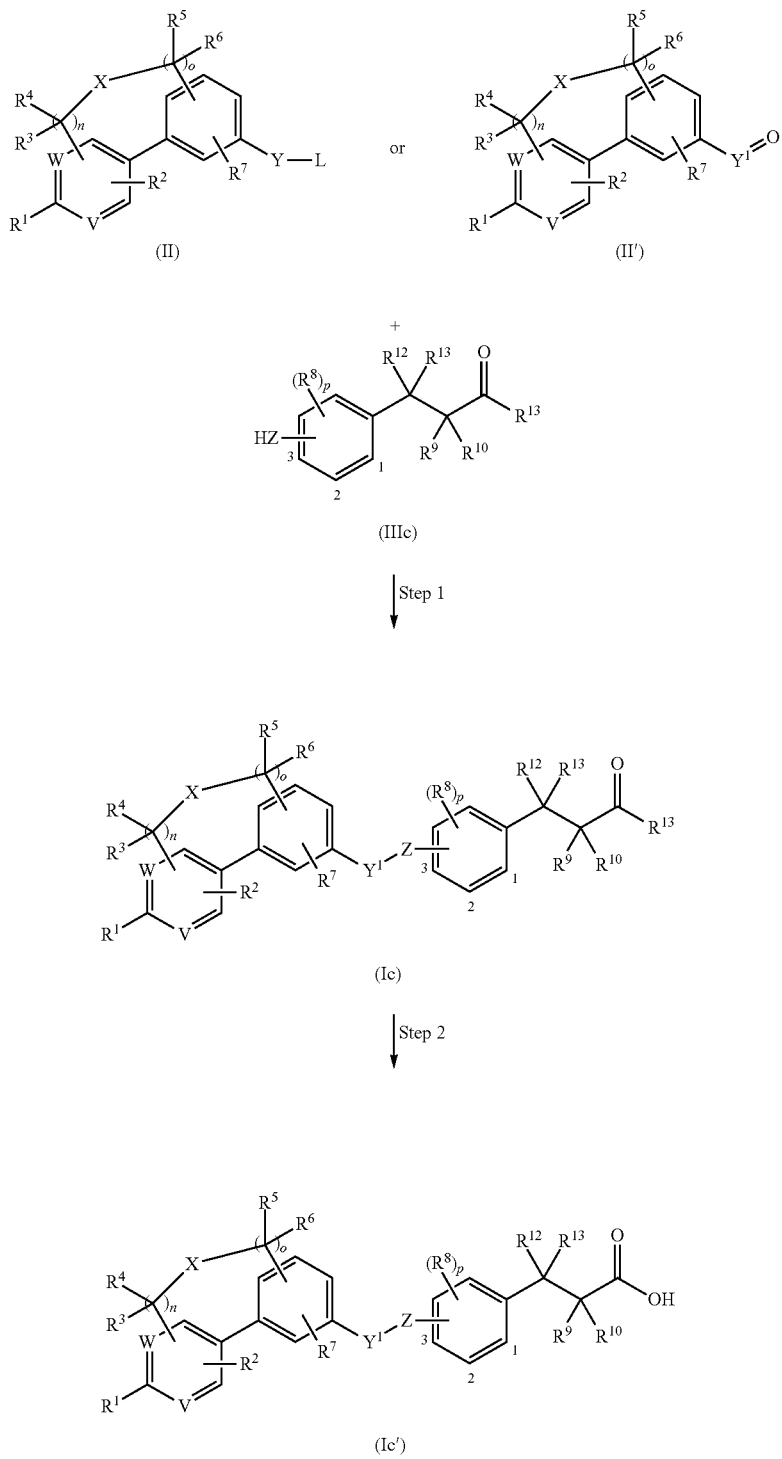

In Schemes 1 and 2, L is a leaving group, or a hydroxyl group, and $Y^1=O$ is in the form of a ketone or aldehyde of Y.

For example, the compound Ia may be synthesized under a binding reaction of intermediates II and IIIa in the presence of a proper base (for example, sodium hydride, potassium carbonate, cesium carbonate, etc.) when L is a leaving group, and may be synthesized under a Mitsunobu reaction when L is a hydroxyl group. Also, the compound Ia may be synthesized under a reductive amination reaction of intermediates II' and IIIa in the presence of a proper reducing agent (for example, sodium cyanoborohydride, sodium triacetoxyborohydride, sodium borohydride, etc.). When imine products as intermediates may be stably isolated from a reaction system, the compound Ia may be synthesized under a separate reduction reaction after the corresponding imine products are obtained.

When R" in compound Ia, Ib, or Ic is not hydroxy, the compound Ia, Ib, or Ic may be hydrolyzed in the presence of a proper acid or base to synthesize compound Ia', Ib' or Ic' containing a carboxyl group.

proper base as shown in Step 3, and may be prepared also under a Suzuki reaction as shown in Step 3', when necessary.

Meanwhile, the intermediate II' may be prepared by oxidizing the intermediate II with a proper oxidizing agent (for example, a manganese oxide, a Des s-Martin reagent (1,1,1-triacetoxy-1,1-dihydro-1,2-benziodoxol-3(1H)-one), etc.).

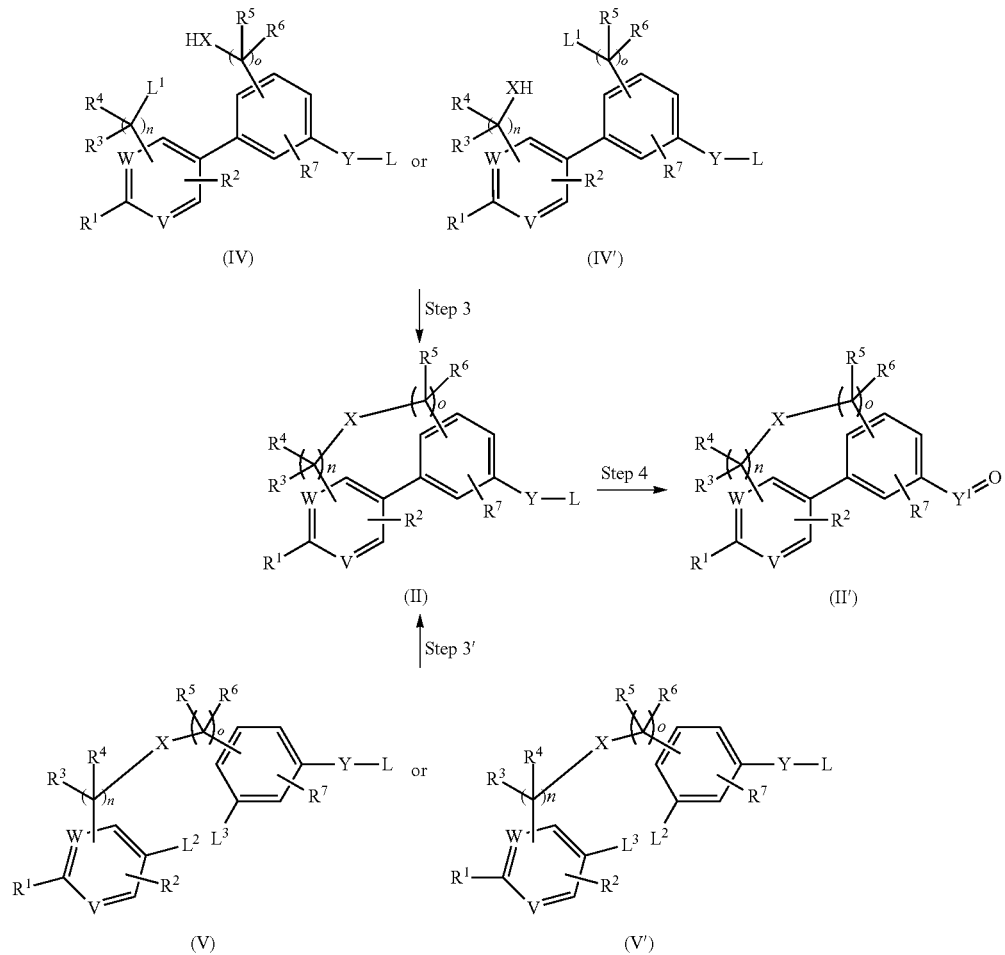

The intermediates II and II' in Scheme 1 may be prepared by the following Scheme 3, or methods similar to Scheme 3. In some cases, the intermediates II and II' may be prepared by means of various known synthesis methods in accordance with the characteristics of the types of the backbone or substituent. In terms of a preparation technique, it may also be effective to substitute a functional group with a proper protective group, that is, a group that may be readily converted into the corresponding functional group, during the steps in which starting materials or intermediates are prepared, depending on the types of the functional groups. Thereafter, the protective group may be optionally removed to provide a desired compound.

The intermediate II of Scheme 1 may be prepared under an intramolecular cyclization reaction in the presence of a In Scheme 3, L, $L^1$, $L^2$, and $L^3$ represent leaving groups.

The intermediates IV and IV' in Scheme 3 may be prepared under a Suzuki reaction or methods similar to the Suzuki reaction, as shown in the following Scheme 4.

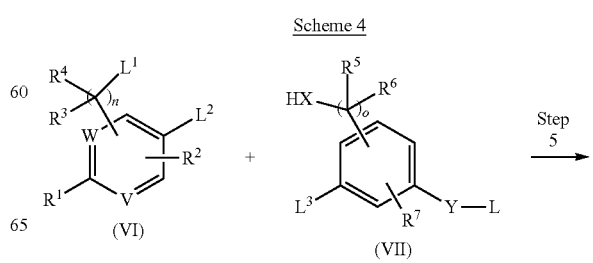

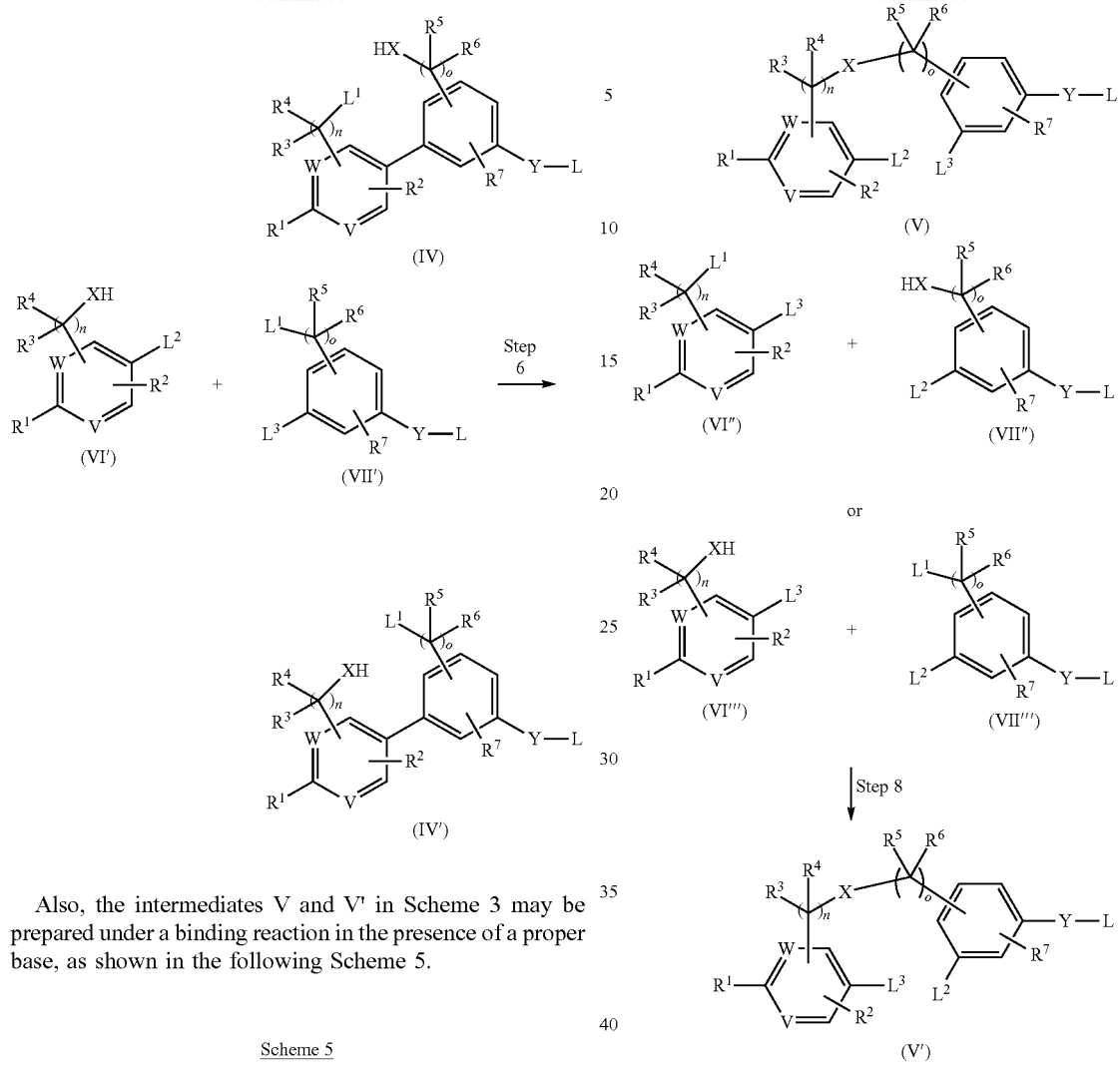

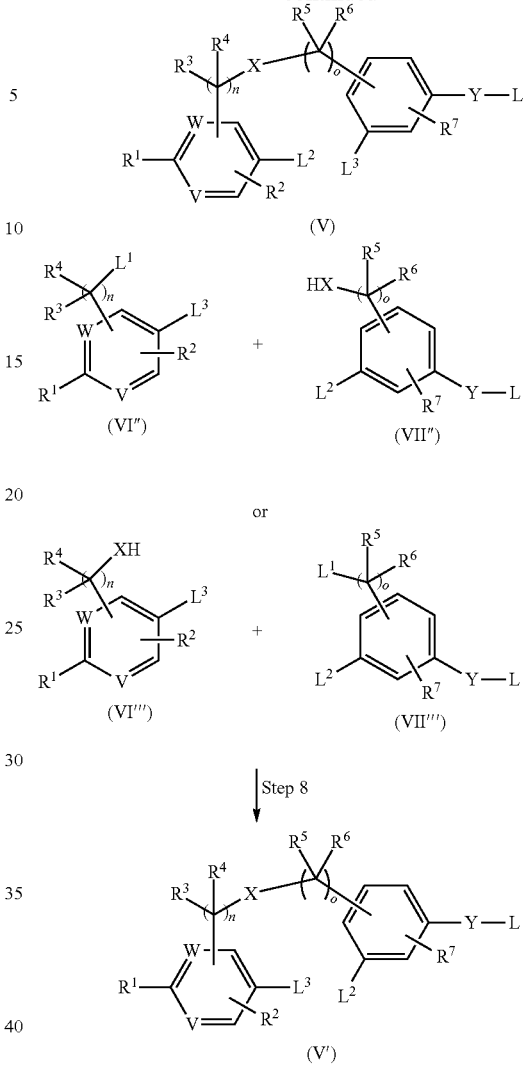

Also, the intermediates V and V' in Scheme 3 may be prepared under a binding reaction in the presence of a proper base, as shown in the following Scheme 5.

Scheme 5

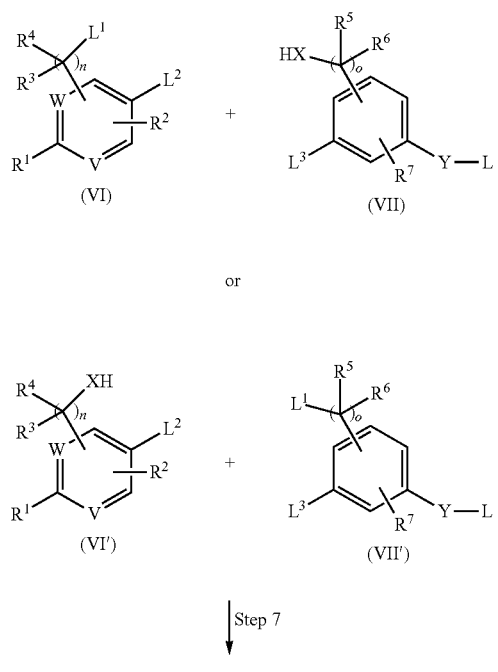

The compounds according to the present invention prepared thus are isolated and purified in a free state, or as salts thereof by performing a salt forming treatment using a conventional method. The isolation/purification is performed by means of conventional chemical processes such as extraction, concentration, distillation, removal, crystallization, filtration, recrystallization, various chromatographies, etc.

Various isomers may be isolated by a conventional method using a difference in physicochemical properties between the isomers. For example, a racemic mixture may be separated into optically pure isomers by using a racemic resolution method, for example, by preparing using a diastereomeric salt with a typical optically-active acid such as tartaric acid to optically resolve the racemic mixture, or various chromatographies. Also, the resulting diastereomeric mixture may be separated, for example, by fractional crystallization or various chromatographies. In addition, the optically active compound may also be prepared by using a proper optically-active starting material.

When the compound of Formula I includes a stereoisomer, both the respective isomers and mixtures of the respective isomers fall under the scope of the present invention. Also, the compound of Formula I may be a hydrate, or a non-hydrate.

The compound of Formula I may be labeled with an isotope (for example, $^3$H, $^{14}$C, $^{35}$S), etc.

The compound selected from the group consisting of the tricyclic compound of Formula I according to the present invention or the pharmaceutically acceptable salt, isomer, solvate and precursor thereof has an ability to modulate GPR40 receptor functions (GPR40 receptor agonist activity and GPR40 receptor antagonist activity), particularly, GPR40 receptor agonist activity, and exhibits low toxicity and fewer side effects (for example, acute toxicity, chronic toxicity, genetic toxicity, developmental toxicity, cardiotoxicity, drug interactions, and carcinogenicity). Therefore, the compounds according to the present invention are useful as a stable GPR40 receptor modulator, preferably a GPR40 agonist.

The compound according to the present invention, or a pharmaceutical composition comprising the compound has an excellent ability to modulate GPR40 receptor functions in mammals (for example, mice, rats, hamsters, rabbits, cats, dogs, cattle, sheep, monkeys, humans, etc.), and is useful as a medicament for modulating the physiological functions in which the GPR40 receptor takes part, or a medicament for preventing or treating diseases in which the GPR40 receptor takes part.

Specifically, the compound according to the present invention, or the pharmaceutical composition comprising the compound is useful as an insulin secretion modulator (preferably an insulin secretagogue), a hypoglycemic agent, and a pancreatic β cell protective agent.

Also, the compound according to one exemplary embodiment of the present invention, or the pharmaceutical composition including the compound is useful as a medicament for preventing or treating diseases such as diabetes, impaired glucose tolerance, ketosis, acidosis, diabetic neuropathy, diabetic nephropathy, diabetic retinopathy, macular edema, hyperlipidemia, genital disorders, skin diseases, arthropathia, osteopenia, arteriosclerosis, thrombotic diseases, dyspepsia, memory and learning difficulties, depression, manic depression, schizophrenia, attention-deficit hyperactivity disorder, visual impairments, appetite dysregulation (for example, hyperorexia), obesity, hypoglycemia, hypertension, edemas, insulin resistance, labile diabetes, lipoatrophia, insulin allergies, insulinoma, lipotoxicity, pancreatic fatigue, hyperinsulinemia, cancers (for example, breast cancer), metabolic syndromes, immune diseases (for example, immunodeficiency), inflammatory diseases (for example, enteritis, arthritis, and allergy), multiple sclerosis, acute renal failure, etc.; particularly diseases such as diabetes, impaired glucose tolerance, ketosis, acidosis, diabetic neuropathy, diabetic nephropathy, diabetic retinopathy, macular edema, hyperlipidemia, genital disorders, skin diseases, arthropathia, osteopenia, arteriosclerosis, thrombotic diseases, dyspepsia, memory and learning difficulties, etc.

Here, the diabetes may include type I diabetes mellitus, type II diabetes mellitus, and gestational diabetes. Also, the hyperlipidemia may include hypertriglyceridemia, hypercholesteremia, hyper-HDL-cholesterolemia, postprandial hyperlipidemia, etc.

According to one exemplary embodiment, the compound of the present invention, or the pharmaceutical composition comprising the compound may be used to prevent or treat type II diabetes mellitus.

The compound according to the present invention may be used in combination with other drugs. Examples of such other drugs that may be used in combination with the compound according to the present invention may include an anti-diabetic agent, an anti-diabetic complication agent, an anti-hyperlipidemic agent, an anti-hypertensive agent, an anti-obesity agent, a diuretic agent, a chemotherapeutic agent, an immunotherapeutic agent, an anti-inflammatory drug, an anti-thrombotic agent, a therapeutic agent for osteoporosis, vitamins, anti-dementia drug, a therapeutic agent for urinary incontinence or urinary frequency, an anti-dysuria agent, etc., but are not limited thereto.

The pharmaceutical composition comprising the compound according to the present invention may be prepared by using a pharmaceutically acceptable carrier, an excipient, and the like, generally used in the relevant art in accordance with a conventional preparation method.

The pharmaceutical composition according to the present invention may be prepared into various types of formulations, and administered. A route of administration of the formulation may include oral administration by a tablet, a pill, a capsule, a granule, a powder, a solution, and the like, or parenteral administration by an intraarticular, intravenous or intramuscular injection, a suppository, eye drops, an oculentum, a liquid for transcutaneous use, an ointment, an adhesive for transcutaneous use, a transmucosal liquid, a transmucosal adhesive, an inhalant, etc.

Examples of a solid formulation for oral administration according to the present invention may include a tablet, a pill, a powder, a granule, etc. Such a formulation is prepared by mixing at least one or two or more active ingredients with at least one pharmacologically inert excipient, for example, lactose, mannitol, glucose, hydroxypropyl cellulose, microcrystalline cellulose, starch, polyvinyl pyrrolidone, and/or magnesium aluminium metasilicate. The formulation may include a pharmacologically inert additive, for example, a lubricant such as magnesium stearate, a disintegrating agent such as carboxymethyl starch sodium, a stabilizing agent, a solubilizing aid, etc. The tablet or the pill may be coated with a sugar coating, or coated with a film made of a gastric juice-soluble material or an enteric material.

Examples of a liquid formulation for oral administration according to the present invention may include an emulsion, a solution, a suspension, a syrup, or an elixir. In this case, the liquid formulation may comprise a conventional inert diluent, for example, purified water or ethanol. In addition, the liquid formulation may comprise a solubilizing agent, a wetting agent, an auxiliary agent such as a suspension, a sweetening agent, a flavoring agent, an aromatic, a preservative, etc.

An injection for parenteral administration includes an aseptic aqueous or non-aqueous solution, suspension or emulsion. For example, injectable distilled water, or a saline solution is included as an aqueous solvent. For example, a non-aqueous solvent may be propylene glycol, polyethylene glycol, a vegetable oil such as olive oil, an alcohol such as ethanol, or Polysorbate 80. Such a composition may further comprise an isotonic agent, a preservative, a wetting agent, an emulsifying agent, a dispersing agent, a stabilizing agent, or a solubilizing aid. These components may, for example, be sterilized by filtration using a bacteria retaining filter, blending of a disinfectant, or irradiation. Also, these components may also be used to prepare an aseptic solid composition, and may be dissolved or suspended in sterile water or an aseptic injectable solvent before use.

Hereinafter, the present invention will be described in further detail with reference to exemplary embodiments thereof.

However, it should be understood that the detailed description herein is given by way of illustration of the present invention only, and is not intended to limit the scope of the present invention. Unless stated otherwise, the abbreviations and chemical symbols used in the following examples have conventional meanings as commonly understood by one of ordinary skill in the art. Unless stated otherwise, the compounds disclosed herein are prepared, isolated and identified by using schemes disclosed herein, and other methods.

Example 1

Preparation of 2-((3S)-6-((11-methyl-9-(3-(methylsulfonyl)propoxy)-6,7-dihydro-5H-dibenzo[a,c][7]annulen-4-yl)methoxy)-2,3-dihydrobenzofuran-3-yl)acetic acid <1-1> Preparation of 2-(3-methoxy-5-methylphenyl)acetaldehyde

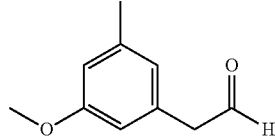

Dess-Martin periodinane (3.25 g, 7.65 mmol) was slowly added to a solution of 2-(3-methoxy-5-methylphenyl)ethanol (prepared according to the method disclosed in the document [Australian Journal of Chemistry, 1999, vol. 52, #11, pp. 1093-1108]; 1.06 g, 6.37 mmol) in dichloromethane (60 mL) at 0° C., and stirred at ambient temperature for 30 minutes. The resulting mixture was diluted with dichloromethane, and washed with a 1 N NaOH aqueous solution and water. An organic layer was dried over sodium sulfate, and concentrated under reduced pressure. The residue was purified using silica gel chromatography to obtain the title compound (pale yellow oil, 749 mg, 4.56 mmol, and 72% yield).

$^1$H NMR (300 MHz, CDCl$_3$) δ 9.72 (t, 1H), 6.65 (d, 2H), 6.56 (s, 1H), 3.79 (s, 3H), 3.61 (d, 2H), 2.33 (s, 3H).

<1-2> Preparation of (2-bromo-6-(methoxycarbonyl)benzyl)triphenylphosphonium bromide

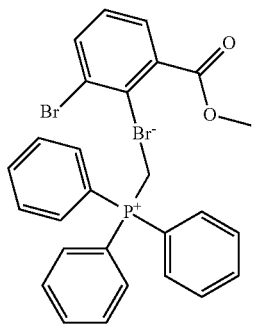

Triphenylphosphine (3.58 g, 13.64 mmol) was added to a solution of methyl 3-bromo-2-(bromomethyl)benzoate (prepared according to the method disclosed in the document [U.S. Pat. No. 6,518,257 B1]; 4.2 g, 13.64 mmol) in toluene (100 mL), and stirred at 95° C. for 15 hours. The resulting compound was cooled to ambient temperature, diluted with hexane (100 mL), and then stirred at ambient temperature for 10 minutes or more. The mixture was filtered, and washed with hexane. Then, the resulting solid was dried in a vacuum to obtain the title compound (white solid, 7.0 g, 12.27 mmol, and 90% yield).

$^1$H NMR (300 MHz, CDCl$_3$) δ 7.88-7.74 (m, 5H), 7.71-7.52 (m, 12H), 7.35 (td, 1H), 5.58 (d, 2H), 3.59 (s, 3H).

<1-3> Preparation of methyl 3-bromo-2-(3-(3-methoxy-5-methylphenyl)prop-1-en-1-yl)benzoate

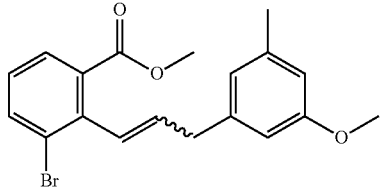 [SMILES: COC(=O)c1cccc(Br)c1C=CCc1cc(C)cc(OC)c1]

The compound (1.57 g, 9.56 mmol) obtained in <1-1> was dissolved in dichloromethane (57 mL) and THF (38 mL), and the compound (5.45 g, 9.56 mmol) obtained in <1-2> was added thereto. Subsequently, K$_2$CO$_3$ (3.97 g, 28.7 mmol) and 18-Crown-6 (505 mg, 1.91 mmol) were added. The mixture was stirred at 70° C. for 1 hour, and the compound (1.09 g, 1.91 mmol) obtained in <1-2> was then added, and stirred for 4 hours. The mixture was cooled to room temperature, and diluted with a saturated EtOAc and NH$_4$Cl aqueous solution. Layers were separated, and an organic layer was dried over magnesium sulfate, filtered, and then concentrated under reduced pressure. The residue was purified using silica gel chromatography to obtain the title compound (an E/Z mixture, colorless oil, 1.11 g, and 31% yield).

E form: $^1$H NMR (300 MHz, CDCl$_3$) δ 7.67 (dd, 1H), 7.54 (dd, 1H), 7.13 (t, 1H), 6.66-6.58 (m, 4H), 5.82 (dt, 1H), 3.80 (d, 3H), 3.67 (d, 3H), 3.50 (d, 2H), 2.32 (t, 3H).

Z form: $^1$H NMR (300 MHz, CDCl$_3$) δ 7.76 (ddd, 2H), 7.22 (m, 1H), 6.62-6.49 (m, 4H), 5.93 (dt, 1H), 3.82 (d, 3H), 3.75 (s, 3H), 3.08 (d, 2H), 2.27 (t, 3H).

<1-4> Preparation of methyl 2-(3-(3-methoxy-5-methylphenyl)propyl)benzoate

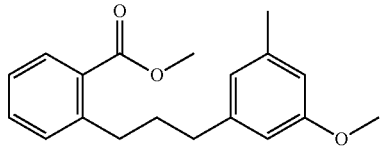 [SMILES: COC(=O)c1ccccc1CCCc1cc(C)cc(OC)c1]

The compound (1.5 g, 3.99 mmol) obtained in <1-3> was dissolved in EtOAc (15 mL), and 10% Pd/C (1.5 g, 1.40 mmol) was added thereto, and stirred for 5 hours under hydrogen gas. The reaction mixture was filtered through Celite, and the filtrate was concentrated under reduced pressure. The residue was purified using silica gel chromatography to obtain the title compound (colorless oil, 984 mg, and 83% yield).

$^1$H NMR (600 MHz, CDCl$_3$) δ 7.86 (d, 1H), 7.41 (t, 1H), 7.28-7.21 (m, 2H), 6.62 (s, 1H), 6.55 (d, 2H), 3.85 (s, 3H), 3.78 (s, 3H), 3.02-2.96 (m, 2H), 2.66-2.60 (m, 2H), 2.30 (s, 3H), 1.96-1.87 (m, 2H).

<1-5> Preparation of methyl 2-(3-(2-bromo-5-methoxy-3-methylphenyl)propyl)benzoate

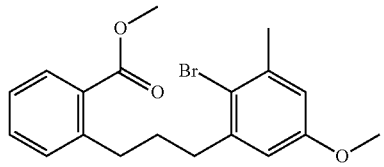 [SMILES: COC(=O)c1ccccc1CCCc1cc(OC)cc(C)c1Br]

The compound (980 mg, 3.29 mmol) obtained in <1-4> was dissolved in CH$_3$CN (30 mL), and N-bromosuccinimide (585 mg, 3.29 mmol) was added thereto, and stirred at ambient temperature for 3 hours. The resulting compound was concentrated under reduced pressure, and the residue was purified using silica gel chromatography to obtain the title compound (colorless oil, 1.2 g, and 97% yield).

$^1$H NMR (300 MHz, CDCl$_3$) δ 7.86 (dd, 1H), 7.41 (m, 1H), 7.30-7.20 (m, 2H), 6.64 (s, 2H), 3.87 (s, 3H), 3.76 (s, 3H), 3.10-2.98 (m, 2H), 2.86-2.74 (m, 2H), 2.38 (s, 3H), 1.99-1.84 (m, 2H).

<1-6> Preparation of methyl 9-methoxy-11-methyl-6,7-dihydro-5H-dibenzo[a,c][7]annulen-4-carboxylate

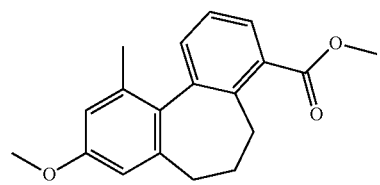

The compound (500 mg, 1.32 mmol) obtained in <1-5>, tricyclohexylphosphine tetrafluoroborate (137 mg, 0.370 mmol), and K$_2$CO$_3$ (365 mg, 2.64 mmol) were mixed with N,N-dimethylacetamide (4 mL), and palladium (II) acetate (42 mg, 0.185 mmol) was added thereto, replaced with nitrogen, and stirred at 150° C. for 15 hours. The mixture was cooled to room temperature, diluted with EtOAc, and washed with a saturated NH$_4$Cl aqueous solution and saline. Thereafter, the mixture was dried over sodium sulfate, and concentrated under reduced pressure. Then, the residue was purified using silica gel chromatography to obtain the title compound (colorless oil, 43 mg, and 11% yield).

$^1$H NMR (300 MHz, CDCl$_3$) δ 7.77-7.66 (m, 1H), 7.42-7.28 (m, 2H), 6.75 (d, 1H), 6.65 (d, 1H), 3.92 (s, 3H), 3.84 (s, 3H), 3.30-3.21 (m, 1H), 2.47 (m, 1H), 2.30 (s, 3H), 2.24-1.95 (m, 4H).

<1-7> Preparation of methyl 9-hydroxy-11-methyl-6,7-dihydro-5H-dibenzo[a,c][7]annulen-4-carboxylate

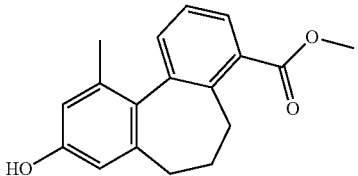 [SMILES: COC(=O)c1cccc2c1CCCc1cc(O)cc(C)c1-2]

The compound (147 mg, 0.5 mmol) obtained in <1-6> was dissolved in dichloromethane (5 mL), and boron tribromide (a 1 M dichloromethane solution, 1 mL, 1 mmol) was slowly added thereto at 0° C., slowly heated, and stirred at ambient temperature for 3 hours. The reaction mixture was diluted with methanol (2 mL) and dichloromethane (15 mL), and washed with a saturated NH$_4$Cl aqueous solution. An organic layer was dried over sodium sulfate, and concentrated under reduced pressure. Then, the residue was purified using silica gel chromatography to obtain the title compound (white foam, 93 mg, and 66% yield).

$^1$H NMR (300 MHz, CDCl$_3$) δ 7.73 (dd, 1H), 7.40-7.28 (m, 2H), 6.69 (d, 1H), 6.58 (d, 1H), 4.67 (s, 1H), 3.92 (s, 3H), 3.30-3.19 (m, 1H), 2.49-2.37 (m, 1H), 2.25 (s, 3H), 2.23-2.10 (m, 3H), 2.05-1.95 (m, 1H).

<1-8> Preparation of methyl 11-methyl-9-(3-(methylsulfonyl)propoxy)-6,7-dihydro-5H-dibenzo[a,c][7]annulen-4-carboxylate

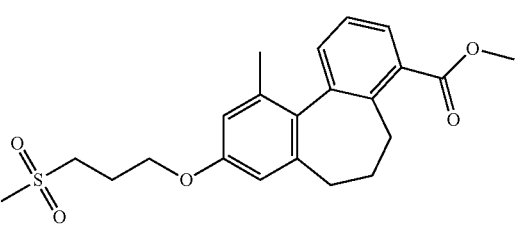

The compound (90 mg, 0.318 mmol) obtained in <1-7> was dissolved in DMF (4 mL), and 3-(methylsulfonyl)propyl 4-methylbenzenesulfonate (112 mg, 0.383 mmol) and K$_2$CO$_3$ (66 mg, 0.478 mmol) were added thereto, and stirred at 90° C. for 15 hours. The reaction mixture was cooled to room temperature, diluted with EtOAc, and then washed with a saturated NH$_4$Cl aqueous solution and saline. An organic layer was dried over sodium sulfate, and concentrated under reduced pressure. Then, the residue was purified using silica gel chromatography to obtain the title compound (white foam, 124 mg, and 97% yield).

$^1$H NMR (300 MHz, CDCl$_3$) δ 7.73 (dd, 1H), 7.40-7.27 (m, 2H), 6.74 (d, 1H), 6.63 (d, 1H), 4.15 (m, 2H), 3.92 (s, 3H), 3.27 (m, 2H), 2.97 (s, 3H), 2.55-2.28 (m, 4H), 2.27 (s, 3H), 2.18 (m, 3H), 2.01 (m, 1H).

<1-9> Preparation of (11-methyl-9-(3-(methylsulfonyl)propoxy)-6,7-dihydro-5H-dibenzo[a,c][7]annulen-4-yl)methanol

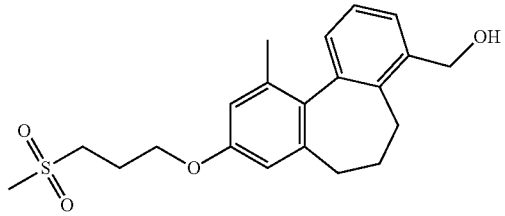 [SMILES: Cc1cc(OCCCS(C)(=O)=O)cc2c1-c1cccc(CO)c1CCC2]

The compound (122 mg, 0.303 mmol) obtained in <1-8> was dissolved in THF (4 mL), and LiAlH₄ (a 1 M THF solution, 455 μL, and 0.455 mmol) was slowly added thereto at 0° C. The reaction mixture was heated slowly, and stirred at ambient temperature for 1 hour. The mixture was diluted with dichloromethane and a saturated sodium sulfate aqueous solution, and layers were separated. An organic layer was dried over MgSO₄, and concentrated under reduced pressure. Then, the residue was purified using silica gel chromatography to obtain the title compound (white foam, 100 mg, and 88% yield).

¹H NMR (300 MHz, CDCl₃) δ 7.34-7.17 (m, 3H), 6.73 (d, 1H), 6.62 (d, 1H), 4.78 (s, 2H), 4.20-4.12 (m, 2H), 3.34-3.22 (m, 2H), 2.97 (s, 3H), 2.87 (dd, 1H), 2.49-2.30 (m, 2H), 2.29 (s, 3H), 2.25-2.04 (m, 2H), 1.67 (br s, 1H).

<1-10> Preparation of methyl 2-((3S)-6-((11-methyl-9-(3-(methylsulfonyl)propoxy)-6,7-dihydro-5H-dibenzo[a,c][7]annulen-4-yl)methoxy)-2,3-dihydrobenzofuran-3-yl)acetate

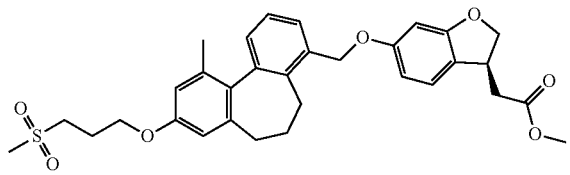

The compound (100 mg, 0.267 mmol) obtained in <1-9>, (S)-methyl 2-(6-hydroxy-2,3-dihydrobenzofuran-3-yl)acetate (prepared according to the method disclosed in the document [WO 2008/001931]; 56 mg, 0.267 mmol), and tributylphosphine (100 μL, 0.4 mmol) were dissolved in THF (3.6 mL), and 1,1'-(azodicarbonyl)dipiperidine (101 mg, 0.4 mmol) was slowly added thereto, and stirred at ambient temperature for 2 hours. The mixture was concentrated, and purified using silica gel chromatography to obtain the title compound (white foam, 126 mg, and 84% yield).

¹H NMR (600 MHz, CDCl₃) δ 7.36 (dd, 1H), 7.29-7.23 (m, 2H), 7.06 (d, 1H), 6.73 (d, 1H), 6.63 (d, 1H), 6.53 (dd, 1H), 6.51 (d, 1H), 5.08 (d, 1H), 5.00 (d, 1H), 4.77 (t, 1H), 4.28 (dd, 1H), 4.15 (m, 2H), 3.87-3.78 (m, 1H), 3.72 (s, 3H), 3.31-3.25 (m, 2H), 2.97 (s, 3H), 2.80-2.75 (m, 1H), 2.75-2.71 (m, 2H), 2.58 (dd, 1H), 2.44 (dd, 1H), 2.40-2.33 (m, 2H), 2.30 (s, 3H), 2.22 (ddt, 2H), 2.09 (m, 1H), 1.99 (m, 1H).

<1-11> Preparation of 2-((3S)-6-((11-methyl-9-(3-(methylsulfonyl)propoxy)-6,7-dihydro-5H-dibenzo[a,c][7]annulen-4-yl)methoxy)-2,3-dihydrobenzofuran-3-yl)acetic acid

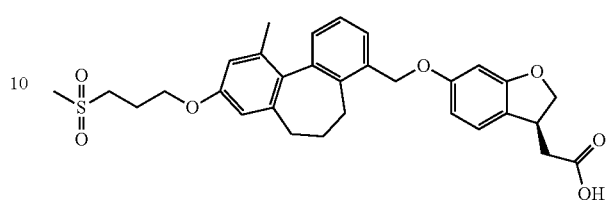

The compound (126 mg, 0.223 mmol) obtained in <1-10> was dissolved in methanol (2.4 mL) and THF (1.2 mL), and 2 N NaOH (330 μL, 0.66 mmol) was added thereto, and stirred at 75° C. for 2 hours. The mixture was cooled to ambient temperature, and water was added to the mixture to adjust a pH value of a 1 N citric acid aqueous solution to pH 5. The mixture was extracted with dichloromethane, dried over sodium sulfate, and concentrated under reduced pressure. Then, the residue was purified using silica gel chromatography to obtain the title compound (white foam, 112 mg, and 91% yield).

MS m/z 549 [M−H]⁻.

¹H NMR (600 MHz, CDCl₃) δ 7.36 (dd, 1H), 7.29-7.23 (m, 2H), 7.10 (d, 1H), 6.74 (d, 1H), 6.63 (d, 1H), 6.55 (dd, 1H), 6.52 (d, 1H), 5.08 (d, 1H), 5.00 (d, 1H), 4.78 (t, 1H), 4.31 (dd, 1H), 4.14 (t, 2H), 3.88-3.79 (m, 1H), 3.31-3.25 (m, 2H), 2.97 (s, 3H), 2.83 (dd, 1H), 2.74 (dd, 1H), 2.64 (dd, 1H), 2.44 (dd, 1H), 2.41-2.33 (m, 2H), 2.30 (s, 3H), 2.22 (ddt, 2H), 2.09 (m, 1H), 1.99 (m, 1H).

Example 2

Preparation of (1S,2S)-2-(4-((9-(3-(methylsulfonyl)propoxy)-6,7-dihydrodibenzo[b,d]oxepin-2-yl)methoxy)phenyl)cyclopropanecarboxylic acid

<2-1> Preparation of 2-(3-methoxy-phenyl)-ethanol

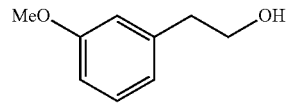

(3-Methoxy-phenyl)-acetic acid methyl ester (2.5 g, 13.9 mmol) was dissolved in EtOH/H₂O (40/10 mL), and CaCl₂ (1.5 g, 13.9 mmol) was added thereto. Thereafter, when the solids were completely dissolved, NaBH₄ (1.1 g, 27.8 mmol) was slowly added. The resulting mixture was stirred for 1 hour and a half, and water and 2 N HCl were added to be adjusted to pH 3 to 4, and then concentrated. The mixture was diluted with water, and extracted with dichloromethane. An organic layer was dried over sodium sulfate, and concentrated under reduced pressure. Then, the residue was purified using silica gel chromatography to obtain the title compound (colorless oil, 1.44 g, and 68% yield).

¹H NMR (300 MHz, CDCl₃) δ 7.24 (t, 1H), 6.78-6.84 (m, 3H), 3.85 (m, 2H), 3.79 (s, 3H), 2.85 (t, 2H), 1.52 (br s, 1H).

<2-2> Preparation of 2-(2-bromo-5-methoxy-phenyl)-ethanol

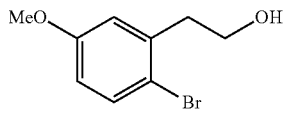

The compound (1.44 g, 9.46 mmol) obtained in <2-1> was dissolved in CH$_3$CN (26 mL), N-bromosuccinimide (1.68 g, 9.46 mmol) was added thereto, and stirred for 1 hour. The reaction mixture was concentrated under reduced pressure, and then purified using silica gel chromatography to obtain the title compound (pale brown oil, 2.1 g, and 96% yield).

$^1$H NMR (300 MHz, CDCl$_3$) δ 7.43 (d, 1H), 6.83 (d, 1H), 6.67 (dd, 1H), 3.88 (q, 2H), 3.79 (s, 3H), 2.99 (t, 2H), 1.41 (t, 1H).

<2-3> Preparation of 4-hydroxy-benzoic acid methyl ester

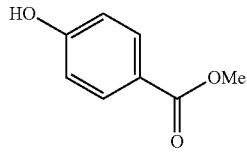 [SMILES: COC(=O)c1ccc(O)cc1]

4-Hydroxy-benzoic acid (10 g, 72.4 mmol) was dissolved in methanol (130 mL), and sulfuric acid (1.9 mL) was added thereto, and stirred for 4 hours under reflux. The reaction mixture was concentrated, diluted with water, and extracted with EtOAc. An organic layer was washed with saline, dried over sodium sulfate, and concentrated under reduced pressure. Then, the residue was purified using silica gel chromatography to obtain the title compound (white solid, 11.01 g, and 99% yield).

$^1$H NMR (300 MHz, CDCl$_3$) δ 7.95 (d, 2H), 6.87 (d, 2H), 3.89 (s, 3H).

<2-4> Preparation of 3-bromo-4-hydroxy-benzoic acid methyl ester

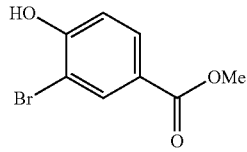 [SMILES: COC(=O)c1ccc(O)c(Br)c1]

The compound (5 g, 32.9 mmol) obtained in <2-3> was dissolved in dichloromethane (350 mL), and a solution obtained by dissolving Br$_2$ (1.7 mL, 32.9 mmol) in dichloromethane (50 mL) was slowly added thereto at 0° C., and stirred at ambient temperature for 1 hour. The mixture was stirred at ambient temperature for another 5 hours, and water and a Na$_2$S$_2$O$_3$ aqueous solution were added thereto. The mixture was extracted with dichloromethane, washed with saline, dried over sodium sulfate, and then concentrated under reduced pressure. The residue was purified using silica gel chromatography to obtain the title compound (white solid, 6.18 g, and 81% yield).

$^1$H NMR (300 MHz, CDCl$_3$) δ 8.19 (d, 1H), 7.92 (dd, 1H), 7.05 (d, 1H), 5.93 (s, 1H), 3.89 (s, 3H).

<2-5> Preparation of 3-bromo-4-methoxymethoxy-benzoic acid methyl ester

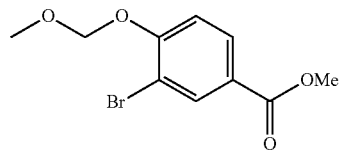

The compound (3 g, 13.0 mmol) obtained in <2-4> was dissolved in acetone (25 mL), and K$_2$CO$_3$ (2.3 g, 16.9 mmol) and chloro-methoxy-methane (1.2 mL, 15.6 mmol) were added thereto, and stirred at ambient temperature. After 3 hours, the mixture was filtered, and concentrated. Then, the residue was purified using silica gel chromatography to obtain the title compound (colorless oil, 3.25 g, and 91% yield).

$^1$H NMR (300 MHz, CDCl$_3$) δ 8.24 (d, 1H), 7.94 (dd, 1H), 7.17 (d, 1H), 5.31 (s, 2H), 3.90 (s, 3H), 3.52 (s, 3H).

<2-6> Preparation of 4-methoxymethoxy-3-(4,4,5,5-tetramethyl-[1,3,2]dioxaborolan-2-yl)-benzoic acid methyl ester

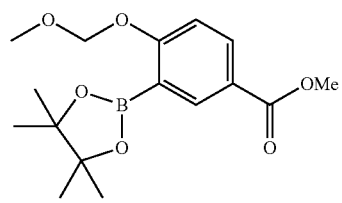 [SMILES: COCOc1ccc(C(=O)OC)cc1B1OC(C)(C)C(C)(C)O1]

The compound (3.2 g, 11.6 mmol) obtained in <2-5>, and bis(pinacolato)diboron (4.4 g, 17.4 mmol) were dissolved in 1,4-dioxane (60 mL), and potassium acetate (3.4 g, 34.8 mmol), and a complex (473 mg, 0.58 mmol) of [1,1'-bis(diphenylphosphino)ferrocene]dichloropalladium (II) with dichloromethane were added thereto, and then replaced with nitrogen. The mixture was stirred at 90° C. for 22 hours, cooled to ambient temperature, and then diluted with saline. The mixture was extracted with EtOAc, dried over magnesium sulfate, filtered through silica gel, and then concentrated under reduced pressure. The residue was purified using silica gel chromatography to obtain the title compound (colorless oil, 2.79 g, and 75% yield).

$^1$H NMR (300 MHz, CDCl$_3$) δ 8.35 (d, 1H), 8.06 (dd, 1H), 7.05 (d, 1H), 5.26 (s, 2H), 3.89 (s, 3H), 3.51 (s, 3H), 1.36 (s, 12H).

<2-7> Preparation of 2'-(2-hydroxy-ethyl)-4'-methoxy-6-methoxymethoxy-biphenyl-3-carboxylic acid methyl ester

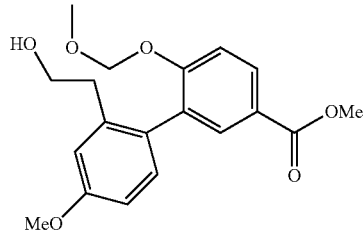 [SMILES: COCOc1ccc(C(=O)OC)cc1-c1ccc(OC)cc1CCO]

The compound (1.67 g, 7.2 mmol) obtained in <2-2>, the compound (2.5 g, 7.8 mmol) obtained in <2-6>, and $K_2CO_3$ (3.4 g, 34.8 mmol) were dissolved in 1,4-dioxane (26 mL), and a complex (294 mg, 0.36 mmol) of [1,1'-bis(diphenylphosphino)ferrocene]dichloropalladium (II) with dichloromethane was added thereto, and replaced with nitrogen. The reaction mixture was stirred at 90° C. for 14 hours, cooled to ambient temperature, and then diluted with saline. The mixture was extracted with EtOAc, dried over magnesium sulfate, and concentrated under reduced pressure. Then, the residue was purified using silica gel chromatography to obtain the title compound (oil, 2.4 g, and 96% yield).

$^1$H NMR (300 MHz, CDCl$_3$) δ 8.01 (dd, 1H), 7.84 (d, 1H), 7.22 (d, 1H), 7.09 (d, 1H), 6.89 (d, 1H), 6.82 (dd, 1H), 5.14 (s, 2H), 3.88 (s, 3H), 3.85 (s, 3H), 3.66 (q, 2H), 3.37 (s, 3H), 2.73 (m, 2H), 1.37 (t, 1H).

<2-8> Preparation of 6-hydroxy-2'-(2-hydroxy-ethyl)-4'-methoxy-biphenyl-3-carboxylic acid methyl ester

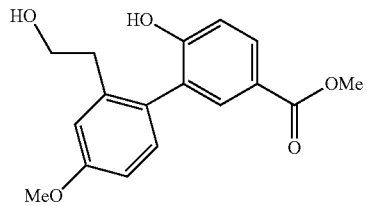 [SMILES: COC(=O)c1ccc(O)c(-c2ccc(OC)cc2CCO)c1]

The compound (2.4 g, 6.9 mmol) obtained in <2-7> was dissolved in methanol (60 mL), and p-TsOH.H$_2$O (4.0 g, 20.8 mmol) was added thereto, and stirred at ambient temperature. After 30 minutes, p-TsOH.H$_2$O (2.0 g, 10.4 mmol) was added, stirred for 14 hours, and then concentrated. The mixture was diluted with water and dichloromethane, and basified with a saturated NaHCO$_3$ aqueous solution, and extraction was then performed. An organic layer was dried over sodium sulfate, and concentrated under reduced pressure. Then, the residue was purified using silica gel chromatography to obtain the title compound (white solid, 1.50 g, and 72% yield).

$^1$H NMR (300 MHz, CDCl$_3$) δ 7.98 (dd, 1H), 7.81 (d, 1H), 7.14 (d, 1H), 7.01 (d, 1H), 6.94 (d, 1H), 6.88 (dd, 1H), 6.00 (br s, 1H), 3.88 (s, 3H), 3.86 (s, 3H), 3.79 (t, 2H), 2.70 (m, 2H), 1.50 (br s, 1H).

<2-9> Preparation of 6-hydroxy-4'-methoxy-2'-[2-(toluene-4-sulfonyloxy)-ethyl]-biphenyl-3-carboxylic acid methyl ester

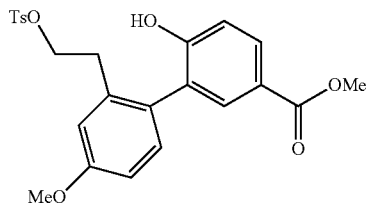 [SMILES: COC(=O)c1ccc(O)c(-c2ccc(OC)cc2CCOS(=O)(=O)c2ccc(C)cc2)c1]

The compound (1.5 g, 4.96 mmol) obtained in <2-8> was dissolved in dichloromethane (60 mL), pyridine (2.0 mL, 24.8 mmol) was added thereto to dissolve solids, and p-TsCl (1.4 g, 7.44 mmol) was added at 0° C. The mixture was slowly heated, stirred at ambient temperature for 16 hours, and diluted with water, and extraction was then performed. An organic layer was dried over sodium sulfate, and concentrated under reduced pressure. Then, the residue was purified using silica gel chromatography to obtain the title compound (white solid, 2.23 g, and 98% yield).

$^1$H NMR (300 MHz, CDCl$_3$) δ 7.95 (dd, 1H), 7.70 (d, 1H), 7.61 (d, 1H), 7.26 (d, 1H), 7.11 (d, 1H), 6.96 (d, 1H), 6.90 (d, 1H), 6.86 (dd, 1H), 5.23 (s, 1H), 4.00 (t, 2H), 3.88 (s, 3H), 3.84 (s, 3H), 2.78 (m, 2H), 2.43 (s, 3H).

<2-10> Preparation of 9-methoxy-6,7-dihydro-5-oxa-dibenzo[a,c]cycloheptene-2-carboxylic acid methyl ester

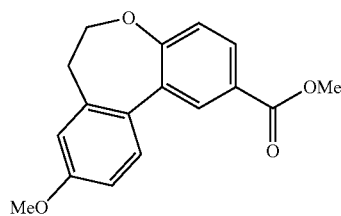 [SMILES: COC(=O)c1ccc2c(c1)-c1ccc(OC)cc1CCO2]

The compound (2.23 g, 4.88 mmol) obtained in <2-9> was dissolved in DMF (60 mL), and K$_2$CO$_3$ (2.0 g, 14.65 mmol) was added thereto, and stirred at 90° C. for 1 hour and 30 minutes. The mixture was diluted with water and saline, filtered, and then washed with water. The resulting solids were dried at 35° C. in a vacuum to obtain the title compound (white solid, 1.26 g, and 91% yield).

$^1$H NMR (300 MHz, CDCl$_3$) δ 8.09 (d, 1H), 7.96 (dd, 1H), 7.43 (d, 1H), 7.14 (d, 1H), 6.94 (d, 1H), 6.83 (d, 1H), 4.62 (t, 2H), 3.92 (s, 3H), 3.86 (s, 3H), 2.81 (t, 2H).

<2-11> Preparation of 9-hydroxy-6,7-dihydro-5-oxa-dibenzo[a,c]cycloheptene-2-carboxylic acid methyl ester

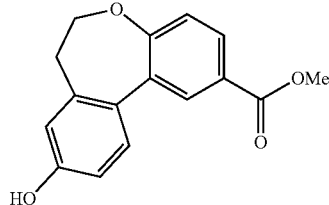 [SMILES: COC(=O)c1ccc2c(c1)-c1ccc(O)cc1CCO2]

The title compound (white solid, 852.2 mg, and 77% yield) was obtained from the compound obtained in <2-10> according to the procedure described in <1-7>.
$^1$H NMR (300 MHz, CDCl$_3$) δ 8.08 (d, 1H), 7.96 (dd, 1H), 7.36 (d, 1H), 7.14 (d, 1H), 6.86 (dd, 1H), 6.78 (d, 1H), 5.18 (s, 1H), 4.61 (t, 2H), 3.93 (s, 3H), 2.78 (t, 2H).

<2-12> Preparation of 9-(3-methanesulfonyl-propoxy)-6,7-dihydro-5-oxa-dibenzo[a,c]cycloheptene-2-carboxylic acid methyl ester

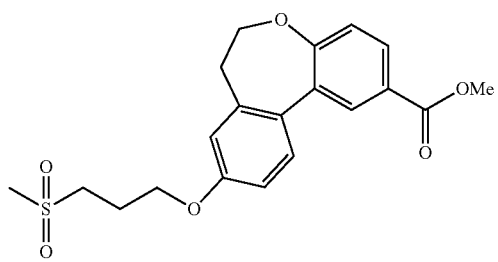 [SMILES: COC(=O)c1ccc2c(c1)-c1ccc(OCCCS(C)(=O)=O)cc1CCO2]

The title compound (colorless oil, 396.7 mg, >100% yield) was obtained from the compound obtained in <2-11> according to the procedure described in <1-8>.
$^1$H NMR (300 MHz, CDCl$_3$) δ 8.08 (d, 1H), 7.97 (dd, 1H), 7.42 (d, 1H), 7.14 (d, 1H), 6.91 (dd, 1H), 6.83 (d, 1H), 4.61 (t, 2H), 4.18 (t, 2H), 3.92 (s, 3H), 3.29 (t, 2H), 2.97 (s, 3H), 2.80 (t, 2H), 2.38 (m, 2H).

<2-13> Preparation of [9-(3-methanesulfonyl-propoxy)-6,7-dihydro-5-oxa-dibenzo[a,c]cycloheptene-2-yl]-methanol

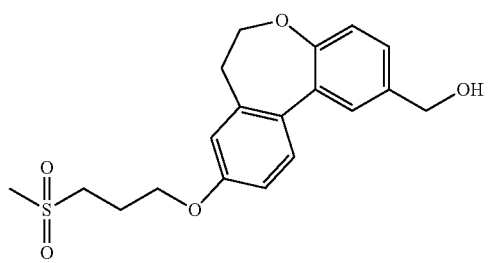 [SMILES: CS(=O)(=O)CCCOc1ccc2c(c1)CCOc1ccc(CO)cc1-2]

The title compound (colorless oil, 294.7 mg, and 86% yield) was obtained from the compound obtained in <2-12> according to the procedure described in <1-9>.

$^1$H NMR (300 MHz, CDCl$_3$) δ 7.39 (d, 1H), 7.37 (dd, 1H), 7.29 (dd, 1H), 7.11 (d, 1H), 6.89 (dd, 1H), 6.83 (d, 1H), 4.72 (d, 2H), 4.55 (t, 2H), 4.16 (t, 2H), 3.28 (t, 2H), 2.97 (s, 3H), 2.77 (t, 2H), 2.37 (m, 2H), 1.75 (br t, 1H).

<2-14> Preparation of (1S,2S)-2-(4-acetoxy-phenyl)-cyclopropanecarboxylic acid ethyl ester

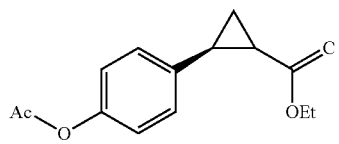 [SMILES: C=C(OCC)C1C[C@@H]1c1ccc(OC(C)=O)cc1]

Chloroform (10 mL) was replaced with argon, and (CuOTf)$_2$-toluene (39.8 mg, 0.077 mmol), and (2R)-4-tert-butyl-2-{1-[(4R)-4-tert-butyl-4,5-dihydro-1,3-oxazol-2-yl]-1-methylethyl}-4,5-dihydro-1,3-oxazole (45.3 mg, 0.154 mmol) were added, and stirred for 1 hour and 10 minutes. Acetic acid 4-vinyl-phenyl ester (2.5 g, 15.4 mmol) was dissolved in chloroform (10 mL), and replaced with argon, and the prepared solution was then added thereto. Diazoacetic acid ethyl ester (2.1 mL, 17.0 mmol) was dissolved in chloroform (30 mL), replaced with argon, and then slowly added to the mixture over 3 hours. The reaction mixture was filtered through silica gel, washed with EtOAc/dichloromethane (1/9 ratio), concentrated under reduced pressure, and then purified using silica gel chromatography to obtain the title compound (colorless oil, 3.6 g, and 94% yield).

<2-15> Preparation of (1S,2S)-2-(4-hydroxy-phenyl)-cyclopropanecarboxylic acid ethyl ester

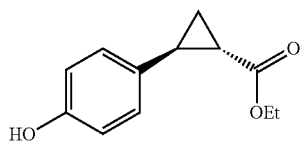 [SMILES: CCOC(=O)[C@H]1C[C@@H]1c1ccc(O)cc1]

The compound (2.6 g, 10.47 mmol) obtained in <2-14> was dissolved in MeOH/H$_2$O (80/20 mL), and NH$_4$OAc (6.46 g, 83.78 mmol) was added thereto, and stirred for 3 hours 30 minutes under reflux. The reaction mixture was cooled to ambient temperature, and concentrated. Thereafter, the reaction mixture was diluted with water, and extracted with EtOAc, and an organic layer was then washed with saline. Subsequently, the organic layer was dried over magnesium sulfate, and concentrated under reduced pressure. Then, the residue was purified using silica gel chromatography to obtain the title compound (colorless oil, 1.77 g, 80% yield, and 97% ee).

$^1$H NMR (300 MHz, CDCl$_3$) δ 7.00 (d, 2H), 6.74 (d, 2H), 4.85 (br s, 1H), 4.16 (q, 2H), 2.47 (m, 1H), 1.81 (m, 1H), 1.55 (m, 1H), 1.28 (t, 3H), 1.24 (m, 1H).

<2-16> Preparation of (1S,2S)-ethyl 2-(4-((9-(3-(methylsulfonyl)propoxy)-6,7-dihydrodibenzo[b,d]oxepin-2-yl)methoxy)phenyl)cyclopropanecarboxylate

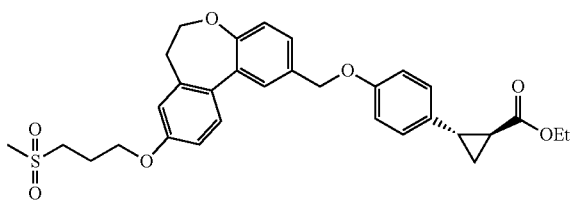 [SMILES: CCOC(=O)[C@H]1C[C@@H]1c1ccc(OCc2ccc3c(c2)-c2ccc(OCCCS(C)(=O)=O)cc2CCO3)cc1]

The compound (88.8 mg, 0.25 mmol) obtained in <2-13>, the compound (50.5 mg, 0.25 mmol) obtained in <2-15>, and PPh$_3$ (96.5 mg, 0.37 mmol) were dissolved in THF (2 mL), and diethyl azodicarboxylate (a 40% toluene solution, 0.17 mL, 0.37 mmol) was slowly added thereto, and stirred for 3 hours 30 minutes. The reaction mixture was concentrated under reduced pressure, and then purified using silica gel chromatography to obtain the title compound (oil, 99.4 mg, and 74% yield).

$^1$H NMR (300 MHz, CDCl$_3$) δ 7.43 (d, 1H), 7.37 (d, 1H), 7.34 (dd, 1H), 7.13 (d, 1H), 7.04 (d, 2H), 6.91 (d, 2H), 6.89 (dd, 1H), 6.83 (d, 1H), 5.05 (s, 2H), 4.56 (t, 2H), 4.18 (t, 2H), 4.15 (q, 2H), 3.28 (t, 2H), 2.97 (s, 3H), 2.78 (t, 2H), 2.47 (m, 1H), 2.37 (m, 2H), 1.82 (m, 1H), 1.55 (m, 1H), 1.26 (t, 3H), 1.24 (m, 1H).

<2-17> Preparation of (1S,2S)-2-(4-((9-(3-(methylsulfonyl)propoxy)-6,7-dihydrodibenzo[b,d]oxepin-2-yl)methoxy)phenyl)cyclopropanecarboxylic acid

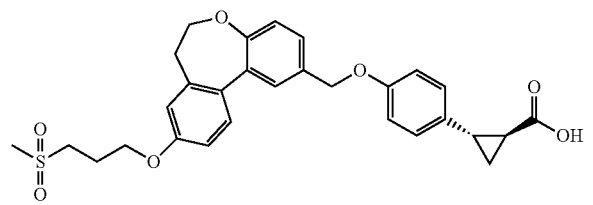 [SMILES: CS(=O)(=O)CCCOc1ccc2c(c1)CCOc1ccc(COc3ccc([C@H]4C[C@@H]4C(=O)O)cc3)cc1-2]

The title compound (white solid, 74.5 mg, 79% yield) was obtained from the compound obtained in <2-16> according to the procedure described in <1-11>.

MS m/z 521 [M−H]$^-$.

$^1$H NMR (300 MHz, CDCl$_3$) δ 7.42 (d, 1H), 7.37 (d, 1H), 7.34 (dd, 1H), 7.13 (d, 1H), 7.05 (d, 2H), 6.91 (d, 2H), 6.90 (dd, 1H), 5.05 (t, 2H), 4.56 (t, 2H), 4.17 (t, 2H), 3.28 (t, 2H), 2.97 (s, 3H), 2.78 (t, 2H), 2.56 (m, 1H), 2.37 (m, 2H), 1.84 (m, 1H), 1.62 (m, 1H), 1.35 (m, 1H).

Example 3

Preparation of (1S,2S)-2-(4-(((9-(2-ethoxyethoxy)-6,7-dihydrodibenzo[b,d]oxepin-2-yl)methyl)amino)phenyl)cyclopropanecarboxylic acid <3-1> Preparation of methyl 9-(2-ethoxyethoxy)-6,7-dihydrodibenzo[b,d]oxepin-2-carboxylate

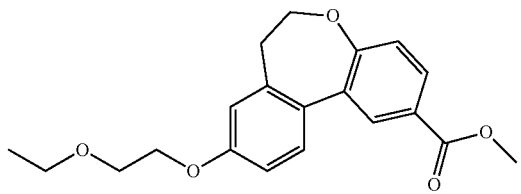 [SMILES: CCOCCOc1ccc2c(c1)CCOc1ccc(C(=O)OC)cc1-2]

The compound (100 mg, 0.37 mmol) obtained in <2-11>, and K$_2$CO$_3$ (61 mg, 0.44 mmol) were dissolved in DMF (1.5 mL), and KI (12 mg, 74 μmol) and 2-chloroethyl ethyl ether (62 μL, 0.56 mmol) were sequentially added to the suspension solution, and then stirred at 80° C. for 18 hours. The mixture was diluted with EtOAc, and washed with a saturated NH$_4$Cl aqueous solution. An organic layer was dried over sodium sulfate, and concentrated under reduced pressure. Then, the residue was purified using silica gel chromatography to obtain the title compound (colorless oil, 94 mg, and 73% yield).

$^1$H NMR (600 MHz, CDCl$_3$) δ 8.09 (d, 1H), 7.96 (dd, 1H), 7.42 (d, 1H), 7.14 (d, 1H), 6.96 (dd, 1H), 6.88 (d, 1H), 4.61 (t, 2H), 4.18 (t, 2H), 3.92 (s, 3H), 3.82 (t, 2H), 3.63 (q, 2H), 2.80 (t, 2H), 1.26 (t, 3H).

<3-2> Preparation of (9-(2-ethoxyethoxy)-6,7-dihydrodibenzo[b,d]oxepin-2-yl)methanol

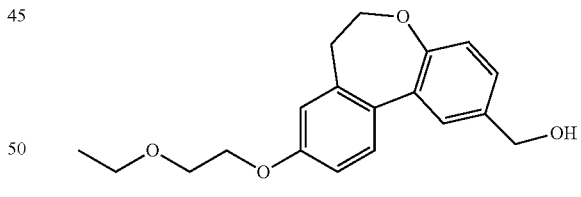

The compound (90 mg, 0.26 mmol) obtained in <3-1> was dissolved in THF (5 mL), and LiAlH$_4$ (0.53 mL, 0.53 mmol) was slowly added thereto at 0° C., and then stirred at room temperature for 1 hour. The reaction mixture was cooled to 0° C., and diluted with a saturated sodium sulfate aqueous solution. Layers were separated, and an organic layer was dried over sodium sulfate, concentrated under reduced pressure, and then purified using silica gel chromatography to obtain the title compound (colorless oil, 80 mg, and 97% yield).

$^1$H NMR (600 MHz, CDCl$_3$) δ 7.38-7.39 (m, 1H), 7.37 (s, 1H), 7.29 (dd, 1H), 7.11 (d, 1H), 6.94 (dd, 1H), 6.88 (d, 1H), 4.73 (d, 2H), 4.55 (t, 2H), 4.18 (t, 2H), 3.82 (t, 2H), 3.63 (q, 2H), 2.77 (t, 2H), 1.67 (t, 1H), 1.26 (t, 3H).

<3-3> Preparation of 9-(2-ethoxyethoxy)-6,7-dihydrodibenzo[b,d]oxepin-2-carbaldehyde

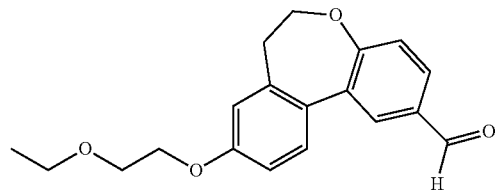 [SMILES: CCOCCOc1ccc2c(c1)CCOc1ccc(C=O)cc1-2]

The compound (80 mg, 0.25 mmol) obtained in <3-2> was dissolved in CH$_3$CN (4 mL), and MnO$_2$ (110 mg, 1.27 mmol) was added thereto, and then stirred at 60° C. for 70 minutes. The reaction mixture was filtered through Celite, concentrated under reduced pressure, and then purified using silica gel chromatography to obtain the title compound (colorless oil, 79 mg, and 100% yield).

$^1$H NMR (600 MHz, CDCl$_3$) δ 10.01 (s, 1H), 7.92 (d, 1H), 7.81 (dd, 1H), 7.43 (d, 1H), 7.23 (d, 1H), 6.97 (dd, 1H), 6.89 (d, 1H), 4.64 (t, 2H), 4.19 (q, 2H), 3.83 (t, 2H), 3.63 (q, 2H), 2.83 (t, 2H), 1.26 (t, 3H).

<3-4> Preparation of (1S,2S)-ethyl 2-(4-(((9-(2-ethoxyethoxy)-6,7-dihydrodibenzo[b,d]oxepin-2-yl)methyl)amino)phenyl)cyclopropanecarboxylate

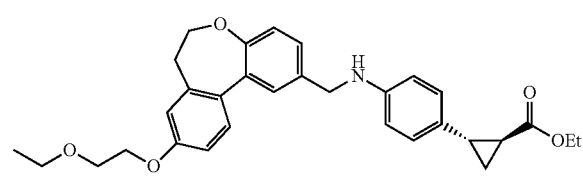 [SMILES: CCOCCOc1ccc2c(c1)CCOc1ccc(CNc3ccc([C@H]4C[C@@H]4C(=O)OCC)cc3)cc1-2]

The compound (79 mg, 0.25 mmol) obtained in <3-3>, and a (1S,2S)-2-(4-amino-phenyl)-cyclopropanecarboxylic acid ethyl ester (prepared according to the method disclosed in the document [Bioorganic & Medicinal Chemistry, 2006, pp. 1840-1845]; 52 mg, 0.25 mmol) were dissolved in dichloromethane (3 mL), and AcOH (29 µL, 0.51 mmol) was added thereto, and stirred at room temperature for 1 hour. The mixture was cooled to 0° C., and Na(OAc)$_3$BH (107 mg, 0.51 mmol) was slowly added. The mixture was stirred at room temperature for 2 hours, and then diluted with water. Layers were separated, and an organic layer was dried over sodium sulfate, concentrated under reduced pressure, and then purified using silica gel chromatography to obtain the title compound (colorless foam, 121 mg, and 95% yield).

$^1$H NMR (600 MHz, CDCl$_3$) δ 7.36 (d, 1H), 7.34 (d, 1H), 7.25-7.27 (m, 1H), 7.08 (d, 1H), 6.90-6.94 (m, 3H), 6.88 (d, 1H), 6.57-6.62 (m, 2H), 4.54 (t, 2H), 4.32 (s, 2H), 4.13-4.18 (m, 4H), 4.00 (br, 1H), 3.81 (t, 2H), 3.63 (q, 2H), 2.76 (t, 2H), 2.42-2.45 (m, 1H), 1.77-1.80 (m, 1H), 1.50-1.53 (m, 1H), 1.24-1.28 (m, 6H), 1.21-1.23 (m, 1H).

<3-5> Preparation of (1S,2S)-2-(4-(((9-(2-ethoxyethoxy)-6,7-dihydrodibenzo[b,d]oxepin-2-yl)methyl)amino)phenyl)cyclopropanecarboxylic acid

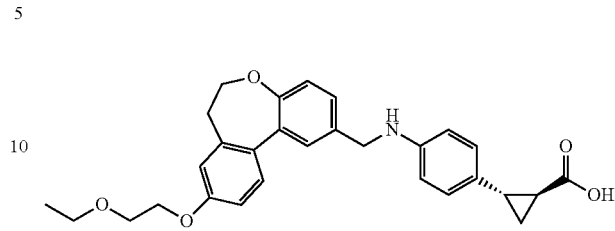

The compound (121 mg, 0.24 mmol) obtained in <3-4> was dissolved in THF (1.5 mL) and MeOH (3 mL), and 2 N NaOH (0.36 mL, 0.72 mmol) was added thereto, and then stirred at 80° C. for 2 hours. The mixture was diluted with a 0.5 M citric acid aqueous solution until the pH value reached approximately pH 3 to 4. Layers were extracted, and an organic layer was dried over sodium sulfate, concentrated under reduced pressure, and then purified using silica gel chromatography to obtain the title compound (colorless foam, 100 mg, and 88% yield).

MS m/z 472 [M−H]$^-$.

$^1$H NMR (600 MHz, CDCl$_3$) δ 7.36 (d, 1H), 7.34 (d, 1H), 7.25-7.27 (m, 1H), 7.08 (d, 1H), 6.92-6.96 (m, 3H), 6.88 (d, 1H), 6.58-6.60 (m, 2H), 4.54 (t, 2H), 4.32 (s, 2H), 4.17 (t, 2H), 3.82 (t, 2H), 3.63 (q, 2H), 2.76 (t, 2H), 2.50-2.53 (m, 1H), 1.77-1.80 (m, 1H), 1.56-1.59 (m, 1H), 1.31-1.34 (m, 1H), 1.26 (t, 3H).

Example 4

Preparation of (1S,2S)-2-(4-(((9-(3-(methylsulfonyl)propoxy)-6,7-dihydrodibenzo[b,d]oxepin-2-yl)methyl)amino)phenyl)cyclopropanecarboxylic acid

<4-1> Preparation of 9-(3-(methylsulfonyl)propoxy)-6,7-dihydrodibenzo[b,d]oxepin-2-carbaldehyde

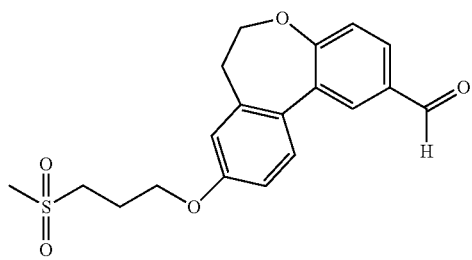 [SMILES: CS(=O)(=O)CCCOc1ccc2c(c1)CCOc1ccc(C=O)cc1-2]

The title compound (white solid, 103.4 mg, and 99% yield) was obtained from the compound obtained in <2-13> according to the procedure described in <3-3>.

$^1$H NMR (300 MHz, CDCl$_3$) δ 10.01 (s, 1H), 7.92 (d, 1H), 7.82 (dd, 1H), 7.43 (d, 1H), 7.23 (d, 1H), 6.93 (dd, 1H), 6.84 (d, 1H), 4.65 (t, 2H), 4.19 (t, 2H), 3.29 (t, 2H), 2.98 (s, 3H), 2.84 (t, 2H), 2.39 (m, 2H).

<4-2> Preparation of (1S,2S)-ethyl 2-(4-(((9-(3-(methylsulfonyl)propoxy)-6,7-dihydrodibenzo[b,d]oxepin-2-yl)methyl)amino)phenyl)cyclopropanecarboxylate

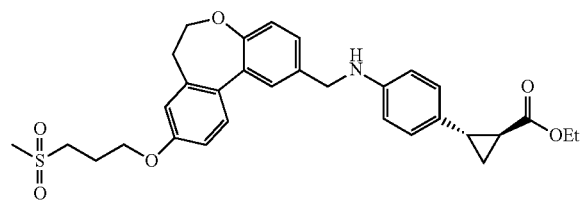 [SMILES: CCOC(=O)[C@H]1C[C@@H]1c1ccc(NCc2ccc3c(c2)-c2ccc(OCCCS(C)(=O)=O)cc2CCO3)cc1]

The title compound (oil, 150.2 mg, and 94% yield) was obtained from the compound obtained in <4-1> according to the procedure described in <3-4>.

$^1$H NMR (300 MHz, CDCl$_3$) δ 7.35 (d, 1H), 7.33 (d, 1H), 7.27 (dd, 1H), 7.07 (d, 1H), 6.93 (d, 2H), 6.87 (dd, 1H), 6.82 (d, 1H), 6.57 (d, 2H), 4.53 (t, 2H), 4.31 (s, 2H), 4.15 (t, 2H), 4.14 (q, 2H), 4.00 (br s, 1H), 3.27 (t, 2H), 2.96 (s, 3H), 2.76 (t, 2H), 2.32-2.46 (m, 3H), 1.77 (m, 1H), 1.50 (m, 1H), 1.26 (t, 3H), 1.21 (m, 1H).

<4-3> Preparation of (1S,2S)-2-(4-(((9-(3-(methylsulfonyl)propoxy)-6,7-dihydrodibenzo[b,d]oxepin-2-yl)methyl)amino)phenyl)cyclopropanecarboxylic acid

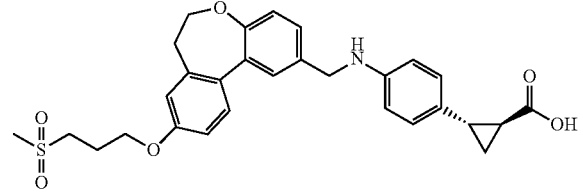 [SMILES: CS(=O)(=O)CCCOc1ccc2c(c1)CCOc1ccc(CNc3ccc([C@H]4C[C@@H]4C(=O)O)cc3)cc1-2]

The title compound (white solid, 68.9 mg, and 49% yield) was obtained from the compound obtained in <4-2> according to the procedure described in <3-5>.

MS m/z 520 [M−H]$^−$.

$^1$H NMR (300 MHz, CDCl$_3$) δ 7.35 (d, 1H), 7.34 (d, 1H), 7.27 (dd, 1H), 7.08 (d, 1H), 6.94 (d, 2H), 6.88 (dd, 1H), 6.83 (d, 1H), 6.58 (d, 2H), 4.55 (t, 2H), 4.33 (s, 2H), 4.16 (t, 2H), 3.28 (t, 2H), 2.97 (s, 3H), 2.77 (t, 2H), 2.52 (m, 1H), 2.38 (m, 2H), 1.79 (m, 1H), 1.58 (m, 1H), 1.32 (m, 1H).

Example 5

Preparation of (S)-2-(6-((9-(3-(methylsulfonyl)propoxy)-6,7-dihydro-5H-dibenzo[a,c][7]annulen-2-yl) methoxy)-2,3-dihydrobenzofuran-3-yl)acetic acid <5-1> Preparation of (2-bromo-4-(methoxycarbonyl)benzyl)triphenylphosphonium bromide

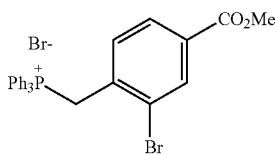

The title compound (white solid, 4.95 g, and 92% yield) was obtained from methyl 3-bromo-4-(bromomethyl)benzoate (prepared according to the method disclosed in the document [Journal of the American Chemical Society, 2002, vol. 124, #50, pp. 14993-15000]; 2.90 g, 9.42 mmol) according to the procedure described in <1-2>.

$^1$H NMR (300 MHz, CDCl$_3$) δ 8.04 (s, 1H), 7.84-7.62 (m, 17H), 5.90 (d, 2H), 3.90 (s, 3H).

<5-2> Preparation of methyl 3-bromo-4-(3-(3-methoxyphenyl)prop-1-en-1-yl)benzoate

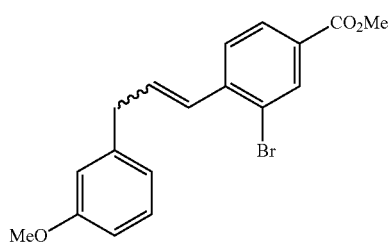 [SMILES: COC(=O)c1ccc(C=CCc2cccc(OC)c2)c(Br)c1]

The title compound (an E/Z mixture, light yellow oil, 3.13 g, and 84% yield) was obtained from the compound obtained in <5-1>, and 2-(3-methoxyphenyl)acetaldehyde according to the procedure described in <1-3>.

E form: $^1$H NMR (300 MHz, CDCl$_3$) δ 8.21 (d, 1H), 7.88 (dd, 1H), 7.54 (d, 1H), 7.23 (d, 1H), 6.90-6.73 (m, 4H), 6.41 (dt, 1H), 3.91 (s, 3H), 3.81 (s, 3H), 3.59 (d, 2H).

Z form: $^1$H NMR (300 MHz, CDCl$_3$) δ 8.28 (d, 1H), 7.94 (dd, 1H), 7.38 (d, 1H), 7.21 (d, 1H), 6.90-6.73 (m, 3H), 6.63 (d, 1H), 6.05 (dt, 1H), 3.93 (s, 3H), 3.80 (s, 3H), 3.49 (d, 2H).

<5-3> Preparation of methyl 3-bromo-4-(3-(3-methoxyphenyl)propyl)benzoate

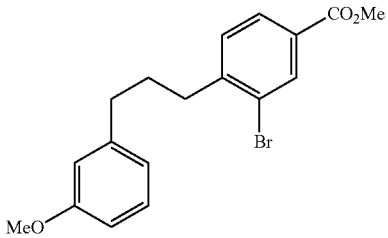 [SMILES: COC(=O)c1ccc(CCCc2cccc(OC)c2)c(Br)c1]

The compound (3.13 g, 8.67 mmol) obtained in <5-2> was dissolved in EtOAc (30 mL), and 10% Pd/C (600 mg, 0.56 mmol) was added thereto, and stirred for 2 hours under hydrogen flow. The reaction mixture was filtered through Celite, and washed with EtOAc, and the filtrate was then concentrated under reduced pressure. The residue was purified using silica gel chromatography to obtain the title compound (colorless oil, 2.39 g, and 76% yield).

$^1$H NMR (300 MHz, CDCl$_3$) δ 8.20 (d, 1H), 7.88 (dd, 1H), 7.27 (d, 1H), 7.24-7.18 (m, 1H), 6.80 (d, 1H), 6.76-6.73 (m, 2H), 3.91 (s, 3H), 3.80 (s, 3H), 2.81 (t, 2H), 2.68 (t, 2H), 2.01-1.91 (m, 2H).

<5-4> Preparation of methyl 4-(3-(3-methoxyphenyl)propyl)-3-(4,4,5,5-tetramethyl-1,3,2-dioxaborolan-2-yl)benzoate

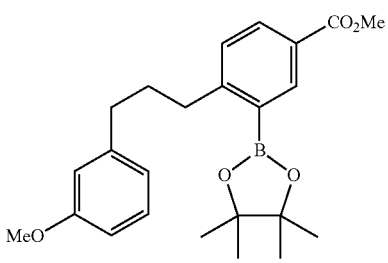 [SMILES: COC(=O)c1ccc(CCCc2cccc(OC)c2)c(B2OC(C)(C)C(C)(C)O2)c1]

The compound (2.39 g, 6.58 mmol) obtained in <5-3> was dissolved in DMF (30 mL), and bis(pinacolato)diboron (2.01 g, 7.90 mmol) and KOAc (1.94 g, 19.74 mmol) were added thereto, and replaced with nitrogen. Thereafter, [1,1'-bis(diphenylphosphino)ferrocene]dichloropalladium (269 mg, 0.33 mmol) was added, and stirred at 100° C. for 10 hours. The reaction mixture was cooled to room temperature, and water was added. The resulting mixture was extracted with EtOAc. An organic layer was washed with saline, dried over sodium sulfate, filtered, and then concentrated under reduced pressure. The residue was purified using silica gel chromatography to obtain the title compound (colorless oil, 1.88 g, and 70% yield).

$^1$H NMR (300 MHz, CDCl$_3$) δ 8.42 (d, 1H), 7.99 (dd, 1H), 7.23 (d, 1H), 7.22-7.16 (m, 1H), 6.78 (d, 1H), 6.73-6.71 (m, 2H), 3.90 (s, 3H), 3.79 (s, 3H), 2.98 (t, 2H), 2.65 (t, 2H), 1.93-1.83 (m, 2H), 1.34 (s, 12H).

<5-5> Preparation of methyl 4-(3-(2-bromo-5-methoxyphenyl)propyl)-3-(4,4,5,5-tetramethyl-1,3,2-dioxaborolan-2-yl)benzoate

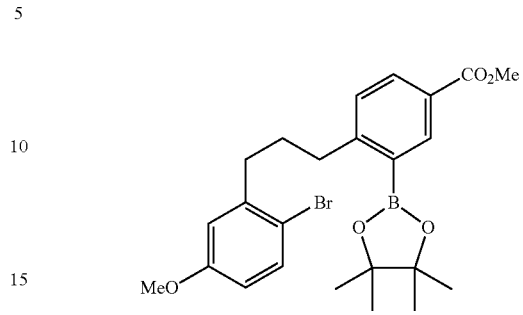

The compound (1.87 g, 4.56 mmol) obtained in <5-4> was dissolved in acetonitrile (30 mL), and N-bromosuccinimide (0.81 g, 4.56 mmol) was added thereto at 0° C., warmed to room temperature, and stirred for 3 hours. The reaction mixture was concentrated under reduced pressure, and water was added. Then, the mixture was extracted with dichloromethane. An organic layer was dried over sodium sulfate, filtered and concentrated under reduced pressure. The residue was purified using silica gel chromatography to obtain the title compound (colorless oil, 1.96 g, and 88% yield).

$^1$H NMR (300 MHz, CDCl$_3$) δ 8.43 (d, 1H), 8.00 (dd, 1H), 7.39 (d, 1H), 7.27 (d, 1H), 6.74 (d, 1H), 6.61 (dd, 1H), 3.90 (s, 3H), 3.76 (s, 3H), 3.03 (t, 2H), 2.74 (t, 2H), 1.93-1.83 (m, 2H), 1.34 (s, 12H).

<5-6> Preparation of methyl 9-methoxy-6,7-dihydro-5H-dibenzo[a,c][7]annulen-2-carboxylate

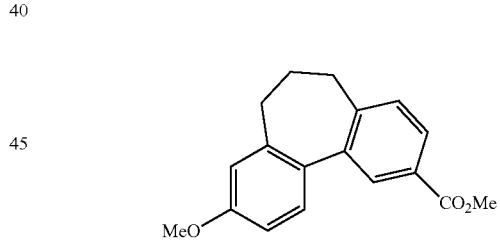

The compound (1.82 g, 3.72 mmol) obtained in <5-5> was dissolved in 1,4-dioxane (25 mL), and K$_2$CO$_3$ (1.54 g, 11.16 mmol) was added thereto, and replaced with nitrogen. Thereafter, PdCl$_2$(dppf) (152 mg, 0.19 mmol) was added, and stirred at 95° C. for 16 hours. The reaction mixture was cooled to room temperature, and a saturated NH$_4$Cl aqueous solution was added. Then, the mixture was extracted with EtOAc. An organic layer was washed with saline, dried over sodium sulfate, filtered, and then concentrated under reduced pressure. The residue was purified using silica gel chromatography to obtain the title compound (colorless oil, 695 mg, and 66% yield).

$^1$H NMR (300 MHz, CDCl$_3$) δ 8.02 (d, 1H), 7.92 (dd, 1H), 7.35 (d, 1H), 7.29 (d, 1H), 6.89 (dd, 1H), 6.81 (d, 1H), 3.93 (s, 3H), 3.86 (s, 3H), 2.55 (t, 2H), 2.46 (t, 2H), 2.25-2.16 (m, 2H).

<5-7> Preparation of methyl 9-hydroxy-6,7-dihydro-5H-dibenzo[a,c][7]annulen-2-carboxylate

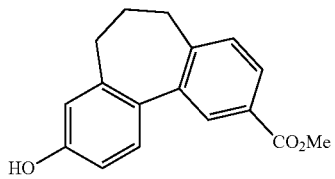

The compound (685 mg, 2.43 mmol) obtained in <5-6> was dissolved in dichloromethane (25 mL), and BBr$_3$ (a 1 M dichloromethane solution, 4.85 mL, 4.85 mmol) was slowly added thereto at 0° C., warmed to room temperature, and stirred for 1 hour. Methanol and water were sequentially added to the reaction mixture at 0° C., and then extracted with dichloromethane. An organic layer was dried over sodium sulfate, filtered, and then concentrated under reduced pressure. The residue was purified using silica gel chromatography to obtain the title compound (colorless foam, 643 mg, and 99% yield).

$^1$H NMR (300 MHz, CDCl$_3$) δ 8.01 (d, 1H), 7.92 (dd, 1H), 7.29 (d, 2H), 6.83 (dd, 1H), 6.75 (d, 1H), 5.08 (s, 1H), 3.93 (s, 3H), 2.54 (t, 2H), 2.43 (t, 2H), 2.24-2.14 (m, 2H).

<5-8> Preparation of methyl 9-(3-(methylsulfonyl)propoxy)-6,7-dihydro-5H-dibenzo[a,c][7]annulen-2-carboxylate

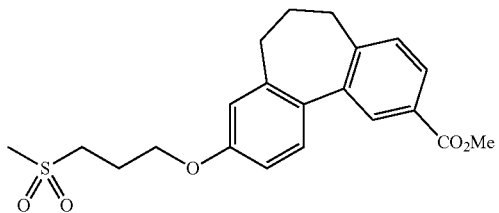 [SMILES: COC(=O)c1ccc2c(c1)-c1ccc(OCCCS(C)(=O)=O)cc1CCC2]

The title compound (white solid, 424 mg, and 98% yield) was obtained from the compound obtained in <5-7> according to the procedure described in <1-8>.

$^1$H NMR (300 MHz, CDCl$_3$) δ 8.01 (d, 1H), 7.93 (dd, 1H), 7.35 (d, 1H), 7.30 (d, 1H), 6.87 (dd, 1H), 6.80 (d, 1H), 4.17 (t, 2H), 3.93 (s, 3H), 3.29 (t, 2H), 2.98 (s, 3H), 2.54 (t, 2H), 2.46 (t, 2H), 2.43-2.34 (m, 2H), 2.25-2.16 (m, 2H).

<5-9> Preparation of (9-(3-(methylsulfonyl)propoxy)-6,7-dihydro-5H-dibenzo[a,c][7]annulen-2-yl)methanol

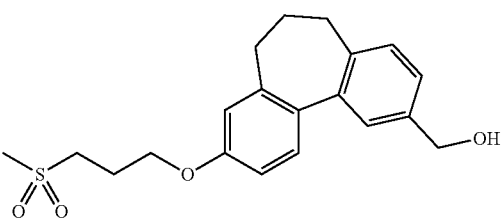 [SMILES: CS(=O)(=O)CCCOc1ccc2c(c1)CCCc1ccc(CO)cc1-2]

The title compound (white solid, 338 mg, and 87% yield) was obtained from the compound obtained in <5-8> according to the procedure described in <1-9>.

$^1$H NMR (300 MHz, CDCl$_3$) δ 7.34 (d, 1H), 7.32 (d, 1H), 7.29-7.21 (m, 2H), 6.85 (dd, 1H), 6.79 (d, 1H), 4.74 (d, 2H), 4.17 (t, 2H), 3.29 (t, 2H), 2.97 (s, 3H), 2.49 (t, 2H), 2.46 (t, 2H), 2.42-2.33 (m, 2H), 2.22-2.13 (m, 2H), 1.65 (t, 1H).

<5-10> Preparation of (S)-methyl 2-(6-((9-(3-(methylsulfonyl)propoxy)-6,7-dihydro-5H-dibenzo[a,c][7]annulen-2-yl)methoxy)-2,3-dihydrobenzofuran-3-yl)acetate

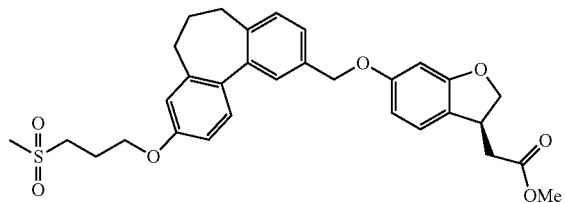 [SMILES: COC(=O)C[C@@H]1COc2cc(OCc3ccc4c(c3)-c3ccc(OCCCS(C)(=O)=O)cc3CCC4)ccc21]

The title compound (white foam, 103 mg, and 84% yield) was obtained from the compound obtained in <5-9> according to the procedure described in <1-10>.

$^1$H NMR (300 MHz, CDCl$_3$) δ 7.38 (d, 1H), 7.31 (d, 2H), 7.23 (d, 1H), 7.03 (d, 1H), 6.85 (dd, 1H), 6.79 (d, 1H), 6.53-6.48 (m, 2H), 5.04 (s, 2H), 4.76 (t, 1H), 4.27 (dd, 1H), 4.17 (t, 2H), 3.86-3.76 (m, 1H), 3.72 (s, 3H), 3.29 (t, 2H), 2.97 (s, 3H), 2.76 (dd, 1H), 2.56 (dd, 1H), 2.50 (t, 2H), 2.47 (t, 2H), 2.42-2.33 (m, 2H), 2.22-2.13 (m, 2H).

<5-11> Preparation of (S)-2-(6-((9-(3-(methylsulfonyl)propoxy)-6,7-dihydro-5H-dibenzo[a,c][7]annulen-2-yl)methoxy)-2,3-dihydrobenzofuran-3-yl)acetic acid

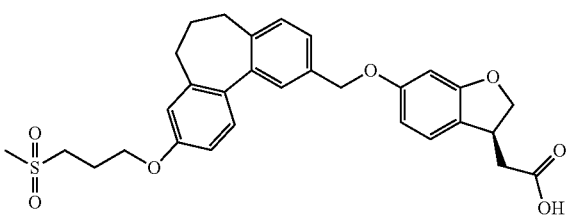

The title compound (white foam, 81 mg, and 83% yield) was obtained from the compound obtained in <5-10> according to the procedure described in <1-11>.

MS m/z 535 [M−H]$^-$.

$^1$H NMR (300 MHz, CDCl$_3$) δ 7.38 (d, 1H), 7.31 (d, 2H), 7.23 (d, 1H), 7.07 (d, 1H), 6.85 (dd, 1H), 6.79 (d, 1H), 6.54-6.49 (m, 2H), 5.04 (s, 2H), 4.77 (t, 1H), 4.29 (dd, 1H), 4.16 (t, 2H), 3.87-3.77 (m, 1H), 3.29 (t, 2H), 2.97 (s, 3H), 2.82 (dd, 1H), 2.62 (dd, 1H), 2.50 (t, 2H), 2.47 (t, 2H), 2.42-2.33 (m, 2H), 2.22-2.13 (m, 2H).

Example 6

Preparation of (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylic acid <6-1> Preparation of 9-(3-(methylsulfonyl)propoxy)-6,7-dihydro-5H-dibenzo[a,c][7]annulen-2-carbaldehyde

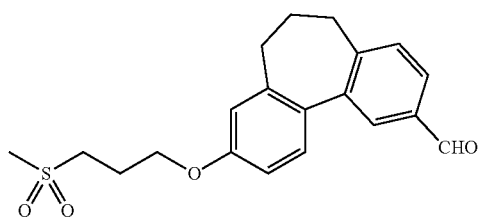 [SMILES: CS(=O)(=O)CCCOc1ccc2c(c1)CCCc1ccc(C=O)cc1-2]

The title compound (white solid, 80 mg, and 89% yield) was obtained from the compound obtained in <5-9> according to the procedure described in <3-3>.

¹H NMR (300 MHz, CDCl₃) δ 10.05 (s, 1H), 7.84 (d, 1H), 7.78 (dd, 1H), 7.40 (d, 1H), 7.35 (d, 1H), 6.89 (dd, 1H), 6.81 (d, 1H), 4.18 (t, 2H), 3.30 (t, 2H), 2.98 (s, 3H), 2.57 (t, 2H), 2.47 (t, 2H), 2.43-2.34 (m, 2H), 2.27-2.18 (m, 2H).

<6-2> Preparation of (1S,2S)-ethyl2-(4-(((9-(3-(methylsulfonyl)propoxy)-6,7-dihydro-5H-dibenzo[a,c][7]annulen-2-yl)methyl)amino)phenyl)cyclopropanecarboxylate

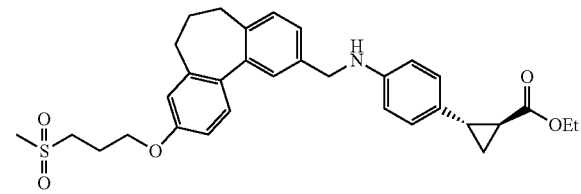

The title compound (white foam, 115 mg, and 97% yield) was obtained from the compound obtained in <6-1> according to the procedure described in <3-4>.

¹H NMR (300 MHz, CDCl₃) δ 7.32 (d, 1H), 7.29-7.18 (m, 3H), 6.93 (d, 2H), 6.84 (dd, 1H), 6.79 (d, 1H), 6.59 (d, 2H), 4.33 (s, 2H), 4.16 (t, 2H), 4.15 (q, 2H), 4.01 (s, 1H), 3.29 (t, 2H), 2.97 (s, 3H), 2.48 (t, 2H), 2.46 (t, 2H), 2.44-2.33 (m, 3H), 2.21-2.12 (m, 2H), 1.81-1.75 (m, 1H), 1.53-1.48 (m, 1H), 1.27 (t, 3H), 1.24-1.19 (m, 1H).

<6-3> Preparation of (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylic acid

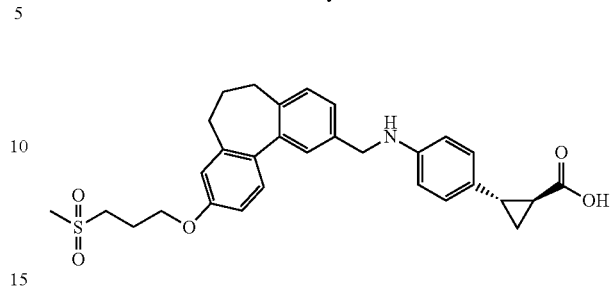

The title compound (white solid, 82 mg, and 77% yield) was obtained from the compound obtained in <6-2> according to the procedure described in <3-5>.

MS m/z 518 [M–H]⁻.

¹H NMR (300 MHz, CDCl₃) δ ppm 7.31 (s, 1H), 7.28-7.17 (m, 3H), 6.94 (d, 2H), 6.84 (dd, 1H), 6.78 (d, 1H), 6.58 (d, 2H), 4.33 (s, 2H), 4.16 (t, 2H), 3.28 (t, 2H), 2.97 (s, 3H), 2.55-2.49 (m, 1H), 2.48 (t, 2H), 2.46 (t, 2H), 2.41-2.32 (m, 2H), 2.21-2.12 (m, 2H), 1.81-1.76 (m, 1H), 1.60-1.54 (m, 1H), 1.35-1.24 (m, 2H).

Example 7

Preparation of 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-yl)acetic acid <7-1> Preparation of methyl 3-bromo-4-(3-(3-methoxy-5-methylphenyl)prop-1-en-1-yl)benzoate

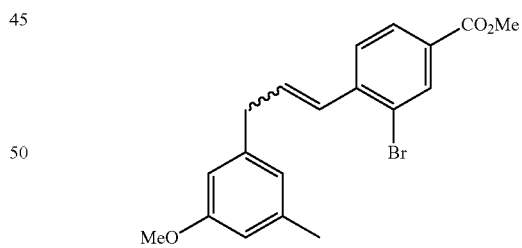

The title compound (E/Z mixture, colorless oil, 3.04 g, and 94% yield) was obtained from the compound obtained in <5-1> and the compound obtained in <1-1>, according to the procedure described in <1-3>.

E form: ¹H NMR (300 MHz, CDCl₃) δ 8.21 (d, 1H), 7.88 (ddd, 1H), 7.55 (d, 1H), 6.84 (d, 1H), 6.67-6.54 (m, 3H), 6.40 (dt, 1H), 3.91 (s, 3H), 3.79 (s, 3H), 3.55 (d, 2H), 2.32 (s, 3H).

Z form: ¹H NMR (300 MHz, CDCl₃) δ 8.28 (d, 1H), 7.93 (dd, 1H), 7.39 (d, 1H), 6.67-6.54 (m, 4H), 6.04 (dt, 1H), 3.93 (s, 3H), 3.78 (s, 3H), 3.45 (d, 2H), 2.31 (s, 3H).

<7-2> Preparation of methyl 3-bromo-4-(3-(3-methoxy-5-methylphenyl)propyl)benzoate

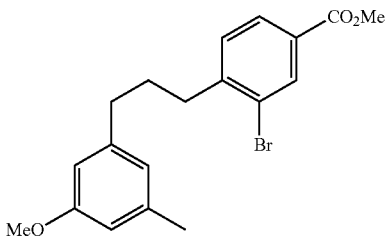 [SMILES: COC(=O)c1ccc(CCCc2cc(C)cc(OC)c2)c(Br)c1]

The title compound (colorless oil, 2.68 g, and 88% yield) was obtained from the compound obtained in <7-1> according to the procedure described in <5-3>.

$^1$H NMR (300 MHz, CDCl$_3$) δ 8.20 (d, 1H), 7.88 (dd, 1H), 7.27 (d, 1H), 6.62 (s, 1H), 6.56 (s, 2H), 3.91 (s, 3H), 3.78 (s, 3H), 2.81 (t, 2H), 2.64 (t, 2H), 2.31 (s, 3H), 2.00-1.89 (m, 2H).

<7-3> Preparation of methyl 4-(3-(3-methoxy-5-methylphenyl)propyl)-3-(4,4,5,5-tetramethyl-1,3,2-dioxaborolan-2-yl)benzoate

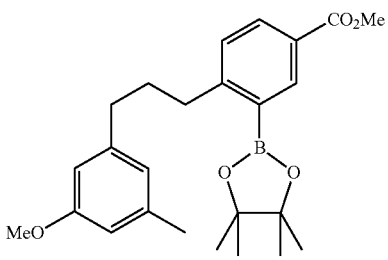 [SMILES: COC(=O)c1ccc(CCCc2cc(C)cc(OC)c2)c(B2OC(C)(C)C(C)(C)O2)c1]

The title compound (colorless oil, 1.21 g, and 40% yield) was obtained from the compound obtained in <7-2> according to the procedure described in <5-4>.

$^1$H NMR (300 MHz, CDCl$_3$) δ 8.42 (d, 1H), 7.99 (dd, 1H), 7.23 (d, 1H), 6.60 (s, 1H), 6.54 (s, 2H), 3.90 (s, 3H), 3.77 (s, 3H), 2.98 (t, 2H), 2.61 (t, 2H), 2.29 (s, 3H), 1.92-1.81 (m, 2H), 1.34 (s, 12H).

<7-4> Preparation of methyl 4-(3-(2-bromo-5-methoxy-3-methylphenyl)propyl)-3-(4,4,5,5-tetramethyl-1,3,2-dioxaborolan-2-yl)benzoate

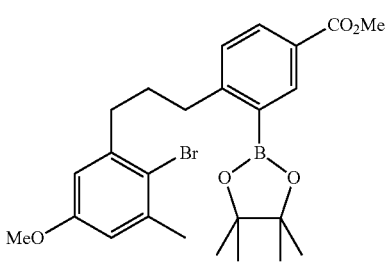 [SMILES: COC(=O)c1ccc(CCCc2cc(OC)cc(C)c2Br)c(B2OC(C)(C)C(C)(C)O2)c1]

The title compound (colorless oil, 1.36 g, and 96% yield) was obtained from the compound obtained in <7-3> according to the procedure described in <5-5>.

$^1$H NMR (300 MHz, CDCl$_3$) δ 8.42 (d, 1H), 8.00 (dd, 1H), 7.27 (d, 1H), 6.65 (d, 1H), 6.59 (d, 1H), 3.90 (s, 3H), 3.75 (s, 3H), 3.03 (t, 2H), 2.78 (t, 2H), 2.38 (s, 3H), 1.93-1.83 (m, 2H), 1.34 (s, 12H).

<7-5> Preparation of methyl 9-methoxy-11-methyl-6,7-dihydro-5H-dibenzo[a,c][7]annulen-2-carboxylate

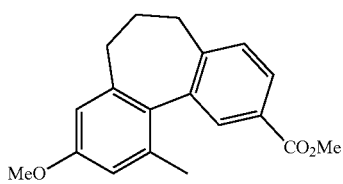

The title compound (colorless oil, 283 mg, and 35% yield) was obtained from the compound obtained in <7-4> according to the procedure described in <5-6>.

$^1$H NMR (300 MHz, CDCl$_3$) δ 7.95 (d, 1H), 7.91 (dd, 1H), 7.30 (d, 1H), 6.76 (d, 1H), 6.65 (d, 1H), 3.91 (s, 3H), 3.84 (s, 3H), 2.60-2.52 (m, 1H), 2.49-2.35 (m, 2H), 2.31 (s, 3H), 2.28-2.17 (m, 1H), 2.12-1.98 (m, 2H).

<7-6> Preparation of methyl 9-hydroxy-11-methyl-6,7-dihydro-5H-dibenzo[a,c][7]annulen-2-carboxylate

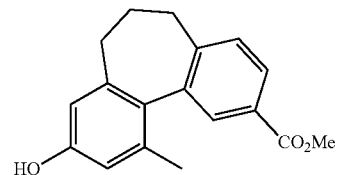 [SMILES: COC(=O)c1ccc2c(c1)-c1c(C)cc(O)cc1CCC2]

The title compound (white foam, 345 mg, and 97% yield) was obtained from the compound obtained in <7-5> according to the procedure described in <5-7>.

$^1$H NMR (300 MHz, CDCl$_3$) δ 7.94 (d, 1H), 7.91 (dd, 1H), 7.30 (d, 1H), 6.70 (d, 1H), 6.58 (d, 1H), 4.79 (s, 1H), 3.91 (s, 3H), 2.59-2.53 (m, 1H), 2.46-2.35 (m, 2H), 2.27 (s, 3H), 2.25-2.14 (m, 1H), 2.10-1.99 (m, 2H).

<7-7> Preparation of methyl 11-methyl-9-(3-(methylsulfonyl)propoxy)-6,7-dihydro-5H-dibenzo[a,c][7]annulen-2-carboxylate

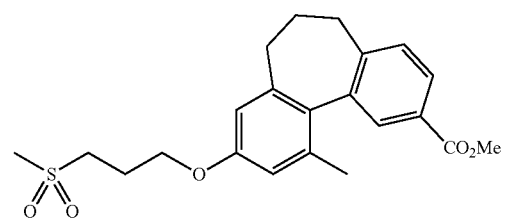 [SMILES: COC(=O)c1ccc2c(c1)-c1c(C)cc(OCCCS(C)(=O)=O)cc1CCC2]

The title compound (white foam, 285 mg, and 93% yield) was obtained from the compound obtained in <7-6> according to the procedure described in <1-8>.

$^1$H NMR (300 MHz, CDCl$_3$) δ 7.93-7.90 (m, 2H), 7.30 (d, 1H), 6.74 (d, 1H), 6.63 (d, 1H), 4.16 (t, 2H), 3.91 (s, 3H), 3.29 (t, 2H), 2.97 (s, 3H), 2.60-2.54 (m, 1H), 2.47-2.32 (m, 4H), 2.30 (s, 3H), 2.27-2.16 (m, 1H), 2.09-2.00 (m, 2H).

<7-8> Preparation of 11-methyl-9-(3-(methylsulfonyl)propoxy)-6,7-dihydro-5H-dibenzo[a,c][7]annulen-2-yl)methanol

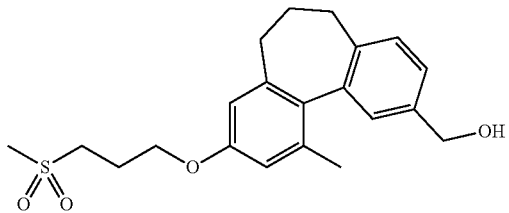 [SMILES: Cc1cc(OCCCS(C)(=O)=O)cc2c1-c1cc(CO)ccc1CCC2]

The title compound (white foam, 212 mg, and 81% yield) was obtained from the compound obtained in <7-7> according to the procedure described in <1-9>.

$^1$H NMR (300 MHz, CDCl$_3$) δ 7.24 (s, 2H), 7.23 (s, 1H), 6.73 (d, 1H), 6.62 (d, 1H), 4.71 (d, 2H), 4.15 (t, 2H), 3.28 (t, 2H), 2.97 (s, 3H), 2.54-2.43 (m, 1H), 2.42-2.31 (m, 4H), 2.30 (s, 3H), 2.26-2.19 (m, 1H), 2.06-1.97 (m, 2H), 1.62 (t, 1H).

<7-9> Preparation of methyl 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-yl)acetate

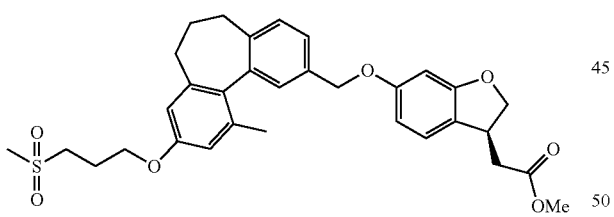

The title compound (white foam, 59 mg, and 36.3% yield) was obtained from the compound obtained in <7-8> according to the procedure described in <1-10>.

$^1$H NMR (600 MHz, CDCl$_3$) δ ppm 7.31-7.26 (m, 2H), 7.25-7.21 (m, 1H), 7.02 (d, 1H), 6.71 (d, 1H), 6.62 (d, 1H), 6.49 (dt, 1H), 6.47-6.45 (m, 1H), 5.04 (s, 2H), 4.75 (t, 1H), 4.28-4.23 (m, 1H), 4.14 (t, 2H), 3.84-3.76 (m, 1H), 3.71 (s, 3H), 3.30-3.24 (m, 2H), 2.97 (s, 3H), 2.74 (dd, 1H), 2.55 (dd, 1H), 2.53-2.48 (m, 1H), 2.45-2.39 (m, 1H), 2.39-2.32 (m, 3H), 2.31-2.25 (m, 1H), 2.24 (s, 3H), 2.06-1.98 (m, 2H).

<7-10> Preparation of 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-yl)acetic acid

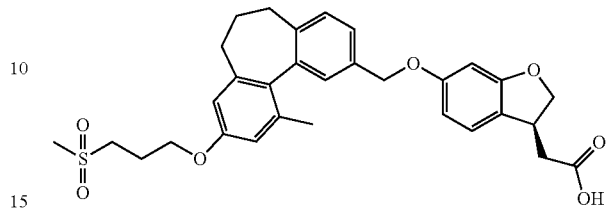

The title compound (white foam, 27 mg, and 47% yield) was obtained from the compound obtained in <7-9> according to the procedure described in <1-11>.

MS m/z 549 [M−H]$^-$.

$^1$H NMR (600 MHz, CDCl$_3$) δ ppm 7.31-7.26 (m, 2H), 7.25-7.21 (m, 1H), 7.05 (d, 1H), 6.71 (d, 1H), 6.62 (d, 1H), 6.50 (dt, 1H), 6.47-6.45 (m, 1H), 5.04 (s, 2H), 4.76 (t, 1H), 4.31-4.25 (m, 1H), 4.14 (t, 2H), 3.86-3.76 (m, 1H), 3.31-3.22 (m, 2H), 2.97 (s, 3H), 2.82 (dd, 2H), 2.61 (dd, 1H), 2.54-2.48 (m, 1H), 2.45-2.39 (m, 1H), 2.38-2.33 (m, 3H), 2.32-2.25 (m, 1H), 2.24 (s, 3H), 2.04-1.97 (m, 2H).

Example 8

Preparation of (1R,2R)-2-(4-(((10-methyl-8-(3-(methylsulfonyl)propoxy)-6H-benzo[c]chromen-4-yl)methyl)amino)phenyl)cyclopropanecarboxylic acid <8-1> Preparation of methyl 2-((2-bromo-5-methoxy-3-methylbenzyl)oxy)benzoate

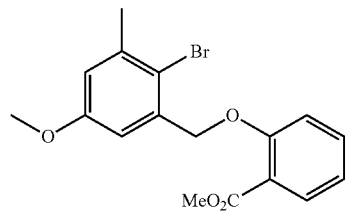 [SMILES: COC(=O)c1ccccc1OCc1cc(OC)cc(C)c1Br]

2-Bromo-1-(bromomethyl)-5-methoxy-3-methylbenzene (prepared according to the method disclosed in the document [Journal of Organic Chemistry, 1994, vol. 59, #16, pp. 4473-4481]; 2.50 g, 8.50 mmol) was dissolved in DMF (25 mL), and K$_2$CO$_3$ (2.35 g, 17.01 mmol) and methyl 2-hydroxybenzoate (1.42 g, 9.35 mmol) were added thereto, and stirred at 65° C. for 15 hours. The reaction mixture was cooled to room temperature, and a saturated NH$_4$Cl aqueous solution was added. Then, the resulting mixture was extracted with EtOAc. An organic layer was washed with saline, dried over sodium sulfate, filtered, and then concentrated under reduced pressure. The residue was purified using silica gel chromatography to obtain the title compound (white solid, 2.71 g, and 87% yield).

$^1$H NMR (300 MHz, CDCl$_3$) δ 7.86 (dd, 1H), 7.47 (ddd, 1H), 7.35 (d, 1H), 7.04 (d, 1H), 7.02 (t, 1H), 6.77 (d, 1H), 5.18 (s, 2H), 3.92 (s, 3H), 3.82 (s, 3H), 2.41 (s, 3H).

<8-2> Preparation of methyl 8-methoxy-10-methyl-6H-benzo[c]chromen-4-carboxylate

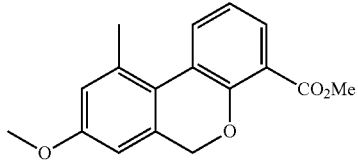 [SMILES: COC(=O)c1cccc2c1OCc1cc(OC)cc(C)c1-2]

The compound (2.70 g, 7.39 mmol) obtained in <8-1>, PCy$_3$-HBF$_4$ (381 mg, 1.04 mmol), and K$_2$CO$_3$ (2.04 g, 14.79 mmol) were suspended in DMA (25 mL), and then replaced with nitrogen. Pd(OAc)$_2$ (116 mg, 0.52 mmol) was added thereto, and stirred at 135° C. for 16 hours. The reaction mixture was cooled to room temperature, and a saturated NH$_4$Cl aqueous solution was added. The resulting mixture was extracted with EtOAc. An organic layer was washed with saline, dried over sodium sulfate, filtered, and then concentrated under reduced pressure. The residue was purified using silica gel chromatography to obtain the title compound (light yellow oil, 1.85 g, and 88% yield).

$^1$H NMR (300 MHz, CDCl$_3$) δ 7.82 (dd, 1H), 7.68 (dd, 1H), 7.08 (t, 1H), 6.79 (d, 1H), 6.62 (d, 1H), 4.99 (s, 2H), 3.92 (s, 3H), 3.83 (s, 3H), 2.59 (s, 3H).

<8-3> Preparation of methyl 2'-(bromomethyl)-2,4'-dihydroxy-6'-methyl-[1,1'-biphenyl]-3-carboxylate

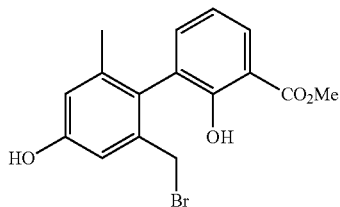 [SMILES: COC(=O)c1cccc(-c2c(C)cc(O)cc2CBr)c1O]

The compound (1.84 g, 6.47 mmol) obtained in <8-2> was dissolved in dichloromethane (25 mL), and BBr$_3$ (a 1 M dichloromethane solution, 19.4 mL, 19.4 mmol) was slowly added thereto at 0° C., warmed to room temperature, and then stirred for 1 hour. Distilled water and a 1 N HCl aqueous solution were sequentially added to the reaction mixture at 0° C., and extracted with 5% methanol/dichloromethane. An organic layer was dried over sodium sulfate, filtered, and then concentrated under reduced pressure. The residue was purified using silica gel chromatography to obtain the title compound (white foam, 1.55 g, and 68% yield).

$^1$H NMR (300 MHz, CDCl$_3$) δ 11.02 (s, 1H), 7.93 (dd, 1H), 7.41 (dd, 1H), 7.00 (t, 1H), 6.85 (d, 1H), 6.75 (d, 1H), 4.86 (s, 1H), 4.30 (d, 1H), 4.07 (d, 1H), 3.98 (s, 3H), 2.01 (s, 3H).

<8-4> Preparation of methyl 10-methyl-8-(3-(methylsulfonyl)propoxy)-6H-benzo[c]chromen-4-carboxylate

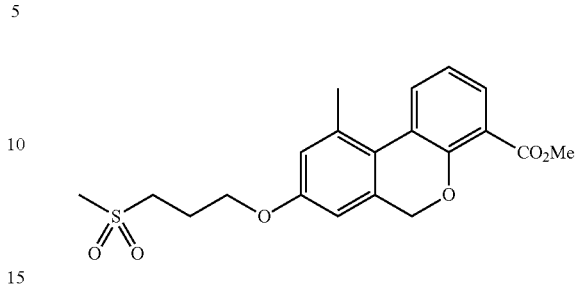

The compound (800 mg, 2.28 mmol) obtained in <8-3> was dissolved in DMF (10 mL), and K$_2$CO$_3$ (945 mg, 6.83 mmol) was added, and stirred at room temperature for 1 hour. 3-(Methylsulfonyl)propyl 4-methylbenzenesulfonate (799 mg, 2.73 mmol) was added thereto, and stirred at 90° C. for 15 hours. The reaction mixture was cooled to room temperature, and a saturated NH$_4$Cl aqueous solution was then added, and extracted with EtOAc. An organic layer was washed with saline, dried over sodium sulfate, filtered, and then concentrated under reduced pressure. The residue was purified using silica gel chromatography to obtain the title compound (white foam, 848 mg, and 95% yield).

$^1$H NMR (300 MHz, CDCl$_3$) δ 7.82 (dd, 1H), 7.69 (dd, 1H), 7.09 (t, 1H), 6.77 (d, 1H), 6.61 (d, 1H), 4.98 (s, 2H), 4.15 (t, 2H), 3.92 (s, 3H), 3.27 (t, 2H), 2.97 (s, 3H), 2.58 (s, 3H), 2.41-2.32 (m, 2H).

<8-5> Preparation of 10-methyl-8-(3-(methylsulfonyl)propoxy)-6H-benzo[c]chromen-4-yl)methanol

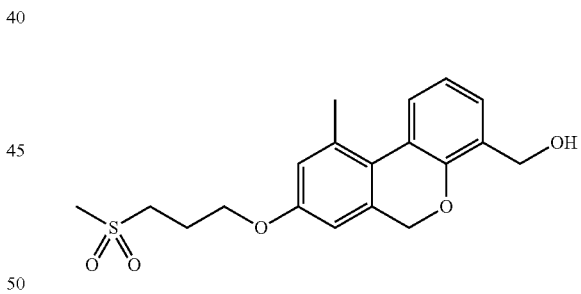

The compound (840 mg, 2.15 mmol) obtained in <8-4> was suspended in THF (25 mL), and LiAlH$_4$ (a 1 M THF solution, 3.23 mL, 3.23 mmol) was added at 0° C., warmed to room temperature, and then stirred for 2 hours. A saturated sodium sulfate aqueous solution was added to the reaction mixture at 0° C., and water was added. The resulting mixture was extracted with dichloromethane. An organic layer was dried over sodium sulfate, filtered, and then concentrated under reduced pressure. The residue was purified using silica gel chromatography to obtain the title compound (white foam, 652 mg, and 84% yield).

$^1$H NMR (300 MHz, CDCl$_3$) δ 7.67 (dd, 1H), 7.23 (dd, 1H), 7.06 (t, 1H), 6.77 (d, 1H), 6.61 (d, 1H), 4.96 (s, 2H), 4.76 (d, 2H), 4.15 (t, 2H), 3.27 (t, 2H), 2.97 (s, 3H), 2.61 (s, 3H), 2.41-2.32 (m, 2H), 2.21 (t, 1H).

<8-6> Preparation of 10-methyl-8-(3-(methylsulfonyl)propoxy)-6H-benzo[c]chromen-4-carbaldehyde

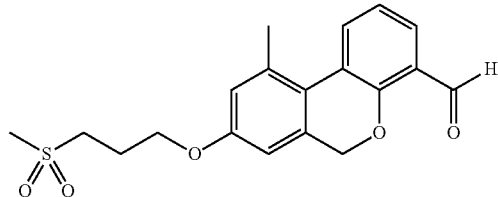 [SMILES: Cc1cc(OCCCS(C)(=O)=O)cc2c1-c1cccc(C=O)c1OC2]

The title compound (white foam, 90.2 mg, and 91% yield) was obtained from the compound obtained in <8-5> according to the procedure described in <3-3>.

<8-7> Preparation of (1R,2R)-ethyl 2-(4-(((10-methyl-8-(3-(methylsulfonyl)propoxy)-6H-benzo[c]chromen-4-yl)methyl)amino)phenyl)cyclopropanecarboxylate

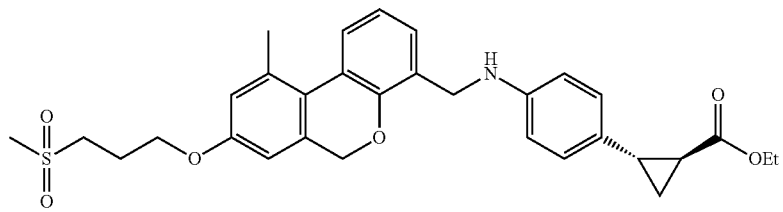 [SMILES: CCOC(=O)[C@H]1C[C@@H]1c1ccc(NCc2cccc3c2OCc2cc(OCCCS(C)(=O)=O)cc(C)c2-3)cc1]

The title compound (white foam, 125.7 mg, and 91% yield) was obtained from the compound obtained in <8-6> according to the procedure described in <3-4>.

$^1$H NMR (300 MHz, CDCl$_3$) δ 7.63 (d, 1H), 7.23 (d, 1H), 7.01 (t, 1H), 6.92 (d, 2H), 6.77 (s, 1H), 6.60 (d, 3H), 4.94 (s, 2H), 4.37 (s, 2H), 4.15 (dt, 4H), 3.32-3.20 (m, 2H), 2.97 (s, 3H), 2.60 (s, 3H), 2.39 (s, 3H), 1.83-1.72 (m, 1H), 1.54-1.44 (m, 1H), 1.26 (t, 4H).

<8-8> Preparation of (1R,2R)-2-(4-(((10-methyl-8-(3-(methylsulfonyl)propoxy)-6H-benzo[c]chromen-4-yl)methyl)amino)phenyl)cyclopropanecarboxylic acid

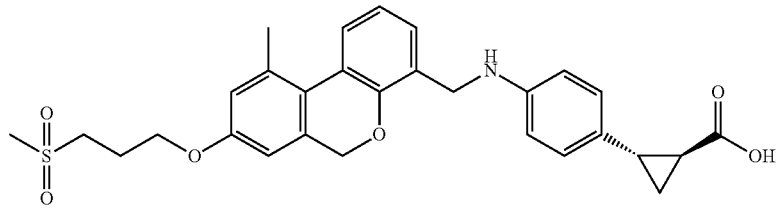 [SMILES: Cc1cc(OCCCS(C)(=O)=O)cc2c1-c1cccc(CNc3ccc([C@H]4C[C@@H]4C(=O)O)cc3)c1OC2]

The title compound (reddish brown foam, 57.5 mg, and 48% yield) was obtained from the compound obtained in <8-7> according to the procedure described in <3-5>.

MS m/z 520 [M−H]$^-$.

$^1$H NMR (300 MHz, CDCl$_3$) δ 7.62 (d, 1H), 7.23 (d, 1H), 7.01 (t, 1H), 6.93 (d, 2H), 6.76 (s, 1H), 6.60 (d, 3H), 4.94 (s, 2H), 4.37 (s, 2H), 4.15 (t, 2H), 3.33-3.20 (m, 2H), 2.97 (s, 3H), 2.60 (s, 3H), 2.50 (s, 1H), 2.44-2.29 (m, 2H), 1.77 (dd, 1H), 1.62-1.50 (m, 1H), 1.30 (d, 1H).

Example 9

Preparation of (1S,2S)-2-(4-(((10-methyl-8-(3-(methylsulfonyl)propoxy)-6H-benzo[c]chromen-2-yl)methyl)amino)phenyl)cyclopropanecarboxylic acid <9-1> Preparation of methyl 2-((2-bromo-5-methoxy-3-methylbenzyl)oxy)benzoate

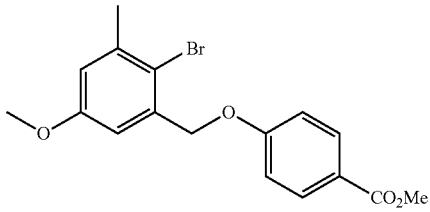 [SMILES: COC(=O)c1ccc(OCc2cc(OC)cc(C)c2Br)cc1]

The title compound (white solid, 2.85 g, and 92% yield) was obtained from 2-bromo-1-(bromomethyl)-5-methoxy-3-methylbenzene and methyl 4-hydroxybenzoate according to the procedure described in <8-1>.

$^1$H NMR (300 MHz, CDCl$_3$) δ 8.00 (d, 2H), 7.00 (d, 2H), 6.93 (d, 1H), 6.78 (d, 1H), 5.17 (s, 2H), 3.89 (s, 3H), 3.77 (s, 3H), 2.42 (s, 3H).

<9-2> Preparation of methyl 8-methoxy-10-methyl-6H-benzo[c]chromen-2-carboxylate

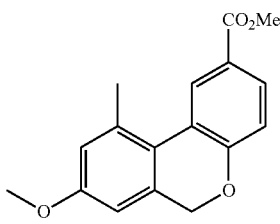 [SMILES: COC(=O)c1ccc2c(c1)-c1c(C)cc(OC)cc1CO2]

The title compound (light yellow solid, 1.99 g, and 91% yield) was obtained from the compound obtained in <9-1> according to the procedure described in <8-2>.

$^1$H NMR (300 MHz, CDCl$_3$) δ 8.45 (d, 1H), 7.89 (dd, 1H), 7.06 (d, 1H), 6.80 (d, 1H), 6.61 (d, 1H), 4.99 (s, 2H), 3.92 (s, 3H), 3.84 (s, 3H), 2.66 (s, 3H).

<9-3> Preparation of 2'-(bromomethyl)-4',6-dihydroxy-6'-methyl-[1,1'-biphenyl]-3-carboxylic acid

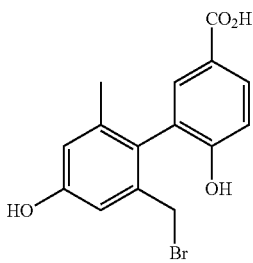 [SMILES: Cc1cc(O)cc(CBr)c1-c1cc(C(=O)O)ccc1O]

The compound (1.98 g, 6.96 mmol) obtained in <9-2> was dissolved in dichloromethane (25 mL), and BBr$_3$ (a 1 M dichloromethane solution, 20.9 mL, 20.9 mmol) was slowly added at 0° C., warmed to room temperature, and then stirred for 3 hours. Water and a 1 N HCl aqueous solution were sequentially added to the reaction mixture at 0° C., and extracted with 10% methanol/dichloromethane. An organic layer was dried over sodium sulfate, filtered, and then concentrated under reduced pressure. The residue was purified using silica gel chromatography to obtain the title compound (light yellow foam, 1.64 g, and 70% yield).

$^1$H NMR (300 MHz, DMSO-d$_6$) δ 10.14 (s, 1H), 9.45 (s, 1H), 7.82 (dd, 1H), 7.60 (d, 1H), 7.00 (d, 1H), 6.77 (d, 1H), 6.67 (d, 1H), 4.40 (d, 1H), 4.05 (d, 1H), 1.88 (s, 3H).

<9-4> Preparation of methyl 2'-(bromomethyl)-4',6-dihydroxy-6'-methyl-[1,1'-biphenyl]-3-carboxylate

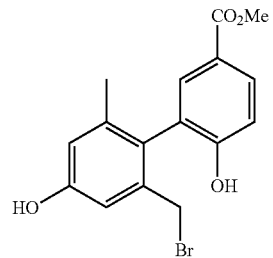 [SMILES: COC(=O)c1ccc(O)c(-c2c(C)cc(O)cc2CBr)c1]

The compound (1.40 g, 4.15 mmol) obtained in <9-3> was dissolved in methanol (20 mL), and SOCl$_2$ (0.6 mL, 8.30 mmol) was slowly added at 0° C., and stirred at 70° C. for 1 hour under reflux. The reaction mixture was neutralized by slowly adding a saturated NaHCO$_3$ aqueous solution to the reaction mixture at 0° C., and then extracted with dichloromethane. An organic layer was dried over sodium sulfate, filtered, and then concentrated under reduced pressure. The residue was purified using silica gel chromatography to obtain the title compound (white solid, 0.92 g, and 63% yield).

$^1$H NMR (300 MHz, CDCl$_3$) δ 8.03 (dd, 1H), 7.81 (d, 1H), 7.06 (d, 1H), 6.90 (d, 1H), 6.79 (d, 1H), 5.55 (s, 1H), 5.18 (s, 1H), 4.21 (d, 1H), 4.09 (d, 1H), 3.90 (s, 3H), 1.97 (s, 3H).

<9-5> Preparation of methyl 2-(10-methyl-8-(3-(methylsulfonyl)propoxy)-6H-benzo[c]chromen-2-yl)acetate

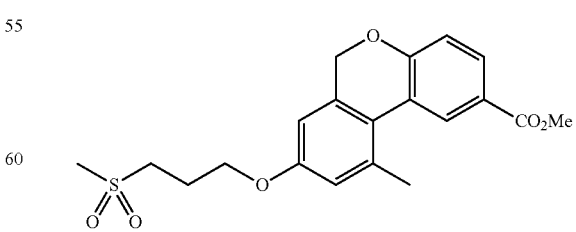

The title compound (white solid, 520 mg, and 99% yield) was obtained from the compound obtained in <9-4> according to the procedure described in <8-4>.

¹H NMR (300 MHz, CDCl₃) δ 8.45 (d, 1H), 7.89 (dd, 1H), 7.06 (d, 1H), 6.79 (d, 1H), 6.60 (d, 1H), 4.98 (s, 2H), 4.16 (t, 2H), 3.92 (s, 3H), 3.27 (t, 2H), 2.97 (s, 3H), 2.66 (s, 3H), 2.42-2.33 (m, 2H).

<9-6> Preparation of (10-methyl-8-(3-(methylsulfonyl)propoxy)-6H-benzo[c]chromen-2-yl)methanol

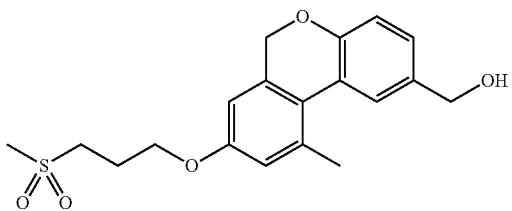 [SMILES: Cc1cc(OCCCS(C)(=O)=O)cc2c1-c1cc(CO)ccc1OC2]

The title compound (white solid, 436 mg, and 82% yield) was obtained from the compound obtained in <9-5> according to the procedure described in <8-5>.

¹H NMR (300 MHz, CDCl₃) δ 7.73 (d, 1H), 7.21 (dd, 1H), 7.04 (d, 1H), 6.77 (d, 1H), 6.60 (d, 1H), 4.92 (s, 2H), 4.70 (d, 2H), 4.15 (t, 2H), 3.27 (t, 2H), 2.97 (s, 3H), 2.63 (s, 3H), 2.41-2.32 (m, 2H), 1.66 (t, 1H).

<9-7> Preparation of 8-(3-methanesulfonylpropoxy)-10-methyl-6H-benzo[c]chromen-2-carbaldehyde The title compound (white solid, 95.2 mg, and 96% yield) was obtained from the compound obtained in <9-6> according to the procedure described in <3-3>.

¹H NMR (300 MHz, CDCl₃) δ 9.95 (s, 1H), 8.25 (d, 1H), 7.72 (dd, 1H), 7.14 (d, 1H), 6.79 (d, 1H), 6.60 (d, 1H), 5.01 (s, 2H), 4.16 (t, 2H), 3.26 (t, 2H), 2.97 (s, 3H), 2.66 (s, 3H), 2.37 (m, 2H).

<9-8> Preparation of (1S,2S)-ethyl 2-(4-(((10-methyl-8-(3-(methylsulfonyl)propoxy)-6H-benzo[c]chromen-2-yl)methyl)amino)phenyl)cyclopropanecarboxylate

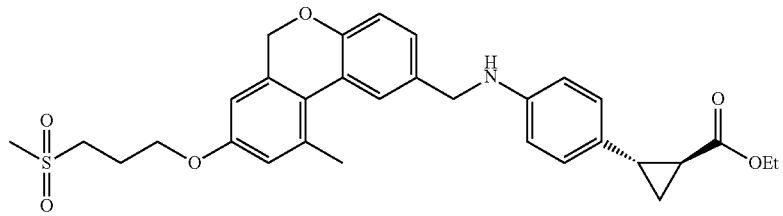 [SMILES: CCOC(=O)[C@H]1C[C@@H]1c1ccc(NCc2ccc3c(c2)-c2c(C)cc(OCCCS(C)(=O)=O)cc2CO3)cc1]

The title compound (white solid, 126.9 mg, and impure) was obtained from the compound obtained in <9-7> according to the procedure described in <3-4>.

¹H NMR (300 MHz, CDCl₃) δ 8.26 (1H, d), 7.74 (dd, 1H), 7.11-7.18 (m, 5H), 6.79 (d, 1H), 6.61 (d, 1H), 4.98 (s, 2H), 4.11-4.22 (m, 6H), 3.27 (t, 2H), 2.97 (s, 3H), 2.69 (s, 3H), 2.54 (m, 1H), 2.37 (m, 2H), 1.91 (m, 1H), 1.62 (m, 1H), 1.32 (m, 1H), 1.30 (t, 3H).

<9-9> Preparation of (1S,2S)-2-(4-(((10-methyl-8-(3-(methylsulfonyl)propoxy)-6H-benzo[c]chromen-2-yl)methyl)amino)phenyl)cyclopropanecarboxylic acid

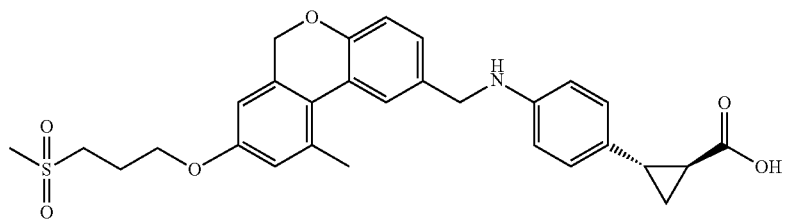 [SMILES: Cc1cc(OCCCS(C)(=O)=O)cc2c1-c1cc(CNc3ccc([C@H]4C[C@@H]4C(=O)O)cc3)ccc1OC2]

The title compound (white solid, 21.7 mg, and 18% yield) was obtained from the compound obtained in <9-8> according to the procedure described in <3-5>.

MS m/z 520 [M−H]⁻.

¹H NMR (300 MHz, CDCl₃) δ 7.67 (d, 1H), 7.17 (dd, 1H), 7.01 (d, 1H), 6.94 (d, 2H), 6.73 (d, 1H), 6.60 (d, 1H), 6.59 (d, 2H), 4.90 (s, 2H), 4.32 (s, 2H), 4.14 (t, 2H), 3.26 (t, 2H), 2.96 (s, 3H), 2.52 (m, 1H), 2.49 (s, 3H), 2.36 (m, 2H), 1.78 (m, 1H), 1.57 (m, 1H), 1.32 (m, 1H).

Example 10

Preparation of (S)-2-(6-((5-methyl-7-(3-(methylsulfonyl)propoxy)-9,10-dihydrophenanthren-1-yl)methoxy)-2,3-dihydrobenzofuran-3-yl)acetic acid <10-1> Preparation of (3-methoxy-5-methylbenzyl)triphenylphosphonium bromide

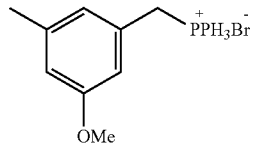

1-(Bromomethyl)-3-methoxy-5-methylbenzene (prepared according to the method disclosed in the document [Australian Journal of Chemistry, 1999, vol. 52, pp. 1093-1108]; 2.3 g, 10.46 mmol), and PPh₃ (2.74 g, 10.46 mmol) were added to toluene (70 mL), and stirred at 95° C. for 16 hours. The reaction mixture was cooled to ambient temperature, and hexane was added, and stirred for 10 minutes. Thereafter, the resulting mixture was filtered, and washed with hexane. Then, the mixture was dried in a vacuum to obtain the title compound (white solid, 3.75 g, and 75% yield).

¹H NMR (300 MHz, CDCl₃) δ 7.84-7.57 (m, 15H), 6.57 (s, 2H), 6.34 (s, 1H), 5.28 (d, 2H), 3.53 (s, 2H), 2.07 (s, 3H).

<10-2> Preparation of methyl 2-(3-methoxy-5-methylstyryl)benzoate

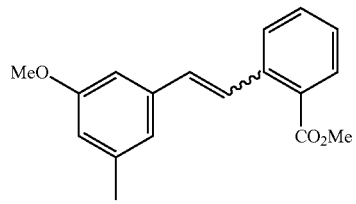 [SMILES: COC(=O)c1ccccc1C=Cc1cc(C)cc(OC)c1]

K₂CO₃ (3.80 g, 27.46 mmol) and 18-Crown-6 (484 mg, 1.83 mmol) were added to a mixture including the compound (4.37 g, 9.15 mmol) obtained in <10-1>, methyl 2-formylbenzoate (1.50 g, 9.15 mmol), THF (92 mL), and dichloromethane (69 mL), and stirred for 3 hours under reflux. The reaction mixture was cooled to ambient temperature, and a saturated NH₄Cl aqueous solution was then added. Thereafter, the mixture was extracted with EtOAc, and an organic layer was then dried over magnesium sulfate. Then, the filtrate was concentrated under reduced pressure. The residue was purified using silica gel chromatography to obtain the title compound (colorless oil, 2.58 g, approximately 100% yield, and an E/Z mixture).

Z-form: ¹H NMR (300 MHz, CDCl₃) δ 8.02-7.97 (m, 1H), 7.36-7.23 (m, 3H), 7.04 (d, 1H), 6.58 (d, 1H), 6.53-6.49 (m, 2H), 6.35 (s, 1H), 3.90 (s, 3H), 3.52 (s, 3H), 2.18 (s, 3H).

E-Form: ¹H NMR (300 MHz, CDCl₃) δ 7.95 (d, 1H), 7.95-7.90 (m, 1H), 7.70 (m, 1H), 7.51 (m, 1H), 7.36-7.28 (m, 1H), 6.99 (m, 1H), 6.95 (d, 1H), 6.89 (s, 1H), 6.66 (s, 1H), 3.93 (s, 3H), 3.83 (s, 3H), 2.36 (s, 3H).

<10-3> Preparation of methyl 2-(3-methoxy-5-methylphenethyl)benzoate

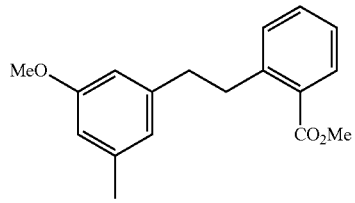 [SMILES: COC(=O)c1ccccc1CCc1cc(C)cc(OC)c1]

The compound (2.65 g, 9.38 mmol) obtained in <10-2> was dissolved in EtOAc (90 mL), and Pd/C (265 mg, based on 10% by weight of a dried product) was added thereto, and stirred for 1 hour under a hydrogen atmosphere. The reaction mixture was filtered through Celite, and washed with EtOAc. The filtrate was concentrated under reduced pressure, and dried in a vacuum to obtain the title compound (yellow oil, 2.43 g, and 91% yield).

¹H NMR (300 MHz, CDCl₃) δ 7.90 (dd, 1H), 7.41 (td, 1H), 7.32-7.17 (m, 2H), 6.65 (s, 1H), 6.57 (s, 2H), 3.91 (s, 3H), 3.77 (s, 3H), 3.23 (m, 2H), 2.83 (m, 2H), 2.31 (s, 3H).

<10-4> Preparation of methyl 2-(2-bromo-5-methoxy-3-methylphenethyl)benzoate

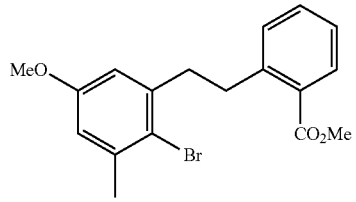 [SMILES: COC(=O)c1ccccc1CCc1cc(OC)cc(C)c1Br]

The compound (2.43 g, 8.54 mmol) obtained in <10-3> was dissolved in CH₃CN (85 mL), and N-bromosuccinimide (1.60 g, 8.97 mmol) was added thereto, and then stirred at ambient temperature for 1 hour. The reaction mixture was concentrated under reduced pressure, and the residue was purified using silica gel chromatography to obtain the title compound (white solid, 2.87 g, and 92% yield).

¹H NMR (300 MHz, CDCl₃) δ 7.89 (dd, 1H), 7.42 (td, 1H), 7.33-7.20 (m, 2H), 6.67 (d, 1H), 6.60 (d, 1H), 3.90 (s, 3H), 3.82 (s, 3H), 3.24 (m, 2H), 3.03 (m, 2H), 2.41 (s, 3H).

<10-5> Preparation of methyl 7-methoxy-5-methyl-9,10-dihydrophenanthren-1-carboxylate

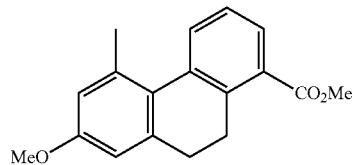 [SMILES: COC(=O)c1cccc2c1CCc1cc(OC)cc(C)c1-2]

The compound (2.87 g, 7.90 mmol) obtained in <10-4> was dissolved in N,N-dimethylacetamide (26 mL), and tricyclohexylphosphine tetrafluoroborate (407 mg, 1.10 mmol) and $K_2CO_3$ (2.18 g, 15.80 mmol) were added thereto, and replaced with nitrogen. Thereafter, palladium (II) acetate (124 mg, 0.55 mmol) was added, and stirred at 135° C. for 15 hours. The reaction mixture was cooled to ambient temperature, and a saturated $NH_4Cl$ aqueous solution and water were added. Subsequently, the mixture was extracted with EtOAc, and an organic layer was washed with saline. The organic layer was dried over magnesium sulfate, filtered, and then concentrated. The resulting residue was purified using silica gel chromatography to obtain the title compound (colorless oil, 1.18 g, and 53% yield).

$^1$H NMR (300 MHz, $CDCl_3$) δ 7.70 (m, 2H), 7.30 (t, 1H), 6.73 (d, 1H), 6.69 (d, 1H), 3.92 (s, 3H), 3.84 (s, 3H), 3.08 (m, 2H), 2.68 (m, 2H), 2.55 (s, 3H).

<10-6> Preparation of methyl 7-hydroxy-5-methyl-9,10-dihydrophenanthren-1-carboxylate

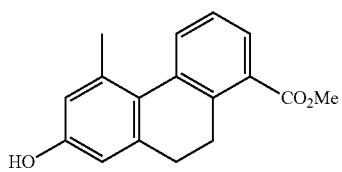 [SMILES: COC(=O)c1cccc2c1CCc1cc(O)cc(C)c1-2]

The compound (1.06 g, 3.75 mmol) obtained in <10-5> was dissolved in dichloromethane (37 mL), and boron tribromide (a 1M MC solution, 7.5 mL, 7.50 mmol) was slowly added dropwise thereto at 0° C., and stirred for 1 hour and 40 minutes. The mixture was warmed to ambient temperature, and stirred for another 20 minutes, and methanol was then added at 0° C. Water was added to the reaction mixture, and the mixture was extracted with dichloromethane, and dried over magnesium sulfate. The filtrate was concentrated under reduced pressure, and purified using silica gel chromatography to obtain the title compound (white foam, 944 mg, and 94% yield).

$^1$H NMR (300 MHz, $CDCl_3$) δ 7.70 (m, 2H), 7.29 (t, 1H), 6.67 (d, 1H), 6.62 (d, 1H), 4.69 (s, 1H), 3.92 (s, 3H), 3.07 (m, 2H), 2.64 (m, 2H), 2.52 (s, 3H).

<10-7> Preparation of methyl 5-methyl-7-(3-(methylsulfonyl)propoxy)-9,10-dihydrophenanthren-1-carboxylate

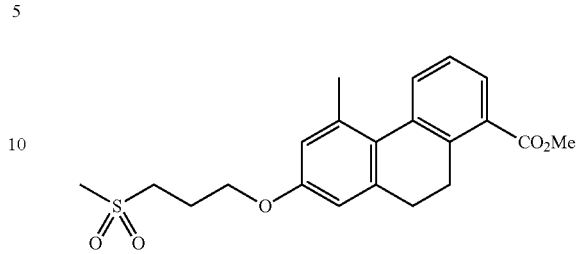

The compound (white foam, 284 mg, and 98% yield) was obtained from the compound obtained in <10-6> according to the procedure described in <1-8>.

$^1$H NMR (300 MHz, $CDCl_3$) δ 7.70 (td, 2H), 7.30 (t, 1H), 6.72 (d, 1H), 6.67 (d, 1H), 4.15 (t, 2H), 3.92 (s, 3H), 3.27 (m, 2H), 3.08 (m, 2H), 2.97 (s, 3H), 2.67 (m, 2H), 2.54 (s, 3H), 2.37 (m, 1H).

<10-8> Preparation of (5-methyl-7-(3-(methylsulfonyl)propoxy)-9,10-dihydrophenanthren-1-yl)methanol

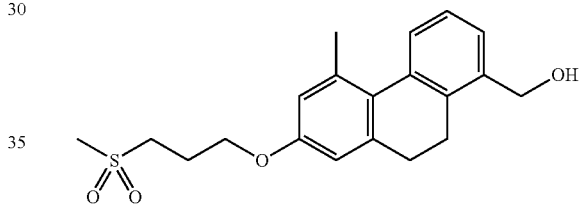

The title compound (white foam, 215 mg, and 82% yield) was obtained from the compound obtained in <10-7> according to the procedure described in <1-9>.

$^1$H NMR (300 MHz, $CDCl_3$) δ 7.56 (m, 1H), 7.33-7.21 (m, 2H), 6.71 (d, 1H), 6.67 (d, 1H), 4.79 (d, 2H), 4.15 (t, 2H), 3.27 (m, 2H), 2.97 (s, 3H), 2.86-2.68 (m, 4H), 2.57 (s, 3H), 2.44-2.28 (m, 2H), 1.55 (t, 1H).

<10-9> Preparation of (S)-methyl 2-(6-((5-methyl-7-(3-(methylsulfonyl)propoxy)-9,10-dihydrophenanthren-1-yl)methoxy)-2,3-dihydrobenzofuran-3-yl)acetate

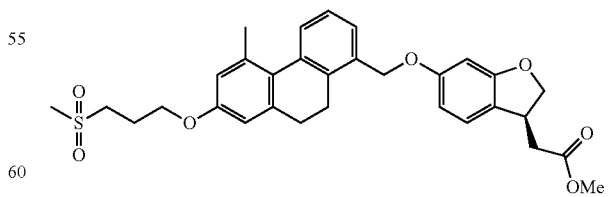

The title compound (white foam, 89 mg, and 79% yield) was obtained from the compound obtained in <10-8> according to the procedure described in <1-10>.

$^1$H NMR (300 MHz, $CDCl_3$) δ 7.59 (dd, 1H), 7.34-7.23 (m, 2H), 7.08 (d, 1H), 6.71 (d, 1H), 6.66 (d, 1H), 6.51 (m,

2H), 5.06 (s, 2H), 4.77 (t, 1H), 4.28 (dd, 1H), 4.15 (t, 2H), 3.81 (m, 1H), 3.27 (m, 2H), 2.97 (s, 3H), 2.84-2.69 (m, 5H), 2.59 (m, 4H), 2.36 (m, 2H).

<10-10> Preparation of (S)-2-(6-((5-methyl-7-(3-(methylsulfonyl)propoxy)-9,10-dihydrophenanthren-1-yl)methoxy)-2,3-dihydrobenzofuran-3-yl)acetic acid

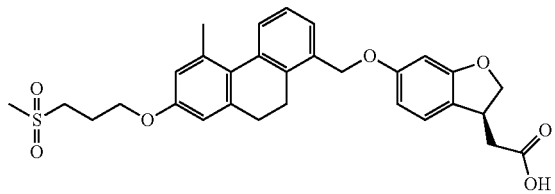 [SMILES: Cc1cc(OCCCS(C)(=O)=O)cc2c1-c1cccc(COc3ccc4c(c3)OC[C@H]4CC(=O)O)c1CC2]

The title compound (white foam, 84 mg, and 99% yield) was obtained from the compound obtained in <10-9> according to the procedure described in <1-11>.

MS m/z 535 [M–H]⁻.

$^1$H NMR (300 MHz, CDCl$_3$) δ 7.59 (dd, 1H), 7.35-7.21 (m, 2H), 7.08 (d, 1H), 6.75 (d, 1H), 6.62 (d, 1H), 6.58-6.46 (m, 2H), 5.06 (s, 2H), 4.78 (t, 1H), 4.30 (dd, 1H), 4.14 (t, 2H), 3.88-3.77 (m, 1H), 3.33-3.21 (m, 2H), 2.97 (s, 3H), 2.87-2.62 (m, 5H), 2.57 (s, 3H), 2.36 (m, 2H).

Example 11

Preparation of (S)-2-(6-((5-methyl-7-(3-(methylsulfonyl)propoxy)-9,10-dihydrophenanthren-3-yl)methoxy)-2,3-dihydrobenzofuran-3-yl)acetic acid <11-1> Preparation of methyl 4-(3-methoxy-5-methylstyryl)benzoate

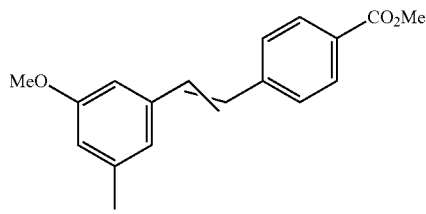

The title compound (white solid, 1.70 g, 96% yield, and an E/Z mixture) was obtained from the compound obtained in <10-1> and methyl 4-formylbenzoate, according to the procedure described in <10-2>.

Z-form: $^1$H NMR (300 MHz, CDCl$_3$) δ 8.02 (d, 2H), 7.55 (d, 2H), 7.15 (d, 2H), 6.96 (s, 1H), 6.88 (s, 1H), 6.68 (s, 1H), 3.93 (s, 3H), 3.84 (s, 3H), 2.36 (s, 3H).

E-form: $^1$H NMR (300 MHz, CDCl$_3$) δ 7.89 (d, 2H), 7.32 (d, 2H), 6.72-6.52 (m, 5H), 3.89 (s, 3H), 3.62 (s, 3H), 2.24 (s, 3H).

<11-2> Preparation of methyl 4-(3-methoxy-5-methylphenethyl)benzoate

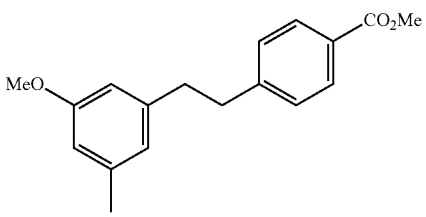 [SMILES: COC(=O)c1ccc(CCc2cc(C)cc(OC)c2)cc1]

The title compound (colorless oil, 1.70 g, and 99% yield) was obtained from the compound obtained in <11-1> according to the procedure described in <10-3>.

$^1$H NMR (300 MHz, CDCl$_3$) δ 7.95 (d, 2H), 7.24 (d, 2H), 6.60 (s, 1H), 6.57 (s, 1H), 6.51 (s, 1H), 3.90 (s, 3H), 3.76 (s, 3H), 3.02-2.79 (m, 4H), 2.30 (s, 3H).

<11-3> Preparation of methyl 4-(2-bromo-5-methoxy-3-methylphenethyl)benzoate

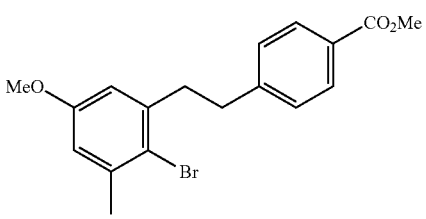 [SMILES: COC(=O)c1ccc(CCc2cc(OC)cc(C)c2Br)cc1]

The title compound (colorless oil, 1.86 g, and 85% yield) was obtained from the compound obtained in <11-2> according to the procedure described in <10-4>.

$^1$H NMR (300 MHz, CDCl$_3$) δ 7.96 (d, 2H), 7.29 (d, 2H), 6.68 (d, 1H) 6.60 (d, 1H), 3.91 (s, 3H), 3.72 (s, 3H), 3.09-2.89 (m, 4H), 2.41 (s, 3H).

<11-4> Preparation of methyl 7-methoxy-5-methyl-9,10-dihydrophenanthren-3-carboxylate

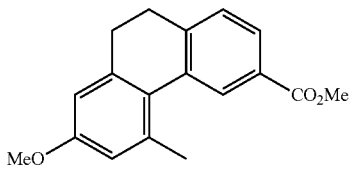 [SMILES: COC(=O)c1ccc2c(c1)-c1c(C)cc(OC)cc1CC2]

The title compound (colorless oil, 1.23 g, and 86% yield) was obtained from the compound obtained in <11-3> according to the procedure described in <10-5>.

$^1$H NMR (300 MHz, CDCl$_3$) δ 8.30 (d, 1H), 7.84 (dd, 1H), 7.31 (d, 1H), 6.75 (d, 1H), 6.68 (s, 1H), 3.93 (s, 3H), 3.84 (s, 3H), 2.84-2.70 (m, 4H), 2.64 (s, 3H).

<11-5> Preparation of methyl 7-hydroxy-5-methyl-9,10-dihydrophenanthren-3-carboxylate

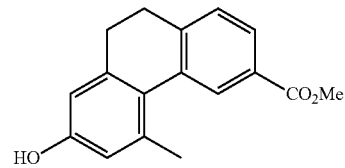 [SMILES: COC(=O)c1ccc2c(c1)-c1c(C)cc(O)cc1CC2]

The title compound (white solid, 768 mg, and 66% yield) was obtained from the compound obtained in <11-4> according to the procedure described in <10-6>.

$^1$H NMR (300 MHz, CDCl$_3$) δ 8.28 (d, 1H), 7.84 (dd, 1H), 7.31 (m, 1H), 6.69 (d, 1H), 6.62 (d, 1H), 4.78 (s, 1H), 3.93 (s, 3H), 2.84-2.65 (m, 4H), 2.60 (s, 3H).

<11-6> Preparation of methyl 5-methyl-7-(3-(methylsulfonyl)propoxy)-9,10-dihydrophenanthren-3-carboxylate

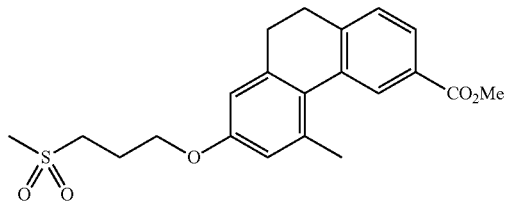 [SMILES: COC(=O)c1ccc2c(c1)-c1c(C)cc(OCCCS(C)(=O)=O)cc1CC2]

The title compound (white solid, 266 mg, and 92% yield) was obtained from the compound obtained in <11-5> according to the procedure described in <1-8>.

$^1$H NMR (300 MHz, CDCl$_3$) δ 8.29 (d, 1H), 7.85 (dd, 1H), 7.32 (d, 1H), 6.73 (d, 1H), 6.67 (d, 1H), 4.15 (t, 2H), 3.93 (s, 2H), 3.28 (m, 2H), 2.97 (s, 3H), 2.76 (m, 2H), 2.36 (m, 2H).

<11-7> Preparation of (5-methyl-7-(3-(methylsulfonyl)propoxy)-9,10-dihydrophenanthren-3-yl)methanol

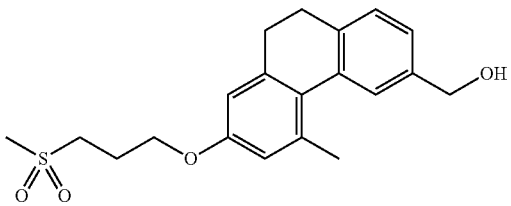 [SMILES: Cc1cc(OCCCS(C)(=O)=O)cc2c1-c1cc(CO)ccc1CC2]

The title compound (white solid, 194 mg, and 79% yield) was obtained from the compound obtained in <11-6> according to the procedure described in <1-9>.

$^1$H NMR (300 MHz, CDCl$_3$) δ 7.61 (d, 1H), 7.30-7.13 (m, 2H), 6.74 (d, 1H), 6.63 (d, 1H), 4.72 (d, 2H), 4.15 (t, 2H), 3.33-3.21 (m, 2H), 2.97 (s, 3H), 2.73 (s, 4H), 2.61 (s, 3H), 2.36 (m, 2H), 1.62 (t, 1H).

<11-8> Preparation of (S)-methyl 2-(6-((5-methyl-7-(3-(methylsulfonyl)propoxy)-9,10-dihydrophenanthren-3-yl)methoxy)-2,3-dihydrobenzofuran-3-yl)acetate

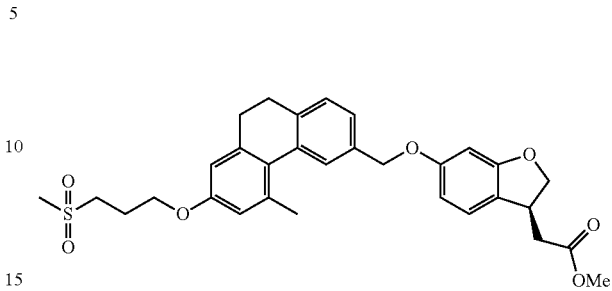

The title compound (colorless oil, 115 mg, and 80% yield) was obtained from the compound obtained in <11-7> according to the procedure described in <1-10>.

$^1$H NMR (300 MHz, CDCl$_3$) δ 7.62 (s, 1H), 7.31-7.19 (m, 2H), 7.03 (d, 1H), 6.72 (d, 1H), 6.62 (d, 1H), 6.55-6.44 (m, 2H), 5.04 (s, 2H), 4.75 (t, 1H), 4.26 (dd, 1H), 4.14 (t, 2H), 3.81 (m, 1H), 3.72 (s, 3H), 3.33-3.21 (m, 2H), 2.96 (s, 3H), 2.82-2.68 (m, 5H), 2.60-2.51 (m, 4H), 2.41-2.30 (m, 2H).

<11-9> Preparation of (S)-2-(6-((5-methyl-7-(3-(methylsulfonyl)propoxy)-9,10-dihydrophenanthren-3-yl)methoxy)-2,3-dihydrobenzofuran-3-yl)acetic acid

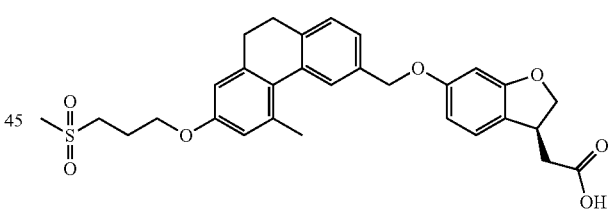

The title compound (white solid, 101 mg, and 92% yield) was obtained from the compound obtained in <11-8> according to the procedure described in <1-11>.

MS m/z 535 [M−H]$^−$.

$^1$H NMR (300 MHz, CDCl$_3$) δ 7.62 (s, 1H), 7.31-7.16 (m, 2H), 7.06 (d, 1H), 6.73 (d, 1H), 6.62 (d, 1H), 6.56-6.45 (m, 2H), 5.05 (s, 2H), 4.76 (t, 1H), 4.29 (dd, 1H), 4.14 (t, 2H), 3.81 (t, 1H), 3.33-3.21 (m, 2H), 2.96 (s, 3H), 2.85-2.77 (m, 1H), 2.73 (s, 3H), 2.66-2.57 (m, 1H), 2.55 (s, 3H), 2.40-2.31 (m, 2H).

Example 12

Preparation of (S)-2-(6-((7-(2-ethoxyethoxy)-5-methyl-9,10-dihydrophenanthren-3-yl)methoxy)-2,3-dihydrobenzofuran-3-yl)acetic acid <12-1> Preparation of methyl 7-(2-ethoxyethoxy)-5-methyl-9,10-dihydrophenanthren-3-carboxylate

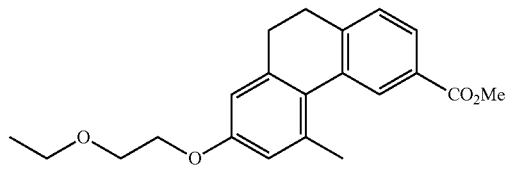 [SMILES: CCOCCOc1cc(C)c2c(c1)CCc1ccc(C(=O)OC)cc1-2]

The title compound (yellow oil, 410 mg, and approximately 100% yield) was obtained from the compound obtained in <11-5> according to the procedure described in <3-1>.

$^1$H NMR (300 MHz, CDCl$_3$) δ 8.29 (d, 1H), 7.84 (dd, 1H), 7.31 (d, 1H), 6.77 (d, 1H), 6.71 (d, 1H), 4.16 (t, 2H), 3.92 (s, 3H), 3.81 (t, 2H), 3.62 (q, 2H), 2.76 (m, 4H), 2.62 (s, 3H), 1.26 (t, 3H).

<12-2> Preparation of (7-(2-ethoxyethoxy)-5-methyl-9,10-dihydrophenanthren-3-yl)methanol

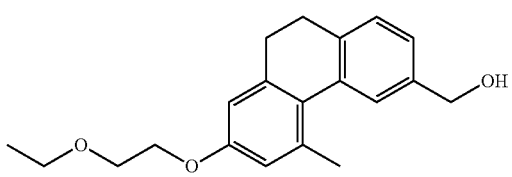 [SMILES: CCOCCOc1cc(C)c2c(c1)CCc1ccc(CO)cc1-2]

The title compound (white solid, 332 mg, and 95% yield) was obtained from the compound obtained in <12-1> according to the procedure described in <3-2>.

$^1$H NMR (300 MHz, CDCl$_3$) δ 7.61 (s, 1H), 7.26-7.15 (m, 2H), 6.79 (d, 1H), 6.67 (d, 1H), 4.71 (s, 2H), 4.15 (t, 2H), 3.80 (t, 2H), 3.62 (q, 2H), 2.72 (s, 4H), 2.61 (s, 3H), 1.25 (t, 3H).

<12-3> Preparation of (S)-methyl 2-(6-((7-(2-ethoxyethoxy)-5-methyl-9,10-dihydrophenanthren-3-yl)methoxy)-2,3-dihydrobenzofuran-3-yl)acetate

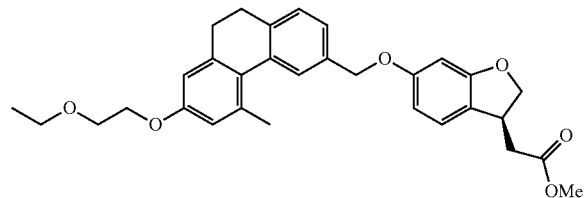 [SMILES: CCOCCOc1cc(C)c2c(c1)CCc1ccc(COc3ccc4c(c3)OC[C@H]4CC(=O)OC)cc1-2]

The title compound (colorless oil, 135 mg, and 84% yield) was obtained from the compound obtained in <12-2> according to the procedure described in <1-10>.

$^1$H NMR (300 MHz, CDCl$_3$) δ 7.62 (s, 1H), 7.30-7.15 (m, 2H), 7.02 (d, 1H), 6.77 (d, 1H), 6.66 (d, 1H), 6.55-6.44 (m, 2H), 5.04 (s, 2H), 4.75 (t, 1H), 4.26 (dd, 1H), 4.15 (t, 2H), 3.85-3.75 (m, 3H), 3.71 (s, 3H), 3.61 (q, 2H), 2.82-2.68 (m, 5H), 2.63-2.47 (m, 4H), 1.25 (t, 3H).

<12-4> Preparation of (S)-2-(6-((7-(2-ethoxyethoxy)-5-methyl-9,10-dihydrophenanthren-3-yl)methoxy)-2,3-dihydrobenzofuran-3-yl)acetic acid

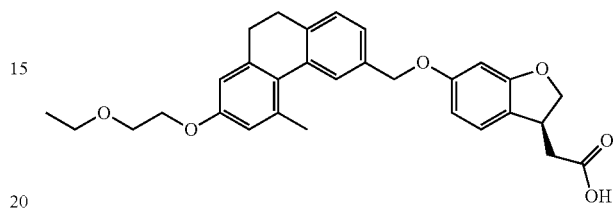

The title compound (white foam, 93 mg, and 77% yield) was obtained from the compound obtained in <12-3> according to the procedure described in <1-11>.

MS m/z 487 [M−H]$^-$.

$^1$H NMR (300 MHz, CDCl$_3$) δ 7.74 (d, 1H), 7.23 (dd, 1H), 7.05 (m, 2H), 6.80 (d, 1H), 6.63 (d, 1H), 6.56-6.45 (m, 2H), 5.02 (s, 2H), 4.92 (s, 2H), 4.76 (t, 1H), 4.29 (dd, 1H), 4.15 (t, 2H), 3.89-3.73 (m, 3H), 3.62 (q, 2H), 2.81 (dd, 1H), 2.69-2.57 (m, 1H), 2.57 (s, 3H), 1.25 (t, 3H).

Example 13

Preparation of 2-((3S)-6-((11-methyl-9-(3-(methylsulfonyl)propoxy)-6,7-dihydrodibenzo[b,d]oxepin-4-yl)methoxy)-2,3-dihydrobenzofuran-3-yl)acetic acid <13-1> Preparation of methyl 3-bromo-2-(3-methoxy-5-methylphenethoxy)benzoate

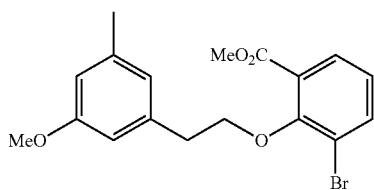 [SMILES: COC(=O)c1cccc(Br)c1OCCc1cc(C)cc(OC)c1]

2-(3-Methoxy-5-methylphenyl)ethanol (prepared according to the method disclosed in the document [Australian Journal of Chemistry, 1999, vol. 52, pp. 1093-1108]; 113 mg, 0.68 mmol), and methyl 3-bromo-2-hydroxybenzoate (see the document [Organic and Biomolecular Chemistry, 2004, vol. 2, pp. 963-964]; 157 mg, 0.68 mmol) were dissolved in THF (7 mL), PPh$_3$ (267 mg, 1.02 mmol) was added thereto, and diethyl azodicarboxylate (40% toluene solution, 0.46 mL, 1.02 mmol) was slowly added dropwise. The reaction mixture was stirred at ambient temperature for 2 hours, concentrated under reduced pressure, and then purified using silica gel chromatography to obtain the title compound (yellow oil, 253 mg, and 98% yield).

$^1$H NMR (300 MHz, CDCl$_3$) δ 7.73 (td, 2H), 7.03 (t, 1H), 6.72 (s, 1H), 6.67 (s, 1H), 6.59 (s, 1H), 4.22 (t, 2H), 3.85 (s, 3H), 3.79 (s, 3H), 3.14 (t, 2H), 2.31 (s, 3H).

<13-2> Preparation of methyl 2-(3-methoxy-5-methylphenethoxy)-3-(4,4,5,5-tetramethyl-1,3,2-dioxaborolan-2-yl)benzoate

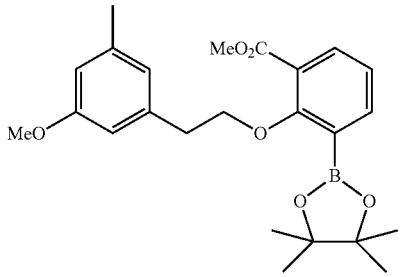 [SMILES: COC(=O)c1cccc(B2OC(C)(C)C(C)(C)O2)c1OCCc1cc(C)cc(OC)c1]

The compound (248 mg, 0.65 mmol) obtained in <13-1>, and bis(pinacolato)diboron (249 mg, 0.98 mmol) were dissolved in 1,4-dioxane (7 mL), and KOAc (193 mg, 1.96 mmol) was added thereto, and replaced with nitrogen. Thereafter, a complex (27 mg, 0.033 mmol) of [1,1'-bis(diphenylphosphino)ferrocene]dichloropalladium (II) with dichloromethane was added, and reacted at 90° C. for 15 hours. The reaction mixture was cooled to ambient temperature, filtered through Celite, and then washed with EtOAc. The filtrate was concentrated under reduced pressure, and then purified using silica gel chromatography to obtain the title compound (colorless oil, 131 mg, and a mixture including the compound obtained in <13-2> and bis(pinacolato)diboron at a ratio of 1.0:0.17).

$^1$H NMR (300 MHz, CDCl$_3$) δ 7.92-7.80 (m, 2H), 7.15 (t, 1H), 6.69 (s, 1H), 6.63 (s, 1H), 6.58 (s, 1H), 4.16 (t, 2H), 3.82 (s, 3H), 3.78 (s, 3H), 3.13 (t, 2H), 2.30 (s, 3H), 1.37 (s, 12H).

<13-3> Preparation of methyl 2-(2-bromo-5-methoxy-3-methylphenethoxy)-3-(4,4,5,5-tetramethyl-1,3,2-dioxaborolan-2-yl)benzoate

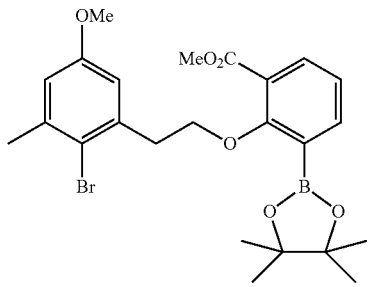

The compound (126 mg; a mixture including the compound obtained in <13-2> and bis(pinacolato)diboron at a ratio of 1.0:0.17) obtained in <13-2> was dissolved in acetonitrile (5 mL), and N-bromosuccinimide (48 mg, 0.26 mmol) was added thereto, and stirred at ambient temperature for 2 hours. The reaction mixture was concentrated under reduced pressure, and purified using silica gel chromatography to obtain the title compound (colorless oil, 109 mg, and 81% yield).

$^1$H NMR (300 MHz, CDCl$_3$) δ 7.86 (m, 2H), 7.15 (t, 1H), 6.80 (d, 1H), 6.68 (d, 1H), 4.20 (t, 2H), 3.83 (s, 3H), 3.77 (s, 3H), 3.33 (t, 2H), 2.39 (s, 3H), 1.36 (s, 12H).

<13-4> Preparation of methyl 9-methoxy-11-methyl-6,7-dihydrodibenzo[b,d]oxepin-4-carboxylate

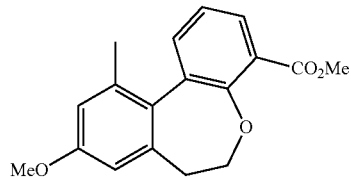 [SMILES: COC(=O)c1cccc2c1OCCc1cc(OC)cc(C)c1-2]

The compound (106 mg, 0.21 mmol) obtained in <13-3> was dissolved in 1,4-dioxane (4 mL), and K$_2$CO$_3$ (87 mg, 0.63 mmol) was added thereto, and replaced with nitrogen. Thereafter, [1,1'-bis(diphenylphosphino)ferrocene]dichloropalladium (II) (15 mg, 0.021 mmol) was added, and stirred at 100° C. for 15 hours. The reaction mixture was cooled to ambient temperature, and water was added. Then, the mixture was extracted with EtOAc. An organic layer was collected, and dried over magnesium sulfate. Subsequently, the filtrate was concentrated under reduced pressure, and purified using silica gel chromatography to obtain the title compound (colorless oil, 8 mg, and 13% yield).

$^1$H NMR (300 MHz, CDCl$_3$) δ 7.72 (dd, 1H), 7.44 (dd, 1H), 7.22 (t, 1H), 6.79 (d, 1H), 6.71 (d, 1H), 4.70 (m, 1H), 4.44 (ddd, 1H), 3.92 (s, 3H), 3.84 (s, 3H), 2.84 (td, 1H), 2.54 (dd, 1H), 2.34 (s, 3H).

<13-5> Preparation of methyl 2'-(2-bromoethyl)-2,4'-dihydroxy-6'-methyl-[1,1'-biphenyl]-3-carboxylate

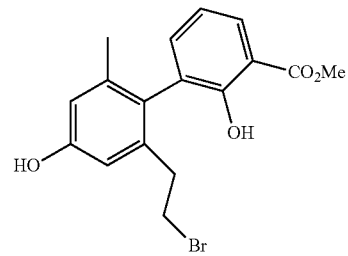 [SMILES: COC(=O)c1cccc(-c2c(C)cc(O)cc2CCBr)c1O]

The compound (8 mg, 0.027 mmol) obtained in <13-4> was dissolved in dichloromethane (2 mL), and boron tribromide (a 1 M MC solution, 54 mL, 0.053 mmol) was slowly added dropwise thereto at 0° C., and stirred at the same temperature for 1 hour and 20 minutes. Thereafter, methanol (0.2 mL) was added at 0° C. Water was added to the reaction mixture, and the mixture was extracted with dichloromethane, and extracted with 5% methanol/dichloromethane again. Then, an organic layer was dried over magnesium sulfate. The filtrate was concentrated under reduced pressure to obtain the title compound (colorless oil, 10 mg, and approximately 100% yield), which was used for the next reaction without any additional purification.

$^1$H NMR (300 MHz, CDCl$_3$) δ 11.00 (s, 1H), 7.91 (dd, 1H), 7.31-7.21 (m, 1H), 6.97 (t, 1H), 6.70 (d, 1H), 6.67 (d, 1H), 4.65 (s, 1H), 3.99 (s, 3H), 3.35 (m, 2H), 2.95-2.78 (m, 2H), 1.98 (s, 3H).

<13-6> Preparation of methyl 11-methyl-9-(3-(methylsulfonyl)propoxy)-6,7-dihydrodibenzo[b,d]oxepin-4-carboxylate

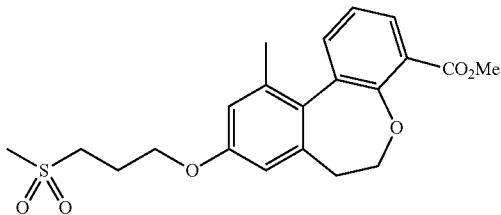 [SMILES: COC(=O)c1cccc2c1OCCc1cc(OCCCS(C)(=O)=O)cc(C)c1-2]

The compound (11 mg, 0.03 mmol) obtained in <13-5> was dissolved in DMF (2 mL), and K₂CO₃ (6 mg, 0.045 mmol) was added thereto, and stirred at ambient temperature for 3 hours. 3-(Methylsulfonyl)propyl 4-methylbenzenesulfonate (11 mg, 0.036 mmol) was added to the reaction mixture, stirred at 90° C. for 16 hours, and then cooled to ambient temperature. The mixture was concentrated under reduced pressure, and purified using silica gel chromatography to obtain the title compound (colorless oil, 10 mg, and 82% yield).

$^1$H NMR (300 MHz, CDCl₃) δ 7.73 (dd, 1H), 7.44 (dd, 1H), 7.23 (t, 1H), 6.77 (d, 1H), 6.69 (d, 1H), 4.69 (dd, 1H), 4.43 (ddd, 1H), 4.16 (t, 2H), 3.92 (s, 3H), 3.28 (m, 2H), 2.97 (s, 3H), 2.83 (td, 1H), 2.41-2.30 (m, 2H), 2.33 (s, 3H).

<13-7> Preparation of (11-methyl-9-(3-(methylsulfonyl)propoxy)-6,7-dihydrodibenzo[b,d]oxepin-4-yl)methanol

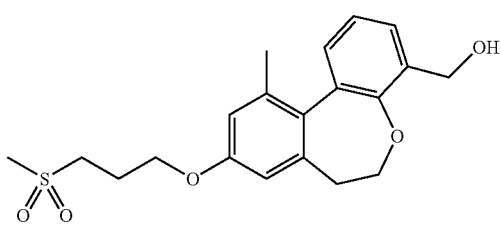 [SMILES: Cc1cc(OCCCS(C)(=O)=O)cc2c1-c1cccc(CO)c1OCC2]

The title compound (colorless oil, 7 mg, and 75% yield) was obtained from the compound obtained in <13-6> according to the procedure described in <1-9>.

$^1$H NMR (300 MHz, CDCl₃) δ 7.34 (dd, 1H), 7.26 (dd, 1H), 7.22 (t, 1H), 6.78 (d, 1H), 6.69 (d, 1H), 4.89 (dd, 1H), 4.64 (dd, 1H), 4.56-4.36 (m, 2H), 4.16 (t, 2H), 3.28 (m, 2H), 2.97 (s, 3H), 2.85 (td, 1H), 2.52 (dd, 1H), 2.44-2.29 (m, 2H), 2.35 (s, 3H), 2.22 (dd, 1H).

<13-8> Preparation of methyl 2-((3S)-6-((11-methyl-9-(3-(methylsulfonyl)propoxy)-6,7-dihydrodibenzo[b,d]oxepin-4-yl)methoxy)-2,3-dihydrobenzofuran-3-yl)acetate

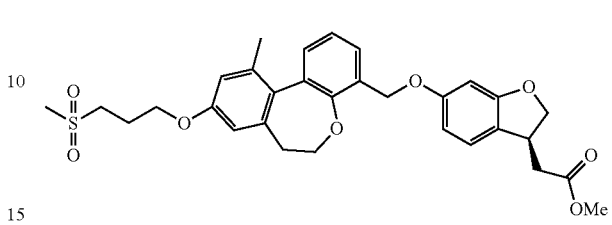

The title compound (colorless oil, 7 mg, and 93% yield) was obtained from the compound obtained in <13-7> according to the procedure described in <1-10>.

$^1$H NMR (300 MHz, CDCl₃) δ 7.45 (dd, 1H), 7.29 (dd, 1H), 7.21 (t, 1H), 7.05 (d, 1H), 6.78 (d, 1H), 6.69 (d, 1H), 6.59-6.48 (m, 2H), 5.20 (d, 1H), 4.99 (d, 1H), 4.77 (t, 1H), 4.53-4.36 (m, 2H), 4.28 (dd, 1H), 4.16 (t, 2H), 3.82 (m, 1H), 3.72 (s, 3H), 3.28 (m, 2H), 2.97 (s, 3H), 2.87 (td, 1H), 2.77 (dd, 1H), 2.65-2.47 (m, 2H), 2.41-2.32 (m, 2H), 2.36 (s, 3H).

<13-9> Preparation of 2-((3S)-6-((11-methyl-9-(3-(methylsulfonyl)propoxy)-6,7-dihydrodibenzo[b,d]oxepin-4-yl)methoxy)-2,3-dihydrobenzofuran-3-yl)acetic acid

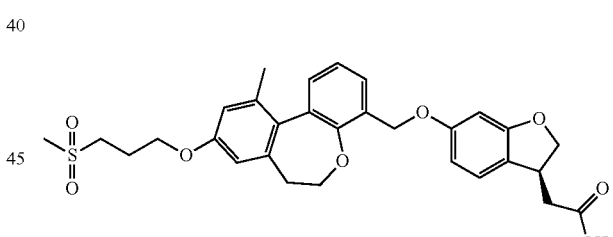

The title compound (white foam, 7 mg, and 72% yield) was obtained from the compound obtained in <13-8> according to the procedure described in <1-11>.

MS m/z 551 [M−H]⁻.

$^1$H NMR (300 MHz, CDCl₃) δ 7.45 (dd, 1H), 7.29 (dd, 1H), 7.21 (t, 1H), 7.08 (d, 1H), 6.78 (d, 1H), 6.69 (d, 1H), 6.60-6.48 (m, 2H), 5.20 (d, 1H), 5.00 (d, 1H), 4.78 (t, 1H), 4.53-4.36 (m, 2H), 4.31 (dd, 1H), 4.16 (t, 2H), 3.82 (m, 1H), 3.28 (m, 2H), 2.97 (s, 3H), 2.92-2.76 (m, 2H), 2.71-2.47 (m, 2H), 2.41-2.31 (m, 2H), 2.36 (s, 3H).

Example 14

Preparation of 2-((3S)-6-((11-methyl-9-(3-(methylsulfonyl)propoxy)-6,7-dihydrodibenzo[b,d]oxepin-2-yl)methoxy)-2,3-dihydrobenzofuran-3-yl)acetic acid <14-1> Preparation of 3-bromo-4-[2-(3-methoxy-5-methyl-phenyl)-ethoxy]-benzoic acidmethyl ester

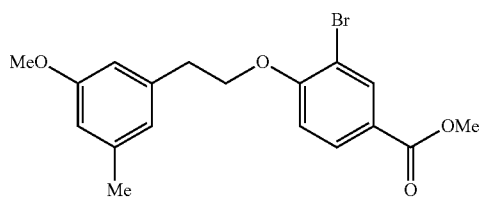 [SMILES: COC(=O)c1ccc(OCCc2cc(C)cc(OC)c2)c(Br)c1]

2-(3-Methoxy-5-methyl-phenyl)-ethanol (prepared according to the method disclosed in the document [Australian Journal of Chemistry, 1999, vol. 52, pp. 1093-1108]; 1.9 g, 11.6 mmol), the compound (2.7 g, 11.6 mmol) obtained in <2-4>, and PPh₃ (4.6 g, 17.4 mmol) were dissolved in THF (85 mL), and diethyl azodicarboxylate (40% toluene solution, 7.9 mL, 17.4 mmol) was slowly added thereto. After 2 hours, the reaction mixture was concentrated, and purified using silica gel chromatography to obtain the title compound (colorless oil, 4.18 g, and 95% yield).

$^1$H NMR (300 MHz, CDCl₃) δ 8.22 (d, 1H), 7.93 (dd, 1H), 6.86 (d, 1H), 6.76 (s, 1H), 6.71 (s, 1H), 6.62 (s, 1H), 4.25 (t, 2H), 3.89 (s, 3H), 3.80 (s, 3H), 3.11 (t, 2H), 2.32 (s, 3H).

<14-2> Preparation of 4-[2-(3-methoxy-5-methyl-phenyl)-ethoxy]-3-(4,4,5,5-tetramethyl-[1,3,2]dioxaborolan-2-yl)-benzoic acidmethyl ester

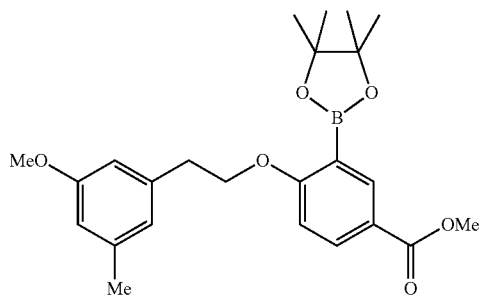 [SMILES: COC(=O)c1ccc(OCCc2cc(C)cc(OC)c2)c(B2OC(C)(C)C(C)(C)O2)c1]

The compound (4.18 g, 11.0 mmol) obtained in <14-1>, and bis(pinacolato)diboron (4.2 g, 16.5 mmol) were dissolved in DMF (60 mL), and potassium acetate (3.2 g, 33 mmol), and a complex of [1,1'-bis(diphenylphosphino)ferrocene]dichloropalladium (II) with dichloromethane were added thereto, and replaced with argon. The reaction mixture was stirred at 100° C. for 20 hours, cooled to ambient temperature, and then diluted with saline. The mixture was extracted with EtOAc, and an organic layer was washed with saline. The organic layer was dried over magnesium sulfate, and concentrated under reduced pressure. Then, the residue was purified using silica gel chromatography to obtain the title compound (oil, 6.1 g, >100% yield).

$^1$H NMR (300 MHz, CDCl₃) δ 8.30 (d, 1H), 8.04 (dd, 1H), 6.82 (d, 1H), 6.72 (s, 1H), 6.70 (s, 1H), 6.59 (s, 1H), 4.21 (t, 2H), 3.87 (s, 3H), 3.77 (s, 3H), 3.08 (t, 2H), 2.31 (s, 3H), 1.36 (s, 12H).

<14-3> Preparation of 4-[2-(2-bromo-5-methoxy-3-methyl-phenyl)-ethoxy]-3-(4,4,5,5-tetramethyl-[1,3,2]dioxaborolan-2-yl)-benzoic acidmethyl ester

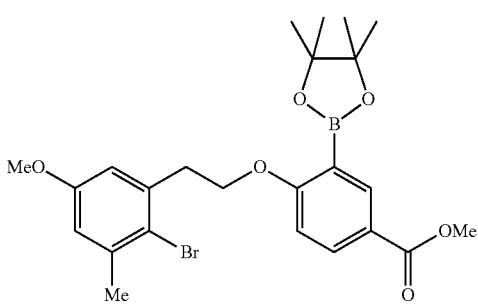 [SMILES: COC(=O)c1ccc(OCCc2cc(OC)cc(C)c2Br)c(B2OC(C)(C)C(C)(C)O2)c1]

The compound (6.1 g, 11.0 mmol) obtained in <14-2> was dissolved in CH₃CN (70 mL), and NBS (1.9 g, 11.0 mmol) was added thereto, and stirred for 2 hours. The reaction mixture was concentrated under reduced pressure, recrystallized from EtOAc/hexane (a mixture including EtOAc and hexane at a ratio of approximately 1:1), and then filtered. The filtrate was concentrated under reduced pressure, and the residue was purified using silica gel chromatography to obtain the title compound (oil, 6.48 g, >100% yield).

$^1$H NMR (300 MHz, CDCl₃) δ 8.30 (d, 1H), 8.05 (dd, 1H), 6.86 (d, 1H), 6.85 (d, 1H), 6.69 (d, 1H), 6.59 (s, 1H), 4.25 (t, 2H), 3.87 (s, 3H), 3.74 (s, 3H), 3.27 (t, 2H), 2.40 (s, 3H), 1.36 (s, 12H).

<14-4> Preparation of 9-methoxy-11-methyl-6,7-dihydro-5-oxa-dibenzo[a,c]cycloheptene-2-carboxylic acid methyl ester

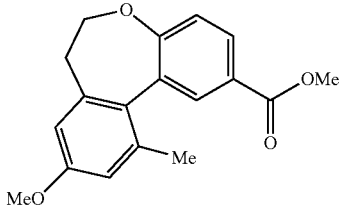 [SMILES: COC(=O)c1ccc2c(c1)-c1c(C)cc(OC)cc1CCO2]

The compound (6.48 g, 11.0 mmol) obtained in <14-3>, and K₂CO₃ (4.5 g, 33.0 mmol) were dissolved in 1,4-dioxane (70 mL), and a complex (718 mg, 0.88 mmol) of [1,1'-bis(diphenylphosphino)ferrocene]dichloropalladium (II) with dichloromethane was added thereto, and replaced with argon. The resulting mixture was stirred at 100° C. for 17 hours, and the reaction mixture was then cooled to ambient temperature, and diluted with water. The mixture was extracted with EtOAc, dried over magnesium sulfate, and concentrated under reduced pressure. The residue was purified using silica gel chromatography to obtain the title compound (white solid, 2.4 g, and 96% yield).

$^1$H NMR (300 MHz, CDCl$_3$) δ 8.03 (d, 1H), 7.97 (dd, 1H), 7.17 (d, 1H), 6.80 (d, 1H), 6.69 (d, 1H), 4.45-4.53 (m, 2H), 3.91 (s, 3H), 3.85 (s, 3H), 2.82 (m, 1H), 2.52 (m, 1H), 2.38 (s, 3H).

<14-5> Preparation of methyl 9-hydroxy-11-methyl-6,7-dihydrodibenzo[b,d]oxepin-2-carboxylate

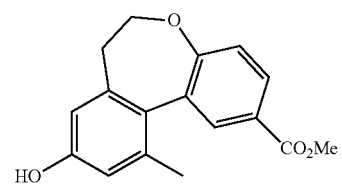 [SMILES: COC(=O)c1ccc2c(c1)-c1c(C)cc(O)cc1CCO2]

The compound (300 mg, 1.01 mmol) obtained in <14-4> was dissolved in dichloromethane (10 mL), and boron tribromide (a 1 M dichloromethane solution, 2.0 mL, 2.01 mmol) was slowly added dropwise thereto at 0° C., and stirred at the same temperature for 3 hours. Thereafter, methanol (4 mL) was added dropwise at 0° C., and water was added. The reaction mixture was extracted with 5% methanol/dichloromethane (40 mL), and an organic layer was then dried over magnesium sulfate. The filtrate was concentrated under reduced pressure, and then purified using silica gel chromatography to obtain the title compound (white solid, 119 mg, and 42% yield).

$^1$H NMR (300 MHz, CDCl$_3$) δ 8.02 (d, 1H), 7.97 (dd, 1H), 7.18 (d, 1H), 6.73 (d, 1H), 6.63 (d, 1H), 4.47 (m, 2H), 3.92 (s, 3H), 2.80 (td, 1H), 2.49 (m, 1H), 2.34 (s, 3H).

<14-6> Preparation of methyl 11-methyl-9-(3-(methylsulfonyl)propoxy)-6,7-dihydrodibenzo[b,d]oxepin-2-carboxylate

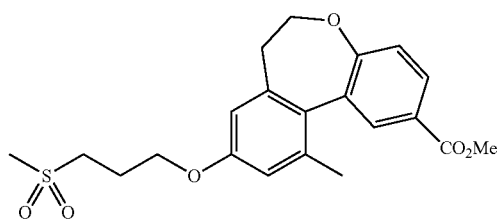 [SMILES: COC(=O)c1ccc2c(c1)-c1c(C)cc(OCCCS(C)(=O)=O)cc1CCO2]

The title compound (white solid, 169 mg, and 63% yield) was obtained from the compound obtained in <14-5> according to the procedure described in <1-8>.

$^1$H NMR (300 MHz, CDCl$_3$) δ 8.02 (d, 1H), 7.98 (dd, 1H), 7.18 (d, 1H), 6.79 (d, 1H), 6.68 (d, 1H), 4.47 (m, 2H), 4.16 (t, 2H), 3.92 (s, 3H), 3.28 (m, 2H), 2.97 (s, 3H), 2.82 (td, 1H), 2.52 (dd, 1H), 2.42-2.33 (m, 2H), 2.37 (s, 3H).

<14-7> Preparation of (11-methyl-9-(3-(methylsulfonyl)propoxy)-6,7-dihydrodibenzo[b,d]oxepin-2-yl)methanol

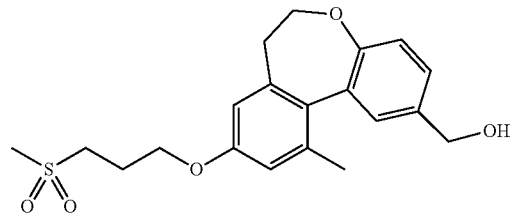 [SMILES: Cc1cc(OCCCS(C)(=O)=O)cc2c1-c1cc(CO)ccc1OCC2]

The title compound (white foam, 266 mg, and 85% yield) was obtained from the compound obtained in <14-6> according to the procedure described in <1-9>.

$^1$H NMR (300 MHz, CDCl$_3$) δ 7.33-7.27 (m, 2H), 7.14 (dd, 1H), 6.77 (d, 1H), 6.68 (d, 1H), 4.71 (d, 2H), 4.41 (m, 2H), 4.15 (t, 2H), 3.27 (m, 2H), 2.97 (s, 3H), 2.81 (m, 1H), 2.52-2.45 (m, 2H), 2.42-2.31 (m, 2H), 2.37 (s, 3H), 1.64 (t, 1H).

<14-8> Preparation of methyl 2-((3S)-6-((11-methyl-9-(3-(methylsulfonyl)propoxy)-6,7-dihydrodibenzo[b,d]oxepin-2-yl)methoxy)-2,3-dihydrobenzofuran-3-yl)acetate

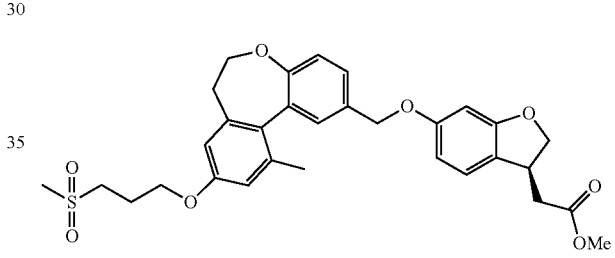

The title compound (white foam, 126 mg, and 84% yield) was obtained from the compound obtained in <14-7> according to the procedure described in <1-10>.

$^1$H NMR (300 MHz, CDCl$_3$) δ 7.36-7.31 (m, 2H), 7.15 (m, 1H), 7.03 (d, 1H), 6.76 (d, 1H), 6.68 (d, 1H), 6.48 (m, 2H), 5.04 (s, 2H), 4.75 (t, 1H), 4.41 (m, 2H), 4.26 (dd, 1H), 4.14 (t, 2H), 3.81 (m, 1H), 3.72 (s, 3H), 3.27 (m, 3H), 2.97 (s, 3H), 2.77 (m, 2H), 2.61-2.45 (m, 2H), 2.36 (m, 2H), 2.31 (s, 3H).

<14-9> Preparation of 2-((3S)-6-((11-methyl-9-(3-(methylsulfonyl)propoxy)-6,7-dihydrodibenzo[b,d]oxepin-2-yl)methoxy)-2,3-dihydrobenzofuran-3-yl)acetic acid

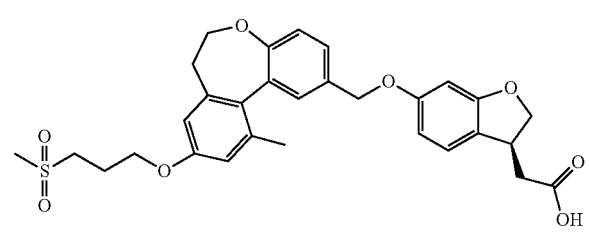 [SMILES: Cc1cc(OCCCS(C)(=O)=O)cc2c1-c1cc(COc3ccc4c(c3)OC[C@H]4CC(=O)O)ccc1OCC2]

The title compound (white foam, 116 mg, and 98% yield) was obtained from the compound obtained in <14-8> according to the procedure described in <1-11>.

MS m/z 551 [M−H]⁻.

¹H NMR (300 MHz, CDCl₃) δ 7.36-7.31 (m, 2H), 7.18-7.03 (m, 2H), 6.76 (d, 1H), 6.68 (d, 1H), 6.49 (m, 2H), 5.04 (s, 2H), 4.76 (t, 1H), 4.42 (m, 2H), 4.29 (dd, 1H), 4.15 (t, 2H), 3.81 (m, 1H), 3.28 (m, 2H), 2.97 (s, 3H), 2.91-2.77 (m, 2H), 2.67-2.45 (m, 2H), 2.36 (m, 2H), 2.31 (s, 3H).

Example 15

Preparation of (1S,2S)-2-(4-(((11-methyl-9-(3-(methylsulfonyl)propoxy)-6,7-dihydrodibenzo[b,d]oxepin-2-yl)methyl)amino)phenyl)cyclopropanecarboxylic acid <15-1> Preparation of 11-methyl-9-(3-(methylsulfonyl)propoxy)-6,7-dihydrodibenzo[b,d]oxepin-2-carbaldehyde

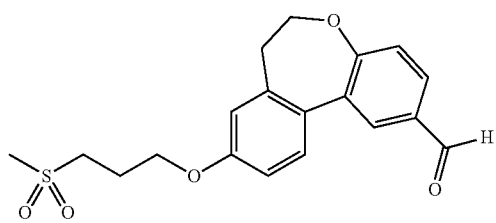 [SMILES: CS(=O)(=O)CCCOc1ccc2c(c1)CCOc1ccc(C=O)cc1-2]

The title compound (colorless oil, 109 mg, and approximately 100% yield) was obtained from the compound obtained in <14-7> according to the procedure described in <3-3>.

¹H NMR (300 MHz, CDCl₃) δ 10.01 (s, 1H), 7.88-7.78 (m, 2H), 7.28 (m, 1H), 6.80 (d, 1H), 6.69 (d, 1H), 5.30 (s, 1H), 4.57-4.45 (m, 2H), 4.17 (t, 2H), 3.28 (m, 2H), 2.98 (s, 3H), 2.84 (td, 1H), 2.54 (m, 1H), 2.46-2.30 (m, 2H), 2.37 (s, 3H).

<15-2> Preparation of (1S,2S)-ethyl 2-(4-(((11-methyl-9-(3-(methylsulfonyl)propoxy)-6,7-dihydrodibenzo[b,d]oxepin-2-yl)methyl)amino)phenyl)cyclopropanecarboxylate

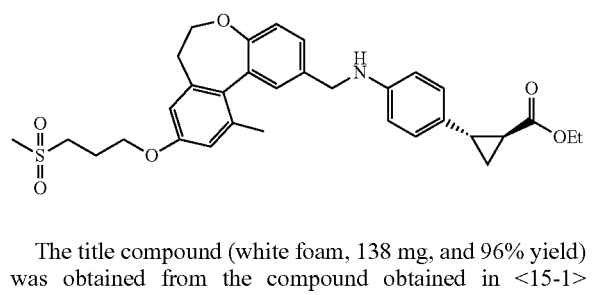

The title compound (white foam, 138 mg, and 96% yield) was obtained from the compound obtained in <15-1> according to the procedure described in <3-4>.

¹H NMR (300 MHz, CDCl₃) δ 7.31-7.23 (m, 2H), 7.11 (m, 1H), 6.93 (m, 2H), 6.75 (d, 1H), 6.67 (d, 1H), 6.62-6.52 (m, 2H), 4.45-4.37 (m, 2H), 4.34 (s, 2H), 4.22-4.11 (m, 4H), 4.03 (s, 1H), 3.27 (m, 2H), 2.97 (s, 3H), 2.82 (m, 1H), 2.54-2.30 (m, 4H), 2.26 (s, 3H), 1.78 (m, 1H), 1.52 (m, 1H), 1.33-1.16 (m, 1H), 1.27 (t, 3H).

<15-3> Preparation of (1S,2S)-2-(4-(((11-methyl-9-(3-(methylsulfonyl)propoxy)-6,7-dihydrodibenzo[b,d]oxepin-2-yl)methyl)amino)phenyl)cyclopropanecarboxylic acid

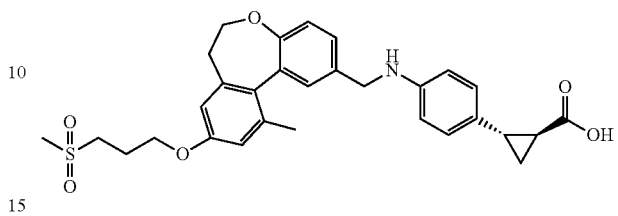

The title compound (white foam, 126 mg, and 97% yield) was obtained from the compound obtained in <15-2> according to the procedure described in <3-5>.

MS m/z 534 [M−H]⁻.

¹H NMR (300 MHz, CDCl₃) δ 7.28-7.24 (m, 2H), 7.11 (m, 1H), 6.93 (m, 2H), 6.74 (d, 1H), 6.61 (d, 1H), 6.57 (m, 2H), 4.40 (m, 2H), 4.34 (s, 2H), 4.14 (t, 2H), 3.27 (m, 2H), 2.96 (s, 3H), 2.81 (m, 1H), 2.50 (m, 2H), 2.36 (m, 2H), 2.25 (s, 3H), 1.77 (m, 1H), 1.57 (dt, 1H), 1.33 (m, 1H).

Example 16

Preparation of (1S,2S)-2-(4-(((8-(2-ethoxyethoxy)-10-methyl-6H-benzo[c]chromen-2-yl)methyl)amino)phenyl)cyclopropanecarboxylic acid <16-1> Preparation of methyl 8-(2-ethoxyethoxy)-10-methyl-6H-benzo[c]chromen-2-carboxylate

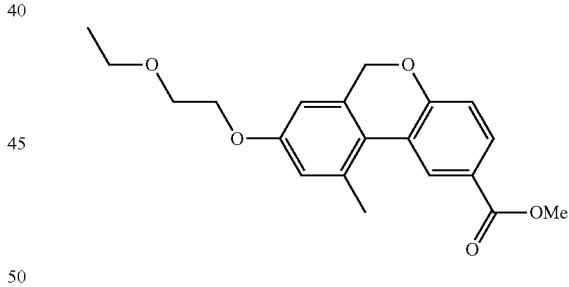

The compound (180 mg, 0.51 mmol) obtained in <9-4> was dissolved in DMF (5 mL), and Cs₂CO₃ (500 mg, 1.54 mmol) was added thereto, and then stirred at ambient temperature for 1 hour. 2-Chloroethyl ethyl ether (67 mL, 0.61 mmol) was added to the mixture, and stirred at 90° C. for 15 hours. The reaction mixture was diluted with EtOAc, and then washed with a saturated NH₄Cl aqueous solution. An aqueous layer was extracted with EtOAc again, and an organic layer was then dried over magnesium sulfate, and concentrated under reduced pressure. The residue was purified using silica gel chromatography to obtain the title compound (white solid, 100 mg, and 57% yield).

¹H NMR (300 MHz, CDCl₃) δ 8.45 (d, 1H), 7.88 (dd, 1H), 7.05 (d, 1H), 6.83 (d, 1H), 6.64 (d, 1H), 4.98 (s, 2H), 4.18-4.13 (m, 2H), 3.92 (s, 3H), 3.83-3.78 (m, 2H), 3.62 (q, 2H), 2.65 (s, 3H), 1.25 (t, 3H).

<16-2> Preparation of (8-(2-ethoxyethoxy)-10-methyl-6H-benzo[c]chromen-2-yl)methanol

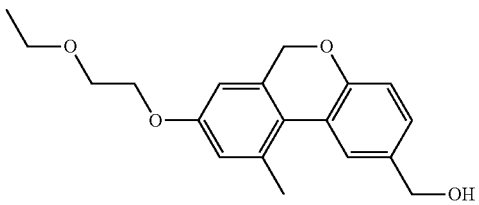 [SMILES: CCOCCOc1cc(C)c2c(c1)COc1ccc(CO)cc1-2]

The title compound (light yellow oil, 207 mg, and 99% yield) was obtained from the compound obtained in <16-1> according to the procedure described in <3-2>.

<16-3> Preparation of 8-(2-ethoxyethoxy)-10-methyl-6H-benzo[c]chromen-2-carbaldehyde

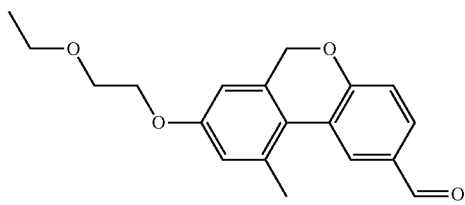 [SMILES: CCOCCOc1cc(C)c2c(c1)COc1ccc(C=O)cc1-2]

The title compound (light yellow oil, 207 mg, and 99% yield) was obtained from the compound obtained in <16-2> according to the procedure described in <3-3>.
$^1$H NMR (300 MHz, CDCl$_3$) δ 9.96 (s, 1H), 8.26 (d, 1H), 7.73 (dd, 1H), 7.15 (d, 1H), 6.85 (d, 1H), 6.65 (d, 1H), 5.01 (s, 2H), 4.19-4.14 (m, 2H), 3.84-3.78 (m, 2H), 3.62 (q, 2H), 2.66 (s, 3H), 1.26 (t, 3H).

<16-4> Preparation of (1S,2S)-ethyl 2-(4-(((8-(2-ethoxyethoxy)-10-methyl-6H-benzo[c]chromen-2-yl)methyl)amino)phenyl)cyclopropanecarboxylate

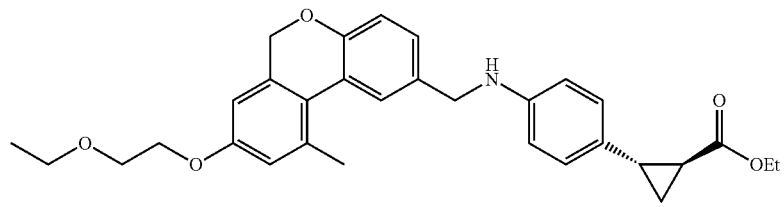 [SMILES: CCOCCOc1cc(C)c2c(c1)COc1ccc(CNc3ccc([C@H]4C[C@@H]4C(=O)OCC)cc3)cc1-2]

The title compound (light yellow oil, 137 mg, and 99% yield) was obtained from the compound obtained in <16-3> according to the procedure described in <3-4>.

$^1$H NMR (300 MHz, CDCl$_3$) δ 7.67 (d, 1H), 7.16 (dd, 1H), 7.00 (d, 1H), 6.93 (d, 2H), 6.78 (d, 1H), 6.63 (d, 1H), 6.59 (d, 2H), 4.90 (s, 2H), 4.31 (s, 2H), 4.15 (q, 2H) 4.11 (q, 2H), 4.00 (s, 1H), 3.82-3.77 (m, 2H), 3.61 (q, 2H), 2.50 (s, 3H), 2.48-2.39 (m, 1H), 1.81-1.73 (m, 1H), 1.51 (dt, 1H), 1.27 (t, 3H), 1.27-1.18 (m, 1H), 1.25 (t, 3H).

<16-5> Preparation of (1S,2S)-2-(4-(((8-(2-ethoxyethoxy)-10-methyl-6H-benzo[c]chromen-2-yl)methyl)amino)phenyl)cyclopropanecarboxylic acid)

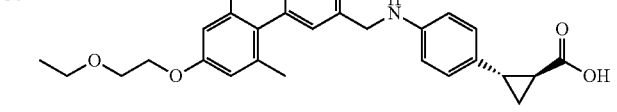

The title compound (light yellow foam, 64 mg, and 50% yield) was obtained from the compound obtained in <16-4> according to the procedure described in <3-5>.

MS m/z 472 [M−H]$^-$.

$^1$H NMR (300 MHz, CDCl$_3$) δ 7.68 (d, 1H), 7.16 (dd, 1H), 7.00 (d, 1H), 6.94 (d, 2H), 6.78 (d, 1H), 6.63 (d, 1H), 6.59 (d, 2H), 4.91 (s, 2H), 4.31 (s, 2H), 4.17-4.12 (m, 2H), 3.82-3.77 (m, 2H), 3.61 (q, 2H), 2.57-2.50 (m, 1H), 2.50 (s, 3H), 1.82-1.74 (m, 1H), 1.58 (dt, 1H), 1.37-1.28 (m, 1H), 1.25 (t, 3H).

Example 17

Preparation of (S)-2-(6-((8-(2-ethoxyethoxy)-10-methyl-6H-benzo[c]chromen-2-yl)methoxy)-2,3-dihydrobenzofuran-3-yl)acetic acid <17-1> Preparation of (S)-methyl 2-(6-((8-(2-ethoxyethoxy)-10-methyl-6H-benzo[c]chromen-2-yl)methoxy)-2,3-dihydrobenzofuran-3-yl)acetate

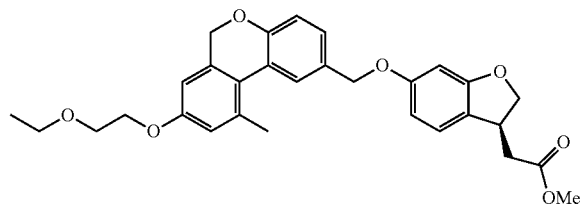 [SMILES: CCOCCOc1cc(C)c2c(c1)COc1ccc(COc3ccc4c(c3)OC[C@H]4CC(=O)OC)cc1-2]

The title compound (colorless oil, 113 mg, and 83% yield) was obtained from the compound obtained in <16-2> according to the procedure described in <1-10>.

$^1$H NMR (300 MHz, CDCl$_3$) δ 7.74 (d, 1H), 7.22 (dd, 1H), 7.03 (m, 2H), 6.79 (d, 1H), 6.63 (d, 1H), 6.54-6.46 (m, 2H), 5.01 (s, 2H), 4.91 (s, 2H), 4.75 (t, 1H), 4.26 (dd, 1H), 4.14 (t, 2H), 3.79 (m, 3H), 3.72 (s, 3H), 3.61 (q, 2H), 2.75 (m, 1H), 2.62-2.50 (m, 1H), 2.56 (s, 3H), 1.25 (t, 3H).

<17-2> Preparation of (S)-2-(6-((8-(2-ethoxyethoxy)-10-methyl-6H-benzo[c]chromen-2-yl)methoxy)-2,3-dihydrobenzofuran-3-yl)acetic acid

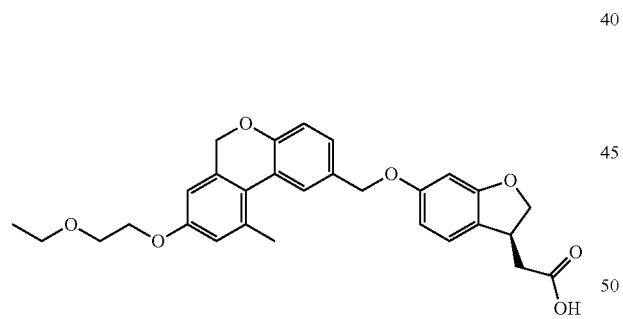

The title compound (white foam, 98 mg, and 89% yield) was obtained from the compound obtained in <17-1> according to the procedure described in <1-11>.

MS m/z 489 [M−H]$^-$.

$^1$H NMR (300 MHz, CDCl$_3$) δ 7.74 (d, 1H), 7.23 (dd, 1H), 7.05 (t, 2H), 6.80 (d, 1H), 6.63 (d, 1H), 6.55-6.46 (m, 2H), 5.02 (s, 2H), 4.92 (s, 2H), 4.76 (t, 1H), 4.29 (dd, 1H), 4.15 (m, 2H), 3.80 (m, 3H), 3.61 (q, 2H), 2.81 (m, 1H), 2.68-2.51 (m, 1H), 2.57 (s, 3H), 1.25 (t, 3H).

Example 18

Preparation of (1S,2S)-2-(4-(((9-(3-(methylsulfonyl)propoxy)-5,7-dihydrodibenzo[c,e]oxepin-2-yl)methyl)amino)phenyl)cyclopropanecarboxylic acid <18-1> Preparation of (2-bromo-5-(methoxymethoxy)phenyl)methanol

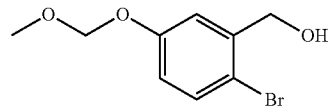

(3-(Methoxymethoxy)phenyl)methanol (prepared according to the method disclosed in the document [Journal of Organic Chemistry, 2006, vol. 71, #9, pp. 3650-3652]; 3.45 g, 20.5 mmol) was dissolved in CH$_3$CN (51.25 mL), and N-bromosuccinimide (4.01 g, 22.55 mmol) was added thereto, and stirred at ambient temperature for 1 hour. The mixture was concentrated, diluted with dichloromethane, and then filtered. The filtrate was purified using silica gel chromatography to obtain the title compound (white solid, 4.63 g, and 91% yield).

$^1$H NMR (300 MHz, CDCl$_3$) δ 7.43 (d, 1H), 7.20 (d, 1H), 6.86 (dd, 1H), 5.17 (s, 2H), 4.71 (d, 2H), 3.47 (s, 3H), 1.97 (t, 1H).

<18-2> Preparation of methyl 4-methyl-3-(4,4,5,5-tetramethyl-1,3,2-dioxaborolan-2-yl)benzoate

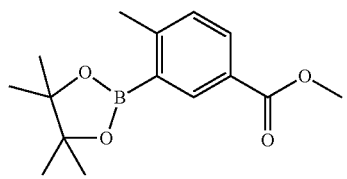

Methyl 3-bromo-4-methylbenzoate (3 mL, 19.2 mmol) was dissolved in 1,4-dioxane (96 mL), and bis(pinacolato)diboron (7.31 g, 28.2 mmol), potassium acetate (5.65 g, 57.6 mmol), and Pd(dppf)Cl$_2$ (2.8 g, 3.84 mmol) were added thereto. The resulting mixture was replaced with argon, and stirred at 90° C. for 16 hours. The mixture was cooled to room temperature, and water was added. Then, the mixture was extracted with EtOAc. An organic layer was dried over magnesium sulfate, concentrated, and then purified using silica gel chromatography to obtain the title compound (off-white solid, 4.46 g, and 84% yield).

$^1$H NMR (300 MHz, CDCl$_3$) δ 8.40 (d, 1H), 7.97 (dd, 1H), 7.23 (d, 1H), 3.94-3.87 (m, 3H), 2.58 (s, 3H), 1.35 (d, 12H).

<18-3> Preparation of methyl 4-(bromomethyl)-3-(4,4,5,5-tetramethyl-1,3,2-dioxaborolan-2-yl)benzoate

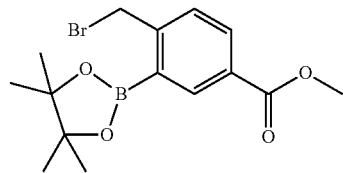

Methyl 4-methyl-3-(4,4,5,5-tetramethyl-1,3,2-dioxaborolan-2-yl)benzoate (1.15 g, 4.16 mmol) was dissolved in ACN (27.7 mL), and N-bromosuccinimide (888 mg, 4.99 mmol) and AIBN (13.6 mg, 0.083 mmol) were added thereto, and then stirred at 90° C. for 4 hours. The mixture was concentrated, diluted with dichloromethane, and then filtered. The filtrate was concentrated, and then purified using silica gel chromatography to obtain the title compound (colorless oil, 1.4 g, and 95% yield).

$^1$H NMR (300 MHz, CDCl$_3$) δ 8.46 (d, 1H), 8.06 (dd, 1H), 7.46 (d, 1H), 4.91 (s, 2H), 3.92 (s, 3H), 1.37 (d, 12H).

<18-4> Preparation of methyl 4-(((2-bromo-5-(methoxymethoxy)benzyl)oxy)methyl)-3-(4,4,5,5-tetramethyl-1,3,2-dioxaborolan-2-yl)benzoate

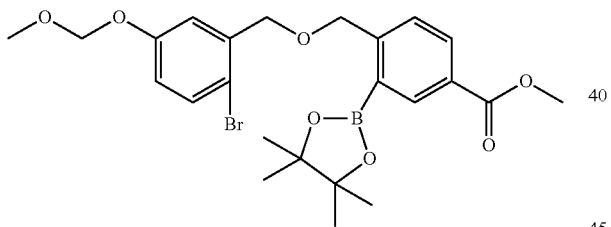

The compound (973.5 mg, 3.94 mmol) obtained in <18-1> was dissolved in DMF (13.1 mL), and NaH (315.2 mg, 7.88 mmol) was slowly added thereto, and stirred for 5 minutes. Meanwhile, the compound (1.4 g, 3.94 mmol) obtained in <18-3> was dissolved in DMF (5 mL), and this solution was slowly added to the mixture, and then stirred at ambient temperature for 3 hours. Water was slowly added to the mixture at 0° C., and saline and EtOAc were added. Then, the resulting mixture was filtered. An organic layer was washed with saline, dried over magnesium sulfate, concentrated, and then purified using silica gel chromatography to obtain the title compound (white solid, 851.1 mg, and 42% yield).

$^1$H NMR (300 MHz, CDCl$_3$) δ 8.46 (d, 1H), 8.11 (dd, 1H), 7.66 (d, 1H), 7.42 (d, 1H), 7.25 (s, 1H), 6.86 (dd, 1H), 5.15 (s, 2H), 4.95 (s, 2H), 4.63 (s, 2H), 3.92 (s, 3H), 3.46 (s, 3H), 1.34 (s, 12H).

<18-5> Preparation of methyl 9-(methoxymethoxy)-5,7-dihydrodibenzo[c,e]oxepin-2-carboxylate

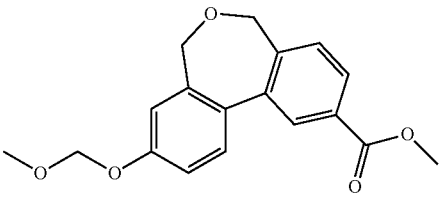

The compound (851 mg, 1.63 mmol) obtained in <18-4> was dissolved in 1,4-dioxane (15 mL), and replaced with argon. K$_2$CO$_3$ (675.8 mg, 4.89 mmol) and [1,1'-bis(diphenylphosphino)ferrocene]dichloropalladium (II) (59.6 mg, 0.082 mmol) were sequentially added thereto, and then replaced with argon. The mixture was stirred at 90° C. for 18 hours. The mixture was cooled to room temperature, filtered through Celite, and then washed with dichloromethane. The filtrate was concentrated, and then purified using silica gel chromatography to obtain the title compound (white solid, 265.3 mg, and 52% yield).

$^1$H NMR (300 MHz, CDCl$_3$) δ 8.19 (d, 1H), 8.04 (dd, 1H), 7.57-7.45 (m, 2H), 7.20 (dd, 1H), 7.14 (d, 1H), 5.25 (s, 2H), 4.40 (s, 2H), 4.33 (s, 2H), 3.96 (s, 3H), 3.52 (s, 3H).

<18-6> Preparation of methyl 9-hydroxy-5,7-dihydrodibenzo[c,e]oxepin-2-carboxylate

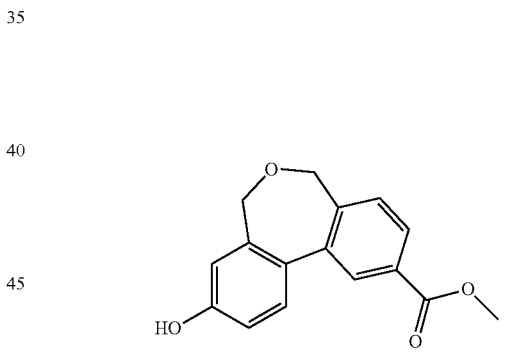

The compound (195.3 mg, 0.62 mmol) obtained in <18-5> was dissolved in methanol (6.2 mL), and p-TsOH.H$_2$O (353.8 mg, 1.86 mmol) was added thereto, and then stirred at ambient temperature for 16 hours. A NaHCO$_3$ aqueous solution was added to the mixture to adjust the pH value of the mixture to approximately pH 8. Then, the mixture was extracted with dichloromethane. An organic layer was collected, dried over magnesium sulfate, concentrated, and then purified using silica gel chromatography to obtain the title compound (white solid, 136 mg, and 81% yield).

$^1$H NMR (300 MHz, CDCl$_3$) δ 8.18 (d, 1H), 8.04 (dd, 1H), 7.50 (dd, 2H), 7.00 (dd, 1H), 6.94 (d, 1H), 5.13 (s, 1H), 4.40 (s, 2H), 4.31 (s, 2H), 3.96 (s, 3H).

<18-7> Preparation of methyl 9-(3-(methylsulfonyl)propoxy)-5,7-dihydrodibenzo[c,e]oxepin-2-carboxylate

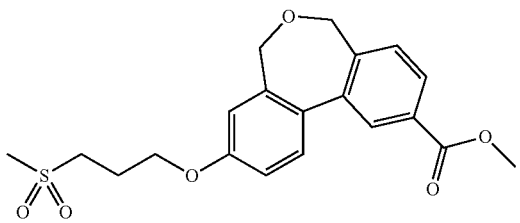

According to the procedures as described in <1-8>, the compound obtained in <18-6> was used to prepare the title compound (white solid, 487.9 mg, 74% yield).

$^1$H NMR (300 MHz, CDCl$_3$) δ 8.18 (d, 1H), 8.04 (dd, 1H), 7.52 (dd, 2H), 7.04 (dd, 1H), 6.98 (d, 1H), 4.39 (s, 2H), 4.32 (s, 2H), 4.21 (t, 2H), 3.96 (s, 3H), 3.35-3.24 (m, 2H), 2.98 (s, 3H), 2.42 (dd, 2H).

<18-8> Preparation of (9-(3-(methylsulfonyl)propoxy)-5,7-dihydrodibenzo[c,e]oxepin-2-yl)methanol

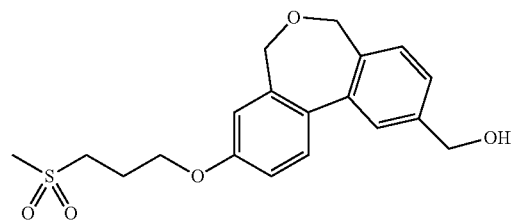 [SMILES: CS(=O)(=O)CCCOc1ccc2c(c1)COCc1ccc(CO)cc1-2]

According to the procedures as described in <1-9>, the compound obtained in <18-7> was used to prepare the title compound (white solid, 417 mg, 92% yield).

$^1$H NMR (300 MHz, CDCl$_3$) δ 7.51 (d, 2H), 7.41 (t, 2H), 7.02 (d, 1H), 6.97 (s, 1H), 4.81 (d, 2H), 4.33 (d, 4H), 4.19 (t, 2H), 3.36-3.17 (m, 2H), 2.98 (s, 3H), 2.49-2.27 (m, 2H), 1.77 (t, 1H).

<18-9> Preparation of 9-(3-(methylsulfonyl)propoxy)-5,7-dihydrodibenzo[c,e]oxepin-2-carbaldehyde

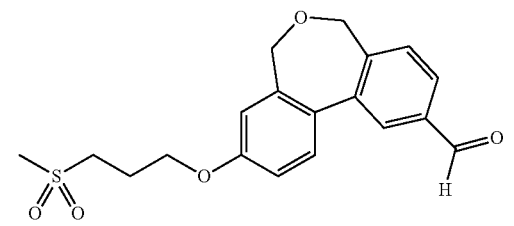 [SMILES: CS(=O)(=O)CCCOc1ccc2c(c1)COCc1ccc(C=O)cc1-2]

According to the procedures as described in <3-3>, the compound obtained in <18-8> was used to prepare the title compound (white solid, 63.3 mg, 83% yield).

$^1$H NMR (300 MHz, CDCl$_3$) δ 10.12 (s, 1H), 8.02 (d, 1H), 7.89 (dd, 1H), 7.57 (dd, 2H), 7.06 (dd, 1H), 6.99 (d, 1H), 4.41 (s, 2H), 4.34 (s, 2H), 4.21 (t, 2H), 3.36-3.23 (m, 2H), 2.99 (s, 3H), 2.42 (d, 2H).

<18-10> Preparation of (1S,2S)-ethyl 2-(4-(((9-(3-(methylsulfonyl)propoxy)-5,7-dihydrodibenzo[c,e]oxepin-2-yl)methyl)amino)phenyl)cyclopropanecarboxylate

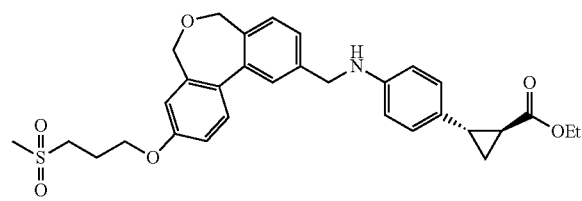 [SMILES: CCOC(=O)[C@H]1C[C@@H]1c1ccc(NCc2ccc3c(c2)-c2ccc(OCCCS(C)(=O)=O)cc2COC3)cc1]

According to the procedures as described in <3-4>, the compound obtained in <18-9> was used to prepare the title compound (off-white foam, 83.8 mg, 85% yield).

$^1$H NMR (300 MHz, CDCl$_3$) δ 7.50 (s, 1H), 7.46 (d, 1H), 7.38 (s, 2H), 7.00 (d, 1H), 6.98-6.90 (m, 3H), 6.59 (d, 2H), 4.40 (s, 2H), 4.34 (s, 2H), 4.31 (s, 2H), 4.23-4.10 (m, 4H), 3.35-3.24 (m, 2H), 2.98 (s, 3H), 2.42 (m, 3H), 1.79 (m, 1H), 1.53-1.47 (m, 1H), 1.25 (m, 4H).

<18-11> Preparation of (1S,2S)-2-(4-(((9-(3-(methylsulfonyl)propoxy)-5,7-dihydrodibenzo[c,e]oxepin-2-yl)methyl)amino)phenyl)cyclopropanecarboxylic acid

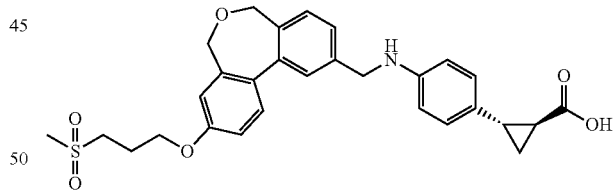

According to the procedures as described in <3-5>, the compound obtained in <18-10> was used to prepare the title compound (white solid, 42.7 mg, 55% yield).

MS m/z 520 [M−H]$^-$.

$^1$H NMR (300 MHz, CDCl$_3$) δ 7.49 (s, 1H), 7.46 (d, 1H), 7.38 (s, 2H), 7.05-6.98 (m, 1H), 6.98-6.90 (m, 3H), 6.60 (d, 2H), 4.40 (s, 2H), 4.34 (s, 2H), 4.32 (s, 2H), 4.19 (t, 2H), 3.35-3.23 (m, 2H), 2.99 (s, 3H), 2.46 (m, 1H), 2.43-2.32 (m, 2H), 1.75 (m, 1H), 1.53 (m, 1H), 1.20 (d, 1H).

Example 19

Preparation of (1S,2S)-2-(4-(((11-methyl-9-(3-(methylsulfonyl)propoxy)-5,7-dihydrodibenzo[c,e]oxepin-4-yl)methyl)amino)phenyl)cyclopropanecarboxylic acid

<19-1> Preparation of 4-bromo-3-(bromomethyl)-5-methylphenol

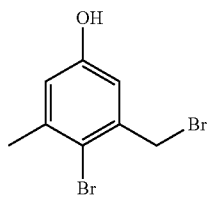

2-Bromo-1-(bromomethyl)-5-methoxy-3-methylbenzene (prepared in accordance with the reference [Chemistry—A European Journal, 2004, vol. 10, #16, p. 3931-3935]; 6.6 g, 22.5 mmol) was dissolved in dichloromethane (34 mL), and $BBr_3$ (34 mL, 34 mmol) was slowly added to the mixture at 0° C. The reaction mixture was stirred at room temperature for 3 hours, and methanol was added to the mixture at 0° C. The mixture was washed with water, and the organic layer was dried over sodium sulfate and concentrated. The residue was purified to obtain the title compound (light yellow solid, 6.0 g, 95% yield).

$^1$H NMR (300 MHz, $CDCl_3$) δ 6.80 (d, 1H), 6.72 (d, 1H), 4.69 (s, 1H), 4.57 (s, 2H), 2.39 (s, 3H).

<19-2> Preparation of 2-bromo-1-(bromomethyl)-5-(methoxymethoxy)-3-methylbenzene

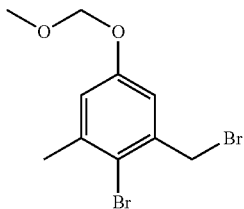

The compound obtained in <19-1> (6 g, 21.4 mmol) was dissolved in acetone (70 mL), which was then added with methyl chloromethyl ether (MOMCl, 2.4 mL, 32.1 mmol) and $K_2CO_3$ (4.8 g, 34.2 mmol). The reaction mixture thus obtained was stirred at room temperature for 2 hours and filtered. The filtered $K_2CO_3$ solid was washed with hexane, concentrated and purified by silica gel chromatography to obtain the title compound (colorless oil, 6.2 g, 89% yield).

$^1$H NMR (300 MHz, $CDCl_3$) δ 6.99 (d, 1H), 6.92 (d, 1H), 5.15 (s, 2H), 4.60 (s, 2H), 3.47 (s, 3H), 2.41 (s, 3H).

<19-3> Preparation of (2-bromo-5-(methoxymethoxy)-3-methylphenyl)methanol

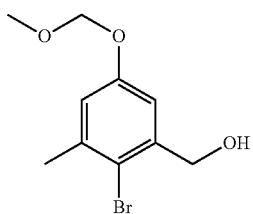

The compound obtained in <19-2> (6.2 g, 19.1 mmol) was dissolved in 1,4-dioxane (50 mL) and water (50 mL), which was then added with $CaCO_3$ (8.6 g, 86.0 mmol), followed by stirring for 18 hours at 100° C. The reaction mixture thus obtained was filtered, and the residue was diluted with EtOAc, washed with water, dried over sodium sulfate, and concentrated. The concentrates were purified by silica gel chromatography to obtain the title compound (white solid, 4.8 g, 96% yield).

$^1$H NMR (300 MHz, $CDCl_3$) δ 7.04 (d, 1H), 6.89 (d, 1H), 5.16 (s, 2H), 4.72 (d, 2H), 3.47 (s, 3H), 2.39 (s, 3H), 2.02 (t, 1H).

<19-4> Preparation of methyl 2-(bromomethyl)-3-(4,4,5,5-tetramethyl-1,3,2-dioxaborolane-2-yl)benzoate

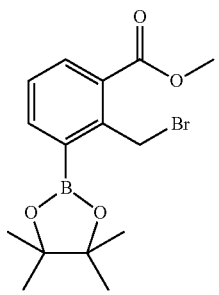

Methyl 2-methyl-3-(4,4,5,5-tetramethyl-1,3,2-dioxaborolane-2-yl)benzoate (prepared in accordance with the reference [EP 2011788 A1]; 2.0 g, 7.1 mmol) was dissolved in $CH_3CN$ (40 mL), which was then added with AIBN (23 mg, 0.14 mmol) and N-bromosuccinimide (1.5 g, 8.5 mmol), followed by stirring for 3 hours at 90° C. The reaction mixture thus obtained was concentrated, and purified by silica gel chromatography to obtain the title compound (colorless oil, 2.2 g, 87% yield).

$^1$H NMR (300 MHz, $CDCl_3$) δ 7.97-7.93 (m, 2H), 7.34 (t, 1H), 5.43 (s, 2H), 3.95 (s, 3H), 1.39 (s, 12H).

<19-5> Preparation of methyl 2-(((2-bromo-5-(methoxymethoxy)-3-methylbenzyl)oxy)methyl)-3-(4,4,5,5-tetramethyl-1,3,2-dioxaborolane-2-yl)benzoate

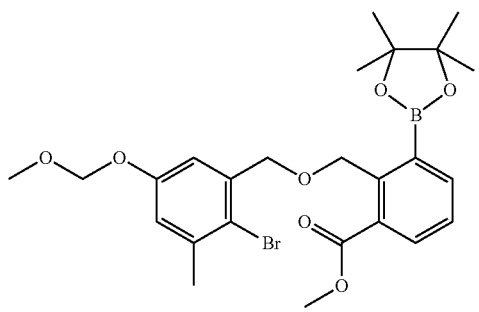

According to the procedures as described in <18-4>, the compounds obtained in <19-3> and <19-4> were used to prepare the title compound (colorless oil, 320 mg, 69% yield).

$^1$H NMR (300 MHz, CDCl$_3$) δ 7.82 (m, 2H), 7.34 (t, 1H), 7.04 (d, 1H), 6.85 (d, 1H), 5.17 (s, 2H), 5.14 (s, 2H), 4.57 (s, 2H), 3.86 (s, 3H), 3.44 (s, 3H), 2.38 (s, 3H), 1.30 (s, 12H).

<19-6> Preparation of methyl 9-(methoxymethoxy)-11-methyl-5,7-dihydrodibenzo[c,e]oxepin-4-carboxylate

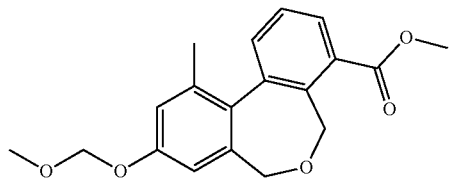

According to the procedures as described in <18-5>, the compound obtained in <19-5> was used to prepare the title compound (colorless oil, 63 mg, 32% yield).

$^1$H NMR (300 MHz, CDCl$_3$) δ 7.88 (dd, 1H), 7.54 (dd, 1H), 7.46 (t, 1H), 7.04 (d, 1H), 6.96 (d, 1H), 5.41 (d, 1H), 5.24 (q, 2H), 4.43 (d, 1H), 4.00-3.84 (m, 5H), 3.52 (s, 3H), 2.38 (s, 3H).

<19-7> Preparation of methyl 9-hydroxy-11-methyl-5,7-dihydrodibenzo[c,e]oxepin-4-carboxylate

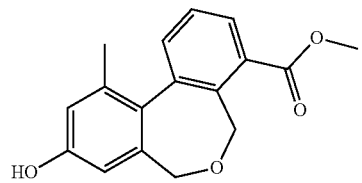 [SMILES: COC(=O)c1cccc2c1COCc1cc(O)cc(C)c1-2]

According to the procedures as described in <18-6>, the compound obtained in <19-6> was used to prepare the title compound (white solid, 53 mg, 97% yield).

$^1$H NMR (300 MHz, CDCl$_3$) δ 7.88 (dd, 1H), 7.55 (dd, 1H), 7.47 (t, 1H), 6.87 (d, 1H), 6.77 (d, 1H), 5.79 (s, 1H), 5.46 (d, 1H), 4.40 (d, 1H), 4.00 (d, 1H), 3.96 (m, 4H), 2.36 (s, 3H).

<19-8> Preparation of methyl 11-methyl-9-(3-(methylsulfonyl)propoxy)-5,7-dihydrodibenzo[c,e]oxepin-4-carboxylate

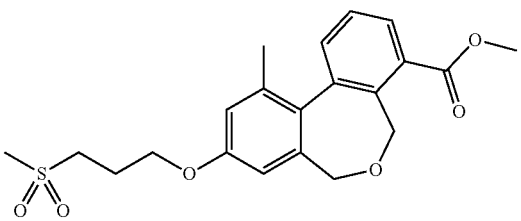

According to the procedures as described in <1-8>, the compound obtained in <19-7> was used to prepare the title compound (white solid, 66 mg, 85% yield).

$^1$H NMR (300 MHz, CDCl$_3$) δ 7.87 (dd, 1H), 7.53 (dd, 1H), 7.46 (t, 1H), 6.89 (d, 1H), 6.80 (d, 1H), 5.41 (d, 1H), 4.41 (d, 1H), 4.17 (t, 2H), 4.02-3.84 (m, 5H), 3.28 (m, 2H), 2.97 (s, 3H), 2.58-2.33 (m, 5H).

<19-9> Preparation of (11-methyl-9-(3-(methylsulfonyl)propoxy)-5,7-dihydrodibenzo[c,e]oxepin-4-yl)methanol

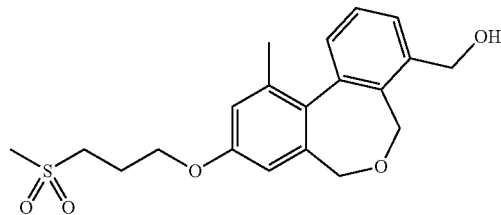

According to the procedures as described in <1-9>, the compound obtained in <19-8> was used to prepare the title compound (white solid, 47 mg, 77% yield).

$^1$H NMR (300 MHz, CDCl$_3$) δ 7.48-7.31 (m, 3H), 6.89 (d, 1H), 6.80 (d, 1H), 4.97-4.79 (m, 3H), 4.38 (d, 1H), 4.18 (t, 2H), 3.97 (d, 1H), 3.93 (d, 1H), 3.35-3.21 (m, 2H), 2.98 (s, 3H), 2.47-2.29 (m, 5H), 1.86 (dd, 1H).

<19-10> Preparation of 11-methyl-9-(3-(methylsulfonyl)propoxy)-5,7-dihydrodibenzo[c,e]oxepin-4-carbaldehyde

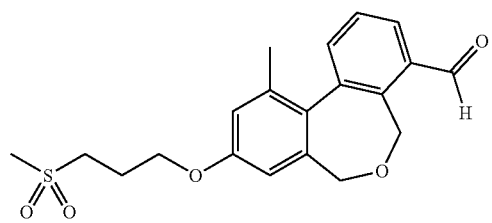 [SMILES: Cc1cc(OCCCS(C)(=O)=O)cc2c1-c1cccc(C=O)c1COC2]

According to the procedures as described in <3-3>, the compound obtained in <19-9> was used to prepare the title compound (white solid, 40 mg, 85% yield).

¹H NMR (300 MHz, CDCl₃) δ 10.45 (s, 1H), 7.93 (dd, 1H), 7.69-7.56 (m, 2H), 6.92 (d, 1H), 6.82 (d, 1H), 5.58 (d, 1H), 4.43 (d, 1H), 4.19 (t, 2H), 3.96 (t, 2H), 3.34-3.23 (m, 2H), 2.98 (s, 3H), 2.49-2.33 (m, 5H).

<19-11> Preparation of (1S,2S)-ethyl 2-(4-(((11-methyl-9-(3-(methylsulfonyl)propoxy)-5,7-dihydrodibenzo[c,e]oxepin-4-yl)methyl)amino)phenyl)cyclopropanecarboxylate

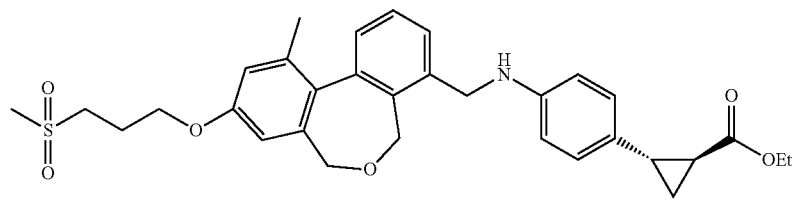 [SMILES: CCOC(=O)[C@H]1C[C@@H]1c1ccc(NCc2cccc3c2COCc2cc(OCCCS(C)(=O)=O)cc(C)c2-3)cc1]

According to the procedures as described in <3-4>, the compound obtained in <19-10> was used to prepare the title compound (white solid, 51 mg, 85% yield).

¹H NMR (300 MHz, CDCl₃) δ 7.44-7.31 (m, 3H), 6.96 (d, 2H), 6.89 (d, 1H), 6.80 (d, 1H), 6.63 (d, 2H), 4.79 (d, 1H), 4.42 (dt, 3H), 4.25-4.04 (m, 6H), 4.00-3.88 (m, 2H), 3.33-3.22 (m, 2H), 2.98 (s, 3H), 2.50-2.31 (m, 6H), 1.86-1.75 (m, 1H), 1.63-1.46 (m, 2H), 1.31-1.18 (m, 6H).

<19-12> Preparation of (1S,2S)-2-(4-(((11-methyl-9-(3-(methylsulfonyl)propoxy)-5,7-dihydrodibenzo[c,e]oxepin-4-yl)methyl)amino)phenyl)cyclopropanecarboxylic acid

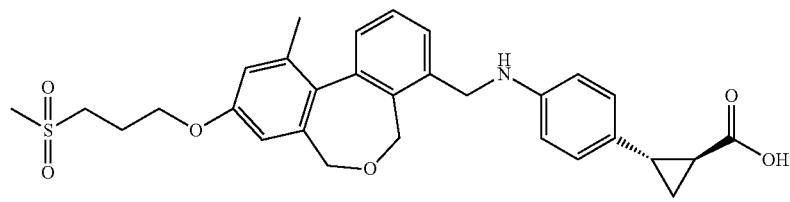 [SMILES: Cc1cc(OCCCS(C)(=O)=O)cc2c1-c1cccc(CNc3ccc([C@H]4C[C@@H]4C(=O)O)cc3)c1COC2]

According to the procedures as described in <3-5>, the compound obtained in <19-11> was used to prepare the title compound (white solid, 27 mg, 57% yield).

MS m/z 534 [M−H]⁻.

¹H NMR (600 MHz, CDCl₃) δ 7.42-7.33 (m, 3H), 6.96 (d, 2H), 6.88 (d, 1H), 6.79 (d, 1H), 6.64-6.60 (m, 2H), 4.78 (d, 1H), 4.45 (d, 1H), 4.40 (q, 2H), 4.20-4.14 (m, 2H), 3.96 (d, 1H), 3.92 (d, 1H), 3.30-3.25 (m, 2H), 2.97 (s, 3H), 2.54-2.49 (m, 1H), 2.42 (s, 3H), 2.40-2.34 (m, 2H), 1.81-1.77 (m, 1H), 1.57 (dt, 1H), 1.35-1.31 (m, 1H).

Example 20

Preparation of (S)-2-(6-((9-(3-(methylsulfonyl)propoxy)-5,7-dihydrodibenzo[c,e]oxepin-2-yl)methoxy)-2,3-dihydrobenzofuran-3-yl)acetic acid <20-1> Preparation of (S)-methyl 2-(6-((9-(3-(methylsulfonyl)propoxy)-5,7-dihydrodibenzo[c,e]oxepin-2-yl)methoxy)-2,3-dihydrobenzofuran-3-yl)acetate

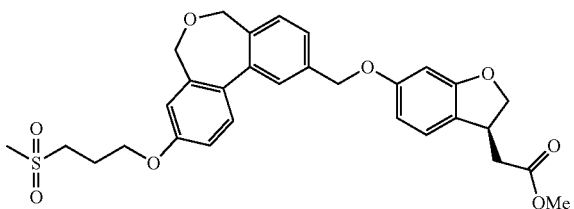

According to the procedures as described in <1-10>, the compound obtained in <18-8> was used to prepare the title compound (off-white foam, 130.1 mg, 87% yield).

$^1$H NMR (300 MHz, CDCl$_3$) δ 7.56 (s, 1H), 7.50 (d, 1H), 7.43 (d, 2H), 7.03 (dd, 2H), 6.97 (d, 1H), 6.51 (dt, 2H), 5.10 (s, 2H), 4.76 (t, 1H), 4.36 (s, 2H), 4.32 (s, 2H), 4.27 (dd, 1H), 4.20 (t, 2H), 3.79 (s, 1H), 3.72 (s, 3H), 3.35-3.23 (m, 2H), 2.98 (s, 3H), 2.76 (dd, 1H), 2.57 (dd, 1H), 2.47-2.32 (m, 2H).

<20-2> Preparation of (S)-2-(6-((9-(3-(methylsulfonyl)propoxy)-5,7-dihydrodibenzo[c,e]oxepin-2-yl)methoxy)-2,3-dihydrobenzofuran-3-yl)acetic acid

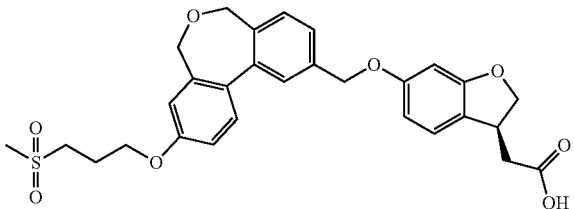 [SMILES: CS(=O)(=O)CCCOc1ccc2c(c1)COCc1ccc(COc3ccc4c(c3)OC[C@H]4CC(=O)O)cc1-2]

According to the procedures as described in <1-11>, the compound obtained in <20-1> was used to prepare the title compound (white solid, 70.2 mg, 55% yield).

MS m/z 537 [M–H]$^-$.

$^1$H NMR (300 MHz, DMSO-d$_6$) δ 7.60 (s, 1H), 7.53 (d, 1H), 7.47 (d, 2H), 7.12 (d, 3H), 6.51 (d, 2H), 5.14 (s, 2H), 4.69 (t, 1H), 4.21 (dd, 7H), 3.68 (s, 1H), 3.30-3.23 (m, 2H), 3.04 (s, 3H), 2.79-2.61 (m, 2H), 2.18 (s, 2H).

Example 21

Preparation of (1S,2S)-2-(4-(((3-(3-(methylsulfonyl)propoxy)-6,7-dihydrodibenzo[b,d]oxepin-10-yl)methyl)amino)phenyl)cyclopropanecarboxylic acid <21-1> Preparation of methyl 3-bromo-4-(2-methoxy-2-oxoethyl)benzoate

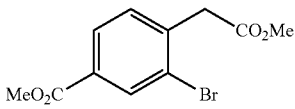

Methyl 3-bromo-4-(cyanomethyl)benzoate (prepared in accordance with the reference [European Journal of Organic Chemistry. 2009, 2, p. 223-237]; 1.82 g, 7.16 mmol) was dissolved in methanol (30 mL), which was then slowly added with sulfuric acid (6 mL) at 0° C., followed by stirring for 12 hours at 100° C. Subsequently, the mixture was further added with sulfuric acid (3 mL), and stirred for 5 hours at 100° C. The reaction mixture thus obtained was cooled to room temperature, added with water at 0° C., and stirred for 1 hour. The solid thus produced was filtered, washed with water, and then dried in vacuo for 1 hour at 45° C. and for 15 hours at room temperature to obtain the title compound (yellow solid, 1.76 g, 85% yield).

$^1$H NMR (300 MHz, CDCl$_3$) δ 8.25 (d, 1H), 7.95 (d, 1H), 7.37 (d, 1H), 3.92 (s, 3H), 3.85 (s, 2H), 3.73 (s, 3H)

<21-2> Preparation of methyl 3-bromo-4-(2-hydroxyethyl)benzoate

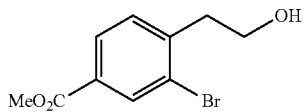 [SMILES: COC(=O)c1ccc(CCO)c(Br)c1]

The compound obtained in <21-1> (1.44 g, 5.02 mmol) was dissolved in dichloromethane (50 mL), which was then slowly added with DIBAL-H (1M dichloromethane solution, 7.5 mL, 7.52 mmol) at −78° C., followed by stirring for 2.5 hours at the same temperature. The reaction mixture was added with a mixture of methanol and water (1:1, 8 mL) and then with a saturated sodium potassium tartrate solution (50 mL), followed by stirring for 1 hour at room temperature. The reaction mixture was diluted dichloromethane, and the aqueous layer was further diluted with dichloromethane one more time. The organic layer was washed with brine, dried over magnesium sulfate, and concentrated under reduced pressure. The residue was added with methanol (50 mL), cooled to 0° C., added with NaBH$_4$ (474 mg, 12.5 mmol), and stirred at room temperature for 2 hours. The reaction mixture thus obtained was added with water, diluted with EtOAc and water, and the layers thus formed were separated. The organic layer was dried over magnesium sulfate, concentrated, and purified by silica gel chromatography to obtain the title compound (yellow oil, 331 mg, 25% yield).

$^1$H NMR (300 MHz, CDCl$_3$) δ 8.23 (d, 1H), 7.91 (dd, 1H), 7.36 (d, 1H), 3.94-3.90 (m, 2H), 3.92 (s, 3H), 3.08 (t, 2H)

<21-3> Preparation of 2-(4-(benzyloxy)-2-methoxyphenyl)-4,4,5,5-tetramethyl-1,3,2-dioxaborolane

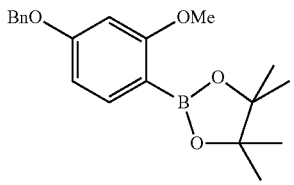 [SMILES: COc1cc(OCc2ccccc2)ccc1B1OC(C)(C)C(C)(C)O1]

According to the procedures as described in <2-6>, 4-(benzyloxy)-1-bromo-2-methoxybenzene (prepared in accordance with the reference [US 2001/7873 A1]) was used to prepare the title compound (colorless oil, 1.32 g, 66% yield).

$^1$H NMR (300 MHz, CDCl$_3$) δ 7.64 (d, 1H), 7.50-7.31 (m, 5H), 6.55 (dd, 1H), 6.49 (d, 1H), 5.08 (s, 2H), 3.80 (s, 3H), 1.33 (s, 12H)

<21-4> Preparation of methyl 4'-(benzyloxy)-6-(2-hydroxyethyl)-2'-methoxy-[1,1'-biphenyl]-3-carboxylate

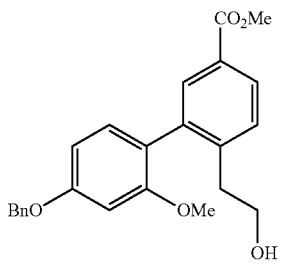 [SMILES: COC(=O)c1ccc(CCO)c(-c2ccc(OCc3ccccc3)cc2OC)c1]

According to the procedures as described in <2-7>, the compound obtained in <21-3> was used to prepare the title compound (yellow oil, 638 mg, 96% yield).

$^1$H NMR (300 MHz, CDCl$_3$) δ 7.97 (dd, 1H), 7.85 (d, 1H), 7.50-7.35 (m, 6H), 7.04 (d, 1H), 6.65-6.60 (m, 2H), 5.11 (s, 2H), 3.89 (s, 3H), 3.70 (s, 3H), 3.70-3.67 (m, 2H), 2.76-2.82 (m, 2H).

<21-5> Preparation of methyl 4'-hydroxy-6-(2-hydroxyethyl)-2'-methoxy-[1,1'-biphenyl]-3-carboxylate

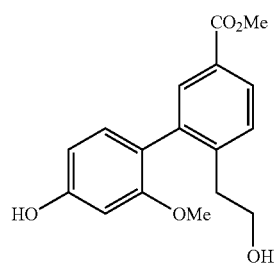

The compound obtained in <21-4> (598 mg, 1.52 mmol) was dissolved in dichloromethane (15 mL), which was then added with BBr$_3$ (1M heptane solution, 1.8 mL, 1.82 mmol) −78° C. After 30 minutes, the reaction mixture was added with methanol (5 mL), slowly heated to room temperature, added with water, and neutralized with a saturated NaHCO$_3$ aqueous solution. The mixture was extracted with dichloromethane, and then the organic layer was dried over magnesium sulfate, concentrated, and purified by silica gel chromatography to obtain the title compound (white foam, 331 mg, 72% yield).

$^1$H NMR (300 MHz, CDCl$_3$) δ 7.97 (dd, 1H), 7.84 (d, 1H), 7.41 (s, 1H), 6.97 (d, 1H), 6.50-6.44 (m, 2H), 5.11 (s, 1H), 3.89 (s, 3H), 3.70 (s, 3H), 3.68-3.73 (m, 2H), 2.82-2.77 (m, 2H)

<21-6> Preparation of methyl 6-(2-hydroxyethyl)-2'-methoxy-4'-(3-(methylsulfonyl)propoxy)-[1,1'-biphenyl]-3-carboxylate

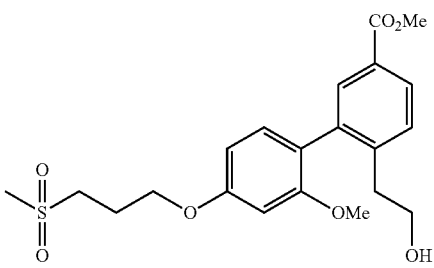 [SMILES: COC(=O)c1ccc(CCO)c(-c2ccc(OCCCS(C)(=O)=O)cc2OC)c1]

The compound obtained in <21-5> (300 mg, 0.99 mmol) was dissolved in DMF (5 mL), added with 3-(methylsulfonyl)propyl 4-methylbenzenesulfonate (318 mg, 1.09 mmol) and Cs$_2$CO$_3$ (354 mg, 1.09 mmol), and then stirred at 50° C. for 1 hour. The reaction mixture was filtered and washed with EtOAc. The filtrate was concentrated and purified by silica gel chromatography to obtain the title compound (white solid, 411 mg, 73% yield).

$^1$H NMR (300 MHz, CDCl$_3$) δ 7.97 (dd, 1H), 7.83 (d, 1H), 7.39 (d, 1H), 7.04 (d, 1H), 6.55-6.51 (m, 2H), 4.17 (t, 2H), 3.89 (s, 3H), 3.72 (s, 3H), 3.72-3.67 (m, 2H), 3.32-3.27 (m, 2H), 2.99 (s, 3H), 2.80-2.75 (m, 2H), 2.43-2.36 (m, 2H).

<21-7> Preparation of methyl 2'-hydroxy-6-(2-hydroxyethyl)-4'-(3-(methylsulfonyl)propoxy)-[1,1'-biphenyl]-3-carboxylate

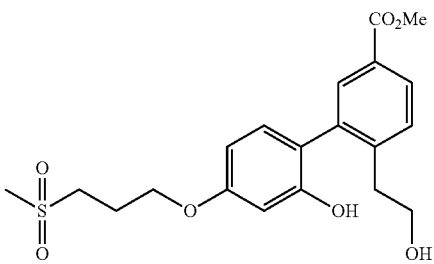 [SMILES: COC(=O)c1ccc(CCO)c(-c2ccc(OCCCS(C)(=O)=O)cc2O)c1]

The compound obtained in <21-6> (157 mg, 0.28 mmol) was dissolved in dichloromethane (4 mL), which was then added with BBr$_3$ (1M dichloromethane solution, 0.69 mmol, 0.70 mL) at 0° C., and stirred for 2 hours. The reaction mixture was added with methanol (2 mL), slowly heated to room temperature, added with water, and neutralized with a saturated NaHCO$_3$ aqueous solution. The mixture was extracted with dichloromethane, and the organic layer was dried over magnesium sulfate, and concentrated under reduced pressure. The residue was purified by silica gel chromatography to obtain the title compound (milky oil, 23.5 mg, 20% yield).

$^1$H NMR (300 MHz, CDCl$_3$) δ 8.03 (dd, 1H), 7.89 (d, 1H), 7.46 (d, 1H), 6.98 (d, 1H), 6.55-6.52 (m, 2H), 4.13 (t, 2H), 3.90 (s, 3H), 3.85-3.80 (m, 2H), 3.30-3.25 (m, 2H), 2.97 (s, 3H), 2.85-2.77 (m, 2H), 2.41-2.32 (m, 2H).

<21-8> Preparation of methyl 2'-hydroxy-4'-(3-(methylsulfonyl)propoxy)-6-(2-(tosyloxy)ethyl)-[1,1'-biphenyl]-3-carboxylate

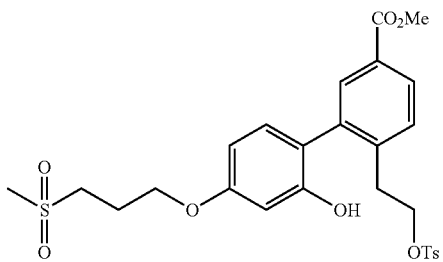 [SMILES: COC(=O)c1ccc(CCOS(=O)(=O)c2ccc(C)cc2)c(-c2ccc(OCCCS(C)(=O)=O)cc2O)c1]

According to the procedures as described in <2-9>, the compound obtained in Example <21-7> was used to prepare the title compound (white solid, 63.5 mg, 79% yield).

$^1$H NMR (300 MHz, CDCl$_3$) δ 7.96 (dd, 1H), 7.87 (d, 1H), 7.61 (d, 2H), 7.34 (d, 1H), 7.27-7.25 (m, 2H), 6.85 (d, 1H), 6.52-6.48 (m, 2H), 4.14 (t, 2H), 4.05 (t, 2H), 3.91 (s, 3H), 3.31-3.25 (m, 2H), 2.98 (s, 3H), 2.93-2.87 (m, 2H), 2.43 (s, 3H), 2.40-2.33 (m, 2H)

<21-9> Preparation of methyl 3-(3-(methylsulfonyl)propoxy)-6,7-dihydrodibenzo[b,d]oxepin-10-carboxylate

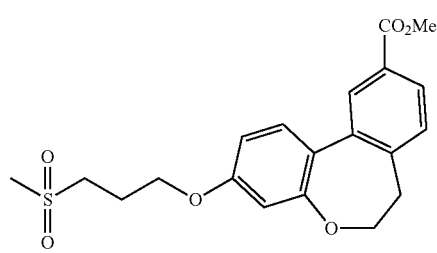 [SMILES: COC(=O)c1ccc2c(c1)-c1ccc(OCCCS(C)(=O)=O)cc1OCC2]

According to the procedures as described in <2-10>, the compound obtained in <21-8> was used to prepare the title compound (white solid, 26 mg, 59% yield).

$^1$H NMR (300 MHz, CDCl$_3$) δ 8.07 (d, 1H), 7.96 (dd, 1H), 7.38 (d, 1H), 7.34 (d, 1H), 6.81 (dd, 1H), 6.69 (d, 1H), 4.58 (t, 2H), 4.16 (t, 2H), 3.93 (s, 3H), 3.31-3.25 (m, 2H), 2.98 (s, 3H), 2.87 (t, 2H), 2.43-2.33 (m, 2H).

<21-10> Preparation of (3-(3-(methylsulfonyl)propoxy)-6,7-dihydrodibenzo[b,d]oxepin-10-yl)methanol

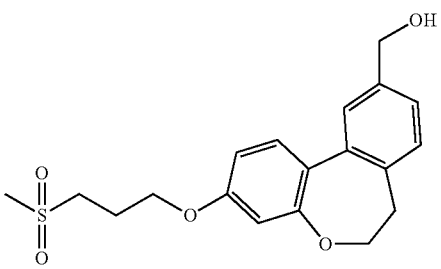 [SMILES: CS(=O)(=O)CCCOc1ccc2c(c1)OCCc1ccc(CO)cc1-2]

According to the procedures as described in <1-9>, the compound obtained in <21-9> was used to prepare the title compound (light yellow oil, 26 mg, 99% yield).

<21-11> Preparation of 3-(3-(methylsulfonyl)propoxy)-6,7-dihydrodibenzo[b,d]oxepin-10-carbaldehyde

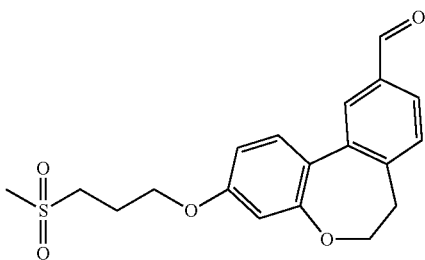 [SMILES: CS(=O)(=O)CCCOc1ccc2c(c1)OCCc1ccc(C=O)cc1-2]

According to the procedures as described in <3-3>, the compound obtained in <21-10> was used to prepare the title compound (light yellow oil, 19 mg, 73% yield).

$^1$H NMR (300 MHz, CDCl$_3$) δ 10.06 (s, 1H), 7.90 (d, 1H), 7.80 (dd, 1H), 7.44 (d, 1H), 7.39 (d, 1H), 6.82 (dd, 1H), 6.71 (d, 1H), 4.60 (t, 2H), 4.17 (t, 2H), 3.31-3.26 (m, 2H), 2.98 (s, 3H), 2.90 (t, 2H), 2.43-2.34 (m, 2H).

<21-12> Preparation of (1S,2S)-ethyl 2-(4-(((3-(3-(methylsulfonyl)propoxy)-6,7-dihydrodibenzo[b,d]oxepin-10-yl)methyl)amino)phenyl)cyclopropanecarboxylate

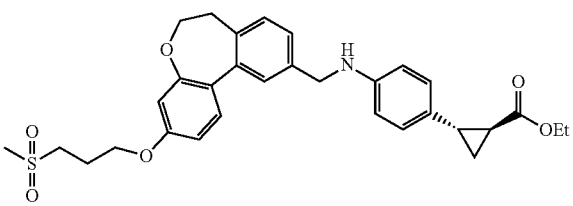 [SMILES: CCOC(=O)[C@H]1C[C@@H]1c1ccc(NCc2ccc3c(c2)-c2ccc(OCCCS(C)(=O)=O)cc2OCC3)cc1]

According to the procedures as described in <3-4>, the compound obtained in <21-11> was used to prepare the title compound (light yellow oil, 15 mg, 51% yield).

$^1$H NMR (300 MHz, CDCl$_3$) δ 7.38 (d, 1H), 7.32-7.21 (m, 3H), 6.94 (d, 2H), 6.77 (dd, 1H), 6.68 (d, 1H), 6.58 (d, 2H), 4.56 (t, 2H), 4.35 (s, 2H), 4.19-4.11 (m, 4H), 3.31-3.24 (m, 2H), 2.97 (s, 3H), 2.80 (t, 2H), 2.45-2.34 (m, 3H), 1.82-1.75 (m, 1H), 1.54-1.47 (m, 1H), 1.27 (t, 3H), 1.28-1.21 (m, 1H)

<21-13> Preparation of (1S,2S)-2-(4-(((3-(3-(methylsulfonyl)propoxy)-6,7-dihydrodibenzo[b,d]oxepin-10-yl)methyl)amino)phenyl)cyclopropanecarboxylic acid

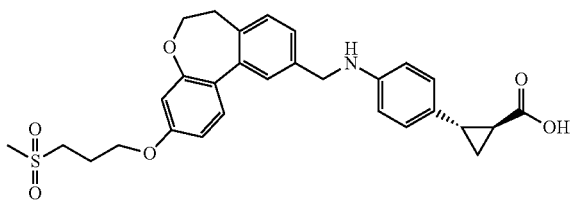

According to the procedures as described in <3-5>, the compound obtained in <21-12> was used to prepare the title compound (white solid, 12 mg, 85% yield).

MS m/z 520 [M-H]⁻

¹H NMR (300 MHz, CDCl₃) δ 7.38-7.37 (m, 1H), 7.31-7.21 (m, 3H), 6.94 (d, 2H), 6.77 (dd, 1H), 6.68 (d, 1H), 6.58 (d, 2H), 4.56 (t, 2H), 4.34 (s, 2H), 4.14 (t, 2H), 3.30-3.24 (m, 2H), 2.97 (s, 3H), 2.80 (t, 2H), 2.55-2.48 (m, 1H), 2.41-2.32 (m, 2H), 1.82-1.75 (m, 1H), 1.61-1.54 (m, 1H), 1.37-1.25 (m, 1H)

Example 22

Preparation of (1S,2S)-2-(4-(((9-(2-ethoxyethoxy)-5,7-dihydrodibenzo[c,e]oxepin-2-yl)methyl)amino)phenyl)cyclopropanecarboxylic acid <22-1> Preparation of methyl 9-(2-ethoxyethoxy)-5,7-dihydrodibenzo[c,e]oxepin-2-carboxylate

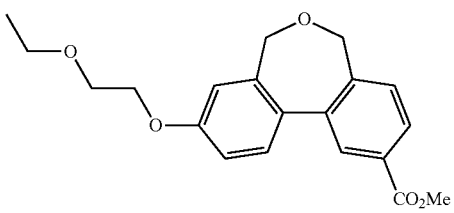 [SMILES: CCOCCOc1ccc2c(c1)COCc1ccc(C(=O)OC)cc1-2]

The compound obtained in <18-6> (180 mg, 0.66 mmol) was dissolved in DMF (6 mL), added with 2-chloroethyl ethyl ether (80 mL, 0.73 mmol) and Cs₂CO₃ (238 mg, 0.73 mmol), and stirred at 90° C. for 15 hours. The reaction mixture was diluted with EtOAc and washed with a saturated NH₄Cl aqueous solution. The aqueous layer was further diluted with EtOAc one more time, and the organic layer was dried over magnesium sulfate and concentrated. The residue was purified by silica gel chromatography to obtain the title compound (white solid, 229 mg, 100% yield).

¹H NMR (300 MHz, CDCl₃) δ 8.18 (d, 1H), 8.03 (dd, 1H), 7.53 (d, 1H), 7.48 (d, 1H), 7.09 (dd, 1H), 7.02 (d, 1H), 4.38 (s, 2H), 4.32 (s, 2H), 4.22-4.19 (m, 2H), 3.96 (s, 3H), 3.85-3.82 (m, 2H), 3.63 (q, 2H), 1.27 (t, 3H)

<22-2> Preparation of (9-(2-ethoxyethoxy)-5,7-dihydrodibenzo[c,e]oxepin-2-yl)methanol

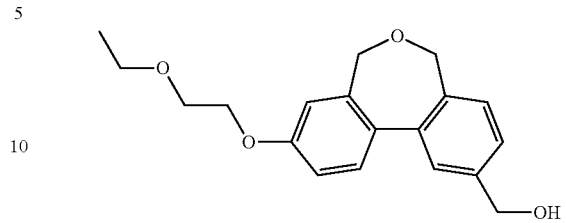

According to the procedures as described in <3-2>, the compound obtained in <22-1> was used to prepare the title compound (light yellow oil, 207 mg, 99% yield).

¹H NMR (300 MHz, CDCl₃) δ 7.52 (m, 1H), 7.49 (d, 1H), 7.43-7.35 (m, 2H), 7.06 (dd, 1H), 7.01 (d, 1H), 4.80 (d, 2H), 4.35 (s, 2H), 4.31 (s, 2H), 4.22-4.17 (m, 2H), 3.86-3.81 (m, 2H), 3.63 (q, 2H), 1.75 (t, 1H), 1.26 (t, 3H)

<22-3> Preparation of 9-(2-ethoxyethoxy)-5,7-dihydrodibenzo[c,e]oxepin-2-carbaldehyde

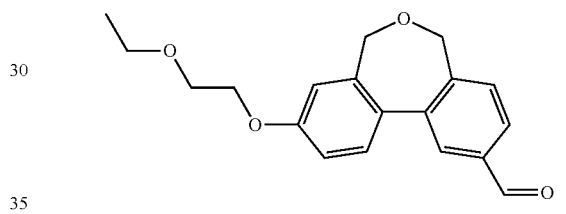

According to the procedures as described in <3-3>, the compound obtained in <22-2> was used to prepare the title compound (light yellow oil, 89 mg, 89% yield).

¹H NMR (300 MHz, CDCl₃) δ 10.12 (s, 1H), 8.02 (d, 1H), 7.88 (dd, 1H), 7.59 (d, 1H), 7.54 (d, 1H), 7.10 (dd, 1H), 7.03 (d, 1H), 4.40 (s, 2H), 4.34 (s, 2H), 4.24-4.19 (m, 2H), 3.87-3.82 (m, 2H), 3.63 (q, 2H), 1.27 (t, 3H)

<22-4> Preparation of (1S,2S)-ethyl 2-(4-(((9-(2-ethoxyethoxy)-5,7-dihydrodibenzo[c,e]oxepin-2-yl)methyl)amino)phenyl)cyclopropanecarboxylate

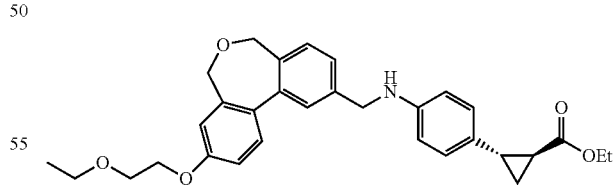

According to the procedures as described in <3-4>, the compound obtained in <22-3> was used to prepare the title compound (light yellow oil, 140 mg, 97% yield).

¹H NMR (300 MHz, CDCl₃) δ 7.50 (m, 1H), 7.45 (d, 1H), 7.37 (m, 2H), 7.05 (dd, 1H), 7.00 (d, 1H), 6.94 (d, 2H), 6.59 (d, 2H), 4.40 (s, 2H), 4.34 (s, 2H), 4.32 (s, 2H), 4.22-4.17 (m, 2H), 4.15 (q, 2H), 3.86-3.80 (m, 2H), 3.63 (q, 2H), 2.47-2.40 (m, 1H), 1.82-1.74 (m, 1H), 1.51 (dt, 1H), 1.27 (t, 3H), 1.26 (t, 3H), 1.26-1.19 (m, 1H)

<22-5> Preparation of (1S,2S)-2-(4-(((9-(2-ethoxyethoxy)-5,7-dihydrodibenzo[c,e]oxepin-2-yl)methyl)amino)phenyl)cyclopropanecarboxylic acid

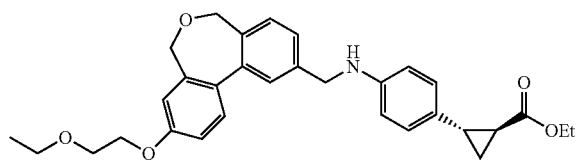 [SMILES: CCOCCOc1ccc2c(c1)COCc1ccc(CNc3ccc([C@H]4C[C@@H]4C(=O)OCC)cc3)cc1-2]

According to the procedures as described in <3-5>, the compound obtained in <22-4> was used to prepare the title compound (light yellow foam, 67 mg, 50% yield).

MS m/z 472 [M−H]⁻

$^1$H NMR (300 MHz, CDCl$_3$) δ 7.50 (m, 1H), 7.44 (d, 1H), 7.38-7.35 (m, 2H), 7.05 (dd, 1H), 7.00 (d, 1H), 6.95 (d, 2H), 6.59 (d, 2H), 4.40 (s, 2H), 4.34 (s, 2H), 4.31 (s, 2H), 4.22-4.17 (m, 2H), 3.85-3.70 (m, 2H), 3.63 (q, 2H), 2.56-2.47 (m, 1H), 1.83-1.75 (m, 1H), 1.58 (dt, 1H), 1.37-1.26 (m, 1H), 1.26 (t, 3H).

Example 23

Preparation of (S)-2-(6-((9-(2-ethoxyethoxy)-5,7-dihydrodibenzo[c,e]oxepin-2-yl)methoxy)-2,3-dihydrobenzofuran-3-yl)acetic acid <23-1> Preparation of (S)-methyl 2-(6-((9-(2-ethoxyethoxy)-5,7-dihydrodibenzo[c,e]oxepin-2-yl)methoxy)-2,3-dihydrobenzofuran-3-yl)acetate

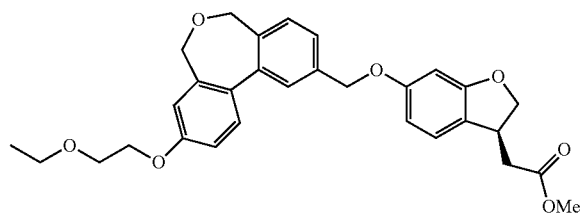 [SMILES: CCOCCOc1ccc2c(c1)COCc1ccc(COc3ccc4c(c3)OC[C@H]4CC(=O)OC)cc1-2]

According to the procedures as described in <1-10>, the compound obtained in <22-2> was used to prepare the title compound (white solid, 114 mg, 72% yield).

$^1$H NMR (300 MHz, CDCl$_3$) δ 7.56 (m, 1H), 7.48 (d, 1H), 7.41-7.42 (m, 2H), 7.09-7.00 (m, 3H), 6.55-6.48 (m, 2H), 5.10 (s, 2H), 4.76 (t, 1H), 4.35 (s, 2H), 4.32 (s, 2H), 4.27 (dd, 1H), 4.23-4.17 (m, 2H), 3.86-3.81 (m, 3H), 3.72 (s, 3H), 3.63 (q, 2H), 2.76 (dd, 1H), 2.56 (dd, 1H), 1.26 (t, 3H)

<23-2> Preparation of (S)-2-(6-((9-(2-ethoxyethoxy)-5,7-dihydrodibenzo[c,e]oxepin-2-yl)methoxy)-2,3-dihydrobenzofuran-3-yl)acetic acid

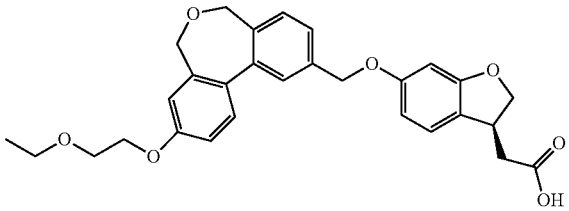 [SMILES: CCOCCOc1ccc2c(c1)COCc1ccc(COc3ccc4c(c3)OC[C@H]4CC(=O)O)cc1-2]

According to the procedures as described in <1-11>, the compound obtained in <23-1> was used to prepare the title compound (white solid, 99 mg, 100% yield).

MS m/z 489 [M−H]⁻

$^1$H NMR (300 MHz, CDCl$_3$) δ 7.56 (m, 1H), 7.48 (d, 1H), 7.42 (m, 2H), 7.09-7.04 (m, 2H), 7.01 (d, 1H), 6.53 (dd, 1H), 6.50 (d, 1H), 5.10 (s, 2H), 4.77 (t, 1H), 4.36 (s, 2H), 4.33 (s, 2H), 4.30 (dd, 1H), 4.22-4.18 (m, 2H), 3.85-3.79 (m, 3H), 3.63 (q, 2H), 2.82 (dd, 1H), 2.63 (dd, 1H), 1.26 (t, 3H).

Example 24

Preparation of (1S,2S)-2-(4-((9-(3-(methylsulfonyl)propoxy)-5,7-dihydrodibenzo[c,e]oxepin-2-yl)methoxy)phenyl)cyclopropanecarboxylic acid <24-1> Preparation of (1S,2S)-ethyl 2-(4-((9-(3-(methylsulfonyl)propoxy)-5,7-dihydrodibenzo[c,e]oxepin-2-yl)methoxy)phenyl)cyclopropanecarboxylate

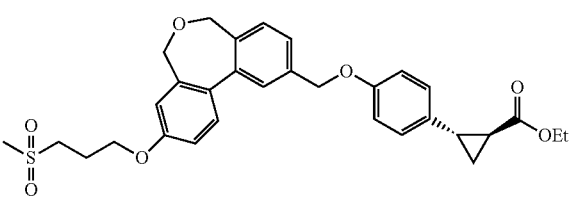 [SMILES: CCOC(=O)[C@H]1C[C@@H]1c1ccc(OCc2ccc3c(c2)-c2ccc(OCCCS(C)(=O)=O)cc2COC3)cc1]

According to the procedures as described in <2-16>, the compound obtained in <18-8> was used to prepare the title compound (light yellow oil, 143 mg, 99% yield).

$^1$H NMR (300 MHz, CDCl$_3$) δ 7.56 (m, 1H), 7.50 (d, 1H), 7.43 (m, 2H), 7.04 (d, 2H), 7.02 (dd, 1H), 6.97 (d, 1H), 6.92 (d, 2H), 5.13 (s, 2H), 4.36 (s, 2H), 4.32 (s, 2H), 4.18 (t, 2H), 4.12 (q, 2H), 3.29 (t, 2H), 2.98 (s, 3H), 2.53-2.43 (m, 1H), 2.43-2.34 (m, 2H), 1.87-1.79 (m, 1H), 1.56 (dt, 1H), 1.30-1.23 (m, 1H), 1.28 (t, 3H)

<24-2> Preparation of (1S,2S)-2-(4-((9-(3-(methyl-sulfonyl)propoxy)-5,7-dihydrodibenzo[c,e]oxepin-2-yl)methoxy)phenyl)cyclopropanecarboxylic acid

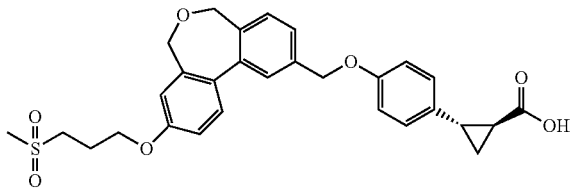 [SMILES: CS(=O)(=O)CCCOc1ccc2c(c1)COCc1ccc(COc3ccc([C@H]4C[C@@H]4C(=O)O)cc3)cc1-2]

According to the procedures as described in <1-11>, the compound obtained in <24-1> was used to prepare the title compound (white foam, 104 mg, 78% yield).

MS m/z 521 [M–H]⁻

¹H NMR (300 MHz, CDCl₃) δ 7.56 (m, 1H), 7.49 (d, 1H), 7.43 (d, 2H), 7.06 (d, 2H), 7.02 (dd, 1H), 6.97 (d, 1H), 6.93 (d, 2H), 5.13 (s, 2H), 4.36 (s, 2H), 4.33 (s, 2H), 4.20 (t, 2H), 3.33-3.26 (m, 2H), 2.98 (s, 3H), 2.61-2.52 (m, 1H), 2.45-2.34 (m, 2H), 1.88-1.80 (m, 1H), 1.63 (dt, 1H), 1.40-1.32 (m, 1H)

Example 25

Preparation of (1S,2S)-2-(4-((9-(3-(methylsulfonyl)propoxy)-6,7-dihydro-5H-dibenzo[a,c][7]annulen-2-yl)methoxy)phenyl)cyclopropanecarboxylic acid <25-1> Preparation of (1S,2S)-ethyl 2-(4-((9-(3-(methylsulfonyl)propoxy)-6,7-dihydro-5H-dibenzo[a,c][7]annulen-2-yl)methoxy)phenyl)cyclopropanecarboxylate

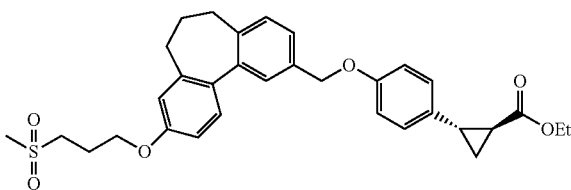 [SMILES: CCOC(=O)[C@H]1C[C@@H]1c1ccc(OCc2ccc3c(c2)-c2ccc(OCCCS(C)(=O)=O)cc2CCC3)cc1]

According to the procedures as described in <2-16>, the compound obtained in <5-9> was used to prepare the title compound (light yellow oil, 111 mg, 87% yield).

¹H NMR (300 MHz, CDCl₃) δ 7.39 (d, 1H), 7.32 (d, 2H), 7.24 (d, 1H), 7.05 (d, 2H), 6.92 (d, 2H), 6.86 (dd, 1H), 6.81 (d, 1H), 5.07 (s, 2H), 4.17 (q, 2H), 4.17 (t, 2H), 3.33-3.26 (m, 2H), 2.98 (s, 3H), 2.54-2.44 (m, 5H), 2.44-2.33 (m, 2H), 2.24-2.15 (m, 2H), 1.87-1.79 (m, 1H), 1.56 (dt, 1H), 1.30-1.23 (m 1H), 1.29 (t, 3H)

<25-2> Preparation of (1S,2S)-2-(4-((9-(3-(methyl-sulfonyl)propoxy)-6,7-dihydro-5H-dibenzo[a,c][7]annulen-2-yl)methoxy)phenyl)cyclopropanecarboxylic acid

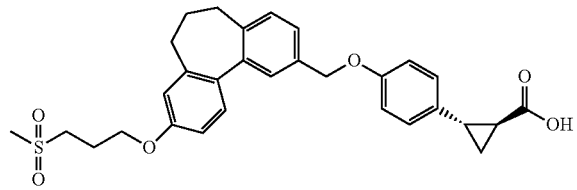 [SMILES: CS(=O)(=O)CCCOc1ccc2c(c1)CCCc1ccc(COc3ccc([C@H]4C[C@@H]4C(=O)O)cc3)cc1-2]

According to the procedures as described in <1-11>, the compound obtained in <25-1> was used to prepare the title compound (white foam, 88.3 mg, 86% yield).

MS m/z 519 [M–H]⁻

¹H NMR (300 MHz, CDCl₃) δ 7.38 (d, 1H), 7.31 (dd, 1H), 7.30 (d, 1H), 7.24 (d, 1H), 7.05 (d, 2H), 6.92 (d, 2H), 6.85 (dd, 1H), 6.79 (d, 1H), 5.07 (s, 2H), 4.17 (t, 2H), 3.32-3.25 (m, 2H), 2.97 (s, 3H), 2.61-2.53 (m, 1H), 2.53-2.43 (m, 4H), 2.42-2.32 (m, 2H), 2.23-2.14 (m, 2H), 1.88-1.80 (m, 1H), 1.66 (dt, 1H), 1.40-1.32 (m, 1H)

Example 26

Preparation of (S)-2-(6-((10-methyl-8-(3-(methyl-sulfonyl)propoxy)-6H-benzo[c]chromen-2-yl)methoxy)-2,3-dihydrobenzofuran-3-yl)acetic acid <26-1> Preparation of (S)-methyl 2-(6-((10-methyl-8-(3-(methylsulfonyl)propoxy)-6H-benzo[c]chromen-2-yl)methoxy)-2,3-dihydrobenzofuran-3-yl)acetate

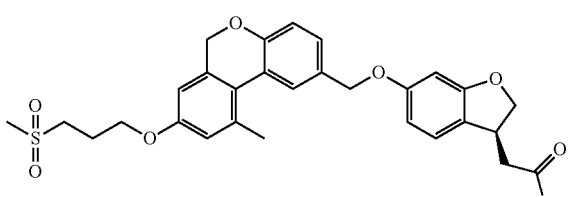

According to the procedures as described in <1-10>, the compound obtained in <9-6> was used to prepare the title compound (colorless oil, 89 mg, 58% yield).

¹H NMR (600 MHz, CDCl₃) δ 7.75 (d, 1H), 7.24 (dd, 1H), 7.04 (t, 1H), 6.75 (d, 1H), 6.59 (d, 1H), 6.51 (dd, 1H), 6.48 (d, 1H), 5.02 (s, 2H), 4.92 (s, 2H), 4.75 (t, 1H), 4.27 (dd, 1H), 4.14 (t, 2H), 3.79-3.83 (m, 1H), 3.72 (s, 3H), 3.25-3.28 (m, 2H), 2.97 (s, 3H), 2.75 (dd, 1H), 2.54-2.58 (m, 4H), 2.35-2.38 (m, 2H).

<26-2> Preparation of (S)-2-(6-((10-methyl-8-(3-(methylsulfonyl)propoxy)-6H-benzo[c]chromen-2-yl)methoxy)-2,3-dihydrobenzofuran-3-yl)acetic acid

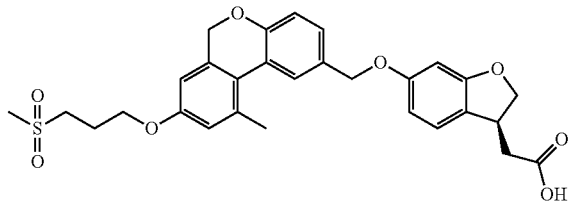 [SMILES: Cc1cc(OCCCS(C)(=O)=O)cc2c1-c1cc(COc3ccc4c(c3)OC[C@H]4CC(=O)O)ccc1OC2]

According to the procedures as described in <1-11>, the compound obtained in <26-1> was used to prepare the title compound (colorless foam, 43 mg, 50% yield).

MS m/z 537 [M−H]⁻.

¹H NMR (600 MHz, CDCl₃) δ ppm 7.75 (d, 1H), 7.24 (dd, 1H), 7.04-7.08 (m, 2H), 6.75 (d, 1H), 6.59 (d, 1H), 6.52 (dd, 1H), 6.49 (d, 1H), 5.02 (s, 2H), 4.92 (s, 2H), 4.77 (t, 1H), 4.29 (dd, 1H), 4.14 (t, 2H), 3.80-3.83 (m, 1H), 3.26 (t, 2H), 2.97 (s, 3H), 2.81 (dd, 1H), 2.63 (dd, 1H), 2.57 (s, 3H), 2.34-2.38 (m, 2H).

Example 27

Preparation of (S)-2-(6-((9-(2-ethoxyethoxy)-6,7-dihydro-5H-dibenzo[a,c][7]annulen-2-yl)methoxy)-2,3-dihydrobenzofuran-3-yl)acetic acid <27-1> Preparation of methyl 9-(2-ethoxyethoxy)-6,7-dihydro-5H-dibenzo[a,c][7]annulene-2-carboxylate

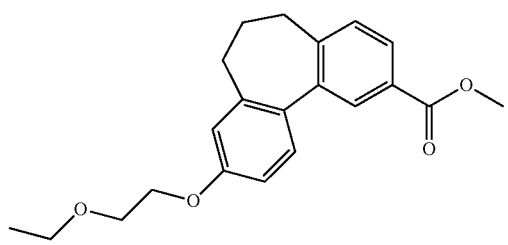 [SMILES: CCOCCOc1ccc2c(c1)CCCc1ccc(C(=O)OC)cc1-2]

According to the procedures as described in <3-1>, the compound obtained in <5-7> was used to prepare the title compound (colorless oil, 210 mg, 87% yield).

¹H NMR (600 MHz, CDCl₃) δ 8.01 (d, 1H), 7.91 (dd, 1H), 7.33 (d, 1H), 7.29 (d, 1H), 6.91 (dd, 1H), 6.85 (d, 1H), 4.18 (t, 2H), 3.92 (s, 3H), 3.83 (t, 2H), 3.63 (q, 2H), 2.53 (t, 2H), 2.45 (t, 2H), 2.71-2.21 (m, 2H), 1.26 (t, 3H).

<27-2> Preparation of (9-(2-ethoxyethoxy)-6,7-dihydro-5H-dibenzo[a,c][7]annulen-2-yl)methanol

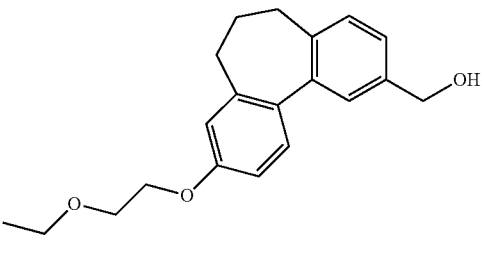 [SMILES: CCOCCOc1ccc2c(c1)CCCc1ccc(CO)cc1-2]

According to the procedures as described in <3-2>, the compound obtained in <27-1> was used to prepare the title compound (white solid, 171 mg, 88% yield).

¹H NMR (600 MHz, CDCl₃) δ 7.34 (d, 1H), 7.30 (d, 1H), 7.25-7.27 (m, 1H), 7.22 (d, 1H), 6.88 (dd, 1H), 6.84 (d, 1H), 4.74 (d, 2H), 4.17 (t, 2H), 3.82 (t, 2H), 3.63 (q, 2H), 2.44-2.59 (m, 4H), 2.14-2.19 (m, 2H), 1.66 (t, 1H), 1.26 (t, 3H)

<27-3> Preparation of (S)-methyl 2-(6-((9-(2-ethoxyethoxy)-6,7-dihydro-5H-dibenzo[a,c][7]annulen-2-yl)methoxy)-2,3-dihydrobenzofuran-3-yl)acetate

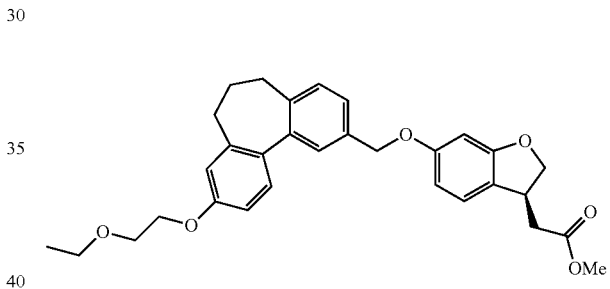

According to the procedures as described in <1-10>, the compound obtained in <27-2> was used to prepare the title compound (white solid, 102 mg, 71% yield).

¹H NMR (600 MHz, CDCl₃) δ 7.38 (d, 1H), 7.29-7.31 (m, 2H), 7.23 (d, 1H), 7.03 (dd, 1H), 6.89 (dd, 1H), 6.84 (d, 1H), 6.51 (dd, 1H), 6.49 (d, 1H), 5.04 (s, 2H), 4.73-4.77 (m, 1H), 4.25-4.28 (m, 1H), 4.17 (t, 2H), 3.78-3.83 (m, 3H), 3.72 (s, 3H), 3.63 (q, 2H), 2.76 (dd, 1H), 2.57 (dd, 1H), 2.45-2.50 (m, 4H), 2.14-2.19 (m, 2H), 1.25 (t, 3H).

<27-4> Preparation of (S)-2-(6-((9-(2-ethoxyethoxy)-6,7-dihydro-5H-dibenzo[a,c][7]annulen-2-yl)methoxy)-2,3-dihydrobenzofuran-3-yl)acetic acid

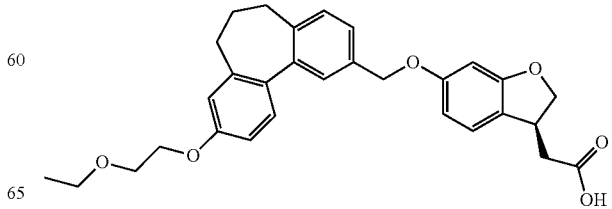

According to the procedures as described in <1-11>, the compound obtained in <27-3> was used to prepare the title compound (white foam, 82 mg, 84% yield).

MS m/z 487 [M−H]⁻.

$^1$H NMR (600 MHz, CDCl$_3$) δ 7.38 (d, 1H), 7.29-7.31 (m, 2H), 7.23 (d, 1H), 7.05-7.7 (m, 1H), 6.89 (dd, 1H), 6.84 (d, 1H), 6.53 (dd, 1H), 6.49 (d, 1H), 5.04 (s, 2H), 4.77 (t, 1H), 4.29 (dd, 1H), 4.17 (t, 2H), 3.80-3.83 (m, 3H), 3.62 (q, 2H), 2.81 (dd, 1H), 2.63 (dd, 1H), 2.45-2.50 (m, 4H), 2.15-2.18 (m, 2H), 1.26 (t, 3H).

Example 28

Preparation of (1S,2S)-2-(4-(((9-(2-ethoxyethoxy)-6,7-dihydro-5H-dibenzo[a,c][7]annulen-2-yl)methyl)amino)phenyl)cyclopropanecarboxylic acid <28-1> Preparation of 9-(2-ethoxyethoxy)-6,7-dihydro-5H-dibenzo[a,c][7]annulene-2-carbaldehyde

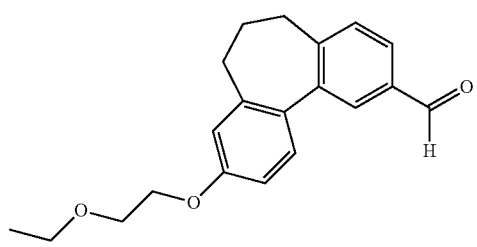 [SMILES: CCOCCOc1ccc2c(c1)CCCc1ccc(C=O)cc1-2]

According to the procedures as described in <3-3>, the compound obtained in <27-2> was used to prepare the title compound (colorless oil, 78 mg, 98% yield).

$^1$H NMR (600 MHz, CDCl$_3$) δ 10.04 (s, 1H), 7.84 (d, 1H), 7.77 (dd, 1H), 7.39 (d, 1H), 7.34 (d, 1H), 6.93 (dd, 1H), 6.86 (d, 1H), 4.19 (t, 2H), 3.83 (t, 2H), 3.64 (q, 2H), 2.57 (t, 2H), 2.46 (t, 2H), 2.19-2.24 (m, 2H), 1.27 (t, 3H).

<28-2> Preparation of (1S,2S)-ethyl 2-(4-(((9-(2-ethoxyethoxy)-6,7-dihydro-5H-dibenzo[a,c][7]annulen-2-yl)methyl)amino)phenyl)cyclopropanecarboxylate

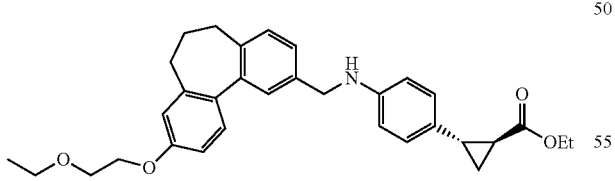

According to the procedures as described in <3-4>, the compound obtained in <28-1> was used to prepare the title compound (white foam, 108 mg, 88% yield).

$^1$H NMR (600 MHz, CDCl$_3$) δ 7.33 (d, 1H), 7.26-7.27 (m, 1H), 7.23-7.24 (m, 1H), 7.19 (d, 1H), 6.93-6.94 (m, 2H), 6.88 (dd, 1H), 6.84 (d, 1H), 6.58-6.59 (m, 2H), 4.33 (s, 2H), 4.13-4.18 (m, 4H), 4.00 (br, 1H), 3.82 (t, 2H), 3.63 (q, 2H), 2.43-2.48 (m, 5H), 2.14-2.18 (m, 2H), 1.77-1.79 (m, 1H), 1.49-1.52 (m, 1H), 1.24-1.28 (m, 6H), 1.21-1.23 (m, 1H).

<28-3> Preparation of (1S,2S)-2-(4-(((9-(2-ethoxyethoxy)-6,7-dihydro-5H-dibenzo[a,c][7]annulen-2-yl)methyl)amino)phenyl)cyclopropanecarboxylic acid

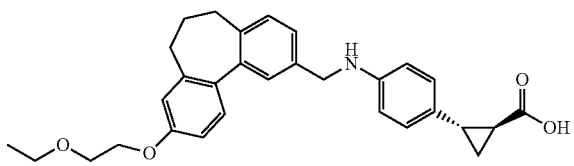 [SMILES: CCOCCOc1ccc2c(c1)CCCc1ccc(CNc3ccc([C@H]4C[C@@H]4C(=O)O)cc3)cc1-2]

According to the procedures as described in <3-5>, the compound obtained in <28-2> was used to prepare the title compound (white foam, 94 mg, 94% yield).

MS m/z 470 [M−H]⁻.

$^1$H NMR (600 MHz, CDCl$_3$) δ ppm 7.32 (s, 1H), 7.23-7.27 (m, 2H), 7.19 (d, 1H), 6.94 (d, 2H), 6.88 (dd, 1H), 6.84 (d, 1H), 6.59 (d, 2H), 4.33 (s, 2H), 4.17 (t, 2H), 3.82 (t, 2H), 3.63 (q, 2H), 2.50-2.53 (m, 1H), 2.44-2.49 (m, 4H), 2.13-2.18 (m, 2H), 1.77-1.80 (m, 1H), 1.56-1.59 (m, 1H), 1.31-1.34 (m, 1H), 1.26 (t, 3H).

Example 29

Preparation of (1S,2S)-2-(4-(((11-methyl-9-(3-(methylsulfonyl)propoxy)-6,7-dihydro-5H-dibenzo[a,c][7]annulen-2-yl)methyl)amino)phenyl)cyclopropanecarboxylic acid <29-1> Preparation of 11-methyl-9-(3-(methylsulfonyl)propoxy)-6,7-dihydro-5H-dibenzo[a,c][7]annulene-2-carbaldehyde

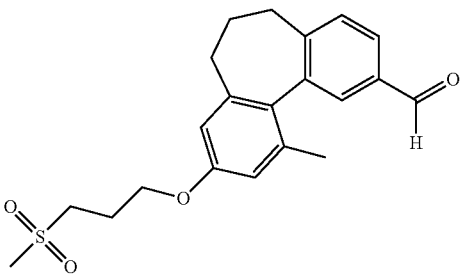 [SMILES: Cc1cc(OCCCS(C)(=O)=O)cc2c1-c1cc(C=O)ccc1CCC2]

According to the procedures as described in <3-3>, the compound obtained in <7-8> was used to prepare the title compound (colorless oil, 100 mg, 100% yield).

$^1$H NMR (600 MHz, CDCl$_3$) δ 10.02 (s, 1H), 7.76-7.77 (m, 2H), 7.40 (d, 1H), 6.75 (d, 1H), 6.64 (d, 1H), 4.16 (t, 2H), 3.28-3.30 (m, 2H), 2.59-2.62 (m, 1H), 2.36-2.45 (m, 4H), 2.31 (s, 3H), 2.19-2.22 (m, 1H), 2.05-2.10 (m, 2H).

<29-2> Preparation of (1S,2S)-ethyl 2-(4-(((11-methyl-9-(3-(methylsulfonyl)propoxy)-6,7-dihydro-5H-dibenzo[a,c][7]annulen-2-yl)methyl)amino)phenyl)cyclopropanecarboxylate

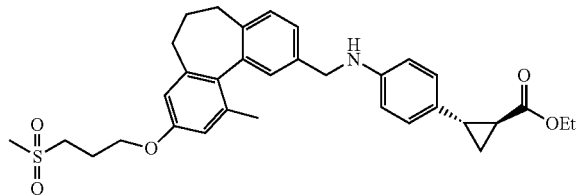 [SMILES: CCOC(=O)[C@H]1C[C@@H]1c1ccc(NCc2ccc3c(c2)-c2c(C)cc(OCCCS(C)(=O)=O)cc2CCC3)cc1]

According to the procedures as described in <3-4>, the compound obtained in <29-1> was used to prepare the title compound (white foam, 116 mg, 79% yield).
¹H NMR (600 MHz, CDCl₃) δ 7.17-7.22 (m, 3H), 6.91 (d, 2H), 6.69 (d, 1H), 6.61 (d, 1H), 6.56 (d, 2H), 4.32 (s, 2H), 4.12-4.16 (m, 4H), 4.00 (br, 1H), 3.25-3.28 (m, 2H), 2.97 (s, 3H), 2.46-2.50 (m, 1H), 2.39-2.43 (m, 2H), 2.20-2.37 (m, 4H), 2.18 (s, 3H), 1.98-2.03 (m, 2H), 1.74-1.77 (m, 1H), 1.48-1.51 (m, 1H), 1.26 (t, 3H), 1.19-1.22 (m, 1H).

<29-3> Preparation of (1S,2S)-2-(4-(((11-methyl-9-(3-(methylsulfonyl)propoxy)-6,7-dihydro-5H-dibenzo[a,c][7]annulen-2-yl)methyl)amino)phenyl)cyclopropanecarboxylic acid

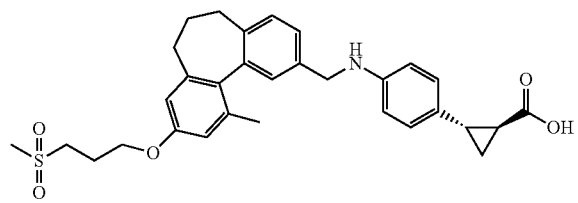 [SMILES: Cc1cc(OCCCS(C)(=O)=O)cc2c1-c1cc(CNc3ccc([C@H]4C[C@@H]4C(=O)O)cc3)ccc1CCC2]

According to the procedures as described in <3-5>, the compound obtained in <29-2> was used to prepare the title compound (white foam, 100 mg, 89% yield).

MS m/z 532 [M−H]⁻

¹H NMR (600 MHz, CDCl₃) δ 7.15-7.19 (m, 3H), 6.87-6.88 (m, 2H), 6.67-6.68 (m, 1H), 6.59-6.60 (m, 1H), 6.51-6.52 (m, 1H), 4.28 (s, 2H), 4.10-4.12 (m, 2H), 3.25 (m, 2H), 2.94 (s, 3H), 2.45-2.49 (m, 2H), 2.38-2.41 (m, 1H), 2.29-2.35 (m, 4H), 2.18-2.23 (m, 1H), 2.16 (s, 3H), 1.97-2.01 (m, 2H), 1.73-1.75 (m, 1H), 1.52-1.54 (m, 1H).

Example 30

Preparation of (1S,2S)-2-(4-((10-methyl-8-(3-(methylsulfonyl)propoxy)-6H-benzo[c]chromen-2-yl)methoxy)phenyl)cyclopropanecarboxylic acid <30-1> Preparation of (1S,2S)-ethyl 2-(4-((10-methyl-8-(3-(methylsulfonyl)propoxy)-6H-benzo[c]chromen-2-yl)methoxy)phenyl)cyclopropanecarboxylate

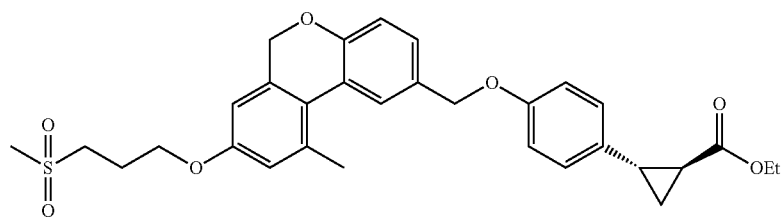 [SMILES: CCOC(=O)[C@H]1C[C@@H]1c1ccc(OCc2ccc3c(c2)-c2c(C)cc(OCCCS(C)(=O)=O)cc2CO3)cc1]

According to the procedures as described in <2-16>, the compound obtained in <9-6> was used to prepare the title compound (white foam, 132 mg, 87% yield).
¹H NMR (600 MHz, CDCl₃) δ 7.74 (d, 1H), 7.24 (dd, 1H), 7.02-7.05 (m, 3H), 6.89-6.92 (m, 2H), 6.75 (d, 1H), 6.59 (d, 1H), 5.04 (s, 2H), 4.92 (s, 2H), 4.12-4.18 (m, 4H), 3.25-3.27 (m, 2H), 2.96 (s, 3H), 2.56 (s, 3H), 2.46-2.50 (m, 1H), 2.34-2.38 (m, 2H), 1.80-1.83 (m, 1H), 1.54-1.57 (m, 1H), 1.23-1.29 (m, 4H).

<30-2> Preparation of (1S,2S)-2-(4-((10-methyl-8-(3-(methylsulfonyl)propoxy)-6H-benzo[c]chromen-2-yl)methoxy)phenyl)cyclopropanecarboxylic acid

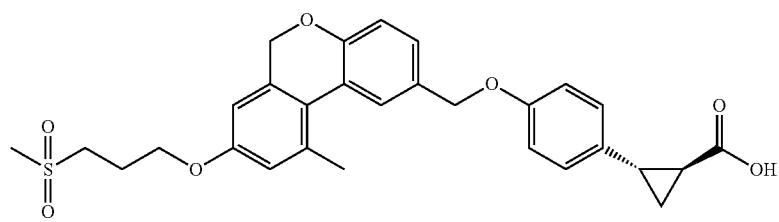 [SMILES: Cc1cc(OCCCS(C)(=O)=O)cc2c1-c1cc(COc3ccc([C@H]4C[C@@H]4C(=O)O)cc3)ccc1OC2]

According to the procedures as described in <1-11>, the compound obtained in <30-1> was used to prepare the title compound (white solid, 105 mg, 84% yield).

MS m/z 521 [M−H]⁻

¹H NMR (600 MHz, CDCl$_3$) δ 7.73 (d, 1H), 7.23 (dd, 1H), 7.02-7.05 (m, 3H), 6.89-6.92 (m, 2H), 6.47 (d, 1H), 6.58 (d, 1H), 5.03 (s, 2H), 4.91 (s, 2H), 4.13 (t, 2H), 3.24-3.27 (m, 2H), 2.96 (s, 3H), 2.54-2.57 (m, 4H), 2.33-2.37 (m, 2H), 1.80-1.83 (m, 1H), 1.59-1.63 (m, 1H), 1.33-1.36 (m, 1H).

Example 31

Preparation of (1S,2S)-2-(4-((5-methyl-7-(3-(methylsulfonyl)propoxy)-9,10-dihydrophenanthren-3-yl)methoxy)phenyl)cyclopropanecarboxylic acid <31-1> Preparation of (1S,2S)-ethyl 2-(4-((5-methyl-7-(3-(methylsulfonyl)propoxy)-9,10-dihydrophenanthren-3-yl)methoxy)phenyl)cyclopropanecarboxylate

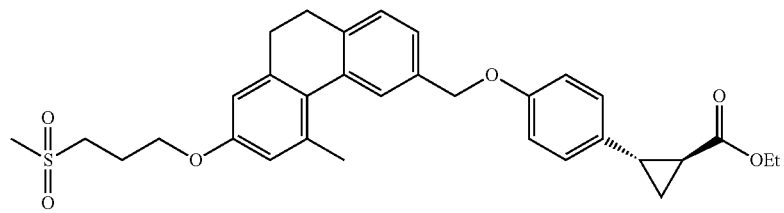 [SMILES: CCOC(=O)[C@H]1C[C@@H]1c1ccc(OCc2ccc3c(c2)-c2c(C)cc(OCCCS(C)(=O)=O)cc2CC3)cc1]

According to the procedures as described in <2-16>, the compound obtained in <11-7> was used to prepare the title compound (white foam, 93 mg, 76% yield).

¹H NMR (600 MHz, CDCl$_3$) δ 7.62 (d, 1H), 7.25-7.27 (m, 1H), 7.21 (dd, 1H), 7.02-7.03 (m, 2H), 6.90-6.92 (m, 2H), 6.69 (d, 1H), 6.66 (d, 1H), 5.07 (s, 2H), 4.13-4.18 (m, 4H), 3.25-3.28 (m, 2H), 2.96 (s, 3H), 2.72 (s, 4H), 2.54 (s, 3H), 2.46-2.48 (m, 2H), 2.34-2.37 (m, 1H), 1.80-1.83 (m, 1H), 1.53-1.56 (m, 1H), 1.23-1.29 (m, 4H).

<31-2> Preparation of (1S,2S)-2-(4-((5-methyl-7-(3-(methylsulfonyl)propoxy)-9,10-dihydrophenanthren-3-yl)methoxy)phenyl)cyclopropanecarboxylic acid

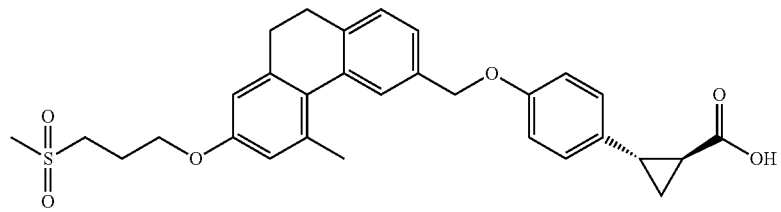 [SMILES: Cc1cc(OCCCS(C)(=O)=O)cc2c1-c1cc(COc3ccc([C@H]4C[C@@H]4C(=O)O)cc3)ccc1CC2]

According to the procedures as described in <1-11>, the compound obtained in <31-1> was used to prepare the title compound (white solid, 73 mg, 85% yield).

MS m/z 519 [M−H]⁻

¹H NMR (600 MHz, CDCl₃) δ 7.62 (d, 1H), 7.25-7.27 (m, 1H), 7.22 (dd, 1H), 7.03-7.05 (m, 2H), 6.90-6.92 (m, 2H), 6.69 (d, 1H), 6.66 (d, 1H), 5.07 (s, 2H), 4.14 (t, 2H), 3.25-3.28 (m, 2H), 2.96 (s, 3H), 2.73 (s, 4H), 2.54-2.57 (m, 4H), 2.33-2.38 (m, 2H), 1.81-1.84 (m, 1H), 1.60-1.63 (m, 1H), 1.33-1.36 (m, 1H).

Example 32

Preparation of (S)-2-(6-((9-(3-(methylsulfonyl)propoxy)-6,7-dihydrodibenzo[b,d]oxepin-2-yl)methoxy)-2,3-dihydrobenzofuran-3-yl)acetic acid <32-1> Preparation of (S)-methyl 2-(6-((9-(3-(methylsulfonyl)propoxy)-6,7-dihydrodibenzo[b,d]oxepin-2-yl)methoxy)-2,3-dihydrobenzofuran-3-yl)acetate

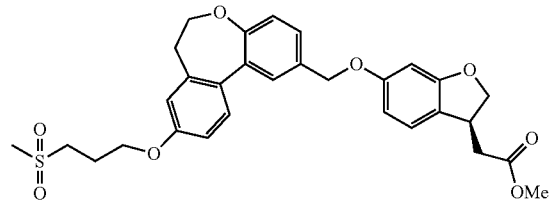 [SMILES: COC(=O)C[C@@H]1COc2cc(OCc3ccc4c(c3)-c3ccc(OCCCS(C)(=O)=O)cc3CCO4)ccc21]

According to the procedures as described in <1-10>, the compound obtained in <2-13> was used to prepare the title compound (white foam, 112 mg, 83% yield).

¹H NMR (600 MHz, CDCl₃) δ 7.42 (d, 1H), 7.38 (d, 1H), 7.34 (dd, 1H), 7.12 (d, 1H), 7.04 (dd, 1H), 6.89 (dd, 1H), 6.83 (d, 1H), 6.51 (dd, 1H), 6.48 (d, 1H), 5.03 (s, 2H), 4.76 (t, 1H), 4.56 (t, 2H), 4.27 (dd, 1H), 4.17 (t, 2H), 3.79-3.84 (m, 1H), 3.72 (s, 3H), 3.27-3.29 (m, 2H), 2.97 (s, 3H), 2.74-2.79 (m, 3H), 2.54-2.59 (m, 1H), 2.35-2.40 (m, 2H).

<32-2> Preparation of (S)-2-(6-((9-(3-(methylsulfonyl)propoxy)-6,7-dihydrodibenzo[b,d]oxepin-2-yl)methoxy)-2,3-dihydrobenzofuran-3-yl)acetic acid

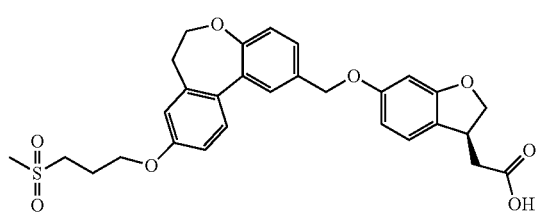 [SMILES: CS(=O)(=O)CCCOc1ccc2c(c1)CCOc1ccc(COc3ccc4c(c3)OC[C@H]4CC(=O)O)cc1-2]

According to the procedures as described in <1-11>, the compound obtained in <32-1> was used to prepare the title compound (white foam, 90 mg, 84% yield).

MS m/z 537 [M−H]⁻

¹H NMR (600 MHz, CDCl₃) δ 7.42 (d, 1H), 7.38 (d, 1H), 7.34 (dd, 1H), 7.13 (d, 1H), 7.07 (d, 1H), 6.89 (dd, 1H), 6.83 (d, 1H), 6.52 (dd, 1H), 6.49 (d, 1H), 5.03 (s, 2H), 4.77 (t, 1H), 4.56 (t, 2H), 4.30 (dd, 1H), 4.17 (t, 2H), 3.79-3.84 (m, 1H), 3.27-3.29 (m, 2H), 2.97 (s, 3H), 2.77-2.83 (m, 3H), 2.61-2.65 (m, 1H), 2.35-2.40 (m, 2H).

Example 33

Preparation of 2-((3S)-6-((11-methyl-9-(3-(methylsulfonyl)propoxy)-5,7-dihydrodibenzo[c,e]oxepin-2-yl)methoxy)-2,3-dihydrobenzofuran-3-yl)acetic acid <33-1> Preparation of methyl 4-(bromomethyl)-3-(4,4,5,5-tetramethyl-1,3,2-dioxaborolane-2-yl)benzoate

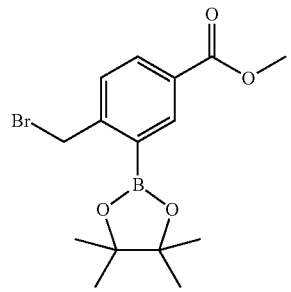 [SMILES: COC(=O)c1ccc(CBr)c(B2OC(C)(C)C(C)(C)O2)c1]

According to the procedures as described in <1-4>, methyl 4-(bromomethyl)-3-(4,4,5,5-tetramethyl-1,3,2-dioxaborolane-2-yl)benzoate (prepared in accordance with the reference [Chemical Communications (Cambridge, United Kingdom), 2012, vol. 48, #34, p. 4115-4117]) was used to prepare the title compound (white solid, 3.0 g, 92% yield).

¹H NMR (300 MHz, CDCl₃) δ 8.46 (d, 1H), 8.06 (dd, 1H), 7.46 (d, 1H), 4.91 (s, 2H), 3.93 (s, 3H), 1.38 (s, 12H).

<33-2> Preparation of methyl 4-(((2-bromo-5-(methoxymethoxy)-3-methylbenzyl)oxy)methyl)-3-(4,4,5,5-tetramethyl-1,3,2-dioxaborolane-2-yl)benzoate

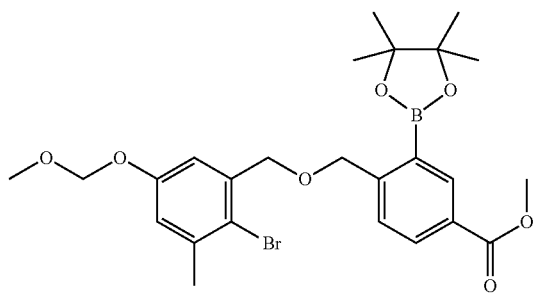

According to the procedures as described in <18-4>, the compounds obtained in <19-3> and <33-1> were used to prepare the title compound (white solid, 1.75 g, 47% yield).

¹H NMR (300 MHz, CDCl₃) δ 8.46 (d, 1H), 8.10 (dd, 1H), 7.67 (d, 1H), 7.11 (d, 1H), 6.89 (d, 1H), 5.15 (s, 2H), 4.96 (s, 2H), 4.64 (s, 2H), 3.92 (s, 3H), 3.46 (s, 3H), 2.39 (s, 3H), 1.34 (s, 13H).

<33-3> Preparation of methyl 9-(methoxymethoxy)-11-methyl-5,7-dihydrodibenzo[c,e]oxepin-2-carboxylate

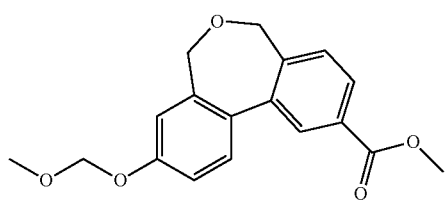

According to the procedures as described in <18-5>, the compound obtained in <33-2> was used to prepare the title compound (colorless oil, 246 mg, 23% yield).

¹H NMR (300 MHz, CDCl₃) δ 8.12 (d, 1H), 8.03 (dd, 1H), 7.50 (d, 1H), 7.05 (d, 1H), 6.96 (d, 1H), 5.23 (q, 2H), 4.51 (d, 1H), 4.41 (d, 1H), 4.16 (d, 1H), 3.97 (d, 1H), 3.94 (s, 3H), 3.51 (s, 3H), 2.43 (s, 3H).

<33-4> Preparation of methyl 9-hydroxy-11-methyl-5,7-dihydrodibenzo[c,e]oxepin-2-carboxylate

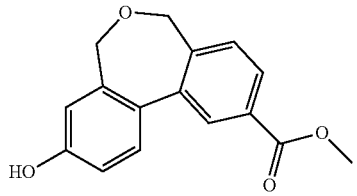 [SMILES: COC(=O)c1ccc2c(c1)-c1ccc(O)cc1COC2]

According to the procedures as described in <18-6>, the compound obtained in <33-3> was used to prepare the title compound (white solid, 187 mg, 88% yield).

¹H NMR (300 MHz, CDCl₃) δ 8.12 (d, 1H), 8.04 (dd, 1H), 7.51 (d, 1H), 6.88 (d, 1H), 6.78 (d, 1H), 5.81 (s, 1H), 4.55 (d, 1H), 4.38 (d, 1H), 4.20 (d, 1H), 3.98 (d, 1H), 3.95 (s, 3H), 2.41 (s, 3H).

<33-5> Preparation of methyl 11-methyl-9-(3-(methylsulfonyl)propoxy)-5,7-dihydrodibenzo[c,e]oxepin-2-carboxylate

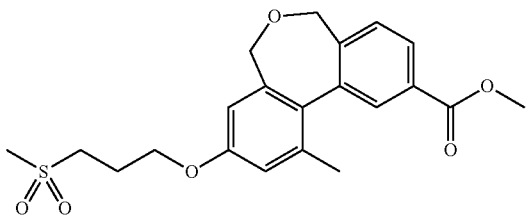

According to the procedures as described in <1-8>, the compound obtained in <33-4> was used to prepare the title compound (white solid, 217 mg, 82% yield).

¹H NMR (300 MHz, CDCl₃) δ 8.11 (d, 1H), 8.03 (dd, 1H), 7.50 (d, 1H), 6.90 (d, 1H), 6.81 (d, 1H), 4.51 (d, 1H), 4.39 (d, 1H), 4.20-4.11 (m, 3H), 3.98 (d, 1H), 3.95 (s, 3H), 3.36-3.22 (m, 2H), 2.98 (s, 3H), 2.50-2.33 (m, 5H).

<33-6> Preparation of (11-methyl-9-(3-(methylsulfonyl)propoxy)-5,7-dihydrodibenzo[c,e]oxepin-2-yl)methanol

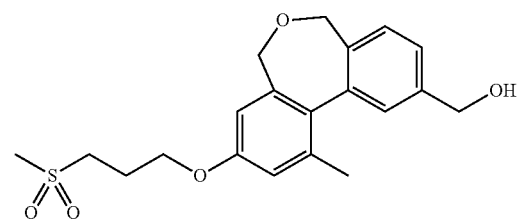 [SMILES: Cc1cc(OCCCS(C)(=O)=O)cc2c1-c1cc(CO)ccc1COC2]

According to the procedures as described in <1-9>, the compound obtained in <33-5> was used to prepare the title compound (white solid, 171 mg, 85% yield).

¹H NMR (300 MHz, CDCl₃) δ 7.46-7.34 (m, 3H), 6.89 (d, 1H), 6.80 (d, 1H), 4.78 (d, 2H), 4.47 (d, 1H), 4.37 (d, 1H), 4.18 (t, 2H), 4.12 (d, 1H), 4.00 (d, 1H), 3.28 (dd, 2H), 2.98 (s, 3H), 2.47-2.32 (m, 5H), 1.71 (t, 1H).

<33-7> Preparation of methyl 2-((3S)-6-((11-methyl-9-(3-(methylsulfonyl)propoxy)-5,7-dihydrodibenzo[c,e]oxepin-2-yl) methoxy)-2,3-dihydrobenzofuran-3-yl)acetate

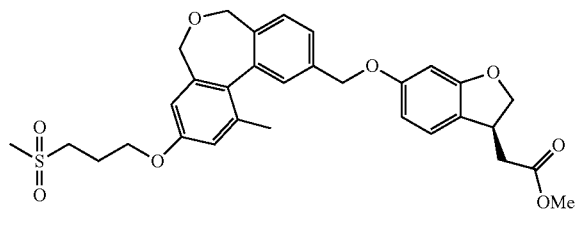 [SMILES: COC(=O)C[C@@H]1COc2cc(OCc3ccc4c(c3)-c3c(C)cc(OCCCS(C)(=O)=O)cc3COC4)ccc21]

According to the procedures as described in <1-10>, the compound obtained in <33-6> was used to prepare the title compound (white solid, 25 mg, 20% yield).

¹H NMR (300 MHz, CDCl₃) δ 7.51-7.37 (m, 3H), 7.03 (d, 1H), 6.87 (d, 1H), 6.80 (d, 1H), 6.54-6.43 (m, 2H), 5.10 (s, 2H), 4.75 (t, 1H), 4.48 (d, 1H), 4.37 (d, 1H), 4.27 (dd, 1H), 4.19-4.09 (m, 4H), 4.01 (d, 1H), 3.86-3.76 (m, 1H), 3.74 (d, 3H), 3.34-3.22 (m, 2H), 2.98 (s, 3H), 2.75 (dd, 1H), 2.56 (dd, 1H), 2.46-2.28 (m, 5H), 2.04 (s, 1H), 1.26 (t, 2H).

<33-8> Preparation of 2-((3S)-6-((11-methyl-9-(3-(methylsulfonyl)propoxy)-5,7-dihydrodibenzo[c,e]oxepin-2-yl) methoxy)-2,3-dihydrobenzofuran-3-yl) acetic acid

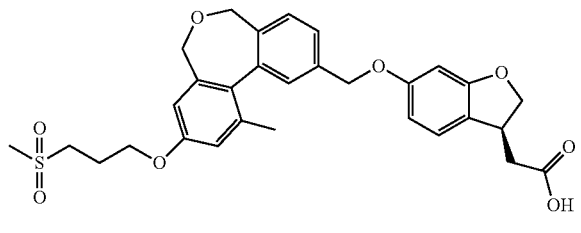 [SMILES: Cc1cc(OCCCS(C)(=O)=O)cc2c1-c1cc(COc3ccc4c(c3)OC[C@H]4CC(=O)O)ccc1COC2]

According to the procedures as described in <1-11>, the compound obtained in <33-7> was used to prepare the title compound (white solid, 11 mg, 46% yield).

MS m/z 551 [M−H]⁻.

¹H NMR (600 MHz, CDCl₃) δ 7.46-7.41 (m, 2H), 7.39 (dd, 1H), 7.05 (d, 1H), 6.86 (d, 1H), 6.78 (d, 1H), 6.49 (ddd, 1H), 6.46 (t, 1H), 5.10 (s, 2H), 4.75 (t, 1H), 4.47 (d, 1H), 4.37 (d, 1H), 4.28 (ddd, 1H), 4.16 (t, 2H), 4.11 (dd, 1H), 4.00 (d, 1H), 3.85-3.75 (m, 1H), 3.30-3.24 (m, 2H), 2.96 (s, 3H), 2.79 (dd, 1H), 2.61 (dd, 1H), 2.40-2.33 (m, 5H).

Example 34

(1S,2S)-2-(4-(((11-methyl-9-(3-(methylsulfonyl)propoxy)-5,7-dihydrodibenzo[c,e]oxepin-2-yl)methyl)amino)phenyl)cyclopropanecarboxylic acid <34-1> Preparation of 11-methyl-9-(3-(methylsulfonyl)propoxy)-5,7-dihydrodibenzo[c,e]oxepin-2-carbaldehyde

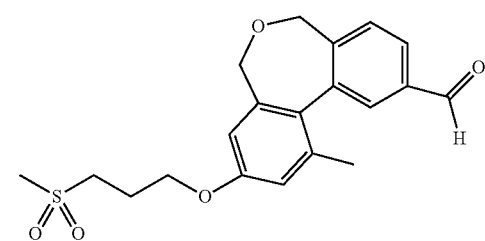 [SMILES: Cc1cc(OCCCS(C)(=O)=O)cc2c1-c1cc(C=O)ccc1COC2]

According to the procedures as described in <3-3>, the compound obtained in <33-6> was used to prepare the title compound (white solid, 57 mg, 67% yield).

¹H NMR (300 MHz, CDCl₃) δ 10.10 (s, 1H), 7.94 (d, 1H), 7.88 (dd, 1H), 7.61 (d, 1H), 6.92 (d, 1H), 6.82 (d, 1H), 4.54 (d, 1H), 4.41 (d, 1H), 4.23-4.10 (m, 3H), 3.99 (d, 1H), 3.36-3.23 (m, 2H), 2.98 (s, 3H), 2.49-2.30 (m, 5H).

<34-2> Preparation of (1S,2S)-ethyl 2-(4-(((11-methyl-9-(3-(methylsulfonyl)propoxy)-5,7-dihydrodibenzo[c,e]oxepin-2-yl)methyl)amino)phenyl)cyclopropanecarboxylate

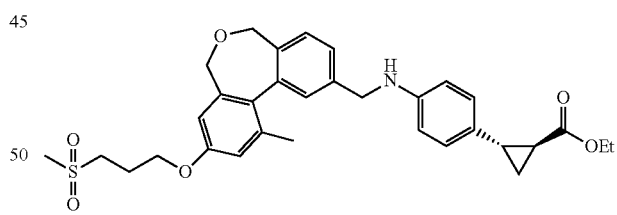

According to the procedures as described in <3-4>, the compound obtained in <34-1> was used prepare the title compound (white solid, 67 mg, 78% yield).

¹H NMR (300 MHz, CDCl₃) δ 7.42-7.30 (m, 3H), 6.92 (d, 2H), 6.85 (d, 1H), 6.78 (d, 1H), 6.57 (d, 2H), 4.46 (d, 1H), 4.40 (s, 2H), 4.36 (d, 1H), 4.23-4.05 (m, 6H), 3.99 (d, 1H), 3.27 (dd, 2H), 2.97 (s, 3H), 2.49-2.31 (m, 3H), 2.29 (s, 3H), 1.84-1.72 (m, 1H), 1.55-1.46 (m, 1H), 1.32-1.16 (m, 4H).

<34-3> Preparation of (1S,2S)-2-(4-(((11-methyl-9-(3-(methylsulfonyl)propoxy)-5,7-dihydrodibenzo[c,e]oxepin-2-yl)methyl)amino)phenyl)cyclopropanecarboxylic acid

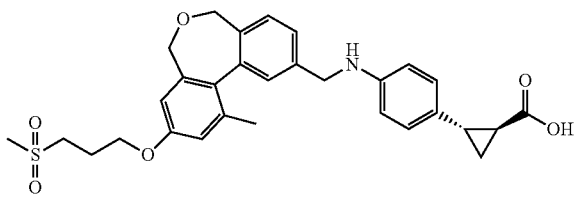 [SMILES: Cc1cc(OCCCS(C)(=O)=O)cc2c1-c1cc(CNc3ccc([C@H]4C[C@@H]4C(=O)O)cc3)ccc1COC2]

According to the procedures as described in <3-5>, the compound obtained in <34-2> was used to prepare the title compound (white solid, 11 mg, 46% yield).
MS m/z 534 [M−H]⁻.
¹H NMR (600 MHz, CDCl₃) δ 7.38 (d, 4H), 7.33 (dd, 2H), 6.92 (d, 4H), 6.84 (d, 2H), 6.77 (d, 2H), 6.59-6.54 (m, 4H), 4.45 (d, 2H), 4.40 (s, 4H), 4.35 (d, 2H), 4.15 (t, 4H), 4.09 (d, 2H), 3.98 (d, 2H), 3.30-3.23 (m, 4H), 2.96 (s, 6H), 2.52-2.48 (m, 2H), 2.38-2.35 (m, 4H), 2.27 (s, 6H), 1.78-1.75 (m, 2H), 1.56 (dt, 3H), 1.34-1.28 (m, 3H), 1.28-1.23 (m, 3H).

Example 35

Preparation of 2-((3S)-6-((9-(2-ethoxyethoxy)-11-methyl-6,7-dihydro-5H-dibenzo[a,c][7]annulen-2-yl)methoxy)-2,3-dihydrobenzofuran-3-yl)acetic acid

<35-1> Preparation of methyl 9-(2-ethoxyethoxy)-11-methyl-6,7-dihydro-5H-dibenzo[a,c][7]annulene-2-carboxylate

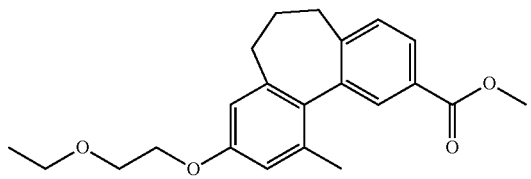 [SMILES: CCOCCOc1cc(C)c2c(c1)CCCc1ccc(C(=O)OC)cc1-2]

According to the procedures as described in <3-1>, the compound obtained in <7-6> was used prepare the title compound (colorless oil, 67 mg, 86% yield).
¹H NMR (300 MHz, CDCl₃) δ 7.94 (d, 1H), 7.91 (dd, 1H), 7.29 (d, 1H), 6.78 (d, 1H), 6.68 (d, 1H), 4.16 (dd, 2H), 3.91 (s, 3H), 3.82 (dd, 2H), 3.63 (q, 2H), 2.61-2.14 (m, 7H), 2.08-1.98 (m, 2H), 1.26 (t, 3H).

<35-2> Preparation of (9-(2-ethoxyethoxy)-11-methyl-6,7-dihydro-5H-dibenzo[a,c][7]annulen-2-yl)methanol

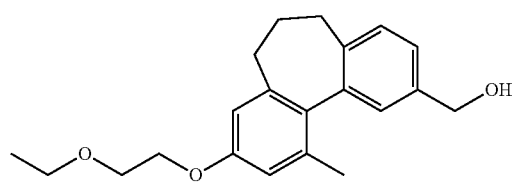 [SMILES: CCOCCOc1cc(C)c2c(c1)CCCc1ccc(CO)cc1-2]

According to the procedures as described in <3-2>, the compound obtained in <35-1> was used to prepare the title compound (colorless oil, 59 mg, 88% yield).
¹H NMR (300 MHz, CDCl₃) δ 7.25-7.20 (m, 3H), 6.77 (d, 1H), 6.67 (d, 1H), 4.70 (s, 2H), 4.16 (dd, 2H), 3.81 (dd, 2H), 3.62 (q, 2H), 2.53-2.18 (m, 7H), 2.04-1.96 (m, 2H), 1.26 (t, 3H).

<35-3> Preparation of methyl 2-((3S)-6-((9-(2-ethoxyethoxy)-11-methyl-6,7-dihydro-5H-dibenzo[a,c][7]annulen-2-yl)methoxy)-2,3-dihydrobenzofuran-3-yl)acetate

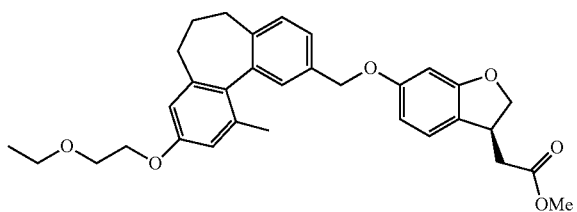 [SMILES: CCOCCOc1cc(C)c2c(c1)CCCc1ccc(COc3ccc4c(c3)OC[C@H]4CC(=O)OC)cc1-2]

According to the procedures as described in <1-10>, the compound obtained in <35-2> was used to prepare the title compound (colorless oil, 80 mg, 93% yield).
¹H NMR (300 MHz, CDCl₃) δ 7.32-7.18 (m, 4H), 7.02 (d, 1H), 6.76 (d, 1H), 6.67 (d, 1H), 6.48 (dd, 2H), 5.04 (s, 2H), 4.75 (t, 1H), 4.26 (dd, 1H), 4.16 (t, 2H), 3.88-3.75 (m, 3H), 3.71 (s, 3H), 3.62 (q, 2H), 2.75 (dd, 1H), 2.59-2.24 (m, 7H), 2.04-1.98 (m, 2H), 1.26 (t, 4H).

<35-4> Preparation of 2-((3S)-6-((9-(2-ethoxyethoxy)-11-methyl-6,7-dihydro-5H-dibenzo[a,c][7]annulen-2-yl)methoxy)-2,3-dihydrobenzofuran-3-yl)acetic acid

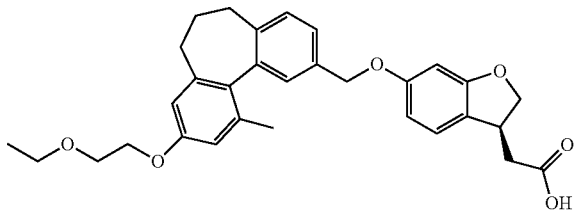 [SMILES: CCOCCOc1cc(C)c2c(c1)CCCc1ccc(COc3ccc4c(c3)OC[C@H]4CC(=O)O)cc1-2]

According to the procedures as described in <1-11>, the compound obtained in <35-3> was used to prepare the title compound (white solid, 56 mg, 71% yield).
MS m/z 501 [M−H]⁻.
¹H NMR (600 MHz, CDCl₃) δ 7.29-7.25 (m, 2H), 7.22 (d, 1H), 7.04 (d, 1H), 6.75 (d, 1H), 6.66 (d, 1H), 6.52-6.48 (m, 1H), 6.46 (d, 1H), 5.03 (s, 2H), 4.75 (t, 1H), 4.32-4.24 (m, 1H), 4.17-4.13 (m, 2H), 3.83-3.77 (m, 3H), 3.61 (q, 2H), 2.79 (dd, 1H), 2.60 (dd, 1H), 2.48 (ddd, 1H), 2.44-2.37 (m, 1H), 2.38-2.31 (m, 1H), 2.31-2.24 (m, 1H), 2.23 (d, 3H), 2.05-1.95 (m, 2H), 1.24 (t, 4H).

Example 36

Preparation of 2-((3S)-6-((9-((1,1-dioxidotetrahydro-2H-thiopyran-4-yl)oxy)-11-methyl-6,7-dihydrodibenzo[b,d]oxepin-2-yl)methoxy)-2,3-dihydrobenzofuran-3-yl)acetic acid <36-1> Preparation of methyl 11-methyl-9-((tetrahydro-2H-thiopyran-4-yl)oxy)-6,7-dihydrodibenzo[b,d]oxepin-2-carboxylate

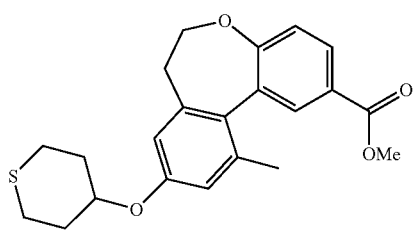 [SMILES: COC(=O)c1ccc2c(c1)-c1c(C)cc(OC3CCSCC3)cc1CCO2]

The compound obtained in <14-5> (80 mg, 0.28 mmol), tetrahydro-2H-thiopyran-4-ol (33.1 mg, 0.28 mmol) and triphenylphosphine (110.2 mg, 0.42 mmol) were dissolved in THF (2.5 mL), which was then slowly added with diethyl azodicarboxylate (DEAD, 191 μL, 0.42 mmol) and stirred at room temperature for 19 hours. The resulting mixture was concentrated and purified by silica gel chromatography to obtain the title compound (white solid, 33.7 mg, 31% yield).

$^1$H NMR (300 MHz, CDCl$_3$) δ 8.02 (d, 1H), 7.97 (dd, 1H), 7.18 (d, 1H), 6.79 (d, 1H), 6.67 (d, 1H), 4.50-4.38 (m, 3H), 3.91 (s, 3H), 3.00-2.92 (m, 2H), 2.87-2.76 (m, 1H), 2.63-2.47 (m, 3H), 2.36 (s, 3H), 2.27-2.17 (m, 2H), 2.12-2.01 (m, 2H)

<36-2> Preparation of methyl 9-((1,1-dioxidotetrahydro-2H-thiopyran-4-yl)oxy)-11-methyl-6,7-dihydrodibenzo[b,d]oxepin-2-carboxylate

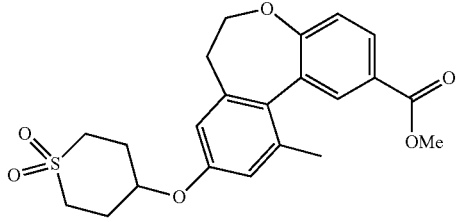 [SMILES: COC(=O)c1ccc2c(c1)-c1c(C)cc(OC3CCS(=O)(=O)CC3)cc1CCO2]

The compound obtained in <36-1> (71.1 mg, 0.18 mmol) was dissolved in dichloromethane (3 mL), which was then added with m-CPBA (87.4 mg, 0.39 mmol) at 0° C. After 20 minutes, the reaction mixture was stirred at room temperature for 30 minutes. The mixture was added with an aqeuous Na$_2$S$_2$O$_3$ solution, diluted with dichloromethane and a saturated sodium sulfate aqueous solution, and the layers thus formed were separated. The aqueous layer was extracted with dichloromethane 2 times, and the organic layer was dried over Na$_2$SO$_4$ and concentrated under reduced pressure. The residue was purified by silica gel chromatography to obtain the title compound (colorless oil, 94.4 mg, 99% yield).

$^1$H NMR (300 MHz, CDCl$_3$) δ 8.01 (d, 1H), 7.96 (dd, 1H), 7.16 (d, 1H), 6.77 (d, 1H), 6.67 (d, 1H), 4.71 (m, 1H), 4.50-4.45 (m, 2H), 3.92 (s, 3H), 3.50-3.39 (m, 2H), 2.95 (m, 2H), 2.88-2.77 (m, 1H), 2.52 (m, 3H), 2.40 (m, 2H), 2.37 (s, 3H)

<36-3> Preparation of 4-((2-(hydroxymethyl)-11-methyl-6,7-dihydrodibenzo[b,d]oxepin-9-yl)oxy)tetrahydro-2H-thiopyran 1,1-dioxide

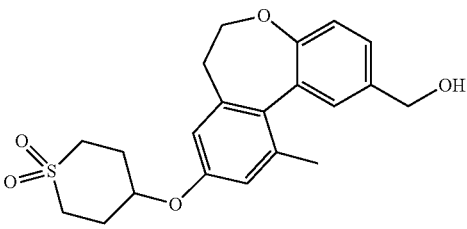 [SMILES: Cc1cc(OC2CCS(=O)(=O)CC2)cc2c1-c1cc(CO)ccc1OCC2]

According to the procedures as described in <1-9>, the compound obtained in <36-2> was used to prepare the title compound (colorless oil, 87.0 mg, 99% yield).

$^1$H NMR (300 MHz, CDCl$_3$) δ 7.32 (s, 1H), 7.27 (d, 1H), 7.13 (d, 1H), 6.80 (d, 1H), 6.71 (d, 1H), 4.71 (m, 3H), 4.43-4.39 (m, 2H), 3.49-3.43 (m, 2H), 2.94 (m, 2H), 2.87-2.76 (m, 1H), 2.54-2.42 (m, 3H), 2.38 (m, 2H), 2.37 (s, 3H), 1.78 (t, 1H)

<36-4> Preparation of methyl 2-((3S)-6-((9-((1,1-dioxidotetrahydro-2H-thiopyran-4-yl)oxy)-11-methyl-6,7-dihydrodibenzo[b,d]oxepin-2-yl)methoxy)-2,3-dihydrobenzofuran-3-yl)acetate

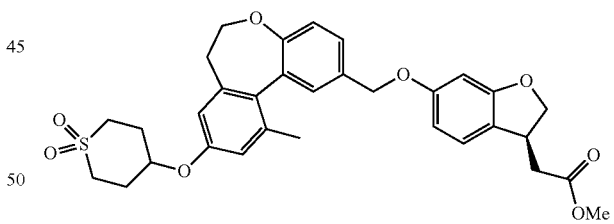

According to the procedures as described in <1-10>, the compound obtained in <36-3> was used to prepare the title compound (colorless oil, 114.4 mg, 88% yield).

$^1$H NMR (300 MHz, CDCl$_3$) δ 7.34 (m, 2H), 7.15 (d, 1H), 7.02 (d, 1H), 6.79 (d, 1H), 6.71 (d, 1H), 6.48 (m, 2H), 5.04 (s, 2H), 4.75 (t, 1H), 4.70 (m, 1H), 4.41 (m, 2H), 4.26 (dd, 1H), 3.81 (m, 1H), 3.72 (s, 3H), 3.44 (m, 2H), 2.94 (m, 2H), 2.87-2.70 (m, 2H), 2.60-2.47 (m, 4H), 2.38 (m, 2H), 2.31 (s, 3H).

<36-5> Preparation of 2-((3S)-6-((9-((1,1-dioxido-tetrahydro-2H-thiopyran-4-yl)oxy)-11-methyl-6,7-dihydrodibenzo[b,d]oxepin-2-yl)methoxy)-2,3-dihydrobenzofuran-3-yl)acetic acid

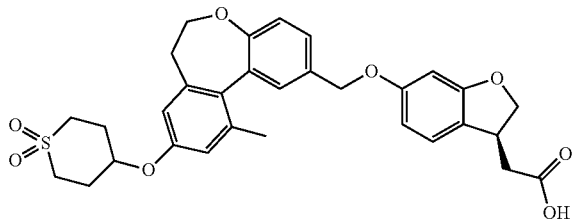 [SMILES: Cc1cc(OC2CCS(=O)(=O)CC2)cc2c1-c1cc(COc3ccc4c(c3)OC[C@H]4CC(=O)O)ccc1OCC2]

According to the procedures as described in <1-11>, the compound obtained in <36-4> was used to prepare the title compound (white foam, 93.3 mg, 83% yield).

MS m/z 563 [M−H]⁻.

¹H NMR (600 MHz, CDCl₃) δ 7.35 (m, 2H), 7.17 (d, 1H), 7.07 (d, 1H), 6.80 (d, 1H), 6.72 (d, 1H), 6.54-6.48 (m, 2H), 5.05 (s, 2H), 4.77 (t, 1H), 4.71 (m, 1H), 4.42 (m, 2H), 4.29 (dd, 1H), 3.82 (m, 1H), 3.45 (m, 2H), 2.96 (m, 2H), 2.84 (m, 1H), 2.79 (d, 1H), 2.62 (dd, 1H), 2.55-2.49 (m, 3H), 2.39 (m, 2H), 2.32 (s, 3H).

Example 37

Preparation of 2-((3S)-6-((9-(2-(1,1-dioxidothiomorpholino)ethoxy)-11-methyl-6,7-dihydrodibenzo[b,d]oxepin-2-yl)methoxy)-2,3-dihydrobenzofuran-3-yl)acetic acid <37-1> Preparation of methyl 9-(2-(1,1-dioxidothiomorpholino)ethoxy)-11-methyl-6,7-dihydrodibenzo[b,d]oxepin-2-carboxylate

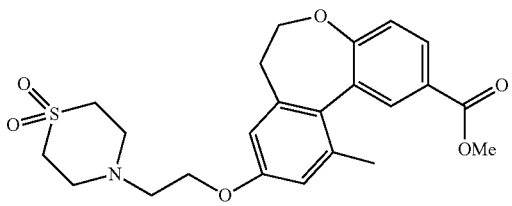 [SMILES: COC(=O)c1ccc2c(c1)-c1c(C)cc(OCCN3CCS(=O)(=O)CC3)cc1CCO2]

The compound obtained in <14-5> (80 mg, 0.28 mmol), 4-(2-hydroxyethyl)thiomorpholine 1,1-dioxide (50.4 mg, 0.28 mmol) and triphenylphosphine (110.2 mg, 0.42 mmol) were dissolved in THF (2.5 mL), which was then slowly added with diethyl azodicarboxylate (DEAD, 191 μL, 0.42 mmol) and stirred at room temperature for 19 hours. The resulting mixture was concentrated and purified by silica gel chromatography to obtain the title compound (white solid, 57.5 mg, 46% yield).

¹H NMR (300 MHz, CDCl₃) δ 8.02 (d, 1H), 7.97 (dd, 1H), 7.18 (d, 1H), 6.79 (d, 1H), 6.67 (d, 1H), 4.49-4.44 (m, 2H), 4.27 (t, 2H), 3.90 (s, 3H), 3.17 (m, 4H), 3.08 (m, 4H), 3.00 (t, 2H), 2.80 (m, 1H), 2.50 (m, 1H), 2.36 (s, 3H)

<37-2> Preparation of 4-(2-((2-(hydroxymethyl)-11-methyl-6,7-dihydrodibenzo[b,d]oxepin-9-yl)oxy)ethyl)thiomorpholine 1,1-dioxide

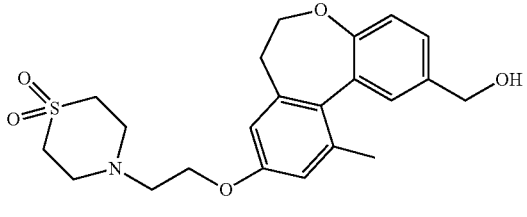 [SMILES: Cc1cc(OCCN2CCS(=O)(=O)CC2)cc2c1-c1cc(CO)ccc1OCC2]

According to the procedures as described in <1-9>, the compound obtained in <37-1> was used to prepare the title compound (white foam, 93.6 mg, 75% yield).

¹H NMR (300 MHz, CDCl₃) δ 7.31 (s, 1H), 7.29 (dd, 1H), 7.14 (d, 1H), 6.77 (d, 1H), 6.68 (d, 1H), 4.71 (d, 1H), 4.40 (m, 2H), 4.14 (t, 2H), 3.18 (m, 4H), 3.09 (m, 4H), 3.01 (t, 2H), 2.81 (m, 1H), 2.48 (m, 1H), 2.38 (s, 3H), 1.65 (s, 1H).

<37-3> Preparation of methyl 2-((3S)-6-((9-(2-(1,1-dioxidothiomorpholino)ethoxy)-11-methyl-6,7-dihydrodibenzo[b,d]oxepin-2-yl)methoxy)-2,3-dihydrobenzofuran-3-ylacetate

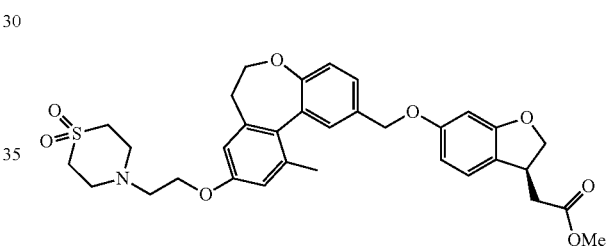

According to the procedures as described in <1-10>, the compound obtained in <37-2> was used to prepare the title compound (colorless oil, 120.2 mg, 88% yield).

¹H NMR (300 MHz, CDCl₃) δ 7.34-7.32 (m, 2H), 7.15 (d, 1H), 7.02 (d, 1H), 6.76 (d, 1H), 6.66 (d, 1H), 6.51-6.46 (m, 2H), 5.03 (s, 2H), 4.75 (t, 1H), 4.41 (m, 2H), 4.26 (dd, 1H), 4.13 (t, 2H), 3.80 (m, 1H), 3.72 (s, 3H), 3.18 (m, 4H), 3.08 (m, 4H), 3.00 (t, 2H), 2.83 (m, 1H), 2.74 (dd, 1H), 2.54 (dd, 1H), 2.48 (dd, 1H), 2.32 (s, 3H).

<37-4> Preparation of 2-((3S)-6-((9-(2-(1,1-dioxidothiomorpholino)ethoxy)-11-methyl-6,7-dihydrodibenzo[b,d]oxepin-2-yl)methoxy)-2,3-dihydrobenzofuran-3-yl)acetic acid

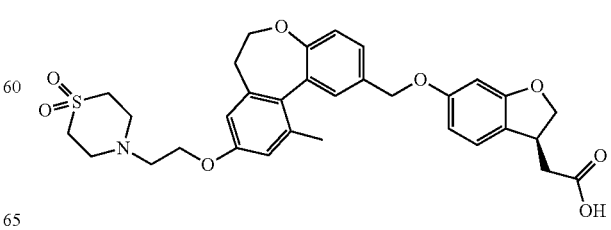

According to the procedures as described in <1-11>, the compound obtained in <37-3> was used to prepare the title compound (white foam, 81.1 mg, 68% yield).

MS m/z 592 [M−H]⁻.

$^1$H NMR (600 MHz, CDCl$_3$) δ 7.35-7.33 (m, 2H), 7.16 (d, 1H), 7.06 (d, 1H), 6.76 (d, 1H), 6.68 (d, 1H), 6.52-6.47 (m, 2H), 5.04 (s, 2H), 4.77 (t, 1H), 4.41 (m, 2H), 4.29 (dd, 1H), 4.14 (t, 2H), 3.80 (m, 1H), 3.20 (m, 4H), 3.11 (m, 4H), 3.02 (t, 2H), 2.87 (m, 1H), 2.80 (dd, 1H), 2.61 (dd, 1H), 2.49 (dd, 1H), 2.32 (s, 3H).

Example 38

Preparation of 2-((3S)-6-((9-(3-(ethylsulfonyl) propoxy)-11-methyl-6,7-dihydrodibenzo[b,d]oxepin-2-yl)methoxy)-2,3-dihydrobenzofuran-3-yl)acetic acid <38-1> Preparation of methyl 9-(3-(ethylsulfonyl) propoxy)-11-methyl-6,7-dihydrodibenzo[b,d]oxepin-2-carboxylate

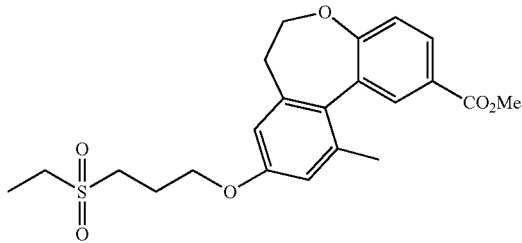 [SMILES: CCS(=O)(=O)CCCOc1cc(C)c2c(c1)CCOc1ccc(C(=O)OC)cc1-2]

A solution of the compound obtained in <14-5> (160 mg, 0.56 mmol) and 1-chloro-3-(ethylsulfonyl)propane (prepared in accordance with the reference [US 2009/270355 A1]; 162 mg, 0.95 mmol) in DMF (1.87 mL) was added with K$_2$CO$_3$ (201 mg, 1.46 mmol) and KI (19 mg, 0.112 mmol), followed by stirring for 5 hours at 90° C. The reaction mixture was cooled to room temperature and extracted with EtOAc. The organic layer was collected and dried over MgSO$_4$. The resulting filtrate was concentrated under reduced pressure and purified by silica gel chromatography to obtain the title compound (yellow oil, 165 mg, 70% yield).

$^1$H NMR (300 MHz, CDCl$_3$) δ 8.02 (d, 1H), 7.98 (dd, 2H), 7.18 (d, 1H), 6.78 (d, 1H), 6.68 (d, 1H), 4.54-4.38 (m, 2H), 4.16 (t, 2H), 3.92 (s, 3H), 3.27-3.16 (m, 2H), 3.06 (q, 2H), 2.87-2.74 (m, 1H), 2.57-2.30 (m, 6H), 1.46 (t, 3H).

<38-2> Preparation of (9-(3-(ethylsulfonyl) propoxy)-11-methyl-6,7-dihydrodibenzo[b,d]oxepin-2-yl)methanol

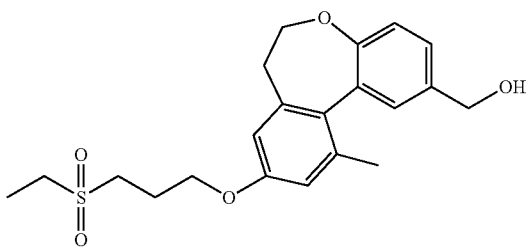 [SMILES: CCS(=O)(=O)CCCOc1cc(C)c2c(c1)CCOc1ccc(CO)cc1-2]

According to the procedures as described in <1-9>, the compound obtained in <38-1> was used to prepare the title compound (colorless oil, 129 mg, 84% yield).

$^1$H NMR (300 MHz, CDCl$_3$) δ 7.33-7.26 (m, 2H), 7.14 (d, 1H), 6.77 (d, 1H), 6.69 (d, 1H), 4.72 (d, 2H), 4.44-4.36 (m, 2H), 4.15 (t, 2H), 3.28-3.15 (m, 2H), 3.05 (q, 2H), 2.80 (m, 1H), 2.49 (m, 1H), 2.41-2.29 (m, 5H), 1.64 (t, 1H), 1.45 (t, 3H).

<38-3> Preparation of methyl 2-((3S)-6-((9-(3-(ethylsulfonyl)propoxy)-11-methyl-6,7-dihydrodibenzo [b,d]oxepin-2-yl) methoxy)-2,3-dihydrobenzofuran-3-ylacetate

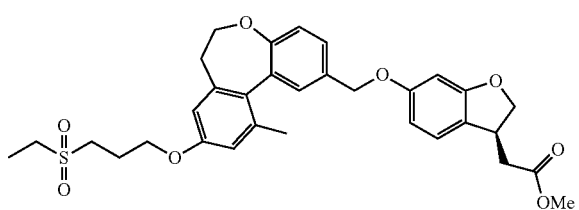 [SMILES: CCS(=O)(=O)CCCOc1cc(C)c2c(c1)CCOc1ccc(COc3ccc4c(c3)OC[C@H]4CC(=O)OC)cc1-2]

According to the procedures as described in <1-10>, the compound obtained in <38-2> was used to prepare the title compound (white foam, 58.7 mg, 56% yield).

$^1$H NMR (300 MHz, CDCl$_3$) δ 7.37-7.29 (m, 2H), 7.15 (d, 1H), 7.03 (d, 1H), 6.76 (d, 1H), 6.68 (d, 1H), 6.52-6.42 (m, 2H), 5.04 (s, 2H), 4.75 (t, 1H), 4.49-4.35 (m, 2H), 4.27 (dd, 1H), 4.15 (t, 2H), 3.81 (m, 1H), 3.72 (s, 3H), 3.27-3.14 (m, 2H), 3.05 (q, 2H), 2.83 (m, 1H), 2.75 (dd, 1H), 2.63-2.42 (m, 2H), 2.36 (m, 2H), 2.31 (s, 3H), 1.45 (t, 3H).

<38-4> Preparation of 2-((3S)-6-((9-(3-(ethylsulfonyl)propoxy)-11-methyl-6,7-dihydrodibenzo[b,d] oxepin-2-yl) methoxy)-2,3-dihydrobenzofuran-3-yl) acetic acid

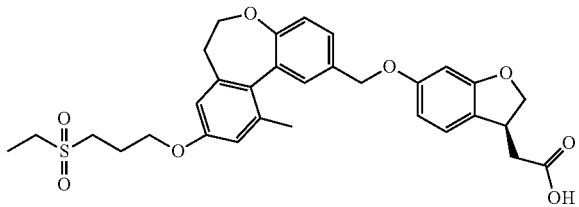 [SMILES: CCS(=O)(=O)CCCOc1cc(C)c2c(c1)CCOc1ccc(COc3ccc4c(c3)OC[C@H]4CC(=O)O)cc1-2]

According to the procedures as described in <1-11>, the compound obtained in <38-3> was used to prepare the title compound (white foam, 49.2 mg, 87% yield).

MS m/z 565 [M−H]⁻.

$^1$H NMR (300 MHz, CDCl$_3$) δ 7.37-7.30 (m, 2H), 7.15 (d, 1H), 7.06 (d, 1H), 6.76 (d, 1H), 6.68 (d, 1H), 6.54-6.44 (m, 2H), 5.04 (s, 2H), 4.77 (t, 1H), 4.46-4.36 (m, 2H), 4.29 (dd, 1H), 4.15 (t, 2H), 3.81 (m, 1H), 3.27-3.16 (m, 2H), 3.05 (q, 2H), 2.92-2.75 (m, 2H), 2.62 (dd, 1H), 2.51 (m, 1H), 2.36 (m, 2H), 2.31 (s, 3H), 1.45 (t, 3H).

Example 39

Preparation of (1S,2S)-2-(4-((11-methyl-9-(3-(methylsulfonyl)propoxy)-6,7-dihydrodibenzo[b,d]oxepin-2-yl)methoxy)phenyl)cyclopropanecarboxylic acid <39-1> Preparation of (1S,2S)-ethyl 2-(4-((11-methyl-9-(3-(methylsulfonyl)propoxy)-6,7-dihydrodibenzo[b,d]oxepin-2-yl)methoxy)phenyl)cyclopropanecarboxylate

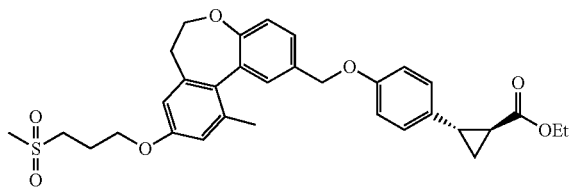 [SMILES: CCOC(=O)[C@H]1C[C@@H]1c1ccc(OCc2ccc3c(c2)-c2c(C)cc(OCCCS(C)(=O)=O)cc2CCO3)cc1]

According to the procedures as described in <2-16>, the compound obtained in <14-7> was used to prepare the title compound (white foam, 66 mg, 45% yield).

$^1$H NMR (300 MHz, CDCl$_3$) δ 7.37-7.31 (m, 2H), 7.15 (d, 1H), 7.03 (d, 2H), 6.89 (d, 2H), 6.76 (d, 1H), 6.68 (d, 1H), 5.06 (s, 2H), 4.45-4.37 (m, 2H), 4.22-4.09 (m, 4H), 3.28 (m, 2H), 2.97 (s, 3H), 2.92-2.74 (m, 1H), 2.55-2.33 (m, 4H), 2.31 (s, 3H), 1.82 (m, 1H), 1.55 (m, 1H), 1.28 (t, 3H), 1.25 (m, 1H).

<39-2> Preparation of (1S,2S)-2-(4-((11-methyl-9-(3-(methylsulfonyl)propoxy)-6,7-dihydrodibenzo[b,d]oxepin-2-yl)methoxy)phenyl)cyclopropanecarboxylic acid

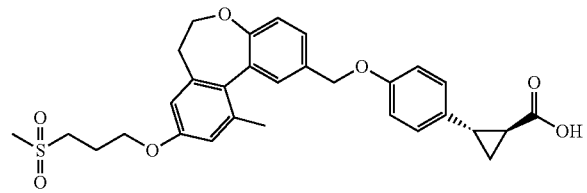 [SMILES: Cc1cc(OCCCS(C)(=O)=O)cc2c1-c1cc(COc3ccc([C@H]4C[C@@H]4C(=O)O)cc3)ccc1OCC2]

According to the procedures as described in <1-11>, the compound obtained in <39-1> was used to prepare the title compound (white foam, 54.6 mg, 85% yield).

MS m/z 535 [M−H]$^-$.

$^1$H NMR (300 MHz, CDCl$_3$) δ 7.37-7.31 (m, 2H), 7.16 (d, 1H), 7.05 (d, 2H), 6.90 (d, 2H), 6.76 (d, 1H), 6.68 (d, 1H), 5.06 (s, 2H), 4.46-4.37 (m, 2H), 4.15 (t, 2H), 3.34-3.22 (m, 2H), 2.97 (s, 3H), 2.91-2.74 (m, 1H), 2.61-2.32 (m, 4H), 2.31 (s, 3H), 1.91-1.78 (m, 1H), 1.60 (m, 1H), 1.42-1.32 (m, 1H).

Example 40

Preparation of (1S,2S)-2-(2-fluoro-4-((11-methyl-9-(3-(methylsulfonyl)propoxy)-6,7-dihydrodibenzo[b,d]oxepin-2-yl)methoxy)phenyl)cyclopropanecarboxylic acid <40-1> Preparation of (1S,2S)-ethyl 2-(2-fluoro-4-((11-methyl-9-(3-(methylsulfonyl)propoxy)-6,7-dihydrodibenzo[b,d]oxepin-2-yl)methoxy)phenyl)cyclopropanecarboxylate

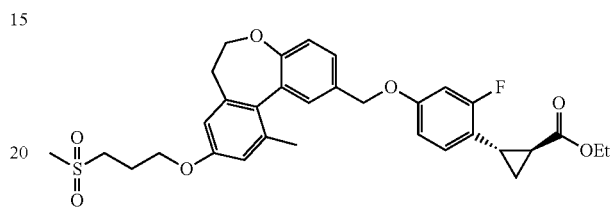

The compound obtained in <14-7> (98.9 mg, 0.26 mmol), (1S,2S)-ethyl 2-(2-fluoro-4-hydroxyphenyl)cyclopropanecarboxylate (56 mg, 0.267 mmol) and tributylphosphine (97.4 μL, 0.39 mmol) were dissolved in THF (1.73 mL), which was then slowly added with 1,1'-(azodicarbonyl)dipiperidine) (98.4 mg, 0.39 mmol) and stirred at room temperature for 1.5 hours. The mixture thus obtained was concentrated and purified by silica gel chromatography to obtain the title compound (yellow foam, 122.2 mg, 81% yield).

$^1$H NMR (300 MHz, CDCl$_3$) δ 7.37-7.29 (m, 2H), 7.16 (d, 1H), 6.87 (d, 1H), 6.77 (d, 1H), 6.71-6.62 (m, 3H), 5.04 (s, 2H), 4.49-4.36 (m, 2H), 4.23-4.08 (m, 4H), 3.32-3.20 (m, 2H), 2.97 (s, 3H), 2.82 (m, 1H), 2.61-2.44 (m, 2H), 2.43-2.33 (m, 2H), 2.31 (s, 3H), 1.91-1.78 (m, 1H), 1.60-1.49 (m, 1H), 1.33-1.23 (m, 4H).

<40-2> Preparation of (1S,2S)-2-(2-fluoro-4-((11-methyl-9-(3-(methylsulfonyl)propoxy)-6,7-dihydrodibenzo[b,d]oxepin-2-yl)methoxy)phenyl)cyclopropanecarboxylic acid

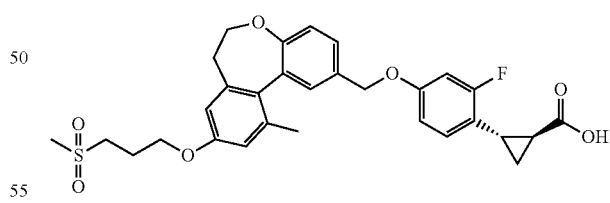

According to the procedures as described in <1-11>, the compound obtained in <40-1> was used to prepare the title compound (white foam, 119.7 mg, 102% yield).

MS m/z 553 [M−H]$^-$.

$^1$H NMR (300 MHz, CDCl$_3$) δ 7.37-7.29 (m, 2H), 7.16 (d, 1H), 6.88 (d, 1H), 6.77 (d, 1H), 6.71-6.64 (m, 3H), 5.05 (s, 2H), 4.49-4.35 (m, 2H), 4.15 (t, 2H), 3.33-3.21 (m, 2H), 2.97 (s, 3H), 2.83 (m, 1H), 2.62 (m, 1H), 2.50 (m, 1H), 2.38 (m, 2H), 2.31 (s, 3H), 1.91-1.80 (m, 1H), 1.68-1.56 (m, 1H), 1.40 (m, 1H).

Example 41

Preparation of (1S,2S)-2-(4-((9-(3-(ethylsulfonyl)propoxy)-11-methyl-6,7-dihydrodibenzo[b,d]oxepin-2-yl)methoxy)-2-fluorophenyl)cyclopropanecarboxylic acid <41-1> Preparation of (1S,2S)-ethyl 2-(4-((9-(3-(ethylsulfonyl)propoxy)-11-methyl-6,7-dihydrodibenzo[b,d]oxepin-2-yl)methoxy)-2-fluorophenyl)cyclopropanecarboxylate

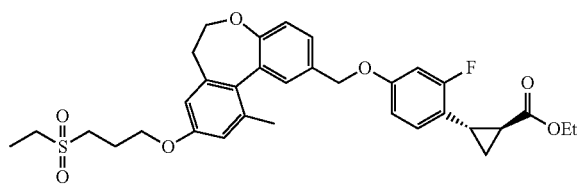 [SMILES: CCOC(=O)[C@H]1C[C@@H]1c1ccc(OCc2ccc3c(c2)-c2c(C)cc(OCCCS(=O)(=O)CC)cc2CCO3)cc1F]

According to the procedures as described in <40-1>, the compound obtained in <38-2> was used to prepare the title compound (off-white foam, 81.9 mg, 91.5% yield).

$^1$H NMR (300 MHz, CDCl$_3$) δ 7.37-7.29 (m, 2H), 7.16 (d, 1H), 6.88 (d, 1H), 6.77 (d, 1H), 6.72-6.62 (m, 3H), 5.04 (s, 2H), 4.45-4.39 (m, 2H), 4.25-4.06 (m, 4H), 3.27-3.14 (m, 2H), 3.05 (q, 2H), 2.82 (m, 1H), 2.62-2.44 (m, 2H), 2.43-2.32 (m, 2H), 2.31 (s, 3H), 1.91-1.80 (m, 1H), 1.60-1.50 (m, 1H), 1.45 (t, 3H), 1.27 (m, 4H).

<41-2> Preparation of (1S,2S)-2-(4-((9-(3-(ethylsulfonyl)propoxy)-11-methyl-6,7-dihydrodibenzo[b,d]oxepin-2-yl)methoxy)-2-fluorophenyl)cyclopropanecarboxylic acid

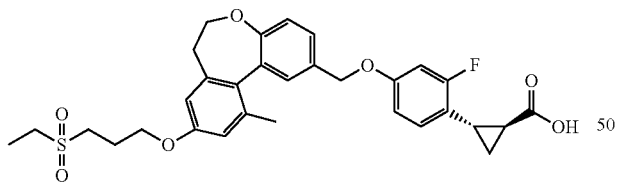

According to the procedures as described in <1-11>, the compound obtained in <41-1> was used to prepare the title compound (white foam, 56.5 mg, 71% yield).

MS m/z 567 [M−H]$^-$.

$^1$H NMR (300 MHz, CDCl$_3$) δ 7.35-7.30 (m, 2H), 7.16 (d, 1H), 6.88 (d, 1H), 6.76 (d, 1H), 6.71-6.65 (m, 3H), 5.05 (s, 2H), 4.47-4.37 (m, 2H), 4.14 (t, 2H), 3.26-3.15 (m, 2H), 3.05 (q, 2H), 2.91-2.75 (m, 1H), 2.64 (m, 1H), 2.52 (m, 1H), 2.34 (m, 2H), 2.31 (s, 3H), 1.85 (m, 1H), 1.67-1.56 (m, 1H), 1.45 (t, 3H), 1.41-1.33 (m, 1H).

Example 42

Preparation of (S)-2-(6-((3-(3-(methylsulfonyl)propoxy)-6,7-dihydrodibenzo[b,d]oxepin-10-yl)methoxy)-2,3-dihydrobenzofuran-3-yl)acetic acid <42-1> Preparation of (S)-methyl 2-(6-((3-(3-(methylsulfonyl)propoxy)-6,7-dihydrodibenzo[b,d]oxepin-10-yl)methoxy)-2,3-dihydrobenzofuran-3-yl)acetate

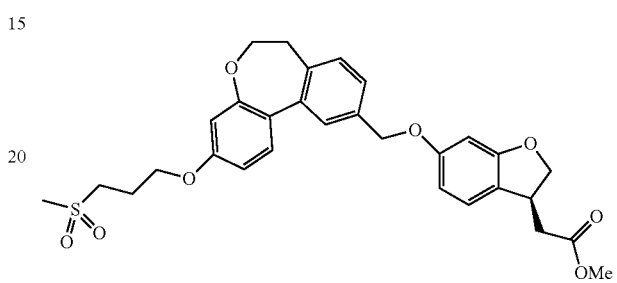

According to the procedures as described in <1-10>, the compound obtained in <21-10> was used to prepare the title compound (white solid, 42 mg, 65.5% yield).

$^1$H NMR (300 MHz, CDCl$_3$) δ 7.44 (s, 1H), 7.38-7.28 (m, 3H), 7.03 (d, 1H), 6.78 (dd, 1H), 6.69 (d, 1H), 6.56-6.43 (m, 2H), 5.05 (s, 2H), 4.76 (t, 1H), 4.57 (t, 2H), 4.27 (dd, 1H), 4.15 (t, 2H), 3.93-3.75 (m, 1H), 3.72 (s, 3H), 3.38-3.18 (m, 2H), 2.97 (s, 3H), 2.82 (t, 2H), 2.76 (dd, 1H), 2.56 (dd, 1H), 2.47-2.27 (m, 2H).

<42-2> Preparation of (S)-2-(6-((3-(3-(methylsulfonyl)propoxy)-6,7-dihydrodibenzo[b,d]oxepin-10-yl)methoxy)-2,3-dihydrobenzofuran-3-yl)acetic acid

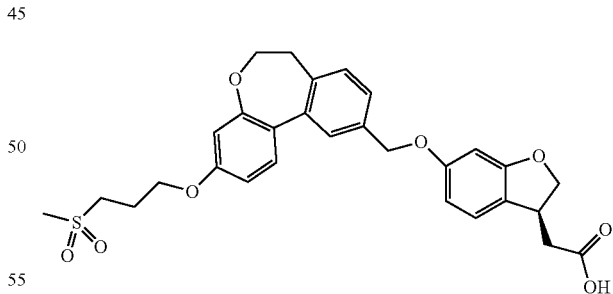

According to the procedures as described in <1-11>, the compound obtained in <42-1> was used to prepare the title compound (white solid, 32 mg, 78.2% yield).

MS m/z 537 [M−H]$^-$.

$^1$H NMR (300 MHz, CDCl$_3$) δ 7.44 (s, 1H), 7.36-7.27 (m, 3H), 7.07 (d, 1H), 6.78 (dd, 1H), 6.69 (d, 1H), 6.54-6.46 (m, 2H), 5.06 (s, 2H), 4.77 (t, 1H), 4.56 (t, 2H), 4.29 (dd, 1H), 4.15 (t, 2H), 3.89-3.75 (m, 1H), 3.28 (m, 2H), 2.97 (s, 3H), 2.87-2.75 (m, 3H), 2.62 (dd, 1H), 2.37 (m, 2H).

Example 43

Preparation of (S)-2-(6-((6,6-dimethyl-9-(3-(methylsulfonyl)propoxy)-6,7-dihydrodibenzo[b,d]oxepin-2-yl)methoxy)-2,3-dihydrobenzofuran-3-yl)acetic acid <43-1> Preparation of 1-(2-bromo-5-methoxyphenyl)-2-methylpropan-2-ol

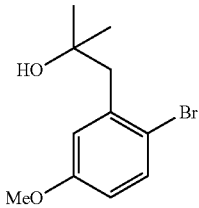

A solution of 1-(3-methoxyphenyl)-2-methylpropan-2-ol (prepared in accordance with the reference [Bioorg. Med. Chem. Lett., 2012, vol. 22, p. 1130-1135]; 1.98 g, 10.98 mmol) in $CH_3CN$ (50 mL) was added with N-bromosuccinimide (1.95 g, 10.98 mmol) and stirred at room temperature for 2 hours. The reaction mixture was concentrated under reduced pressure and purified by silica gel chromatography to obtain the title compound (yellow oil, 1.826 g, 64% yield).

$^1$H NMR (300 MHz, $CDCl_3$) δ 7.45 (d, 1H), 6.91 (d, 1H), 6.68 (dd, 1H), 3.79 (s, 3H), 2.97 (s, 2H), 1.29 (s, 6H).

<43-2> Preparation of methyl 2'-(2-hydroxy-2-methylpropyl)-4'-methoxy-2-(methoxymethoxy)-[1,1'-biphenyl]-4-carboxylate

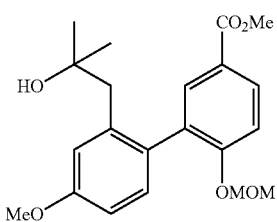

A solution of the compounds obtained in <43-1> (1.63 g, 6.301 mmol) and <2-6> (2.03 g, 6.301 mmol) in 1,4-dioxane (30 mL) was added with $K_2CO_3$ (2.61 g, 18.903 mmol) and substituted with nitrogen. The mixture was added with Pd(dppf)Cl$_2$.MC (257 mg, 0.315 mmol) and allowed to react at 90° C. for 13 hours. The reaction mixture was cooled to room temperature, added with distilled water and brine, and then extracted with EtOAc. The organic layer was dried over $MgSO_4$, concentrated under reduced pressure, and purified by silica gel chromatography to obtain the title compound (yellow oil, 2.25 g, 96% yield).

$^1$H NMR (300 MHz, $CDCl_3$) δ 8.00 (dd, 1H), 7.85 (d, 1H), 7.22 (d, 1H), 7.11 (d, 1H), 6.97 (d, 1H), 6.85 (dd, 1H), 5.21-5.07 (m, 2H), 3.88 (s, 3H), 3.85 (s, 3H), 3.38 (s, 2H), 2.88-2.55 (m, 2H), 1.03 (s, 3H), 0.99 (s, 3H).

<43-3> Preparation of methyl 2-hydroxy-2'-(2-hydroxy-2-methylpropyl)-4'-methoxy-[1,1'-biphenyl]-4-carboxylate

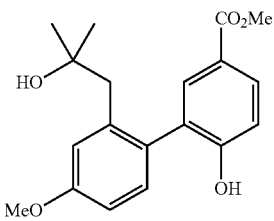 [SMILES: COC(=O)c1ccc(O)c(-c2ccc(OC)cc2CC(C)(C)O)c1]

A solution of the compound obtained in <43-2> (2.24 g, 6.780 mmol) in MeOH (35 mL) was added with p-toluenesulfonic acid monohydrate (3.87 g, 20.341 mmol) and stirred at room temperature for 19 hours. The reaction mixture was added with distilled water and neutralized by adding a saturated $NaHCO_3$ aqueous solution. The organic layer extracted with $CH_2Cl_2$ was collected, dried over $MgSO_4$, concentrated under reduced pressure, and purified by silica gel chromatography to obtain the title compound (yellow foam, 1.35 g, 68% yield).

$^1$H NMR (300 MHz, $CDCl_3$) δ 7.94 (dd, 1H), 7.79 (d, 1H), 7.14 (d, 1H), 7.00 (d, 1H), 6.97 (d, 1H), 6.89 (dd, 1H), 6.40 (br s, 1H), 3.87 (s, 3H), 3.85 (s, 3H), 2.85-2.52 (m, 2H), 1.12 (s, 6H).

<43-4> Preparation of methyl 9-methoxy-6,6-dimethyl-6,7-dihydrodibenzo[b,d]oxepin-2-carboxylate

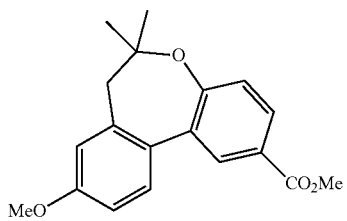 [SMILES: COC(=O)c1ccc2c(c1)-c1ccc(OC)cc1CC(C)(C)O2]

A solution of the compound <43-3> (1.35 g, 4.086 mmol) in THF (40 mL) was consecutively added with PBu$_3$ (1.5 mL, 6.129 mmol) and 1,1'-(azodicarbonyl)dipiperidine (1.547 g, 6.129 mmol), and then stirred at room temperature for 1.5 hours. The reaction mixture was concentrated under reduced pressure and purified by silica gel chromatography to obtain the title compound (white foam, 767 mg, 60% yield).

$^1$H NMR (300 MHz, $CDCl_3$) δ 8.11 (d, 1H), 7.96 (dd, 1H), 7.44 (d, 1H), 7.07 (d, 1H), 6.94 (dd, 1H), 6.80 (d, 1H), 3.92 (s, 3H), 3.87 (s, 3H), 2.59 (s, 2H), 1.42 (s, 6H).

<43-5> Preparation of methyl 9-hydroxy-6,6-dimethyl-6,7-dihydrodibenzo[b,d]oxepin-2-carboxylate

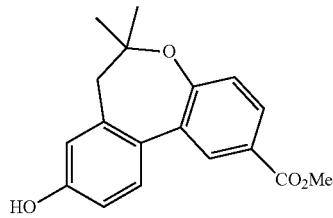 [SMILES: COC(=O)c1ccc2c(c1)-c1ccc(O)cc1CC(C)(C)O2]

To a solution of the compound obtained in <43-4> (784 mg, 2.510 mmol) in CH$_2$Cl$_2$ (20 mL) at 0° C. was slowly added dropwise BBr$_3$ (1.0M CH$_2$Cl$_2$ solution, 4.4 mL, 4.380 mmol). At the same temperature, the mixture was stirred for 2.5 hours and slowly added dropwise with MeOH. Then, the mixture was added with distilled water, extracted with CH$_2$Cl$_2$, and the organic layer was collected and dried over MgSO$_4$. The filtrate was concentrated under reduced pressure and purified by silica gel chromatography to obtain the title compound (white foam, 377 mg, 50% yield).

$^1$H NMR (300 MHz, CDCl$_3$) δ 8.11 (d, 1H), 7.96 (dd, 1H), 7.37 (d, 1H), 7.07 (d, 1H), 6.87 (dd, 1H), 6.75 (d, 1H), 5.11 (s, 1H), 3.93 (s, 3H), 2.56 (s, 2H), 1.42 (s, 6H).

<43-6> Preparation of methyl 6,6-dimethyl-9-(3-(methylsulfonyl)propoxy)-6,7-dihydrodibenzo[b,d]oxepin-2-carboxylate

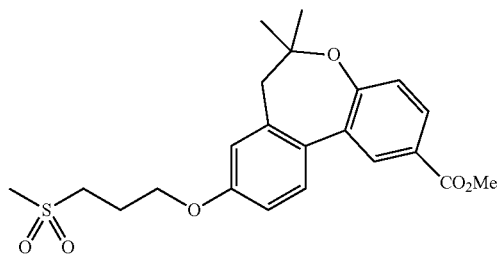 [SMILES: COC(=O)c1ccc2c(c1)-c1ccc(OCCCS(C)(=O)=O)cc1CC(C)(C)O2]

According to the procedures as described in <1-8>, the compound obtained in <43-5> was used to prepare the title compound (colorless oil, 137 mg, 88% yield).

$^1$H NMR (300 MHz, CDCl$_3$) δ 8.10 (d, 1H), 7.97 (dd, 1H), 7.44 (d, 1H), 7.07 (d, 1H), 6.92 (dd, 1H), 6.78 (d, 1H), 4.18 (t, 2H), 3.92 (s, 3H), 3.34-3.21 (m, 2H), 2.97 (s, 3H), 2.58 (s, 2H), 2.45-2.30 (m, 2H), 1.42 (s, 6H).

<43-7> Preparation of (6,6-dimethyl-9-(3-(methylsulfonyl)propoxy)-6,7-dihydrodibenzo[b,d]oxepin-2-yl)methanol

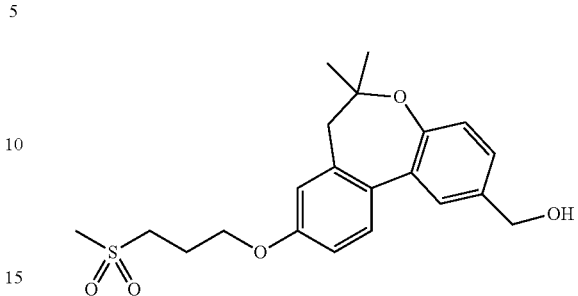

According to the procedures as described in <1-9>, the compound obtained in <43-6> was used to prepare the title compound (white foam, 105 mg, 83% yield).

$^1$H NMR (300 MHz, CDCl$_3$) δ 7.40 (s, 1H), 7.38 (d, 1H), 7.27 (d, 1H), 7.02 (d, 1H), 6.88 (dd, 1H), 6.77 (d, 1H), 4.71 (d, 2H), 4.14 (t, 2H), 3.34-3.19 (m, 2H), 2.95 (s, 3H), 2.55 (s, 2H), 2.46-2.23 (m, 2H), 1.91 (t, 1H), 1.40 (s, 6H).

<43-8> Preparation of (S)-methyl 2-(6-((6,6-dimethyl-9-(3-(methylsulfonyl)propoxy)-6,7-dihydrodibenzo[b,d]oxepin-2-yl)methoxy)-2,3-dihydrobenzofuran-3-yl)acetate

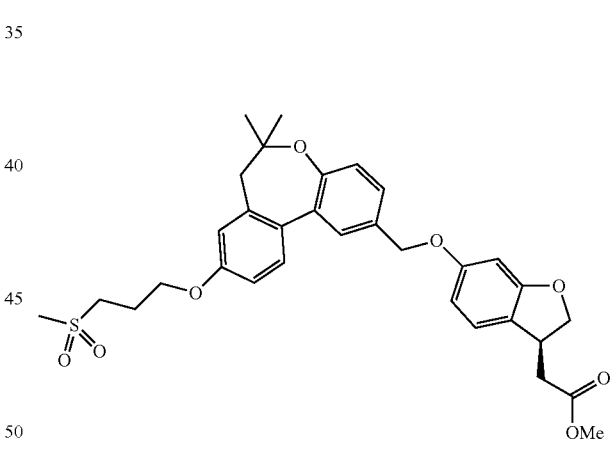

According to the procedures as described in <1-10>, the compound obtained in <43-7> was used to prepare the title compound (colorless oil, 141 mg, 90% yield).

$^1$H NMR (300 MHz, CDCl$_3$) δ 7.44 (d, 1H), 7.39 (d, 1H), 7.33 (d, 1H), 7.04 (dd, 2H), 6.89 (dd, 1H), 6.78 (d, 1H), 6.57-6.41 (m, 2H), 5.02 (s, 2H), 4.76 (t, 1H), 4.27 (dd, 1H), 4.17 (t, 2H), 3.91-3.75 (m, 1H), 3.72 (s, 3H), 3.39-3.20 (m, 2H), 2.97 (d, 3H), 2.76 (dd, 1H), 2.65-2.47 (m, 3H), 2.47-2.27 (m, 2H), 1.41 (s, 6H).

<43-9> Preparation of (S)-2-(6-((6,6-dimethyl-9-(3-(methylsulfonyl)propoxy)-6,7-dihydrodibenzo[b,d]oxepin-2-yl)methoxy)-2,3-dihydrobenzofuran-3-yl)acetic acid

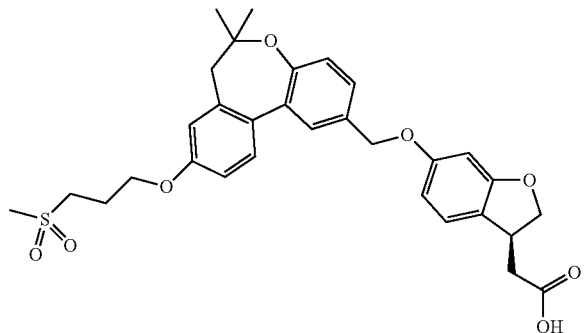 [SMILES: CC1(C)Cc2cc(OCCCS(C)(=O)=O)ccc2-c2cc(COc3ccc4c(c3)OC[C@H]4CC(=O)O)ccc2O1]

According to the procedures as described in <1-11>, the compound obtained in <43-8> was used to prepare the title compound (white foam, 126 mg, 92% yield).

MS m/z 565 [M−H]⁻.

¹H NMR (300 MHz, CDCl₃) δ 7.44 (d, 1H), 7.39 (d, 1H), 7.33 (dd, 1H), 7.09-7.02 (m, 2H), 6.89 (dd, 1H), 6.78 (d, 2H), 6.56-6.42 (m, 2H), 5.03 (s, 2H), 4.77 (t, 1H), 4.30 (dd, 1H), 4.17 (t, 2H), 3.82 (m, 1H), 3.36-3.21 (m, 2H), 2.97 (s, 3H), 2.82 (dd, 1H), 2.63 (dd, 1H), 2.57 (s, 2H), 2.45-2.29 (m, 2H), 1.41 (s, 6H).

Example 44

Preparation of (S)-2-(6-((5-ethyl-9-(3-(methylsulfonyl)propoxy)-6,7-dihydro-5H-dibenzo[b,d]azepin-2-yl)methoxy)-2,3-dihydrobenzofuran-3-yl)acetic acid

<44-1> Preparation of ethyl 3-bromo-4-nitrobenzoate

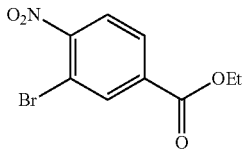 [SMILES: CCOC(=O)c1ccc([N+](=O)[O-])c(Br)c1]

Ethyl 4-amino-3-bromobenzoate (prepared in accordance with the reference [Journal of the American Chemical Society, 2002, vol. 124, p. 5350-5364]; 2.20 g, 9.01 mmol) was dissolved in CF₃CO₂H (40 mL), which was then added with hydrogen peroxide (5.67 mL, 30% aqueous solution, 50.0 mmol) and stirred for 15 hours at 60° C. The reaction mixture was concentrated, diluted with EtOAc, washed with 2N NaOH aqueous solution, NaHCO₃ aqueous solution and brine. The organic layer was dried over magnesium sulfate, concentrated under reduced pressure. The residue thus obtained was purified by silica gel chromatography to obtain the title compound (pale yellow solid, 1.94 g, 79% yield).

¹H NMR (600 MHz, CDCl₃) δ 8.39 (s, 1H), 8.10 (d, 1H), 7.85 (d, 1H), 4.44 (q, 2H), 1.43 (t, 3H).

<44-2> Preparation of ethyl 4-nitro-3-(4,4,5,5-tetramethyl-1,3,2-dioxaboran-2-yl)benzoate

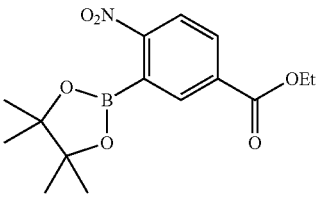 [SMILES: CCOC(=O)c1ccc([N+](=O)[O-])c(B2OC(C)(C)C(C)(C)O2)c1]

The compound obtained in <44-1> (820 mg, 2.99 mmol) and bis(pinacolato)diboron (1.14 g, 4.49 mmol) were dissolved in 1,4-dioxane (16 mL). The mixture was added with potassium acetate (881 mg, 8.89 mmol) and [1,1'-bis(diphenylphosphino)ferrocene]dichloropalladium(II) complex with dichloromethane (122 mg, 0.15 mmol), and then substituted with nitrogen. The mixture was stirred at 90° C. for 15 hours, cooled to room temperature and diluted with brine. Then, the mixture was extracted with EtOAc, dried over magnesium sulfate, filtered and concentrated under reduced pressure. The residue thus obtained was purified by silica gel chromatography to obtain the title compound (pale yellow solid, 610 mg, 64% yield).

¹H NMR (600 MHz, CDCl₃) δ 8.21-8.18 (m, 3H), 4.44 (q, 2H), 1.44 (s, 12H), 1.42 (t, 3H).

<44-3> Preparation of ethyl 2'-(2-hydroxyethyl)-4'-methoxy-2-nitro-[1,1'-biphenyl]-4-carboxylate

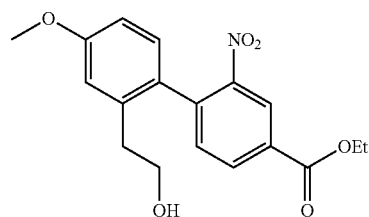 [SMILES: CCOC(=O)c1ccc(-c2ccc(OC)cc2CCO)c([N+](=O)[O-])c1]

The compound obtained in <44-2> (432 mg, 1.87 mmol) and the compound obtained in <2-2> (600 mg, 1.87 mmol) were dissolved in 1,4-dioxane (8 mL), which was then added with K₂CO₃ (775 g, 5.61 mmol) and substituted with nitrogen. Subsequently, the mixture was added with [1,1'-bis(diphenylphosphino)ferrocene]dichloropalladium(II) complex with dichloromethane (76 mg, 0.093 mmol) and stirred at 90° C. for 15 hours. The reaction mixture was cooled room temperature, added with a saturated NH₄Cl aqueous solution, and extracted with EtOAc. The organic layer was washed with brine, dried over sodium sulfate, filtered and concentrated under reduced pressure. The filtrate thus obtained was purified by silica gel chromatography to obtain the title compound (pale brown oil, 379 mg, 59% yield).

¹H NMR (600 MHz, CDCl₃) δ 8.16 (d, 1H), 8.04 (s, 1H), 7.94 (d, 1H), 7.03 (d, 1H), 6.92 (s, 1H), 6.82 (dd, 1H), 4.44-4.40 (m, 2H), 3.85 (s, 3H), 3.70 (q, 2H), 2.81-2.76 (m, 1H), 2.69-2.65 (m, 1H), 1.47 (t, 1H), 1.41 (t, 3H).

<44-4> Preparation of ethyl 2'-(2-bromoethyl)-4'-methoxy-2-nitro-[1,1'-biphenyl]-4-carboxylate

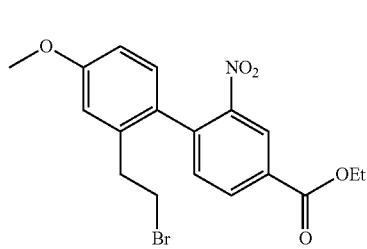 [SMILES: CCOC(=O)c1ccc(-c2ccc(OC)cc2CCBr)c([N+](=O)[O-])c1]

The compound obtained in <44-3> (370 mg, 1.07 mmol) was dissolved in dichloromethane (5 mL), which was then added with triphenylphosphine (463 mg, 1.77 mmol), pyridine (0.51 mL, 6.21 mmol), and tetrabromomethane (532 mg, 1.61 mmol) at 0° C. The reaction mixture was stirred at room temperature for 5 hours, concentrated under reduced pressure and purified by silica gel chromatography to obtain the title compound (pale yellow oil, 405 mg, 93% yield).

$^1$H NMR (600 MHz, CDCl$_3$) δ 8.18 (d, 1H), 8.04 (s, 1H), 7.96 (d, 1H), 7.03 (d, 1H), 6.89 (s, 1H), 6.83 (dd, 1H), 4.45-4.41 (m, 2H), 3.85 (s, 3H), 3.42 (t, 2H), 3.07-3.03 (m, 1H), 2.93-2.88 (m, 1H), 1.41 (t, 3H).

<44-5> Preparation of ethyl 9-methoxy-6,7-dihydro-5H-dibenzo[b,d]azepin-2-carboxylate

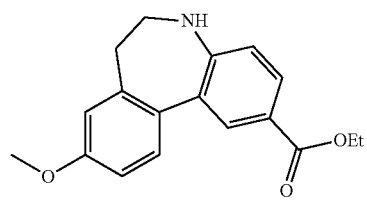 [SMILES: CCOC(=O)c1ccc2c(c1)-c1ccc(OC)cc1CCN2]

The compound obtained in <44-4> (400 mg, 0.98 mmol) was dissolved in methanol (5 mL), which was then added with 10% Pd/C (40 mg, 0.38 mmol) and stirred under a hydrogen atmosphere for 15 hours. The reaction mixture was filtered through Celite, washed with EtOAc, and the resulting filtrate was concentrated under reduced pressure. The residue thus obtained was purified by silica gel chromatography to obtain the title compound (white foam, 179 mg, 61% yield).

$^1$H NMR (600 MHz, CDCl$_3$) δ 8.04 (s, 1H), 7.79 (d, 1H), 7.43 (d, 1H), 6.90 (d, 1H), 6.74 (d, 1H), 6.68 (d, 1H), 4.36 (q, 2H), 3.85 (s, 3H), 3.80 (t, 2H), 2.89 (t, 2H), 1.38 (t, 3H).

<44-6> Preparation of ethyl 5-ethyl-9-methoxy-6,7-dihydro-5H-dibenzo[b,d]azepin-2-carboxylate

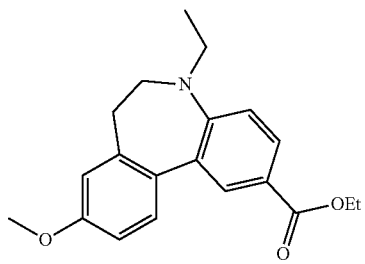 [SMILES: CCOC(=O)c1ccc2c(c1)-c1ccc(OC)cc1CCN2CC]

The compound obtained in <44-5> (35 mg, 0.118 mmol) was dissolved in DMF (1 mL), which was then slowly added with NaH (7.06 mg, 0.177 mmol) at 0° C. and stirred for 30 minutes. The mixture thus obtained was slowly added with iodoethane (14 μL, 0.177 mmol) and stirred at room temperature for 3 hours. The reaction mixture was added with water at 0° C. and extracted with EtOAc. The organic layer was dried over magnesium sulfate, and the resulting filtrate was concentrated under reduced pressure. The residue thus obtained was purified by silica gel chromatography to obtain the title compound (colorless oil, 19 mg, 50% yield).

$^1$H NMR (600 MHz, CDCl$_3$) δ 7.96-7.93 (m, 2H), 7.34 (d, 1H), 7.01 (d, 1H), 6.90 (d, 1H), 6.79 (d, 1H), 4.36 (q, 2H), 3.86 (s, 1H), 3.54 (t, 2H), 3.17 (q, 2H), 2.72 (t, 2H), 1.38 (t, 3H), 1.09 (t, 3H).

<44-7> Preparation of ethyl 5-ethyl-9-hydroxy-6,7-dihydro-5H-dibenzo[b,d]azepin-2-carboxylate

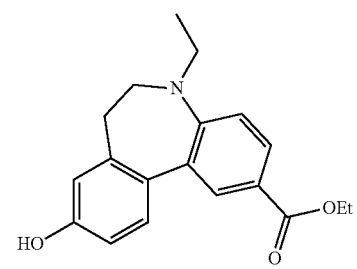 [SMILES: CCOC(=O)c1ccc2c(c1)-c1ccc(O)cc1CCN2CC]

According to the procedures as described in <1-7>, the compound obtained in <44-6> was used to prepare the title compound (white foam, 90 mg, 42% yield).

$^1$H NMR (600 MHz, CDCl$_3$) δ 7.96-7.93 (m, 2H), 7.28 (d, 1H), 7.01 (d, 1H), 6.83 (d, 1H), 6.73 (d, 1H), 5.01 (s, 1H), 4.38 (q, 2H), 3.53 (t, 2H), 3.17 (q, 2H), 2.69 (t, 2H), 1.39 (t, 3H), 1.10 (t, 3H).

<44-8> Preparation of ethyl 5-ethyl-9-(3-(methylsulfonyl)propoxy)-6,7-dihydro-5H-dibenzo[b,d]azepin-2-carboxylate

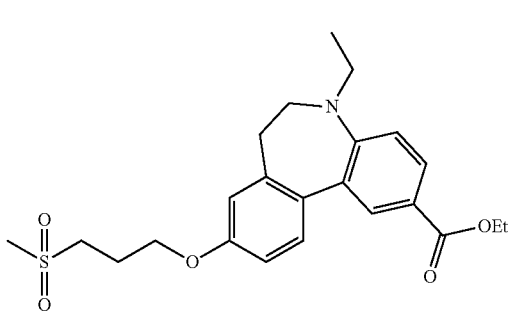 [SMILES: CCOC(=O)c1ccc2c(c1)-c1ccc(OCCCS(C)(=O)=O)cc1CCN2CC]

According to the procedures as described in <1-8>, the compound obtained in <44-7> was used to prepare the title compound (white foam, 329 mg, 85% yield).

$^1$H NMR (600 MHz, CDCl$_3$) δ 7.95-7.93 (m, 2H), 7.34-7.32 (m, 1H), 7.02 (d, 1H), 6.87 (dd, 1H), 6.77 (d, 1H), 4.37 (q, 1H), 4.17 (t, 2H), 3.55-3.52 (m, 2H), 3.29 (t, 2H), 3.17 (q, 2H), 2.97 (s, 3H), 2.72 (t, 2H), 2.37-2.35 (m, 2H), 1.38 (t, 3H), 1.09 (t, 3H).

<44-9> Preparation of (5-ethyl-9-(3-(methylsulfonyl)propoxy)-6,7-dihydro-5H-dibenzo[b,d]azepin-2-yl)methanol

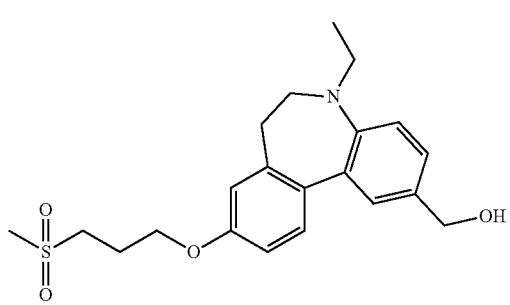 [SMILES: CCN1CCc2cc(OCCCS(C)(=O)=O)ccc2-c2cc(CO)ccc21]

According to the procedures as described in <1-9>, the compound obtained in <44-8> was used to prepare the title compound (white foam, 229 mg, 80% yield).

$^1$H NMR (600 MHz, CDCl$_3$) δ 7.31-7.29 (m, 3H), 7.04 (d, 1H), 6.86 (dd, 1H), 6.78 (d, 1H), 4.68 (d, 2H), 4.16 (t, 2H), 4.43 (t, 2H), 3.28 (t, 2H), 3.10 (q, 2H), 2.97 (s, 3H), 2.65 (t, 2H), 2.39-2.36 (m, 2H), 1.61 (t, 1H), 1.04 (t, 3H).

<44-10> Preparation of (S)-methyl 2-(6-((5-ethyl-9-(3-(methylsulfonyl)propoxy)-6,7-dihydro-5H-dibenzo[b,d]azepin-2-yl)methoxy)-2,3-dihydrobenzofuran-3-yl)acetate

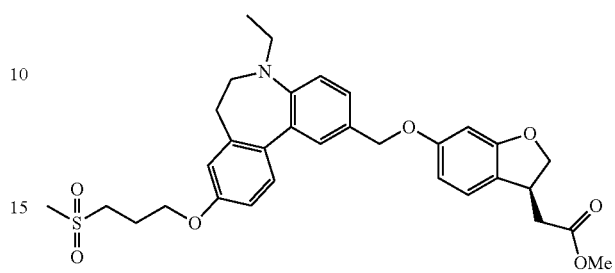

According to the procedures as described in <1-10>, the compound obtained in <44-9> was used to prepare the title compound (white foam, 33 mg, 22% yield).

$^1$H NMR (600 MHz, CDCl$_3$) δ 7.34-7.32 (m, 2H), 7.29 (d, 1H), 7.03 (d, 1H), 6.85 (dd, 1H), 6.77 (d, 1H), 6.50 (d, 1H), 6.48 (s, 1H), 4.98 (s, 2H), 4.75 (t, 2H), 4.26 (dd, 1H), 4.14 (t, 2H), 3.83-3.78 (m, 1H), 3.71 (s, 3H), 3.42 (t, 2H), 3.27 (t, 2H), 3.09 (q, 2H), 2.97 (s, 3H), 2.75 (dd, 1H), 2.65 (t, 2H), 2.55 (dd, 1H), 2.38-2.33 (m, 2H), 1.03 (t, 3H).

<44-11> Preparation of (S)-2-(6-((5-ethyl-9-(3-(methylsulfonyl)propoxy)-6,7-dihydro-5H-dibenzo[b,d]azepin-2-yl)methoxy)-2,3-dihydrobenzofuran-3-yl)acetic acid

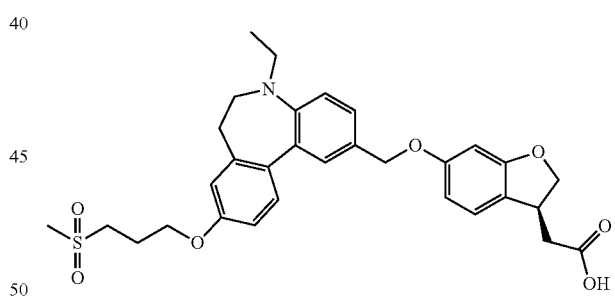

According to the procedures as described in <1-11>, the compound obtained in <44-10> was used to prepare the title compound (white foam, 58 mg, 92% yield).

MS m/z 565 [M−H]$^−$.

$^1$H NMR (600 MHz, CDCl$_3$) δ 7.35-7.34 (m, 2H), 7.30 (d, 1H), 7.05 (d, 2H), 6.85 (dd, 1H), 6.78 (d, 1H), 6.52 (d, 1H), 6.50 (s, 1H), 4.99 (s, 2H), 4.77 (t, 2H), 4.29 (dd, 1H), 4.16 (t, 2H), 3.83-3.80 (m, 1H), 3.45 (s, 3H), 3.28 (t, 2H), 3.10 (q, 2H), 2.97 (s, 3H), 2.80 (dd, 1H), 2.66 (t, 2H), 2.60 (dd, 1H), 2.39-2.35 (m, 2H), 1.75-1.70 (m, 1H), 1.57-1.53 (m, 1H), 1.43-1.39 (m, 1H), 1.04 (t, 3H).

Example 45

Preparation of (1S,2S)-2-(4-((5-ethyl-9-(3-(methylsulfonyl)propoxy)-6,7-dihydro-5H-dibenzo[b,d]azepin-2-yl)methoxy)phenyl)cyclopropanecarboxylic acid <45-1> Preparation of (1S,2S)-ethyl 2-(4-((5-ethyl-9-(3-(methylsulfonyl)propoxy)-6,7-dihydro-5H-dibenzo[b,d]azepin-2-yl)methoxy)phenyl)cyclopropanecarboxylate

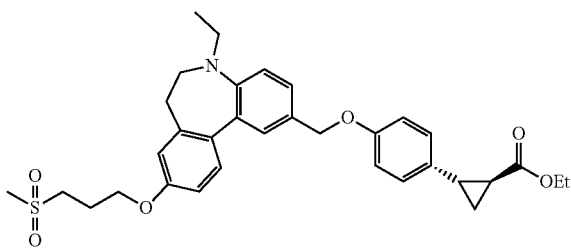

According to the procedures as described in <2-16>, the compound obtained in <44-9> was used to prepare the title compound (white foam, 98 mg, 55% yield).

$^1$H NMR (600 MHz, CDCl$_3$) δ 7.35-7.34 (m, 2H), 7.30 (d, 1H), 7.04 (d, 3H), 6.91 (d, 2H), 6.85 (dd, 1H), 6.79 (d, 1H), 5.01 (s, 2H), 4.18-4.14 (m, 4H), 3.42 (t, 2H), 3.28 (t, 2H), 3.09 (q, 2H), 2.97 (s, 3H), 2.66 (t, 2H), 2.50-2.46 (m, 1H), 2.39-2.35 (m, 2H), 1.84-1.81 (m, 1H), 1.57-1.54 (m, 2H), 1.29-1.25 (m, 5H), 1.04 (t, 3H).

<45-2> Preparation of (1S,2S)-2-(4-((5-ethyl-9-(3-(methylsulfonyl)propoxy)-6,7-dihydro-5H-dibenzo[b,d]azepin-2-yl)methoxy)phenyl)cyclopropanecarboxylic acid

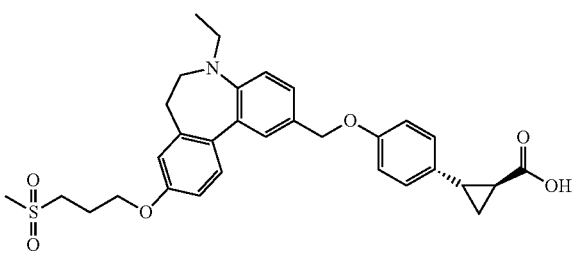

According to the procedures as described in <1-11>, the compound obtained in <45-1> was used to prepare the title compound (white foam, 69 mg, 77% yield).

MS m/z 549 [M−H]$^−$.

$^1$H NMR (600 MHz, CDCl$_3$) δ 7.34-7.33 (m, 2H), 7.28 (d, 1H), 7.05-7.02 (m, 3H), 6.92 (d, 2H), 6.84 (dd, 1H), 6.78 (d, 1H), 5.01 (s, 2H), 4.14 (t, 4H), 3.42 (t, 2H), 3.27 (t, 2H), 3.08 (q, 2H), 2.96 (s, 3H), 2.66 (t, 2H), 2.57-2.54 (m, 1H), 2.38-2.33 (m, 2H), 1.84-1.81 (m, 1H), 1.62-1.59 (m, 1H), 1.36-1.33 (m, 1H), 1.03 (t, 3H).

Example 46

Preparation of 2-((3S)-6-((9-((4-hydroxy-1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid <46-1> Preparation of methyl 9-((4-hydroxytetrahydro-2H-thiopyran-4-yl)methoxy)-11-methyl-6,7-dihydrodibenzo[b,d]oxepin-2-carboxylate

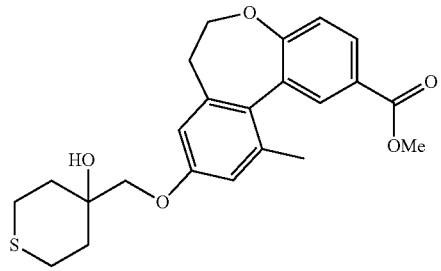 [SMILES: COC(=O)c1ccc2c(c1)-c1c(C)cc(OCC3(O)CCSCC3)cc1CCO2]

The compound obtained in <14-5> (105.6 mg, 0.37 mmol) was dissolved in DMF (4 mL), which was then added with 1-oxa-6-thiaspiro[2.5]octane 6,6-dioxide (49.3 mg, 0.38 mmol) and K$_2$CO$_3$ (77 mg, 0.56 mmol), followed by stirring at 90° C. for 12 hours. The reaction mixture was cooled to room temperature, diluted with EtOAc, and washed with a saturated NH$_4$Cl aqueous solution and brine. The organic layer was dried over Na$_2$SO$_4$, concentrated under reduced pressure, and the residue thus obtained was purified by silica gel chromatography to obtain the title compound (colorless oil, 50.7 mg, 33% yield).

$^1$H NMR (300 MHz, CDCl$_3$) δ 8.05 (d, 1H), 7.98 (dd, 1H), 7.18 (d, 1H), 6.81 (d, 1H), 6.70 (d, 1H), 4.52-4.42 (m, 2H), 3.92 (s, 3H), 3.82 (s, 2H), 3.11 (m, 2H), 2.88-2.72 (m, 1H), 2.50 (m, 3H), 2.37 (s, 3H), 2.10 (m, 2H), 1.84 (m, 2H)

<46-2> Preparation of methyl 9-((4-hydroxy-1,1-dioxidotetrahydro-2H-thiopyran-4-yl)methoxy)-11-methyl-6,7-dihydrodibenzo[b,d]oxepin-2-carboxylate

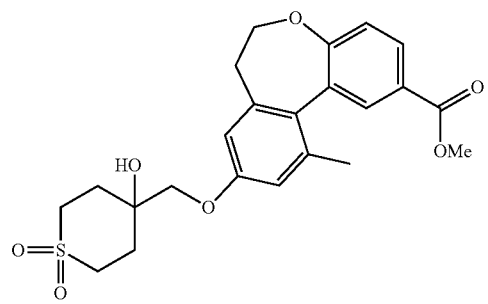 [SMILES: COC(=O)c1ccc2c(c1)-c1c(C)cc(OCC3(O)CCS(=O)(=O)CC3)cc1CCO2]

According to the procedures as described in <36-2>, the compound obtained in <46-1> was used to prepare the title compound (white foam, 84.6 mg, 92% yield).

$^1$H NMR (300 MHz, CDCl$_3$) δ 8.02 (d, 1H), 7.99 (dd, 1H), 7.19 (d, 1H), 6.81 (d, 1H), 6.70 (d, 1H), 4.50-4.45 (m, 2H), 3.92 (s, 3H), 3.91 (s, 2H), 3.50 (m, 2H), 2.96 (m, 2H), 2.83 (m, 1H), 2.52 (m, 1H), 2.38 (s, 3H), 2.27 (m, 4H)

<46-3> Preparation of 4-hydroxy-4-(((2-(hydroxymethyl)-11-methyl-6,7-dihydrodibenzo[b,d]oxepin-9-yl)oxy)methyl)tetrahydro-2H-thiopyran 1,1-dioxide

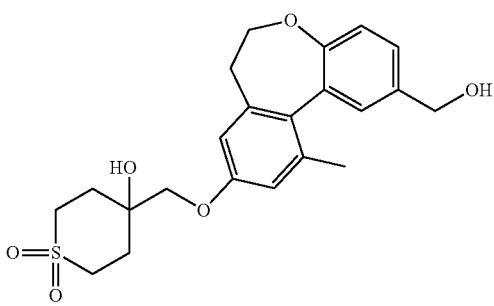 [SMILES: Cc1cc(OCC2(O)CCS(=O)(=O)CC2)cc2c1-c1cc(CO)ccc1OCC2]

According to the procedures as described in <1-9>, the compound obtained in <46-2> was used to prepare the title compound (white foam, 83.9 mg, 106% yield).

$^1$H NMR (300 MHz, CDCl$_3$) δ 7.32 (d, 1H), 7.30 (dd, 1H), 7.14 (d, 1H), 6.79 (d, 1H), 6.71 (d, 1H), 4.71 (d, 2H), 4.40 (m, 2H), 3.90 (s, 2H), 3.55-3.45 (m, 2H), 2.96 (m, 2H), 2.88-2.77 (m, 1H), 2.48 (m, 1H), 2.38 (s, 3H), 2.28 (m, 4H), 1.68 (t, 1H)

<46-4> Preparation of methyl 2-((3S)-6-((9-((4-hydroxy-1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-ylacetate

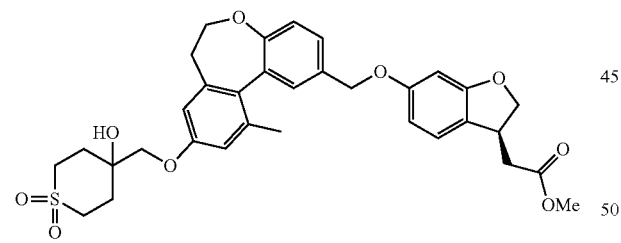

According to the procedures as described in <1-10>, the compound obtained in <46-3> was used to prepare the title compound (colorless oil, 45.2 mg, 69% yield).

$^1$H NMR (300 MHz, CDCl$_3$) δ 7.35 (dd, 1H), 7.33 (d, 1H), 7.15 (d, 1H), 7.02 (d, 1H), 6.78 (d, 1H), 6.70 (d, 1H), 6.48 (dd, 1H), 6.46 (d, 1H), 5.04 (s, 2H), 4.75 (t, 1H), 4.41 (m, 2H), 4.26 (dd, 1H), 3.90 (s, 2H), 3.81 (m, 1H), 3.72 (s, 3H), 3.55-3.45 (m, 2H), 2.95 (m, 2H), 2.84 (m, 1H), 2.75 (dd, 1H), 2.55 (dd, 1H), 2.49 (m, 1H), 2.32 (s, 3H), 2.26 (m, 4H).

<46-5> Preparation of 2-((3S)-6-((9-((4-hydroxy-1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid

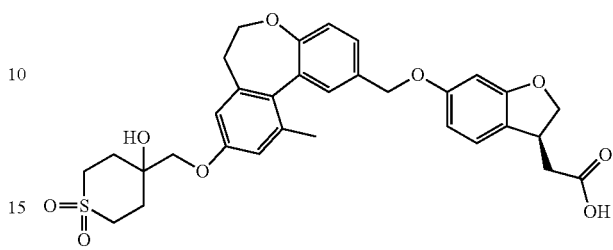

According to the procedures as described in <1-11>, the compound obtained in <46-4> was used to prepare the title compound (white foam, 20.1 mg, 46% yield).

MS m/z 593 [M−H]$^-$.

$^1$H NMR (600 MHz, CDCl$_3$) δ 7.34 (dd, 1H), 7.33 (d, 1H), 7.15 (d, 1H), 7.06 (d, 1H), 6.78 (d, 1H), 6.70 (d, 1H), 6.49 (dd, 1H), 6.46 (d, 1H), 5.04 (s, 2H), 4.77 (t, 1H), 4.41 (m, 2H), 4.29 (dd, 1H), 3.90 (s, 2H), 3.79 (m, 1H), 3.55-3.44 (m, 2H), 2.95 (m, 2H), 2.85 (m, 1H), 2.80 (dd, 1H), 2.61 (dd, 1H), 2.49 (m, 1H), 2.32 (s, 3H), 2.26 (m, 4H)

Example 47

Preparation of 2-((3S)-6-((9-((1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid

<47-1> Preparation of methyl 9-((1,1-dioxidotetrahydro-2H-thiopyran-4-yl)methoxy)-11-methyl-6,7-dihydrodibenzo[b,d]oxepin-2-carboxylate

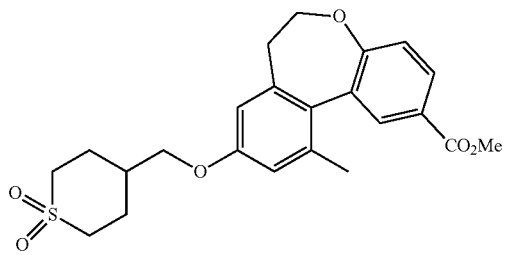 [SMILES: COC(=O)c1ccc2c(c1)-c1c(C)cc(OCC3CCS(=O)(=O)CC3)cc1CCO2]

A solution of the compound obtained in <14-5> (80 mg, 0.28 mmol) and (1,1-dioxidotetrahydro-2H-thiopyran-4-yl)methyl 4-methylbenzenesulfonate (prepared in accordance with the reference [Bioorganic and Medicinal Chemistry Letters, 2011, vol. 21, p. 1748-1753]; 108 mg, 0.34 mmol) in DMF (1 mL) was added with K$_2$CO$_3$ (50 mg, 0.36 mmol), followed by stirring at 90° C. for 14 hours. The reaction mixture was cooled to room temperature, added with distilled water, and extracted with EtOAc. The organic layer was dried over MgSO$_4$. The filtrate thus obtained was concentrated under reduced pressure and purified by silica gel chromatography (white foam, 133 mg, 110% yield).

$^1$H NMR (300 MHz, CDCl$_3$) δ 8.05-7.96 (m, 2H), 7.18 (d, 1H), 6.78 (d, 1H), 6.67 (d, 1H), 4.55-4.43 (m, 2H), 3.94-3.86

(m, 4H), 3.21-2.98 (m, 4H), 2.81 (m, 1H), 2.51 (m, 1H), 2.37 (s, 3H), 2.36-2.26 (m, 2H), 2.18-2.01 (m, 3H).

<47-2> Preparation of 4-(((2-(hydroxymethyl)-11-methyl-6,7-dihydrodibenzo[b,d]oxepin-9-yl)oxy)methyl)tetrahydro-2H-thiopyran 1,1-dioxide

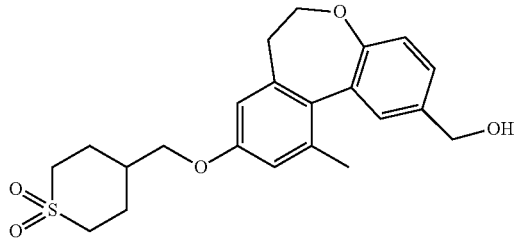 [SMILES: Cc1cc(OCC2CCS(=O)(=O)CC2)cc2c1-c1cc(CO)ccc1OCC2]

According to the procedures as described in <1-9>, the compound obtained in <47-1> was used to prepare the title compound (white foam, 57.3 mg, 51% yield).

¹H NMR (300 MHz, CDCl₃) δ 7.34-7.28 (m, 2H), 7.14 (d, 1H), 6.76 (d, 1H), 6.68 (d, 1H), 5.30 (s, 2H), 4.72 (d, 2H), 4.46-4.37 (m, 2H), 3.92 (d, 2H), 3.21-2.98 (m, 4H), 2.81 (m, 1H), 2.49 (m, 1H), 2.38 (s, 3H), 2.36-2.27 (m, 2H), 2.13-1.96 (m, 3H), 1.64 (t, 1H).

<47-3> Preparation of methyl 2-((3S)-6-((9-((1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-ylacetate

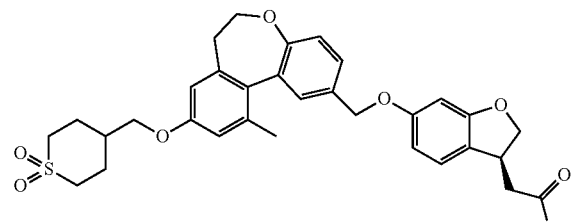

According to the procedures as described in <1-10>, the compound obtained in <47-2> was used to prepare the title compound (white foam, 71 mg, 85% yield).

¹H NMR (300 MHz, CDCl₃) δ 7.37-7.31 (m, 2H), 7.15 (d, 1H), 7.03 (d, 1H), 6.75 (d, 1H), 6.68 (d, 1H), 6.51-6.45 (m, 2H), 5.04 (s, 2H), 4.76 (t, 1H), 4.49-4.36 (m, 2H), 4.27 (d, 1H), 3.90 (d, 2H), 3.81 (m, 1H), 3.72 (s, 3H), 3.22-2.98 (m, 4H), 2.83 (m, 1H), 2.75 (dd, 1H), 2.62-2.44 (m, 2H), 2.38-2.25 (m, 5H), 2.14-1.96 (m, 3H).

<47-4> Preparation of 2-((3S)-6-((9-((1,1-dioxido-tetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid

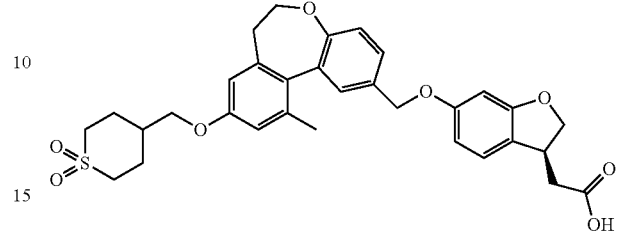

According to the procedures as described in <1-11>, the compound obtained in <47-3> was used to prepare the title compound (white foam, 47.9 mg, 69% yield).

MS m/z 577 [M−H]⁻.

¹H NMR (300 MHz, CDCl₃) δ 7.37-7.30 (m, 2H), 7.15 (d, 1H), 7.06 (d, 1H), 6.75 (d, 1H), 6.68 (d, 1H), 6.53-6.44 (m, 2H), 5.04 (s, 2H), 4.76 (t, 1H), 4.46-4.35 (m, 2H), 4.29 (d, 1H), 3.91 (d, 2H), 3.81 (m, 1H), 3.20-2.95 (m, 4H), 2.94-2.73 (m, 2H), 2.62 (dd, 1H), 2.48 (m, 1H), 2.38-2.23 (m, 5H), 2.13-1.95 (m, 3H).

Example 48

Preparation of (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)phenyl)cyclopropanecarboxylic acid <48-1> Preparation of (1S,2S)-ethyl 2-(4-((9-((1,1-dioxidotetrahydro-2H-thiopyran-4-yl)oxy)-11-methyl-6,7-dihydrodibenzo[b,d]oxepin-2-yl)methoxy)phenyl)cyclopropanecarboxylate

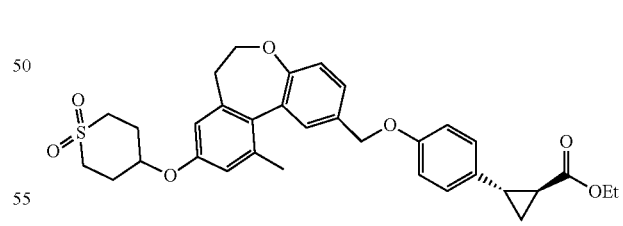

According to the procedures as described in <2-16>, the compound obtained in <36-3> was used to prepare the title compound (white foam, 42.0 mg, 52% yield).

¹H NMR (300 MHz, CDCl₃) δ 7.38-7.32 (m, 2H), 7.16 (d, 1H), 7.03 (d, 2H), 6.89 (d, 2H), 6.79 (d, 1H), 6.72 (d, 1H), 5.06 (s, 2H), 4.70 (m, 1H), 4.46-4.37 (m, 2H), 4.16 (q, 2H), 3.45 (m, 2H), 3.01-2.74 (m, 3H), 2.60-2.26 (m, 9H), 1.82 (m, 1H), 1.56 (m, 1H), 1.33-1.20 (m, 4H).

<48-2> Preparation of (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)phenyl)cyclopropanecarboxylic acid

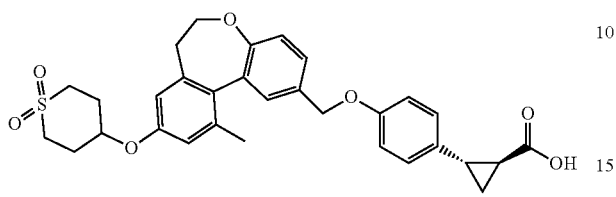

According to the procedures as described in <1-11>, the compound obtained in <48-1> was used to prepare the title compound (white foam, 36.6 mg, 91% yield).

MS m/z 571 [M+Na]⁺.

¹H NMR (300 MHz, CDCl₃) δ 7.38-7.31 (m, 2H), 7.16 (d, 1H), 7.05 (d, 2H), 6.90 (d, 2H), 6.80 (d, 1H), 6.72 (d, 1H), 5.07 (s, 2H), 4.70 (m, 1H), 4.42 (m, 2H), 3.44 (m, 2H), 3.00-2.75 (m, 3H), 2.61-2.27 (m, 9H), 1.83 (m, 1H), 1.69-1.56 (m, 1H), 1.36 (m, 1H).

Example 49

Preparation of (1S,2S)-2-(4-((9-(3-(ethylsulfonyl)propoxy)-11-methyl-6,7-dihydrodibenzo[b,d]oxepin-2-yl)methoxy)phenyl)cyclopropanecarboxylic acid <49-1> Preparation of (1S,2S)-ethyl 2-(4-((9-(3-(ethylsulfonyl)propoxy)-11-methyl-6,7-dihydrodibenzo[b,d]oxepin-2-yl)methoxy)phenyl)cyclopropanecarboxylate

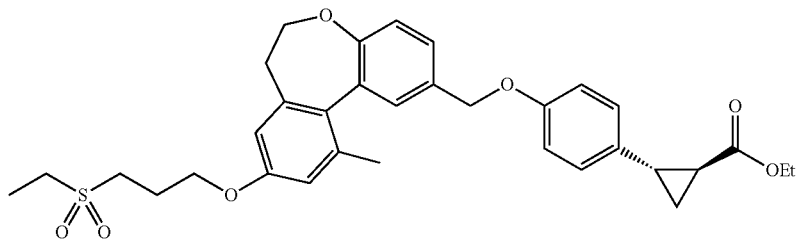 [SMILES: CCOC(=O)[C@H]1C[C@@H]1c1ccc(OCc2ccc3c(c2)-c2c(C)cc(OCCCS(=O)(=O)CC)cc2CCO3)cc1]

According to the procedures as described in <2-16>, the compound obtained in <38-2> was used to prepare the title compound (white foam, 105.8 mg, 76% yield).

¹H NMR (300 MHz, CDCl₃) δ 7.37-7.31 (m, 2H), 7.15 (d, 1H), 7.03 (d, 2H), 6.89 (d, 2H), 6.76 (d, 1H), 6.68 (d, 1H), 5.06 (s, 2H), 4.41 (d, 2H), 4.21-4.06 (m, 4H), 3.27-3.14 (m, 2H), 3.05 (q, 2H), 2.82 (m, 1H), 2.53-2.43 (m, 2H), 2.40-2.28 (m, 5H) 1.87-1.76 (m, 1H), 1.61-1.49 (m, 1H), 1.44 (t, 3H), 1.32-1.19 (m, 4H).

<49-2> Preparation of (1S,2S)-2-(4-((9-(3-(ethylsulfonyl)propoxy)-11-methyl-6,7-dihydrodibenzo[b,d]oxepin-2-yl)methoxy)phenyl)cyclopropanecarboxylic acid

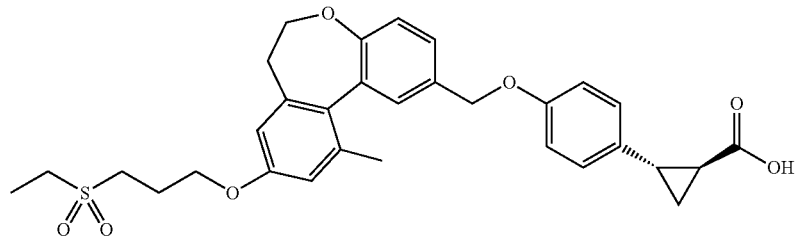 [SMILES: CCS(=O)(=O)CCCOc1cc(C)c2c(c1)CCOc1ccc(COc3ccc([C@H]4C[C@@H]4C(=O)O)cc3)cc1-2]

According to the procedures as described in <1-11>, the compound obtained in <49-1> was used to prepare the title compound (white foam, 85.8 mg, 92% yield).

MS m/z 573 [M+Na]⁺.

¹H NMR (300 MHz, CDCl₃) δ 7.39-7.30 (m, 2H), 7.15 (d, 1H), 7.04 (d, 2H), 6.90 (d, 2H), 6.76 (d, 1H), 6.68 (d, 1H), 5.06 (s, 2H), 4.41 (m, 2H), 4.14 (q, 2H), 3.26-3.13 (m, 2H), 3.05 (q, 2H), 2.82 (m, 1H), 2.63-2.43 (m, 2H), 2.43-2.25 (m, 5H), 1.89-1.76 (m, 1H), 1.69-1.56 (m, 1H), 1.44 (t, 3H), 1.35 (m, 1H).

Example 50

Preparation of (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)-2-fluorophenyl)cyclopropanecarboxylic acid <50-1> Preparation of (1S,2S)-ethyl 2-(4-((9-((1,1-dioxidotetrahydro-2H-thiopyran-4-yl)oxy)-11-methyl-6,7-dihydrodibenzo[b,d]oxepin-2-yl)methoxy)-2-fluorophenyl)cyclopropanecarboxylate

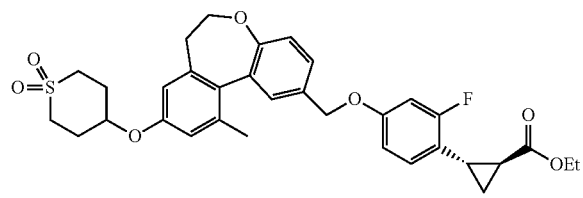 [SMILES: CCOC(=O)[C@H]1C[C@@H]1c1ccc(OCc2ccc3c(c2)-c2c(C)cc(OC4CCS(=O)(=O)CC4)cc2CCO3)cc1F]

According to the procedures as described in <40-1>, the compound obtained in <36-3> was used to prepare the title compound (white foam, 38.2 mg, 76% yield).

$^1$H NMR (300 MHz, CDCl$_3$) δ 7.37-7.31 (m, 2H), 7.17 (d, 1H), 6.88 (d, 1H), 6.80 (d, 1H), 6.72 (d, 1H), 6.70-6.63 (m, 2H), 5.05 (s, 2H), 4.69 (m, 1H), 4.42 (m, 2H), 4.16 (q, 2H), 3.45 (m, 2H), 3.01-2.78 (m, 3H), 2.60-2.27 (m, 9H), 1.84 (m, 1H), 1.60-1.51 (m, 1H), 1.33-1.22 (m, 3H).

<50-2> Preparation of (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)-2-fluorophenyl)cyclopropanecarboxylic acid

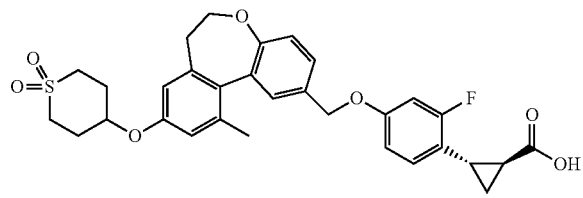 [SMILES: Cc1cc(OC2CCS(=O)(=O)CC2)cc2c1-c1cc(COc3ccc([C@H]4C[C@@H]4C(=O)O)c(F)c3)ccc1OCC2]

According to the procedures as described in <1-11>, the compound obtained in <50-1> was used to prepare the title compound (white foam, 31.9 mg, 88% yield).

MS m/z 565 [M−H]$^-$.

$^1$H NMR (300 MHz, CDCl$_3$) δ 7.37-7.30 (m, 2H), 7.17 (d, 1H), 6.88 (d, 1H), 6.80 (d, 1H), 6.72 (d, 1H), 6.74-6.64 (m, 2H), 5.05 (s, 2H), 4.70 (m, 1H), 4.42 (m, 2H), 3.44 (m, 2H), 2.95 (m, 2H), 2.90-2.76 (m, 1H), 2.68-2.59 (m, 1H), 2.57-2.26 (m, 8H), 1.85 (m, 1H), 1.61 (m, 1H), 1.37 (m, 1H).

Example 51

Preparation of (1S,2S)-2-{2-fluoro-4-[9-(4-hydroxy-1,1-dioxido-hexahydro-thiopyran-4-ylmethoxy)-11-methyl-6,7-dihydro-5-oxa-dibenzo[a,c]cyclohepten-2-ylmethoxy]-phenyl}-cyclopropanecarboxylic acid <51-1> Preparation of (1S,2S)-ethyl 2-{2-fluoro-4-[9-(4-hydroxy-1,1-dioxido-hexahydro-thiopyran-4-ylmethoxy)-11-methyl-6,7-dihydro-5-oxa-dibenzo[a,c]cyclohepten-2-ylmethoxyl]-phenyl}-cyclopropanecarboxylate

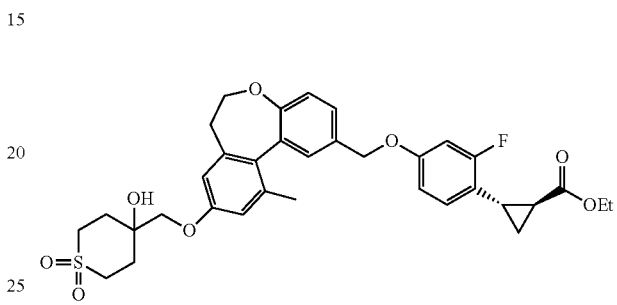

According to the procedures as described in <40-1>, the compound obtained in <46-3> was used to prepare the title compound (colorless oil, 16.3 mg, 28% yield).

$^1$H NMR (300 MHz, CDCl$_3$) δ 7.34 (dd, 1H), 7.32 (d, 1H), 7.16 (d, 1H), 7.02 (d, 1H), 6.88 (t, 1H), 6.79 (d, 1H), 6.70 (m, 2H), 6.65 (m, 1H), 5.05 (s, 2H), 4.42 (m, 2H), 4.12 (q, 2H), 3.91 (s, 2H), 3.49 (m, 2H), 2.96 (m, 2H), 2.85 (m, 1H), 2.56 (m, 1H), 2.50 (m, 1H), 2.31 (s, 3H), 2.27 (m, 4H), 1.85 (m, 1H), 1.29 (t, 3H), 1.25 (m, 1H).

<51-2> Preparation of (1S,2S)-2-{2-fluoro-4-[9-(4-hydroxy-1,1-dioxido-hexahydro-thiopyran-4-yl-methoxy)-11-methyl-6,7-dihydro-5-oxa-dibenzo[a,c]cyclohepten-2-ylmethoxyl]-phenyl}-cyclopropanecarboxylic acid

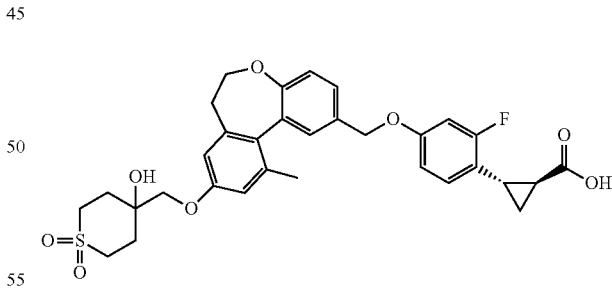

According to the procedures as described in <1-11>, the compound obtained in <51-1> was used to prepare the title compound (white foam, 3.9 mg, 25% yield).

MS m/z 595 [M−H]$^-$.

$^1$H NMR (300 MHz, CDCl$_3$) δ 7.34 (dd, 1H), 7.32 (d, 1H), 7.16 (d, 1H), 7.02 (d, 1H), 6.89 (t, 1H), 6.79 (d, 1H), 6.70 (m, 2H), 6.65 (m, 1H), 5.05 (s, 2H), 4.42 (m, 2H), 3.90 (s, 2H), 3.49 (m, 2H), 2.96 (m, 2H), 2.84 (m, 1H), 2.49 (m, 1H), 2.31 (s, 3H), 2.27 (m, 4H), 1.85 (m, 1H), 1.57 (m, 1H), 1.37 (m, 1H).

Example 52

Preparation of (1S,2S)-2-(4-(((9-((1,1-dioxidotetra-hydro-2H-thiopyran-4-yl)oxy)-11-methyl-6,7-dihydrodibenzo[b,d]oxepin-2-yl)methyl)amino)-2-fluorophenyl)cyclopropanecarboxylic acid <52-1> Preparation of 9-((1,1-dioxidotetrahydro-2H-thiopyran-4-yl)oxy)-11-methyl-6,7-dihydrodibenzo[b,d]oxepin-2-carbaldehyde

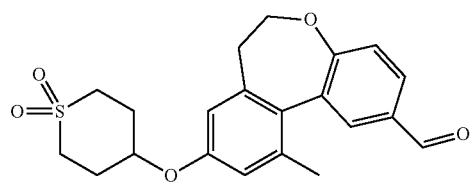 [SMILES: Cc1cc(OC2CCS(=O)(=O)CC2)cc2c1-c1cc(C=O)ccc1OCC2]

According to the procedures as described in <3-3>, the compound obtained in <36-3> was used to prepare the title compound (white foam, 31.9 mg, 88% yield).

$^1$H NMR (300 MHz, CDCl$_3$) δ 10.01 (s, 1H), 7.89-7.77 (m, 2H), 7.29 (d, 1H), 6.84 (s, 1H), 6.73 (d, 1H), 4.72 (m, 1H), 4.58-4.41 (m, 2H), 4.12 (q, 5H), 3.42 (m, 2H), 2.96 (m, 2H), 2.91-2.75 (m, 1H), 2.51 (m, 2H), 2.46-2.32 (m, 2H), 2.38 (s, 3H).

<52-2> Preparation of (1S,2S)-ethyl 2-(4-(((9-((1,1-dioxidotetrahydro-2H-thiopyran-4-yl)oxy)-11-methyl-6,7-dihydrodibenzo[b,d]oxepin-2-yl)methyl)amino)-2-fluorophenyl)cyclopropanecarboxylate

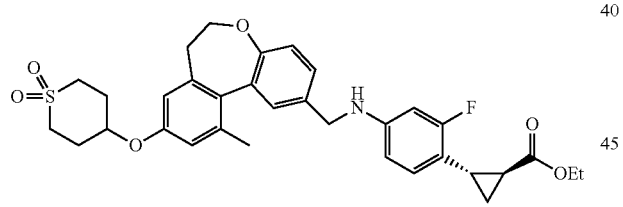

The compound obtained in <52-1> (25 mg, 0.065 mmol) and (1S,2S)-ethyl 2-(4-amino-2-fluorophenyl)cyclopropanecarboxylate (14.5 mg, 0.065 mmol) were dissolved in dichloromethane (1 mL), which was then added with AcOH (7.44 μL, 0.13 mmol) and slowly added with Na(OAc)$_3$BH (27.5 mg, 0.13 mmol) while stirring. The mixture thus obtained was stirred at room temperature for 17 hours, and then diluted with water and CH$_2$Cl$_2$. The layers thus formed were separated, and the organic layer was dried over sodium sulfate, concentrated under reduced pressure, and purified by silica gel chromatography to obtain the title compound (white foam, 29.6 mg, 77% yield).

$^1$H NMR (300 MHz, CDCl$_3$) δ 7.29-7.22 (m, 2H), 7.12 (d, 1H), 6.79 (d, 1H), 6.74 (d, 1H), 6.71 (d, 1H), 6.35-6.26 (m, 2H), 4.69 (m, 1H), 4.40 (m, 2H), 4.31 (d, 2H), 4.16 (q, 2H), 3.43 (m, 2H), 2.94 (m, 2H), 2.88-2.72 (m, 1H), 2.58-2.29 (m, 6H), 2.26 (s, 3H), 1.78 (s, 1H), 1.51 (m, 1H), 1.33-1.18 (m, 4H).

<52-3> Preparation of (1S,2S)-2-(4-(((9-((1,1-dioxidotetrahydro-2H-thiopyran-4-yl)oxy)-11-methyl-6,7-dihydrodibenzo[m]oxepin-2-yl)methyl)amino)-2-fluorophenyl)cyclopropanecarboxylic acid

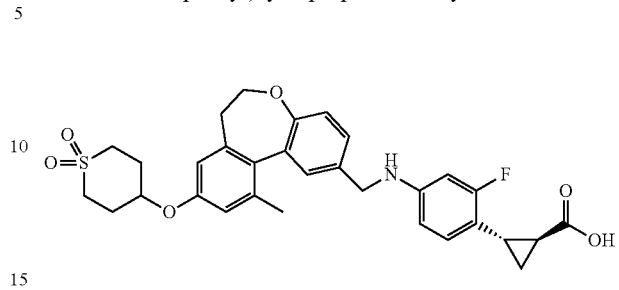

According to the procedures as described in <1-11>, the compound obtained in <52-2> was used to prepare the title compound (white foam, 23.2 mg, 82% yield).

MS m/z 564 [M–H]$^-$.

$^1$H NMR (300 MHz, CDCl$_3$) δ 7.29-7.22 (m, 2H), 7.13 (d, 1H), 6.83-6.73 (m, 2H), 6.71 (d, 1H), 6.38-6.23 (m, 2H), 4.69 (m, 1H), 4.41 (m, 2H), 4.33 (s, 2H), 3.43 (m, 2H), 2.95 (m, 2H), 2.82 (m, 1H), 2.65-2.30 (m, 6H), 2.26 (s, 3H), 1.78 (m, 1H), 1.58 (m, 1H), 1.37 (m, 1H).

Example 53

Preparation of (1S,2S)-2-(4-(((9-(3-(ethylsulfonyl)propoxy)-11-methyl-6,7-dihydrodibenzo[b,d]oxepin-2-yl)methyl)amino)-2-fluorophenyl)cyclopropanecarboxylic acid <53-1> Preparation of 9-(3-(ethylsulfonyl)propoxy)-11-methyl-6,7-dihydrodibenzo[b,d]oxepin-2-carbaldehyde

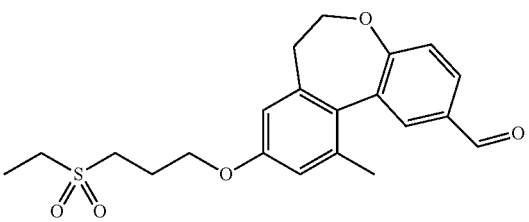 [SMILES: CCS(=O)(=O)CCCOc1cc(C)c2c(c1)CCOc1ccc(C=O)cc1-2]

According to the procedures as described in <3-3>, the compound obtained in <38-2> was used to prepare the title compound (white foam, 86.3 mg, 97% yield).

$^1$H NMR (300 MHz, CDCl$_3$) δ 10.01 (s, 1H), 7.87-7.79 (m, 2H), 7.28 (d, 1H), 6.80 (d, 1H), 6.69 (d, 1H), 4.58-4.43 (m, 2H), 4.17 (t, 2H), 3.28-3.15 (m, 2H), 3.06 (q, 2H), 2.82 (m, 1H), 2.55 (m, 1H), 2.42-2.30 (m, 2H), 2.37 (s, 3H), 1.45 (t, 3H).

<53-2> Preparation of (1S,2S)-ethyl 2-(4-(((9-(3-(ethylsulfonyl)propoxy)-11-methyl-6,7-dihydrodibenzo[b,d]oxepin-2-yl)methyl)amino)-2-fluorophenyl)cyclopropanecarboxylate

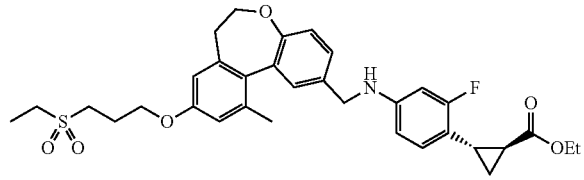 [SMILES: CCOC(=O)[C@H]1C[C@@H]1c1ccc(NCc2ccc3c(c2)-c2c(C)cc(OCCCS(=O)(=O)CC)cc2CCO3)cc1F]

According to the procedures as described in <52-2>, the compound obtained in <53-1> was used to prepare the title compound (white foam, 96.0 mg, 73% yield).

$^1$H NMR (300 MHz, CDCl$_3$) δ 7.28-7.20 (m, 2H), 7.15-7.07 (m, 1H), 6.79-6.71 (m, 2H), 6.67 (d, 1H), 6.37-6.24 (m, 2H), 4.40 (m, 2H), 4.31 (d, 2H), 4.24-4.04 (m, 4H), 3.27-3.14 (m, 2H), 3.04 (q, 2H), 2.81 (m, 1H), 2.55-2.43 (m, 2H), 2.42-2.29 (m, 2H), 2.26 (s, 3H), 1.86-1.73 (m, 1H), 1.51 (m, 1H), 1.44 (t, 3H), 1.34-1.17 (m, 4H).

<53-3> Preparation of (1S,2S)-2-(4-(((9-(3-(ethylsulfonyl)propoxy)-11-methyl-6,7-dihydrodibenzo[b,d]oxepin-2-yl)methyl)amino)-2-fluorophenyl)cyclopropanecarboxylic acid

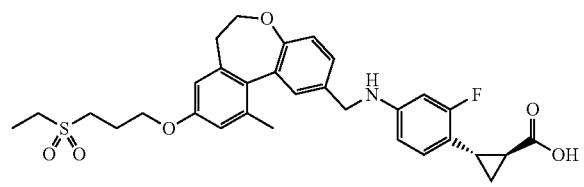 [SMILES: CCS(=O)(=O)CCCOc1cc(C)c2c(c1)CCOc1ccc(CNc3ccc([C@H]4C[C@@H]4C(=O)O)c(F)c3)cc1-2]

According to the procedures as described in <1-11>, the compound obtained in <53-2> was used to prepare the title compound (white foam, 79.8 mg, 88% yield).

MS m/z 566 [M–H]$^-$.

$^1$H NMR (300 MHz, CDCl$_3$) δ 7.28-7.22 (m, 2H), 7.12 (d, 1H), 6.82-6.72 (m, 2H), 6.68 (d, 1H), 6.36-6.27 (m, 2H), 4.40 (m, 2H), 4.32 (s, 2H), 4.13 (t, 2H), 3.27-3.15 (m, 2H), 3.05 (q, 2H), 2.80 (m, 1H), 2.59 (m, 1H), 2.49 (m, 1H), 2.34 (m, 2H), 2.26 (s, 3H), 1.79 (m, 1H), 1.63-1.51 (m, 1H), 1.44 (t, 3H), 1.36 (m, 1H).

Example 54

Preparation of 2-((3S)-6-((6,6,11-trimethyl-9-(3-(methylsulfonyl)propoxy)-6,7-dihydrodibenzo[b,d]oxepin-2-yl)methoxy)-2,3-dihydrobenzofuran-3-yl)acetic acid

<54-1> Preparation of methyl 2-(3-methoxy-5-methylphenyl)acetate

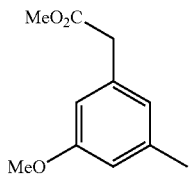

A solution of 2-(3-methoxy-5-methylphenyl)acetonitrile (prepared in accordance with the reference [Australian Journal of Chemistry, 1999, vol. 52, #11, p. 1093-1108]; 8.80 g, 54.591 mmol) in MeOH (150 mL) was slowly added dropwise with sulfuric acid (50 mL) and refluxed for 15 hours. The reaction mixture was cooled to room temperature, added with distilled water, and extracted with CH$_2$Cl$_2$. The organic layer was collected, dried over MgSO$_4$, and the filtrate thus obtained was concentrated under reduced pressure and purified by silica gel chromatography to obtain the title compound (colorless oil, 8.26 g, 78% yield).

$^1$H NMR (300 MHz, CDCl$_3$) δ 6.69 (s, 1H), 6.63 (s, 1H), 3.78 (s, 3H), 3.69 (s, 3H), 3.56 (s, 2H), 2.31 (s, 3H).

<54-2> Preparation of 1-(3-methoxy-5-methylphenyl)-2-methylpropan-2-ol

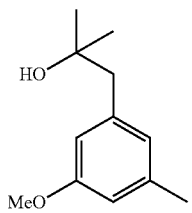

To a solution of the compound obtained <54-1> (9.66 g, 49.735 mmol) in THF (160 mL) 0° C. was added dropwise MeMgBr (3.0M Et$_2$O solution, 57 mL, 169.902 mmol). The mixture was heated to room temperature and stirred for 4.5 hours. Then, the mixture slowly added with a saturated NH$_4$Cl aqueous solution at 0° C. The reaction mixture thus obtained was added with EtOAc, a saturated NH$_4$Cl aqueous solution and distilled water, and the layers thus formed were separated. The aqueous layer was extracted with EtOAc one more time, and the organic layer was collected and dried over MgSO$_4$. The filtrate was concentrated under reduced pressure and purified by silica gel chromatography to obtain the title compound (yellow oil, 9.07 g, 94% yield).

$^1$H NMR (300 MHz, CDCl$_3$) δ 6.66-6.59 (m, 2H), 6.57 (s, 1H), 3.79 (d, 3H), 2.70 (s, 2H), 2.32 (s, 3H), 1.43 (s, 1H), 1.24 (s, 6H).

<54-3> Preparation of 1-(2-bromo-5-methoxy-3-methylphenyl)-2-methylpropan-2-ol

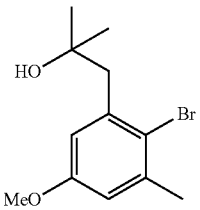

According to the procedures as described in <43-1>, the compound obtained in <54-2> was used to prepare the title compound (yellow oil, 11.93 g, 98% yield).
$^1$H NMR (600 MHz, CDCl$_3$) δ 6.74 (d, 1H), 6.70 (d, 1H), 3.76 (s, 3H), 3.03 (s, 2H), 2.40 (s, 3H), 1.54 (d, 1H), 1.28 (s, 6H).

<54-4> Preparation of methyl 2'-(2-hydroxy-2-methylpropyl)-4'-methoxy-2-(methoxymethoxy)-6'-methyl-[1,1'-biphenyl]-4-carboxylate

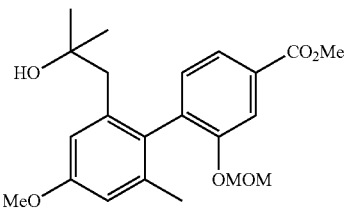

A mixed solution of the compounds obtained in <54-3> (1 g, 3.661 mmol) and <2-6> (1.77 g, 5.491 mmol) in toluene (23 mL) and distilled water (2.3 mL) was added with K$_3$PO$_4$ (301 mg, 0.732 mmol) and substituted with nitrogen. The mixture was added with Pd(OAc)$_2$ (82 mg, 0.366 mmol) and stirred at 100° C. for 18 hours. The reaction mixture thus obtained was cooled to room temperature, added with distilled water and brine, and then extracted with EtOAc. The organic layer was collected and dried over MgSO$_4$. The filtrate was concentrated under reduced pressure and purified by silica gel chromatography to obtain the title compound (yellow oil, 388 mg, 27% yield).
$^1$H NMR (300 MHz, CDCl$_3$) δ 8.02 (dd, 1H), 7.75 (d, 1H), 7.25 (d, 1H), 6.83 (d, 1H), 6.74 (d, 1H), 5.17-5.09 (m, 1H), 3.88 (s, 3H), 3.84 (s, 3H), 3.39 (s, 3H), 2.70-2.50 (m, 1H), 1.99 (s, 3H), 1.07 (s, 3H), 1.04 (s, 3H).

<54-5> Preparation of methyl 2-hydroxy-2'-(2-hydroxy-2-methylpropyl)-4'-methoxy-6'-methyl-[1,1'-biphenyl]-4-carboxylate

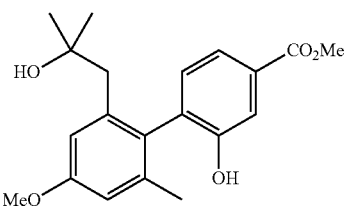 [SMILES: COC(=O)c1ccc(-c2c(C)cc(OC)cc2CC(C)(C)O)c(O)c1]

According to the procedures as described in <43-3>, the compound obtained in <54-4> was used to prepare the title compound (yellow oil, 301 mg, 83% yield).
$^1$H NMR (300 MHz, CDCl$_3$) δ 7.98 (dd, 1H), 7.71 (d, 1H), 7.02 (d, 1H), 6.86 (d, 1H), 6.78 (d, 1H), 6.03 (br s, 1H), 3.88 (s, 3H), 3.85 (s, 3H), 2.70 (d, 1H), 2.49 (d, 1H), 1.98 (s, 3H), 1.17 (s, 3H), 1.13 (s, 3H).

<54-6> Preparation of methyl 9-methoxy-6,6,11-trimethyl-6,7-dihydrodibenzo[b,d]oxepin-2-carboxylate

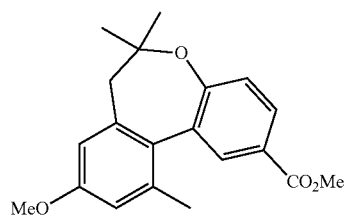 [SMILES: COC(=O)c1ccc2c(c1)-c1c(C)cc(OC)cc1CC(C)(C)O2]

According to the procedures as described in <43-4>, the compound obtained in <54-5> was used to prepare the title compound (colorless oil, 82 mg, 29% yield).
$^1$H NMR (300 MHz, CDCl$_3$) δ 8.05 (d, 1H), 7.96 (dd, 1H), 7.09 (d, 1H), 6.80 (d, 1H), 6.64 (d, 1H), 3.92 (s, 3H), 3.85 (s, 3H), 2.60 (d, 1H), 2.39 (s, 3H), 2.35 (d, 1H), 1.38 (s, 3H), 1.33 (s, 3H).

<54-7> Preparation of methyl 9-hydroxy-6,6,11-trimethyl-6,7-dihydrobenzo[b,d]oxepin-2-carboxylate

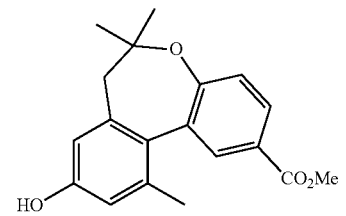 [SMILES: COC(=O)c1ccc2c(c1)-c1c(C)cc(O)cc1CC(C)(C)O2]

According to the procedures as described in <43-5>, the compound obtained in <54-6> was used to prepare the title compound (colorless oil, 52 mg, 72% yield).
$^1$H NMR (300 MHz, CDCl$_3$) δ 8.04 (d, 1H), 7.96 (dd, 1H), 7.09 (dd, 1H), 6.73 (d, 1H), 6.58 (d, 1H), 5.03 (s, 1H), 3.92 (s, 3H), 2.57 (d, 1H), 2.34 (s, 3H), 2.32 (d, 1H), 1.37 (s, 3H), 1.33 (s, 3H).

<54-8> Preparation of methyl 6,6,11-trimethyl-9-(3-(methylsulfonyl)propoxy)-6,7-dihydrodibenzo[b,d]oxepin-2-carboxylate

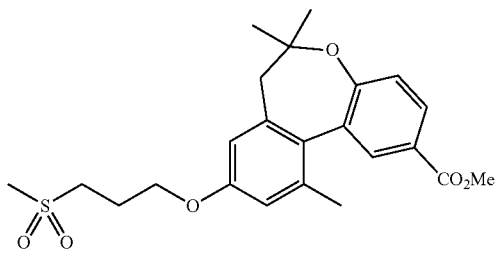 [SMILES: COC(=O)c1ccc2c(c1)-c1c(C)cc(OCCCS(C)(=O)=O)cc1CC(C)(C)O2]

According to the procedures as described in <1-8>, the compound obtained in <54-7> was used to prepare the title compound (colorless oil, 71 mg, 99% yield).

$^1$H NMR (300 MHz, CDCl$_3$) δ 8.04 (d, 1H), 7.97 (dd, 1H), 7.09 (d, 1H), 6.78 (d, 1H), 6.62 (d, 1H), 4.16 (t, 2H), 3.92 (s, 3H), 3.29 (m, 2H), 2.98 (s, 3H), 2.59 (d, 1H), 2.45-2.28 (m, 6H), 1.38 (d, 3H), 1.33 (d, 3H).

<54-9> Preparation of (6,6,11-trimethyl-9-(3-(methylsulfonyl)propoxy)-6,7-dihydrodibenzo[b,d]oxepin-2-yl)methanol

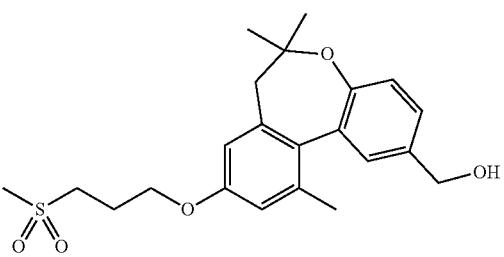 [SMILES: Cc1cc(OCCCS(C)(=O)=O)cc2c1-c1cc(CO)ccc1OC(C)(C)C2]

According to the procedures as described in <1-9>, the compound obtained in <54-8> was used to prepare the title compound (colorless oil, 60 mg, 90% yield).

$^1$H NMR (300 MHz, CDCl$_3$) δ 7.32 (d, 1H), 7.27 (d, 1H), 7.04 (d, 1H), 6.76 (d, 1H), 6.61 (d, 1H), 4.70 (s, 2H), 4.15 (t, 2H), 3.37-3.18 (m, 2H), 2.96 (s, 3H), 2.59 (d, 1H), 2.40-2.28 (m, 6H), 1.36 (s, 3H), 1.30 (s, 3H).

<54-10> Preparation of methyl 2-((3S)-6-((6,6,11-trimethyl-9-(3-(methylsulfonyl)propoxy)-6,7-dihydrodibenzo[b,d]oxepin-2-yl)methoxy)-2,3-dihydrobenzofuran-3-ylacetate

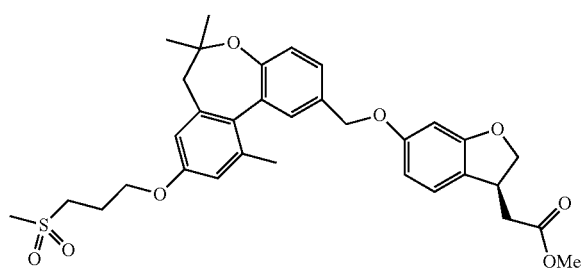 [SMILES: COC(=O)C[C@@H]1COc2cc(OCc3ccc4c(c3)-c3c(C)cc(OCCCS(C)(=O)=O)cc3CC(C)(C)O4)ccc21]

According to the procedures as described in <1-10>, the compound obtained in <54-9> was used to prepare the title compound (colorless oil, 68 mg, 77% yield).

$^1$H NMR (300 MHz, CDCl$_3$) δ 7.36 (d, 1H), 7.32 (dd, 1H), 7.09-6.99 (m, 2H), 6.75 (d, 1H), 6.61 (d, 1H), 6.53-6.45 (m, 2H), 5.03 (s, 2H), 4.76 (t, 1H), 4.35-4.23 (m, 1H), 4.15 (t, 2H), 3.87-3.75 (m, 1H), 3.72 (s, 3H), 3.34-3.21 (m, 2H), 2.97 (s, 3H), 2.75 (m, 1H), 2.68-2.50 (m, 2H), 2.42-2.23 (m, 6H), 1.37 (s, 3H), 1.31 (s, 3H).

<54-11> Preparation of 2-((3S)-6-((6,6,11-trimethyl-9-(3-(methylsulfonyl)propoxy)-6,7-dihydrodibenzo[b,d]oxepin-2-yl)methoxy)-2,3-dihydrobenzofuran-3-yl)acetic acid

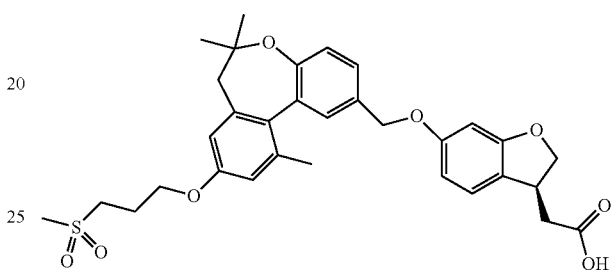

According to the procedures as described in <1-11>, the compound obtained in <54-10> was used to prepare the title compound (white foam, 57 mg, 86% yield).

MS m/z 579 [M−H]$^−$.

$^1$H NMR (300 MHz, CDCl$_3$) δ 7.35 (d, 1H), 7.31 (dd, 1H), 7.06 (dd, 2H), 6.75 (d, 1H), 6.61 (d, 1H), 6.54-6.45 (m, 2H), 5.03 (s, 2H), 4.77 (t, 1H), 4.29 (dd, 1H), 4.15 (t, 2H), 3.90-3.75 (m, 1H), 3.34-3.22 (m, 2H), 2.97 (s, 3H), 2.82 (dd, 1H), 2.68-2.56 (m, 2H), 2.44-2.25 (m, 6H), 1.37 (s, 3H), 1.30 (s, 3H).

Example 55

Preparation of 2-((3S)-6-((9-((1,1-dioxidotetrahydro-2H-thiopyran-4-yl)oxy)-11-methyl-6,7-dihydro-5H-dibenzo[a,c][7]annulen-2-yl)methoxy)-2,3-dihydrobenzofuran-3-yl)acetic acid <55-1> Preparation of methyl 9-((1,1-dioxidotetrahydro-2H-thiopyran-4-yl)oxy)-11-methyl-6,7-dihydro-5H-dibenzo[a,c][7]annulene-2-carboxylate

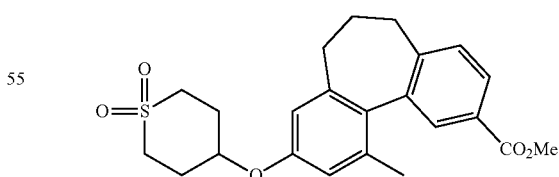

A solution of the compound obtained in <7-6> (180 mg, 0.638 mmol) and 1,1-dioxidotetrahydro-2H-thiopyran-4-yl 4-methylbenzenesulfonate (388 mg, 1.275 mmol) in DMF (3.2 mL) was added with K$_2$CO$_3$ (176 mg, 1.275 mmol), followed by stirring at 90° C. for 14 hours. The reaction mixture was cooled to room temperature, added with a saturated NH$_4$Cl aqueous solution and distilled water, and then extracted with EtOAc. The organic layer was dried over MgSO$_4$. The filtrate was concentrated under reduced pressure and purified by silica gel chromatography to obtain the title compound (white foam, 213 mg, 81% yield).

$^1$H NMR (300 MHz, CDCl$_3$) δ 7.96-7.89 (m, 2H), 7.31 (d, 1H), 6.78 (d, 1H), 6.67 (d, 1H), 4.70 (m, 1H), 3.92 (s, 3H), 3.46 (t, 2H), 3.03-2.89 (m, 2H), 2.65-2.14 (m, 11H), 2.05 (m, 2H).

<55-2> Preparation of 4-((10-(hydroxymethyl)-1-methyl-6,7-dihydro-5H-dibenzo[a,c][7]annulen-3-yl)oxy)tetrahydro-2H-thiopyran 1,1-dioxide

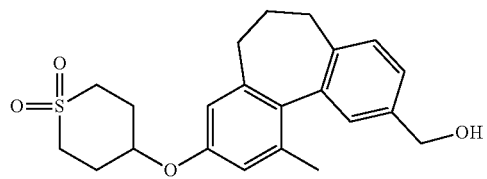 [SMILES: Cc1cc(OC2CCS(=O)(=O)CC2)cc2c1-c1cc(CO)ccc1CCC2]

According to the procedures as described in <1-9>, the compound obtained in <55-1> was used to prepare the title compound (colorless oil, 158 mg, 80% yield).

$^1$H NMR (300 MHz, CDCl$_3$) δ 7.29-7.20 (m, 3H), 6.77 (d, 1H), 6.66 (d, 1H), 4.70 (m, 3H), 3.46 (t, 2H), 2.95 (m, 2H), 2.59-2.17 (m, 11H), 2.11-1.95 (m, 2H), 1.76 (br s, 1H).

<55-3> Preparation of methyl 2-((3S)-6-((9-((1,1-dioxidotetrahydro-2H-thiopyran-4-yl)oxy)-11-methyl-6,7-dihydro-5H-dibenzo[a,c][7]annulen-2-yl)methoxy)-2,3-dihydrobenzofuran-3-ylacetate

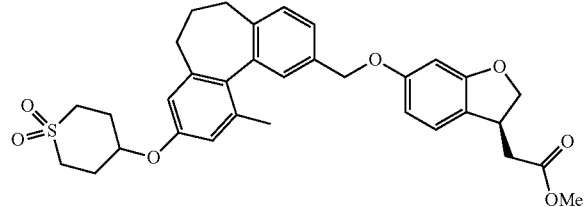 [SMILES: COC(=O)C[C@@H]1COc2cc(OCc3ccc4c(c3)-c3c(C)cc(OC5CCS(=O)(=O)CC5)cc3CCC4)ccc21]

According to the procedures as described in <1-10>, the compound obtained in <55-2> was used to prepare the title compound (white foam, 103 mg, 88% yield).

$^1$H NMR (300 MHz, CDCl$_3$) δ 7.35-7.19 (m, 3H), 7.02 (d, 1H), 6.75 (d, 1H), 6.66 (d, 1H), 6.54-6.42 (m, 2H), 5.04 (s, 2H), 4.75 (t, 1H), 4.69 (m, 1H), 4.26 (dd, 1H), 3.87-3.74 (m, 1H), 3.72 (s, 3H), 3.46 (t, 2H), 2.95 (m, 2H), 2.75 (dd, 1H), 2.62-2.28 (m, 9H), 2.24 (s, 3H), 2.05 (m, 2H).

<55-4> Preparation of 2-((3S)-6-((9-((1,1-dioxido-tetrahydro-2H-thiopyran-4-yl)oxy)-11-methyl-6,7-dihydro-5H-dibenzo[a,c][7]annulen-2-yl)methoxy)-2,3-dihydrobenzofuran-3-yl)acetic acid

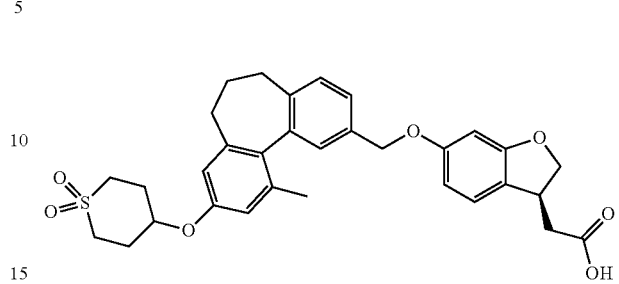

According to the procedures as described in <1-11>, the compound obtained in <55-3> was used to prepare the title compound (white foam, 84 mg, 84% yield).

MS m/z 561 [M−H]$^−$.

$^1$H NMR (300 MHz, CDCl$_3$) δ 7.33-7.20 (m, 3H), 7.06 (d, 1H), 6.75 (d, 1H), 6.66 (d, 1H), 6.54-6.43 (m, 2H), 5.05 (s, 2H), 4.76 (t, 1H), 4.69 (m, 1H), 4.29 (dd, 1H), 3.81 (m, 1H), 3.46 (t, 2H), 3.03-2.89 (m, 2H), 2.81 (dd, 1H), 2.62 (dd, 1H), 2.57-2.28 (m, 8H), 2.24 (s, 3H), 2.04 (m, 2H).

Example 56

Preparation of 2-((3S)-6-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)-2,3-dihydrobenzofuran-3-yl) acetic acid <56-1> Preparation of methyl 9-((4-hydroxytetrahydro-2H-thiopyran-4-yl)methoxy)-11-methyl-6,7-dihydro-5H-dibenzo[a,c][7]annulene-2-carboxylate

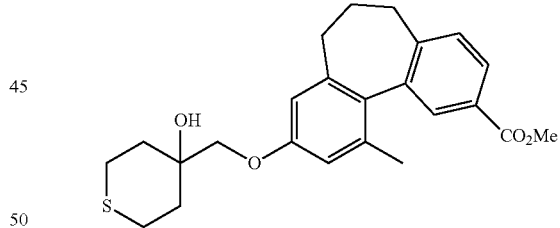

A solution of the compound obtained in <7-6> (240 mg, 0.850 mmol) and 1-oxa-6-thiaspiro[2.5]octane (prepared in accordance with the reference [WO 2005/63729 A1]; 363 mg, 2.787 mmol) in DMF (4.3 mL) was added with K$_2$CO$_3$ (235 mg, 1.700 mmol) and KI (28 mg, 0.170 mmol), followed by stirring at 90° C. for 15 hours. The reaction mixture was cooled to room temperature, added with a saturated NH$_4$Cl aqueous solution and distilled water, and extracted with EtOAc. The organic layer was collected, washed with brine and dried over MgSO$_4$. The filtrate was concentrated under reduced pressure and purified by silica gel chromatography to obtain the title compound (white foam, 317 mg, 90% yield).

$^1$H NMR (300 MHz, CDCl$_3$) δ 7.95-7.88 (m, 2H), 7.30 (d, 1H), 6.77 (d, 1H), 6.66 (d, 1H), 3.91 (d, 3H), 3.82 (s, 2H), 3.21-3.02 (m, 2H), 2.63-2.33 (m, 5H), 2.31 (s, 3H), 2.28-2.18 (m, 1H), 2.17 (s, 1H), 2.16-1.96 (m, 4H), 1.91-1.76 (m, 2H).

<56-2> Preparation of methyl 9-((4-hydroxy-1,1-dioxidotetrahydro-2H-thiopyran-4-yl)methoxy)-11-methyl-6,7-dihydro-5H-dibenzo[a,c][7]annulen-2-carboxylate

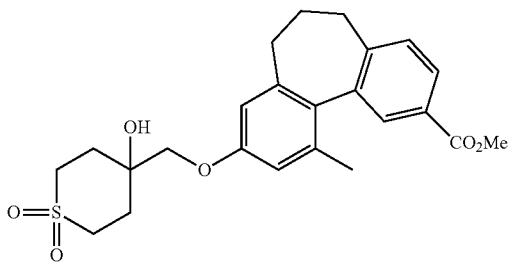 [SMILES: COC(=O)c1ccc2c(c1)-c1c(C)cc(OCC3(O)CCS(=O)(=O)CC3)cc1CCC2]

A solution of the compound obtained in <56-1> (314 mg, 0.761 mmol) in CH$_2$Cl$_2$ (8 mL) was added with MCPBA (<77%, 358 mg, 1.598 mmol) at 0° C., and then stirred at the same temperature for 2 hours. The mixture was slowly added dropwise with a saturated Na$_2$S$_2$O$_3$ aqueous solution at 0° C. and then added with distilled water. The reaction mixture was added with a saturated NaHCO$_3$ aqueous solution so that the pH was adjusted to 8, and then extracted with CH$_2$Cl$_2$. The organic layer was collected, dried over MgSO$_4$, and then the filtrate thus obtained was concentrated under reduced pressure and silica gel chromatography to obtain the title compound (white foam, 338 mg, ~100% yield).

$^1$H NMR (300 MHz, CDCl$_3$) δ 7.99-7.88 (m, 2H), 7.31 (d, 1H), 6.77 (d, 1H), 6.65 (d, 1H), 3.91 (s, 3H), 3.61-3.40 (m, 2H), 3.06-2.87 (m, 2H), 2.58 (m, 1H), 2.52-2.16 (m, 11H), 2.11-1.99 (m, 2H).

<56-3> Preparation of 4-hydroxy-4-(((10-(hydroxymethyl)-1-methyl-6,7-dihydro-5H-dibenzo[a,c][7]annulen-3-yl)oxy)methyl)tetrahydro-2H-thiopyran 1,1-dioxide

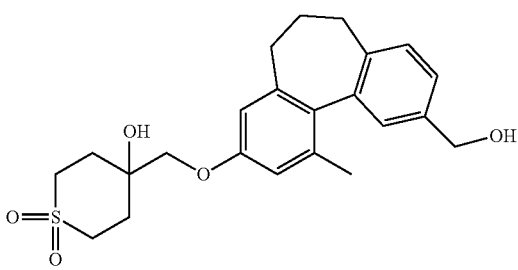 [SMILES: Cc1cc(OCC2(O)CCS(=O)(=O)CC2)cc2c1-c1cc(CO)ccc1CCC2]

According to the procedures as described in <1-9>, the compound obtained in <56-2> was used to prepare the title compound (white foam, 288 mg, 92% yield).

$^1$H NMR (300 MHz, CDCl$_3$) δ 7.28-7.21 (m, 3H), 6.75 (d, 1H), 6.65 (d, 1H), 4.72 (d, 2H), 3.90 (s, 2H), 3.57-3.42 (m, 2H), 3.05-2.86 (m, 2H), 2.60-2.18 (m, 12H), 2.08-1.96 (m, 2H), 1.63 (t, 1H).

<56-4> Preparation of methyl 2-((3S)-6-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)-2,3-dihydrobenzofuran-3-ylacetate

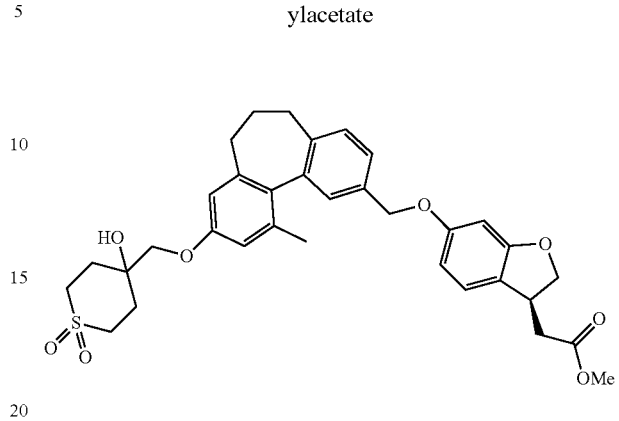

According to the procedures as described in <1-10>, the compound obtained in <56-3> was used to prepare the title compound (white foam, 86 mg, 84% yield).

$^1$H NMR (300 MHz, CDCl$_3$) δ 7.34-7.20 (m, 3H), 7.02 (d, 1H), 6.74 (d, 1H), 6.65 (d, 1H), 6.52-6.42 (m, 2H), 5.04 (s, 2H), 4.75 (t, 1H), 4.26 (dd, 1H), 3.90 (s, 2H), 3.86-3.75 (m, 1H), 3.72 (s, 3H), 3.59-3.41 (m, 2H), 2.96 (m, 2H), 2.75 (dd, 1H), 2.62-2.37 (m, 4H), 2.37-2.16 (m, 9H), 2.08-1.96 (m, 2H).

<56-5> Preparation of 2-((3S)-6-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)-2,3-dihydrobenzofuran-3-yl)acetic acid

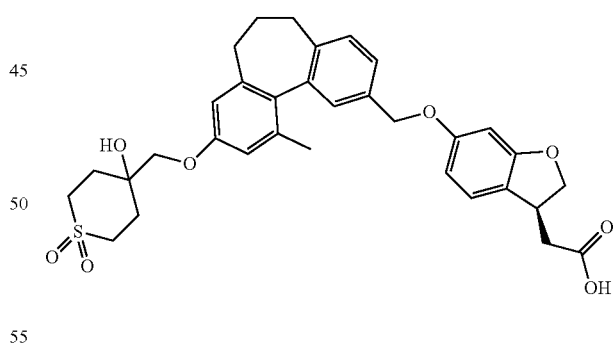

According to the procedures as described in <1-11>, the compound obtained in <56-4> was used to prepare the title compound (white foam, 49 mg, 58% yield).

MS m/z 591 [M−H]$^-$.

$^1$H NMR (300 MHz, CDCl$_3$) δ 7.33-7.20 (m, 3H), 7.05 (d, 1H), 6.74 (d, 1H), 6.65 (d, 1H), 6.55-6.42 (m, 2H), 5.05 (s, 2H), 4.76 (t, 1H), 4.29 (dd, 1H), 3.90 (s, 2H), 3.81 (m, 1H), 3.60-3.40 (m, 2H), 3.03-2.89 (m, 2H), 2.81 (dd, 1H), 2.62 (dd, 1H), 2.57-2.17 (m, 11H), 2.05 (m, 2H).

Example 57

Preparation of 2-((3S)-6-((9-(3-(ethylsulfonyl)propoxy)-11-methyl-6,7-dihydro-5H-dibenzo[a,c][7]annulen-2-yl)methoxy)-2,3-dihydrobenzofuran-3-yl)acetic acid <57-1> Preparation of methyl 9-(3-(ethylsulfonyl)propoxy)-11-methyl-6,7-dihydro-5H-dibenzo[a,c][7]annulene-2-carboxylate

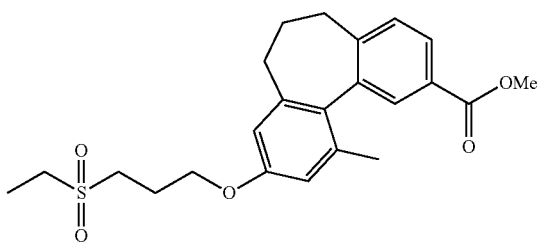 [SMILES: CCS(=O)(=O)CCCOc1cc(C)c2c(c1)CCCc1ccc(C(=O)OC)cc1-2]

The compound obtained in <7-6> (130 mg, 0.46 mmol) was in DMF (5 mL), which was added with 1-chloro-3-(ethylsulfonyl)propane (143 mg, 0.84 mmol), K₂CO₃ (371 mg, 1.38 mmol) and KI (30 mg, 0.18 mmol), followed by stirring at 90° C. for 7 hours. The reaction mixture was cooled to room temperature, diluted with EtOAc and a saturated ammonium chloride aqueous solution, followed by extraction. The organic layer was dried over sodium sulfate, concentrated under reduced pressure, and the residue thus obtained was purified by silica gel chromatography to obtain the title compound (colorless oil, 172 mg, 90% yield).

¹H NMR (300 MHz, CDCl₃) δ 7.93-7.90 (m, 2H), 7.30 (d, 1H), 6.74 (d, 1H), 6.63 (d, 1H), 4.15 (t, 2H), 3.91 (s, 3H), 3.22 (dd, 2H), 3.06 (q, 2H), 2.60-2.16 (m, 6H), 2.30 (s, 3H), 2.09-1.97 (m, 2H), 1.45 (t, 3H).

<57-2> Preparation of (9-(3-(ethylsulfonyl)propoxy)-11-methyl-6,7-dihydro-5H-dibenzo[a,c][7]annulen-2-yl)methanol

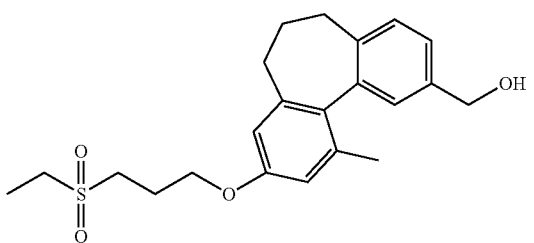 [SMILES: CCS(=O)(=O)CCCOc1cc(C)c2c(c1)CCCc1ccc(CO)cc1-2]

According to the procedures as described in <1-9>, the compound obtained in <57-1> was used to prepare the title compound (white foam, 138 mg, 86% yield).

¹H NMR (300 MHz, CDCl₃) δ 7.27-7.23 (m, 3H), 6.73 (d, 1H), 6.62 (d, 1H), 4.71 (d, 2H), 4.15 (t, 2H), 3.21 (dd, 2H), 3.05 (q, 2H), 2.54-2.19 (m, 6H), 2.30 (s, 3H), 2.05-1.96 (m, 2H), 1.61 (t, 1H), 1.45 (t, 3H).

<57-3> Preparation of methyl 2-((3S)-6-((9-(3-(ethylsulfonyl)propoxy)-11-methyl-6,7-dihydro-5H-dibenzo[a,c][7]annulen-2-yl)methoxy)-2,3-dihydrobenzofuran-3-yl)acetate

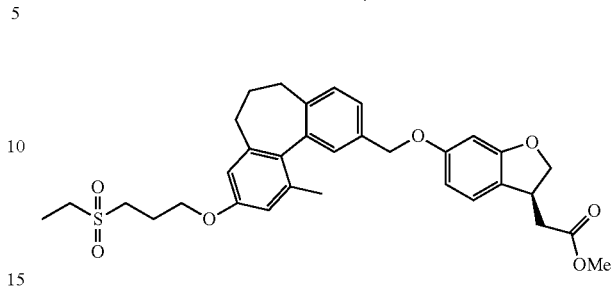

According to the procedures as described in <1-10>, the compound obtained in <57-2> was used to prepare the title compound (white foam, 83 mg, 86% yield).

¹H NMR (300 MHz, CDCl₃) δ 7.30-7.22 (m, 3H), 7.02 (d, 1H), 6.72 (d, 1H), 6.62 (d, 1H), 6.51-6.45 (m, 2H), 5.04 (s, 2H), 4.75 (t, 1H), 4.26 (dd, 1H), 4.14 (t, 2H), 3.84-3.77 (m, 1H), 3.72 (s, 3H), 3.22 (dd, 2H), 3.05 (q, 2H), 2.75 (dd, 1H), 2.60-2.21 (m, 7H), 2.24 (s, 3H), 2.07-1.95 (m, 2H), 1.45 (t, 3H).

<57-4> Preparation of 2-((3S)-6-((9-(3-(ethylsulfonyl)propoxy)-11-methyl-6,7-dihydro-5H-dibenzo[a,c][7]annulen-2-yl)methoxy)-2,3-dihydrobenzofuran-3-yl)acetic acid

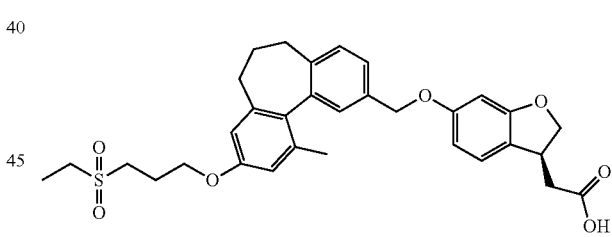

According to the procedures as described in <1-11>, the compound obtained in <57-3> was used to prepare the title compound (white foam, 53 mg, 67% yield).

MS m/z 563 [M−H]⁻.

¹H NMR (300 MHz, CDCl₃) δ 7.30-7.22 (m, 3H), 7.05 (d, 1H), 6.72 (d, 1H), 6.62 (d, 1H), 6.52-6.47 (m, 2H), 5.05 (s, 2H), 4.76 (t, 1H), 4.28 (dd, 1H), 4.14 (t, 2H), 3.84-3.78 (m, 1H), 3.21 (dd, 2H), 3.05 (q, 2H), 2.81 (dd, 1H), 2.61 (dd, 1H), 2.53-2.21 (m, 6H), 2.24 (s, 3H), 2.07-1.96 (m, 2H), 1.44 (t, 3H).

Example 58

Preparation of (1S,2S)-2-(4-((1-methyl-9-(3-(methylsulfonyl)propoxy)-6,7-dihydro-5H-dibenzo[a,c][7]annulen-2-yl)methoxy)phenyl)cyclopropanecarboxylic acid <58-1> Preparation of (1S,2S)-ethyl 2-(4-((11-methyl-9-(3-(methylsulfonyl)propoxy)-6,7-dihydro-5H-dibenzo[a,c][7]annulen-2-yl)methoxy)phenyl)cyclopropanecarboxylate

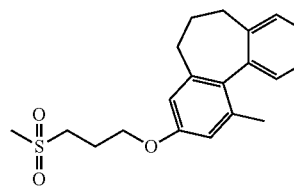

According to the procedures as described in <2-16>, the compound obtained in <7-8> was used to prepare the title compound (white foam, 77 mg, 79% yield).

$^1$H NMR (300 MHz, CDCl$_3$) δ 7.30-7.22 (m, 3H), 7.02 (d, 2H), 6.89 (d, 2H), 6.72 (d, 1H), 6.62 (d, 1H), 5.06 (s, 2H), 4.20-4.11 (m, 4H), 3.28 (dd, 2H), 2.97 (s, 3H), 2.54-2.20 (m, 7H), 2.24 (s, 3H), 2.07-1.96 (m, 2H), 1.84-1.78 (m, 1H), 1.58-1.52 (m, 1H), 1.28 (t, 3H), 1.27-1.21 (m, 1H).

<58-2> Preparation of (1S,2S)-2-(4-((11-methyl-9-(3-(methylsulfonyl)propoxy)-6,7-dihydro-5H-dibenzo[a,c][7]annulen-2-yl)methoxy)phenyl)cyclopropanecarboxylic acid

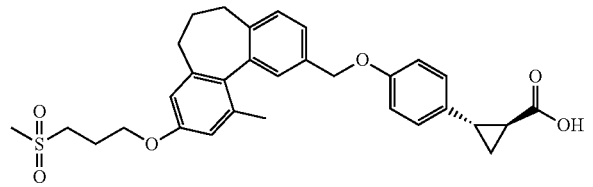 [SMILES: Cc1cc(OCCCS(C)(=O)=O)cc2c1-c1cc(COc3ccc([C@H]4C[C@@H]4C(=O)O)cc3)ccc1CCC2]

According to the procedures as described in <1-11>, the compound obtained in <58-1> was used to prepare the title compound (white foam, 54 mg, 76% yield).

MS m/z 533 [M−H]$^-$.

$^1$H NMR (300 MHz, CDCl$_3$) δ 7.30-7.22 (m, 3H), 7.03 (d, 2H), 6.90 (d, 2H), 6.72 (d, 1H), 6.62 (d, 1H), 5.07 (s, 2H), 4.14 (t, 2H), 3.28 (dd, 2H), 2.97 (s, 3H), 2.59-2.21 (m, 7H), 2.23 (s, 3H), 2.07-1.96 (m, 2H), 1.85-1.79 (m, 1H), 1.64-1.58 (m, 1H), 1.38-1.32 (m, 1H).

Example 59

Preparation of (1S,2S)-2-(4-((9-((1,1-dioxidotetrahydro-2H-thiopyran-4-yl)oxy)-11-methyl-6,7-dihydro-5H-dibenzo[a,c][7]annulen-2-yl)methoxy)phenyl)cyclopropanecarboxylic acid <59-1> Preparation of (1S,2S)-ethyl 2-(4-((9-((1,1-dioxidotetrahydro-2H-thiopyran-4-yl)oxy)-11-methyl-6,7-dihydro-5H-dibenzo[a,c][7]annulen-2-yl)methoxy)phenyl)cyclopropanecarboxylate

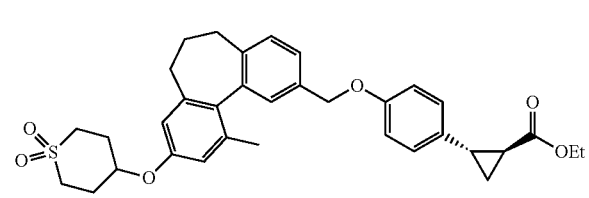 [SMILES: CCOC(=O)[C@H]1C[C@@H]1c1ccc(OCc2ccc3c(c2)-c2c(C)cc(OC4CCS(=O)(=O)CC4)cc2CCC3)cc1]

According to the procedures as described in <2-16>, the compound obtained in <55-2> was used to prepare the title compound (white foam, 97 mg, 82% yield).

$^1$H NMR (300 MHz, CDCl$_3$) δ 7.35-7.21 (m, 3H), 7.03 (m, 2H), 6.94-6.84 (m, 2H), 6.75 (d, 1H), 6.66 (d, 1H), 5.07 (s, 2H), 4.69 (m, 1H), 4.16 (q, 2H), 3.46 (t, 2H), 3.03-2.88 (m, 2H), 2.61-2.27 (m, 9H), 2.24 (s, 3H), 2.12-1.94 (m, 2H), 1.81 (m, 1H), 1.61-1.49 (m, 1H), 1.32-1.21 (m, 4H).

<59-2> Preparation of (1S,2S)-2-(4-((9-((1,1-dioxidotetrahydro-2H-thiopyran-4-yl)oxy)-11-methyl-6,7-dihydro-5H-dibenzo[a,c][7]annulen-2-yl)methoxy)phenyl)cyclopropanecarboxylic acid

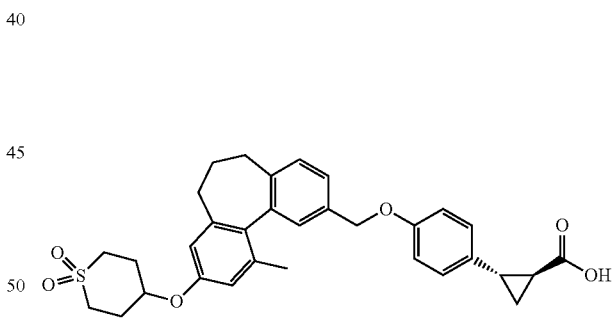

According to the procedures as described in <1-11>, the compound obtained in <59-1> was used to prepare the title compound (white foam, 82 mg, 89% yield).

MS m/z 545 [M−H]$^-$.

$^1$H NMR (300 MHz, CDCl$_3$) δ 7.34-7.20 (m, 3H), 7.07-6.99 (m, 2H), 6.94-6.85 (m, 2H), 6.75 (d, 1H), 6.66 (d, 1H), 5.07 (s, 2H), 4.69 (m, 1H), 3.46 (t, 2H), 3.03-2.87 (m, 2H), 2.61-2.27 (m, 9H), 2.23 (s, 3H), 2.11-1.96 (m, 2H), 1.81 (m, 1H), 1.62 (m, 1H), 1.35 (m, 1H).

Example 60

Preparation of (1S,2S)-2-(4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid <60-1> Preparation of (1S,2S)-ethyl 2-(4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylate

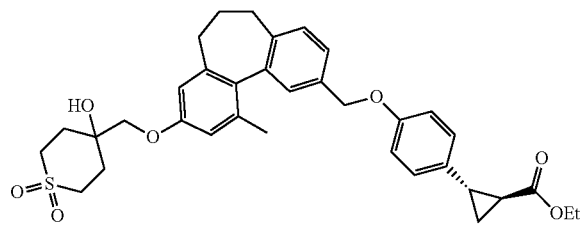 [SMILES: CCOC(=O)[C@H]1C[C@@H]1c1ccc(OCc2ccc3c(c2)-c2c(C)cc(OCC4(O)CCS(=O)(=O)CC4)cc2CCC3)cc1]

According to the procedures as described in <1-10>, the compound obtained in <56-3> was used to prepare the title compound (colorless oil, 84 mg, 83% yield).

¹H NMR (300 MHz, CDCl₃) δ 7.33-7.20 (m, 3H), 7.06-6.96 (m, 2H), 6.93-6.83 (m, 2H), 6.74 (d, 1H), 6.65 (d, 1H), 5.06 (s, 2H), 4.14 (q, 2H), 3.90 (s, 2H), 3.58-3.38 (m, 2H), 3.07-2.85 (m, 2H), 2.59-2.16 (m, 13H), 2.05 (m, 2H), 1.89-1.76 (m, 1H), 1.58-1.50 (m, 2H), 1.27 (m, 4H).

<60-2> Preparation of (1S,2S)-2-(4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid

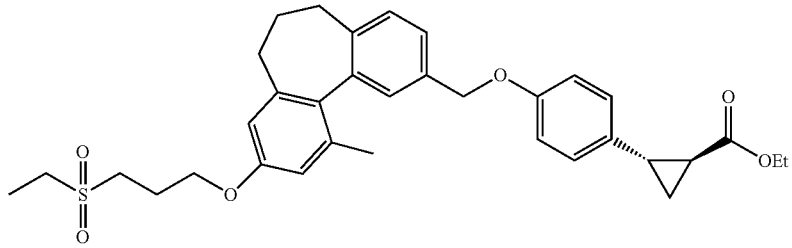 [SMILES: CCOC(=O)[C@H]1C[C@@H]1c1ccc(OCc2ccc3c(c2)-c2c(C)cc(OCCCS(=O)(=O)CC)cc2CCC3)cc1]

According to the procedures as described in <1-11>, the compound obtained in <60-1> was used to prepare the title compound (white foam, 47 mg, 59% yield).

MS m/z 575 [M–H]⁻.

¹H NMR (300 MHz, CDCl₃) δ 7.34-7.20 (m, 3H), 7.10-6.96 (m, 2H), 6.95-6.82 (m, 2H), 6.74 (d, 1H), 6.65 (d, 1H), 5.07 (s, 2H), 3.90 (s, 2H), 3.60-3.36 (m, 2H), 3.05-2.86 (m, 2H), 2.63-2.16 (m, 12H), 2.03 (m, 2H), 1.82 (m, 1H), 1.62 (m, 1H), 1.35 (m, 1H).

Example 61

Preparation of (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylic acid <61-1> Preparation of (1S,2S)-ethyl 2-(4-((9-(3-(ethylsulfonyl)propoxy)-11-methyl-6,7-dihydro-5H-dibenzo[a,c][7]annulen-2-yl)methoxy)phenyl)cyclopropanecarboxylate

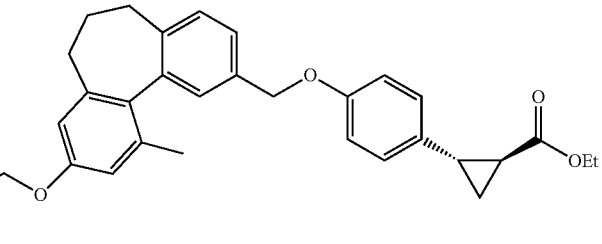

According to the procedures as described in <2-16>, the compound obtained in <57-2> was used to prepare the title compound (white foam, 89 mg, 86% yield).

¹H NMR (300 MHz, CDCl₃) δ 7.30-7.22 (m, 3H), 7.02 (d, 2H), 6.89 (d, 2H), 6.72 (d, 1H), 6.62 (d, 1H), 5.06 (s, 2H), 4.20-4.13 (m, 4H), 3.21 (dd, 2H), 3.05 (q, 2H), 2.53-2.21 (m, 7H), 2.24 (s, 3H), 2.07-1.97 (m, 2H), 1.84-1.78 (m, 1H), 1.58-1.52 (m, 1H), 1.45 (t, 3H), 1.28 (t, 3H), 1.27-1.21 (m, 1H).

<61-2> Preparation of (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylic acid

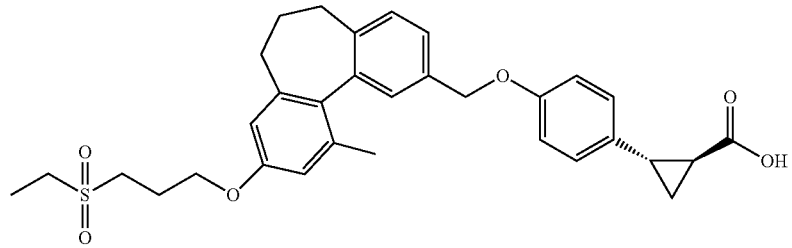 [SMILES: CCS(=O)(=O)CCCOc1cc(C)c2c(c1)CCCc1ccc(COc3ccc([C@H]4C[C@@H]4C(=O)O)cc3)cc1-2]

According to the procedures as described in <1-11>, the compound obtained in <61-1> was used to prepare the title compound (white foam, 59 mg, 72% yield).

MS m/z 547 [M−H]⁻.

¹H NMR (300 MHz, CDCl₃) δ 7.30-7.22 (m, 3H), 7.03 (d, 2H), 6.90 (d, 2H), 6.72 (d, 1H), 6.62 (d, 1H), 5.07 (s, 2H), 4.14 (t, 2H), 3.21 (dd, 2H), 3.05 (q, 2H), 2.59-2.21 (m, 7H), 2.23 (s, 3H), 2.07-1.96 (m, 2H), 1.85-1.79 (m, 1H), 1.65-1.58 (m, 1H), 1.45 (t, 3H), 1.38-1.32 (m, 1H).

Example 62

Preparation of (1S,2S)-2-(2-fluoro-4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid <61-1> Preparation of (1S,2S)-ethyl 2-(2-fluoro-4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylate

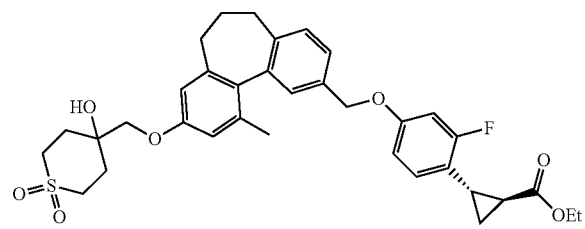 [SMILES: CCOC(=O)[C@H]1C[C@@H]1c1ccc(OCc2ccc3c(c2)-c2c(C)cc(OCC4(O)CCS(=O)(=O)CC4)cc2CCC3)cc1F]

According to the procedures as described in <40-1>, the compound obtained in <56-3> was used to prepare the title compound (colorless oil, 85 mg, 81% yield).

¹H NMR (300 MHz, CDCl₃) δ 7.33-7.20 (m, 3H), 6.87 (t, 1H), 6.74 (d, 1H), 6.71-6.60 (m, 3H), 5.05 (s, 2H), 4.23-4.06 (q, 2H), 3.90 (s, 2H), 3.50 (m, 2H), 3.03-2.87 (m, 2H), 2.64-2.17 (m, 13H), 2.05 (m, 2H), 1.85 (m, 1H), 1.54 (m, 1H), 1.35-1.20 (m, 4H).

<62-2> Preparation of (1S,2S)-2-(2-fluoro-4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid

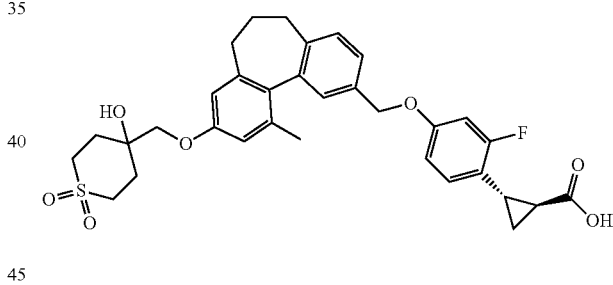

According to the procedures as described in <1-11>, the compound obtained in <62-1> was used to prepare the title compound (white foam, 39 mg, 48% yield).

MS m/z 593 [M−H]⁻.

¹H NMR (300 MHz, CDCl₃) δ 7.33-7.20 (m, 3H), 6.88 (t, 1H), 6.75 (d, 1H), 6.71-6.60 (m, 3H), 5.06 (s, 2H), 3.90 (s, 2H), 3.48 (m, 2H), 2.96 (m, 2H), 2.64 (m, 1H), 2.58-2.15 (m, 11H), 2.03 (m, 2H), 1.90-1.79 (m, 1H), 1.62 (m, 1H), 1.44-1.31 (m, 1H).

Example 63

Preparation of (1S,2S)-2-(2-fluoro-4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid <63-1> Preparation of 9-((4-hydroxy-1,1-dioxidotetrahydro-2H-thiopyran-4-yl)methoxy)-11-methyl-6,7-dihydro-5H-dibenzo[a,c][7]annulen-2-carbaldehyde

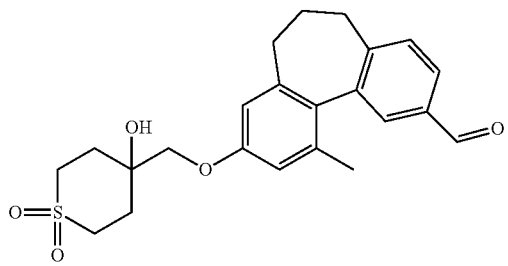 [SMILES: Cc1cc(OCC2(O)CCS(=O)(=O)CC2)cc2c1-c1cc(C=O)ccc1CCC2]

According to the procedures as described in <3-3>, the compound obtained in <56-3> was used to prepare the title compound (colorless oil, 72 mg, ~100% yield).

$^1$H NMR (300 MHz, CDCl$_3$) δ 10.02 (s, 1H), 7.86-7.67 (m, 2H), 7.42 (d, 1H), 6.78 (d, 1H), 6.67 (d, 1H), 3.92 (s, 2H), 3.62-3.41 (m, 2H), 3.06-2.88 (m, 2H), 2.69-2.05 (m, 14H).

<63-2> Preparation of (1S,2S)-ethyl 2-(2-fluoro-4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylate

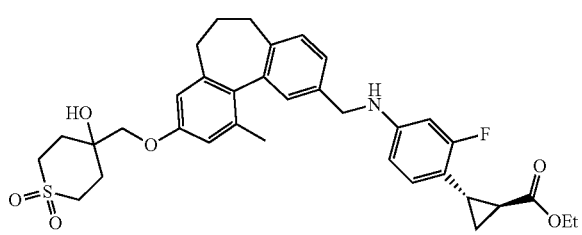 [SMILES: CCOC(=O)[C@H]1C[C@@H]1c1ccc(NCc2ccc3c(c2)-c2c(C)cc(OCC4(O)CCS(=O)(=O)CC4)cc2CCC3)cc1F]

According to the procedures as described in <52-2>, the compound obtained in <63-1> was used to prepare the title compound (colorless oil, 97 mg, 90% yield).

$^1$H NMR (300 MHz, CDCl$_3$) δ 7.23-7.14 (m, 3H), 6.80-6.68 (m, 2H), 6.64 (d, 1H), 6.37-6.22 (m, 2H), 4.32 (s, 2H), 4.14 (q, 2H), 3.89 (s, 2H), 3.58-3.36 (m, 2H), 3.04-2.85 (m, 2H), 2.58-2.22 (m, 10H), 2.20 (s, 3H), 2.05 (m, 2H), 1.79 (m, 1H), 1.50 (m, 1H), 1.27 (m, 4H).

<63-3> Preparation of (1S,2S)-2-(2-fluoro-4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid

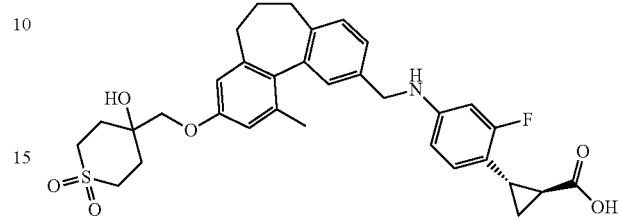

According to the procedures as described in <1-11>, the compound obtained in <63-2> was used to prepare the title compound (white foam, 69 mg, 74% yield).

MS m/z 592 [M−H]$^-$.

$^1$H NMR (300 MHz, CDCl$_3$) δ 7.23-7.13 (m, 3H), 6.81-6.68 (m, 2H), 6.64 (d, 1H), 6.30 (m, 2H), 4.33 (s, 2H), 3.89 (s, 2H), 3.59-3.39 (m, 2H), 2.96 (m, 2H), 2.65-2.13 (m, 12H), 2.03 (d, 2H), 1.84-1.74 (m, 1H), 1.57 (m, 1H), 1.35 (m, 1H).

Example 64

Preparation of (S)-2-(6-((9-((1,1-dioxidotetrahydro-2H-thiopyran-4-yl)oxy)-6,7-dihydro-5H-dibenzo[a,c][7]annulen-2-yl)methoxy)-2,3-dihydrobenzofuran-3-yl)acetic acid <64-1> Preparation of methyl 9-((1,1-dioxidotetrahydro-2H-thiopyran-4-yl)oxy)-6,7-dihydro-5H-dibenzo[a,c][7]annulen-2-carboxylate

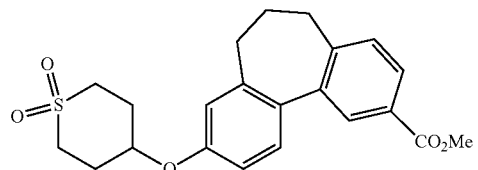

According to the procedures as described in <55-1>, the compound obtained in <5-7> was used to prepare the title compound (colorless oil, 467 mg, 131% yield).

$^1$H NMR (300 MHz, CDCl$_3$) δ 8.01 (d, 1H), 7.94 (dd, 1H), 7.34 (d, 1H), 7.29 (d, 1H), 6.89 (dd, 1H), 6.83 (d, 1H), 4.72 (s, 1H), 3.93 (s, 3H), 3.53-3.41 (m, 2H), 2.90 (m, 2H), 2.59-2.30 (m, 8H), 2.22 (m, 2H).

<64-2> Preparation of 4-((10-(hydroxymethyl)-6,7-dihydro-5H-dibenzo[a,c][7]annulen-3-yl)oxy)tetrahydro-2H-thiopyran 1,1-dioxide

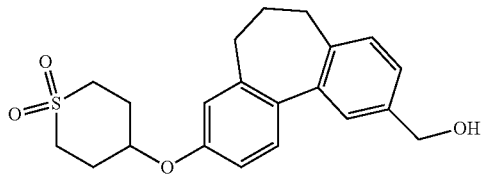 [SMILES: O=S1(=O)CCC(Oc2ccc3c(c2)CCCc2ccc(CO)cc2-3)CC1]

According to the procedures as described in <1-9>, the compound obtained in <64-1> was used to prepare the title compound (white foam, 329.5 mg, 87% yield).

¹H NMR (300 MHz, CDCl₃) δ 7.38-7.20 (m, 3H), 6.89 (dd, 1H), 6.83 (d, 1H), 4.73 (m, 3H), 3.58-3.37 (m, 2H), 2.96 (m, 2H), 2.47 (m, 8H), 2.19 (m, 2H), 1.69 (t, 1H).

<64-3> Preparation of (S)-methyl 2-(6-((9-((1,1-dioxidotetrahydro-2H-thiopyran-4-yl)oxy)-6,7-dihydro-5H-dibenzo[a,c][7]annulen-2-yl)methoxy)-2,3-dihydrobenzofuran-3-yl)acetate

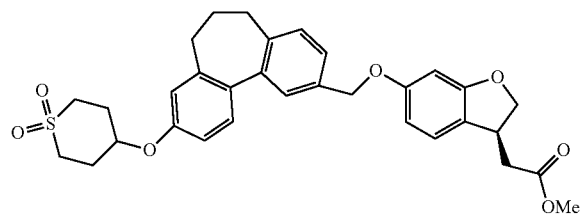 [SMILES: COC(=O)C[C@@H]1COc2cc(OCc3ccc4c(c3)-c3ccc(OC5CCS(=O)(=O)CC5)cc3CCC4)ccc21]

According to the procedures as described in <1-10>, the compound obtained in <64-2> was used to prepare the title compound (yellow foam, 140.5 mg, 83% yield).

¹H NMR (300 MHz, CDCl₃) δ=7.39-7.30 (m, 3H), 7.24 (d, 1H), 7.04 (d, 1H), 6.88 (dd, 1H), 6.83 (d, 1H), 6.55-6.44 (m, 2H), 5.04 (s, 2H), 4.76 (t, 1H), 4.71 (br s, 1H), 4.27 (dd, 1H), 3.81 (m, 1H), 3.72 (s, 3H), 3.53-3.38 (m, 2H), 2.96 (m, 2H), 2.76 (dd, 1H), 2.63-2.24 (m, 9H), 2.18 (m, 2H).

<64-4> Preparation of (S)-2-(6-((9-((1,1-dioxidotetrahydro-2H-thiopyran-4-yl)oxy)-6,7-dihydro-5H-dibenzo[a,c][7]annulen-2-yl)methoxy)-2,3-dihydrobenzofuran-3-yl)acetic acid

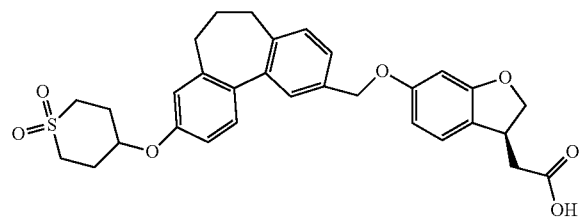 [SMILES: O=C(O)C[C@@H]1COc2cc(OCc3ccc4c(c3)-c3ccc(OC5CCS(=O)(=O)CC5)cc3CCC4)ccc21]

According to the procedures as described in <1-11>, the compound obtained in <64-3> (white foam, 51.4 mg, 38% yield).

MS m/z 547 [M−H]⁻.

¹H NMR (300 MHz, DMSO-d₆) δ=7.36 (s, 1H), 7.34-7.24 (m, 3H), 7.11 (d, 1H), 7.05-6.94 (m, 2H), 6.53-6.42 (m, 2H), 5.07 (s, 2H), 4.77 (m, 1H), 4.68 (t, 1H), 4.19 (m, 1H), 3.68 (m, 1H), 3.21 (t, 4H), 2.70 (dd, 1H), 2.56-2.46 (m, 1H), 2.45-2.32 (m, 4H), 2.32-2.17 (m, 4H), 2.12 (m, 2H).

Example 65

Preparation of (S)-2-(6-((9-((4-hydroxy-1,1-dioxido-tetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid

<65-1> Preparation of methyl 9-((4-hydroxytetrahydro-2H-thiopyran-4-yl)methoxy)-6,7-dihydro-5H-dibenzo[a,c][7]annulen-2-carboxylate

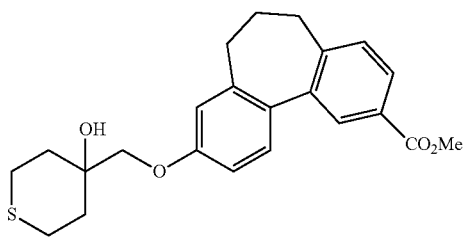 [SMILES: COC(=O)c1ccc2c(c1)-c1ccc(OCC3(O)CCSCC3)cc1CCC2]

According to the procedures as described in <56-1>, the compound obtained in <5-7> was used to prepare the title compound (white foam, 290 mg, 81% yield).

¹H NMR (300 MHz, CDCl₃) δ 8.01 (d, 1H), 7.93 (dd, 1H), 7.35 (d, 1H), 7.30 (d, 1H), 6.89 (dd, 1H), 6.82 (d, 1H), 3.93 (s, 3H), 3.84 (s, 2H), 3.20-3.03 (m, 2H), 2.61-2.40 (m, 6H), 2.27-2.07 (m, 5H), 1.92-1.77 (m, 2H).

<65-2> Preparation of methyl 9-((4-hydroxy-1,1-dioxidotetrahydro-2H-thiopyran-4-yl)methoxy)-6,7-dihydro-5H-dibenzo[a,c][7]annulene-2-carboxylate

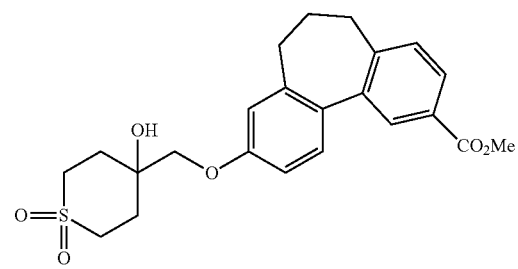

According to the procedures as described in <56-2>, the compound obtained in <65-1> was used to prepare the title compound (white foam, 292 mg, 94% yield).

¹H NMR (300 MHz, CDCl₃) δ 8.01 (d, 1H), 7.94 (dd, 1H), 7.37 (d, 1H), 7.31 (d, 1H), 6.89 (dd, 1H), 6.83 (d, 1H), 3.93 (s, 3H), 3.51 (m, 2H), 2.97 (m, 2H), 2.55 (t, 2H), 2.50-2.42 (m, 3iH), 2.36-2.16 (m, 6H).

<65-3> Preparation of 4-hydroxy-4-(((10-(hydroxymethyl)-6,7-dihydro-5H-dibenzo[a,c][7]annulen-3-yl)oxy)methyl)tetrahydro-2H-thiopyran 1,1-dioxide

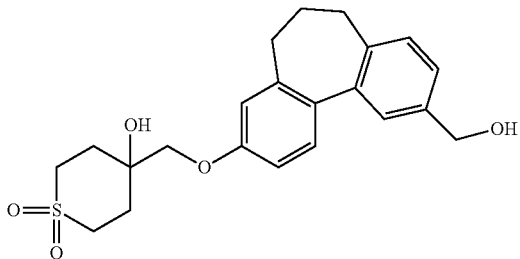 [SMILES: O=S1(=O)CCC(O)(COc2ccc3c(c2)CCCc2ccc(CO)cc2-3)CC1]

According to the procedures as described in <1-9>, the compound obtained in <65-2> was used to prepare the title compound (white foam, 256 mg, 94% yield).

$^1$H NMR (300 MHz, CDCl$_3$) δ 7.37-7.20 (m, 4H), 6.87 (dd, 1H), 6.82 (d, 1H), 4.74 (d, 2H), 3.92 (s, 2H), 3.58-3.41 (m, 2H), 3.03-2.87 (m, 2H), 2.55-2.40 (m, 5H), 2.35-2.11 (m, 6H), 1.67 (t, 1H).

<65-4> Preparation of (S)-methyl 2-(6-((9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-ylacetate

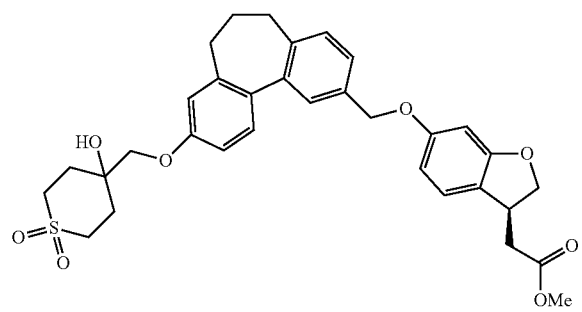 [SMILES: COC(=O)C[C@@H]1COc2cc(OCc3ccc4c(c3)-c3ccc(OCC5(O)CCS(=O)(=O)CC5)cc3CCC4)ccc21]

According to the procedures as described in <1-10>, the compound obtained in <65-3> was used to prepare the title compound (colorless oil, 103 mg, 88% yield).

$^1$H NMR (300 MHz, CDCl$_3$) δ 7.41-7.28 (m, 3H), 7.24 (d, 1H), 7.03 (d, 1H), 6.87 (dd, 1H), 6.82 (d, 1H), 6.56-6.44 (m, 2H), 5.04 (s, 2H), 4.76 (t, 1H), 4.27 (dd, 1H), 3.92 (s, 2H), 3.87-3.76 (m, 1H), 3.72 (s, 3H), 3.59-3.40 (m, 2H), 2.96 (m, 2H), 2.76 (dd, 1H), 2.64-2.39 (m, 6H), 2.36-2.09 (m, 6H).

<65-5> Preparation of (S)-2-(6-((9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid

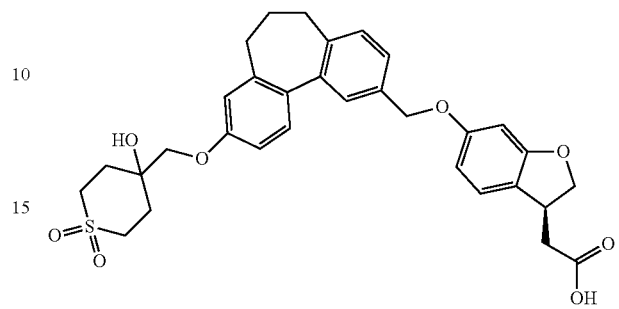

According to the procedures as described in <1-11>, the compound obtained in <65-4> was used to prepare the title compound (white foam, 57 mg, 57% yield).

MS m/z 577 [M−H]$^-$.

$^1$H NMR (300 MHz, CDCl$_3$) δ 7.40-7.20 (m, 4H), 7.07 (d, 1H), 6.87 (dd, 1H), 6.82 (d, 1H), 6.57-6.46 (m, 2H), 5.05 (s, 2H), 4.77 (t, 1H), 4.30 (dd, 1H), 3.92 (s, 2H), 3.82 (m, 1H), 3.59-3.42 (m, 2H), 2.97 (m, 2H), 2.82 (dd, 1H), 2.63 (dd, 1H), 2.49 (m, 4H), 2.35-2.12 (m, 6H).

Example 66

Preparation of (S)-2-(6-((9-(3-(ethylsulfonyl)propoxy)-6,7-dihydro-5H-dibenzo[a,c][7]annulen-2-yl)methoxy)-2,3-dihydrobenzofuran-3-yl)acetic acid <66-1> Preparation of methyl 9-(3-(ethylsulfonyl)propoxy)-6,7-dihydro-5H-dibenzo[a,c][7]annulen-2-carboxylate

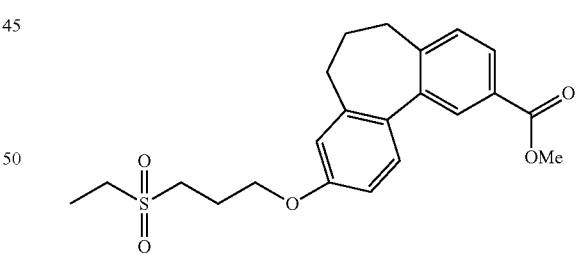

The compound obtained in <5-7> (240 mg, 0.89 mmol) was dissolved in DMF (5 mL), which was then added with 1-chloro-3-(ethylsulfonyl)propane (306 mg, 1.79 mmol) and K$_2$CO$_3$ (371 mg, 2.68 mmol), followed by stirring at 90° C. for 3 hours. The reaction mixture was cooled to room temperature, diluted with EtOAc and water, followed by extraction. The aqueous layer was extracted with EtOAc one more time. The organic layer was dried over sodium sulfate and concentrated under reduced pressure, and the residue thus obtained was purified by silica gel chromatography to obtain the title compound (white foam, 390 mg, 108% yield), which was used in the next step.

<66-2> Preparation of (9-(3-(ethylsulfonyl) propoxy)-6,7-dihydro-5H-dibenzo[a,c][7]annulen-2-yl)methanol

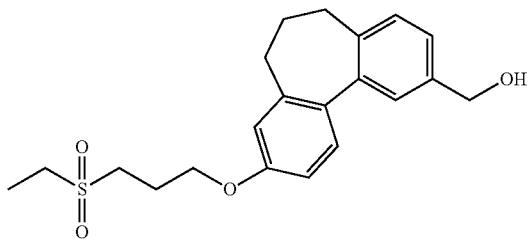 [SMILES: CCS(=O)(=O)CCCOc1ccc2c(c1)CCCc1ccc(CO)cc1-2]

According to the procedures as described in <1-9>, the compound obtained in <66-1> was used to prepare the title compound (white foam, 275 mg, 82% yield).

¹H NMR (600 MHz, CDCl₃) δ 7.34 (d, 1H), 7.31 (d, 1H), 7.27 (d, 1H), 7.22 (d, 1H), 6.85 (dd, 1H), 6.79 (d, 1H), 4.73 (d, 2H), 4.16 (t, 2H), 3.23 (m, 2H), 3.05 (q, 2H), 2.49 (t, 2H), 2.46 (t, 2H), 2.39-2.35 (m, 2H), 2.17 (m, 2H), 1.65 (t, 1H), 1.45 (t, 3H).

<66-3> Preparation of (S)-methyl 2-(6-((9-(3-(ethylsulfonyl)propoxy)-6,7-dihydro-5H-dibenzo[a,c][7]annulen-2-yl)methoxy)-2,3-dihydrobenzofuran-3-ylacetate

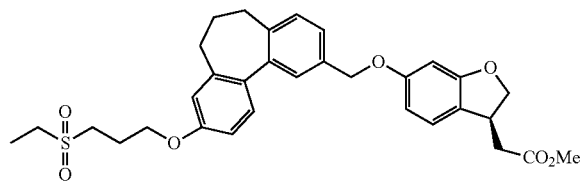 [SMILES: CCS(=O)(=O)CCCOc1ccc2c(c1)CCCc1ccc(COc3ccc4c(c3)OC[C@H]4CC(=O)OC)cc1-2]

According to the procedures as described in <1-10>, the compound obtained in <66-2> was used to prepare the title compound (white foam, 92 mg, 68% yield), which was used in the next step.

<66-4> Preparation of (S)-2-(6-((9-(3-(ethylsulfonyl)propoxy)-6,7-dihydro-5H-dibenzo[a,c][7]annulen-2-yl)methoxy)-2,3-dihydrobenzofuran-3-yl)acetic acid

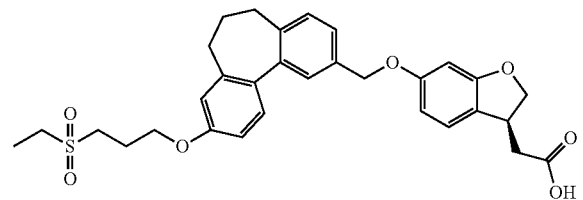 [SMILES: CCS(=O)(=O)CCCOc1ccc2c(c1)CCCc1ccc(COc3ccc4c(c3)OC[C@H]4CC(=O)O)cc1-2]

According to the procedures as described in <1-11>, the compound obtained in <66-3> was used to prepare the title compound (white foam, 41 mg, 45% yield).

MS m/z 549 [M−H]⁻.

¹H NMR (600 MHz, CDCl₃) δ 7.38 (d, 1H), 7.31 (m, 2H), 7.23 (d, 1H), 7.06 (d, 1H), 6.85 (dd, 1H), 6.79 (d, 1H), 6.52 (dd, 2H), 6.49 (d, 1H), 5.04 (s, 2H), 4.77 (t, 1H), 4.29 (dd, 1H), 4.16 (t, 2H), 3.82 (m, 1H), 3.23 (m, 2H), 3.05 (q, 2H), 2.82 (dd, 1H), 2.63 (dd, 1H), 2.48 (m, 4H), 2.39-2.34 (m, 2H), 2.17 (m, 2H), 1.45 (t, 3H).

Example 67

Preparation of (1S,2S)-2-(4-((9-((1,1-dioxidotetrahydro-2H-thiopyran-4-yl)oxy)-6,7-dihydro-5H-dibenzo[a,c][7]annulen-2-yl)methoxy)phenyl)cyclopropanecarboxylic acid

<67-1> Preparation of (1S,2S)-ethyl 2-(4-((9-((1,1-dioxidotetrahydro-2H-thiopyran-4-yl)oxy)-6,7-dihydro-5H-dibenzo[a,c][7]annulen-2-yl)methoxy)phenyl)cyclopropanecarboxylate

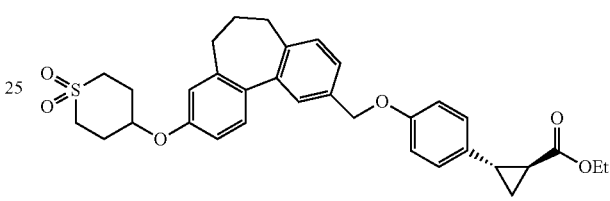

According to the procedures as described in <2-16>, the compound obtained in <64-2> was used to prepare the title compound (yellow oil, 106.3 mg, 68% yield).

¹H NMR (300 MHz, CDCl₃) δ 7.38 (s, 1H), 7.33 (d, 2H), 7.25 (d, 1H), 7.04 (d, 2H), 6.94-6.81 (m, 4H), 5.07 (s, 2H), 4.71 (br s, 1H), 4.17 (q, 2H), 3.54-3.35 (m, 2H), 2.96 (m, 2H), 2.58-2.26 (m, 9H), 2.19 (m, 2H), 1.87-1.77 (m, 1H), 1.58-1.50 (m, 1H), 1.33-1.17 (m, 4H).

<67-2> Preparation of (1S,2S)-2-(4-((9-((1,1-dioxidotetrahydro-2H-thiopyran-4-yl)oxy)-6,7-dihydro-5H-dibenzo[a,c][7]annulen-2-yl)methoxy)phenyl)cyclopropanecarboxylic acid

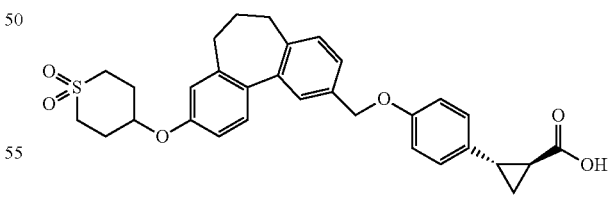

According to the procedures as described in <1-11>, the compound obtained in <67-1> was used to prepare the title compound (white foam, 55.8 mg, 58% yield).

MS m/z 531 [M−H]⁻.

¹H NMR (300 MHz, CDCl₃) δ 7.41-7.21 (m, 4H), 7.05 (d, 2H), 6.97-6.81 (m, 4H), 5.07 (s, 2H), 4.71 (br s, 1H), 3.46 (m, 2H), 2.96 (m, 2H), 2.66-2.31 (m, 9H), 2.19 (m, 2H), 1.88-1.78 (m, 1H), 1.63 (dd, 1H), 1.42-1.30 (m, 1H).

Example 68

Preparation of (1S,2S)-2-(4-((9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid <68-1> Preparation of (1S,2S)-ethyl 2-(4-((9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylate

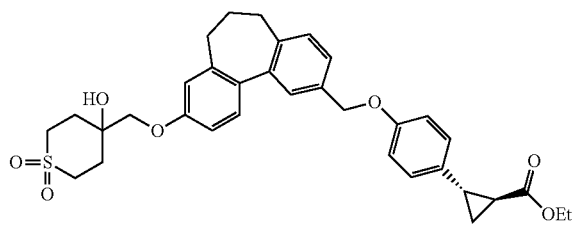 [SMILES: CCOC(=O)[C@H]1C[C@@H]1c1ccc(OCc2ccc3c(c2)-c2ccc(OCC4(O)CCS(=O)(=O)CC4)cc2CCC3)cc1]

According to the procedures as described in <2-16>, the compound obtained in <65-3> was used to prepare the title compound (white foam, 99 mg, 84% yield).

$^1$H NMR (300 MHz, CDCl$_3$) δ 7.42-7.28 (m, 3H), 7.24 (d, 1H), 7.07-6.97 (m, 2H), 6.96-6.89 (m, 2H), 6.87 (dd, 1H), 6.82 (d, 1H), 5.06 (s, 2H), 4.14 (q, 2H), 3.92 (s, 2H), 3.63-3.38 (m, 2H), 3.07-2.85 (m, 2H), 2.60-2.38 (m, 6H), 2.39-2.10 (m, 6H), 1.82 (m, 1H), 1.67-1.51 (m, 2H), 1.33-1.20 (m, 4H).

<68-2> Preparation of (1S,2S)-2-(4-((9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid

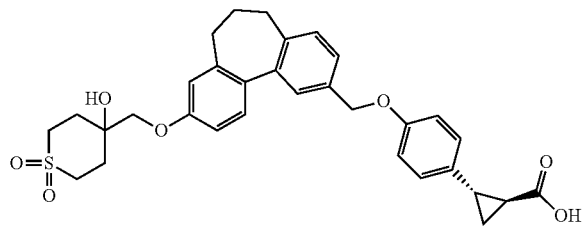 [SMILES: O=C(O)[C@H]1C[C@@H]1c1ccc(OCc2ccc3c(c2)-c2ccc(OCC4(O)CCS(=O)(=O)CC4)cc2CCC3)cc1]

According to the procedures as described in <1-11>, the compound obtained in <68-1> was used to prepare the title compound (white foam, 67 mg, 71% yield).

MS m/z 561 [M−H]$^-$.

$^1$H NMR (300 MHz, CDCl$_3$) δ 7.41-7.29 (m, 3H), 7.26 (d, 1H), 7.09-7.01 (m, 2H), 6.92 (m, 2H), 6.87 (dd, 1H), 6.82 (d, 1H), 5.07 (s, 2H), 3.92 (s, 2H), 3.58-3.40 (m, 2H), 2.96 (m, 2H), 2.63-2.41 (m, 5H), 2.36-2.11 (m, 6H), 1.83 (m, 1H), 1.62 (m, 1H), 1.36 (m, 1H).

Example 69

Preparation of (1S,2S)-2-(4-((9-(3-(ethylsulfonyl)propoxy)-6,7-dihydro-5H-dibenzo[a,c][7]annulen-2-yl)methoxy)phenyl)cyclopropanecarboxylic acid <69-1> Preparation of (1S,2S)-ethyl 2-(4-((9-(3-(ethylsulfonyl)propoxy)-6,7-dihydro-5H-dibenzo[a,c][7]annulen-2-yl)methoxy)phenyl)cyclopropanecarboxylate

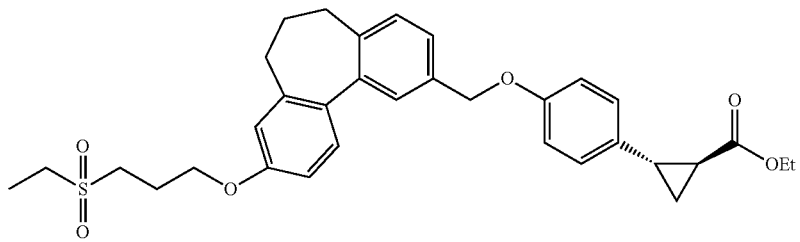 [SMILES: CCOC(=O)[C@H]1C[C@@H]1c1ccc(OCc2ccc3c(c2)-c2ccc(OCCCS(=O)(=O)CC)cc2CCC3)cc1]

According to the procedures as described in <2-16>, the compound obtained in <66-2> was used to prepare the title compound (white foam, 108 mg, 80% yield).

$^1$H NMR (300 MHz, CDCl$_3$) δ 7.38 (d, 1H), 7.30 (m, 2H), 7.23 (d, 1H), 7.04 (d, 2H), 6.91 (d, 2H), 6.85 (dd, 1H), 6.79 (d, 1H), 5.06 (s, 2H), 4.16 (m, 4H), 3.22 (m, 2H), 3.06 (q, 2H), 2.47 (m, 4H), 2.37 (m, 2H), 2.17 (m, 2H), 1.82 (m, 1H), 1.56 (m, 1H), 1.45 (t, 2H), 1.27 (t, 2H), 1.26 (m, 1H)-

<69-2> Preparation of (1S,2S)-2-(4-((9-(3-(ethylsulfonyl)propoxy)-6,7-dihydro-5H-dibenzo[a,c][7]annulen-2-yl) methoxy)phenyl)cyclopropanecarboxylic acid

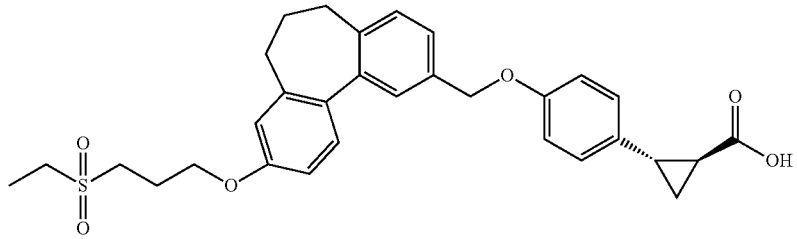 [SMILES: CCS(=O)(=O)CCCOc1ccc2c(c1)CCCc1ccc(COc3ccc([C@H]4C[C@@H]4C(=O)O)cc3)cc1-2]

According to the procedures as described in <1-11>, the compound obtained in <69-1> was used to prepare the title compound (white foam, 79 mg, 76% yield).

MS m/z 533 [M−H]⁻

¹H NMR (600 MHz, CDCl₃) δ 7.37 (d, 1H), 7.30 (dd, 1H), 7.29 (d, 1H), 7.23 (d, 1H), 7.04 (d, 2H), 6.91 (d, 2H), 6.84 (dd, 1H), 6.78 (d, 1H), 5.06 (s, 2H), 4.15 (t, 2H), 3.22 (m, 2H), 3.05 (q, 2H), 2.57-2.54 (m, 1H), 2.50-2.44 (m, 4H), 2.37-2.34 (m, 2H), 2.17 (m, 2H), 1.82 (m, 1H), 1.61 (m, 1H), 1.44 (t, 3H), 1.36-1.33 (m, 1H)

Example 70

Preparation of (1S,2S)-2-(4-(((9-((1,1-dioxidotetrahydro-2H-thiopyran-4-yl)oxy)-6,7-dihydro-5H-dibenzo[a,c][7]annulen-2-yl)methyl)amino)phenyl)cyclopropanecarboxylic acid <70-1> Preparation of 9-((1,1-dioxidotetrahydro-2H-thiopyran-4-yl)oxy)-6,7-dihydro-5H-dibenzo[a,c][7]annulene-2-carbaldehyde

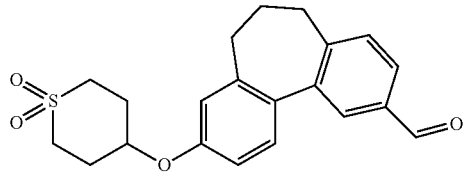 [SMILES: O=Cc1ccc2c(c1)-c1ccc(OC3CCS(=O)(=O)CC3)cc1CCC2]

According to the procedures as described in <3-3>, the compound obtained in <64-2> was used to prepare the title compound (white solid, 55.4 mg, 50% yield).

¹H NMR (300 MHz, CDCl₃) δ 10.05 (s, 1H), 7.84 (s, 1H), 7.79 (d, 1H), 7.41 (d, 1H), 7.37 (d, 1H), 6.92 (dd, 1H), 6.85 (d, 1H), 4.73 (m, 1H), 3.47 (m, 2H), 2.97 (m, 2H), 2.66-2.32 (m, 8H), 2.23 (m, 2H).

<70-2> Preparation of (1S,2S)-ethyl 2-(4-(((9-((1,1-dioxidotetrahydro-2H-thiopyran-4-yl)oxy)-6,7-dihydro-5H-dibenzo[a,c][7]annulen-2-yl)methyl)amino)phenyl)cyclopropanecarboxylate

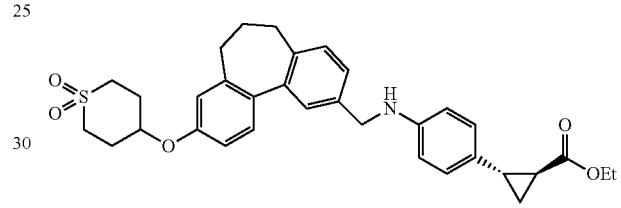

According to the procedures as described in <3-4>, the compound obtained in <70-1> was used to prepare the title compound (white foam, 109.6 mg, 98% yield).

¹H NMR (300 MHz, CDCl₃) δ 7.34-7.23 (m, 3H), 7.20 (d, 1H), 6.93 (d, 2H), 6.87 (dd, 1H), 6.83 (d, 1H), 6.58 (d, 2H), 4.70 (br s, 1H), 4.34 (s, 2H), 4.14 (q, 2H), 4.03 (br s, 1H), 3.46 (m, 2H), 2.96 (m, 2H), 2.59-2.31 (m, 9H), 2.25-2.11 (m, 2H), 1.78 (m, 1H), 1.55-1.46 (m, 1H), 1.31-1.16 (m, 4H).

<70-3> Preparation of (1S,2S)-2-(4-(((9-((1,1-dioxidotetrahydro-2H-thiopyran-4-yl)oxy)-6,7-dihydro-5H-dibenzo[a,c][7]annulen-2-yl)methyl)amino)phenyl)cyclopropanecarboxylic acid

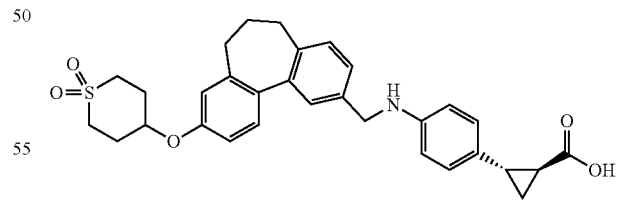

According to the procedures as described in <1-11>, the compound obtained in <70-2> was used to prepare the title compound (white foam, 92.2 mg, 84.5% yield).

MS m/z 530 [M−H]⁻.

¹H NMR (300 MHz, CDCl₃) δ 7.34-7.24 (m, 3H), 7.20 (d, 1H), 6.94 (d, 2H), 6.87 (dd, 1H), 6.83 (d, 1H), 6.59 (d, 2H), 4.70 (br s, 1H), 4.34 (s, 2H), 3.53-3.37 (m, 2H), 2.96 (m, 2H), 2.58-2.31 (m, 9H), 2.17 (m, 2H), 1.83-1.73 (m, 1H), 1.58 (m, 1H), 1.33 (m, 1H).

Example 71

Preparation of (1S,2S)-2-(4-(((9-((4-hydroxy-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid <71-1> Preparation of 9-((4-hydroxy-1,1-dioxido-tetrahydro-2H-thiopyran-4-yl)methoxy)-6,7-dihydro-5H-dibenzo[a,c][7]annulene-2-carbaldehyde

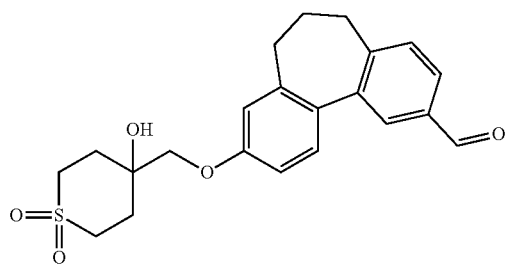 [SMILES: O=Cc1ccc2c(c1)-c1ccc(OCC3(O)CCS(=O)(=O)CC3)cc1CCC2]

According to the procedures as described in <3-3>, the compound obtained in <65-3> was used to prepare the title compound (colorless oil, 83 mg, 92% yield).

¹H NMR (300 MHz, CDCl₃) δ 10.04 (s, 1H), 7.84 (d, 1H), 7.78 (dd, 1H), 7.41 (d, 1H), 7.36 (d, 1H), 6.91 (dd, 1H), 6.84 (d, 1H), 3.93 (s, 2H), 3.51 (m, 2H), 2.97 (m, 2H), 2.64 (s, 1H), 2.57 (t, 2H), 2.47 (t, 2H), 2.36-2.15 (m, 6H).

<71-2> Preparation of (1S,2S)-ethyl 2-(4-(((9-((4-hydroxy-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylate

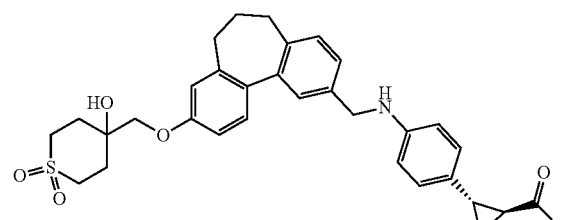

According to the procedures as described in <3-4>, the compound obtained in <71-1> was used to prepare the title compound (white foam, 100 mg, 82% yield).

¹H NMR (300 MHz, CDCl₃) δ 7.36-7.16 (m, 4H), 6.99-6.90 (m, 2H), 6.86 (dd, 1H), 6.82 (d, 1H), 6.63-6.53 (m, 2H), 4.34 (s, 2H), 4.14 (q, 2H), 4.02 (br s, 1H), 3.91 (s, 2H), 3.60-3.40 (m, 2H), 3.03-2.87 (m, 2H), 2.55-2.38 (m, 6H), 2.36-2.11 (m, 6H), 2.05 (s, 2H), 1.83-1.72 (m, 1H), 1.55-1.44 (m, 1H), 1.34-1.18 (m, 4H).

<71-3> Preparation of (1S,2S)-2-(4-(((9-((4-hydroxy-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid

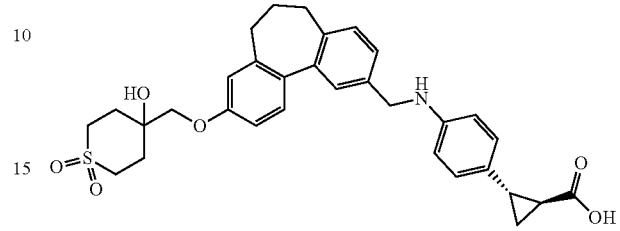

According to the procedures as described in <1-11>, the compound obtained in <71-2> was used to prepare the title compound (white foam, 68 mg, 71% yield).

MS m/z 560 [M−H]⁻.

¹H NMR (300 MHz, CDCl₃) δ 7.35-7.23 (m, 3H), 7.20 (d, 1H), 6.94 (m, 2H), 6.86 (dd, 1H), 6.81 (d, 1H), 6.59 (m, 2H), 4.34 (s, 2H), 3.91 (d, 2H), 3.62-3.38 (m, 2H), 2.96 (m, 2H), 2.61-2.38 (m, 5H), 2.36-2.09 (m, 6H), 1.78 (m, 1H), 1.58 (m, 1H), 1.39-1.28 (m, 1H).

Example 72

Preparation of (1S,2S)-2-(4-(((9-(3-(ethylsulfonyl)propoxy)-6,7-dihydro-5H-dibenzo[a,c][7]annulen-2-yl)methyl)amino)phenyl)cyclopropanecarboxylic acid <72-1> Preparation of 9-(3-(ethylsulfonyl)propoxy)-6,7-dihydro-5H-dibenzo[a,c][7]annulene-2-carbaldehyde

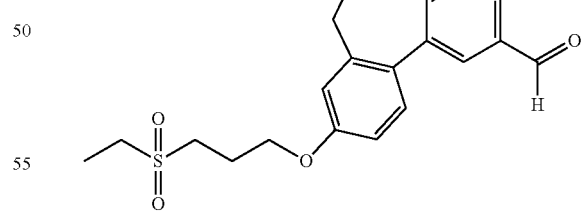

According to the procedures as described in <3-3>, the compound obtained in <66-2> was used to prepare the title compound (white solid, 82 mg, 91% yield).

¹H NMR (300 MHz, CDCl₃) δ 10.05 (s, 1H), 7.84 (d, 1H), 7.78 (dd, 1H), 7.40 (d, 1H), 7.35 (d, 1H), 6.89 (dd, 1H), 6.81 (d, 1H), 4.18 (t, 2H), 3.28 (t, 2H), 3.06 (q, 2H), 2.57 (t, 2H), 2.47 (t, 2H), 2.42-2.34 (m, 2H), 2.25 (m, 2H), 1.45 (t, 3H).

<72-2> Preparation of (1S,2S)-ethyl 2-(4-(((9-(3-(ethylsulfonyl)propoxy)-6,7-dihydro-5H-dibenzo[a,c][7]annulen-2-yl)methyl)amino)phenyl)cyclopropanecarboxylate

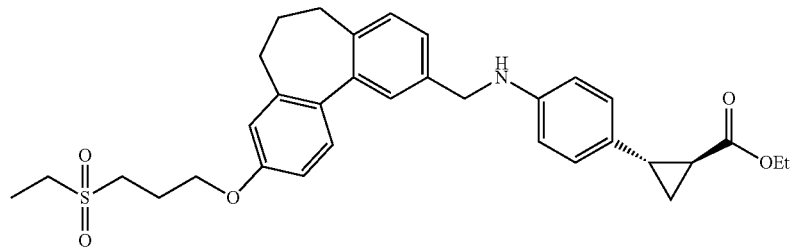 [SMILES: CCOC(=O)[C@H]1C[C@@H]1c1ccc(NCc2ccc3c(c2)-c2ccc(OCCCS(=O)(=O)CC)cc2CCC3)cc1]

According to the procedures as described in <3-4>, the compound obtained in <72-1> was used to prepare the title compound (white solid, 122 mg, 100% yield).

$^1$H NMR (300 MHz, CDCl$_3$) δ 7.32 (d, 1H), 7.29-7.24 (m, 2H), 7.19 (d, 1H), 6.93 (d, 2H), 6.84 (dd, 1H), 6.78 (d, 1H), 6.58 (d, 2H), 4.33 (s, 2H), 4.16 (t, 2H), 4.15 (q, 2H), 3.22 (dd, 2H), 3.05 (q, 2H), 2.46 (m, 4H), 2.36 (m, 2H), 2.17 (m, 2H), 1.77 (m, 1H), 1.81-1.75 (m, 1H), 1.53 (m, 1H), 1.45 (t, 3H), 1.27 (t, 3H), 1.23 (m, 1H).

<72-3> Preparation of (1S,2S)-2-(4-(((9-(3-(ethylsulfonyl)propoxy)-6,7-dihydro-5H-dibenzo[a,c][7]annulen-2-yl)methyl)amino)phenyl)cyclopropanecarboxylic acid

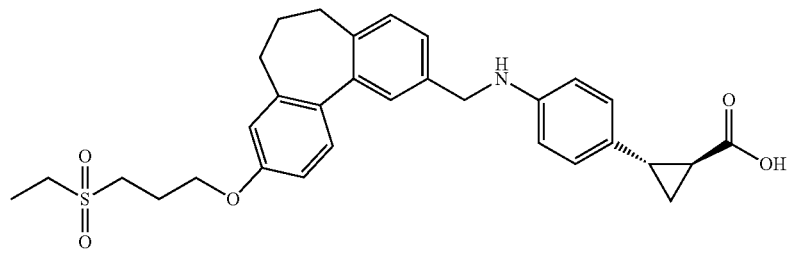 [SMILES: CCS(=O)(=O)CCCOc1ccc2c(c1)CCCc1ccc(CNc3ccc([C@H]4C[C@@H]4C(=O)O)cc3)cc1-2]

According to the procedures as described in <3-5>, the compound obtained in <72-2> was used to prepare the title compound (white foam, 105 mg, 91% yield).

MS m/z 532 [M−H]$^-$.

$^1$H NMR (600 MHz, CDCl$_3$) δ 7.31 (d, 1H), 7.26 (d, 1H), 7.23 (dd, 1H), 7.18 (d, 1H), 6.93 (d, 2H), 6.82 (dd, 1H), 6.78 (d, 1H), 6.58 (d, 2H), 4.32 (s, 2H), 4.15 (t, 2H), 3.21 (dd, 2H), 3.04 (q, 2H), 2.51-2.49 (m, 1H), 2.46 (m, 4H), 2.37-2.33 (m, 2H), 2.16 (m, 2H), 1.77 (m, 1H), 1.57 (m, 1H), 1.43 (t, 3H), 1.34-1.30 (m, 1H).

Example 73

Preparation of (1S,2S)-2-(4-(((9-((1,1-dioxidotetrahydro-2H-thiopyran-4-yl)oxy)-11-methyl-6,7-dihydrodibenzo[b,d]oxepin-2-yl)methyl)amino)phenyl)cyclopropanecarboxylic acid <73-1> Preparation of (1S,2S)-ethyl 2-(4-(((9-((1,1-dioxidotetrahydro-2H-thiopyran-4-yl)oxy)-11-methyl-6,7-dihydrodibenzo[b,d]oxepin-2-yl)methyl)amino)phenyl)cyclopropanecarboxylate

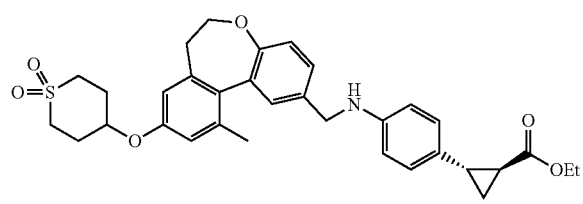 [SMILES: CCOC(=O)[C@H]1C[C@@H]1c1ccc(NCc2ccc3c(c2)-c2c(C)cc(OC4CCS(=O)(=O)CC4)cc2CCO3)cc1]

According to the procedures as described in <3-4>, the compound obtained in <52-1> (white foam, 54.6 mg, 95% yield).

$^1$H NMR (300 MHz, CDCl$_3$) δ 7.31-7.24 (m, 2H), 7.12 (d, 1H), 6.93 (d, 2H), 6.78 (d, 1H), 6.71 (d, 1H), 6.57 (d, 2H), 4.69 (br s, 1H), 4.41 (m, 2H), 4.34 (s, 2H), 4.15 (q, 2H), 4.05 (br s, 1H), 3.43 (m, 2H), 2.95 (m, 2H), 2.89-2.73 (m, 1H), 2.58-2.30 (m, 6H), 2.26 (s, 3H), 1.76 (m, 1H), 1.55-1.47 (m, 1H), 1.32-1.17 (m, 4H).

<73-2> Preparation of (1S,2S)-2-(4-(((9-((1,1-dioxidotetrahydro-2H-thiopyran-4-yl)oxy)-11-methyl-6,7-dihydrodibenzo[b,d]oxepin-2-yl)methyl)amino)phenyl)cyclopropanecarboxylic acid

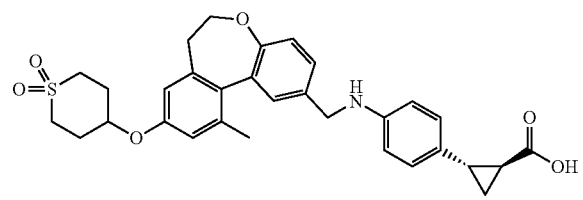 [SMILES: Cc1cc(OC2CCS(=O)(=O)CC2)cc2c1-c1cc(CNc3ccc([C@H]4C[C@@H]4C(=O)O)cc3)ccc1OCC2]

According to the procedures as described in <1-11>, the compound obtained in <73-1> was used to prepare the title compound (white foam, 45.2 mg, 87% yield).

MS m/z 570 [M+Na]$^+$.

$^1$H NMR (300 MHz, CDCl$_3$) δ 7.31-7.23 (m, 2H), 7.12 (d, 1H), 6.93 (d, 2H), 6.78 (d, 1H), 6.71 (d, 1H), 6.57 (d, 2H), 4.69 (br s, 1H), 4.41 (m, 2H), 4.34 (s, 2H), 3.43 (m, 2H), 2.95 (m, 2H), 2.82 (m, 1H), 2.58-2.30 (m, 6H), 2.25 (s, 3H), 1.76 (m, 1H), 1.59 (m, 1H), 1.33 (m, 1H).

Example 74

Preparation of (1S,2S)-2-(4-(((9-(3-(ethylsulfonyl)propoxy)-11-methyl-6,7-dihydro-5H-dibenzo[a,c][7]annulen-2-yl)methyl)amino)phenyl)cyclopropanecarboxylic acid <74-1> Preparation of 9-(3-(ethylsulfonyl)propoxy)-11-methyl-6,7-dihydro-5H-dibenzo[a,c][7]annulene-2-carbaldehyde

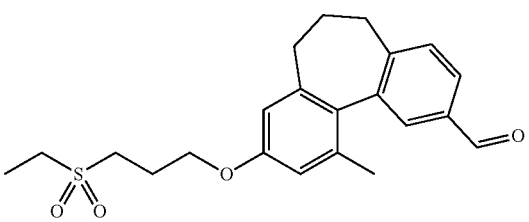 [SMILES: CCS(=O)(=O)CCCOc1cc(C)c2c(c1)CCCc1ccc(C=O)cc1-2]

According to the procedures as described in <3-3>, the compound obtained in <57-2> was used to prepare the title compound (colorless oil, 124 mg, ~100% yield).

$^1$H NMR (300 MHz, CDCl$_3$) δ 10.02 (s, 1H), 7.81-7.69 (m, 2H), 7.45-7.34 (m, 1H), 6.76 (d, 1H), 6.65 (d, 1H), 5.51 (s, 1H), 4.16 (t, 2H), 3.31-3.16 (m, 2H), 3.07 (q, 2H), 2.61 (m, 1H), 2.53-1.96 (m, 10H), 1.45 (t, 3H).

<74-2> Preparation of (1S,2S)-ethyl 2-(4-(((9-(3-(ethylsulfonyl)propoxy)-11-methyl-6,7-dihydro-5H-dibenzo[a,c][7]annulen-2-yl)methyl)amino)phenyl)cyclopropanecarboxylate

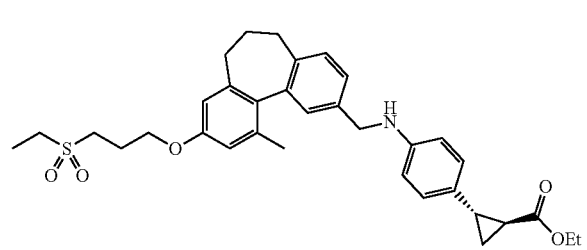 [SMILES: CCOC(=O)[C@H]1C[C@@H]1c1ccc(NCc2ccc3c(c2)-c2c(C)cc(OCCCS(=O)(=O)CC)cc2CCC3)cc1]

According to the procedures as described in <3-4>, the compound obtained in <74-1> was used to prepare the title compound (white foam, 142 mg, 77% yield).

$^1$H NMR (300 MHz, CDCl$_3$) δ 7.25-7.15 (m, 3H), 6.96-6.85 (m, 2H), 6.70 (d, 1H), 6.62 (d, 1H), 6.60-6.49 (m, 2H), 4.33 (s, 2H), 4.20-4.00 (m, 5H), 3.27-3.15 (m, 2H), 3.05 (q, 2H), 2.55-2.14 (m, 9H), 2.08-1.94 (m, 2H), 1.77 (m, 1H), 1.51 (m, 1H), 1.44 (t, 3H), 1.32-1.15 (m, 4H).

<74-3> Preparation of (1S,2S)-2-(4-(((9-(3-(ethyl-sulfonyl)propoxy)-11-methyl-6,7-dihydro-5H-dibenzo[a,c][7]annulen-2-yl)methyl)amino)phenyl)cyclopropanecarboxylic acid

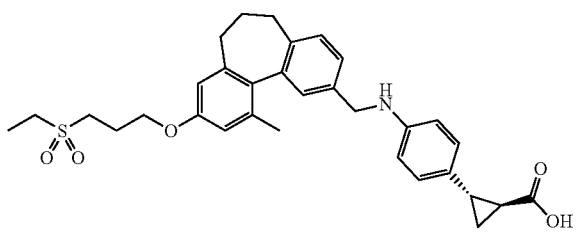 [SMILES: CCS(=O)(=O)CCCOc1cc(C)c2c(c1)CCCc1ccc(CNc3ccc([C@H]4C[C@@H]4C(=O)O)cc3)cc1-2]

According to the procedures as described in <1-11>, the compound obtained in <74-2> was used to prepare the title compound (white foam, 125 mg, 93% yield).

MS m/z 546 [M−H]⁻.

¹H NMR (300 MHz, CDCl₃) δ 7.25-7.15 (m, 3H), 6.97-6.87 (m, 2H), 6.70 (d, 1H), 6.62 (d, 1H), 6.60-6.51 (m, 2H), 4.33 (s, 2H), 4.12 (t, 2H), 3.26-3.15 (m, 2H), 3.05 (q, 2H), 2.56-2.21 (m, 7H), 2.19 (s, 3H), 2.03 (m, 3H), 1.82-1.73 (m, 1H), 1.57 (m, 1H), 1.44 (t, 3H), 1.37-1.29 (m, 1H).

Example 75

Preparation of (1S,2S)-2-(4-(((9-((1,1-dioxidotetra-hydro-2H-thiopyran-4-yl)methoxy)-11-methyl-6,7-dihydro-5H-dibenzo[a,c][7]annulen-2-yl)methyl)amino)phenyl)cyclopropanecarboxylic acid <75-1> Preparation of methyl 9-((1,1-dioxidotetra-hydro-2H-thiopyran-4-yl)methoxy)-11-methyl-6,7-dihydro-5H-dibenzo[a,c][7]annulene-2-carboxylate

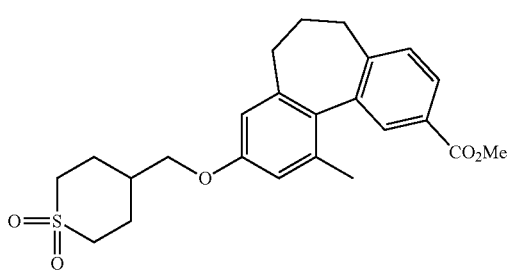 [SMILES: COC(=O)c1ccc2c(c1)-c1c(C)cc(OCC3CCS(=O)(=O)CC3)cc1CCC2]

According to the procedures as described in <47-1>, the compound obtained in <7-6> was used to prepare the title compound (colorless oil, 143 mg, 94% yield).

¹H NMR (300 MHz, CDCl₃) δ 7.96-7.88 (m, 2H), 7.31 (d, 1H), 6.74 (d, 1H), 6.63 (d, 1H), 3.96-3.86 (m, 5H), 3.23-2.97 (m, 4H), 2.63-2.52 (m, 1H), 2.52-2.16 (m, 8H), 2.14-1.97 (m, 5H).

<75-2> Preparation of 4-(((10-(hydroxymethyl)-1-methyl-6,7-dihydro-5H-dibenzo[a,c][7]annulen-3-yl)oxy)methyl)tetrahydro-2H-thiopyran 1,1-dioxide

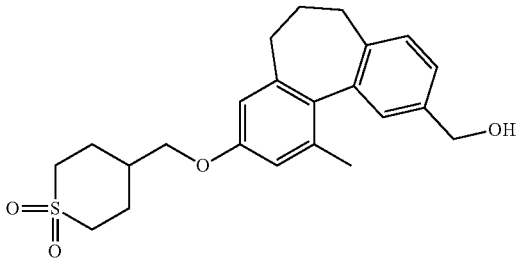 [SMILES: Cc1cc(OCC2CCS(=O)(=O)CC2)cc2c1-c1cc(CO)ccc1CCC2]

According to the procedures as described in <1-9>, the compound obtained in <75-1> was used to prepare the title compound (colorless oil, 121 mg, 91% yield).

¹H NMR (300 MHz, CDCl₃) δ 7.28-7.20 (m, 3H), 6.72 (d, 1H), 6.62 (d, 1H), 4.71 (d, 2H), 3.90 (d, 2H), 3.22-2.94 (m, 4H), 2.58-2.19 (m, 9H), 2.15-1.93 (m, 5H), 1.68 (t, 1H).

<75-3> Preparation of 9-((1,1-dioxidotetrahydro-2H-thiopyran-4-yl)methoxy)-11-methyl-6,7-dihydro-5H-dibenzo[a,c][7]annulene-2-carbaldehyde

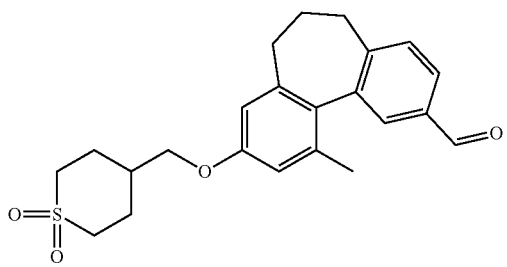 [SMILES: Cc1cc(OCC2CCS(=O)(=O)CC2)cc2c1-c1cc(C=O)ccc1CCC2]

According to the procedures as described in <3-3>, the compound obtained in <75-2> was used to prepare the title compound (white foam, 100 mg, 83% yield).

¹H NMR (300 MHz, CDCl₃) δ 10.02 (s, 1H), 7.81-7.70 (m, 2H), 7.46-7.35 (m, 1H), 6.75 (d, 1H), 6.64 (d, 1H), 3.91 (d, 2H), 3.25-2.93 (m, 4H), 2.61 (m, 1H), 2.55-2.16 (m, 8H), 2.16-2.00 (m, 5H).

<75-4> Preparation of (1S,2S)-ethyl 2-(4-(((9-((1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylate

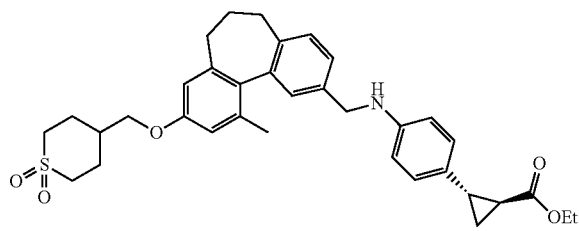 [SMILES: CCOC(=O)[C@H]1C[C@@H]1c1ccc(NCc2ccc3c(c2)-c2c(C)cc(OCC4CCS(=O)(=O)CC4)cc2CCC3)cc1]

According to the procedures as described in <3-4>, the compound obtained in <75-3> was used to prepare the title compound (colorless oil, 130 mg, 88% yield).

¹H NMR (300 MHz, CDCl₃) δ 7.25-7.16 (m, 3H), 6.95-6.87 (m, 2H), 6.69 (d, 1H), 6.61 (d, 1H), 6.59-6.51 (m, 2H), 4.33 (s, 2H), 4.14 (q, 2H), 4.03 (br s, 1H), 3.89 (d, 2H), 3.20-2.95 (m, 4H), 2.56-2.22 (m, 7H), 2.20 (s, 3H), 2.12-1.95 (m, 5H), 1.76 (m, 1H), 1.50 (m, 1H), 1.30-1.18 (m, 4H).

<75-5> Preparation of (1S,2S)-2-(4-(((9-((1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid

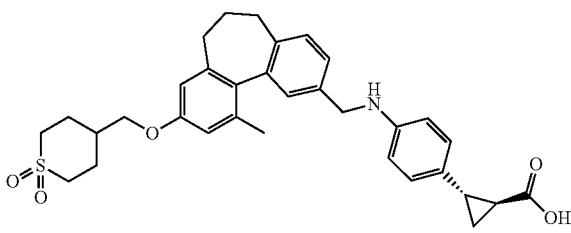 [SMILES: Cc1cc(OCC2CCS(=O)(=O)CC2)cc2c1-c1cc(CNc3ccc([C@H]4C[C@@H]4C(=O)O)cc3)ccc1CCC2]

According to the procedures as described in <1-11>, the compound obtained in <75-4> was used to prepare the title compound (yellow foam, 99 mg, 80% yield).

MS m/z 558 [M−H]⁻.

¹H NMR (300 MHz, CDCl₃) δ 7.25-7.15 (m, 3H), 6.95-6.87 (m, 2H), 6.69 (d, 1H), 6.61 (d, 1H), 6.60-6.50 (m, 2H), 4.33 (s, 2H), 3.89 (d, 2H), 3.20-2.95 (m, 4H), 2.59-2.21 (m, 7H), 2.19 (s, 3H), 2.10-1.95 (m, 5H), 1.75 (m, 1H), 1.57 (m, 1H), 1.39-1.30 (m, 1H).

Example 76

Preparation of (1S,2S)-2-(4-(((9-((1,1-dioxidotetrahydro-2H-thiopyran-4-yl)oxy)-11-methyl-6,7-dihydro-5H-dibenzo[a,c][7]annulen-2-yl)methyl)amino)phenyl)cyclopropanecarboxylic acid <76-1> Preparation of 9-((1,1-dioxidotetrahydro-2H-thiopyran-4-yl)oxy)-11-methyl-6,7-dihydro-5H-dibenzo[a,c][7]annulene-2-carbaldehyde

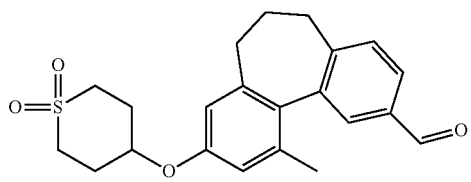 [SMILES: Cc1cc(OC2CCS(=O)(=O)CC2)cc2c1-c1cc(C=O)ccc1CCC2]

According to the procedures as described in <3-3>, the compound obtained in <55-2> was used to prepare the title compound (white foam, 112 mg, 96% yield).

¹H NMR (300 MHz, CDCl₃) δ 10.02 (s, 1H), 7.80-7.72 (m, 2H), 7.42 (d, 1H), 6.80 (d, 1H), 6.68 (d, 1H), 4.72 (m, 1H), 3.46 (t, 2H), 2.96 (m, 2H), 2.68-2.34 (m, 7H), 2.31 (s, 3H), 2.29-2.00 (m, 3H).

<76-2> Preparation of (1S,2S)-ethyl 2-(4-(((9-((1,1-dioxidotetrahydro-2H-thiopyran-4-yl)oxy)-11-methyl-6,7-dihydro-5H-dibenzo[a,c][7]annulen-2-yl)methyl)amino)phenyl)cyclopropanecarboxylate

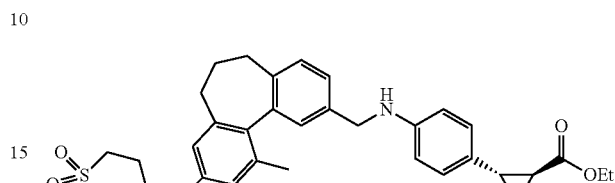

According to the procedures as described in <3-4>, the compound obtained in <76-1> was used to prepare the title compound (white foam, 139 mg, 83% yield).

¹H NMR (300 MHz, CDCl₃) δ 7.26-7.15 (m, 3H), 6.98-6.87 (m, 2H), 6.74 (d, 1H), 6.65 (d, 1H), 6.61-6.50 (m, 2H), 4.68 (m, 1H), 4.33 (s, 2H), 4.14 (q, 2H), 4.03 (s, 1H), 3.45 (t, 2H), 3.04-2.84 (m, 2H), 2.59-2.13 (m, 12H), 2.05 (m, 2H), 1.82-1.72 (m, 1H), 1.51 (m, 1H), 1.32-1.17 (m, 4H).

<76-3> Preparation of (1S,2S)-2-(4-(((9-((1,1-dioxidotetrahydro-2H-thiopyran-4-yl)oxy)-11-methyl-6,7-dihydro-5H-dibenzo[a,c][7]annulen-2-yl)methyl)amino)phenyl)cyclopropanecarboxylic acid

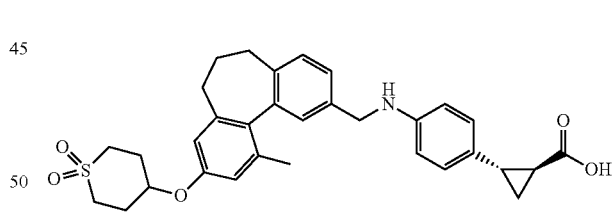

According to the procedures as described in <1-11>, the compound obtained in <76-2> was used to prepare the title compound (white foam, 120 mg, 91% yield).

MS m/z 544 [M−H]⁻.

¹H NMR (300 MHz, CDCl₃) δ 7.25-7.17 (m, 3H), 6.98-6.84 (m, 2H), 6.74 (d, 1H), 6.65 (d, 1H), 6.60-6.48 (m, 2H), 4.68 (m, 1H), 4.34 (s, 2H), 3.45 (t, 2H), 3.04-2.84 (m, 2H), 2.55-2.20 (m, 9H), 2.18 (s, 3H), 2.05 (m, 2H), 1.85-1.68 (m, 1H), 1.57 (m, 1H), 1.39-1.29 (m, 1H).

Example 77

Preparation of (1S,2S)-2-(4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid <77-1> Preparation of (1S,2S)-ethyl 2-(4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylate

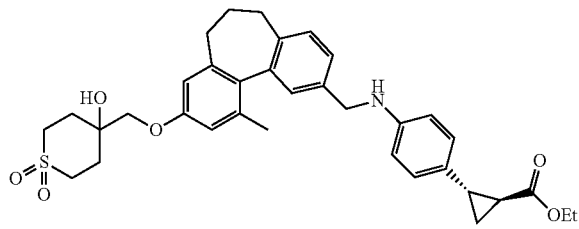 [SMILES: CCOC(=O)[C@H]1C[C@@H]1c1ccc(NCc2ccc3c(c2)-c2c(C)cc(OCC4(O)CCS(=O)(=O)CC4)cc2CCC3)cc1]

According to the procedures as described in <3-4>, the compound obtained in <63-1> was used to prepare the title compound (colorless oil, 76 mg, 90% yield).

¹H NMR (300 MHz, CDCl₃) δ 7.25-7.17 (m, 3H), 6.96-6.86 (m, 2H), 6.73 (d, 1H), 6.64 (d, 1H), 6.59-6.50 (m, 2H), 4.33 (s, 2H), 4.15 (q, 2H), 4.05 (br s, 1H), 3.89 (s, 2H), 3.61-3.39 (m, 2H), 3.03-2.85 (m, 2H), 2.58-2.13 (m, 12H), 2.02 (m, 2H), 1.84-1.72 (m, 1H), 1.51 (m, 1H), 1.35-1.17 (m, 4H).

<77-2> Preparation of (1S,2S)-2-(4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid

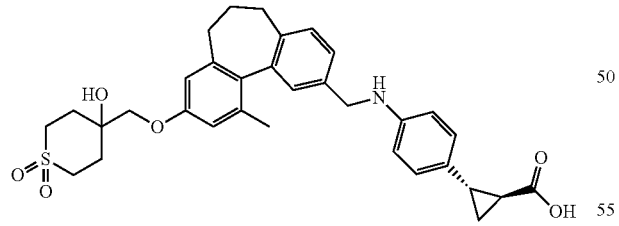

According to the procedures as described in <1-11>, the compound obtained in <77-1> was used to prepare the title compound (yellow foam, 48 mg, 66% yield).

MS m/z 574 [M−H]⁻.

¹H NMR (300 MHz, CDCl₃) δ 7.25-7.17 (m, 3H), 6.92 (m, 2H), 6.72 (d, 1H), 6.64 (d, 1H), 6.60-6.51 (m, 2H), 4.34 (s, 2H), 3.89 (s, 2H), 3.57-3.38 (m, 2H), 2.95 (m, 2H), 2.58-2.21 (m, 9H), 2.18 (s, 3H), 2.00 (m, 2H), 1.76 (m, 1H), 1.57 (m, 1H), 1.39-1.29 (m, 1H).

Example 78

Preparation of (1S,2S)-2-(4-(((9-((1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid <78-1> Preparation of methyl 9-((1,1-dioxidotetrahydro-2H-thiopyran-4-yl)methoxy)-6,7-dihydro-5H-dibenzo[a,c][7]annulene-2-carboxylate

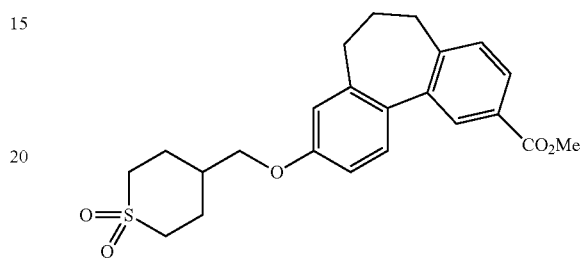

According to the procedures as described in <47-1>, the compound obtained in <5-7> was used to prepare the title compound (white foam, 130.4 mg, 105% yield).

¹H NMR (300 MHz, CDCl₃) δ 8.01 (d, 1H), 7.93 (dd, 1H), 7.35 (d, 1H), 7.30 (d, 1H), 6.86 (dd, 1H), 6.79 (d, 1H), 3.93 (s, 5H), 3.26-2.96 (m, 4H), 2.55 (t, 2H), 2.46 (t, 2H), 2.31 (m, 2H), 2.27-2.14 (m, 2H), 2.13-2.05 (m, 3H).

<78-2> Preparation of 4-(((10-(hydroxymethyl)-6,7-dihydro-5H-dibenzo[a,c][7]annulen-3-yl)oxy)methyl)tetrahydro-2H-thiopyran 1,1-dioxide

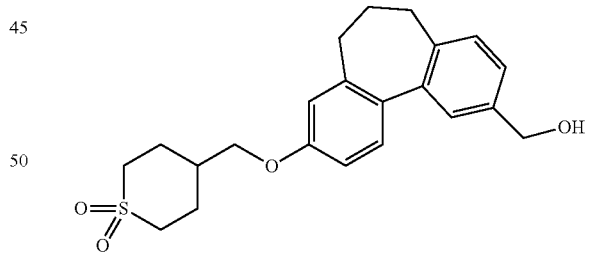

According to the procedures as described in <1-9>, the compound obtained in <78-1> was used to prepare the title compound (white solid, 70.7 mg, 68% yield).

¹H NMR (300 MHz, CDCl₃) δ 7.37-7.19 (m, 3H), 6.84 (dd, 1H), 6.79 (d, 1H), 4.74 (d, 2H), 3.92 (d, 2H), 3.26-2.92 (m, 4H), 2.48 (m, 4H), 2.33 (m, 2H), 2.24-1.96 (m, 5H), 1.68 (t, 1H).

<78-3> Preparation of 9-((1,1-dioxidotetrahydro-2H-thiopyran-4-yl)methoxy)-6,7-dihydro-5H-dibenzo[a,c][7]annulene-2-carbaldehyde

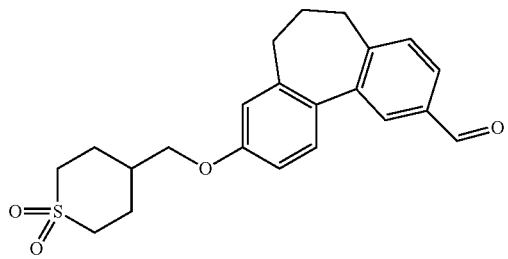 [SMILES: O=Cc1ccc2c(c1)-c1ccc(OCC3CCS(=O)(=O)CC3)cc1CCC2]

According to the procedures as described in <3-3>, the compound obtained in <78-2> was used to prepare the title compound (white foam, 95.8 mg, 89% yield).

$^1$H NMR (300 MHz, CDCl$_3$) δ 10.05 (s, 1H), 7.84 (d, 1H), 7.78 (dd, 1H), 7.40 (d, 1H), 7.35 (d, 1H), 6.88 (dd, 1H), 6.81 (d, 1H), 3.93 (d, 2H), 3.24-2.95 (m, 4H), 2.58 (t, 2H), 2.48 (t, 2H), 2.32 (m, 2H), 2.24 (m, 2H), 2.15-1.96 (m, 3H).

<78-4> Preparation of (1S,2S)-ethyl 2-(4-(((9-((1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylate

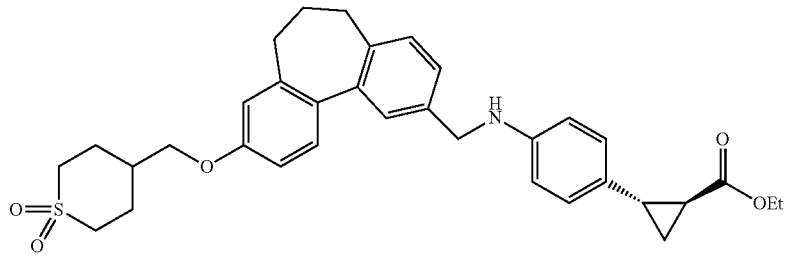 [SMILES: CCOC(=O)[C@H]1C[C@@H]1c1ccc(NCc2ccc3c(c2)-c2ccc(OCC4CCS(=O)(=O)CC4)cc2CCC3)cc1]

According to the procedures as described in <3-4>, the compound obtained in <78-3> was used to prepare the title compound (white foam, 124.8 mg, 87% yield).

$^1$H NMR (300 MHz, CDCl$_3$) δ 7.34-7.22 (m, 3H), 7.19 (d, 1H), 6.93 (d, 2H), 6.83 (dd, 1H), 6.78 (d, 1H), 6.59 (d, 2H), 4.33 (s, 2H), 4.14 (q, 2H), 4.02 (s, 1H), 3.91 (d, 2H), 3.20-2.98 (m, 4H), 2.54-2.38 (m, 5H), 2.31 (m, 2H), 2.23-2.12 (m, 2H), 2.13-1.96 (m, 3H), 1.84-1.73 (m, 1H), 1.55-1.45 (m, 1H), 1.33-1.17 (m, 4H).

<78-5> Preparation of (1S,2S)-2-(4-(((9-((1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid

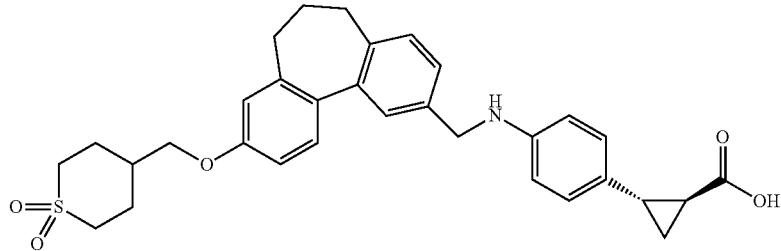 [SMILES: O=C(O)[C@H]1C[C@@H]1c1ccc(NCc2ccc3c(c2)-c2ccc(OCC4CCS(=O)(=O)CC4)cc2CCC3)cc1]

According to the procedures as described in <1-11>, the compound obtained in <78-4> was used to prepare the title compound (white foam, 129.3 mg, 108% yield).

MS m/z 544 [M−H]$^−$.

$^1$H NMR (300 MHz, CDCl$_3$) δ 7.34-7.17 (m, 4H), 6.94 (d, 2H), 6.84 (dd, 1H), 6.79 (d, 1H), 6.60 (d, 2H), 4.34 (s, 2H), 3.91 (d, 2H), 3.21-2.96 (m, 4H), 2.57-2.39 (m, 5H), 2.30 (m, 2H), 2.24-2.13 (m, 2H), 2.12-1.98 (m, 3H), 1.78 (m, 1H), 1.63-1.52 (m, 1H), 1.33 (m, 1H).

Example 79

Preparation of 2-((S)-6-(((R)-6-methyl-9-(3-(methylsulfonyl)propoxy)-6,7-dihydrodibenzo[b,d]oxepin-2-yl)methoxy)-2,3-dihydrobenzofuran-3-yl)acetic acid <79-1> Preparation of 1-(benzyloxy)-3-bromobenzene

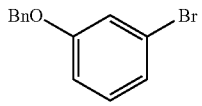

A solution of 3-bromophenol (3 g, 17.34 mmol) in acetone (100 mL) was added with benzyl bromide (2.2 mL, 19.07 mmol) and $K_2CO_3$ (7.0 g, 52.02 mmol), and the resulting mixture was refluxed for 15 hours. The reaction mixture was cooled to room temperature, filtered, and washed with acetone. The filtrate was concentrated and purified by silica gel chromatography to obtain the title compound (white solid, 5.1 g, 100% yield).

$^1$H NMR (300 MHz, $CDCl_3$) δ 7.50-7.30 (m, 5H), 7.20-7.01 (m, 3H), 6.98-6.80 (m, 1H), 5.05 (s, 2H).

<79-2> Preparation of (S)-1-(3-(benzyloxy)phenyl)propan-2-ol

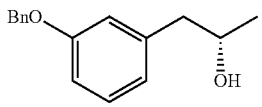

A solution of the compound obtained in <79-1> (3.37 g, 12.8 mmol) in THF (100 mL) was cooled to −78° C., slowly added with n-BuLi (1.6M hexene solution, 8.4 mL, 13.44 mmol), and stirred for 20 minutes. The reaction mixture was added with (S)-(−)propylene oxide (985 L, 14.08 mmol) and $BF_3 \cdot Et_2O$ (2.3 mL, 19.2 mmol), followed by stirring at the same temperature for 1.5 hours. The mixture was added with a saturated $NH_4Cl$ aqueous solution, slowly heated to room temperature, and then extracted with EtOAc two times. The organic layer was dried over $MgSO_4$, concentrated, and purified by silica gel chromatography to obtain the title compound (colorless oil, 2.3 g, 74.6% yield).

$^1$H NMR (300 MHz, $CDCl_3$) δ 7.52-7.29 (m, 5H), 7.25-7.18 (m, 1H), 6.91-6.75 (m, 3H), 5.06 (s, 2H), 4.01 (m, 1H), 2.77 (dd, 1H), 2.66 (dd, 1H), 1.51 (d, 1H), 1.24 (d, 3H).

<79-3> Preparation of (S)-1-(5-(benzyloxy)-2-bromophenyl)propan-2-ol

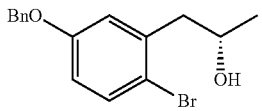

A solution of the compound obtained in <79-2> (2.2 g, 9.07 mmol) in acetonitrile (90 mL) was cooled to 0° C., added with NBS (1.6 g, 9.07 mmol) and stirred at room temperature for 4 hours. The reaction mixture was concentrated and purified by silica gel chromatography to obtain the title compound (white solid, 2.48 g, 85.1% yield).

$^1$H NMR (300 MHz, $CDCl_3$) δ 7.49-7.28 (m, 5H), 6.90 (d, 1H), 6.74 (dd, 1H), 5.04 (s, 2H), 4.12 (m, 1H), 2.92 (dd, 1H), 2.78 (dd, 1H), 1.47 (d, 1H), 1.27 (d, 3H).

<79-4> Preparation of (S)-methyl 4'-(benzyloxy)-2'-(2-hydroxypropyl)-6-(methoxymethoxy)-[1,1'-biphenyl]-3-carboxylate

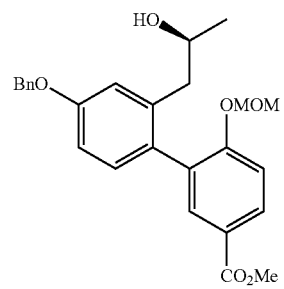

A solution of the compound obtained in <79-3> (2.00 g, 6.22 mmol) in 1,4-dioxane (50 mL) was added with methyl 4-(methoxymethoxy)-3-(4,4,5,5-tetramethyl-1,3,2-dioxaboran-2-yl)benzoate (1.67 g, 5.18 mmol), Pd(dppf)Cl$_2$ (211 mg, 0.259 mmol) and $K_2CO_3$ (2.15 g, 15.4 mmol), and then stirred at 90° C. for 15 hours. The reaction mixture was filtered through Celite and washed with ethyl acetate (EA). The filtrate was concentrated and purified by silica gel chromatography to obtain the title compound (brown oil, 1.84 g, 81.7% yield).

$^1$H NMR (300 MHz, $CDCl_3$) δ 8.01 (dd, 1H), 7.84 (s, 1H), 7.50-7.30 (m, 5H), 7.23 (d, 1H), 7.09 (d, 1H), 6.97 (d, 1H), 6.91 (dd, 1H), 5.22-5.04 (m, 4H), 3.88 (s, 3H), 3.81 (br s, 1H), 3.37 (s, 3H), 2.74-2.48 (m, 2H), 1.92 (s, 1H), 1.03 (d, 3H).

<79-5> Preparation of (S)-methyl 4'-(benzyloxy)-6-hydroxy-2'-(2-hydroxypropyl)-[1,1'-biphenyl]-3-carboxylate

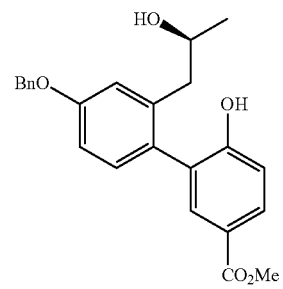 [SMILES: COC(=O)c1ccc(O)c(-c2ccc(OCc3ccccc3)cc2C[C@H](C)O)c1]

A solution of the compound obtained in <79-4> (268 mg, 0.614 mmol) in MeOH (6 mL) was added with p-TsOH·H$_2$O (350 mg, 1.84 mmol) and stirred at 50° C. for 2 hours. The reaction mixture was cooled to room temperature, diluted with distilled water, and neutralized with a saturated $NaHCO_3$ aqueous solution. The aqueous layer was extracted with $CH_2Cl_2$ two times, and the organic layer was collected, dried over MgSO₄, and purified by silica gel chromatography to obtain the title compound (yellow oil, 225 mg, 93.3% yield).

¹H NMR (300 MHz, CDCl₃) δ 7.98 (dd, 1H), 7.86-7.74 (m, 1H), 7.50-7.30 (m, 5H), 7.14 (d, 1H), 7.06-6.93 (m, 3H), 5.12 (s, 2H), 4.07 (m, 1H), 3.88 (s, 3H), 2.74-2.42 (m, 4H), 1.20 (d, 3H).

<79-6> Preparation of (R)-methyl 9-(benzyloxy)-6-methyl-6,7-dihydrodibenzo[b,d]oxepin-2-carboxylate

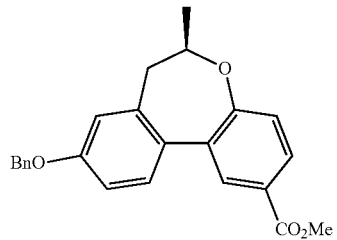 [SMILES: COC(=O)c1ccc2c(c1)-c1ccc(OCc3ccccc3)cc1C[C@@H](C)O2]

A solution of the compound obtained in <79-5> (225 mg, 0.573 mmol) in THF (5 mL) was added with PBu₃ (0.021 mL, 0.860 mmol) and ADD (217 mg, 0.860 mmol), and then stirred at room temperature for 3 hours. The reaction mixture was concentrated and purified by silica gel chromatography to obtain the title compound (pale yellow oil, 150 mg, 69.9% yield).

¹H NMR (300 MHz, CDCl₃) δ 8.10 (d, 1H), 7.96 (dd, 1H), 7.52-7.30 (m, 6H), 7.12 (d, 1H), 7.01 (dd, 1H), 6.91 (d, 1H), 5.13 (s, 2H), 4.97-4.78 (m, 1H), 3.92 (s, 3H), 2.82 (dd, 1H), 2.52 (dd, 1H), 1.39 (d, 3H).

<79-7> Preparation of (R)-methyl 9-hydroxy-6-methyl-6,7-dihydrodibenzo[b,d]oxepin-2-carboxylate

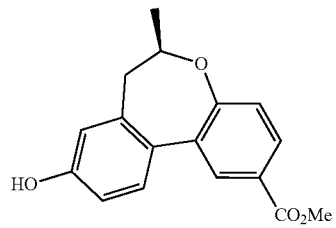

A solution of the compound obtained in <79-6> (153 mg, 0.408 mmol) in MeOH (4 mL) was added with Pd—C (30 mg) and stirred under a hydrogen atmosphere for 15 hours. The reaction mixture was filtered through Celite and washed with EA. The filtrate thus obtained was concentrated and purified by silica gel chromatography to obtain the title compound (yellow oil, 114 mg, 98.2% yield).

¹H NMR (300 MHz, CDCl₃) δ 8.09 (d, 1H), 7.96 (dd, 1H), 7.38 (d, 1H), 7.12 (d, 1H), 6.87 (dd, 1H), 6.77 (d, 1H), 4.98 (s, 1H), 4.95-4.79 (m, 1H), 3.93 (s, 3H), 2.80 (dd, 1H), 2.50 (dd, 1H), 1.40 (d, 3H).

<79-8> Preparation of (R)-methyl 6-methyl-9-(3-(methylsulfonyl)propoxy)-6,7-dihydrodibenzo[b,d]oxepin-2-carboxylate

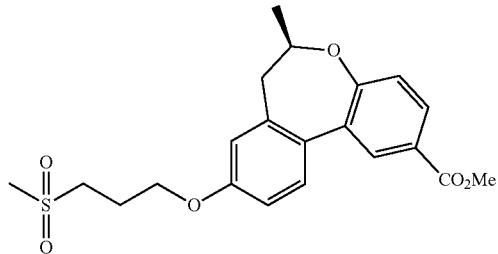 [SMILES: COC(=O)c1ccc2c(c1)-c1ccc(OCCCS(C)(=O)=O)cc1C[C@@H](C)O2]

According to the procedures as described in <1-8>, the compound obtained in <79-7> was used to prepare the title compound (white solid, 204 mg, 99.0% yield).

¹H NMR (300 MHz, CDCl₃) δ 8.09 (d, 1H), 7.97 (dd, 1H), 7.43 (d, 1H), 7.12 (d, 1H), 6.92 (dd, 1H), 6.81 (d, 1H), 4.88 (m, 1H), 4.18 (t, 2H), 3.93 (s, 3H), 3.40-3.21 (m, 2H), 2.98 (s, 3H), 2.82 (dd, 1H), 2.52 (dd, 1H), 2.45-2.32 (m, 2H), 1.40 (d, 3H).

<79-9> Preparation of (R)-(6-methyl-9-(3-(methylsulfonyl)propoxy)-6,7-dihydrodibenzo[b,d]oxepin-2-yl)methanol

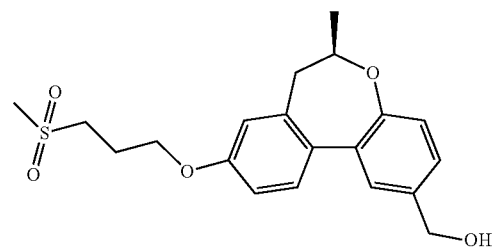 [SMILES: C[C@@H]1Cc2cc(OCCCS(C)(=O)=O)ccc2-c2cc(CO)ccc2O1]

According to the procedures as described in <1-9>, the compound obtained in <79-8> was used to prepare the title compound (pale yellow oil, 142 mg, 76.3% yield).

¹H NMR (300 MHz, CDCl₃) δ 7.43-7.36 (m, 2H), 7.29 (dd, 1H), 7.08 (d, 1H), 6.90 (d, 1H), 6.81 (d, 1H), 4.88-4.77 (m, 1H), 4.73 (d, 2H), 4.17 (t, 2H), 3.40-3.16 (m, 2H), 2.98 (s, 3H), 2.80 (dd, 1H), 2.49 (dd, 1H), 2.44-2.28 (m, 2H), 1.69 (t, 1H), 1.38 (d, 3H).

<79-10> Preparation of methyl 2-((S)-6-(((R)-6-methyl-9-(3-(methylsulfonyl)propoxy)-6,7-dihydrodibenzo[b,d]oxepin-2-yl)methoxy)-2,3-dihydrobenzofuran-3-yl)acetate

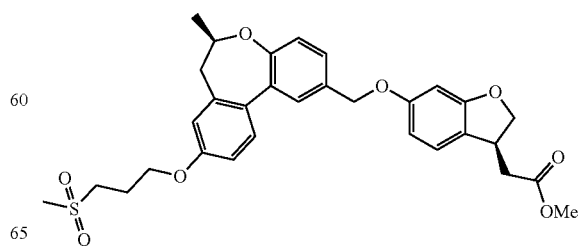

According to the procedures as described in <1-10>, the compound obtained in <79-9> was used to prepare the title compound (white foam, 126 mg, 69.2% yield).

¹H NMR (300 MHz, CDCl3) δ 7.45-7.30 (m, 1H), 7.12-7.01 (m, 2H), 6.90 (dd, 1H), 6.81 (d, 1H), 6.54-6.45 (m, 2H), 5.03 (s, 2H), 4.89-4.71 (m, 3H), 4.27 (dd, 1H), 4.17 (t, 2H), 4.01-3.75 (m, 2H), 3.72 (s, 3H), 3.28 (m, 2H), 2.97 (s, 3H), 2.85-2.71 (m, 2H), 2.63-2.44 (m, 1H), i2.44-2.31 (m, 2H), 1.38 (d, 3H).

<79-11> Preparation of 2-((S)-6-(((R)-6-methyl-9-(3-(methylsulfonyl)propoxy)-6,7-dihydrodibenzo[b,d]oxepin-2-yl)methoxy)-2,3-dihydrobenzofuran-3-yl)acetic acid

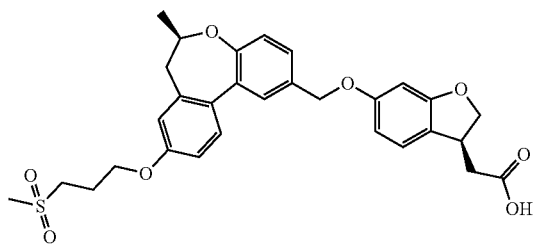 [SMILES: C[C@@H]1Cc2cc(OCCCS(C)(=O)=O)ccc2-c2cc(COc3ccc4c(c3)OC[C@H]4CC(=O)O)ccc2O1]

According to the procedures as described in <1-11>, the compound obtained in <79-10> was used to prepare the title compound (white foam, 129 mg, 88.0% yield).

MS m/z 551 [M−H]⁻.

¹H NMR (300 MHz, CDCl3) δ 7.43 (d, 1H), 7.38 (d, 1H), 7.34 (dd, 1H), 7.16-7.01 (m, 2H), 6.90 (dd, 1H), 6.81 (d, 1H), 6.58-6.45 (m, 2H), 5.03 (s, 2H), 4.89-4.71 (m, 2H), 4.30 (dd, 1H), 4.17 (t, 2H), 3.82 (m, 1H), 3.43-3.18 (m, 2H), 2.97 (s, 3H), 2.82 (m, 2H), 2.62 (dd, 1H), 2.51 (dd, 1H), 2.45-2.28 (m, 2H), 1.38 (d, 3H).

Example 80

Preparation of (S)-2-(6-((9-(3-(methylsulfonyl)propoxy)dibenzo[d,f][1,3]dioxepin-2-yl)methoxy)-2,3-dihydrobenzofuran-3-yl)acetic acid <80-1> Preparation of methyl 4'-(benzyloxy)-2',6-bis(methoxymethoxy)-[1,1'-biphenyl]-3-carboxylate

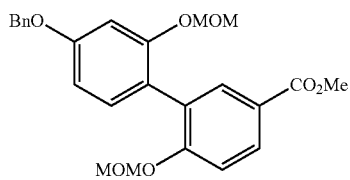

A solution of 4-(benzyloxy)-1-bromo-2-(methoxymethoxy)benzene (prepared in accordance with the reference [Synthesis, 1999, #6, p. 1017-1021]; 4.82 g, 14.921 mmol) and the compound obtained in <2-6> (4.37 g, 13.564 mmol) in 1,4-dioxane (70 mL) was added with K₂CO₃ (5.62 g, 40.693 mmol) and substituted with nitrogen. The reaction mixture was added with Pd(dppf)Cl₂.MC (554 mg, 0.678 mmol) and stirred at 100° C. for 13 hours. The reaction mixture was cooled to room temperature, filtered through Celite, and washed with CH₂Cl₂. The filtrate thus obtained was concentrated under reduced pressure and purified by silica gel chromatography to obtain the title compound (yellow oil, 2.61 g, 44% yield).

¹H NMR (300 MHz, CDCl₃) δ 7.98 (dd, 1H), 7.94 (d, 1H), 7.50-7.31 (m, 5H), 7.23 (d, 1H), 7.15 (d, 1H), 6.91 (d, 1H), 6.70 (dd, 1H), 5.15 (s, 2H), 5.09 (s, 2H), 5.05 (s, 2H), 3.88 (d, 3H), 3.39 (d, 3H), 3.34 (d, 3H).

<80-2> Preparation of methyl 4'-(benzyloxy)-2',6-dihydroxy-[1,1'-biphenyl]-3-carboxylate

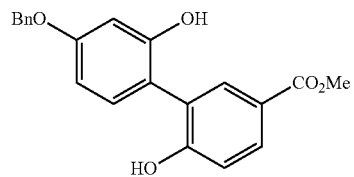 [SMILES: COC(=O)c1ccc(O)c(-c2ccc(OCc3ccccc3)cc2O)c1]

According to the procedures as described in <43-3>, the compound obtained in <80-1> was used to prepare the title compound (white foam, 1.99 g, 95% yield).

¹H NMR (300 MHz, CDCl₃) δ 8.00 (dd, 1H), 7.96 (d, 1H), 7.49-7.31 (m, 5H), 7.17 (d, 1H), 7.06 (d, 1H), 6.72 (dd, 1H), 6.67 (d, 1H), 5.96 (br s, 1H), 5.43 (br s, 1H), 5.10 (s, 2H), 3.89 (d, 2H).

<80-3> Preparation of methyl 9-(benzyloxy)dibenzo[d,f][1,3]dioxepin-2-carboxylate

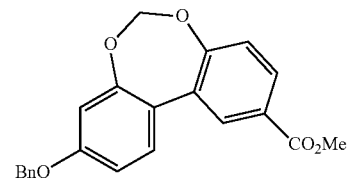 [SMILES: COC(=O)c1ccc2c(c1)-c1ccc(OCc3ccccc3)cc1OCO2]

A mixed solution of the compound obtained in <80-2> (1.99 g, 5.680 mmol), K₂CO₃ (4.71 g, 34.079 mmol) and NaI (426 mg, 2.840 mmol) in DMF (20 mL) was added with dibromoethane (1.2 mL, 17.040 mmol) and stirred 80° C. for 13 hours. The reaction mixture was diluted with EtOAc, consecutively washed with distilled water, a saturated NH₄Cl aqueous solution and brine, and then dried over MgSO₄. The filtrate was concentrated under reduced pressure and purified by silica gel chromatography to obtain the title compound (white solid, 1.68 g, 82% yield).

¹H NMR (300 MHz, CDCl₃) δ 8.43 (d, 1H), 7.88 (dd, 1H), 7.76 (d, 1H), 7.49-7.30 (m, 5H), 7.12 (d, 1H), 6.88 (dd, 1H), 6.74 (d, 1H), 5.57 (s, 2H), 5.10 (s, 2H), 3.93 (s, 3H).

<80-4> Preparation of methyl 9-hydroxydibenzo[d,f][1,3]dioxepin-2-carboxylate

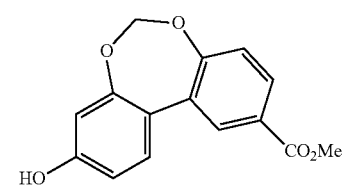 [SMILES: COC(=O)c1ccc2c(c1)-c1ccc(O)cc1OCO2]

A solution of the compound obtained in <80-3> (1.68 g, 4.636 mmol) in CH$_2$Cl$_2$ (25 mL) and MeOH (25 mL) was added with Pd/C (10 wt % loading dry basis, 340 mg) and stirred under a hydrogen atmosphere for 3 hours. The reaction mixture was filtered, and the filtrate was concentrated under reduced pressure, diluted with CH$_2$Cl$_2$, stirred for 10 minutes, and then filtered. The solid thus obtained was dried in vacuo to obtain the title compound (white solid, 1.12 g, 89% yield).

$^1$H NMR (300 MHz, CDCl$_3$) δ 8.41 (d, 1H), 7.86 (dd, 1H), 7.69 (d, 1H), 7.11 (dd, 1H), 6.74 (dd, 1H), 6.61 (dd, 1H), 5.56 (d, 2H), 3.94 (d, 3H).

<80-5> Preparation of methyl 9-(3-(methylsulfonyl)propoxy)dibenzo[d,f][1,3]dioxepin-2-carboxylate

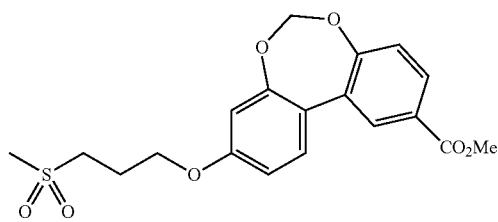 [SMILES: COC(=O)c1ccc2c(c1)-c1ccc(OCCCS(C)(=O)=O)cc1OCO2]

According to the procedures as described in <1-8>, the compound obtained in <80-4> was used to prepare the title compound (white solid, 442 mg, ~100% yield).

$^1$H NMR (300 MHz, CDCl$_3$) δ 8.42 (d, 1H), 7.89 (dd, 1H), 7.76 (d, 1H), 7.13 (d, 1H), 6.78 (dd, 1H), 6.65 (d, 1H), 5.57 (s, 2H), 4.15 (t, 2H), 3.94 (s, 3H), 3.34-3.23 (m, 2H), 2.98 (s, 3H), 2.46-2.29 (m, 2H).

<80-6> Preparation of (9-(3-(methylsulfonyl)propoxy)dibenzo[d,f][1,3]dioxepin-2-yl)methanol

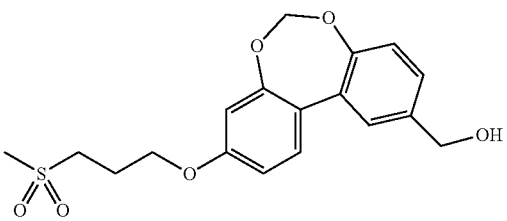 [SMILES: CS(=O)(=O)CCCOc1ccc2c(c1)OCOc1ccc(CO)cc1-2]

According to the procedures as described in <1-9>, the compound obtained in <80-5> was used to prepare the title compound (white solid, 353 mg, 88% yield).

$^1$H NMR (300 MHz, CDCl$_3$) δ 7.72-7.60 (m, 2H), 7.25 (dd, 1H), 7.11 (d, 1H), 6.76 (dd, 1H), 6.66 (d, 1H), 5.57 (s, 2H), 4.73 (d, 2H), 4.15 (t, 2H), 3.39-3.19 (m, 2H), 2.97 (s, 3H), 2.45-2.30 (m, 2H), 1.68 (t, 1H).

<80-7> Preparation of (S)-methyl 2-(6-((9-(3-(methylsulfonyl)propoxy)dibenzo[d,f][1,3]dioxepin-2-yl)methoxy)-2,3-dihydrobenzofuran-3-yl)acetate

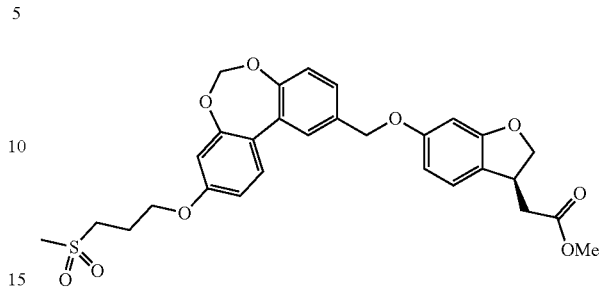

According to the procedures as described in <1-10>, the compound obtained in <80-6> was used to prepare the title compound (white solid, 137 mg, 87% yield).

$^1$H NMR (300 MHz, CDCl$_3$) δ 7.69 (d, 1H), 7.63 (d, 1H), 7.29 (dd, 1H), 7.12 (d, 1H), 7.04 (d, 1H), 6.76 (dd, 1H), 6.65 (d, 1H), 6.54-6.45 (m, 2H), 5.57 (s, 2H), 5.02 (s, 2H), 4.76 (t, 1H), 4.34-4.22 (dd, 1H), 4.14 (t, 2H), 3.82 (m, 1H), 3.72 (s, 3H), 3.34-3.20 (m, 2H), 2.97 (s, 3H), 2.76 (dd, 1H), 2.57 (dd, 1H), 2.43-2.32 (m, 2H).

<80-8> Preparation of (S)-2-(6-((9-(3-(methylsulfonyl)propoxy)dibenzo[d,f][1,3]dioxepin-2-yl)methoxy)-2,3-dihydrobenzofuran-3-yl)acetic acid

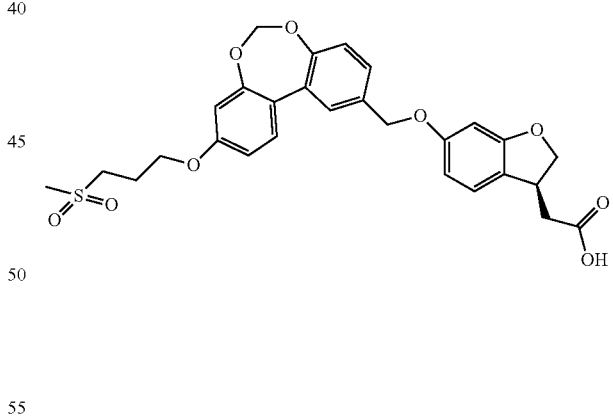

According to the procedures as described in <1-11>, the compound obtained in <80-7> was used to prepare the title compound (white solid, 114 mg, 90% yield).

MS m/z 539 [M−H]$^-$.

$^1$H NMR (300 MHz, CDCl$_3$) δ 7.69 (d, 1H), 7.63 (d, 1H), 7.29 (dd, 1H), 7.12 (d, 1H), 7.08 (d, 1H), 6.76 (dd, 1H), 6.65 (d, 1H), 6.57-6.43 (m, 2H), 5.57 (s, 2H), 5.03 (s, 2H), 4.78 (t, 1H), 4.30 (dd, 1H), 4.14 (t, 2H), 3.83 (m, 1H), 3.34-3.19 (m, 2H), 2.97 (s, 3H), 2.82 (dd, 1H), 2.63 (dd, 1H), 2.45-2.30 (m, 2H).

Example 81

Preparation of 2-((3S)-6-((1-methyl-3-morpholino-6,7-dihydro-5H-benzo[3,4]cyclohepta[1,2-d]pyrimidin-10-yl)methoxy)-2,3-dihydrobenzofuran-3-yl) acetic acid <81-1> Preparation of 4-allyl-2-chloro-6-methylpyrimidine

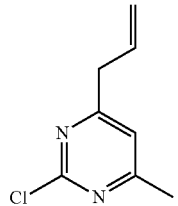

2,4-dichloro-6-methylpyrimidine (10 g, 60.350 mmol), 2-allyl-4,4,5,5-tetramethyl-1,3,2-dioxaborolane (11.5 mL, 61.350 mmol), K₃PO₄ (26.0 g, 122.699 mmol), THF (240 mL), distilled water (30 mL) were substituted with nitrogen for a few minutes while stirring. The mixture was added with Pd(PPh₃)₂Cl₂ (2.15 g, 3.067 mmol) and allowed to react at 80° C. for 17 hours. The reaction mixture was cooled to room temperature and added with EtOAc and distilled water. The organic layer was separated and the aqueous layer was extracted with EtOAc one more time. The organic layer was collected, dried over MgSO₄, and the filtrate thus obtained was concentrated under reduced pressure and purified by silica gel chromatography to obtain the title compound (yellow oil, 5.93 g, 57% yield).

¹H NMR (300 MHz, CDCl₃) δ 7.00 (s, 1H), 6.06-5.90 (m, 1H), 5.26-5.14 (m, 2H), 3.51 (m, 2H), 2.51 (s, 3H).

<81-2> Preparation of methyl 3-bromo-4-(3-(2-chloro-6-methylpyrimidin-4-yl)propyl)benzoate

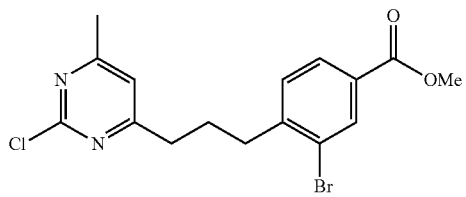 [SMILES: COC(=O)c1ccc(CCCc2cc(C)nc(Cl)n2)c(Br)c1]

A solution of the compound obtained in <81-1> (5.02 g, 29.771 mmol) in THF (35 mL) was added with 9-BBN (0.5M THF solution, 65.5 mL, 32.748 mmol) and stirred at room temperature for 2.5 hours. The mixture was added with DMF (100 mL), methyl 3-bromo-4-iodobenzoate (11.17 g, 32.748 mmol) and K₂CO₃ (12.34 g, 89.313 mmol), and then substituted with nitrogen for a few minutes. Then, the mixture was added with Pd(dppf)Cl₂.MC (1.22 g, 1.489 mmol) and allowed to react at 100° C. for 16 hours. After cooled to room temperature, the reaction mixture was added with distilled water and brine, and then extracted with EtOAc. The organic layer was collected and dried over MgSO₄. The filtrate thus obtained was concentrated under reduced pressure and purified by silica gel chromatography to obtain the title compound (yellow oil, 5.38 g, 47% yield).

¹H NMR (300 MHz, CDCl₃) δ 8.20 (d, 1H), 7.90 (dd, 1H), 7.29 (d, 1H), 6.98 (s, 1H), 3.92 (s, 3H), 2.90-2.74 (m, 4H), 2.50 (s, 3H), 2.17-1.99 (m, 2H).

<81-3> Preparation of methyl 3-bromo-4-(3-(6-methyl-2-morpholinopyrimidin-4-yl)propyl)benzoate

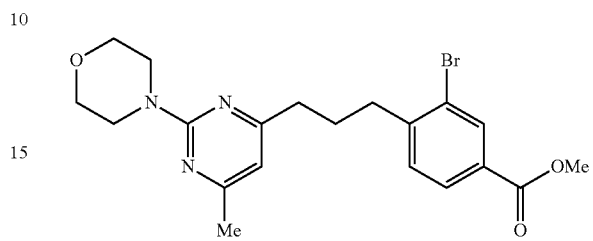

Methyl 3-bromo-4-(3-(2-chloro-6-methylpyrimidin-4-yl)propyl)benzoate obtained in <81-2> (500 mg, 1.30 mmol) was dissolved in CH₃CN (5 mL), which was then added with morpholine (228 μL, 2.60 mmol) and i-Pr₂NEt (340 μL, 1.95 mmol), followed by stirring at 60° C. for 1 hour. The mixture was added with morpholine (228 μL, 2.60 mmol) and further added with morpholine (228 μL, 2.60 mmol) 13 hours thereafter. After 3 hours later, the reaction mixture was cooled to room temperature, diluted with EtOAc, and extracted with brine three times. The organic layer was dried over MgSO₄, concentrated under reduced pressure, and the residue thus obtained was purified by silica gel chromatography to obtain the title compound (colorless solid, 519.9 mg, 92% yield).

¹H NMR (300 MHz, CDCl₃) δ 8.20 (d, 1H), 7.88 (dd, 1H), 7.29 (d, 1H), 6.30 (s, 1H), 3.91 (s, 3H), 3.78 (m, 8H), 2.83 (t, 2H), 2.61 (t, 2H), 2.30 (s, 3H), 2.03 (m, 2H)

<81-4> Preparation of methyl 4-(3-(6-methyl-2-morpholinopyrimidin-4-yl)propyl)-3-(4,4,5,5-tetramethyl-1,3,2-dioxaboran-2-yl)benzoate

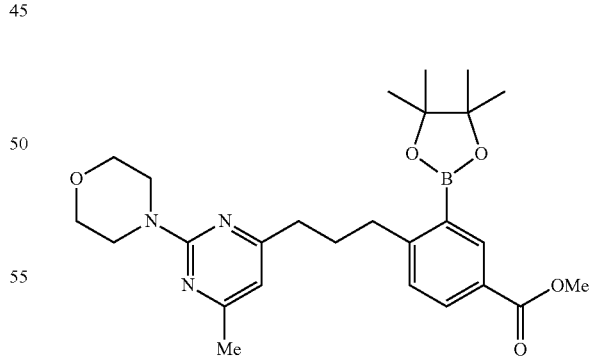

According to the procedures as described in <5-4>, the compound obtained in <81-3> was used to prepare the title compound (pale green oil, 508.4 mg, 88% yield).

¹H NMR (300 MHz, CDCl₃) δ 8.43 (d, 1H), 7.99 (dd, 1H), 7.24 (d, 1H), 6.27 (s, 1H), 3.91 (s, 3H), 3.77 (m, 8H), 2.99 (t, 2H), 2.58 (t, 2H), 2.29 (s, 3H), 1.94 (m, 2H), 1.35 (s, 12H)

<81-5> Preparation of methyl 4-(3-(5-bromo-6-methyl-2-morpholinopyrimidin-4-yl)propyl)-3-(4,4,5,5-tetramethyl-1,3,2-dioxaboran-2-yl)benzoate

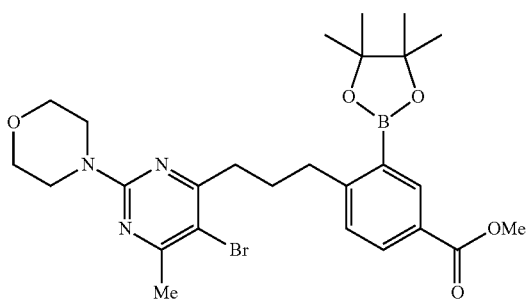 [SMILES: COC(=O)c1ccc(CCCc2nc(N3CCOCC3)nc(C)c2Br)c(B2OC(C)(C)C(C)(C)O2)c1]

According to the procedures as described in <5-5>, the compound obtained in <81-4> was used to prepare the title compound (colorless oil, 528.2 mg, 89% yield).

$^1$H NMR (300 MHz, CDCl$_3$) δ 8.43 (d, 1H), 7.99 (dd, 1H), 7.27 (d, 1H), 3.90 (s, 3H), 3.74 (m, 8H), 3.03 (t, 2H), 2.80 (t, 2H), 2.44 (s, 3H), 1.96 (m, 2H), 1.34 (s, 12H)

<81-6> Preparation of methyl 1-methyl-3-morpholino-6,7-dihydro-5H-benzo[3,4]cyclohepta[1,2-d]pyrimidine-10-carboxylate

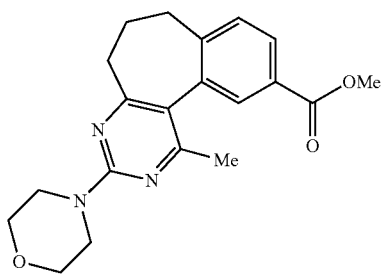 [SMILES: COC(=O)c1ccc2c(c1)-c1c(C)nc(N3CCOCC3)nc1CCC2]

According to the procedures as described in <5-6>, the compound obtained in <81-5> was used to prepare the title compound (colorless oil, 104.8 mg, 32% yield).

$^1$H NMR (300 MHz, CDCl$_3$) δ 7.95 (dd, 1H), 7.76 (d, 1H), 7.36 (d, 1H), 3.89 (s, 3H), 3.71 (m, 8H), 2.61-2.39 (m, 6H), 2.40 (s, 3H), 1.81 (m, 2H)

<81-7> Preparation of (1-methyl-3-morpholino-6,7-dihydro-5H-benzo[3,4]cyclohepta[1,2-d]pyrimidin-10-yl)methanol

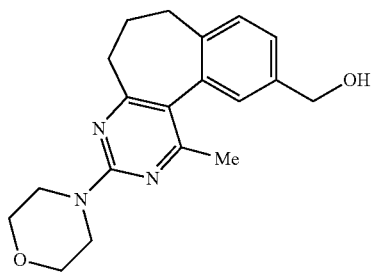 [SMILES: Cc1nc(N2CCOCC2)nc2c1-c1cc(CO)ccc1CCC2]

According to the procedures as described in <1-9>, the compound obtained in <81-6> was used to prepare the title compound (colorless oil, 88.2 mg, 90% yield).

$^1$H NMR (300 MHz, CDCl$_3$) δ 7.13-7.30 (m, 3H), 4.71 (d, 2H), 3.88-3.74 (m, 8H), 2.66-2.34 (m, 4H), 2.37 (s, 3H), 2.25-2.01 (m, 2H)

<81-8> Preparation of methyl 2-((3S)-6-((9-((4-hydroxy-1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-ylacetate

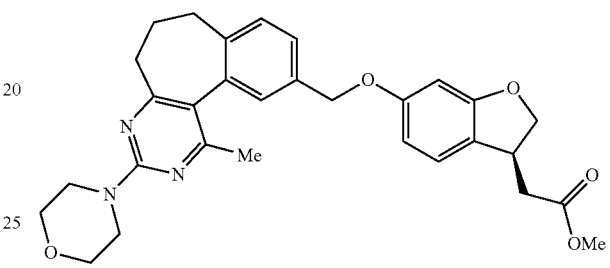

According to the procedures as described in <1-10>, the compound obtained in <81-7> was used to prepare the title compound (colorless oil, 84.5 mg, 61% yield).

$^1$H NMR (300 MHz, CDCl$_3$) δ 7.32-7.19 (m, 3H), 7.02 (d, 1H), 6.51-6.46 (m, 2H), 5.05 (s, 2H), 4.75 (t, 1H), 4.26 (dd, 1H), 3.88-3.74 (m, 9H), 3.72 (s, 3H), 2.74 (dd, 1H), 2.61-2.32 (m, 5H), 2.30 (s, 3H), 2.25-2.02 (m, 2H)

<81-9> Preparation of 2-((3S)-6-((1-methyl-3-morpholino-6,7-dihydro-5H-benzo[3,4]cyclohepta[1,2-d]pyrimidin-10-yl)methoxy)-2,3-dihydrobenzofuran-3-yl)acetic acid

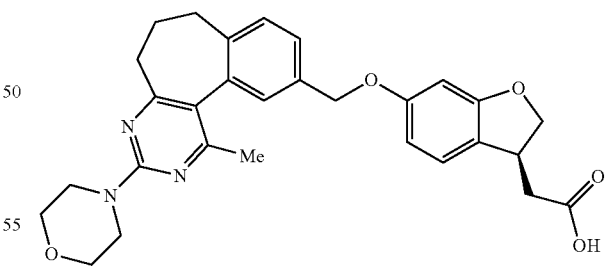

According to the procedures as described in <1-11>, the compound obtained in <81-8> was used to prepare the title compound (white foam, 76.4 mg, 95% yield).

MS m/z 502 [M+H].

$^1$H NMR (300 MHz, CDCl$_3$) δ 7.32-7.21 (m, 3H), 7.05 (d, 1H), 6.52-6.46 (m, 2H), 5.05 (s, 2H), 4.76 (t, 1H), 4.28 (dd, 1H), 3.74-3.87 (m, 9H), 2.79 (dd, 1H), 2.65-2.36 (m, 5H), 2.30 (s, 3H), 2.25-2.02 (m, 2H)

Example 82

Preparation of (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-yl)acetic acid <82-1> Preparation of (S)-methyl 2-(6-(((9-(3-(methylsulfonyl)propoxy)-6,7-dihydro-5H-dibenzo[a,c][7]annulen-2-yl)methyl)amino)-2,3-dihydrobenzofuran-3-ylacetate

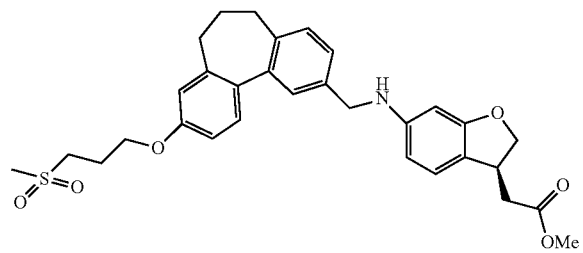 [SMILES: COC(=O)C[C@@H]1COc2cc(NCc3ccc4c(c3)-c3ccc(OCCCS(C)(=O)=O)cc3CCC4)ccc21]

A solution of the compound obtained in <6-1> (80 mg, 0.223 mmol) and (S)-methyl 2-(6-amino-2,3-dihydrobenzofuran-3-ylacetate (prepared in accordance with the reference [WO 2010/143733 A1]; 46 mg, 0.223 mmol) in CH$_2$Cl$_2$ (2 mL) was added with AcOH (0.03 mL, 0.446 mmol), stirred at room temperature for 20 minutes, added with NaBH(OAc)$_3$ (95 mg, 0.446 mmol), and further stirred for 3.5 hours. The reaction mixture was added with distilled water, extracted with CH$_2$Cl$_2$, and the organic layer was collected and dried over MgSO$_4$. The filtrate thus obtained was concentrated under reduced pressure and purified by silica gel chromatography to obtain the title compound (white foam, 124 mg, >100% yield).

$^1$H NMR (300 MHz, CDCl$_3$) δ 7.34-7.21 (m, 3H), 7.19 (d, 1H), 6.93 (d, 1H), 6.84 (dd, 1H), 6.79 (d, 1H), 6.22-6.10 (m, 2H), 4.70 (t, 1H), 4.31 (s, 2H), 4.26-4.00 (m, 4H), 3.76 (m, 1H), 3.71 (s, 3H), 3.35-3.21 (m, 2H), 2.97 (s, 3H), 2.73 (dd, 1H), 2.59-2.42 (m, 5H), 2.42-2.30 (m, 2H), 2.18 (m, 2H).

<82-2> Preparation of (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-yl)acetic acid

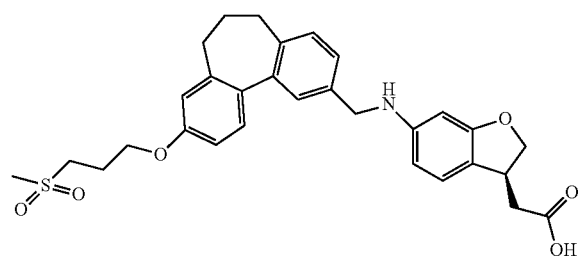 [SMILES: CS(=O)(=O)CCCOc1ccc2c(c1)CCCc1ccc(CNc3ccc4c(c3)OC[C@H]4CC(=O)O)cc1-2]

According to the procedures as described in <1-11>, the compound obtained in <82-1> was used to prepare the title compound (yellow foam, 102 mg, 84% yield).

MS m/z 534 [M−H]$^-$.

$^1$H NMR (300 MHz, CDCl$_3$) δ 7.33-7.21 (m, 3H), 7.19 (d, 1H), 6.96 (d, 1H), 6.84 (dd, 1H), 6.79 (d, 1H), 6.24-6.11 (m, 2H), 4.72 (t, 1H), 4.32 (s, 2H), 4.24 (dd, 1H), 4.16 (t, 2H), 3.77 (m, 1H), 3.33-3.23 (m, 2H), 2.97 (s, 3H), 2.79 (dd, 1H), 2.59 (dd, 1H), 2.47 (m, 4H), 2.37 (m, 2H), 2.17 (m, 2H).

Example 83

Preparation of (S)-2-(6-(((9-((1,1-dioxidotetrahydro-2H-thiopyran-4-yl)methoxy)-6,7-dihydro-5H-dibenzo[a,c][7]annulen-2-yl)methyl)amino)-2,3-dihydrobenzofuran-3-yl)acetic acid <83-1> Preparation of (S)-methyl 2-(6-(((9-((1,1-dioxidotetrahydro-2H-thiopyran-4-yl)methoxy)-6,7-dihydro-5H-dibenzo[a,c][7]annulen-2-yl)methyl)amino)-2,3-dihydrobenzofuran-3-ylacetate

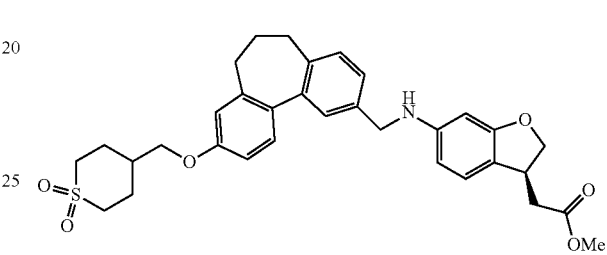

According to the procedures as described in <82-1>, the compound obtained in <78-3> was used to prepare the title compound (off-white foam, 164.1 mg, 109% yield).

$^1$H NMR (300 MHz, CDCl$_3$) δ=7.34-7.23 (m, 3H), 7.19 (d, 1H), 6.93 (d, 1H), 6.83 (dd, 1H), 6.78 (d, 1H), 6.21-6.13 (m, 2H), 4.71 (t, 1H), 4.31 (s, 2H), 4.22 (dd, 1H), 4.07 (br s, 1H), 3.91 (d, 2H), 3.77 (m, 1H), 3.71 (s, 3H), 3.21-2.96 (m, 4H), 2.73 (dd, 1H), 2.58-2.39 (m, 5H), 2.31 (m, 2H), 2.24-2.13 (m, 2H), 2.12-1.95 (m, 3H).

<83-2> Preparation of (S)-2-(6-(((9-((1,1-dioxidotetrahydro-2H-thiopyran-4-yl)methoxy)-6,7-dihydro-5H-dibenzo[a,c][7]annulen-2-yl)methyl)amino)-2,3-dihydrobenzofuran-3-yl)acetic acid

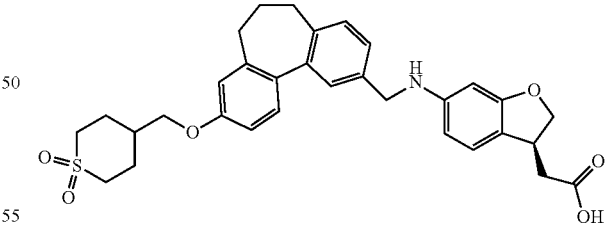

According to the procedures as described in <1-11>, the compound obtained in <83-1> was used to prepare the title compound (off-white foam, 154.8 mg, 98% yield).

MS m/z 562 [M+H]$^+$.

$^1$H NMR (300 MHz, CDCl$_3$) δ=7.34-7.23 (m, 3H), 7.19 (d, 1H), 6.97 (d, 1H), 6.83 (dd, 1H), 6.78 (d, 1H), 6.23-6.11 (m, 2H), 4.72 (t, 1H), 4.32 (s, 2H), 4.24 (dd, 1H), 3.92 (d, 2H), 3.77 (m, 1H), 3.21-2.97 (m, 4H), 2.79 (dd, 1H), 2.59 (dd, 1H), 2.48 (m, 4H), 2.31 (m, 2H), 2.18 (m, 2H), 2.13-1.97 (m, 3H).

Example 84

Preparation of (S)-2-(6-((9-((1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid <84-1> Preparation of (S)-methyl 2-(6-((9-((1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetate

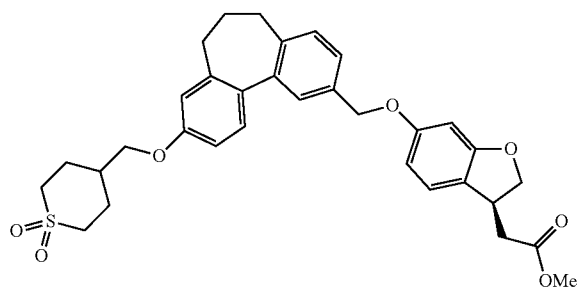 [SMILES: COC(=O)C[C@@H]1COc2cc(OCc3ccc4c(c3)-c3ccc(OCC5CCS(=O)(=O)CC5)cc3CCC4)ccc21]

According to the procedures as described in <1-10>, the compound obtained in <84-2> was used to prepare the title compound (colorless oil, 190 mg, 104% yield).

$^1$H NMR (300 MHz, CDCl$_3$) δ 7.40-7.27 (m, 3H), 7.23 (d, 1H), 7.03 (dd, 1H), 6.84 (dd, 1H), 6.79 (d, 1H), 6.54-6.43 (m, 2H), 5.04 (s, 2H), 4.76 (t, 1H), 4.27 (dd, 1H), 3.91 (d, 2H), 3.80 (m, 1H), 3.72 (s, 3H), 3.24-2.93 (m, 4H), 2.76 (dd, 1H), 2.65-2.41 (m, 5H), 2.32 (m, 2H), 2.17 (m, 2H), 2.12-1.97 (m, 3H).

<84-2> Preparation of (S)-2-(6-((9-((1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid

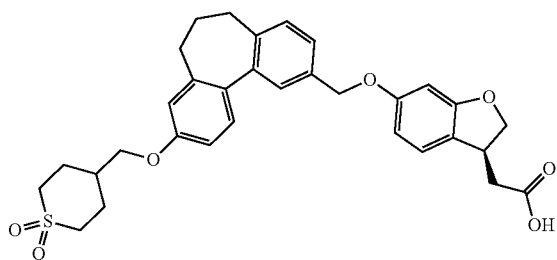 [SMILES: O=C(O)C[C@@H]1COc2cc(OCc3ccc4c(c3)-c3ccc(OCC5CCS(=O)(=O)CC5)cc3CCC4)ccc21]

According to the procedures as described in <1-11>, the compound obtained in <84-1> was used to prepare the title compound (white solid, 93 mg, 52% yield).

MS m/z 561 [M−H]$^-$.

$^1$H NMR (300 MHz, DMSO-d$_6$) δ 7.37-7.22 (m, 4H), 7.11 (d, 1H), 6.95-6.87 (m, 2H), 6.51-6.45 (m, 2H), 5.07 (s, 2H), 4.68 (t, 1H), 4.19 (m, 1H), 3.93 (d, 2H), 3.67 (m, 1H), 3.27-3.00 (m, 4H), 2.70 (dd, 1H), 2.54-2.30 (m, 5H), 2.22-2.00 (m, 5H), 1.87-1.68 (m, 2H).

Example 85

Preparation of (S)-2-(6-((9-((1,1-dioxidotetrahydro-2H-thiopyran-4-yl)methoxy)-3-fluoro-6,7-dihydro-5H-dibenzo[a,c][7]annulen-2-yl)methoxy)-2,3-dihydrobenzofuran-3-yl)acetic acid <85-1> Preparation of methyl 4-amino-5-bromo-2-fluorobenzoate

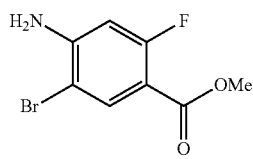 [SMILES: COC(=O)c1cc(Br)c(N)cc1F]

Methyl 4-amino-2-fluorobenzoate (prepared in accordance with the reference [Bioorganic and Medicinal Chemistry, 2009, vol. 17, p. 7042-7051]; 7.93 g, 46.9 mmol) was dissolved in CHCl$_3$ (140 mL), added with N-bromosuccinimide (8.34 g, 46.9 mmol) at 0° C., and then stirred at room temperature for 1 hour. The reaction mixture was concentrated, and the residue thus obtained was purified by silica gel chromatography to obtain the title compound (white solid, 8.70 g, 75% yield).

$^1$H NMR (600 MHz, CDCl$_3$) δ 8.04 (d, 1H), 6.45 (d, 1H), 4.61 (br s, 2H), 3.88 (s, 3H).

<85-2> Preparation of methyl 5-bromo-2-fluoro-4-iodobenzoate

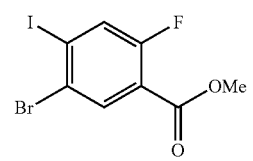 [SMILES: COC(=O)c1cc(Br)c(I)cc1F]

The compound obtained in <85-1> (8.7 g, 35.1 mmol) was dissolved in acetone, which was then added with 6N HCl aqueous solution (58.5 mL, 351 mmol) at 0° C. and stirred for 5 minutes. The reaction mixture was added with 3.5M NaNO$_2$ aqueous solution (15 mL, 52.6 mmol) and stirred for 60 minutes. The reaction mixture was slowly added with 3.5M KI aqueous solution (20 mL, 70.1 mmol) and stirred for 2 hours. Then, the mixture was diluted with a saturated Na$_2$S$_2$O$_3$ aqueous solution and extracted with EtOAc. The organic layer was washed with brine, dried over sodium sulfate, filtered and concentrated under reduced pressure. The residue thus obtained was purified by silica gel chromatography to obtain the title compound (white solid, 8.81 g, 70% yield).

$^1$H NMR (600 MHz, CDCl$_3$) δ 8.14 (d, 1H), 7.68 (d, 1H), 3.93 (s, 3H).

<85-3> Preparation of methyl 5-bromo-2-fluoro-4-(3-(3-methoxyphenyl)propyl)benzoate

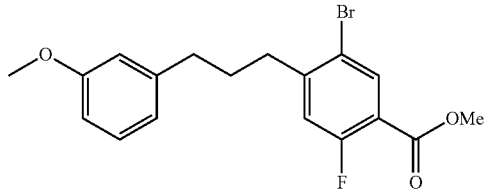 [SMILES: COC(=O)c1cc(Br)c(CCCc2cccc(OC)c2)cc1F]

1-Allyl-3-methoxybenzene (prepared in accordance with the reference [Journal of Organic Chemistry, 2013, vol. 78, p. 9772-9780]; 2.44 g, 16.5 mmol) was dissolved in THF (19 mL), slowly added with 9-BBN (0.5M THF solution, 39.5 mL, 19.8 mmol), and stirred at room temperature for 2 hours. The reaction mixture was added with the compound obtained in <88-2> (6.5 g, 18.1 mmol), $K_2CO_3$ (6.83 g, 49.3 mmol) and DMF (38 mL), and then substituted with nitrogen. Subsequently, the mixture was added with [1,1'-bis(diphenylphosphino)ferrocene]dichloropalladium(II) complex with dichloromethane (672 mg, 0.823 mmol), and then stirred at 110° C. for 15 hours. The reaction mixture was cooled to room temperature, added with a saturated $NH_4Cl$ aqueous solution, and extracted with EtOAc. The organic layer was washed with brine, dried over sodium sulfate, filtered and concentrated under reduced pressure. The residue thus obtained was purified by silica gel chromatography to obtain the title compound (colorless oil, 3.49 g, 55% yield).

$^1$H NMR (600 MHz, $CDCl_3$) δ 8.09 (d, 1H), 7.21 (t, 1H), 7.00 (d, 1H), 6.79 (d, 1H), 6.76-6.74 (m, 2H), 3.92 (s, 3H), 3.80 (s, 3H), 2.76 (dd, 2H), 2.68 (t, 2H), 1.98-1.93 (m, 2H).

<85-4> Preparation of methyl 2-fluoro-4-(3-(3-methoxyphenyl)propyl)-5-(4,4,5,5-tetramethyl-1,3,2-dioxaboran-2-yl)benzoate

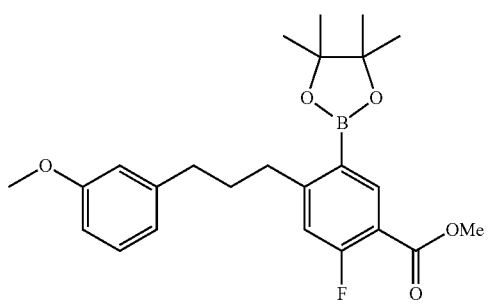 [SMILES: COC(=O)c1cc(B2OC(C)(C)C(C)(C)O2)c(CCCc2cccc(OC)c2)cc1F]

According to the procedures as described in <5-4>, the compound obtained in <85-3> was used to prepare the title compound (white foam, 5.02 g, 77% yield).

$^1$H NMR (600 MHz, $CDCl_3$) δ 8.34 (d, 1H), 7.20 (t, 1H), 6.93 (d, 1H), 6.77 (d, 1H), 6.74-6.72 (m, 2H), 3.91 (s, 3H), 3.79 (s, 3H), 2.96 (dd, 2H), 2.65 (t, 2H), 1.89-1.86 (m, 2H).

<85-5> Preparation of methyl 4-(3-(2-bromo-5-methoxyphenyl)propyl)-2-fluoro-5-(4,4,5,5-tetramethyl-1,3,2-dioxaboran-2-yl)benzoate

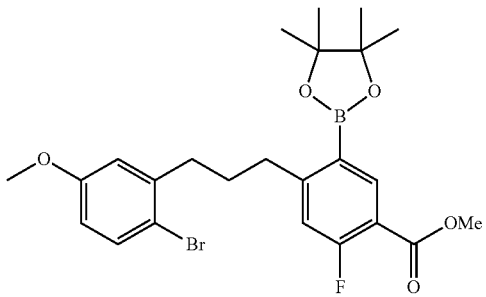 [SMILES: COC(=O)c1cc(B2OC(C)(C)C(C)(C)O2)c(CCCc2cc(OC)ccc2Br)cc1F]

According to the procedures as described in <5-5>, the compound obtained in <85-4> was used to prepare the title compound (white foam, 5.5 g, 93% yield).

$^1$H NMR (600 MHz, $CDCl_3$) δ 8.35 (d, 1H), 7.39 (d, 1H), 6.97 (d, 1H), 6.74 (d, 1H), 6.62 (dd, 2H), 3.91 (s, 3H), 3.77 (s, 3H), 3.00 (dd, 2H), 2.74 (t, 2H), 1.89-1.86 (m, 2H).

<85-6> Preparation of methyl 3-fluoro-9-methoxy-6,7-dihydro-5H-dibenzo[a,c][7]annulene-2-carboxylate

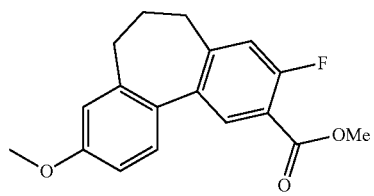 [SMILES: COC(=O)c1cc2c(cc1F)CCCc1cc(OC)ccc1-2]

According to the procedures as described in <5-6>, the compound obtained in <85-5> was used to prepare the title compound (white foam, 1.89 g, 58% yield).

$^1$H NMR (600 MHz, $CDCl_3$) δ 7.89 (d, 1H), 7.30 (d, 1H), 7.02 (d, 1H), 6.88 (dd, 1H), 6.80 (d, 1H), 3.94 (s, 3H), 3.86 (s, 3H), 2.51 (t, 2H), 2.46 (t, 2H), 2.21-2.18 (m, 2H).

<85-7> Preparation of methyl 3-fluoro-9-hydroxy-6,7-dihydro-5H-dibenzo[a,c][7]annulene-2-carboxylate

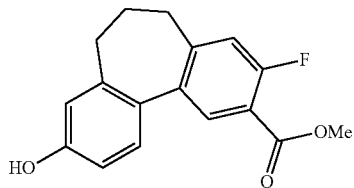 [SMILES: COC(=O)c1cc2c(cc1F)CCCc1cc(O)ccc1-2]

According to the procedures as described in <5-7>, the compound obtained in <85-6> was used to prepare the title compound (white foam, 1.69 g, 94% yield).

$^1$H NMR (600 MHz, $CDCl_3$) δ 7.89 (d, 1H), 7.24 (d, 1H), 7.02 (d, 1H), 6.81 (dd, 1H), 6.74 (d, 1H), 4.98 (s, 1H), 3.94 (s, 3H), 2.51 (t, 2H), 2.43 (t, 2H), 2.22-2.15 (m, 2H).

<85-8> Preparation of methyl 9-((1,1-dioxidotetrahydro-2H-thiopyran-4-yl)methoxy)-3-fluoro-6,7-dihydro-5H-dibenzo[a,c][7]annulene-2-carboxylate

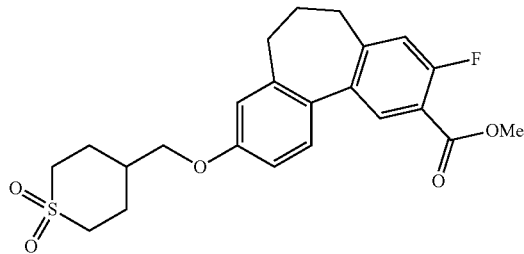 [SMILES: COC(=O)c1cc2c(cc1F)CCCc1cc(OCC3CCS(=O)(=O)CC3)ccc1-2]

The compound obtained in <85-7> (80 mg, 0.279 mmol) was dissolved in DMF (1 mL), which was then added with (1,1-dioxidotetrahydro-2H-thiopyran-4-yl)methyl 4-methylbenzenesulfonate (prepared in accordance with the reference [Bioorganic and Medicinal Chemistry Letters, 2011, vol. 21, p. 1748-1753]; 133 mg, 0.419 mmol) and $K_2CO_3$ (58 mg, 0.419 mmol), and then stirred at 90° C. for 15 hours. The reaction mixture was cooled to room temperature, diluted with EtOAc, and washed with a saturated $NH_4Cl$ aqueous solution and brine. The organic layer was dried over sodium sulfate and concentrated under reduced pressure, and the residue thus obtained was purified by silica gel chromatography to obtain the title compound (white foam, 118 mg, 98% yield).

$^1$H NMR (600 MHz, CDCl$_3$) δ 7.89 (d, 1H), 7.30 (d, 1H), 7.03 (d, 1H), 6.85 (dd, 1H), 6.78 (d, 1H), 3.94 (s, 3H), 3.92 (d, 2H), 3.18-3.14 (m, 2H), 3.08-3.05 (m, 2H), 2.51 (t, 2H), 2.46 (t, 2H), 2.33-2.31 (m, 2H), 2.22-2.17 (m, 2H), 2.09-2.05 (m, 2H).

<85-9> Preparation of 4-(((9-fluoro-10-(hydroxymethyl)-6,7-dihydro-5H-dibenzo[a,c][7]annulen-3-yl)oxy)methyl)tetrahydro-2H-thiopyran 1,1-dioxide

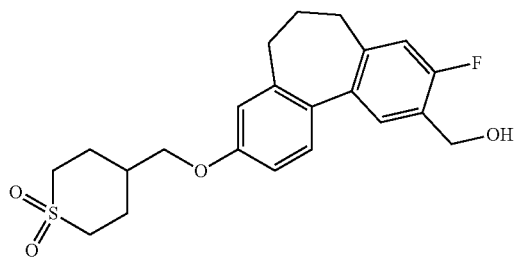 [SMILES: O=S1(=O)CCC(COc2ccc3c(c2)CCCc2cc(F)c(CO)cc2-3)CC1]

According to the procedures as described in <1-9>, the compound obtained <85-8> was used to prepare the title compound (white foam, 103 mg, 95% yield).

$^1$H NMR (600 MHz, CDCl$_3$) δ 7.35 (d, 1H), 7.28 (d, 1H), 6.95 (d, 1H), 6.84 (dd, 1H), 6.78 (d, 1H), 4.79 (d, 2H), 3.92 (d, 2H), 3.18-3.13 (m, 2H), 3.08-3.03 (m, 2H), 2.48-2.44 (m, 4H), 2.34-2.30 (m, 2H), 2.19-2.14 (m, 2H), 2.10-2.04 (m, 2H), 1.83 (t, 1H).

<85-10> Preparation of (S)-methyl 2-(6-((9-((1,1-dioxidotetrahydro-2H-thiopyran-4-yl)methoxy)-3-fluoro-6,7-dihydro-5H-dibenzo[a,c][7]annulen-2-yl)methoxy)-2,3-dihydrobenzofuran-3-yl)acetate

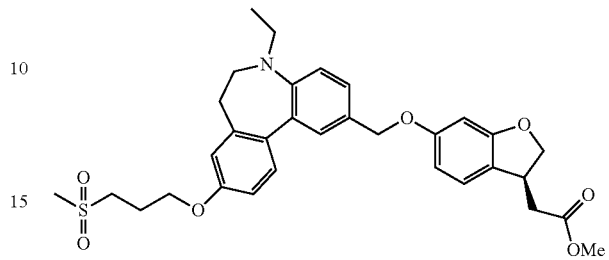

According to the procedures as described in <1-10>, the compound obtained in <85-9> was used to prepare the title compound (white foam, 139 mg, 92% yield).

$^1$H NMR (600 MHz, CDCl$_3$) δ 7.41 (d, 1H), 7.26 (d, 1H), 7.04 (d, 1H), 6.97 (d, 1H), 6.83 (dd, 1H), 6.77 (d, 1H), 6.51 (dd, 1H), 6.49 (d, 1H), 5.10 (s, 2H), 4.78 (t, 1H), 4.27 (dd, 1H), 3.90 (d, 2H), 3.83-3.80 (m, 1H), 3.72 (s, 3H), 3.17-3.14 (m, 2H), 3.07-3.03 (m, 2H), 2.75 (dd, 1H), 2.56 (dd, 1H), 2.48-2.44 (m, 4H), 2.34-2.30 (m, 2H), 2.19-2.14 (m, 2H), 2.09-2.04 (m, 2H).

<85-11> Preparation of (S)-2-(6-((9-((1,1-dioxidotetrahydro-2H-thiopyran-4-yl)methoxy)-3-fluoro-6,7-dihydro-5H-dibenzo[a,c][7]annulen-2-yl)methoxy)-2,3-dihydrobenzofuran-3-yl)acetic acid

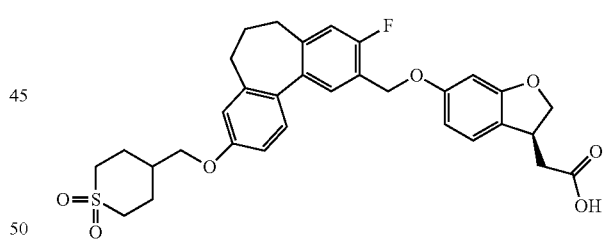

According to the procedures as described in <1-11>, the compound obtained in <85-10> was used to prepare the title compound (white foam, 125 mg, 94% yield).

MS m/z 580 [M−H]$^-$.

$^1$H NMR (600 MHz, CDCl$_3$) δ 7.41 (d, 1H), 7.25 (d, 1H), 7.07 (d, 1H), 6.97 (d, 1H), 6.83 (dd, 1H), 6.77 (d, 1H), 6.52 (dd, 1H), 6.49 (d, 1H), 5.10 (s, 2H), 4.77 (t, 1H), 4.29 (dd, 1H), 3.90 (d, 2H), 3.83-3.80 (m, 1H), 3.17-3.13 (m, 2H), 3.08-3.03 (m, 2H), 2.81 (dd, 1H), 2.62 (dd, 1H), 2.48-2.44 (m, 4H), 2.34-2.30 (m, 2H), 2.19-2.15 (m, 2H), 2.09-2.04 (m, 2H).

Example 86

Preparation of (1S,2S)-2-(4-(((9-((1,1-dioxidotetrahydro-2H-thiopyran-4-yl)methoxy)-3-fluoro-6,7-dihydro-5H-dibenzo[a,c][7]annulen-2-yl)methyl)amino)phenyl)cyclopropanecarboxylic acid <86-1> Preparation of 9-((1,1-dioxidotetrahydro-2H-thiopyran-4-yl)methoxy)-3-fluoro-6,7-dihydro-5H-dibenzo[a,c][7]annulene-2-carbaldehyde

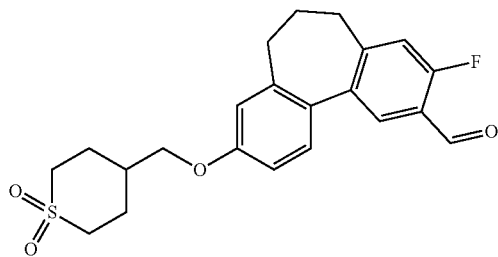 [SMILES: O=Cc1cc2c(cc1F)CCCc1cc(OCC3CCS(=O)(=O)CC3)ccc1-2]

According to the procedures as described in <3-3>, the compound obtained in <85-9> was used to prepare the title compound (white foam, 89 mg, 88% yield).

$^1$H NMR (600 MHz, CDCl$_3$) δ 10.37 (s, 1H), 7.80 (d, 1H), 7.28 (d, 1H), 7.06 (d, 1H), 6.84 (dd, 1H), 6.77 (d, 1H), 4.79 (d, 2H), 3.90 (d, 2H), 3.17-3.13 (m, 2H), 3.08-3.03 (m, 2H), 2.53 (t, 2H), 2.45 (t, 2H), 2.34-2.30 (m, 2H), 2.22-2.16 (m, 2H), 2.80-2.03 (m, 2H), 1.83 (t, 1H).

<86-2> Preparation of (1S,2S)-ethyl 2-(4-(((9-((1,1-dioxidotetrahydro-2H-thiopyran-4-yl)methoxy)-3-fluoro-6,7-dihydro-5H-dibenzo[a,c][7]annulen-2-yl)methyl)amino)phenyl)cyclopropanecarboxylate

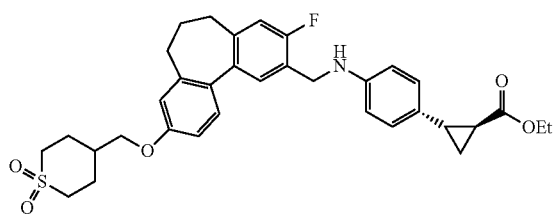

According to the procedures as described in <3-4>, the compound obtained in <86-1> was used to prepare the title compound (white foam, 121 mg, 95% yield).

$^1$H NMR (600 MHz, CDCl$_3$) δ 7.29 (d, 1H), 7.18 (d, 1H), 6.95-6.92 (m, 3H), 6.81 (dd, 1H), 6.76 (d, 1H), 6.60 (d, 2H), 4.39 (s, 2H), 4.15 (q, 2H), 4.02 (br s, 1H), 3.89 (d, 2H), 3.17-3.13 (m, 2H), 3.07-3.03 (m, 2H), 2.46-2.41 (m, 4H), 2.33-2.29 (m, 2H), 2.18-2.15 (m, 2H), 2.08-2.04 (m, 2H), 1.79-1.76 (m, 1H), 1.53-1.49 (m, 1H), 1.28-1.24 (m, 4H), 1.23-1.21 (m, 1H).

<86-3> Preparation of (1S,2S)-2-(4-(((9-((1,1-dioxidotetrahydro-2H-thiopyran-4-yl)methoxy)-3-fluoro-6,7-dihydro-5H-dibenzo[a,c][7]annulen-2-yl)methyl)amino)phenyl)cyclopropanecarboxylic acid

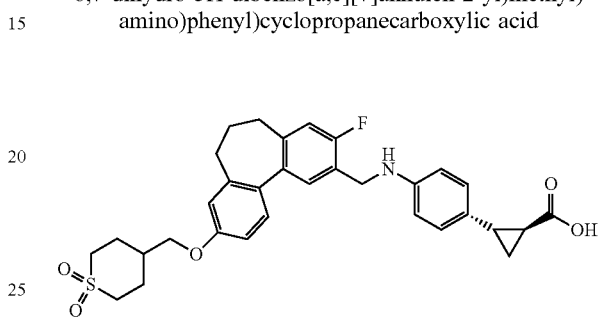

According to the procedures as described in <3-5>, the compound obtained in <86-2> was used to prepare the title compound (white foam, 98 mg, 86% yield).

MS m/z 563 [M−H]$^-$.

$^1$H NMR (600 MHz, CDCl$_3$) δ 7.28 (d, 1H), 7.17 (d, 1H), 6.95-6.92 (m, 3H), 6.80 (dd, 1H), 6.76 (d, 1H), 6.59 (d, 2H), 4.39 (s, 2H), 3.90 (d, 2H), 3.16-3.13 (m, 2H), 3.07-3.02 (m, 2H), 2.52-2.48 (m, 1H), 2.46-2.42 (m, 4H), 2.33-2.29 (m, 2H), 2.18-2.15 (m, 2H), 2.08-2.04 (m, 2H), 1.79-1.76 (m, 1H), 1.58-1.55 (m, 1H), 1.33-1.30 (m, 1H).

Example 87

Preparation of (1S,2S)-2-(4-(((9-(3-(ethylsulfonyl)propoxy)-11-methyl-6,7-dihydrodibenzo[b,d]oxepin-2-yl)methyl)amino)phenyl)cyclopropanecarboxylic acid <87-1> Preparation of (1S,2S)-ethyl 2-(4-(((9-(3-(ethylsulfonyl)propoxy)-11-methyl-6,7-dihydrodibenzo[b,d]oxepin-2-yl)methyl)amino)phenyl)cyclopropanecarboxylate

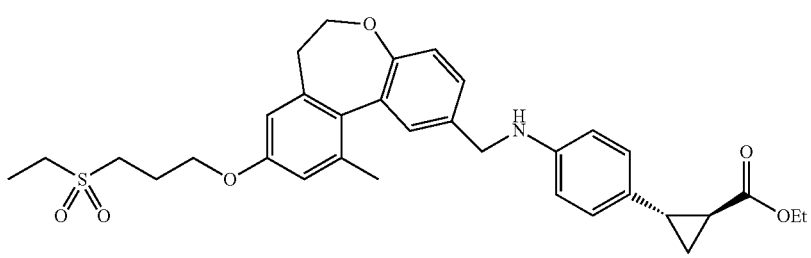 [SMILES: CCOC(=O)[C@H]1C[C@@H]1c1ccc(NCc2ccc3c(c2)-c2c(C)cc(OCCCS(=O)(=O)CC)cc2CCO3)cc1]

According to the procedures as described in <3-4>, the compound obtained in <53-1> was used to prepare the title compound (white foam, 89.6 mg, 103% yield) the compound obtained in.

¹H NMR (300 MHz, CDCl₃) δ 7.31-7.22 (m, 2H), 7.11 (d, 1H), 6.93 (d, 2H), 6.74 (d, 1H), 6.67 (d, 1H), 6.57 (d, 2H), 4.40 (m, 2H), 4.33 (s, 2H), 4.22-4.07 (m, 4H), 4.03 (br s, 1H), 3.26-3.14 (m, 2H), 3.05 (q, 2H), 2.80 (m, 1H), 2.54-2.29 (m, 4H), 2.26 (s, 3H), 1.82-1.73 (m, 1H), 1.52 (m, 1H), 1.44 (t, 3H), 1.32-1.17 (m, 4H).

<87-2> Preparation of (1S,2S)-2-(4-(((9-(3-(ethylsulfonyl)propoxy)-11-methyl-6,7-dihydrodibenzo[b,d]oxepin-2-yl)methyl)amino)phenyl)cyclopropanecarboxylic acid

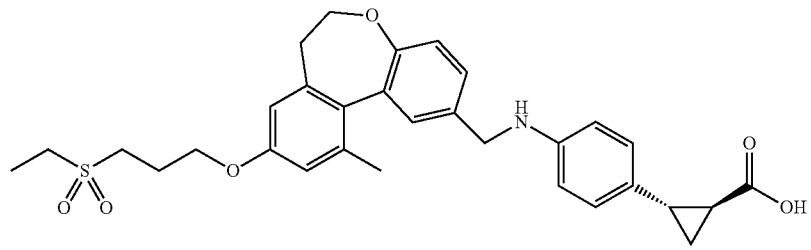 [SMILES: CCS(=O)(=O)CCCOc1cc(C)c2c(c1)CCOc1ccc(CNc3ccc([C@H]4C[C@@H]4C(=O)O)cc3)cc1-2]

According to the procedures as described in <1-11>, the compound obtained in <87-1> was used to prepare the title compound (white foam, 72.8 mg, 88% yield).

MS m/z 550 [M+H]⁺.

¹H NMR (300 MHz, CDCl₃) δ 7.31-7.22 (m, 2H), 7.11 (d, 1H), 6.93 (d, 2H), 6.74 (d, 1H), 6.67 (d, 1H), 6.57 (d, 2H), 4.40 (m, 2H), 4.34 (s, 2H), 4.13 (t, 2H), 3.28-3.14 (m, 2H), 3.05 (q, 2H), 2.81 (m, 1H), 2.56-2.42 (m, 2H), 2.42-2.28 (m, 2H), 2.25 (s, 3H), 1.76 (m, 1H), 1.58 (m, 1H), 1.44 (t, 3H), 1.38-1.30 (m, 1H).

Example 88

Preparation of 2-((3S)-6-((9-(2-ethoxyethoxy)-11-methyl-6,7-dihydrodibenzo[b,d]oxepin-2-yl)methoxy)-2,3-dihydrobenzofuran-3-yl)acetic acid <88-1> Preparation of methyl 9-(2-ethoxyethoxy)-11-methyl-6,7-dihydrodibenzo[b,d]oxepin-2-carboxylate

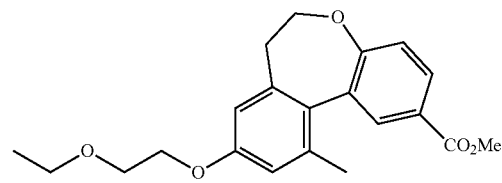 [SMILES: CCOCCOc1cc(C)c2c(c1)CCOc1ccc(C(=O)OC)cc1-2]

According to the procedures as described in <3-1>, the compound obtained in <14-5> was used to prepare the title compound (yellow oil, 143 mg, >100% yield).

¹H NMR (300 MHz, CDCl₃) δ 8.02 (d, 1H), 7.97 (dd, 1H), 7.18 (d, 1H), 6.83 (d, 1H), 6.73 (d, 1H), 4.55-4.39 (m, 2H), 4.17 (t, 2H), 3.92 (s, 3H), 3.82 (m, 2H), 3.63 (q, 2H), 2.88-2.73 (m, 1H), 2.52 (m, 1H), 2.37 (s, 3H), 1.26 (t, 3H).

<88-2> Preparation of (9-(2-ethoxyethoxy)-11-methyl-6,7-dihydrodibenzo[b,d]oxepin-2-yl)methanol

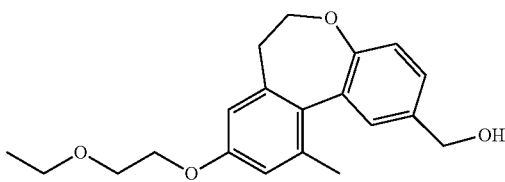 [SMILES: CCOCCOc1cc(C)c2c(c1)CCOc1ccc(CO)cc1-2]

According to the procedures as described in <1-9>, the compound obtained in <88-1> was used to prepare the title compound (colorless oil, 110 mg, 95% yield).

¹H NMR (300 MHz, CDCl₃) δ 7.34-7.27 (m, 2H), 7.13 (d, 1H), 6.82 (d, 1H), 6.73 (d, 1H), 4.71 (d, 2H), 4.41 (m, 2H), 4.16 (t, 2H), 3.86-3.76 (m, 2H), 3.62 (q, 2H), 2.81 (m, 1H), 2.53-2.43 (m, 1H), 2.37 (s, 3H), 1.67 (t, 1H), 1.26 (t, 3H).

<88-3> Preparation of methyl 2-((3S)-6-((9-(2-ethoxyethoxy)-11-methyl-6,7-dihydrodibenzo[b,d]oxepin-2-yl)methoxy)-2,3-dihydrobenzofuran-3-ylacetate

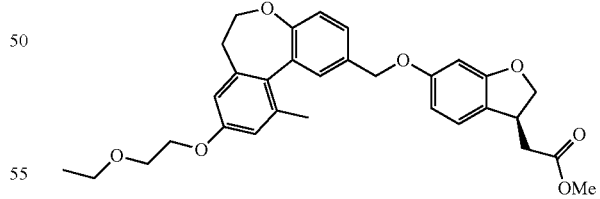

According to the procedures as described in <1-10>, the compound obtained in <88-2> was used to prepare the title compound (white foam, 129 mg, 77% yield).

¹H NMR (300 MHz, CDCl₃) δ 7.36-7.30 (m, 2H), 7.14 (d, 1H), 7.02 (d, 1H), 6.80 (d, 1H), 6.73 (d, 1H), 6.54-6.42 (m, 2H), 5.03 (s, 2H), 4.75 (t, 1H), 4.41 (m, 2H), 4.26 (dd, 1H), 4.16 (m, 2H), 3.81 (m, 3H), 3.72 (s, 3H), 3.62 (q, 2H), 2.91-2.68 (m, 2H), 2.63-2.41 (m, 2H), 2.31 (s, 3H), 1.26 (t, 3H).

225

<88-4> Preparation of 2-((3S)-6-((9-(2-ethoxy-ethoxy)-11-methyl-6,7-dihydrodibenzo[b,d]oxepin-2-yl)methoxy)-2,3-dihydrobenzofuran-3-yl)acetic acid

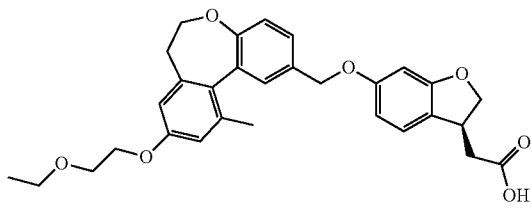 [SMILES: CCOCCOc1cc(C)c2c(c1)CCOc1ccc(COc3ccc4c(c3)OC[C@H]4CC(=O)O)cc1-2]

According to the procedures as described in <1-11>, the compound obtained in <88-3> was used to prepare the title compound (white foam, 121 mg, 96% yield).

MS m/z 503 [M–H]⁻.

¹H NMR (300 MHz, CDCl₃) δ 7.36-7.30 (m, 2H), 7.15 (d, 1H), 7.06 (d, 1H), 6.80 (d, 1H), 6.73 (d, 1H), 6.54-6.43 (m, 2H), 5.04 (s, 2H), 4.76 (t, 1H), 4.42 (m, 2H), 4.29 (dd, 1H), 4.20-4.12 (m, 2H), 3.81 (m, 3H), 3.62 (q, 2H), 2.90-2.75 (m, 2H), 2.61 (dd, 1H), 2.53-2.43 (m, 1H), 2.31 (s, 3H), 1.26 (t, 3H).

Example 89

Preparation of (1S,2S)-2-(4-((1-methyl-3-morpholino-6,7-dihydro-5H-benzo[3,4]cyclohepta[1,2-d]pyrimidin-10-yl)methoxy)phenyl)cyclopropanecarboxylic acid <89-1> Preparation of (1S,2S)-ethyl 2-(4-((1-methyl-3-morpholino-6,7-dihydro-5H-benzo[3,4]cyclohepta[1,2-d]pyrimidin-10-yl)methoxy)phenyl)cyclopropanecarboxylate

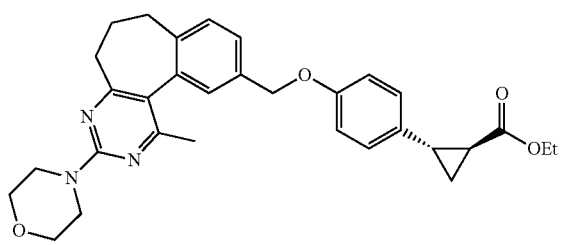 [SMILES: CCOC(=O)[C@H]1C[C@@H]1c1ccc(OCc2ccc3c(c2)-c2c(C)nc(N4CCOCC4)nc2CCC3)cc1]

According to the procedures as described in <2-16>, the compound obtained in <89-7> was used to prepare the title compound (white foam, 123 mg, 79% yield).

¹H NMR (600 MHz, CDCl₃) δ 7.28 (m, 1H), 7.25-7.23 (m, 2H), 7.01 (d, 2H), 6.87 (d, 2H), 5.05 (s, 2H), 4.15 (q, 2H), 3.85 (m, 4H), 3.77 (m, 4H), 2.58-2.54 (m, 1H), 2.52-2.37 (m, 4H), 2.28 (s, 3H), 2.23-2.15 (m, 1H), 2.11-2.05 (m, 1H), 1.80 (m, 1H), 1.54 (m, 1H), 1.26 (t, 3H), 1.24 (m, 1H)

226

<89-2> Preparation of (1S,2S)-2-(4-((1-methyl-3-morpholino-6,7-dihydro-5H-benzo[3,4]cyclohepta[1,2-d]pyrimidin-10-yl)methoxy)phenyl)cyclopropanecarboxylic acid

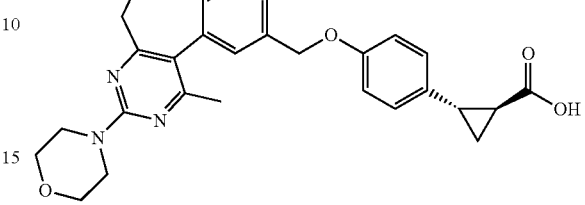

According to the procedures as described in <1-11>, the compound obtained in <89-1> was used to prepare the title compound (white foam, 71 mg, 71% yield).

MS m/z 484 [M–H]⁻

¹H NMR (600 MHz, CDCl₃) δ 7.28 (m, 1H), 7.25-7.23 (m, 2H), 7.03 (d, 2H), 6.88 (d, 2H), 5.06 (s, 2H), 3.85 (m, 4H), 3.78 (m, 4H), 2.58-2.49 (m, 3H), 2.46-2.37 (m, 2H), 2.28 (s, 3H), 2.23-2.16 (m, 1H), 2.11-2.05 (m, 1H), 1.81 (m, 1H), 1.60 (m, 1H), 1.33 (m, 1H)

Example 90

Preparation of 2-((3S)-6-((1-methyl-3-(3-(methylsulfonyl)propoxy)-6,7-dihydro-5H-benzo[3,4]cyclohepta[1,2-d]pyrimidin-10-yl)methoxy)-2,3-dihydrobenzofuran-3-yl)acetic acid <90-1> Preparation of 4-chloro-N,N-bis(4-methoxybenzyl)-6-methylpyrimidine-2-amine

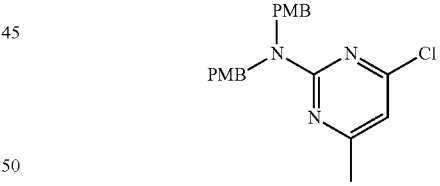

A solution of 4-chloro-6-methylpyrimidine-2-amine (10.0 g, 69.6 mmol) in DMF (200 mL) was added with NaH (60%, mineral oil dispersion, 7.24 g, 181 mmol), stirred for 15 minutes, added with 1-(chloromethyl)-4-methoxybenzene (24.6 mL, 181 mmol), and stirred at room temperature 2.5 hours. The mixture was slowly added with distilled water, further added with EtOAc, consecutively washed with distilled water and brine, and the organic layer thus obtained was dried over MgSO₄. The filtrate was concentrated under reduced pressure and purified by silica gel chromatography (white solid, 19.6 g, 73% yield).

¹H NMR (300 MHz, CDCl₃) δ 7.21-7.12 (m, 4H), 6.87-6.79 (m, 4H), 6.44 (s, 1H), 4.74 (s, 4H), 3.80 (s, 6H), 2.31 (s, 3H).

<90-2> Preparation of 4-allyl-N,N-bis(4-methoxy-benzyl)-6-methylpyrimidine-2-amine

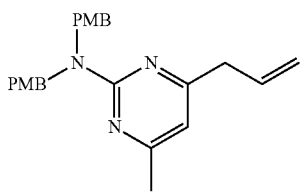

According to the procedures as described in <81-1>, the compound obtained in <90-1> was used to prepare the title compound (colorless oil, 5.89 g, 42% yield).
¹H NMR (300 MHz, CDCl₃) δ 7.23-7.14 (m, 4H), 6.86-6.78 (m, 4H), 6.29 (s, 1H), 6.10-5.95 (m, 1H), 5.21-5.07 (m, 2H), 4.77 (s, 4H), 3.79 (d, 6H), 3.36-3.28 (m, 2H), 2.30 (s, 3H).

<90-3> Preparation of methyl 4-(3-(2-(bis(4-methoxybenzyl)amino)-6-methylpyrimidin-4-yl)propyl)-3-bromobenzoate

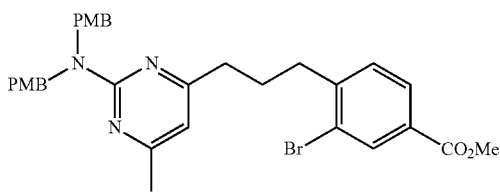

According to the procedures as described in <81-2>, the compound obtained in <90-2> was used to prepare the title compound (yellow solid, 5.78 g, 63% yield).
¹H NMR (300 MHz, CDCl₃) δ 8.18 (d, 1H), 7.83 (dd, 1H), 7.18 (m, 5H), 6.85-6.76 (m, 4H), 6.29 (s, 1H), 4.79 (s, 4H), 3.90 (s, 3H), 3.78 (s, 6H), 2.82-2.73 (m, 2H), 2.60 (t, 2H), 2.31 (s, 3H), 2.07-1.95 (m, 2H).

<90-4> Preparation of methyl 4-(3-(2-(bis(4-methoxybenzyl)amino)-6-methylpyrimidin-4-yl)propyl)-3-(4,4,5,5-tetramethyl-1,3,2-dioxaboran-2-yl)benzoate

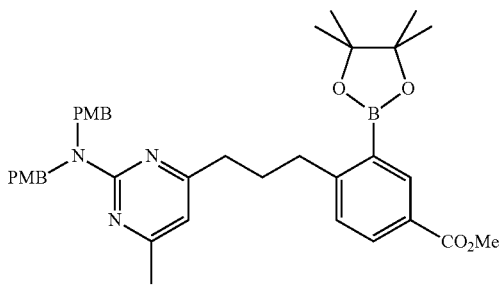

According to the procedures as described in <5-4>, the compound obtained in <90-3> was used to prepare the title compound (yellow oil, 3.38 g, 54% yield).
¹H NMR (300 MHz, CDCl₃) δ 8.41 (d, 1H), 7.96 (dd, 1H), 7.18 (m, 5H), 6.81 (m, 4H), 6.26 (s, 1H), 4.77 (s, 4H), 3.90 (s, 3H), 3.78 (s, 6H), 3.00-2.93 (m, 2H), 2.58 (t, 2H), 2.29 (s, 3H), 1.94 (m, 1H), 1.31 (s, 12H).

<90-5> Preparation of methyl 4-(3-(2-(bis(4-methoxybenzyl)amino)-5-bromo-6-methylpyrimidin-4-yl)propyl)-3-(4,4,5,5-tetramethyl-1,3,2-diboxaboran-2-yl)benzoate

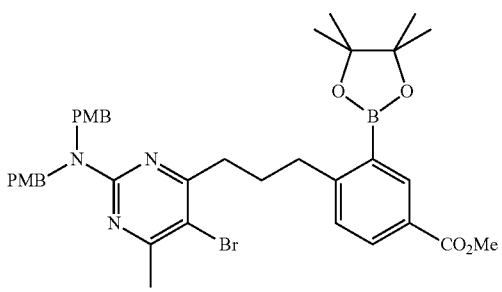

According to the procedures as described in <5-5>, the compound obtained in <90-4> was used to prepare the title compound (yellow oil, 3.60 g, 95% yield).
¹H NMR (300 MHz, CDCl₃) δ 8.41 (d, 1H), 7.95 (dd, 1H), 7.20-7.10 (m, 5H), 6.90-6.75 (m, 4H), 4.73 (s, 4H), 3.89 (s, 3H), 3.77 (s, 6H), 3.04-2.94 (m, 2H), 2.85-2.74 (m, 2H), 2.46 (s, 3H), 1.95 (m, 2H), 1.30 (s, 12H).

<90-6> Preparation of methyl 3-(bis(4-methoxybenzyl)amino)-1-methyl-6,7-dihydro-5H-benzo[3,4]cyclohepta[1,2-d]pyrimidine-10-carboxylate

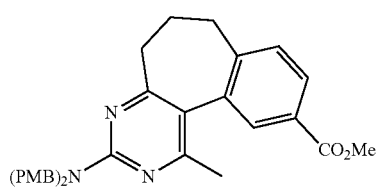

According to the procedures as described in <5-6>, the compound obtained in <90-5> was used to prepare the title compound (white foam, 453 mg, 18% yield).
¹H NMR (300 MHz, CDCl₃) δ 7.96 (d, 1H), 7.91 (dd, 1H), 7.32 (d, 1H), 7.26-7.21 (m, 4H), 6.89-6.83 (m, 4H), 4.83 (m, 4H), 3.93 (s, 3H), 3.81 (s, 6H), 2.71-2.48 (m, 3H), 2.39 (s, 3H), 2.36-2.03 (m, 3H).

<90-7> Preparation of methyl 3-amino-1-methyl-6,7-dihydro-5H-benzo[3,4]cyclohepta[1,2-d]pyrimidine-10-carboxylate

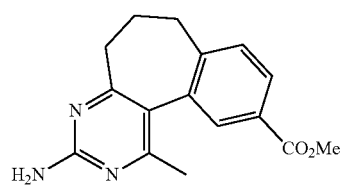 [SMILES: COC(=O)c1ccc2c(c1)-c1c(C)nc(N)nc1CCC2]

A solution of the compound obtained in <90-6> (347 mg, 0.663 mmol) in CH$_2$Cl$_2$ (7 mL) at 0° C. was consecutively added with TFA (7 mL) and H$_2$SO$_4$ (15 drops). After about 10 minutes, the mixture was heated to room temperature and stirred for 4.5 hours. The reaction mixture was concentrated under reduced pressure, and added with distilled water at 0° C. The mixture was added with NH$_4$OH (pH 8-9), extracted with CH$_2$Cl$_2$, and the organic layer was collected and dried over MgSO$_4$. The filtrate was concentrated under reduced pressure and purified by silica gel chromatography to obtain the title compound (white foam, 169 mg, 90% yield).

$^1$H NMR (300 MHz, CDCl$_3$) δ 7.99-7.88 (m, 2H), 7.38-7.29 (m, 1H), 5.06 (s, 2H), 3.93 (s, 3H), 2.66 (m, 1H), 2.56-2.42 (m, 2H), 2.38 (s, 3H), 2.37-2.07 (m, 3H).

<90-8> Preparation of methyl 3-hydroxy-1-methyl-6,7-dihydro-5H-benzo[3,4]cyclohepta[1,2-d]pyrimidine-10-carboxylate

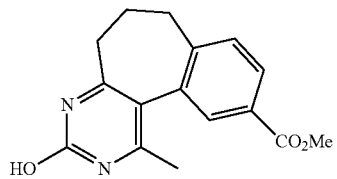 [SMILES: COC(=O)c1ccc2c(c1)-c1c(C)nc(O)nc1CCC2]

A solution of the compound obtained in <90-7> (343 mg, 1.211 mmol) in acetic acid (8.4 mL) and distilled water (1.8 mL) at 60° C. was added dropwise with a solution of NaNO$_2$ (125 mg, 1.816 mmol)/distilled water (1.8 mL) over a 20 minute period, and then stirred at the same temperature for 3 hours. The reaction mixture was cooled to room temperature, added with distilled water, and extracted with EtOAc. The organic layer was collected and dried over MgSO$_4$. The filtrate thus obtained was concentrated under reduced pressure and purified by silica gel chromatography to obtain the title compound (yellow foam, 194 mg, 53% yield).

$^1$H NMR (300 MHz, CDCl$_3$) δ 7.99 (dd, 1H), 7.90 (s, 1H), 7.36 (d, 1H), 3.94 (s, 3H), 2.83-2.50 (m, 3H), 2.48 (s, 3H), 2.44-2.08 (m, 3H).

<90-9> Preparation of methyl 1-methyl-3-(3-(methylsulfonyl)propoxy)-6,7-dihydro-5H-benzo[3,4]cyclohepta[1,2-d]pyrimidine-10-carboxylate

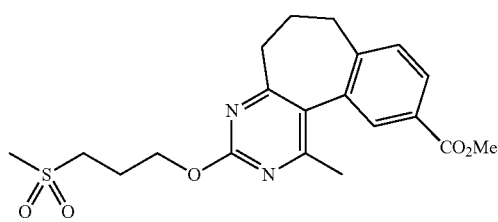 [SMILES: COC(=O)c1ccc2c(c1)-c1c(C)nc(OCCCS(C)(=O)=O)nc1CCC2]

According to the procedures as described in <1-8>, the compound obtained in <90-8> was used to prepare the title compound (yellow foam, 242 mg, 69% yield).

$^1$H NMR (300 MHz, CDCl$_3$) δ 7.99 (dd, 1H), 7.95 (d, 1H), 7.36 (d, 1H), 4.57 (m, 2H), 3.94 (s, 3H), 3.36-3.26 (m, 2H), 2.96 (s, 3H), 2.68 (m, 2H), 2.48 (s, 3H), 2.46-2.34 (m, 4H), 2.24 (m, 2H).

<90-10> Preparation of (1-methyl-3-(3-(methylsulfonyl)propoxy)-6,7-dihydro-5H-benzo[3,4]cyclohepta[1,2-d]pyrimidin-10-yl)methanol

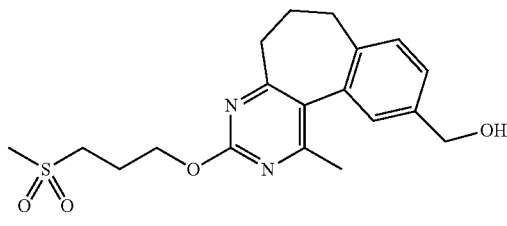 [SMILES: Cc1nc(OCCCS(C)(=O)=O)nc2c1-c1cc(CO)ccc1CCC2]

According to the procedures as described in <1-9>, the compound obtained in <90-9> was used to prepare the title compound (white foam, 157 mg, 70% yield).

$^1$H NMR (300 MHz, CDCl$_3$) δ 7.35-7.23 (m, 3H), 4.75 (d, 2H), 4.56 (m, 2H), 3.37-3.25 (m, 2H), 2.96 (s, 3H), 2.63 (m, 2H), 2.48 (s, 3H), 2.45-2.31 (m, 4H), 2.19 (m, 2H), 1.79 (t, 1H).

<90-11> Preparation of methyl 2-((3S)-6-((1-methyl-3-(3-(methylsulfonyl)propoxy)-6,7-dihydro-5H-benzo[3,4]cyclohepta[1,2-d]pyrimidin-10-yl)methoxy)-2,3-dihydrobenzofuran-3-yl)acetate

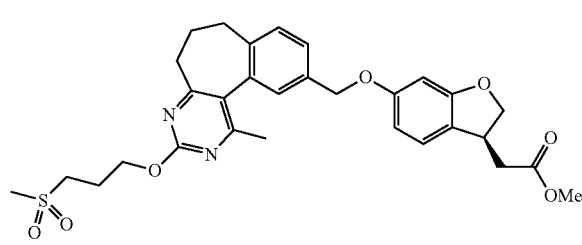 [SMILES: COC(=O)C[C@@H]1COc2cc(OCc3ccc4c(c3)-c3c(C)nc(OCCCS(C)(=O)=O)nc3CCC4)ccc21]

According to the procedures as described in <1-10>, the compound obtained in <90-10> was used to prepare the title compound (white foam, 131 mg, 87% yield).

$^1$H NMR (300 MHz, CDCl$_3$) δ 7.38-7.25 (m, 3H), 7.04 (d, 1H), 6.48 (m, 2H), 5.07 (s, 2H), 4.75 (t, 1H), 4.56 (t, 2H), 4.27 (dd, 1H), 3.81 (m, 1H), 3.72 (s, 3H), 3.39-3.24 (m, 2H), 2.96 (s, 3H), 2.75 (dd, 1H), 2.69-2.43 (m, 4H), 2.43-2.31 (m, 6H), 2.30-2.10 (m, 2H).

<90-12> Preparation of 2-((3S)-6-((1-methyl-3-(3-(methylsulfonyl)propoxy)-6,7-dihydro-5H-benzo[3,4]cyclohepta[1,2-d]pyrimidin-10-yl)methoxy)-2,3-dihydrobenzofuran-3-yl)acetic acid

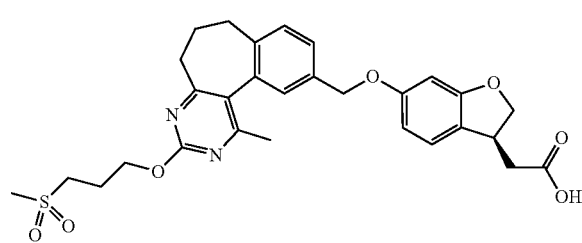 [SMILES: Cc1nc(OCCCS(C)(=O)=O)nc2c1-c1cc(COc3ccc4c(c3)OC[C@H]4CC(=O)O)ccc1CCC2]

According to the procedures as described in <1-11>, the compound obtained in <90-11> was used to prepare the title compound (white foam, 89 mg, 70% yield).

MS m/z 551 [M−H]−.

1H NMR (300 MHz, CDCl3) δ 7.38-7.27 (m, 3H), 7.07 (d, 1H), 6.54-6.41 (m, 2H), 5.07 (s, 2H), 4.77 (t, 1H), 4.55 (t, 2H), 4.34-4.23 (m, 1H), 3.82 (m, 1H), 3.40-3.25 (m, 2H), 2.96 (s, 3H), 2.80 (dd, 1H), 2.70-2.5 (m, 3H), 2.55-1.75 (m, 9H).

Example 91

Preparation of (S)-2-(6-(((9-(2-ethoxyethoxy)-6,7-dihydro-5H-dibenzo[a,c][7]annulen-2-yl)methyl)amino)-2,3-dihydrobenzofuran-3-yl)acetic acid <91-1> Preparation of (S)-methyl 2-(6-(((9-(2-ethoxyethoxy)-6,7-dihydro-5H-dibenzo[a,c][7]annulen-2-yl)methyl)amino)-2,3-dihydrobenzofuran-3-ylacetate

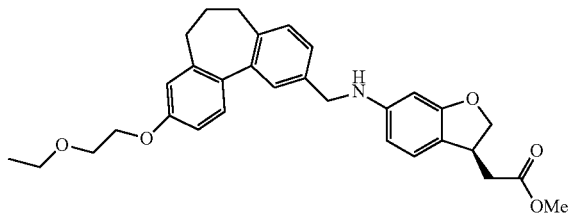 [SMILES: CCOCCOc1ccc2c(c1)CCCc1ccc(CNc3ccc4c(c3)OC[C@H]4CC(=O)OC)cc1-2]

According to the procedures as described in <82-1>, the compound obtained in <28-1> was used to prepare the title compound (yellow oil, 122.3 mg, 79% yield).

1H NMR (300 MHz, CDCl3) δ 7.34-7.21 (m, 3H), 7.18 (d, 1H), 6.93 (d, 1H), 6.88 (dd, 1H), 6.84 (d, 1H), 6.21-6.11 (m, 2H), 4.71 (t, 1H), 4.31 (s, 2H), 4.25-4.14 (m, 3H), 4.05 (br s, 1H), 3.85-3.73 (m, 3H), 3.71 (s, 3H), 3.62 (q, 2H), 2.73 (dd, 1H), 2.60-2.39 (m, 5H), 2.22-2.08 (m, 2H), 1.26 (t, 3H).

<91-2> Preparation of (S)-2-(6-(((9-(2-ethoxyethoxy)-6,7-dihydro-5H-dibenzo[a,c][7]annulen-2-yl)methyl)amino)-2,3-dihydrobenzofuran-3-yl)acetic acid According to the procedures as described in <1-11>, the compound obtained <91-1> was used to prepare the title compound (off-white foam, 92.4 mg, 79% yield).

MS m/z 486 [M−H]−.

1H NMR (300 MHz, CDCl3) δ=7.34-7.21 (m, 3H), 7.18 (d, 1H), 6.96 (d, 1H), 6.87 (d, 1H), 6.84 (d, 1H), 6.22-6.12 (m, 2H), 4.72 (t, 1H), 4.31 (s, 2H), 4.24 (dd, 1H), 4.17 (t, 2H), 3.85-3.71 (m, 3H), 3.62 (q, 2H), 2.78 (dd, 1H), 2.58 (dd, 1H), 2.47 (m, 4H), 2.22-2.07 (m, 2H), 1.25 (t, 3H).

Example 92

Preparation of (S)-2-(6-(((9-(3-(ethylsulfonyl)propoxy)-6,7-dihydro-5H-dibenzo[a,c][7]annulen-2-yl)methyl)amino)-2,3-dihydrobenzofuran-3-yl)acetic acid <92-1> Preparation of (S)-methyl 2-(6-(((9-(3-(ethylsulfonyl)propoxy)-6,7-dihydro-5H-dibenzo[a,c][7]annulen-2-yl)methyl)amino)-2,3-dihydrobenzofuran-3-ylacetate

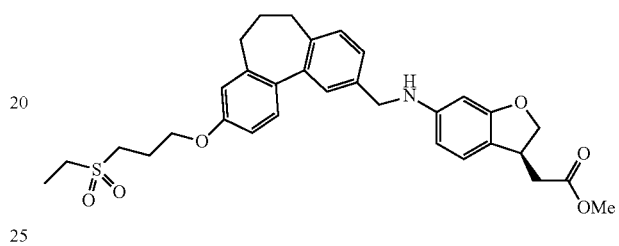

According to the procedures as described in <82-1>, the compound obtained in <72-1> was used to prepare the title compound (white foam, 162 mg, 103% yield).

1H NMR (300 MHz, CDCl3) δ=7.34-7.22 (m, 3H), 7.19 (d, 1H), 6.93 (d, 1H), 6.83 (dd, 1H), 6.79 (d, 1H), 6.22-6.13 (m, 2H), 4.70 (t, 1H), 4.31 (s, 2H), 4.21 (dd, 1H), 4.16 (t, 2H), 4.09 (s, 1H), 3.76 (m, 1H), 3.70 (s, 3H), 3.28-3.16 (m, 2H), 3.05 (q, 2H), 2.73 (dd, 1H), 2.60-2.42 (m, 5H), 2.42-2.29 (m, 2H), 2.24-2.09 (m, 2H), 1.44 (t, 3H).

<92-2> Preparation of (S)-2-(6-(((9-(3-(ethylsulfonyl)propoxy)-6,7-dihydro-5H-dibenzo[a,c][7]annulen-2-yl)methyl)amino)-2,3-dihydrobenzofuran-3-yl)acetic acid

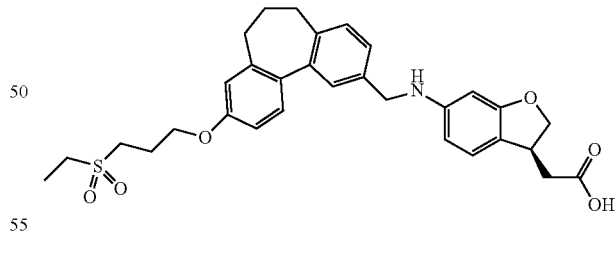

According to the procedures as described in <1-11>, the compound obtained in <92-1> was used to prepare the title compound (off-white foam, 150.4 mg, 94% yield).

MS m/z 548 [M−H]−.

1H NMR (300 MHz, CDCl3) δ=7.39-7.21 (m, 3H), 7.18 (d, 1H), 6.96 (d, 1H), 6.84 (dd, 1H), 6.78 (d, 1H), 6.23-6.10 (m, 2H), 4.71 (t, 1H), 4.31 (s, 2H), 4.28-4.19 (m, 1H), 4.15 (t, 2H), 3.76 (m, 1H), 3.28-3.16 (m, 2H), 3.05 (q, 2H), 2.75 (dd, 1H), 2.61 (dd, 1H), 2.47 (m, 4H), 2.41-2.28 (m, 2H), 2.24-2.08 (m, 2H), 1.44 (t, 3H).

Example 93

Preparation of (S)-2-(6-((9-((4-methyl-1,1-dioxido-tetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid

<93-1> Preparation of 4-methyltetrahydro-2H-thiopyran-4-carbonitrile

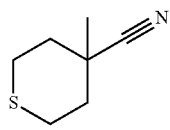

A solution of tetrahydro-2H-thiopyran-4-carbonitrile (1.27 g, 10.0 mmol) in THF (30 mL) was slowly added dropwise with LDA (2M THF/heptane solution, 6.5 mL, 13.0 mmol). After 30 minutes, the mixture was added with MeI (811 µL, 13.0 mmol) and stirred for 50 minutes. Then, the reaction mixture was slowly added with water, diluted with Et$_2$O and brine, and extracted. The organic layer was dried over sodium sulfate, the filtrate thus obtained was concentrated under reduced pressure, and then the residue was purified by silica gel chromatography to obtain the title compound (colorless oil, 1.07 g, 76% yield).

$^1$H NMR (300 MHz, CDCl$_3$) δ 3.03-2.94 (m, 2H), 2.57 (m, 2H), 2.20 (m, 2H), 1.69-1.59 (m, 2H), 1.37 (s, 3H).

<93-2> Preparation of 4-methyltetrahydro-2H-thiopyran-4-carboxylic acid

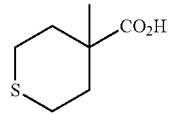

A solution of the compound obtained in <93-1> (1.07 g, 7.58 mmol) in THF/H$_2$O (14/7 mL) was added with NaOH (3.0 g, 75.8 mmol), stirred at 100° C. for 24 hours, and concentrated. The reaction mixture was diluted with Et$_2$O and water, and then extracted. The aqueous layer was acidified to ~pH 1 by using concentrated hydrochloric acid and extracted with EtOAc. The organic layer was dried over sodium sulfate and concentrated under reduced pressure. The residue thus obtained was purified by silica gel chromatography to obtain the title compound (colorless oil, 992.2 mg, 82% yield).

$^1$H NMR (300 MHz, CDCl$_3$) δ 2.78-2.70 (m, 2H), 2.59-2.51 (m, 2H), 2.40-2.32 (m, 2H), 1.65-1.58 (m, 2H), 1.24 (s, 3H).

<93-3> Preparation of (4-methyltetrahydro-2H-thiopyran-4-yl)methanol

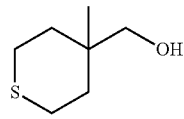

To a solution of the compound obtained in <93-2> (992 mg, 6.191 mmol) in THF (25 mL) was slowly added dropwise BH$_3$.THF (1.0M THF solution, 7.4 mL, 7.429 mmol). The mixture was stirred at 70° C. for 2.5 hours, slowly added with distilled water at 0° C., and concentrated under reduced pressure. The concentrated reaction mixture was added with distilled water and 1M HCl aqueous solution (pH 3), and then extracted with CH$_2$Cl$_2$. The organic layer was collected and dried over MgSO$_4$. The filtrate thus obtained was concentrated in vacuo to obtain the title compound (colorless oil, 856 mg, 95% yield).

$^1$H NMR (300 MHz, CDCl$_3$) δ 3.37 (d, 2H), 2.74 (m, 2H), 2.58-2.47 (m, 2H), 1.78-1.58 (m, 4H), 1.32 (t, 1H), 0.94 (s, 3H).

<93-4> Preparation of (4-methyltetrahydro-2H-thiopyran-4-yl)methyl 4-methylbenzenesulfonate

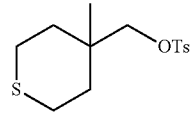 [SMILES: Cc1ccc(S(=O)(=O)OCC2(C)CCSCC2)cc1]

To a solution of the compound obtained in <93-3> (413 mg, 2.824 mmol) in CH$_2$Cl$_2$ (10 mL) at 0° C. was consecutively added with pyridine (5 mL) and m-toluenesulfonyl chloride (1.62 g, 8.472 mmol). After 10 minutes, the mixture was heated to room temperature, stirred for 4 hours, added with cold distilled water at 0° C., and extracted with EtOAc. The organic layer was collected, consecutively washed with 1M HCl aqueous solution, distilled water and brine, and then dried over MgSO$_4$. The filtrate thus obtained was concentrated under reduced pressure reduced pressure and purified by silica gel chromatography to obtain the title compound (colorless oil, 733 mg, 86% yield).

$^1$H NMR (300 MHz, CDCl$_3$) δ 7.82-7.73 (m, 2H), 7.36 (m, 2H), 3.71 (s, 2H), 2.65 (m, 2H), 2.50-2.36 (m, 5H), 1.71-1.52 (m, 4H), 0.93 (s, 3H).

<93-5> Preparation of (4-methyl-1,1-dioxidotetrahydro-2H-thiopyran-4-yl)methyl 4-methylbenzenesulfonate

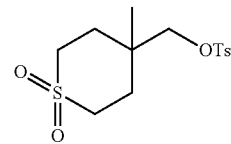 [SMILES: Cc1ccc(S(=O)(=O)OCC2(C)CCS(=O)(=O)CC2)cc1]

To a solution of the compound obtained in <93-4> (733 mg, 2.440 mmol) in CH$_2$Cl$_2$ (15 mL) at 0° C. was added MCPBA (>77%, 1.15 g, 5.123 mmol). The mixture was stirred at the same temperature for 2.5 hours. The reaction mixture was added with distilled water and a saturated NaHCO$_3$ aqueous solution, and then extracted with CH$_2$Cl$_2$. The organic layer was collected, washed with brine and dried over MgSO$_4$. The filtrate was concentrated under reduced pressure and recrystallized using CH$_2$Cl$_2$/hexane to obtain the title compound (white solid, 695 mg, 83% yield).

$^1$H NMR (300 MHz, CDCl$_3$) δ 7.85-7.71 (m, 2H), 7.45-7.30 (m, 2H), 3.79 (s, 2H), 3.05-2.84 (m, 2H), 2.47 (s, 3H), 2.09-1.94 (m, 2H), 1.91-1.79 (m, 2H), 1.08 (s, 3H).

<93-6> Preparation of methyl 9-((4-methyl-1,1-dioxidotetrahydro-2H-thiopyran-4-yl)methoxy)-6,7-dihydro-5H-dibenzo[a,c][7]annulene-2-carboxylate

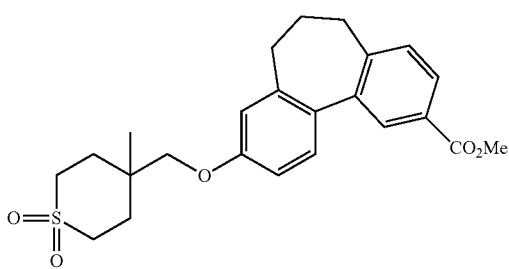 [SMILES: COC(=O)c1ccc2c(c1)-c1ccc(OCC3(C)CCS(=O)(=O)CC3)cc1CCC2]

A mixed solution of the compounds obtained in <5-7> (200 mg, 0.745 mmol) and <93-5> (372 mg, 1.118 mmol), K$_2$CO$_3$ (155 mg, 1.118 mmol) and KI (25 mg, 0.185 mmol) in DMF (4 mL) was stirred at 90° C. for 33 hours. The reaction mixture was cooled to room temperature, added with a saturated NH$_4$Cl aqueous solution and distilled water, and extracted with EtOAc. The organic layer was collected, washed with brine, and dried over MgSO$_4$. The filtrate was concentrated under reduced pressure and purified by silica gel chromatography to obtain the title compound (yellow foam, 162 mg, 51% yield).

$^1$H NMR (300 MHz, CDCl$_3$) δ 8.01 (d, 1H), 7.93 (dd, 1H), 7.35 (d, 1H), 7.30 (d, 1H), 6.88 (dd, 1H), 6.82 (d, 1H), 3.93 (d, 3H), 3.83 (s, 2H), 3.11 (m, 4H), 2.55 (t, 2H), 2.46 (t, 2H), 2.37-2.13 (m, 4H), 2.10-1.94 (m, 2H), 1.21 (s, 3H).

<93-7> Preparation of 4-(((10-(hydroxymethyl)-6,7-dihydro-5H-dibenzo[a,c][7]annulen-3-yl)oxy)methyl)-4-methyltetrahydro-2H-thiopyran 1,1-dioxide

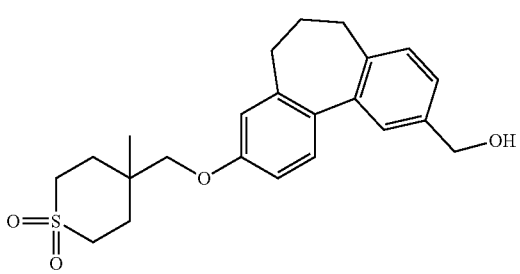 [SMILES: CC1(COc2ccc3c(c2)CCCc2ccc(CO)cc2-3)CCS(=O)(=O)CC1]

According to the procedures as described in <1-9>, the compound obtained in <93-6> was used to prepare the title compound (white foam, 238 mg, 94% yield).

$^1$H NMR (300 MHz, CDCl$_3$) δ 7.36-7.20 (m, 4H), 6.86 (dd, 1H), 6.81 (d, 1H), 4.74 (d, 2H), 3.82 (s, 3H), 3.11 (m, 4H), 2.48 (q, 4H), 2.36-2.22 (m, 2H), 2.18 (m, 2H), 2.05 (m, 2H), 1.72 (t, 1H), 1.21 (s, 3H).

<93-8> Preparation of (S)-methyl 2-(6-((9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetate

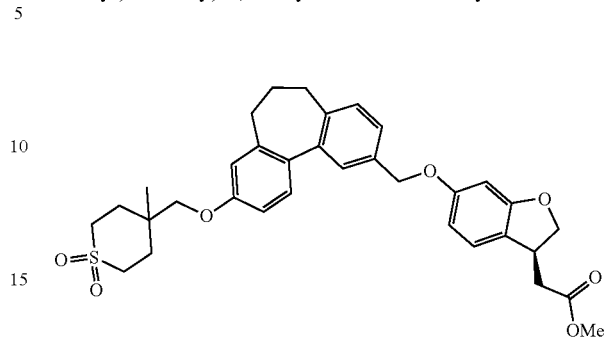

According to the procedures as described in <1-10>, the compound obtained in <93-7> was used to prepare the title compound (colorless oil, 159 mg, 90% yield).

$^1$H NMR (300 MHz, CDCl$_3$) δ 7.40-7.27 (m, 3H), 7.26 (d, 1H), 7.03 (d, 1H), 6.86 (dd, 1H), 6.81 (d, 1H), 6.55-6.43 (m, 2H), 5.04 (s, 2H), 4.76 (t, 1H), 4.27 (dd, 1H), 3.82 (m, 3H), 3.72 (s, 3H), 3.22-3.01 (m, 4H), 2.76 (dd, 1H), 2.63-2.40 (m, 5H), 2.35-2.10 (m, 4H), 2.11-1.94 (m, 2H), 1.21 (s, 3H).

<93-9> Preparation of (S)-2-(6-((9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid

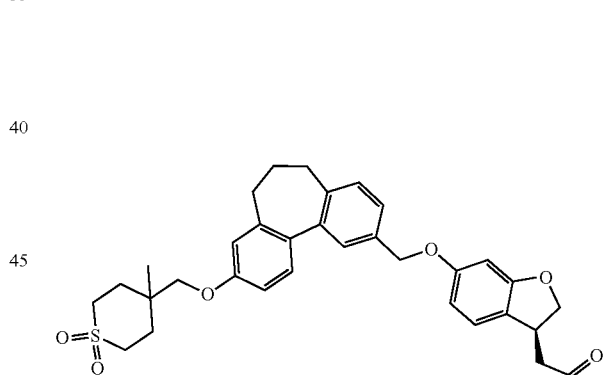

According to the procedures as described in <1-11>, the compound obtained in <93-8> was used to prepare the title compound (white foam, 114 mg, 73% yield).

MS m/z 575 [M−H]$^−$.

$^1$H NMR (300 MHz, CDCl$_3$) δ 7.40-7.28 (m, 3H), 7.24 (d, 1H), 7.07 (d, 1H), 6.86 (dd, 1H), 6.81 (d, 1H), 6.55-6.45 (m, 2H), 5.05 (s, 2H), 4.77 (t, 1H), 4.30 (dd, 1H), 3.82 (m, 2H), 3.22-3.01 (m, 4H), 2.82 (dd, 1H), 2.62 (dd, 1H), 2.49 (m, 4H), 2.35-2.12 (m, 4H), 2.11-1.98 (m, 2H), 1.21 (s, 3H).

Example 94

Preparation of (1S,2S)-2-(4-(((9-((4-methyl-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid <94-1> Preparation of 9-((4-methyl-1,1-dioxidotetrahydro-2H-thiopyran-4-yl)methoxy)-6,7-dihydro-5H-dibenzo[a,c][7]annulene-2-carbaldehyde

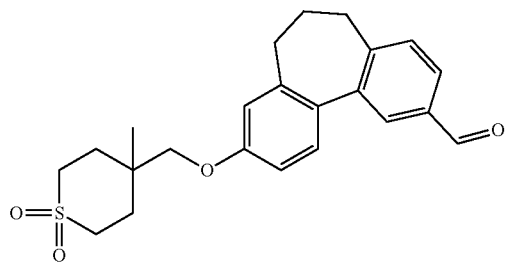 [SMILES: CC1(COc2ccc3c(c2)CCCc2ccc(C=O)cc2-3)CCS(=O)(=O)CC1]

According to the procedures as described in <3-3>, the compound obtained in <93-7> was used to prepare the title compound (colorless oil, 101 mg, 87% yield).

$^1$H NMR (300 MHz, CDCl$_3$) δ 10.05 (s, 1H), 7.84 (d, 1H), 7.78 (dd, 1H), 7.40 (d, 1H), 7.36 (d, 1H), 6.90 (dd, 1H), 6.83 (d, 1H), 3.83 (s, 2H), 3.11 (m, 4H), 2.58 (t, 2H), 2.48 (t, 2H), 2.35-2.16 (m, 4H), 2.11-1.97 (m, 2H), 1.23 (s, 3H).

<94-2> Preparation of (1S,2S)-ethyl 2-(4-(((9-((4-methyl-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylate

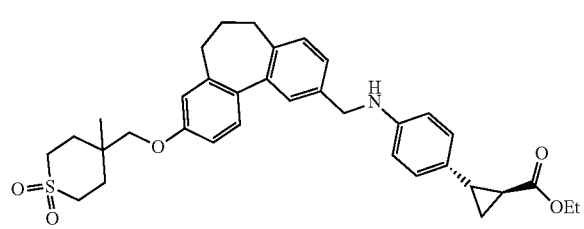

According to the procedures as described in <3-4>, the compound obtained in <94-1> was used to prepare the title compound (white foam, 192 mg, 130% yield).

$^1$H NMR (300 MHz, CDCl$_3$) δ 7.35-7.22 (m, 3H), 7.19 (d, 1H), 6.97-6.89 (m, 2H), 6.85 (dd, 1H), 6.81 (d, 1H), 6.63-6.52 (m, 2H), 4.33 (s, 2H), 4.16 (q, 2H), 4.02 (s, 1H), 3.81 (s, 2H), 3.10 (m, 4H), 2.56-2.37 (m, 5H), 2.35-2.11 (m, 4H), 2.05 (m, 2H), 1.78 (m, 1H), 1.51 (m, 1H), 1.26-1.20 (m, 4H), 1.20 (s, 3H).

<94-3> Preparation of (1S,2S)-2-(4-(((9-((4-methyl-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid

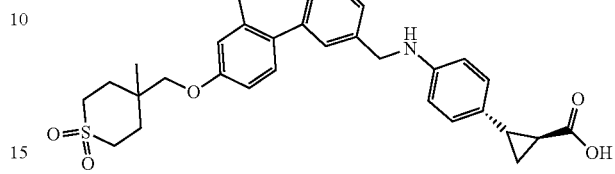

According to the procedures as described in <1-11>, the compound obtained in <94-2> was used to prepare the title compound (yellow foam, 108 mg, 59% yield).

MS m/z 558 [M−H]$^-$.

$^1$H NMR (300 MHz, CDCl$_3$) δ 7.33-7.16 (m, 4H), 6.99-6.89 (m, 2H), 6.85 (dd, 1H), 6.81 (d, 1H), 6.64-6.54 (m, 2H), 4.34 (s, 2H), 3.82 (s, 2H), 3.10 (m, 4H), 2.56-2.40 (m, 5H), 2.35-2.11 (m, 4H), 2.04 (m, 2H), 1.84-1.74 (m, 1H), 1.58 (m, 1H), 1.33 (m, 1H), 1.20 (s, 3H).

Example 95

Preparation of (S)-2-(6-((3-fluoro-9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid <95-1> Preparation of methyl 3-fluoro-9-((4-methyl-1,1-dioxidotetrahydro-2H-thiopyran-4-yl)methoxy)-6,7-dihydro-5H-dibenzo[a,c][7]annulene-2-carboxylate

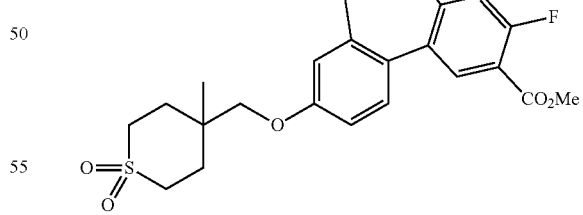

According to the procedures as described in <93-5>, the compound obtained in <85-7> was used to prepare the title compound (white foam, 155.8 mg, 61% yield).

$^1$H NMR (300 MHz, CDCl$_3$) δ 7.88 (d, 1H), 7.31 (d, 1H), 7.03 (d, 1H), 6.86 (d, 1H), 6.81 (d, 1H), 3.94 (s, 3H), 3.82 (s, 2H), 3.19-3.06 (m, 4H), 2.55-2.40 (m, 4H), 2.35-2.13 (m, 4H), 2.09-2.03 (m, 2H), 1.21 (s, 3H).

<95-2> Preparation of 4-(((9-fluoro-10-(hydroxymethyl)-6,7-dihydro-5H-dibenzo[a,c][7]annulen-3-yl)oxy)methyl)-4-methyltetrahydro-2H-thiopyran 1,1-dioxide

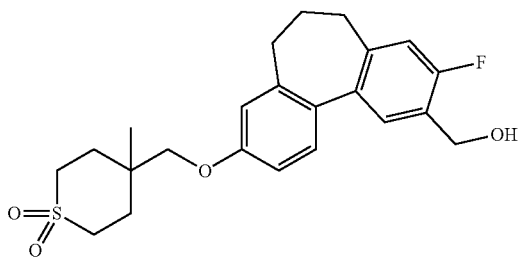 [SMILES: CC1(COc2ccc3c(c2)CCCc2cc(F)c(CO)cc2-3)CCS(=O)(=O)CC1]

According to the procedures as described in <1-9>, the compound obtained in <95-1> was used to prepare the title compound (white foam, 131.2 mg, 90% yield).

$^1$H NMR (300 MHz, CDCl$_3$) δ 7.36 (d, 1H), 7.29 (d, 1H), 6.95 (d, 1H), 6.86 (dd, 1H), 6.81 (d, 1H), 4.80 (d, 2H), 3.82 (s, 2H), 3.20-3.01 (m, 4H), 2.51-2.39 (m, 4H), 2.35-2.22 (m, 2H), 2.22-2.11 (m, 2H), 2.10-2.02 (m, 2H), 1.80 (t, 1H), 1.21 (s, 3H).

<95-3> Preparation of (S)-methyl 2-(6-((3-fluoro-9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-ylacetate

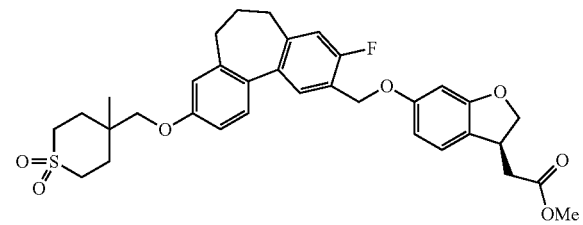 [SMILES: COC(=O)C[C@@H]1COc2cc(OCc3cc4c(cc3F)CCCc3cc(OCC5(C)CCS(=O)(=O)CC5)ccc3-4)ccc21]

According to the procedures as described in <1-10>, the compound obtained in <95-2> was used to prepare the title compound (yellow foam, 193.5 mg, 102% yield).

$^1$H NMR (300 MHz, CDCl$_3$) δ=7.38 (d, 1H), 7.27 (d, 1H), 7.04 (d, 1H), 6.97 (d, 1H), 6.85 (dd, 1H), 6.80 (d, 1H), 6.54-6.47 (m, 2H), 5.10 (s, 2H), 4.76 (t, 1H), 4.27 (dd, 1H), 3.88-3.74 (m, 3H), 3.71 (s, 3H), 3.67 (m, 2H), 3.19-3.01 (m, 4H), 2.76 (dd, 1H), 2.56 (dd, 1H), 2.51-2.40 (m, 4H), 2.28 (m, 2H), 2.19 (m, 2H), 2.09-1.96 (m, 2H), 1.21 (s, 3H).

<95-4> Preparation of (S)-2-(6-((3-fluoro-9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid

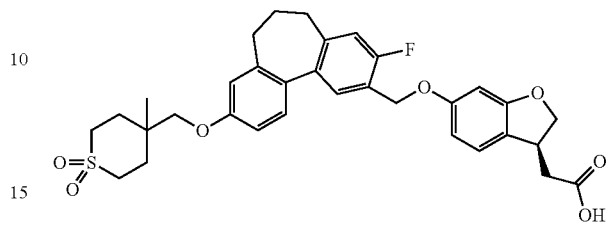

According to the procedures as described in <1-11>, the compound obtained in <95-3> was used to prepare the title compound (white foam, 63.3 mg, 34% yield).

MS m/z 617 [M+Na]$^+$.

$^1$H NMR (300 MHz, CDCl$_3$) δ=7.42 (d, 1H), 7.26 (d, 1H), 7.08 (d, 1H), 6.97 (d, 1H), 6.85 (dd, 1H), 6.80 (d, 1H), 6.57-6.46 (m, 2H), 5.10 (s, 2H), 4.77 (t, 1H), 4.30 (dd, 1H), 3.89-3.76 (m, 3H), 3.19-3.01 (m, 4H), 2.82 (dd, 1H), 2.62 (dd, 1H), 2.47 (t, 4H), 2.28 (m, 2H), 2.19 (m, 2H), 2.09-1.98 (m, 2H), 1.20 (s, 3H).

Example 96

Preparation of (S)-2-(6-((3-fluoro-9-(3-(methylsulfonyl)propoxy)-6,7-dihydro-5H-dibenzo[a,c][7]annulen-2-yl)methoxy)-2,3-dihydrobenzofuran-3-yl)acetic acid

<96-1> Preparation of methyl 3-fluoro-9-(3-(methylsulfonyl)propoxy)-6,7-dihydro-5H-dibenzo[a,c][7]annulene-2-carboxylate

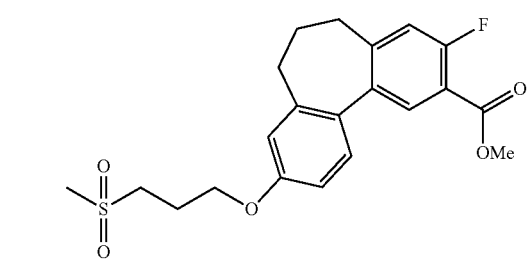 [SMILES: COC(=O)c1cc2c(cc1F)CCCc1cc(OCCCS(C)(=O)=O)ccc1-2]

According to the procedures as described in <1-8>, the compound obtained in <85-7> was used to prepare the title compound (white solid, 471 mg, >100% yield).

$^1$H NMR (600 MHz, CDCl$_3$) δ 7.87 (d, 1H), 7.28 (d, 1H), 7.01 (d, 1H), 6.84 (dd, 1H), 6.77 (d, 1H), 4.15 (t, 2H), 3.93 (s, 3H), 3.28 (t, 2H), 2.96 (s, 3H), 2.49 (t, 2H), 2.44 (t, 2H), 2.38-2.35 (m, 2H), 2.18 (m, 2H).

<96-2> Preparation of (3-fluoro-9-(3-(methylsulfonyl)propoxy)-6,7-dihydro-5H-dibenzo[a,c][7]annulen-2-yl)methanol

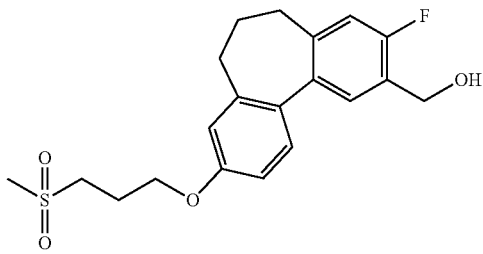 [SMILES: CS(=O)(=O)CCCOc1ccc2c(c1)CCCc1cc(F)c(CO)cc1-2]

According to the procedures as described in <1-9>, the compound obtained in <96-1> was used to prepare the title compound (white solid, 314 mg, 81% yield).

$^1$H NMR (300 MHz, CDCl$_3$) δ 7.34 (d, 1H), 7.26 (d, 1H), 6.93 (d, 1H), 6.83 (dd, 1H), 6.77 (d, 1H), 4.78 (d, 2H), 4.15 (t, 2H), 3.28 (t, 2H), 2.96 (s, 3H), 2.45 (t, 2H), 2.44 (t, 2H), 2.38-2.34 (m, 2H), 2.16 (m, 2H), 1.76 (t, 1H).

<96-3> Preparation of (S)-methyl 2-(6-((3-fluoro-9-(3-(methylsulfonyl)propoxy)-6,7-dihydro-5H-dibenzo[a,c][7]annulen-2-yl)methoxy)-2,3-dihydrobenzofuran-3-ylacetate

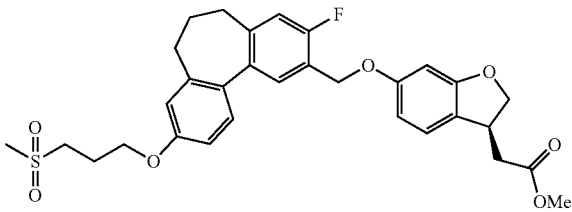 [SMILES: COC(=O)C[C@@H]1COc2cc(OCc3cc4c(cc3F)CCCc3cc(OCCCS(C)(=O)=O)ccc3-4)ccc21]

According to the procedures as described in <1-10>, the compound obtained in <96-2> (white solid, 96 mg, 61% yield).

$^1$H NMR (300 MHz, CDCl$_3$) δ 7.42 (d, 1H), 7.25 (d, 1H), 7.04 (d, 1H), 6.97 (d, 1H), 6.83 (dd, 1H), 6.79 (d, 1H), 6.53-6.50 (m, 2H), 5.10 (s, 2H), 4.76 (t, 1H), 4.27 (dd, 1H), 4.17 (t, 2H), 3.86-3.76 (m, 1H), 3.72 (s, 3H), 3.29 (t, 2H), 2.97 (s, 3H), 2.76 (dd, 1H), 2.56 (dd, 1H), 2.47 (m, 4H), 2.37 (m, 2H), 2.17 (m, 2H).

<96-4> Preparation of (S)-2-(6-((3-fluoro-9-(3-(methylsulfonyl)propoxy)-6,7-dihydro-5H-dibenzo[a,c][7]annulen-2-yl)methoxy)-2,3-dihydrobenzofuran-3-yl)acetic acid

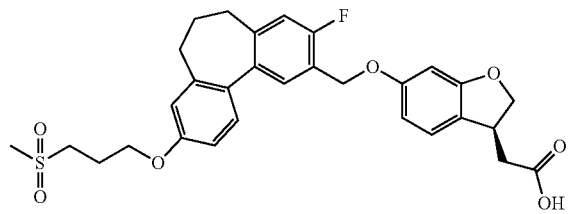 [SMILES: CS(=O)(=O)CCCOc1ccc2c(c1)CCCc1cc(F)c(COc3ccc4c(c3)OC[C@H]4CC(=O)O)cc1-2]

According to the procedures as described in <1-11>, the compound obtained in <96-3> (white solid, 76 mg, 81% yield).

MS m/z 553 [M−H]$^-$.

$^1$H NMR (300 MHz, CDCl$_3$) δ 7.42 (d, 1H), 7.25 (d, 1H), 7.07 (d, 1H), 6.97 (d, 1H), 6.83 (dd, 1H), 6.78 (d, 1H), 6.52 (dd, 1H), 6.50 (d, 1H), 5.10 (s, 2H), 4.77 (t, 1H), 4.29 (dd, 1H), 4.16 (t, 2H), 3.83-3.80 (m, 1H), 3.29 (t, 2H), 2.97 (s, 3H), 2.81 (dd, 1H), 2.62 (dd, 1H), 2.47 (m, 4H), 2.39-2.35 (m, 2H), 2.17 (m, 2H).

Example 97

Preparation of (S)-2-(6-((9-(3-(ethylsulfonyl)propoxy)-3-fluoro-6,7-dihydro-5H-dibenzo[a,c][7]annulen-2-yl)methoxy)-2,3-dihydrobenzofuran-3-yl)acetic acid

<97-1> Preparation of methyl 9-(3-(ethylsulfonyl)propoxy)-3-fluoro-6,7-dihydro-5H-dibenzo[a,c][7]annulene-2-carboxylate

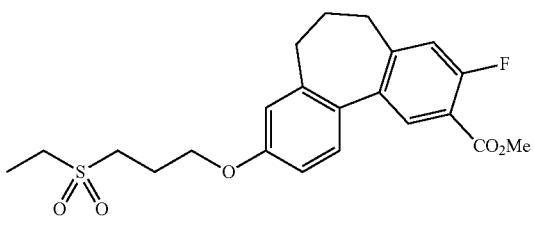 [SMILES: CCS(=O)(=O)CCCOc1ccc2c(c1)CCCc1cc(F)c(C(=O)OC)cc1-2]

According to the procedures as described in <38-1>, the compound obtained in <85-7> was used to prepare the title compound (white solid, 281.5 mg, 96% yield).

$^1$H NMR (300 MHz, CDCl$_3$) δ 7.88 (d, 1H), 7.30 (d, 1H), 7.03 (d, 1H), 6.86 (dd, 1H), 6.79 (d, 1H), 4.17 (t, 2H), 3.94 (s, 3H), 3.30-3.20 (m, 2H), 3.05 (q, 2H), 2.57-2.29 (m, 6H), 2.20 (m, 2H), 1.45 (t, 3H).

<97-2> Preparation of (9-(3-(ethylsulfonyl)propoxy)-3-fluoro-6,7-dihydro-5H-dibenzo[a,c][7]annulen-2-yl)methanol

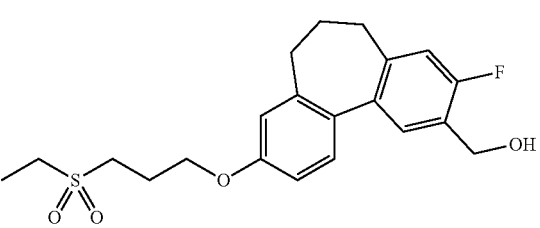 [SMILES: CCS(=O)(=O)CCCOc1ccc2c(c1)CCCc1cc(F)c(CO)cc1-2]

According to the procedures as described in <1-9>, the compound obtained in <97-1> was used to prepare the title compound (white solid, 194.2 mg, 74% yield).

$^1$H NMR (300 MHz, CDCl$_3$) δ 7.36 (d, 1H), 7.28 (d, 1H), 6.95 (d, 1H), 6.84 (dd, 1H), 6.78 (d, 1H), 4.79 (d, 2H), 4.16 (t, 2H), 3.27-3.15 (m, 2H), 3.05 (q, 2H), 2.52-2.29 (m, 6H), 2.17 (m, 2H), 1.79 (t, 1H), 1.45 (t, 3H).

<97-3> Preparation of (S)-methyl 2-(6-((9-(3-(ethylsulfonyl)propoxy)-3-fluoro-6,7-dihydro-5H-dibenzo[a,c][7]annulen-2-yl) methoxy)-2,3-dihydrobenzofuran-3-yl)acetate

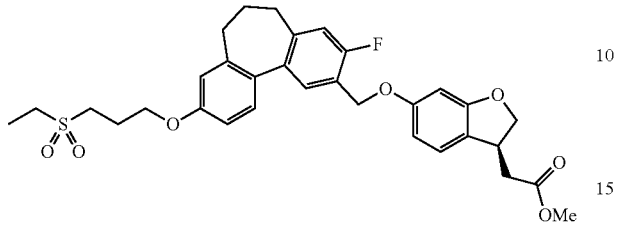

According to the procedures as described in <1-10>, the compound obtained in <97-2> was used to prepare the title compound (white solid, 150.4 mg, 99% yield).

¹H NMR (300 MHz, CDCl₃) δ 7.42 (d, 1H), 7.26 (d, 1H), 7.04 (d, 1H), 6.97 (d, 1H), 6.84 (dd, 1H), 6.79 (d, 1H), 6.55-6.47 (m, 2H), 5.10 (s, 2H), 4.77 (t, 1H), 4.28 (dd, 1H), 4.16 (t, 2H), 3.84-3.74 (m, 1H), 3.72 (s, 3H), 3.28-3.15 (m, 2H), 3.06 (q, 2H), 2.76 (dd, 1H), 2.57 (dd, 1H), 2.51-2.41 (m, 4H), 2.41-2.29 (m, 2H), 2.24-2.09 (m, 2H), 1.45 (t, 3H).

<97-4> Preparation of (S)-2-(6-((9-(3-(ethylsulfonyl)propoxy)-3-fluoro-6,7-dihydro-5H-dibenzo[a,c][7]annulen-2-yl)methoxy)-2,3-dihydrobenzofuran-3-yl)acetic acid

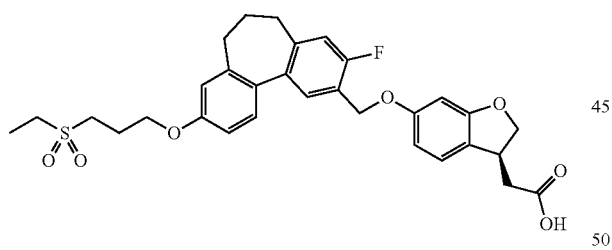

According to the procedures as described in <1-11>, the compound obtained in <97-3> was used to prepare the title compound (white foam, 120.8 mg, 82% yield).

MS m/z 567 [M−H]⁻.

¹H NMR (300 MHz, CDCl₃) δ 7.42 (d, 1H), 7.26 (d, 1H), 7.08 (d, 1H), 6.97 (d, 1H), 6.84 (dd, 1H), 6.78 (d, 1H), 6.56-6.46 (m, 2H), 5.10 (s, 2H), 4.77 (t, 1H), 4.30 (dd, 1H), 4.16 (t, 2H), 3.82 (m, 1H), 3.28-3.16 (m, 2H), 3.06 (q, 2H), 2.82 (dd, 1H), 2.63 (dd, 1H), 2.47 (m, 4H), 2.42-2.29 (m, 2H), 2.18 (m, 2H), 1.45 (t, 3H).

Example 98

Preparation of (S)-2-(6-((9-((1,1-dioxidotetrahydro-2H-thiopyran-4-yl)oxy)-3-fluoro-6,7-dihydro-5H-dibenzo[a,c][7]annulen-2-yl)methoxy)-2,3-dihydrobenzofuran-3-yl)acetic acid

<98-1> Preparation of methyl 9-((1,1-dioxidotetrahydro-2H-thiopyran-4-yl)oxy)-3-fluoro-6,7-dihydro-5H-dibenzo[a,c][7]annulene-2-carboxylate

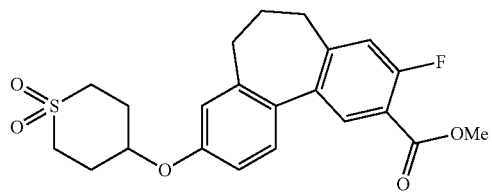 [SMILES: COC(=O)c1cc2c(cc1F)CCCc1cc(OC3CCS(=O)(=O)CC3)ccc1-2]

The compound obtained in <85-7> (200 mg, 0.699 mmol) was dissolved in DMF (4 mL), which was then added with 1,1-dioxidotetrahydro-2H-thiopyran-4-yl 4-methylbenzenesulfonate (425 mg, 1.4 mmol) and K₂CO₃ (193 mg, 1.4 mmol) and stirred at 90° C. for 15 hours. The reaction mixture was cooled to room temperature, diluted with EtOAc, and washed with a saturated NH₄Cl aqueous solution and brine. The organic layer was dried over sodium sulfate, concentrated under reduced pressure, and the residue thus obtained was purified by silica gel chromatography to obtain the title compound (white foam, 234 mg, 80% yield).

¹H NMR (600 MHz, CDCl₃) δ 7.89 (d, 1H), 7.33 (d, 1H), 7.03 (d, 1H), 6.89 (dd, 1H), 6.83 (d, 1H), 4.73-4.70 (m, 1H), 3.94 (s, 3H), 3.45 (td, 2H), 2.96 (dd, 2H), 2.53 (t, 2H), 2.45 (t, 2H), 2.41 (t, 2H), 2.22-2.15 (m, 2H).

<98-2> Preparation of 4-((9-fluoro-10-(hydroxymethyl)-6,7-dihydro-5H-dibenzo[a,c][7]annulen-3-yl)oxy)tetrahydro-2H-thiopyran 1,1-dioxide

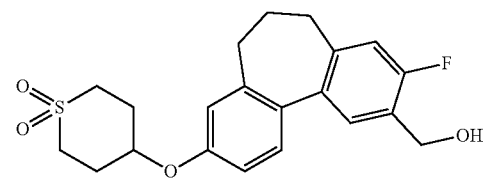 [SMILES: O=S1(=O)CCC(Oc2ccc3c(c2)CCCc2cc(F)c(CO)cc2-3)CC1]

According to the procedures as described in <1-9>, the compound obtained in <98-1> was used to prepare the title compound (white foam, 170 mg, 79% yield).

¹H NMR (600 MHz, CDCl₃) δ 7.36 (d, 1H), 7.30 (d, 1H), 6.95 (d, 1H), 6.88 (dd, 1H), 6.82 (d, 1H), 4.79 (d, 1H), 4.72-4.69 (m, 1H), 3.45 (td, 2H), 2.97 (dd, 2H), 2.54-2.45 (m, 5H), 2.42-2.37 (m, 2H), 2.19-2.16 (m, 2H), 1.85 (t, 1H).

<98-3> Preparation of (S)-methyl 2-(6-((9-((1,1-dioxidotetrahydro-2H-thiopyran-4-yl)oxy)-3-fluoro-6,7-dihydro-5H-dibenzo[a,c][7]annulen-2-yl)methoxy)-2,3-dihydrobenzofuran-3-yl)acetate

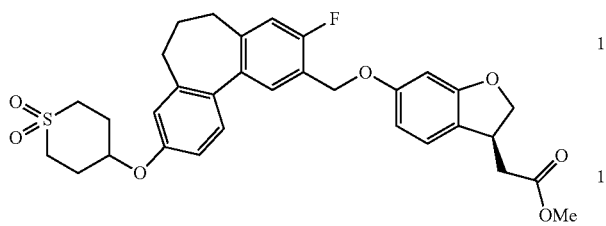

According to the procedures as described in <1-10>, the compound obtained in <98-2> was used to prepare the title compound (white foam, 97 mg, 77% yield).

$^1$H NMR (600 MHz, CDCl$_3$) δ 7.42 (d, 1H), 7.27 (d, 1H), 7.04 (d, 1H), 6.98 (d, 1H), 6.88 (dd, 1H), 6.82 (d, 1H), 6.52 (dd, 1H), 6.49 (d, 1H), 5.10 (s, 2H), 4.76 (t, 1H), 4.72-4.69 (m, 1H), 4.27 (dd, 1H), 3.84-3.79 (m, 1H), 3.72 (s, 3H), 3.45 (td, 2H), 2.98-2.93 (m, 2H), 2.75 (dd, 1H), 2.57 (dd, 1H), 2.53-2.45 (m, 6H), 2.39 (t, 2H), 2.20-2.15 (m, 2H).

<98-4> Preparation of (S)-2-(6-((9-((1,1-dioxidotetrahydro-2H-thiopyran-4-yl)oxy)-3-fluoro-6,7-dihydro-5H-dibenzo[a,c][7]annulen-2-yl)methoxy)-2,3-dihydrobenzofuran-3-yl)acetic acid

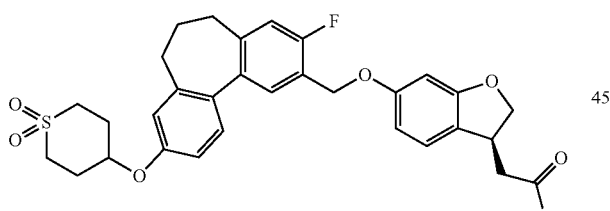

According to the procedures as described in <1-11>, the compound obtained in <98-3> was used to prepare the title compound (white foam, 82 mg, 88% yield).

MS m/z 566 [M−H]$^-$.

$^1$H NMR (600 MHz, CDCl$_3$) δ 7.41 (d, 1H), 7.27 (d, 1H), 7.07 (d, 1H), 6.98 (d, 1H), 6.88 (dd, 1H), 6.82 (d, 1H), 6.52 (dd, 1H), 6.49 (d, 1H), 5.10 (s, 2H), 4.77 (t, 1H), 4.71-4.69 (m, 1H), 4.29 (dd, 1H), 3.84-3.79 (m, 1H), 3.45 (td, 2H), 2.98-2.94 (m, 2H), 2.81 (dd, 1H), 2.62 (dd, 1H), 2.53-2.45 (m, 6H), 2.42-2.36 (m, 2H), 2.20-2.15 (m, 2H).

Example 99

Preparation of (S)-2-(6-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid

<99-1> Preparation of methyl 3-fluoro-9-((4-hydroxytetrahydro-2H-thiopyran-4-yl)methoxy)-6,7-dihydro-5H-dibenzo[a,c][7]annulene-2-carboxylate

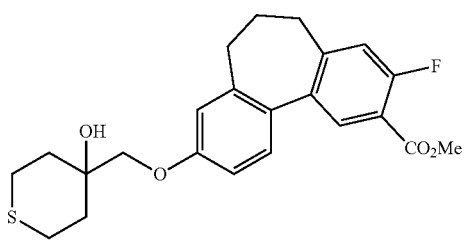 [SMILES: COC(=O)c1cc2c(cc1F)CCCc1cc(OCC3(O)CCSCC3)ccc1-2]

According to the procedures as described in <56-1>, the compound obtained in <85-7> was used to prepare the title compound (white foam, 219 mg, 59% yield).

$^1$H NMR (300 MHz, CDCl$_3$) δ 7.89 (d, 1H), 7.31 (d, 1H), 7.03 (d, 1H), 6.88 (dd, 1H), 6.82 (d, 1H), 3.94 (s, 3H), 3.83 (s, 2H), 3.17-3.04 (m, 2H), 2.56-2.41 (m, 6H), 2.25-2.07 (m, 5H), 1.85 (m, 2H).

<99-2> Preparation of methyl 3-fluoro-9-((4-hydroxy-1,1-dioxidotetrahydro-2H-thiopyran-4-yl)methoxy)-6,7-dihydro-5H-dibenzo[a,c][7]annulene-2-carboxylate

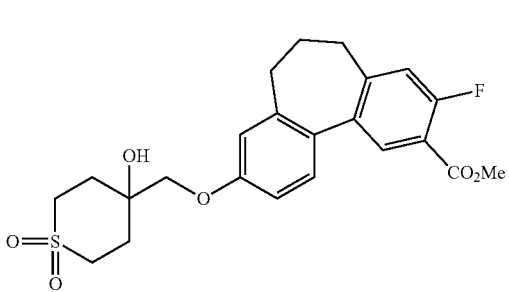 [SMILES: COC(=O)c1cc2c(cc1F)CCCc1cc(OCC3(O)CCS(=O)(=O)CC3)ccc1-2]

According to the procedures as described in <56-2>, the compound obtained in <99-1> was used to prepare the title compound (colorless oil, 382 mg, 107% yield).

$^1$H NMR (300 MHz, CDCl$_3$) δ 7.88 (d, 1H), 7.31 (d, 1H), 7.03 (d, 1H), 6.88 (dd, 1H), 6.82 (d, 1H), 3.94 (s, 3H), 3.92 (s, 2H), 3.51 (m, 2H), 3.02-2.88 (m, 2H), 2.71 (s, 1H), 2.48 (m, 4H), 2.33-2.25 (m, 4H), 2.21 (m, 2H).

247

<99-3> Preparation of 4-(((9-fluoro-10-(hydroxymethyl)-6,7-dihydro-5H-dibenzo[a,c][7]annulen-3-yl)oxy)methyl)-4-hydroxytetrahydro-2H-thiopyran 1,1-dioxide

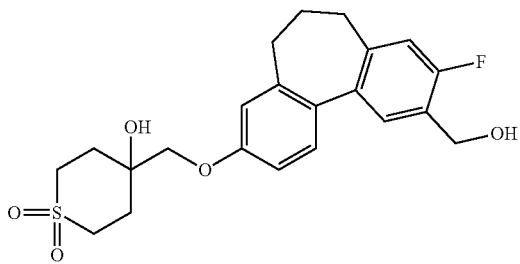 [SMILES: O=S1(=O)CCC(O)(COc2ccc3c(c2)CCCc2cc(F)c(CO)cc2-3)CC1]

According to the procedures as described in <1-9>, the compound obtained in <99-2> was used to prepare the title compound (white foam, 294 mg, 82% yield).

$^1$H NMR (300 MHz, CDCl$_3$) δ 7.36 (d, 1H), 7.29 (dd, 1H), 6.94 (d, 1H), 6.85 (dd, 1H), 6.81 (d, 1H), 4.78 (d, 2H), 3.90 (s, 2H), 3.49 (m, 2H), 3.01-2.87 (m, 2H), 2.75 (s, 1H), 2.45 (t, 4H), 2.27 (m, 4H), 2.17 (m, 3H).

<99-4> Preparation of (S)-methyl 2-(6-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetate

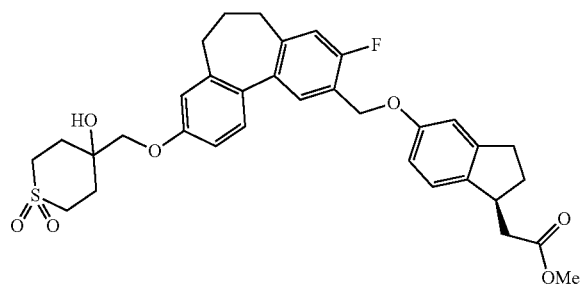 [SMILES: COC(=O)C[C@@H]1CCc2cc(OCc3cc4c(cc3F)CCCc3cc(OCC5(O)CCS(=O)(=O)CC5)ccc3-4)ccc21]

According to the procedures as described in <1-10>, the compound obtained in <99-3> was used to prepare the title compound (colorless oil, 138 mg, 72% yield).

$^1$H NMR (300 MHz, CDCl$_3$) δ 7.41 (d, 1H), 7.27 (d, 1H), 7.04 (d, 1H), 6.97 (d, 1H), 6.85 (dd, 1H), 6.81 (d, 1H), 6.56-6.43 (m, 2H), 5.09 (s, 2H), 4.75 (t, 1H), 4.26 (dd, 1H), 3.90 (s, 2H), 3.84-3.73 (m, 1H), 3.71 (s, 3H), 3.50 (m, 2H), 2.94 (m, 2H), 2.75 (dd, 1H), 2.56 (dd, 1H), 2.46 (t, 4H), 2.32-2.22 (m, 4H), 2.18 (m, 2H).

248

<99-5> Preparation of (S)-2-(6-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid

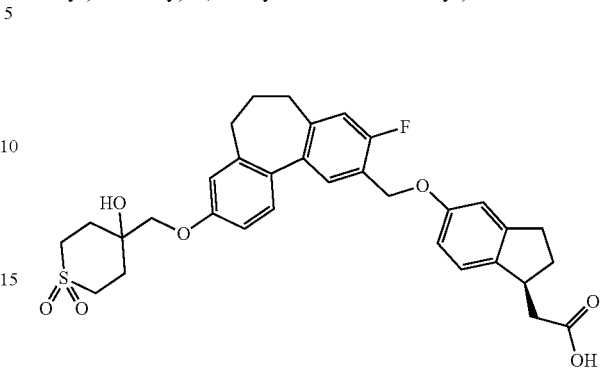

According to the procedures as described in <1-11>, the compound obtained in <99-4> was used to prepare the title compound (white foam, 103 mg, 76% yield).

MS m/z 595 [M−H]$^−$.

$^1$H NMR (300 MHz, CDCl$_3$) δ 7.42 (d, 1H), 7.28 (d, 1H), 7.07 (d, 1H), 6.98 (d, 1H), 6.86 (dd, 1H), 6.81 (d, 1H), 6.56-6.43 (m, 2H), 5.10 (s, 2H), 4.77 (t, 1H), 4.30 (dd, 1H), 3.91 (s, 2H), 3.83 (m, 1H), 3.59-3.41 (m, 2H), 3.03-2.89 (m, 2H), 2.80 (dd, 1H), 2.62 (dd, 1H), 2.47 (t, 4H), 2.29 (m, 4H), 2.17 (m, 2H).

Example 100

Preparation of (1S,2S)-2-(4-((9-((1,1-dioxidotetrahydro-2H-thiopyran-4-yl)oxy)-3-fluoro-6,7-dihydro-5H-dibenzo[a,c][7]annulen-2-yl)methoxy)phenyl)cyclopropanecarboxylic acid <100-1> Preparation of (1S,2S)-ethyl 2-(4-((9-((1,1-dioxidotetrahydro-2H-thiopyran-4-yl)oxy)-3-fluoro-6,7-dihydro-5H-dibenzo[a,c][7]annulen-2-yl)methoxy)phenyl)cyclopropanecarboxylate

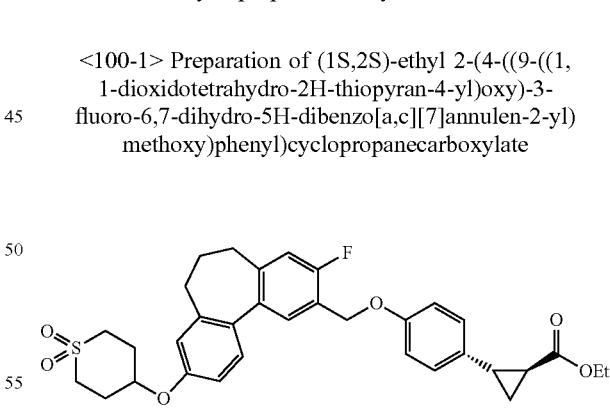

According to the procedures as described in <2-16>, the compound obtained in <98-2> was used to prepare the title compound (white foam, 82 mg, 65% yield).

$^1$H NMR (600 MHz, CDCl$_3$) δ 7.42 (d, 1H), 7.27 (d, 1H), 7.04 (d, 2H), 6.98 (d, 1H), 6.92 (d, 2H), 6.87 (dd, 1H), 6.82 (d, 1H), 5.12 (s, 2H), 4.72-4.69 (m, 1H), 4.16 (q, 2H), 3.45 (td, 2H), 2.98-2.93 (m, 2H), 2.50-2.45 (m, 7H), 2.39 (t, 2H), 2.20-2.15 (m, 2H), 1.83-1.81 (m, 1H), 1.56-1.54 (m, 1H), 1.29-1.24 (m, 4H).

249

<100-2> Preparation of (1S,2S)-2-(4-((9-((1,1-dioxidotetrahydro-2H-thiopyran-4-yl)oxy)-3-fluoro-6,7-dihydro-5H-dibenzo[a,c][p]annulen-2-yl)methoxy)phenyl)cyclopropanecarboxylic acid

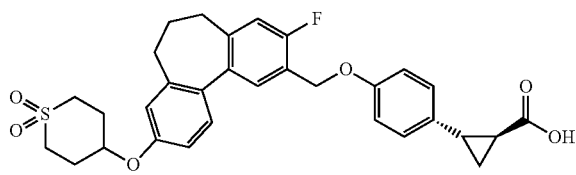

According to the procedures as described in <2-17>, the compound obtained in <100-1> was used to prepare the title compound (white foam, 77 mg, 98% yield).

MS m/z 550 [M−H]⁻.

¹H NMR (600 MHz, CDCl₃) δ 7.41 (d, 1H), 7.26 (d, 1H), 7.05 (d, 2H), 6.98 (d, 1H), 6.93 (d, 2H), 6.88 (dd, 1H), 6.82 (d, 1H), 5.13 (s, 2H), 4.72-4.69 (m, 1H), 3.45 (td, 2H), 2.98-2.94 (m, 2H), 2.56-2.54 (m, 1H), 2.53-2.43 (m, 6H), 2.42-2.36 (m, 2H), 2.20-2.15 (m, 2H), 1.85-1.82 (m, 1H), 1.65-1.60 (m, 1H), 1.36-1.34 (m, 1H).

Example 101

Preparation of (1S,2S)-2-(4-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid <101-1> Preparation of (1S,2S)-ethyl 2-(4-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylate

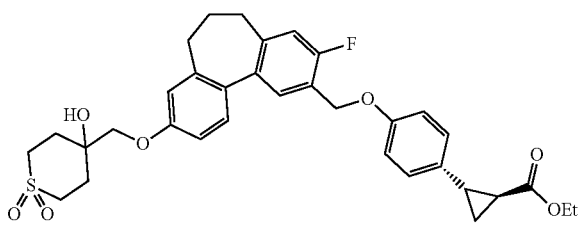

According to the procedures as described in <2-16>, the compound obtained in <99-3> was used to prepare the title compound (white foam, 148 mg, 71% yield).

¹H NMR (300 MHz, CDCl₃) δ 7.42 (d, 1H), 7.27 (d, 1H), 7.07-7.00 (m, 2H), 6.98 (d, 1H), 6.95-6.89 (m, 2H), 6.86 (dd, 1H), 6.81 (d, 1H), 5.12 (s, 2H), 4.16 (q, 2H), 3.90 (s, 2H), 3.50 (m, 2H), 3.01-2.85 (m, 2H), 2.53-2.38 (m, 5H), 2.27 (m, 4H), 2.18 (m, 2H), 1.82 (m, 1H), 1.54 (m, 1H), 1.31-1.20 (m, 3H).

250

<101-2> Preparation of (1S,2S)-2-(4-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid

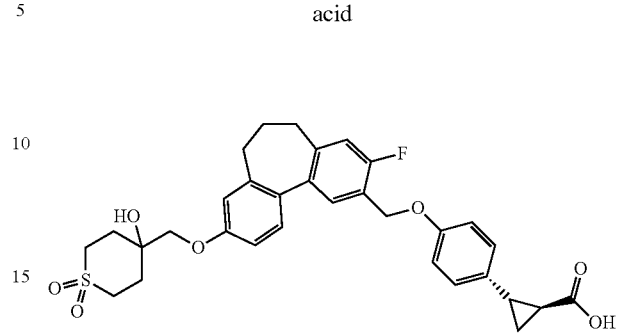

According to the procedures as described in <1-11>, the compound obtained in <101-1> was used to prepare the title compound (white foam, 128 mg, 91% yield).

MS m/z 579 [M−H]⁻.

¹H NMR (300 MHz, CDCl₃) δ 7.42 (d, 1H), 7.27 (d, 1H), 7.10-7.02 (m, 2H), 6.98 (d, 1H), 6.96-6.90 (m, 2H), 6.86 (dd, 1H), 6.81 (d, 1H), 5.13 (s, 2H), 3.91 (s, 2H), 3.59-3.40 (m, 2H), 2.96 (m, 2H), 2.64-2.53 (m, 1H), 2.47 (t, 4H), 2.35-2.23 (m, 4H), 2.23-2.11 (m, 2H), 1.89-1.77 (m, 1H), 1.62 (m, 1H), 1.36 (m, 1H).

Example 102

Preparation of (1S,2S)-2-(4-((3-fluoro-9-(3-(methylsulfonyl)propoxy)-6,7-dihydro-5H-dibenzo[a,c][7]annulen-2-yl)methoxy)phenyl)cyclopropanecarboxylic acid <102-1> Preparation of (1S,2S)-ethyl 2-(4-((3-fluoro-9-(3-(methylsulfonyl)propoxy)-6,7-dihydro-5H-dibenzo[a,c][7]annulen-2-yl)methoxy)phenyl)cyclopropanecarboxylate

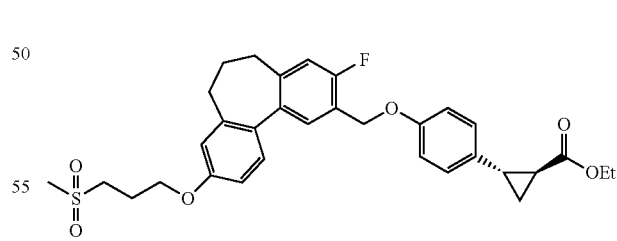

According to the procedures as described in <2-16>, the compound obtained in <96-2> was used to prepare the title compound (white foam, 90 mg, 58% yield).

¹H NMR (300 MHz, CDCl₃) δ 7.42 (d, 1H), 7.24 (d, 1H), 7.04 (d, 2H), 6.97 (d, 1H), 6.92 (d, 2H), 6.83 (dd, 1H), 6.78 (d, 1H), 5.11 (s, 2H), 4.16 (q, 2H), 4.15 (t, 2H), 3.28 (m, 2H), 2.97 (s, 3H), 2.51-2.41 (m, 5H), 2.41-2.32 (m, 2H), 2.17 (m, 2H), 1.81 (m, 1H), 1.55 (m, 1H), 1.27 (t, 3H), 1.25 (m, 1H)

<102-2> Preparation of (1S,2S)-2-(4-((3-fluoro-9-(3-(methylsulfonyl)propoxy)-6,7-dihydro-5H-dibenzo[a,c][7]annulen-2-yl)methoxy)phenyl)cyclopropanecarboxylic acid

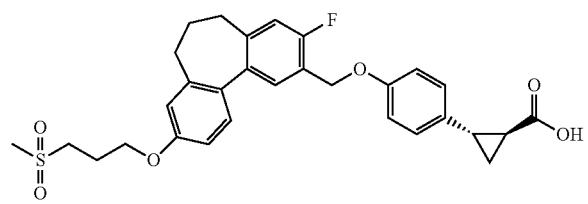 [SMILES: CS(=O)(=O)CCCOc1ccc2c(c1)CCCc1cc(F)c(COc3ccc([C@H]4C[C@@H]4C(=O)O)cc3)cc1-2]

According to the procedures as described in <1-11>, the compound obtained in <102-1> was used to prepare the title compound (white foam, 81 mg, 94% yield).

MS m/z 537 [M−H]⁻

$^1$H NMR (600 MHz, CDCl$_3$) δ 7.41 (d, 1H), 7.23 (d, 1H), 7.05 (d, 2H), 6.96 (d, 1H), 6.92 (d, 2H), 6.83 (dd, 1H), 6.77 (d, 1H), 5.11 (s, 2H), 4.14 (t, 2H), 3.27 (m, 2H), 2.96 (s, 3H), 2.57-2.54 (m, 1H), 2.45 (m, 4H), 2.37-2.35 (m, 2H), 2.16 (m, 2H), 1.82 (m, 1H), 1.61 (m, 1H), 1.35 (m, 1H)

Example 103

Preparation of (1S,2S)-2-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)cyclopropanecarboxylic acid

<103-1> Preparation of (1S,2S)-ethyl 2-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)cyclopropanecarboxylate

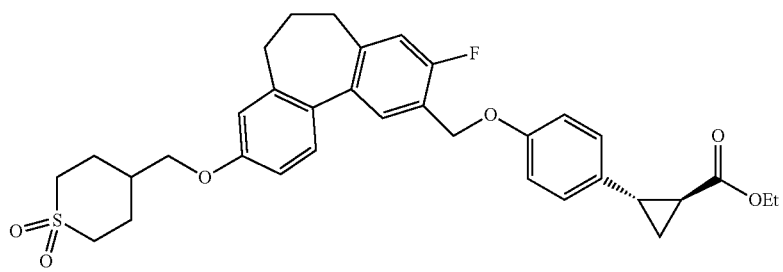 [SMILES: CCOC(=O)[C@H]1C[C@@H]1c1ccc(OCc2cc3c(cc2F)CCCc2cc(OCC4CCS(=O)(=O)CC4)ccc2-3)cc1]

According to the procedures as described in <2-16>, the compound obtained in <85-9> was used to prepare the title compound (white foam, 124.3 mg, 61% yield).

$^1$H NMR (300 MHz, CDCl$_3$) δ 7.42 (d, 1H), 7.25 (d, 1H), 7.04 (d, 2H), 6.97 (d, 1H), 6.92 (d, 2H), 6.83 (dd, 1H), 6.77 (d, 1H), 5.12 (s, 2H), 4.16 (q, 2H), 3.90 (d, 2H), 3.21-2.89 (m, 4H), 2.53-2.41 (m, 5H), 2.30 (m, 2H), 2.25-2.12 (m, 2H), 2.12-1.99 (m, 3H), 1.88-1.77 (m, 1H), 1.60-1.50 (m, 1H), 1.32-1.25 (m, 4H).

<103-2> Preparation of (1S,2S)-2-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)cyclopropanecarboxylic acid

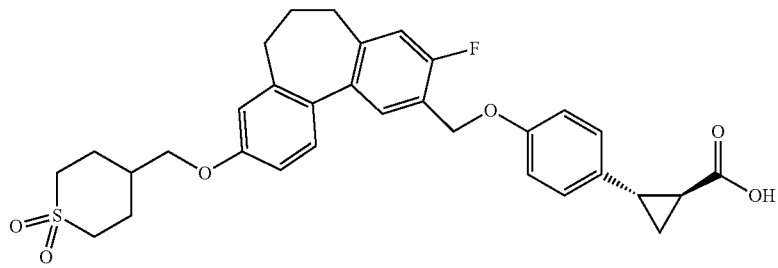 [SMILES: O=C(O)[C@H]1C[C@@H]1c1ccc(OCc2cc3c(cc2F)CCCc2cc(OCC4CCS(=O)(=O)CC4)ccc2-3)cc1]

According to the procedures as described in <1-11>, the compound obtained in <103-1> was used to prepare the title compound (white foam, 94.2 mg, 79% yield).

MS m/z 587 [M+Na]⁺.

$^1$H NMR (300 MHz, CDCl$_3$) δ 7.42 (d, 1H), 7.25 (d, 1H), 7.06 (d, 2H), 6.98 (d, 1H), 6.93 (d, 2H), 6.83 (dd, 1H), 6.78 (d, 1H), 5.12 (s, 2H), 3.91 (d, 2H), 3.21-2.97 (m, 4H), 2.56 (m, 1H), 2.47 (m, 4H), 2.30 (m, 2H), 2.23-2.13 (m, 2H), 2.13-2.00 (m, 3H), 1.89-1.77 (m, 1H), 1.62 (m, 1H), 1.36 (m, 1H).

Example 104

Preparation of (1S,2S)-2-(4-(((3-fluoro-9-(3-(methylsulfonyl)propoxy)-6,7-dihydro-5H-dibenzo[a,c][7]annulen-2-yl)methyl)amino)phenyl)cyclopropanecarboxylic acid <104-1> Preparation of 3-fluoro-9-(3-(methylsulfonyl)propoxy)-6,7-dihydro-5H-dibenzo[a,c][7]annulene-2-carbaldehyde According to the procedures as described in <3-3>, the compound obtained in <96-2> was used to prepare the title compound (white solid, 77 mg, 74% yield), which was used in the next step.

<104-2> Preparation of (1S,2S)-ethyl 2-(4-(((3-fluoro-9-(3-(methylsulfonyl)propoxy)-6,7-dihydro-5H-dibenzo[a,c][7]annulen-2-yl)methyl)amino)phenyl)cyclopropanecarboxylate

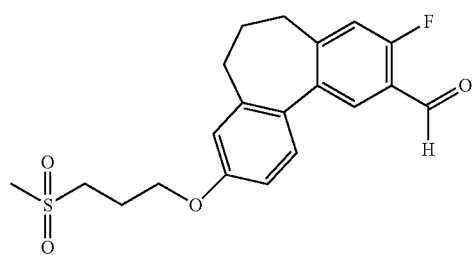 [SMILES: CS(=O)(=O)CCCOc1ccc2c(c1)CCCc1cc(F)c(C=O)cc1-2]

According to the procedures as described in <3-4>, the compound obtained in <104-1> was used to prepare the title compound (white foam, 92 mg, 80% yield).

¹H NMR (300 MHz, CDCl₃) δ 7.27 (d, 1H), 7.17 (d, 1H), 6.94 (d, 1H), 6.93 (d, 2H), 6.81 (dd, 1H), 6.76 (d, 1H), 6.59 (d, 2H), 4.38 (s, 2H), 4.15 (q, 2H), 4.14 (t, 2H), 3.27 (t, 2H), 2.96 (s, 3H), 2.46-2.33 (m, 6H), 2.15 (m, 2H), 1.77 (m, 1H), 1.50 (m, 1H), 1.26 (t, 3H), 1.21 (m, 1H).

<104-3> Preparation of (1S,2S)-2-(4-(((3-fluoro-9-(3-(methylsulfonyl)propoxy)-6,7-dihydro-5H-dibenzo[a,c][7]annulen-2-yl)methyl)amino)phenyl)cyclopropanecarboxylic acid According to the procedures as described in <3-5>, the compound obtained in <104-2> was used to prepare the title compound (white foam, 82 mg, 93% yield).

MS m/z 536 [M−H]⁻.

¹H NMR (600 MHz, CDCl₃) δ 7.27 (d, 1H), 7.16 (d, 1H), 6.93 (d, 1H), 6.92 (d, 2H), 6.80 (dd, 1H), 6.76 (d, 1H), 6.59 (d, 2H), 4.38 (s, 2H), 4.14 (t, 2H), 3.27 (t, 2H), 2.96 (s, 3H), 2.51-2.47 (m, 1H), 2.43 (m, 4H), 2.37-2.33 (m, 2H), 2.14 (m, 2H), 1.77 (m, 1H), 1.56 (m, 1H), 1.32 (m, 1H).

Example 105

Preparation of (1S,2S)-2-(4-(((9-(3-(ethylsulfonyl)propoxy)-3-fluoro-6,7-dihydro-5H-dibenzo[a,c][7]annulen-2-yl)methyl)amino)phenyl)cyclopropanecarboxylic acid <105-1> Preparation of 9-(3-(ethylsulfonyl)propoxy)-3-fluoro-6,7-dihydro-5H-dibenzo[a,c][7]annulene-2-carbaldehyde According to the procedures as described in <3-3>, the compound obtained in <97-2> was used to prepare the title compound (white solid, 73.2 mg, 81% yield).

¹H NMR (300 MHz, CDCl₃) δ 10.38 (s, 1H), 7.81 (d, 1H), 7.30 (d, 1H), 7.07 (d, 1H), 6.87 (dd, 1H), 6.80 (d, 1H), 4.17 (t, 2H), 3.29-3.16 (m, 2H), 3.06 (q, 2H), 2.55 (t, 2H), 2.45 (t, 2H), 2.42-2.32 (m, 2H), 2.22 (m, 2H), 1.45 (t, 3H).

<105-2> Preparation of (1S,2S)-ethyl 2-(4-(((9-(3-(ethylsulfonyl)propoxy)-3-fluoro-6,7-dihydro-5H-dibenzo[a,c][7]annulen-2-yl)methyl)amino)phenyl)cyclopropanecarboxylate

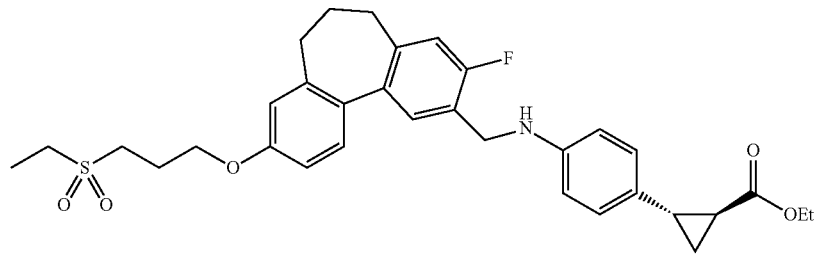 [SMILES: CCOC(=O)[C@H]1C[C@@H]1c1ccc(NCc2cc3c(cc2F)CCCc2cc(OCCCS(=O)(=O)CC)ccc2-3)cc1]

According to the procedures as described in <3-4>, the compound obtained in <105-1> was used to prepare the title compound (white foam, 116.7 mg, 106% yield).
$^1$H NMR (300 MHz, CDCl$_3$) δ 7.31 (d, 1H), 7.19 (d, 1H), 6.99-6.88 (m, 3H), 6.82 (dd, 1H), 6.78 (d, 1H), 6.62 (d, 2H), 4.39 (s, 2H), 4.21-4.09 (m, 4H), 3.28-3.16 (m, 2H), 3.06 (q, 2H), 2.51-2.31 (m, 7H), 2.15 (m, 2H), 1.84-1.73 (m, 1H), 1.56-1.48 (m, 1H), 1.45 (t, 3H), 1.32-1.18 (m, 4H).

<105-3> Preparation of (1S,2S)-2-(4-(((9-(3-(ethylsulfonyl)propoxy)-3-fluoro-6,7-dihydro-5H-dibenzo[a,c][7]annulen-2-yl)methyl)amino)phenyl)cyclopropanecarboxylic acid

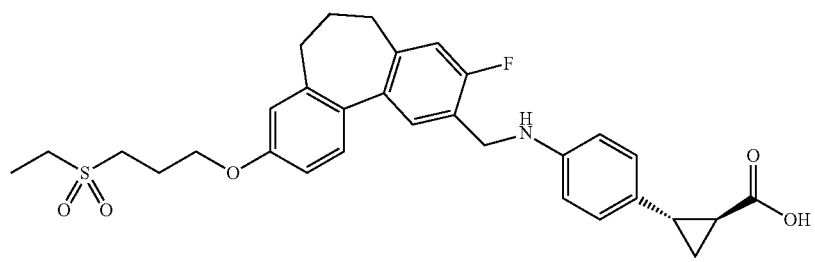 [SMILES: CCS(=O)(=O)CCCOc1ccc2c(c1)CCCc1cc(F)c(CNc3ccc([C@H]4C[C@@H]4C(=O)O)cc3)cc1-2]

According to the procedures as described in <1-11>, the compound obtained in <105-2> was used to prepare the title compound (white foam, 92.4 mg, 84% yield).

MS m/z 550 [M−H]$^−$.

$^1$H NMR (300 MHz, CDCl$_3$) δ=7.29 (d, 1H), 7.17 (d, 1H), 6.99-6.87 (m, 3H), 6.82 (dd, 1H), 6.77 (d, 1H), 6.60 (d, 2H), 4.39 (s, 2H), 4.13 (t, 2H), 3.30-3.12 (m, 2H), 3.05 (q, 2H), 2.56-2.27 (m, 7H), 2.13 (m, 2H), 1.83-1.72 (m, 1H), 1.58 (m, 1H), 1.44 (t, 3H), 1.32 (m, 1H).

Example 106

Preparation of 2-((S)-6-((3-fluoro-9-(((R)-tetrahydrofuran-3-yl)oxy)-6,7-dihydro-5H-dibenzo[a,c][7]annulen-2-yl)methoxy)-2,3-dihydrobenzofuran-3-yl)acetic acid <106-1> Preparation of (R)-methyl 3-fluoro-9-((tetrahydrofuran-3-yl)oxy)-6,7-dihydro-5H-dibenzo[a,c][7]annulene-2-carboxylate

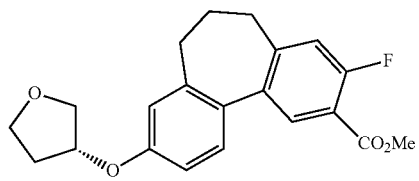 [SMILES: COC(=O)c1cc2c(cc1F)CCCc1cc(O[C@@H]3CCOC3)ccc1-2]

The compound obtained in <85-7> (100 mg, 0.349 mmol) was dissolved in DMF (1 mL), which was then added with (S)-tetrahydrofuran-3-yl methanesulfonate (prepared in accordance with the reference [Journal of the American Chemical Society, 1993, vol. 115, p. 801-803]; 87 mg, 0.524 mmol) and $Cs_2CO_3$ (171 mg, 0.524 mmol), and stirred at 90° C. for 15 hours. The reaction mixture was cooled to room temperature, extracted with EtOAc, a saturated $NH_4Cl$ aqueous solution and brine. The organic layer was dried over sodium sulfate, concentrated under reduced pressure, and the residue thus obtained was purified by silica gel chromatography to obtain the title compound (white foam, 108 mg, 87% yield).

$^1$H NMR (600 MHz, $CDCl_3$) δ 7.87 (d, 1H), 7.28 (d, 1H), 7.01 (d, 1H), 6.81 (dd, 1H), 6.75 (d, 1H), 4.99-4.95 (m, 1H), 4.04-3.98 (m, 3H), 3.94-3.91 (m, 4H), 2.50 (t, 2H), 2.44 (t, 2H), 2.22-2.16 (m, 4H).

<106-2> Preparation of (R)-(3-fluoro-9-((tetrahydrofuran-3-yl)oxy)-6,7-dihydro-5H-dibenzo[a,c][7]annulen-2-yl) methanol

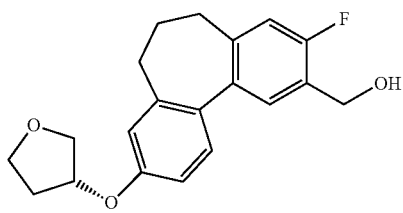

According to the procedures as described in <1-9>, the compound obtained in <106-1> was used to prepare the title compound (white foam, 170 mg, 79% yield).

$^1$H NMR (600 MHz, $CDCl_3$) δ 7.36 (d, 1H), 7.27 (d, 1H), 6.94 (d, 1H), 6.81 (dd, 1H), 6.76 (d, 1H), 4.99-4.97 (m, 1H), 4.79 (d, 2H), 4.05-4.00 (m, 3H), 3.95-3.91 (m, 1H), 2.48-2.44 (m, 4H), 2.25-2.15 (m, 4H), 1.84 (t, 1H).

<106-3> Preparation of methyl 2-((S)-6-((3-fluoro-9-(((R)-tetrahydrofuran-3-yl)oxy)-6,7-dihydro-5H-dibenzo[a,c][7]annulen-2-yl)methoxy)-2,3-dihydrobenzofuran-3-yl)acetate

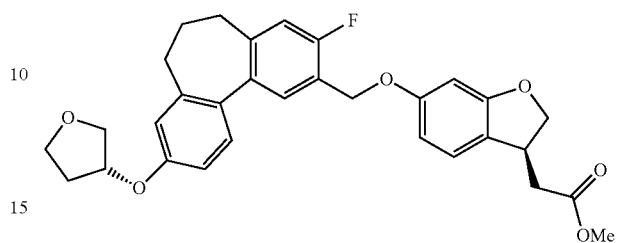

According to the procedures as described in <1-10>, the compound obtained in <106-2> was used to prepare the title compound (white foam, 139 mg, 92% yield).

$^1$H NMR (600 MHz, $CDCl_3$) δ 7.42 (d, 1H), 7.25 (d, 1H), 7.04 (d, 1H), 6.97 (d, 1H), 6.81 (dd, 1H), 6.76 (d, 1H), 6.53 (dd, 1H), 6.50 (d, 1H), 5.10 (s, 2H), 4.98-4.96 (m, 1H), 4.76 (t, 1H), 4.27 (dd, 1H), 4.05-3.99 (m, 3H), 3.94-3.91 (m, 1H), 3.83-3.80 (m, 1H), 3.72 (s, 3H), 2.76 (dd, 1H), 2.57 (dd, 1H), 2.49-2.45 (m, 4H), 2.24-2.15 (m, 4H).

<106-4> Preparation of 2-((S)-6-((3-fluoro-9-(((R)-tetrahydrofuran-3-yl)oxy)-6,7-dihydro-5H-dibenzo[a,c][7]annulen-2-yl)methoxy)-2,3-dihydrobenzofuran-3-yl)acetic acid

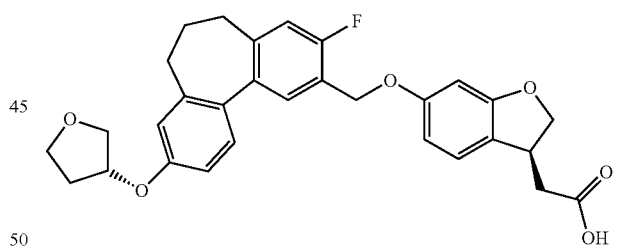

According to the procedures as described in <1-11>, the compound obtained in <106-3> was used to prepare the title compound (white foam, 118 mg, 99% yield).

MS m/z 504 [M−H]$^−$.

$^1$H NMR (600 MHz, $CDCl_3$) δ 7.42 (d, 1H), 7.25 (d, 1H), 7.07 (d, 1H), 6.97 (d, 1H), 6.81 (dd, 1H), 6.76 (d, 1H), 6.53 (dd, 1H), 6.50 (d, 1H), 5.10 (s, 2H), 4.98-4.96 (m, 1H), 4.77 (t, 1H), 4.30 (dd, 1H), 4.05-3.99 (m, 3H), 3.95-3.91 (m, 1H), 3.83-3.80 (m, 1H), 2.81 (dd, 1H), 2.62 (dd, 1H), 2.48-2.45 (m, 4H), 2.25-2.15 (m, 4H).

Example 107

Preparation of (S)-2-(6-((3-fluoro-9-(2-morpholinoethoxy)-6,7-dihydro-5H-dibenzo[a,c][7]annulen-2-yl)methoxy)-2,3-dihydrobenzofuran-3-yl)acetic acid <107-1> Preparation of (3-fluoro-9-(2-morpholinoethoxy)-6,7-dihydro-5H-dibenzo[a,c][7]annulen-2-yl)methanol

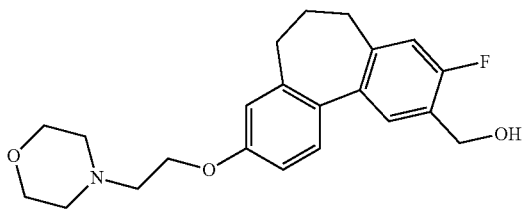 [SMILES: OCc1cc2c(cc1F)CCCc1cc(OCCN3CCOCC3)ccc1-2]

A solution of the compound obtained in <85-7> (100 mg, 0.349 mmol) in DMF (3.5 mL) was added with 4-(2-chloroethyl)morpholine.HCl (98 mg, 0.524 mmol) and Cs$_2$CO$_3$ (284 mg, 0.873 mmol) and stirred at 90° C. for 15 hours. The reaction mixture was cooled, added with a saturated NH$_4$Cl aqueous solution, and extracted with EtOAc two times. The organic layer was collected, dried over MgSO$_4$, concentrated, and purified by silica gel chromatography to obtain methyl 2-(3-fluoro-9-(2-morpholinoethoxy)-6,7-dihydro-5H-dibenzo[a,c][7]annulen-2-ylacetate (white solid, 138 mg, 98.9% yield). According to the procedures as described in <1-9>, methyl 2-(3-fluoro-9-(2-morpholinoethoxy)-6,7-dihydro-5H-dibenzo[a,c][7]annulen-2-ylacetate (138 mg, 0.345 mmol) was used to obtain the title compound (pale yellow oil, 122 mg, 95.2% yield).

$^1$H NMR (300 MHz, CDCl$_3$) δ 7.36 (d, 1H), 7.28-7.25 (m, 1H), 6.94 (d, 1H), 6.87 (dd, 1H), 6.81 (d, 1H), 4.79 (s, 2H), 4.16 (t, 2H), 3.88-3.62 (m, 4H), 2.83 (t, 2H), 2.73-2.54 (m, 4H), 2.46 (m, 4H), 2.17 (m, 2H).

<107-2> Preparation of (S)-methyl 2-(6-((3-fluoro-9-(2-morpholinoethoxy)-6,7-dihydro-5H-dibenzo[a,c][7]annulen-2-yl)methoxy)-2,3-dihydrobenzofuran-3-ylacetate

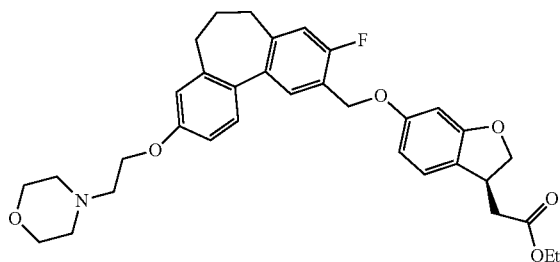 [SMILES: CCOC(=O)C[C@@H]1COc2cc(OCc3cc4c(cc3F)CCCc3cc(OCCN5CCOCC5)ccc3-4)ccc21]

According to the procedures as described in <1-10>, the compound obtained in <107-1> was used to prepare the title compound (white solid, 221 mg, 99% yield).

$^1$H NMR (300 MHz, CDCl3) δ 7.42 (d, 1H), 7.25 (d, 1H), 7.03 (d, 1H), 6.96 (d, 1H), 6.86 (dd, 1H), 6.80 (d, 1H), 6.57-6.38 (m, 2H), 5.09 (s, 2H), 4.76 (t, 1H), 4.27 (dd, 1H), 4.15 (t, 2H), 3.79-3.73 (m, 5H), 3.71 (s, 3H), 2.83 (t, 2H), 2.76 (dd, 1H), 2.63-2.41 (m, 9H), 2.22-2.09 (m, 2H).

<107-3> Preparation of (S)-2-(6-((3-fluoro-9-(2-morpholinoethoxy)-6,7-dihydro-5H-dibenzo[a,c][7]annulen-2-yl) methoxy)-2,3-dihydrobenzofuran-3-yl)acetic acid

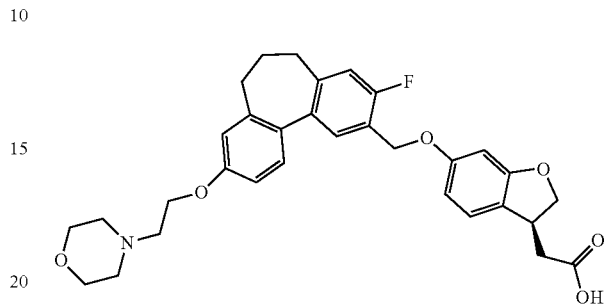

According to the procedures as described in <1-11>, the compound obtained in <107-2> was used to prepare the title compound (white solid, 132 mg, 62.1% yield).

MS m/z 594 [M−H]$^-$.

$^1$H NMR (300 MHz, CDCl$_3$) δ 7.39 (d, 1H), 7.23 (s, 1H), 7.05 (d, 1H), 6.95 (d, 1H), 6.85 (dd, 1H), 6.79 (d, 1H), 6.48 (d, 2H), 5.06 (s, 2H), 4.74 (t, 1H), 4.35-4.15 (m, 3H), 3.87-3.71 (m, 5H), 2.92 (t, 2H), 2.80-2.69 (m, 5H), 2.63-2.40 (m, 13H), 2.23-2.10 (m, 2H).

Example 108

Preparation of (S)-3-(4-((9-(3-(methylsulfonyl)propoxy)-6,7-dihydro-5H-dibenzo[a,c][7]annulen-2-yl) methoxy)phenyl)hex-4-ynoic acid <108-1> Preparation of 1-allyl-3-methoxybenzene

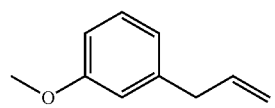

A solution of (3-methoxyphenyl)magnesium bromide (1M toluene/THF solution, 100 mL, 100.0 mmol) in THF (150 mL) at 0° C. was slowly added with allyl bromide (13.0 mL, 150.0 mmol), which was then heated to room temperature and stirred for 18 hours. The mixture was added with a saturated NH$_4$Cl aqueous solution and extracted with Et$_2$O. The organic layer was dried over sodium sulfate, filtered, and concentrated under reduced pressure. The residue thus obtained was purified by silica gel chromatography to obtain the title compound (colorless oil, 12.0 g, 81% yield).

$^1$H NMR (300 MHz, CDCl$_3$) δ 7.21 (dd, 1H), 6.78 (d, 2H), 6.74 (s, 1H), 5.97 (m, 1H), 5.12-5.05 (m, 2H), 3.80 (s, 3H), 3.38 (d, 2H)

<108-2> Preparation of methyl 3-bromo-4-(3-(3-methoxyphenyl)propyl)benzoate

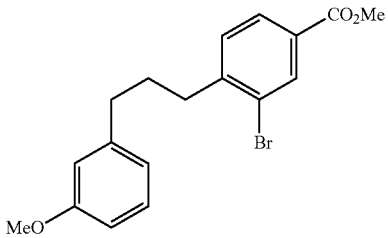 [SMILES: COC(=O)c1ccc(CCCc2cccc(OC)c2)c(Br)c1]

The compound obtained in <108-1> (6.22 g, 42.0 mmol) was dissolved in THF (42 mL), added with 9-BBN (0.5 mol THF solution, 100 mL, 50.0 mmol), stirred for 3 hours. The mixture was added with DMF (100 mL), $K_2CO_3$ (17.5 g, 126.0 mmol), methyl 3-bromo-4-iodobenzoate (15.7 g, 46.0 mmol) and $PdCl_2(dppf)$ (1.72 g, 2.1 mmol), substituted with nitrogen, and stirred at 110° C. for 18 hours. The reaction mixture was cooled to room temperature, added with a saturated $NH_4Cl$ aqueous solution, and extracted with EtOAc. The organic layer was washed with brine, dried over sodium sulfate, filtered and concentrated under reduced pressure. The residue thus obtained was purified by silica gel chromatography to obtain the title compound (colorless oil, 10.6 g, 69% yield).

$^1$H NMR (300 MHz, $CDCl_3$) δ 8.20 (s, 1H), 7.88 (d, 1H), 7.26 (d, 1H), 7.21 (m, 1H), 6.78 (d, 1H), 6.75-6.73 (m, 2H), 3.90 (s, 3H), 3.79 (s, 3H), 2.81 (t, 2H), 2.68 (t, 2H), 1.99-1.93 (m, 2H)

<108-3> Preparation of methyl 4-(3-(3-methoxyphenyl)propyl)-3-(4,4,5,5-tetramethyl-1,3,2-dioxaborolane-2-yl)benzoate

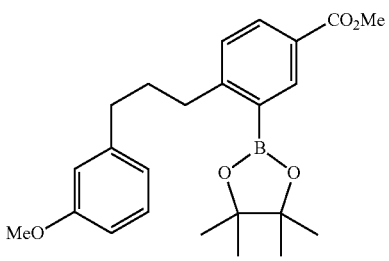 [SMILES: COC(=O)c1ccc(CCCc2cccc(OC)c2)c(B2OC(C)(C)C(C)(C)O2)c1]

The compound obtained in <108-2> (10.6 g, 29.2 mmol) was dissolved in DMF (30 mL), added with bis(pinacolato)diboron (8.9 g, 35.0 mmol), KOAc (8.6 g, 87.6 mmol) and $PdCl_2(dppf)$ (1.22 g, 1.5 mmol), and then substituted with nitrogen. After stirring at 110° C. for 16 hours, the reaction mixture was cooled to room temperature, added with a saturated $NH_4Cl$ aqueous solution, and extracted with EtOAc. The organic layer was dried over sodium sulfate, filtered and concentrated under reduced pressure. The residue thus obtained was purified by silica gel chromatography to obtain the title compound (pale green oil, 13.0 g, 100% yield).

$^1$H NMR (300 MHz, $CDCl_3$) δ 8.42 (d, 1H), 7.98 (dd, 1H), 7.23 (d, 1H), 7.22-7.16 (m, 1H), 6.78 (d, 1H), 6.74-6.72 (m, 2H), 3.90 (s, 3H), 3.79 (s, 3H), 2.98 (t, 2H), 2.65 (t, 2H), 1.93-1.83 (m, 2H), 1.34 (s, 12H).

<108-4> Preparation of methyl 4-(3-(2-bromo-5-methoxyphenyl)propyl)-3-(4,4,5,5-tetramethyl-1,3,2-dioxaborolane-2-yl)benzoate

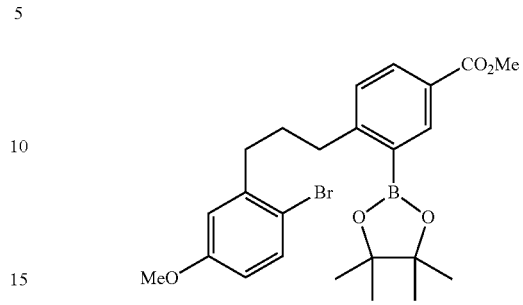

The compound obtained in <108-3> (13.0 g, 29.2 mmol) was dissolved in acetonitrile (150 mL), added with N-bromosuccinimide (5.2 g, 29.2 mmol) at 0° C., heated to room temperature, and stirred for 2 hours. The reaction mixture thus obtained was concentrated under reduced pressure, added with hexane, and filtered. The filtrate was concentrated under reduced pressure, and the residue thus obtained was purified by silica gel chromatography to obtain the title compound (pale green oil, 13.6 g, 95% yield).

$^1$H NMR (300 MHz, $CDCl_3$) δ 8.43 (d, 1H), 8.00 (dd, 1H), 7.39 (d, 1H), 7.27 (d, 1H), 6.74 (d, 1H), 6.61 (dd, 1H), 3.90 (s, 3H), 3.76 (s, 3H), 3.03 (t, 2H), 2.74 (t, 2H), 1.93-1.83 (m, 2H), 1.34 (s, 12H).

<108-5> Preparation of methyl 9-methoxy-6,7-dihydro-5H-dibenzo[a,c][7]annulene-2-carboxylate

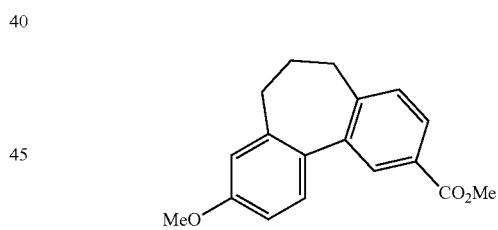

The compound obtained in <108-4> (13.6 g, 27.7 mmol) was dissolved in 1,4-dioxane (140 mL), added with $K_2CO_3$ (11.5 g, 83.2 mmol) and $PdCl_2(dppf)$ (1.1 g, 1.4 mmol), substituted with nitrogen, and stirred at 110° C. for 16 hours. The reaction mixture was cooled to room temperature, concentrated under reduced pressure, diluted with dichloromethane, filtered through Celite, and concentrated under reduced pressure. The residue thus obtained was purified by silica gel chromatography to obtain the title compound (colorless oil, 4.6 g, 58% yield).

$^1$H NMR (300 MHz, $CDCl_3$) δ 8.02 (d, 1H), 7.92 (dd, 1H), 7.35 (d, 1H), 7.29 (d, 1H), 6.89 (dd, 1H), 6.81 (d, 1H), 3.93 (s, 3H), 3.86 (s, 3H), 2.55 (t, 2H), 2.46 (t, 2H), 2.25-2.16 (m, 2H).

<108-6> Preparation of methyl 9-hydroxy-6,7-dihydro-5H-dibenzo[a,c][7]annulene-2-carboxylate

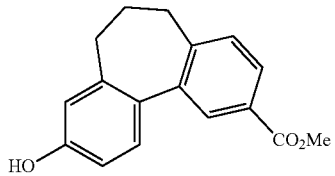 [SMILES: COC(=O)c1ccc2c(c1)-c1ccc(O)cc1CCC2]

The compound obtained in <108-5> (685 mg, 2.43 mmol) was dissolved in dichloromethane (25 mL), slowly added with BBr$_3$ (1M dichloromethane solution, 4.85 mL, 4.85 mmol) at 0° C., heated to room temperature, and stirred for 1 hour. The reaction mixture was consecutively added with methanol and water at 0° C., and then extracted with dichloromethane. The organic layer was dried over sodium sulfate, filtered, and concentrated under reduced pressure. The residue thus obtained was purified by silica gel chromatography to obtain the title compound (colorless foam, 643 mg, 99% yield).

$^1$H NMR (300 MHz, CDCl$_3$) δ 8.01 (d, 1H), 7.92 (dd, 1H), 7.29 (d, 2H), 6.83 (dd, 1H), 6.75 (d, 1H), 5.08 (s, 1H), 3.93 (s, 3H), 2.54 (t, 2H), 2.43 (t, 2H), 2.24-2.14 (m, 2H).

<108-7> Preparation of methyl 9-(3-(methylsulfonyl)propoxy)-6,7-dihydro-5H-dibenzo[a,c][7]annulene-2-carboxylate

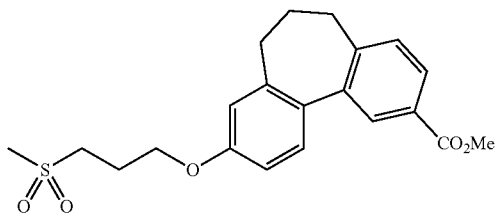 [SMILES: COC(=O)c1ccc2c(c1)-c1ccc(OCCCS(C)(=O)=O)cc1CCC2]

The compound obtained in <108-6> (100 mg, 0.37 mmol) was dissolved in DMF (4 mL), added with 3-(methylsulfonyl)propyl 4-methylbenzenesulfonate (131 mg, 0.45 mmol) and Cs$_2$CO$_3$ (182 mg, 0.56 mmol), and stirred at 50° C. for 15 hours. The reaction mixture was cooled to room temperature, diluted with EtOAc, and washed with a saturated NH$_4$Cl aqueous solution and brine. The organic layer was dried over magnesium sulfate, concentrated under reduced pressure, and the residue thus obtained was purified by silica gel chromatography to obtain the title compound (white foam, 165 mg, 99% yield).

$^1$H NMR (300 MHz, CDCl$_3$) δ 8.01 (d, 1H), 7.93 (dd, 1H), 7.35 (d, 1H), 7.30 (d, 1H), 6.87 (dd, 1H), 6.80 (d, 1H), 4.17 (t, 2H), 3.93 (s, 3H), 3.29 (t, 2H), 2.98 (s, 3H), 2.54 (t, 2H), 2.46 (t, 2H), 2.43-2.34 (m, 2H), 2.25-2.16 (m, 2H).

<108-8> Preparation of (9-(3-(methylsulfonyl)propoxy)-6,7-dihydro-5H-dibenzo[a,c][7]annulen-2-yl)methanol

The compound obtained in <108-7> (165 mg, 0.43 mmol) was dissolved in THF (4 mL) and slowly added with LiAlH$_4$ (1M THF solution, 849 μL, 0.85 mmol) at 0° C. After stirring for 2 hours, the mixture was added with a saturated NH$_4$Cl aqueous solution and filtered. The filtrate was washed with brine, and the organic layer was dried over magnesium sulfate and concentrated under reduced pressure. The residue thus obtained was purified by silica gel chromatography to obtain the title compound (white foam, 124 mg, 81% yield).

$^1$H NMR (300 MHz, CDCl$_3$) δ 7.34 (d, 1H), 7.32 (d, 1H), 7.29-7.21 (m, 2H), 6.85 (dd, 1H), 6.79 (d, 1H), 4.74 (d, 2H), 4.17 (t, 2H), 3.29 (t, 2H), 2.97 (s, 3H), 2.49 (t, 2H), 2.46 (t, 2H), 2.42-2.33 (m, 2H), 2.22-2.13 (m, 2H), 1.65 (t, 1H).

<108-9> Preparation of (S)-methyl 3-(4-((9-(3-(methylsulfonyl)propoxy)-6,7-dihydro-5H-dibenzo[a,c][7]annulen-2-yl)methoxy)phenyl)hex-4-ynoate

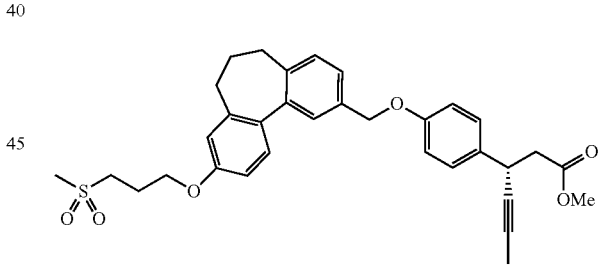

The compound obtained in <108-8> (124 mg, 0.34 mmol), (S)-methyl 3-(4-hydroxyphenyl)hex-4-ynoate (prepared in accordance with the reference [Bioorganic & Medicinal Chemistry Letters, 2012, 22, p. 1267-1270]; 75 mg, 0.34 mmol) and tributylphosphine (129 μL, 0.52 mmol) were dissolved in THF (3.5 mL), which was then added with 1,1'-(azodicarbonyl)dipiperidine) (130 mg, 0.52 mmol) and stirred at room temperature for 2 hours. The mixture was concentrated and purified by silica gel chromatography to obtain the title compound (white foam, 145 mg, 75% yield).

$^1$H NMR (300 MHz, CDCl$_3$) δ 7.39 (d, 1H), 7.32 (d, 1H), 7.31 (d, 1H), 7.28 (d, 2H), 7.24 (d, 2H), 6.94 (d, 2H), 6.85 (dd, 1H), 6.79 (d, 1H), 5.07 (s, 2H), 4.17 (t, 2H), 4.06 (m, 1H), 3.66 (s, 3H), 3.29 (t, 2H), 2.98 (s, 3H), 2.71 (m, 2H), 2.49 (m, 4H), 2.38 (m, 2H), 2.18 (m, 2H), 1.82 (d, 3H).

<108-10> Preparation of (S)-3-(4-((9-(3-(methylsulfonyl)propoxy)-6,7-dihydro-5H-dibenzo[a,c][7]annulen-2-yl)methoxy)phenyl)hex-4-ynoic acid

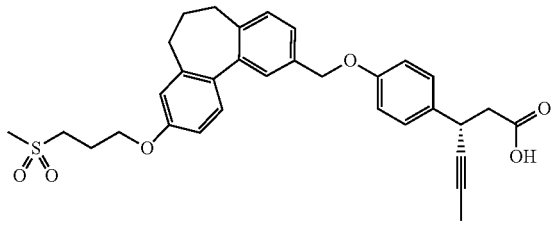 [SMILES: CC#C[C@@H](CC(=O)O)c1ccc(OCc2ccc3c(c2)-c2ccc(OCCCS(C)(=O)=O)cc2CCC3)cc1]

The compound obtained in <108-9> (142 mg, 0.25 mmol) was dissolved in methanol (2 mL) and THF (1 mL), added with 2N NaOH (380 μL, 0.76 mmol), and stirred at 75° C. for 2 hours. The mixture was cooled to room temperature, added with water, and then added with 0.5M citric acid aqueous solution so that the pH was adjusted to ~4. The mixture was extracted with dichloromethane, dried over magnesium sulfate, and the residue thus obtained was purified by silica gel chromatography to obtain the title compound (white foam, 88 mg, 64% yield).

MS m/z 545 [M−H]−.

$^1$H NMR (300 MHz, CDCl$_3$) δ 7.38 (d, 1H), 7.32 (d, 2H), 7.31 (d, 1H), 7.30 (d, 1H), 7.24 (d, 1H), 6.95 (d, 2H), 6.85 (dd, 1H), 6.79 (d, 1H), 5.07 (s, 2H), 4.17 (t, 2H), 4.06 (m, 1H), 3.29 (s, 3H), 2.97 (s, 3H), 2.76 (m, 2H), 2.49 (m, 4H), 2.38 (m, 2H), 2.19 (m, 2H), 1.84 (d, 3H).

Example 109

Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoic acid <109-1> Preparation of methyl 9-((1,1-dioxidotetrahydro-2H-thiopyran-4-yl)methoxy)-6,7-dihydro-5H-dibenzo[a,c][7]annulene-2-carboxylate

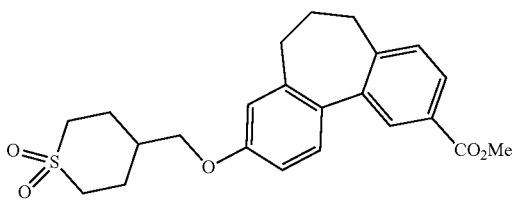 [SMILES: COC(=O)c1ccc2c(c1)-c1ccc(OCC3CCS(=O)(=O)CC3)cc1CCC2]

The compound obtained in <108-6> (100 mg, 0.37 mmol) was dissolved in DMF (4 mL), added with (1,1-dioxidotetrahydro-2H-thiopyran-4-yl)methyl 4-methylbenzenesulfonate (142 mg, 0.45 mmol) and Cs$_2$CO$_3$ (182 mg, 0.56 mmol), and then stirred at 50° C. for 2.5 hours. The reaction mixture was cooled to room temperature, diluted with EtOAc, and then washed with a saturated NH$_4$Cl aqueous solution. The organic layer was dried over magnesium sulfate, concentrated under reduced pressure, and the residue thus obtained was purified by silica gel chromatography to obtain the title compound (white foam, 148 mg, 96% yield).

$^1$H NMR (300 MHz, CDCl$_3$) δ 8.00 (d, 1H), 7.92 (dd, 1H), 7.35 (d, 1H), 7.29 (d, 1H), 6.86 (dd, 1H), 6.78 (d, 1H), 3.92 (s, 3H), 3.91 (d, 2H), 3.10 (m, 4H), 2.54 (t, 2H), 2.44 (t, 2H), 2.32 (m, 2H), 2.20 (m, 2H), 2.07 (m, 2H).

<109-2> Preparation of 4-(((10-(hydroxymethyl)-6,7-dihydro-5H-dibenzo[a,c][7]annulen-3-yl)oxy)methyl)tetrahydro-2H-thiopyran 1,1-dioxide

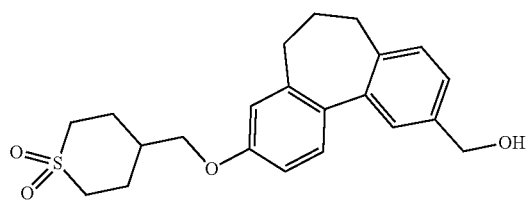 [SMILES: O=S1(=O)CCC(COc2ccc3c(c2)CCCc2ccc(CO)cc2-3)CC1]

The compound obtained in <109-1> (147 mg, 0.36 mmol) was dissolved in THF (3.5 mL) and slowly added with LiAlH$_4$ (1M THF solution, 709 μL, 0.71 mmol) at 0° C. After stirring for 1.5 hours, the mixture was added with a saturated NH$_4$Cl aqueous solution and filtered. The filtrate thus obtained was washed with brine, and the organic layer was dried over magnesium sulfate, concentrated under reduced pressure. The residue was purified by silica gel chromatography to obtain the title compound (white foam, 112 mg, 82% yield).

$^1$H NMR (300 MHz, CDCl$_3$) δ 7.34 (d, 1H), 7.32 (d, 1H), 7.27 (d, 1H), 7.23 (d, 1H), 6.84 (dd, 1H), 6.79 (d, 1H), 4.74 (d, 2H), 3.92 (d, 2H), 3.12 (m, 4H), 2.48 (m, 4H), 2.33 (m, 2H), 2.19 (m, 2H), 2.07 (m, 3H), 1.64 (t, 1H).

<109-3> Preparation of 4-(((10-(bromomethyl)-6,7-dihydro-5H-dibenzo[a,c][7]annulen-3-yl)oxy)methyl)tetrahydro-2H-thiopyran 1,1-dioxide

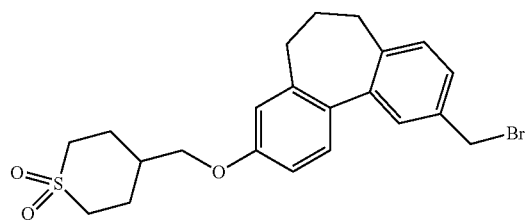 [SMILES: O=S1(=O)CCC(COc2ccc3c(c2)CCCc2ccc(CBr)cc2-3)CC1]

The compound obtained in <109-2> (680 mg, 1.76 mmol) was dissolved in dichloromethane (14 mL), which was then slowly added with DMF (68 μL, 0.88 mmol) and thionyl bromide (0.15 mL, 1.94 mmol), and stirred at room temperature for 1 hour. The reaction mixture was concentrated and purified by silica gel chromatography to obtain the title compound (white solid, 618 mg, 78% yield).

$^1$H NMR (600 MHz, CDCl$_3$) δ 7.35 (d, 1H), 7.31 (d, 1H), 7.29 (d, 1H), 7.20 (d, 1H), 6.85 (dd, 1H), 6.78 (d, 1H), 4.56 (s, 2H), 3.91 (d, 2H), 3.71-3.13 (m, 2H), 3.08-3.03 (m, 2H), 2.50-2.45 (m, 4H), 2.34-2.31 (m, 2H), 2.19-2.16 (m, 2H), 2.09-2.05 (m, 3H).

<109-4> Preparation of (S)-methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoate

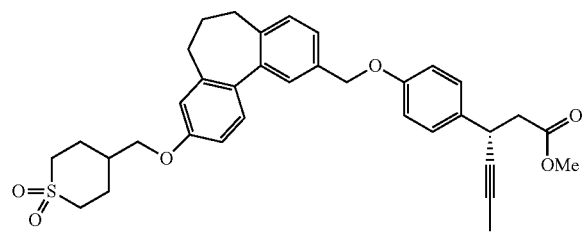

Method 1: The compound obtained in <109-2> (110 mg, 0.29 mmol), (S)-methyl 3-(4-hydroxyphenyl)hex-4-ynoate (prepared in accordance with the reference [Bioorganic & Medicinal Chemistry Letters, 2012, 22, p. 1267-1270]; 62 mg, 0.29 mmol) and tributylphosphine (106 μL, 0.43 mmol) were dissolved in THF (3.5 mL), which was then added with 1,1'-(azodicarbonyl)dipiperidine) (108 mg, 0.43 mmol) and stirred at room temperature for 2 hours. The mixture was concentrated and purified by silica gel chromatography to obtain the title compound (white foam, 103 mg, 62% yield).

Method 2: the compound obtained in <109-3> (100 mg, 0.22 mmol) and (S)-methyl 3-(4-hydroxyphenyl)hex-4-ynoate (prepared in accordance with the reference [Bioorganic & Medicinal Chemistry Letters, 2012, 22, p. 1267-1270]; 58 mg, 0.27 mmol) were dissolved in acetone (3 mL), which was then added with $Cs_2CO_3$ (87 mg, 0.27 mmol) and stirred at room temperature for 16 hours. The reaction mixture was filtered, and the filtrate thus obtained was concentrated and purified by silica gel chromatography to obtain the title compound (white foam, 120 mg, 92% yield).

$^1$H NMR (300 MHz, $CDCl_3$) δ 7.39 (d, 1H), 7.32 (d, 1H), 7.31 (d, 1H), 7.30 (d, 2H), 7.24 (d, 1H), 6.94 (d, 2H), 6.84 (dd, 1H), 6.79 (d, 1H), 5.07 (s, 2H), 4.06 (m, 1H), 3.91 (d, 2H), 3.67 (s, 3H), 3.10 (m, 4H), 2.72 (m, 2H), 2.49 (m, 4H), 2.34 (m, 2H), 2.18 (m, 2H), 2.08 (m, 3H), 1.83 (d, 3H).

<109-5> Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoic acid

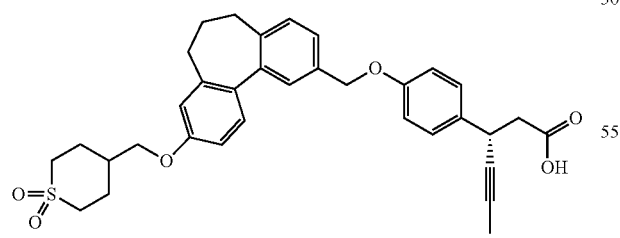

The compound obtained in <109-4> (103 mg, 0.18 mmol) was dissolved in methanol (1.5 mL) and THF (0.8 mL), which was then added with 2N NaOH (263 μL, 0.53 mmol) and stirred at 75° C. for 2 hours. The mixture was cooled to room temperature, added with water, and then further added with 0.5M citric acid aqueous solution so that the pH was adjusted to ~4. The mixture was extracted with dichloromethane, dried over magnesium sulfate, and concentrated under reduced pressure. The residue thus obtained was purified by silica gel chromatography to obtain the title compound (white foam, 73 mg, 72% yield).

MS m/z 571 [M−H]$^−$.

$^1$H NMR (300 MHz, $CDCl_3$) δ 7.39 (d, 1H), 7.32 (d, 2H), 7.31 (m, 2H), 7.24 (d, 1H), 6.96 (d, 2H), 6.84 (dd, 1H), 6.79 (d, 1H), 5.07 (s, 2H), 4.06 (m, 1H), 3.92 (d, 2H), 3.19-3.12 (m, 4H), 2.76 (m, 2H), 2.49 (m, 4H), 2.33 (m, 2H), 2.18 (m, 2H), 2.07 (m, 3H), 1.83 (d, 3H).

Example 110

Preparation of (S)-3-(4-((9-((1,1-dioxidotetrahydro-2H-thiopyran-4-yl)oxy)-6,7-dihydro-5H-dibenzo[a,c][7]annulen-2-yl)methoxy)phenyl)hex-4-ynoic acid <110-1> Preparation of 4-((10-(bromomethyl)-6,7-dihydro-5H-dibenzo[a,c][7]annulen-3-yl)oxy)tetrahydro-2H-thiopyran 1,1-dioxide

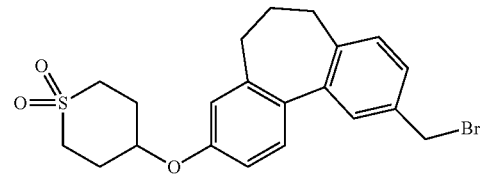 [SMILES: O=S1(=O)CCC(Oc2ccc3c(c2)CCCc2ccc(CBr)cc2-3)CC1]

The compound obtained in <64-2> (83 mg, 0.22 mmol) was dissolved in dichloromethane (2.2 mL), which was then slowly added with DMF (8.5 μL, 0.11 mmol) and thionyl bromide (18.6 μL, 0.24 mmol), and the mixture thus formed was stirred at room temperature for 2 hours. The reaction mixture was concentrated and purified by silica gel chromatography to obtain the title compound (white foam, 93 mg, 97% yield).

$^1$H NMR (300 MHz, $CDCl_3$) δ 7.36-7.29 (m, 3H), 7.20 (d, 1H), 6.89 (dd, 1H), 6.83 (d, 1H), 4.74-4.68 (m, 1H), 4.56 (s, 2H), 3.51-3.41 (m, 2H), 3.00-2.92 (m, 2H), 2.55-2.35 (m, 8H), 2.22-2.15 (m, 2H).

<110-2> Preparation of (S)-methyl 3-(4-((9-((1,1-dioxidotetrahydro-2H-thiopyran-4-yl)oxy)-6,7-dihydro-5H-dibenzo[a,c][7]annulen-2-yl)methoxy)phenyl)hex-4-ynoate

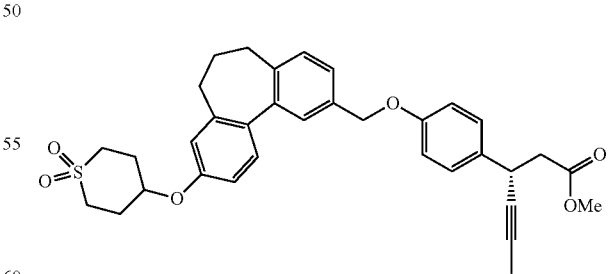

The compound obtained in <110-1> (93 mg, 0.21 mmol) and (S)-methyl 3-(4-hydroxyphenyl)hex-4-ynoate (prepared in accordance with the reference [Bioorganic & Medicinal Chemistry Letters, 2012, 22, p. 1267-1270]; 55 mg, 0.25 mmol) was dissolved in acetone (1 mL), added with $Cs_2CO_3$ (81 mg, 0.25 mmol), and the mixture thus formed was stirred at room temperature for 16 hours. The reaction mixture was filtered, and the filtrate thus obtained was purified by silica gel chromatography to obtain the title compound (white foam, 114 mg, 95% yield).

¹H NMR (300 MHz, CDCl₃) δ 7.40-7.22 (m, 6H), 6.97-6.83 (m, 4H), 5.07 (s, 2H), 4.73-4.68 (m, 1H), 4.11-4.03 (m, 1H), 3.66 (s, 3H), 3.52-3.41 (m, 2H), 2.99-2.92 (m, 2H), 2.80-2.62 (m, 2H), 2.55-2.35 (m, 7H), 2.23-2.14 (m, 2H), 1.84-1.82 (m, 3H).

<110-3> Preparation of (S)-3-(4-((9-((1,1-dioxido-tetrahydro-2H-thiopyran-4-yl)oxy)-6,7-dihydro-5H-dibenzo[a,c][7]annulen-2-yl)methoxy)phenyl)hex-4-ynoic acid

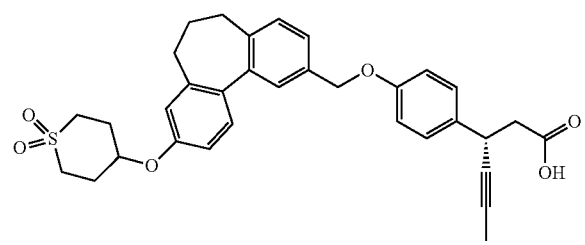 [SMILES: CC#C[C@@H](CC(=O)O)c1ccc(OCc2ccc3c(c2)-c2ccc(OC4CCS(=O)(=O)CC4)cc2CCC3)cc1]

According to the procedures as described in <1-11>, the compound obtained in <110-2> was used to prepare the title compound (white foam, 83 mg, 74% yield).

MS m/z 557 [M–H]⁻.

¹H NMR (300 MHz, CDCl₃) δ 7.39-7.23 (m, 6H), 6.97-6.83 (m, 4H), 5.07 (s, 2H), 4.73-4.68 (m, 1H), 4.11-4.03 (m, 1H), 3.52-3.40 (s, 2H), 3.00-2.92 (m, 2H), 2.85-2.67 (m, 2H), 2.58-2.32 (m, 7H), 2.23-2.14 (m, 2H), 1.84-1.82 (m, 3H).

Example 111

Preparation of (S)-3-(4-((9-(3-(ethylsulfonyl)propoxy)-6,7-dihydro-5H-dibenzo[a,c][7]annulen-2-yl)methoxy)phenyl)hex-4-ynoic acid <111-1> Preparation of (S)-methyl 3-(4-((9-(3-(ethylsulfonyl)propoxy)-6,7-dihydro-5H-dibenzo[a,c][7]annulen-2-yl)methoxy)phenyl)hex-4-ynoate

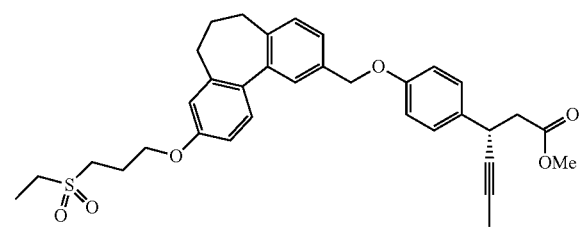

According to the procedures as described in <108-3>, the compound obtained in <66-2> was used to prepare the title compound (yellow oil, 57 mg, 66% yield).

¹H NMR (300 MHz, CDCl₃) δ 7.39 (d, 1H), 7.34-7.23 (m, 5H), 6.97-6.93 (m, 2H), 6.85 (dd, 1H), 6.79 (d, 1H), 5.07 (s, 2H), 4.17 (t, 2H), 4.10-4.04 (m, 1H), 3.67 (s, 3H), 3.25-3.20 (m, 2H), 3.10-3.02 (m, 2H), 2.81-2.62 (m, 2H), 2.52-2.46 (m, 4H), 2.42-2.33 (m, 2H), 2.22-2.16 (m, 2H), 1.83 (d, 3H), 1.45 (t, 3H).

<111-2> Preparation of (S)-3-(4-((9-(3-(ethylsulfonyl)propoxy)-6,7-dihydro-5H-dibenzo[a,c][7]annulen-2-yl)methoxy)phenyl)hex-4-ynoic acid

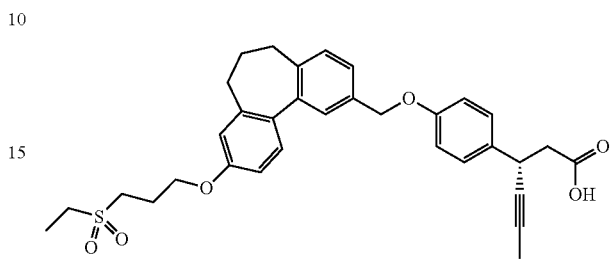

According to the procedures as described in <1-11>, the compound obtained in <111-1> was used to prepare the title compound (white foam, 33 mg, 58% yield).

MS m/z 559 [M–H]⁻.

¹H NMR (300 MHz, CDCl₃) δ 7.39 (d, 1H), 7.34-7.23 (m, 5H), 6.98-6.93 (m, 2H), 6.85 (dd, 1H), 6.79 (d, 1H), 5.07 (s, 2H), 4.17 (t, 2H), 4.10-4.04 (m, 1H), 3.25-3.20 (m, 2H), 3.09-3.02 (m, 2H), 2.85-2.67 (m, 2H), 2.52-2.46 (m, 4H), 2.42-2.33 (m, 2H), 2.22-2.16 (m, 2H), 1.83 (d, 3H), 1.45 (t, 3H).

Example 112

Preparation of (S)-3-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)hex-4-ynoic acid <112-1> Preparation of (S)-methyl 3-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)hex-4-ynoate

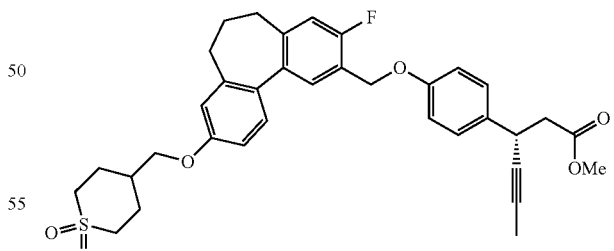

According to the procedures as described in <108-3>, the compound obtained in <85-9> was used to prepare the title compound (yellow oil, 112.8 mg, 64% yield).

¹H NMR (300 MHz, CDCl₃) δ 7.44-7.24 (m, 4H), 6.99-6.77 (m, 5H), 5.13 (s, 2H), 4.10-4.04 (m, 1H), 3.91 (m, 2H), 3.67 (m, 3H), 3.18-3.00 (m, 4H), 2.80-2.62 (m, 2H), 2.50-2.43 (m, 4H), 2.36-2.28 (m, 2H), 2.20-2.14 (m, 2H), 2.10-2.05 (m, 3H), 1.82 (m, 3H).

<112-2> Preparation of (S)-3-(4-((9-((1,1-dioxido-tetrahydro-2H-thiopyran-4-yl)methoxy)-3-fluoro-6,7-dihydro-5H-dibenzo[a,c][7]annulen-2-yl)methoxy)phenyl)hex-4-ynoic acid

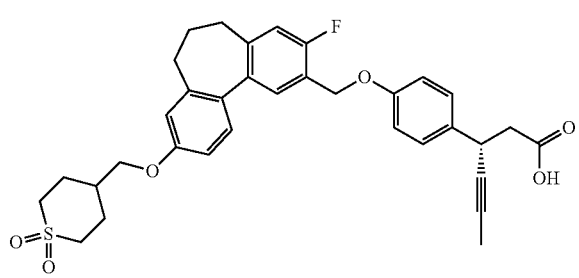 [SMILES: CC#C[C@@H](CC(=O)O)c1ccc(OCc2cc3c(cc2F)CCCc2cc(OCC4CCS(=O)(=O)CC4)ccc2-3)cc1]

According to the procedures as described in <1-11>, the compound obtained in <112-1> was used to prepare the title compound (white foam, 55 mg, 49% yield).

MS m/z 589 [M-H]⁻.

¹H NMR (300 MHz, CDCl₃) δ 7.44-7.24 (m, 4H), 6.99-6.94 (m, 3H), 6.85-6.77 (m, 2H), 5.13 (s, 2H), 4.10-4.04 (m, 1H), 3.90 (m, 2H), 3.18-3.00 (m, 4H), 2.85-2.65 (m, 2H), 2.50-2.43 (m, 4H), 2.33-2.27 (m, 2H), 2.20-2.13 (m, 2H), 2.10-2.04 (m, 3H), 1.83 (m, 3H).

Example 113

Preparation of (S)-3-(4-((9-((1,1-dioxidotetrahydro-2H-thiopyran-4-yl)methoxy)-6,7-dihydrodibenzo[b,d]oxepin-2-yl)methoxy)phenyl)hex-4-ynoic acid <113-1> Preparation of methyl 9-((1,1-dioxidotetrahydro-2H-thiopyran-4-yl)methoxy)-6,7-dihydrodibenzo[b,d]oxepin-2-carboxylate

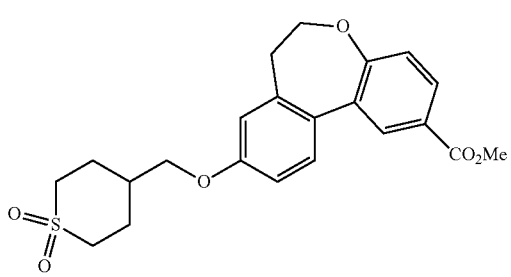 [SMILES: COC(=O)c1ccc2c(c1)-c1ccc(OCC3CCS(=O)(=O)CC3)cc1CCO2]

According to the procedures as described in <47-1>, the compound obtained in <2-11> was used to prepare the title compound (white foam, 155 mg, 100% yield).

¹H NMR (600 MHz, CDCl₃) δ 8.08 (d, 1H), 7.97 (dd, 1H), 7.43 (d, 1H), 7.15 (d, 1H), 6.91 (dd, 1H), 6.81 (d, 1H), 4.61 (t, 2H), 3.94-3.90 (m, 5H), 3.17-3.14 (m, 2H), 3.08-3.03 (m, 2H), 2.80 (t, 2H), 2.34-2.30 (m, 2H), 2.10-2.05 (m, 3H).

<113-2> Preparation of 4-(((2-(hydroxymethyl)-6,7-dihydrodibenzo[b,d]oxepin-9-yl)oxy)methyl)tetrahydro-2H-thiopyran 1,1-dioxide

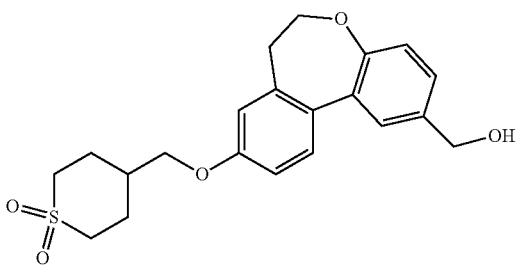 [SMILES: O=S1(=O)CCC(COc2ccc3c(c2)CCOc2ccc(CO)cc2-3)CC1]

According to the procedures as described in <1-9>, the compound obtained in <113-1> was used to prepare the title compound (white solid, 122 mg, 85% yield).

¹H NMR (600 MHz, CDCl₃) δ 7.40-7.38 (m, 2H), 7.29 (dd, 1H), 7.10 (d, 1H), 6.90 (dd, 1H), 6.84 (d, 1H), 4.68 (s, 2H), 4.55 (t, 2H), 3.93 (d, 2H), 3.19-3.14 (m, 2H), 3.12-3.07 (m, 2H), 2.77 (t, 2H), 2.35-2.31 (m, 2H), 2.11-2.03 (m, 3H).

<113-3> Preparation of (S)-methyl 3-(4-((9-((1,1-dioxidotetrahydro-2H-thiopyran-4-yl)methoxy)-6,7-dihydrodibenzo[b,d]oxepin-2-yl)methoxy)phenyl)hex-4-ynoate

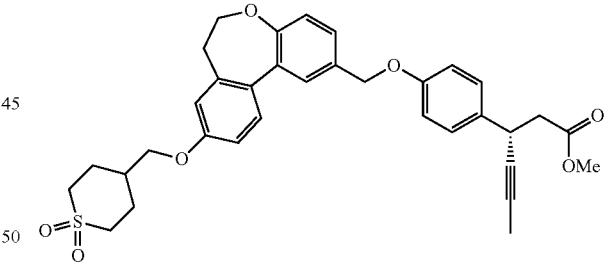

According to the procedures as described in <108-3>, the compound obtained in <113-2> was used to prepare the title compound (white foam, 125 mg, 70% yield).

¹H NMR (600 MHz, CDCl₃) δ 7.42 (d, 1H), 7.35 (d, 1H), 7.34 (dd, 1H), 7.29-7.27 (m, 2H), 7.12 (d, 1H), 6.94-6.92 (m, 2H), 6.88 (dd, 1H), 6.82 (d, 1H), 5.04 (s, 2H), 4.55 (t, 2H), 4.06-4.04 (m, 1H), 3.91 (d, 2H), 3.65 (s, 3H), 3.16-3.12 (m, 2H), 3.06-3.02 (m, 2H), 2.79-2.73 (m, 3H), 2.67-2.63 (m, 1H), 2.31-2.29 (m, 2H), 2.08-2.03 (m, 3H), 1.81 (d, 3H).

<113-4> Preparation of (S)-3-(4-((9-((1,1-dioxido-tetrahydro-2H-thiopyran-4-yl)methoxy)-6,7-dihydrodibenzo[b,d]oxepin-2-yl)methoxy)phenyl)hex-4-ynoic acid

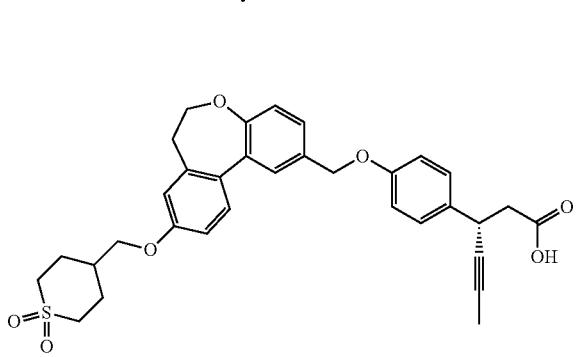

According to the procedures as described in <1-11>, the compound obtained in <113-3> was used to prepare the title compound (white foam, 104 mg, 88% yield).

MS m/z 573 [M−H]⁻.

¹H NMR (600 MHz, CDCl₃) δ 7.41 (d, 1H), 7.36 (d, 1H), 7.33 (dd, 1H), 7.31-7.29 (m, 2H), 7.12 (d, 1H), 6.95-6.92 (m, 2H), 6.88 (dd, 1H), 6.82 (d, 1H), 5.04 (s, 2H), 4.55 (t, 2H), 4.06-4.03 (m, 1H), 3.91 (d, 2H), 3.65 (s, 3H), 3.16-3.12 (m, 2H), 3.06-3.01 (m, 2H), 2.81-2.76 (m, 3H), 2.72-2.68 (m, 1H), 2.32-2.28 (m, 2H), 2.09-2.01 (m, 3H), 1.81 (d, 3H).

Example 114

Preparation of (S)-3-(4-((3-((1,1-dioxidotetrahydro-2H-thiopyran-4-yl)methoxy)-6,7-dihydro-5H-benzo[3,4]cyclohepta[1,2-b]pyridin-10-yl)methoxy)phenyl)hex-4-ynoic acid <114-1> Preparation of 2-allyl-6-methoxypyridine

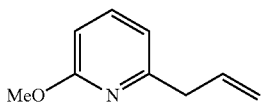

A mixture of 2-bromo-6-methoxypyridine (2 mL, 16.488 mmol), 2-allyl-4,4,5,5-tetramethyl-1,3,2-dioxaborolane (3.4 mL, 18.136 mmol), CsF (7.51 g, 49.463 mmol) and THF (60 mL) was substituted with nitrogen for a few minutes while stirring. The mixture was added with Pd(PPh₃)₄ (1.91 g, 1.649 mmol) and refluxed for 20 hours. After cooled to room temperature, the reaction mixture was added with distilled water and extracted with EtOAc. The organic layer was collected, dried over MgSO₄, concentrated, and purified by silica gel chromatography to obtain the title compound (colorless oil, 1.838 g, 75% yield).

¹H NMR (300 MHz, CDCl₃) δ 7.48 (t, 1H), 6.73 (d, 1H), 6.56 (d, 1H), 6.08 (m, 1H), 5.21-5.03 (m, 2H), 3.92 (s, 3H), 3.47 (d, 2H).

<114-2> Preparation of methyl 3-bromo-4-(3-(6-methoxypyridin-2-yl)propyl)benzoate

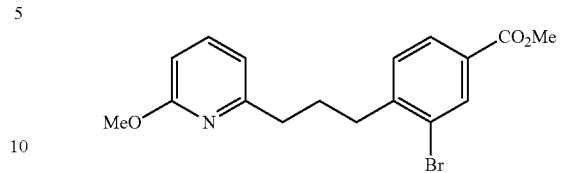

<108-2>, the compound obtained in <114-1> was used to prepare the title compound (colorless oil, 2.368 g, 53% yield).

¹H NMR (300 MHz, CDCl₃) δ 8.20 (d, 1H), 7.88 (dd, 1H), 7.47 (dd, 1H), 7.31 (d, 1H), 6.72 (dd, 1H), 6.56 (d, 1H), 3.92 (s, 3H), 3.91 (s, 3H), 2.90-2.81 (m, 2H), 2.77 (t, 2H), 2.15-2.02 (m, 2H).

<114-3> Preparation of methyl 4-(3-(6-methoxypyridin-2-yl)propyl)-3-(4,4,5,5-tetramethyl-1,3,2-dioxaboran-2-yl)benzoate

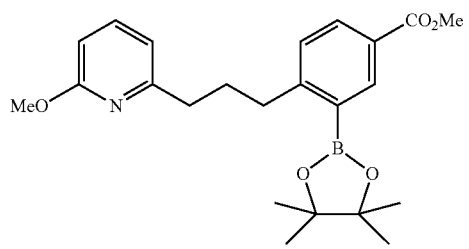 [SMILES: COC(=O)c1ccc(CCCc2cccc(OC)n2)c(B2OC(C)(C)C(C)(C)O2)c1]

According to the procedures as described in <108-3>, the compound obtained in <114-2> was used to prepare the title compound (white solid, 1.671 g, 63% yield).

¹H NMR (300 MHz, CDCl₃) δ 8.42 (d, 1H), 7.99 (dd, 1H), 7.44 (t, 1H), 7.40 (m, 1H), 7.27 (d, 1H), 6.69 (d, 1H), 6.53 (d, 1H), 3.91 (s, 1H), 3.90 (s, 3H), 3.06-2.96 (m, 2H), 2.80-2.66 (m, 2H), 1.99 (m, 2H), 1.34 (s, 12H).

<114-4> Preparation of methyl 4-(3-(3-bromo-6-methoxypyridin-2-yl)propyl)-3-(4,4,5,5-tetramethyl-1,3,2-dioxaboran-2-yl)benzoate

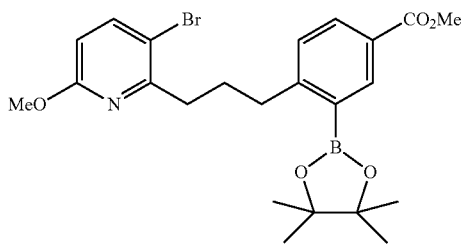 [SMILES: COC(=O)c1ccc(CCCc2nc(OC)ccc2Br)c(B2OC(C)(C)C(C)(C)O2)c1]

A solution of the compound obtained in <114-3> (1.44 g, 3.501 mmol) in THF (35 mL) 0° C. was added with 1,3-dibromo-5,5-dimethylhydantoin (1.00 g, 3.501 mmol), heated to room temperature, and stirred for 63 hours. The reaction mixture was added with a saturated Na₂S₂O₃ aqueous solution and distilled water, and then extracted with EtOAc. The organic layer was collected, dried over Na₂SO₄, concentrated, and purified by silica gel chromatography to obtain the title compound (colorless oil, 1.838 g, 75% yield).

¹H NMR (300 MHz, CDCl₃) δ 8.43 (d, 1H), 8.00 (dd, 1H), 7.60 (d, 1H), 7.29 (d, 1H), 6.45 (d, 1H), 3.90 (s, 3H), 3.88 (s, 3H), 3.10-2.99 (m, 2H), 2.96-2.83 (m, 2H), 2.00 (m, 2H), 1.34 (s, 12H).

<114-5> Preparation of methyl 3-methoxy-6,7-dihydro-5H-benzo[3,4]cyclohepta[1,2-b]pyridine-10-carboxylate

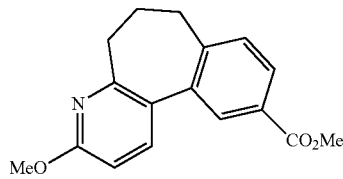 [SMILES: COC(=O)c1ccc2c(c1)-c1ccc(OC)nc1CCC2]

According to the procedures as described in <108-5>, the compound obtained in <114-4> was used to prepare the title compound (white solid, 416 mg, 64% yield).

¹H NMR (300 MHz, CDCl₃) δ 7.98 (d, 1H), 7.94 (dd, 1H), 7.63 (d, 1H), 7.33 (d, 1H), 6.74 (d, 1H), 3.99 (s, 3H), 3.93 (s, 3H), 2.61 (m, 4H), 2.43-2.27 (m, 2H).

<114-6> Preparation of methyl 3-hydroxy-6,7-dihydro-5H-benzo[3,4]cyclohepta[1,2-b]pyridine-10-carboxylate

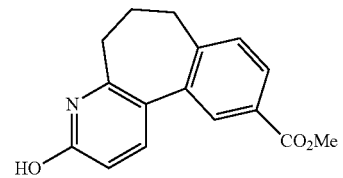 [SMILES: COC(=O)c1ccc2c(c1)-c1ccc(O)nc1CCC2]

According to the procedures as described in <108-6>, the compound obtained in <114-5> was used to prepare the title compound (off-white solid, 278 mg, 59% yield).

¹H NMR (300 MHz, CDCl₃) δ 7.95 (d, 1H), 7.92 (dd, 1H), 7.63 (d, 1H), 7.33 (d, 1H), 6.60 (d, 1H), 3.93 (s, 3H), 2.64 (t, 2H), 2.61 (t, 2H), 2.41 (m, 2H).

<114-7> methyl 3-((1,1-dioxidotetrahydro-2H-thiopyran-4-yl)methoxy)-6,7-dihydro-5H-benzo[3,4]cyclohepta[1,2-b]pyridine-10-carboxylate

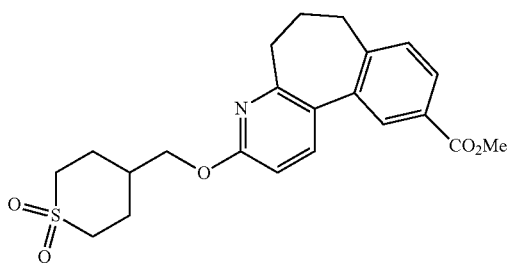 [SMILES: COC(=O)c1ccc2c(c1)-c1ccc(OCC3CCS(=O)(=O)CC3)nc1CCC2]

According to the procedures as described in <47-1>, the compound obtained in <114-6> was used to prepare the title compound (colorless oil, 119 mg, 74% yield).

¹H NMR (300 MHz, CDCl₃) δ 7.98-7.91 (m, 2H), 7.64 (d, 1H), 7.34 (d, 1H), 6.72 (d, 1H), 4.29 (d, 2H), 3.93 (s, 3H), 3.20-2.97 (m, 4H), 2.60 (m, 4H), 2.33 (m, 2H), 2.06 (m, 3H).

<114-8> Preparation of 4-(((10-(hydroxymethyl)-6,7-dihydro-5H-benzo[3,4]cyclohepta[1,2-b]pyridin-3-yl)oxy)methyl)tetrahydro-2H-thiopyran 1,1-dioxide

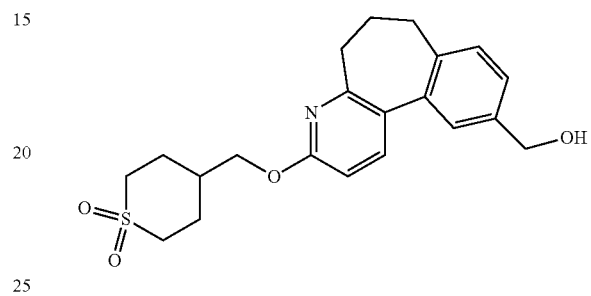

According to the procedures as described in <1-9>, the compound obtained in <114-7> was used to prepare the title compound (white foam, 87 mg, 83% yield).

¹H NMR (300 MHz, CDCl₃) δ 7.61 (d, 1H), 7.33-7.22 (m, 3H), 6.70 (d, 1H), 4.75 (d, 2H), 4.28 (d, 2H), 3.19-2.97 (m, 4H), 2.62 (t, 2H), 2.53 (t, 2H), 2.37-2.23 (m, 4H), 2.14-1.98 (m, 3H), 1.66 (t, 1H).

<114-9> Preparation of (S)-methyl 3-(4-((3-((1,1-dioxidotetrahydro-2H-thiopyran-4-yl)methoxy)-6,7-dihydro-5H-benzo[3,4]cyclohepta[1,2-b]pyridin-10-yl)methoxy)phenyl)hex-4-ynoate

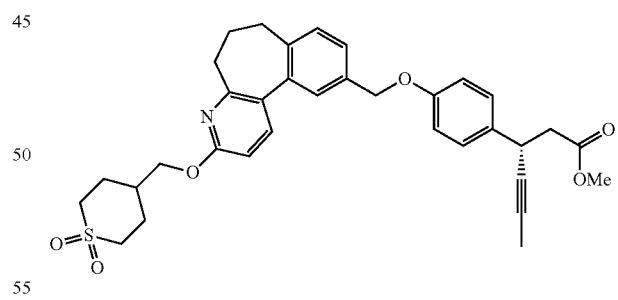

According to the procedures as described in <108-9>, the compound obtained in <114-8> was used to prepare the title compound (white foam, 72 mg, 55% yield).

¹H NMR (300 MHz, CDCl₃) δ 7.60 (d, 1H), 7.39-7.23 (m, 7H), 6.98-6.88 (m, 2H), 6.70 (d, 1H), 5.07 (s, 2H), 4.28 (d, 2H), 4.09 (m, 1H), 3.66 (s, 3H), 3.20-2.95 (m, 4H), 2.73 (m, 2H), 2.63 (t, 2H), 2.54 (t, 2H), 2.30 (m, 4H), 2.06 (m, 3H), 1.83 (d, 3H).

<114-10> Preparation of (S)-3-(4-((3-((1,1-dioxido-tetrahydro-2H-thiopyran-4-yl)methoxy)-6,7-dihydro-5H-benzo[3,4]cyclohepta[1,2-b]pyridin-10-yl)methoxy)phenyl)hex-4-ynoic acid

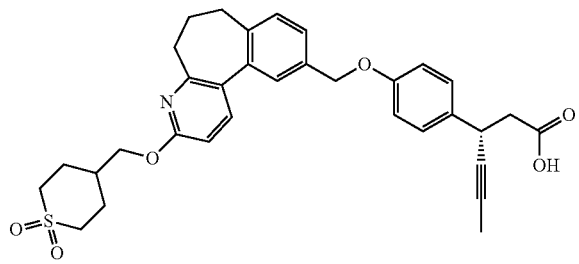 [SMILES: CC#C[C@@H](CC(=O)O)c1ccc(OCc2ccc3c(c2)-c2ccc(OCC4CCS(=O)(=O)CC4)nc2CCC3)cc1]

According to the procedures as described in <1-11>, the compound obtained in <114-9> was used to prepare the title compound (white foam, 78 mg, 85% yield).

MS m/z 572 [M–H]⁻.

$^1$H NMR (300 MHz, CDCl$_3$) δ 7.60 (d, 1H), 7.37-7.20 (m, 7H), 6.98-6.88 (m, 2H), 6.70 (d, 1H), 5.07 (s, 2H), 4.28 (d, 2H), 4.06 (m, 1H), 3.20-1.95 (m, 4H), 2.76 (m, 2H), 2.63 (t, 2H), 2.54 (t, 2H), 2.30 (m, 4H), 2.07 (m, 3H), 1.83 (d, 3H).

Example 115

Preparation of (R)-3-cyclopropyl-3-(3-((9-((1,1-dioxidotetrahydro-2H-thiopyran-4-yl)methoxy)-6,7-dihydro-5H-dibenzo[a,c][7]annulen-2-yl)methoxy)phenyl)propanoic acid <115-1> Preparation of (R)-methyl 3-cyclopropyl-3-(3-((9-((1,1-dioxidotetrahydro-2H-thiopyran-4-yl)methoxy)-6,7-dihydro-5H-dibenzo[a,c][7]annulen-2-yl)methoxy)phenyl)propanoate

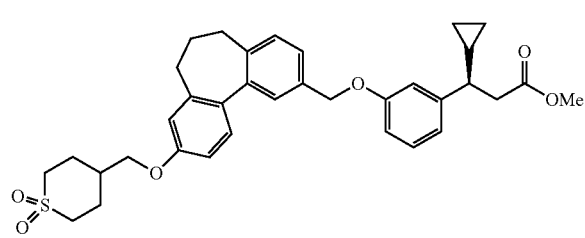 [SMILES: COC(=O)C[C@@H](c1cccc(OCc2ccc3c(c2)-c2ccc(OCC4CCS(=O)(=O)CC4)cc2CCC3)c1)C1CC1]

According to the procedures as described in <110-2>, the compound obtained in <109-3> and (R)-methyl 3-cyclopropyl-3-(3-hydroxyphenyl)propanoate (prepared in accordance with the reference [ACS Medicinal Chemistry Letters, 2012, vol. 3, p. 726-730]) were used to prepare the title compound (white foam, 98.5 mg, 93% yield).

$^1$H NMR (300 MHz, CDCl$_3$) δ 7.41 (s, 1H), 7.41 (s, 1H), 7.36-7.29 (m, 2H), 7.27-7.19 (m, 2H), 6.90-6.75 (m, 5H), 5.07 (s, 2H), 3.92 (d, 2H), 3.60 (s, 3H), 3.21-2.96 (m, 4H), 2.73 (dd, 2H), 2.49 (m, 4H), 2.41-2.25 (m, 3H), 2.25-2.13 (m, 2H), 2.12-1.96 (m, 3H), 1.01 (m, 1H), 0.56 (m, 1H), 0.40 (m, 1H), 0.25 (m, 1H), 0.14 (m, 1H).

<115-2> Preparation of (R)-3-cyclopropyl-3-(3-((9-((1,1-dioxidotetrahydro-2H-thiopyran-4-yl)methoxy)-6,7-dihydro-5H-dibenzo[a,c][7]annulen-2-yl)methoxy)phenyl)propanoic acid

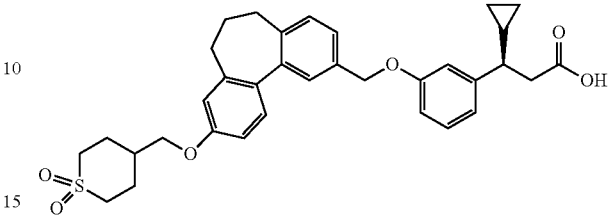

According to the procedures as described in <1-11>, the compound obtained in <115-1> was used to prepare the title compound (white foam, 74.7 mg, 76% yield).

MS m/z 573 [M–H]⁻.

$^1$H NMR (300 MHz, CDCl$_3$) δ 7.41 (s, 1H), 7.37-7.28 (m, 2H), 7.28-7.20 (m, 2H), 6.92-6.81 (m, 4H), 6.79 (s, 1H), 5.07 (s, 2H), 3.91 (s, 2H), 3.23-2.92 (m, 4H), 2.78 (d, 2H), 2.49 (m, 4H), 2.41-2.24 (m, 3H), 2.24-2.12 (m, 2H), 2.12-1.97 (m, 3H), 1.00 (m, 1H), 0.58 (m, 1H), 0.41 (m, 1H), 0.28 (m, 1H), 0.16 (m, 1H).

Example 116

Preparation of 3-cyclopropyl-3-(4-((9-((1,1-dioxido-tetrahydro-2H-thiopyran-4-yl)methoxy)-6,7-dihydro-5H-dibenzo[a,c][7]annulen-2-yl)methoxy)phenyl)propanoic acid <116-1> Preparation of methyl 3-cyclopropyl-3-(4-((9-((1,1-dioxidotetrahydro-2H-thiopyran-4-yl)methoxy)-6,7-dihydro-5H-dibenzo[a,c][7]annulen-2-yl)methoxy)phenyl)propanoate

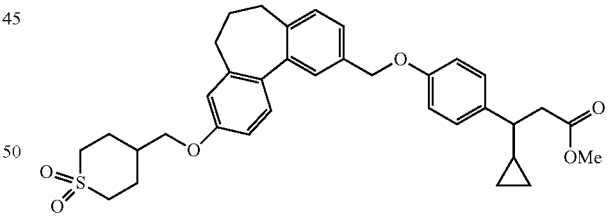

According to the procedures as described in <110-2>, the compound obtained in <109-3> and methyl 3-cyclopropyl-3-(4-hydroxyphenyl)propanoate (prepared in accordance with the reference [WO 2008/130514 A1]) were used to prepare the title compound (white foam, 98.5 mg, 93% yield).

$^1$H NMR (300 MHz, CDCl$_3$) δ 7.39 (d, 1H), 7.35-7.29 (m, 2H), 7.25 (d, 1H), 7.16 (d, 2H), 6.94 (d, 2H), 6.85 (dd, 1H), 6.79 (d, 1H), 5.06 (s, 2H), 3.92 (d, 2H), 3.59 (s, 3H), 3.23-2.95 (m, 4H), 2.82-2.62 (m, 2H), 2.56-2.40 (m, 4H), 2.38-2.26 (m, 3H), 2.25-2.12 (m, 2H), 2.13-1.98 (m, 3H), 0.99 (m, 1H), 0.57 (m, 1H), 0.42 (m, 1H), 0.31-0.19 (m, 1H), 0.19-0.06 (m, 1H).

<116-2> Preparation of 3-cyclopropyl-3-(4-((9-((1,1-dioxidotetrahydro-2H-thiopyran-4-yl)methoxy)-6,7-dihydro-5H-dibenzo[a,c][7]annulen-2-yl)methoxy)phenyl)propanoic acid

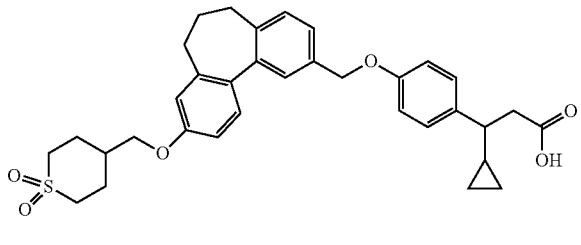 [SMILES: COC(=O)CC(c1ccc(OCc2ccc3c(c2)-c2ccc(OCC4CCS(=O)(=O)CC4)cc2CCC3)cc1)C1CC1]

According to the procedures as described in <1-11>, the compound obtained in <116-1> was used to prepare the title compound (white foam, 74.7 mg, 76% yield).

MS m/z 573 [M–H]⁻.

¹H NMR (300 MHz, CDCl₃) δ 7.39 (s, 1H), 7.35-7.28 (m, 2H), 7.24 (d, 1H), 7.16 (d, 2H), 6.94 (d, 2H), 6.84 (dd, 1H), 6.79 (d, 1H), 5.06 (s, 2H), 3.91 (d, 2H), 3.22-2.94 (m, 4H), 2.76 (m, 2H), 2.49 (m, 4H), 2.41-2.25 (m, 3H), 2.19 (m, 2H), 2.12-1.97 (m, 3H), 1.03 (m, 1H), 0.88 (m, 1H), 0.58 (m, 1H), 0.42 (m, 1H), 0.26 (m, 1H), 0.16 (m, 1H).

Example 117

Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hexanoic acid

<117-1> Preparation of (S)-methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)hexanoate

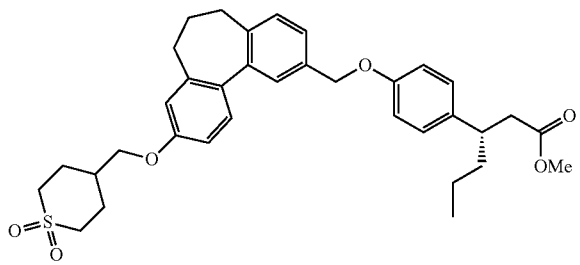 [SMILES: CCC[C@@H](CC(=O)O)c1ccc(OCc2ccc3c(c2)-c2ccc(OCC4CCS(=O)(=O)CC4)cc2CCC3)cc1]

According to the procedures as described in <110-2>, the compound obtained in <109-3> and (S)-methyl 3-(4-hydroxyphenyl)hexanoate (prepared in accordance with the reference [WO2008/130514 A1]) were used to prepare the title compound (colorless oil, 41 mg, 48% yield).

¹H NMR (300 MHz, CDCl₃) δ 7.39 (d, 1H), 7.36-7.20 (m, 3H), 7.10 (m, 2H), 6.97-6.89 (m, 2H), 6.84 (dd, 1H), 6.79 (d, 1H), 5.05 (s, 2H), 3.91 (d, 2H), 3.58 (s, 3H), 3.22-2.97 (m, 5H), 2.63-2.42 (m, 6H), 2.31 (m, 2H), 2.18 (m, 2H), 2.13-2.00 (m, 3H), 1.62-1.47 (m, 2H), 1.22-1.12 (m, 2H), 0.85 (t, 3H).

<117-2> Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hexanoic acid

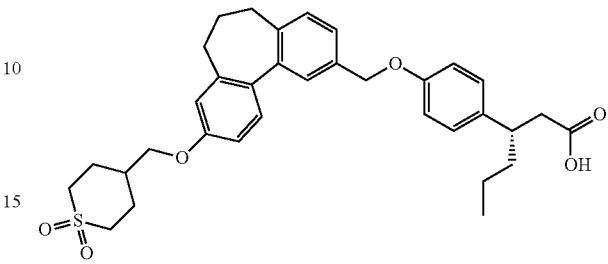

According to the procedures as described in <1-11>, the compound obtained in <117-1> was used to prepare the title compound (white foam, 27 mg, 71% yield).

MS m/z 575 [M–H]⁻.

¹H NMR (300 MHz, CDCl₃) δ 7.38 (s, 1H), 7.35-7.28 (m, 2H), 7.24 (d, 2H), 7.11 (d, 2H), 6.93 (d, 2H), 6.83 (dd, 1H), 6.79 (d, 1H), 5.05 (s, 2H), 3.91 (d, 2H), 3.21-2.96 (m, 5H), 2.60 (t, 2H), 2.49 (m, 4H), 2.30 (m, 2H), 2.18 (m, 2H), 2.12-1.96 (m, 3H), 1.59 (m, 2H), 1.18 (m, 2H), 0.85 (t, 3H).

Example 118

Preparation of (R,Z)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-enoic acid

<118-1> Preparation of (R,Z)-methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-enoate

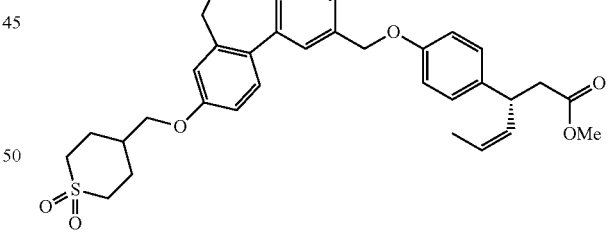

A solution of the compound <109-4> (173 mg, 0.295 mmol) in EtOAc (3 mL) was added with Pd/C (10 wt % loading dry basis, 21 mg), which was then stirred under a hydrogen atmosphere for 6 hours. The reaction mixture was filtered through Celite, washed EtOAc, concentrated, and then purified by silica gel chromatography to obtain the title compound (white foam, 57 mg, 29% yield).

¹H NMR (300 MHz, CDCl₃) δ 7.38 (d, 1H), 7.35-7.27 (m, 2H), 7.24 (d, 1H), 7.19-7.09 (m, 2H), 6.98-6.87 (m, 2H), 6.84 (dd, 1H), 6.79 (d, 1H), 5.58-5.45 (m, 2H), 5.05 (s, 2H), 4.21-4.05 (m, 1H), 3.92 (d, 2H), 3.62 (s, 3H), 3.12 (m, 4H), 2.77-2.55 (m, 2H), 2.49 (m, 4H), 2.32 (m, 2H), 2.18 (m, 2H), 2.06 (m, 3H), 1.69 (d, 3H).

<118-2> Preparation of (R,Z)-3-(4-((9-((1,1-dioxi-dotetrahydro-2H-thiopyran-4-yl)methoxy)-6,7-dihydro-5H-dibenzo[a,c][7]annulen-2-yl)methoxy)phenyl)hex-4-enoic acid

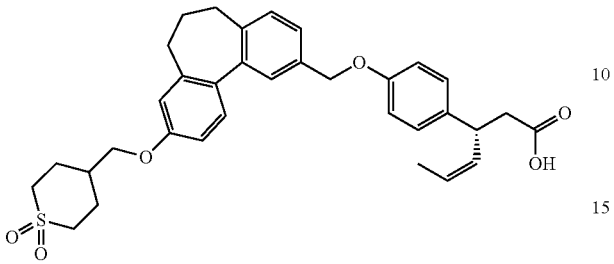

According to the procedures as described in <1-11>, the compound obtained in <118-1> was used to prepare the title compound (white foam, 45 mg, 84% yield).

MS m/z 573 [M−H]⁻.

¹H NMR (300 MHz, CDCl3) δ 7.38 (d, 1H), 7.35-7.27 (m, 2H), 7.24 (d, 1H), 7.20-7.10 (m, 2H), 6.97-6.88 (m, 2H), 6.84 (dd, 1H), 6.79 (d, 1H), 5.61-5.44 (m, 2H), 5.05 (s, 2H), 4.20-4.07 (m, 1H), 3.91 (d, 2H), 3.12 (m, 4H), 2.80-2.58 (m, 2H), 2.49 (m, 4H), 2.30 (m, 2H), 2.18 (m, 2H), 2.06 (m, 3H), 1.69 (d, 3H).

Example 119

Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(5-methylisoxazol-3-yl)propanoic acid <119-1> Preparation of (S)-methyl 3-(4-(benzyloxy)phenyl)hex-4-ynoate

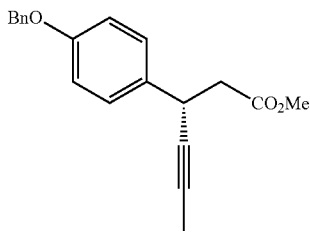

A mixture of (S)-methyl 3-(4-hydroxyphenyl)hex-4-ynoate (prepared in accordance with the reference [Bioorganic & Medicinal Chemistry Letters, 2012, 22, p. 1267-1270]; 1.06 g, 4.857 mmol) and Cs₂CO₃ (1.90 g, 5.828 mmol) in acetone (25 mL) was added with benzyl bromide (0.64 mL, 5.342 mmol), and stirred at room temperature for 17.5 hours. The reaction mixture was filtered and washed with acetone. The filtrate thus obtained was concentrated under reduced pressure, added with EtOAc (50 mL) and piperazine (1.26 g, 14.570 mmol), and then stirred at room temperature for 2 hours. The solid thus obtained was filtered, consecutively washed with EtOAc, 1M HCl aqueous solution, a saturated NaHCO₃ aqueous solution and brine, dried over MgSO₄, and then concentrated. The residue was purified by silica gel chromatography to obtain the title compound (yellow solid, 1.38 g, 92% yield).

¹H NMR (300 MHz, CDCl₃) δ 7.46-7.26 (m, 7H), 6.96-6.87 (m, 2H), 5.04 (s, 2H), 4.06 (m, 1H), 3.66 (s, 3H), 2.85-2.59 (m, 2H), 1.82 (d, 3H).

<119-2> Preparation of (R,Z)-methyl 3-(4-(benzyloxy)phenyl)hex-4-enoate

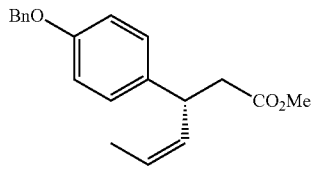 [SMILES: C/C=C\[C@@H](CC(=O)OC)c1ccc(OCc2ccccc2)cc1]

According to the procedures as described in <118-1>, the compound obtained in <119-1> was used to prepare the title compound (white solid, 1.40 g, 94% yield).

¹H NMR (300 MHz, CDCl₃) δ 7.46-7.28 (m, 5H), 7.18-7.12 (m, 2H), 6.95-6.85 (m, 2H), 5.57-5.44 (m, 2H), 5.03 (s, 2H), 4.19-4.08 (m, 1H), 3.62 (s, 3H), 3.58 (s, 3H), 2.77-2.55 (m, 2H), 1.69 (d, 3H).

<119-3> Preparation of (S)-methyl 3-(4-(benzyloxy)phenyl)-4-oxobutanoate

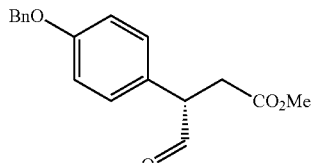

A mixture of the compound obtained in <119-2> (1.398 g, 4.504 mmol) in 1,4-dioxane (40 mL)/distilled water (10 mL) was added with 2,6-lutidine (1.05 mL, 9.008 mmol), and then slowly added with OsO₄ (4 wt % aqueous solution, 0.55 mL, 0.0901 mmol). After 2 minutes, the mixture was added with a solution of NaIO₄ (3.85 g, 18.016 mmol) in distilled water (20 mL), and stirred at room temperature for 4 hours. The reaction mixture was added with EtOAc, 0.5M HCl aqueous solution, and the layers thus formed were separated. The organic layer was consecutively washed with 0.5M HCl aqueous solution, a saturated NaHCO₃ aqueous solution and brine, dried over Na₂SO₄, and concentrated. The residue thus obtained was purified by silica gel chromatography to obtain the title compound (yellow solid, 746 mg, 60% yield).

¹H NMR (300 MHz, CDCl₃) δ 9.66 (s, 1H), 7.39 (m, 5H), 7.15-7.05 (m, 2H), 7.03-6.93 (m, 2H), 5.06 (s, 2H), 4.10 (dd, 1H), 3.66 (s, 3H), 3.13 (dd, 1H), 2.58 (dd, 1H).

<119-4> Preparation of (S)-methyl 3-(4-(benzyloxy)phenyl)-4-(hydroxyimino)butanoate

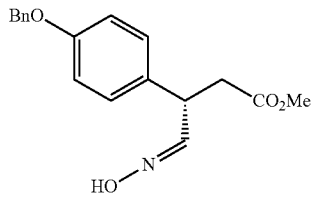 [SMILES: COC(=O)C[C@H](C=NO)c1ccc(OCc2ccccc2)cc1]

A solution of the compound obtained in <119-3> (203 mg, 0.680 mmol) in EtOH (14 mL) was consecutively added with NH₂OH.HCl (71 mg, 1.021 mmol) and distilled water (0.4 mL), and then stirred at room temperature for 1 hour. The reaction mixture thus obtained was concentrated under reduced pressure, added with EtOAc and distilled water, and the layers thus formed were separated. The aqueous layer was extracted with EtOAc one more time, and the organic layer was collected, dried over MgSO₄, and concentrated. The residue thus obtained was purified by silica gel chromatography to obtain the title compound (yellow solid, 184 mg, 86% yield).

¹H NMR (300 MHz, CDCl₃) δ 7.52 (d, 1H), 7.48-7.29 (m, 5H), 7.17-7.11 (m, 2H), 7.05 (s, 1H), 6.97-6.91 (m, 2H), 5.05 (s, 2H), 4.06 (m, 1H), 3.64 (s, 3H), 2.98 (dd, 1H), 2.67 (dd, 1H).

<119-5> Preparation of (S)-methyl 3-(4-(benzyloxy)phenyl)-3-(5-methylisoxazol-3-yl)propanoate

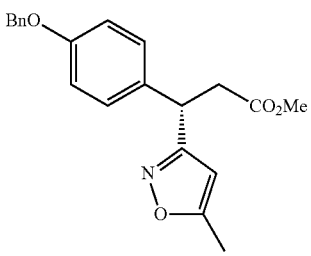 [SMILES: COC(=O)C[C@@H](c1ccc(OCc2ccccc2)cc1)c1cc(C)on1]

A solution of the compound obtained in <119-4> (107 mg, 0.341 mmol) in DMF (1.5 mL) was added with NCS (46 mg, 0.341 mmol) and stirred at room temperature for 3 hours. The mixture was added with EtOAc and distilled water, and the layers thus formed were separated. The organic layer was washed with brine, dried over Na₂SO₄, and the filtrate was concentrated and dried. The residue was added with CH₂Cl₂ (4.3 mL) and dissolved to form a solution, which was then added with propyne (3 wt % heptane solution), stirred and slowly added with triethylamine (0.095 mL, 0.683 mmol). The reaction mixture thus obtained was stirred at room temperature for 17 hours. The reaction mixture was diluted by adding EtOAc, and then consecutively washed with a saturated NH₄Cl aqueous solution and brine. The resultant was dried over Na₂SO₄, concentrated and purified by silica gel chromatography to obtain the title compound (white solid, 37 mg, 31% yield).

¹H NMR (300 MHz, CDCl₃) δ 7.46-7.28 (m, 5H), 7.21-7.11 (m, 2H), 6.95-6.84 (m, 2H), 5.70 (s, 1H), 5.03 (s, 2H), 4.49 (t, 1H), 3.63 (s, 3H), 3.26 (dd, 1H), 2.89 (dd, 1H), 2.33 (d, 3H).

<119-6> Preparation of (S)-methyl 3-(4-hydroxyphenyl)-3-(5-methylisoxazol-3-yl)propanoate

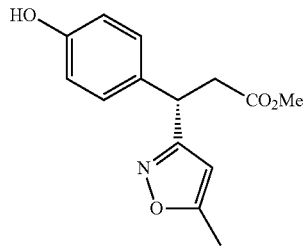 [SMILES: COC(=O)C[C@@H](c1ccc(O)cc1)c1cc(C)on1]

A solution of the compound obtained in <119-5> (25.6 mg, 0.0729 mmol) in CH₂Cl₂ (1.5 mL) at 0° C. was added with BCl₃ (1.0M CH₂Cl₂ solution, 0.115 mL, 0.146 mmol), heated to room temperature and stirred for 2 hours. The mixture was slowly added with MeOH at 0° C., further added with distilled water and extracted with CH₂Cl₂. The organic layer was collected, dried over Na₂SO₄, concentrated and purified by silica gel chromatography to obtain the title compound (colorless oil, 18.7 mg, 98% yield).

¹H NMR (300 MHz, CDCl₃) δ 7.16-7.04 (m, 2H), 6.80-6.68 (m, 2H), 5.71 (s, 1H), 5.51 (s, 1H), 4.47 (t, 1H), 3.62 (s, 3H), 3.24 (dd, 1H), 2.90 (dd, 1H), 2.33 (d, 3H).

<119-7> Preparation of methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(5-methylisoxazol-3-yl)propanoate

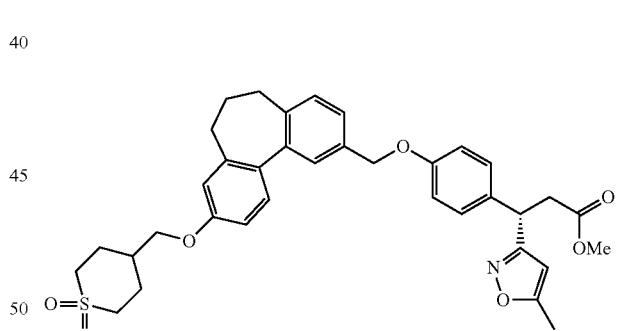

According to the procedures as described in <110-2>, the compounds obtained in <109-3> and <119-6> were used to prepare the title compound (colorless oil, 108 mg, 126% yield).

¹H NMR (300 MHz, CDCl3) δ 7.38 (d, 1H), 7.34-7.22 (m, 3H), 7.21-7.13 (m, 2H), 6.97-6.88 (m, 2H), 6.84 (dd, 1H), 6.79 (d, 1H), 5.71 (s, 1H), 5.05 (s, 2H), 4.49 (t, 1H), 3.92 (d, 2H), 3.63 (s, 3H), 3.26 (dd, 1H), 3.20-2.97 (m, 4H), 2.90 (dd, 1H), 2.48 (m, 4H), 2.38-2.25 (m, 5H), 2.18 (m, 2H), 2.06 (m, 3H).

<119-8> Preparation of (S)-3-(4-((9-((1,1-dioxido-tetrahydro-2H-thiopyran-4-yl)methoxy)-6,7-dihydro-5H-dibenzo[a,c][7]annulen-2-yl)methoxy)phenyl)-3-(5-methylisoxazol-3-yl)propanoic acid

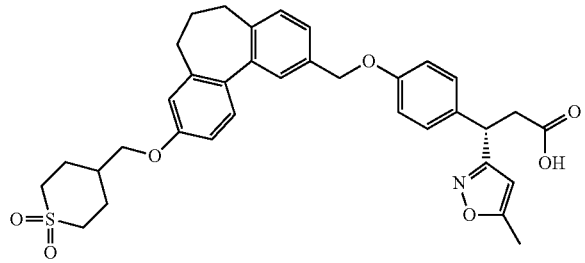 [SMILES: Cc1cc([C@@H](CC(=O)O)c2ccc(OCc3ccc4c(c3)-c3ccc(OCC5CCS(=O)(=O)CC5)cc3CCC4)cc2)no1]

According to the procedures as described in <1-11>, the compound obtained in <119-7> was used to prepare the title compound (white foam, 58 mg, 55% yield).

MS m/z 614 [M−H]⁻.

¹H NMR (300 MHz, CDCl₃) δ 7.38 (d, 1H), 7.33-7.21 (m, 3H), 7.21-7.13 (m, 2H), 6.97-6.88 (m, 2H), 6.84 (dd, 1H), 6.79 (d, 1H), 5.70 (s, 1H), 5.05 (s, 2H), 4.46 (t, 1H), 3.92 (d, 2H), 3.30 (dd, 1H), 3.21-2.98 (m, 4H), 2.93 (dd, 1H), 2.48 (m, 4H), 2.38-2.24 (m, 5H), 2.17 (m, 2H), 2.06 (m, 3H).

Example 120

Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(isoxazol-3-yl)propanoic acid

<120-1> Preparation of (S)-ethyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(isoxazol-3-yl)propanoate

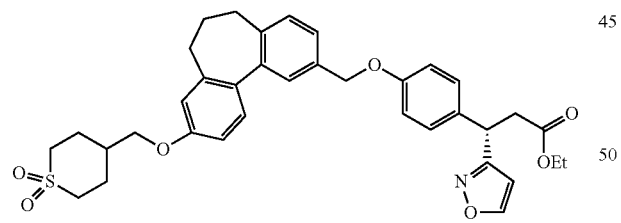

According to the procedures as described in <110-2>, the compound obtained in <109-3> and (S)-ethyl 3-(4-hydroxyphenyl)-3-(isoxazol-3-yl)propanoate (prepared in accordance with the reference [WO 2008/30520 A1]; 42 mg, 0.16 mmol) were used to prepare the title compound (white foam, 80 mg, 95% yield).

¹H NMR (600 MHz, CDCl₃) δ 8.27 (d, 1H), 7.37 (d, 1H), 7.32-7.29 (m, 2H), 7.23 (d, 1H), 7.20-7.17 (m, 2H), 6.96-6.93 (m, 2H), 6.84 (dd, 1H), 6.79 (d, 1H), 6.08 (d, 1H), 5.05 (s, 2H), 4.58 (t, 1H), 4.10-4.06 (m, 2H), 3.91 (d, 2H), 3.29-3.25 (m, 1H), 3.17-3.13 (m, 2H), 3.07-3.03 (m, 2H), 2.95-2.91 (m, 1H), 2.51-2.46 (m, 4H), 2.34-2.31 (m, 2H), 2.19-2.17 (m, 2H), 2.09-2.05 (m, 3H), 1.17 (t, 3H).

<120-2> Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(isoxazol-3-yl)propanoic acid

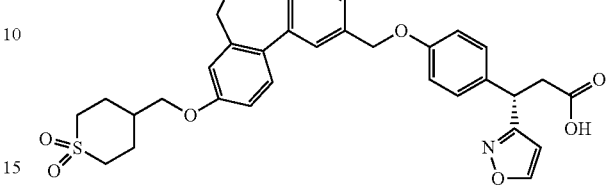

According to the procedures as described in <1-11>, the compound obtained in <120-1> was used to prepare the title compound (white foam, 71 mg, 93% yield).

MS m/z 600 [M−H]⁻.

¹H NMR (600 MHz, CDCl₃) δ 8.29 (d, 1H), 7.37 (d, 1H), 7.32-7.29 (m, 2H), 7.23 (d, 1H), 7.19-7.17 (m, 2H), 6.96-6.93 (m, 2H), 6.84 (dd, 1H), 6.79 (d, 1H), 6.07 (d, 1H), 5.05 (s, 2H), 4.55 (t, 1H), 3.91 (d, 2H), 3.37-3.33 (m, 1H), 3.17-3.13 (m, 2H), 3.07-3.03 (m, 2H), 3.00-2.96 (m, 1H), 2.51-2.46 (m, 4H), 2.33-2.30 (m, 2H), 2.20-2.15 (m, 2H), 2.09-2.04 (m, 3H).

Example 121

Preparation of 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(3-methylisoxazol-5-yl)propanoic acid

<121-1> Preparation of methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(3-methylisoxazol-5-yl)propanoate

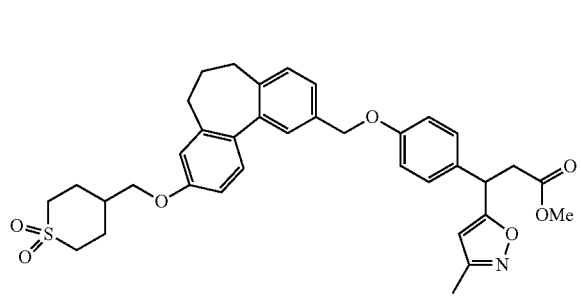 [SMILES: COC(=O)CC(c1ccc(OCc2ccc3c(c2)-c2ccc(OCC4CCS(=O)(=O)CC4)cc2CCC3)cc1)c1cc(C)no1]

According to the procedures as described in <110-2>, the compound obtained in <109-3> was used to prepare the title compound (white foam, 64.6 mg, >100% yield).

¹H NMR (300 MHz, CDCl₃) δ 7.37 (d, 1H), 7.30 (m, 2H), 7.23 (d, 1H), 7.18 (d, 2H), 6.93 (d, 2H), 6.83 (dd, 1H), 6.78 (d, 1H), 5.79 (s, 1H), 5.05 (s, 2H), 4.58 (t, 1H), 3.90 (d, 2H), 3.62 (s, 3H), 3.18-3.01 (m, 5H), 2.91 (dd, 1H), 2.48 (m, 4H), 2.32 (m, 2H), 2.23 (s, 3H), 2.17 (m, 2H), 2.06 (m, 3H).

<121-2> Preparation of 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(3-methylisoxazol-5-yl)propanoic acid

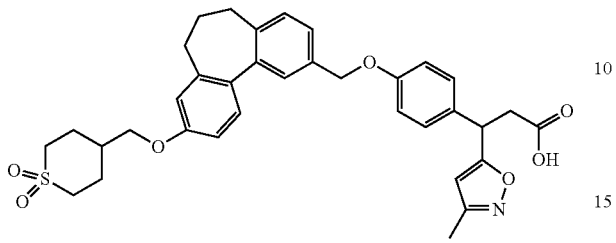

According to the procedures as described in <1-11>, the compound obtained in <121-1> was used to prepare the title compound (white foam, 40.9 mg, 66% yield).

MS m/z 637 [M+Na]+.

¹H NMR (300 MHz, CDCl₃) δ 7.37 (d, 1H), 7.30 (m, 2H), 7.23 (d, 1H), 7.18 (d, 2H), 6.94 (d, 2H), 6.83 (dd, 1H), 6.78 (d, 1H), 5.80 (s, 1H), 5.05 (s, 2H), 4.58 (t, 1H), 3.90 (d, 2H), 3.22-3.05 (m, 5H), 2.94 (dd, 1H), 2.48 (m, 4H), 2.32 (m, 2H), 2.23 (s, 3H), 2.17 (m, 2H), 2.06 (m, 3H).

Example 122

Preparation of (S)-3-(4-((3-(3-(methylsulfonyl)propoxy)-6,7-dihydro-5H-benzo[3,4]cyclohepta[1,2-b]pyridin-10-yl)methoxy)phenyl)hex-4-ynoic acid <122-1> Preparation of methyl 3-(3-(methylsulfonyl)propoxy)-6,7-dihydro-5H-benzo[3,4]cyclohepta[1,2-b]pyridine-10-carboxylate

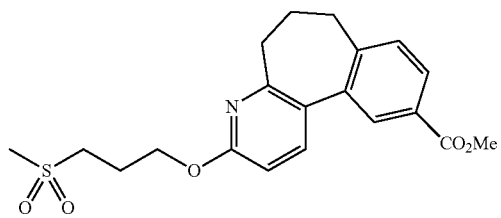 [SMILES: COC(=O)c1ccc2c(c1)-c1ccc(OCCCS(C)(=O)=O)nc1CCC2]

According to the procedures as described in <1-8>, the compound obtained in <116-6> was used to prepare the title compound (white solid, 94 mg, 72% yield).

¹H NMR (300 MHz, CDCl₃) δ 8.01-7.90 (m, 2H), 7.64 (d, 1H), 7.33 (d, 1H), 6.72 (d, 1H), 4.51 (t, 2H), 3.93 (s, 3H), 3.32-3.19 (m, 2H), 2.96 (s, 3H), 2.59 (m, 4H), 2.44-2.24 (m, 4H).

<122-2> Preparation of (3-(3-(methylsulfonyl)propoxy)-6,7-dihydro-5H-benzo[3,4]cyclohepta[1,2-b]pyridin-10-yl)methanol

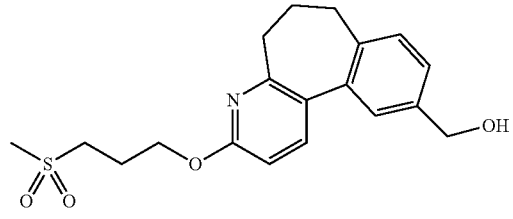 [SMILES: CS(=O)(=O)CCCOc1ccc2c(n1)CCCc1ccc(CO)cc1-2]

According to the procedures as described in <1-9>, the compound obtained in <122-1> was used to prepare the title compound (white solid, 65 mg, 72% yield).

¹H NMR (300 MHz, CDCl₃) δ 7.61 (d, 1H), 7.35-7.21 (m, 3H), 6.70 (d, 1H), 4.74 (d, 2H), 4.50 (t, 2H), 3.33-3.20 (m, 2H), 2.96 (s, 3H), 2.61 (t, 2H), 2.53 (t, 2H), 2.44-2.20 (m, 4H), 1.81 (t, 1H).

<122-3> Preparation of 10-(bromomethyl)-3-(3-(methylsulfonyl)propoxy)-6,7-dihydro-5H-benzo[3,4]cyclohepta[1,2-b]pyridine

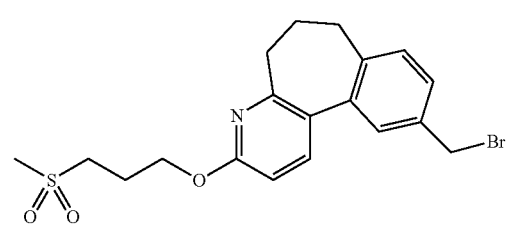 [SMILES: CS(=O)(=O)CCCOc1ccc2c(n1)CCCc1ccc(CBr)cc1-2]

According to the procedures as described in <110-1>, the compound obtained in <122-2> was used to prepare the title compound (white solid, 74.8 mg, 95% yield).

¹H NMR (300 MHz, CDCl₃) δ 7.60 (d, 1H), 7.35-7.19 (m, 3H), 6.71 (d, 1H), 4.56 (s, 2H), 4.51 (t, 2H), 3.35-3.21 (m, 2H), 2.96 (s, 3H), 2.62 (t, 2H), 2.52 (t, 2H), 2.44-2.33 (m, 2H), 2.33-2.21 (m, 2H).

<122-4> Preparation of (S)-methyl 3-(4-((3-(3-(methylsulfonyl)propoxy)-6,7-dihydro-5H-benzo[3,4]cyclohepta[1,2-b]pyridin-10-yl)methoxy)phenyl)hex-4-ynoate

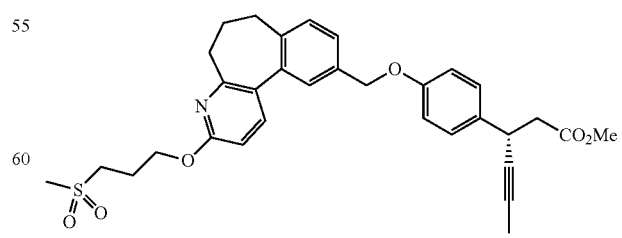

According to the procedures as described in <110-2>, the compound obtained in <122-3> was used to prepare the title compound (white solid, 86 mg, 87% yield).

¹H NMR (300 MHz, CDCl₃) δ 7.60 (d, 1H), 7.39-7.22 (m, 5H), 6.99-6.89 (m, 2H), 6.70 (d, 1H), 5.07 (s, 2H), 4.50 (t, 2H), 4.08 (m, 1H), 3.66 (s, 3H), 3.33-3.16 (m, 2H), 2.96 (s, 3H), 2.82-2.65 (m, 2H), 2.62 (t, 2H), 2.53 (t, 2H), 2.44-2.23 (m, 4H), 1.83 (d, 3H).

<122-5> Preparation of (S)-3-(4-((3-(3-(methylsulfonyl)propoxy)-6,7-dihydro-5H-benzo[3,4]cyclohepta[1,2-b]pyridin-10-yl)methoxy)phenyl)hex-4-ynoic acid

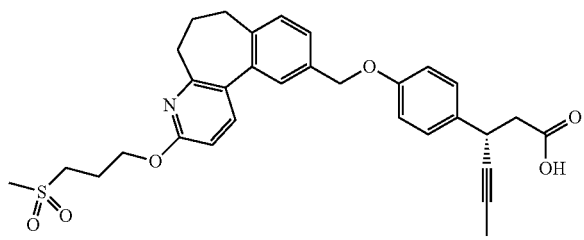 [SMILES: CC#C[C@@H](CC(=O)O)c1ccc(OCc2ccc3c(c2)-c2ccc(OCCCS(C)(=O)=O)nc2CCC3)cc1]

According to the procedures as described in <1-11>, the compound obtained in <122-4> was used to prepare the title compound (white foam, 71 mg, 85% yield).

MS m/z 570 [M+Na]⁺.

¹H NMR (300 MHz, CDCl₃) δ 7.60 (d, 1H), 7.38-7.27 (m, 5H), 7.00-6.87 (m, 2H), 6.70 (d, 1H), 5.07 (s, 2H), 4.50 (t, 2H), 4.06 (m, 1H), 3.31-3.21 (m, 2H), 2.96 (s, 3H), 2.76 (m, 2H), 2.62 (t, 2H), 2.53 (t, 2H), 2.42-2.21 (m, 4H), 1.83 (d, 3H).

Example 123

Preparation of (S)-3-(4-((3-(3-(ethylsulfonyl)propoxy)-6,7-dihydro-5H-benzo[3,4]cyclohepta[1,2-b]pyridin-10-yl)methoxy)phenyl)hex-4-ynoic acid <123-1> Preparation of methyl 3-(3-(ethylsulfonyl)propoxy)-6,7-dihydro-5H-benzo[3,4]cyclohepta[1,2-b]pyridine-10-carboxylate

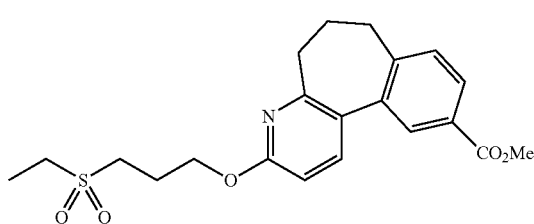 [SMILES: CCS(=O)(=O)CCCOc1ccc2c(n1)CCCc1ccc(C(=O)OC)cc1-2]

According to the procedures as described in <38-1>, the compound obtained in <116-6> was used to prepare the title compound (white solid, 102 mg, 75% yield).

¹H NMR (300 MHz, CDCl₃) δ 8.01-7.89 (m, 2H), 7.64 (d, 1H), 7.33 (d, 1H), 6.72 (d, 1H), 4.51 (t, 2H), 3.93 (s, 3H), 3.25-3.15 (m, 2H), 3.05 (q, 2H), 2.59 (m, 4H), 2.43-2.23 (m, 4H), 1.43 (t, 3H).

<123-2> Preparation of (3-(3-(ethylsulfonyl)propoxy)-6,7-dihydro-5H-benzo[3,4]cyclohepta[1,2-b]pyridin-10-yl) methanol

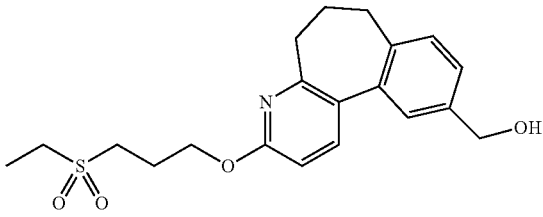 [SMILES: CCS(=O)(=O)CCCOc1ccc2c(n1)CCCc1ccc(CO)cc1-2]

According to the procedures as described in <1-9>, the compound obtained in <123-1> was used to prepare the title compound (colorless oil, 74 mg, 80% yield).

¹H NMR (300 MHz, CDCl₃) δ 7.60 (d, 1H), 7.35-7.22 (m, 3H), 6.69 (d, 1H), 4.74 (d, 2H), 4.49 (t, 2H), 3.26-3.16 (m, 2H), 3.04 (q, 2H), 2.61 (t, 2H), 2.53 (t, 2H), 2.44-2.21 (m, 4H), 1.74 (t, 1H), 1.43 (t, 3H).

<123-3> Preparation of 10-(bromomethyl)-3-(3-(ethylsulfonyl)propoxy)-6,7-dihydro-5H-benzo[3,4]cyclohepta[1,2-b]pyridine

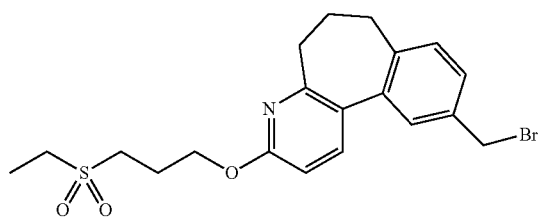 [SMILES: CCS(=O)(=O)CCCOc1ccc2c(n1)CCCc1ccc(CBr)cc1-2]

According to the procedures as described in <109-3>, the compound obtained in <123-2> was used to prepare the title compound (white foam, 80.7 mg, 99% yield).

¹H NMR (300 MHz, CDCl₃) δ 7.60 (d, 1H), 7.35-7.18 (m, 3H), 6.71 (d, 1H), 4.55 (s, 2H), 4.50 (t, 2H), 3.25-3.15 (m, 2H), 3.05 (q, 2H), 2.61 (t, 2H), 2.52 (t, 2H), 2.41-2.20 (m, 4H), 1.44 (t, 3H).

<123-4> Preparation of (S)-methyl 3-(4-((3-(3-(ethylsulfonyl)propoxy)-6,7-dihydro-5H-benzo[3,4]cyclohepta[1,2-b]pyridin-10-yl)methoxy)phenyl)hex-4-ynoate

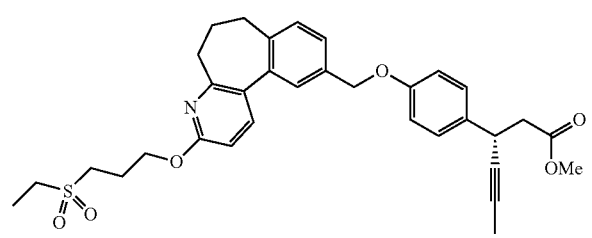 [SMILES: CC#C[C@@H](CC(=O)OC)c1ccc(OCc2ccc3c(c2)-c2ccc(OCCCS(=O)(=O)CC)nc2CCC3)cc1]

According to the procedures as described in <110-2>, the compound obtained in <123-3> was used to prepare the title compound (white foam, 94 mg, 89% yield).

¹H NMR (300 MHz, CDCl₃) δ 7.60 (d, 1H), 7.38-7.21 (m, 5H), 6.99-6.87 (m, 2H), 6.70 (d, 1H), 5.07 (s, 2H), 4.50 (t, 2H), 4.07 (m, 1H), 3.66 (s, 3H), 3.29-3.15 (m, 2H), 3.04 (q, 2H), 2.84-2.66 (m, 2H), 2.63 (t, 2H), 2.53 (t, 2H), 2.43-2.20 (m, 4H), 1.83 (d, 3H), 1.43 (t, 3H).

<123-5> Preparation of (S)-3-(4-((3-(3-(ethylsulfonyl)propoxy)-6,7-dihydro-5H-benzo[3,4]cyclohepta[1,2-b]pyridin-10-yl)methoxy)phenyl)hex-4-ynoic acid

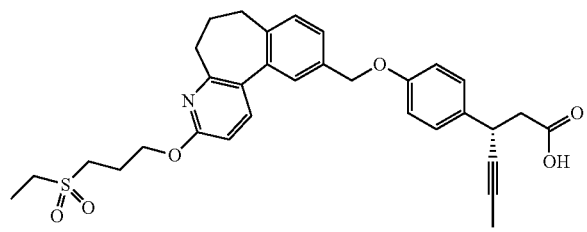 [SMILES: CC#C[C@@H](CC(=O)O)c1ccc(OCc2ccc3c(c2)-c2ccc(OCCCS(=O)(=O)CC)nc2CCC3)cc1]

According to the procedures as described in <1-11>, the compound obtained in <123-4> was used to prepare the title compound (white foam, 85 mg, 93% yield).

MS m/z 584 [M+Na]⁺.

¹H NMR (300 MHz, CDCl₃) δ 7.60 (d, 1H), 7.38-7.25 (m, 5H), 7.00-6.89 (m, 2H), 6.70 (d, 1H), 5.07 (s, 2H), 4.49 (t, 2H), 4.11-3.99 (m, 1H), 3.29-3.14 (m, 2H), 3.05 (q, 2H), 2.76 (m, 2H), 2.62 (t, 2H), 2.53 (t, 2H), 2.33 (m, 4H), 1.83 (dd, 3H), 1.43 (t, 3H).

Example 124

Preparation of (S)-3-(4-((3-((1,1-dioxidotetrahydro-2H-thiopyran-4-yl)oxy)-6,7-dihydro-5H-benzo[3,4]cyclohepta[1,2-b]pyridin-10-yl)methoxy)phenyl)hex-4-ynoic acid <124-1> Preparation of methyl 3-((1,1-dioxidotetrahydro-2H-thiopyran-4-yl)oxy)-6,7-dihydro-5H-benzo[3,4]cyclohepta[1,2-b]pyridine-10-carboxylate

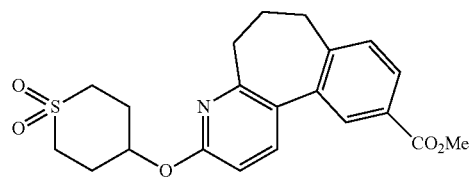 [SMILES: COC(=O)c1ccc2c(c1)-c1ccc(OC3CCS(=O)(=O)CC3)nc1CCC2]

According to the procedures as described in <55-1>, the compound obtained in <116-6> was used to prepare the title compound (yellow solid, 116 mg, 81% yield).

¹H NMR (300 MHz, CDCl₃) δ 7.99-7.91 (m, 2H), 7.66 (d, 1H), 7.37-7.30 (d, 1H), 6.75 (d, 1H), 5.53 (m, 1H), 3.93 (s, 3H), 3.50-3.33 (m, 2H), 3.05-2.90 (m, 2H), 2.65-2.51 (m, 6H), 2.44 (m, 2H), 2.40-2.25 (m, 2H).

<124-2> Preparation of 4-((10-(hydroxymethyl)-6,7-dihydro-5H-benzo[3,4]cyclohepta[1,2-b]pyridin-3-yl)oxy)tetrahydro-2H-thiopyran 1,1-dioxide

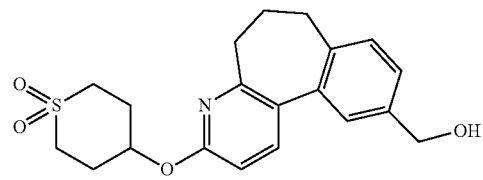 [SMILES: O=S1(=O)CCC(Oc2ccc3c(n2)CCCc2ccc(CO)cc2-3)CC1]

According to the procedures as described in <1-9>, the compound obtained in <124-1> was used to prepare the title compound (white foam, 100 mg, 90% yield).

¹H NMR (300 MHz, CDCl₃) δ 7.63 (d, 1H), 7.35-7.21 (m, 3H), 6.72 (d, 1H), 5.59-5.46 (m, 1H), 4.74 (d, 2H), 3.42 (m, 2H), 3.08-2.91 (m, 2H), 2.65-2.34 (m, 8H), 2.29 (m, 2H), 1.74 (t, 1H).

<124-3> Preparation of 4-((10-(bromomethyl)-6,7-dihydro-5H-benzo[3,4]cyclohepta[1,2-b]pyridin-3-yl)oxy)tetrahydro-2H-thiopyran 1,1-dioxide

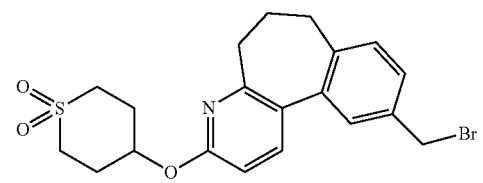 [SMILES: O=S1(=O)CCC(Oc2ccc3c(n2)CCCc2ccc(CBr)cc2-3)CC1]

According to the procedures as described in <110-1>, the compound obtained in <124-2> was used to prepare the title compound (white foam, 110.6 mg, 87% yield).

¹H NMR (300 MHz, CDCl₃) δ 7.63 (d, 1H), 7.35-7.28 (m, 2H), 7.24 (d, 1H), 6.73 (d, 1H), 5.52 (m, 1H), 4.55 (s, 2H), 3.50-3.34 (m, 2H), 3.04-2.91 (m, 2H), 2.65-2.49 (m, 6H), 2.48-2.35 (m, 2H), 2.29 (m, 2H).

<124-4> Preparation of (S)-methyl 3-(4-((3-((1,1-dioxidotetrahydro-2H-thiopyran-4-yl)oxy)-6,7-dihydro-5H-benzo[3,4]cyclohepta[1,2-b]pyridin-10-yl)methoxy)phenyl)hex-4-ynoate

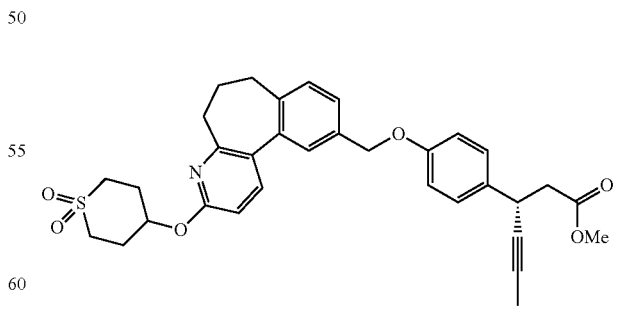

According to the procedures as described in <110-2>, the compound obtained in <124-3> was used to prepare the title compound (white foam, 124 mg, 87% yield).

¹H NMR (300 MHz, CDCl₃) δ 7.62 (d, 1H), 7.41-7.26 (m, 5H), 7.00-6.90 (m, 2H), 6.73 (d, 1H), 5.52 (m, 1H), 5.07 (s,

2H), 4.06 (m, 1H), 3.66 (s, 3H), 3.52-3.31 (m, 2H), 2.99 (m, 2H), 2.83-2.48 (m, 8H), 2.49-2.35 (m, 2H), 2.29 (m, 2H), 1.83 (d, 3H).

<124-5> Preparation of (S)-3-(4-((3-((1,1-dioxido-tetrahydro-2H-thiopyran-4-yl)oxy)-6,7-dihydro-5H-benzo[3,4]cyclohepta[1,2-b]pyridin-10-yl)methoxy)phenyl)hex-4-ynoic acid

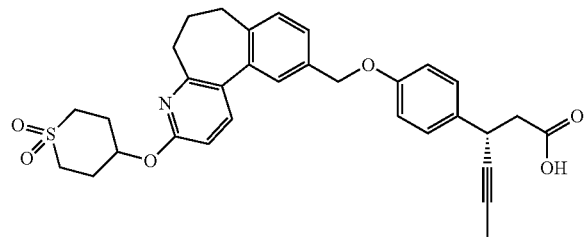 [SMILES: CC#C[C@@H](CC(=O)O)c1ccc(OCc2ccc3c(c2)-c2ccc(OC4CCS(=O)(=O)CC4)nc2CCC3)cc1]

According to the procedures as described in <1-11>, the compound obtained in <124-4> was used to prepare the title compound (white foam, 115 mg, 95% yield).

MS m/z 560 [M+H]⁺.

¹H NMR (300 MHz, CDCl₃) δ 7.62 (d, 1H), 7.40-7.25 (m, 5H), 7.02-6.86 (m, 2H), 6.73 (d, 1H), 5.52 (m, 1H), 5.07 (s, 2H), 4.06 (m, 1H), 3.53-3.32 (m, 2H), 2.99 (m, 2H), 2.66-2.49 (m, 6H), 2.48-2.35 (m, 2H), 2.30 (m, 2H), 1.83 (d, 3H).

Example 125

Preparation of (S)-3-(4-((5-methyl-7-(3-(methylsulfonyl)propoxy)-9,10-dihydrophenanthren-3-yl)methoxy)phenyl)hex-4-ynoic acid <125-1> Preparation of 6-(bromomethyl)-4-methyl-2-(3-(methylsulfonyl)propoxy)-9,10-dihydrophenanthrene

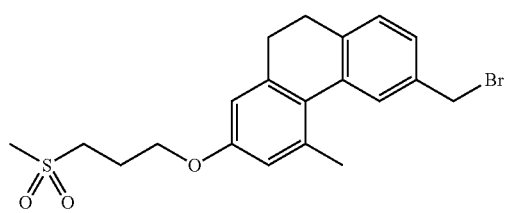 [SMILES: Cc1cc(OCCCS(C)(=O)=O)cc2c1-c1cc(CBr)ccc1CC2]

According to the procedures as described in <110-1>, the compound obtained in <11-7> was used to prepare the title compound (white solid, 104 mg, 89% yield).

¹H NMR (300 MHz, CDCl₃) δ 7.61 (s, 1H), 7.25-7.14 (m, 2H), 6.71 (d, 1H), 6.66 (d, 1H), 4.55 (s, 2H), 4.15 (t, 2H), 3.27 (m, 2H), 2.97 (s, 3H), 2.72 (s, 4H), 2.61 (s, 3H), 2.44-2.28 (m, 2H).

<125-2> Preparation of (S)-methyl 3-(4-((5-methyl-7-(3-(methylsulfonyl)propoxy)-9,10-dihydrophenanthren-3-yl)methoxy)phenyl)hex-4-ynoate

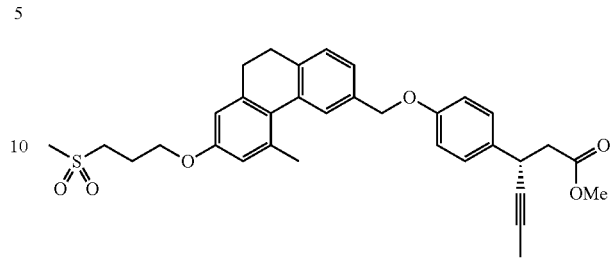

According to the procedures as described in <110-2>, the compound obtained in <125-1> was used to prepare the title compound (white foam, 55 mg, 84% yield).

¹H NMR (300 MHz, CDCl₃) δ 7.63 (s, 1H), 7.34-7.19 (m, 4H), 6.93 (m, 2H), 6.68 (d, 1H), 6.66 (d, 1H), 5.07 (s, 2H), 4.14 (t, 2H), 4.06 (m, 1H), 3.66 (s, 3H), 3.34-3.21 (m, 2H), 2.96 (s, 3H), 2.81-2.60 (m, 6H), 2.54 (s, 3H), 2.42-2.27 (m, 2H), 1.82 (d, 3H).

<125-3> Preparation of (S)-3-(4-((5-methyl-7-(3-(methylsulfonyl)propoxy)-9,10-dihydrophenanthren-3-yl)methoxy)phenyl)hex-4-ynoic acid

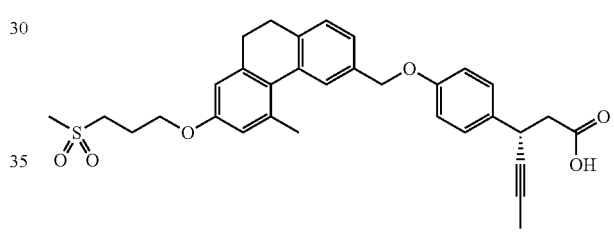

According to the procedures as described in <1-11>, the compound obtained in <125-2> was used to prepare the title compound (white foam, 37.2 mg, 73% yield).

MS m/z 569 [M+Na]⁺.

¹H NMR (600 MHz, CDCl₃) δ 7.62 (d, 1H), 7.31-7.27 (m, 2H), 7.25 (d, 1H), 7.21 (dd, 1H), 6.96-6.90 (m, 2H), 6.68 (d, 1H), 6.65 (d, 1H), 5.06 (s, 2H), 4.12 (t, 2H), 4.07-4.00 (m, 1H), 3.29-3.22 (m, 2H), 2.95 (s, 3H), 2.79 (dd, 1H), 2.74-2.66 (m, 5H), 2.52 (s, 3H), 2.38-2.30 (m, 2H), 1.82 (d, 3H).

Example 126

Preparation of (S)-3-(4-((7-(2-ethoxyethoxy)-5-methyl-9,10-dihydrophenanthren-3-yl)methoxy)phenyl)hex-4-ynoic acid <126-1> Preparation of 6-(bromomethyl)-2-(2-ethoxyethoxy)-4-methyl-9,10-dihydrophenanthrene

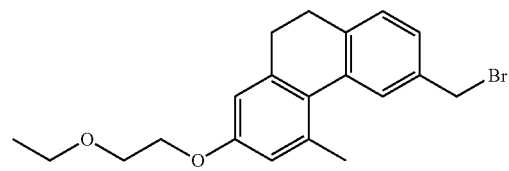 [SMILES: CCOCCOc1cc(C)c2c(c1)CCc1ccc(CBr)cc1-2]

According to the procedures as described in <110-1>, the compound obtained in <12-2> was used to prepare the title compound (white foam, 228 mg, 85% yield).

¹H NMR (600 MHz, CDCl₃) δ 7.61 (d, 1H), 7.22-7.15 (m, 2H), 6.75 (d, 1H), 6.69 (d, 1H), 4.54 (s, 2H), 4.17-4.11 (m, 2H), 3.84-3.75 (m, 2H), 3.61 (q, 2H), 2.71 (s, 4H), 2.59 (s, 3H), 1.24 (t, 3H).

<126-2> Preparation of (S)-methyl 3-(4-((7-(2-ethoxyethoxy)-5-methyl-9,10-dihydrophenanthren-3-yl)methoxy)phenyl)hex-4-ynoate

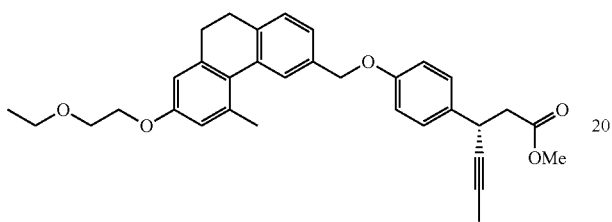

According to the procedures as described in <110-2>, the compound obtained in <126-1> was used to prepare the title compound (colorless oil, 110 mg, 122% yield).

¹H NMR (300 MHz, CDCl₃) δ 7.63 (s, 1H), 7.33-7.17 (m, 4H), 6.98-6.90 (m, 2H), 6.74 (d, 1H), 6.71 (d, 1H), 5.07 (s, 2H), 4.15 (m, 2H), 4.06 (m, 1H), 3.81 (m, 2H), 3.66 (s, 3H), 3.61 (q, 2H), 2.82-2.59 (m, 6H), 2.53 (s, 3H), 1.83 (d, 3H), 1.26 (t, 3H).

<126-3> Preparation of (S)-3-(4-((7-(2-ethoxyethoxy)-5-methyl-9,10-dihydrophenanthren-3-yl)methoxy)phenyl)hex-4-ynoic acid

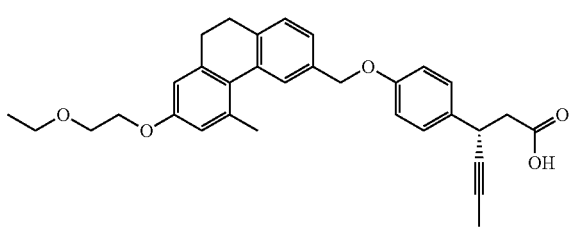 [SMILES: CC#C[C@@H](CC(=O)O)c1ccc(OCc2ccc3c(c2)-c2c(C)cc(OCCOCC)cc2CC3)cc1]

According to the procedures as described in <1-11>, the compound obtained in <126-2> was used to prepare the title compound (white foam, 72 mg, 67% yield).

MS m/z 521 [M+Na]⁺.

¹H NMR (600 MHz, CDCl₃) δ 7.62 (d, 1H), 7.31-7.27 (m, 2H), 7.26-7.23 (m, 1H), 7.20 (dd, 1H), 6.96-6.91 (m, 2H), 6.73 (d, 1H), 6.69 (d, 1H), 5.06 (s, 2H), 4.19-4.09 (m, 2H), 4.04 (m, 1H), 3.82-3.75 (m, 2H), 3.61 (q, 2H), 2.79 (dd, 1H), 2.74-2.66 (m, 5H), 2.52 (s, 3H), 1.82 (d, 3H), 1.24 (t, 3H).

Example 127

Preparation of (S)-3-(4-((5-methyl-7-(3-(methylsulfonyl)propoxy)-9,10-dihydrophenanthren-1-yl)methoxy)phenyl)hex-4-ynoic acid <127-1> Preparation of 1-(bromomethyl)-5-methyl-7-(3-(methylsulfonyl)propoxy)-9,10-dihydrophenanthrene

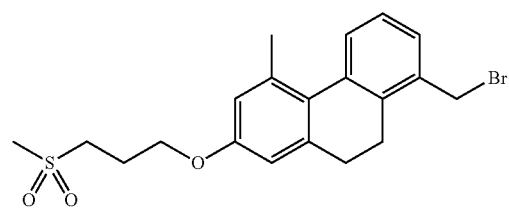 [SMILES: Cc1cc(OCCCS(C)(=O)=O)cc2c1-c1cccc(CBr)c1CC2]

According to the procedures as described in <110-1>, the compound obtained in <10-8> was used to prepare the title compound (white foam, 126 mg, 95% yield).

¹H NMR (600 MHz, CDCl₃) δ 7.54 (dd, 1H), 7.28-7.18 (m, 2H), 6.69 (d, 1H), 6.67 (d, 1H), 4.59 (s, 2H), 4.13 (t, 2H), 3.30-3.22 (m, 2H), 2.96 (s, 3H), 2.83-2.76 (m, 2H), 2.76-2.71 (m, 2H), 2.55 (s, 3H), 2.39-2.32 (m, 2H).

<127-2> Preparation of (S)-methyl 3-(4-((5-methyl-7-(3-(methylsulfonyl)propoxy)-9,10-dihydrophenanthren-1-yl)methoxy)phenyl)hex-4-ynoate

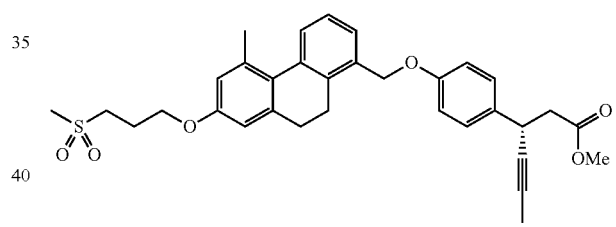

According to the procedures as described in <110-2>, the compound obtained in <127-1> was used to prepare the title compound (white foam, 50 mg, 76% yield).

¹H NMR (300 MHz, CDCl₃) δ 7.60 (dd, 1H), 7.34-7.26 (m, 5H), 6.95 (m, 2H), 6.71 (d, 1H), 6.66 (d, 1H), 5.09 (s, 2H), 4.17-4.02 (m, 3H), 3.67 (s, 3H), 3.32-3.21 (m, 2H), 2.97 (s, 3H), 2.84-2.61 (m, 6H), 2.57 (s, 3H), 2.36 (m, 2H), 1.83 (d, 3H).

<127-3> Preparation of (S)-3-(4-((5-methyl-7-(3-(methylsulfonyl)propoxy)-9,10-dihydrophenanthren-1-yl)methoxy)phenyl)hex-4-ynoic acid

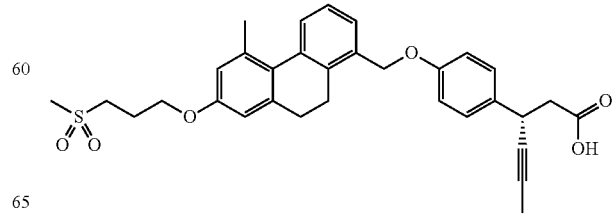

According to the procedures as described in <1-11>, the compound obtained in <127-2> was used to prepare the title compound (white foam, 39.1 mg, 85% yield).

MS m/z 569 [M+Na]+.

$^1$H NMR (600 MHz, CDCl$_3$) δ 7.59 (dd, 1H), 7.34-7.30 (m, 2H), 7.30-7.25 (m, 2H), 6.95 (m, 2H), 6.70 (d, 1H), 6.65 (d, 1H), 5.08 (s, 2H), 4.13 (t, 2H), 4.06 (m, 1H), 3.26 (m, 2H), 2.96 (s, 3H), 2.81 (dd, 1H), 2.77-2.67 (m, 5H), 2.56 (s, 3H), 2.34 (m, 2H), 1.83 (d, 3H).

Example 128

Preparation of (S)-3-(4-((11-methyl-9-(3-(methylsulfonyl)propoxy)-6,7-dihydro-5H-dibenzo[a,c][7]annulen-2-yl)methoxy)phenyl)hex-4-ynoic acid <128-1> Preparation of 10-(bromomethyl)-1-methyl-3-(3-(methylsulfonyl)propoxy)-6,7-dihydro-5H-dibenzo[a,c][7]annulene

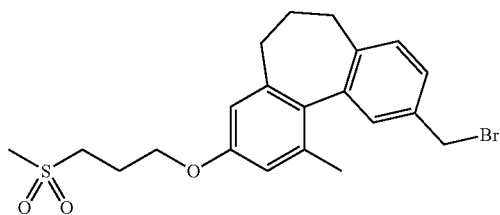 [SMILES: Cc1cc(OCCCS(C)(=O)=O)cc2c1-c1cc(CBr)ccc1CCC2]

According to the procedures as described in <110-1>, the compound obtained in <5-9> was used to prepare the title compound (white foam, 98 mg, 81% yield).

$^1$H NMR (600 MHz, CDCl$_3$) δ 7.30-7.22 (m, 2H), 7.19 (d, 1H), 6.72 (d, 1H), 6.61 (d, 1H), 4.57-4.49 (m, 2H), 4.14 (t, 2H), 3.30-3.24 (m, 2H), 2.96 (s, 3H), 2.49 (ddd, 1H), 2.41 (ddd, 1H), 2.39-2.20 (m, 7H), 2.07-1.95 (m, 2H).

<128-2> Preparation of (S)-methyl 3-(4-((11-methyl-9-(3-(methylsulfonyl)propoxy)-6,7-dihydro-5H-dibenzo[a,c][7]annulen-2-yl)methoxy)phenyl)hex-4-ynoate

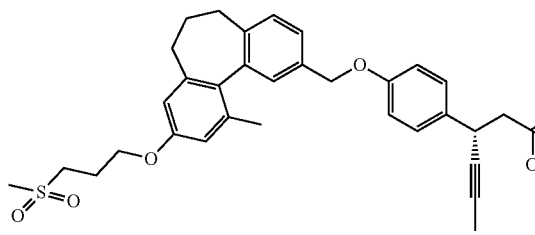

According to the procedures as described in <110-2>, the compound obtained in <128-1> was used to prepare the title compound (white foam, 63 mg, 100% yield).

$^1$H NMR (300 MHz, CDCl$_3$) δ 7.34-7.18 (m, 5H), 6.92 (m, 2H), 6.71 (d, 1H), 6.62 (d, 1H), 5.07 (s, 2H), 4.18-4.00 (m, 3H), 3.66 (s, 3H), 3.28 (m, 2H), 2.97 (s, 3H), 2.82-2.59 (m, 2H), 2.56-2.19 (m, 9H), 2.08-1.95 (m, 2H), 1.82 (d, 3H).

<128-3> Preparation of (S)-3-(4-((11-methyl-9-(3-(methylsulfonyl)propoxy)-6,7-dihydro-5H-dibenzo[a,c][7]annulen-2-yl)methoxy)phenyl)hex-4-ynoic acid

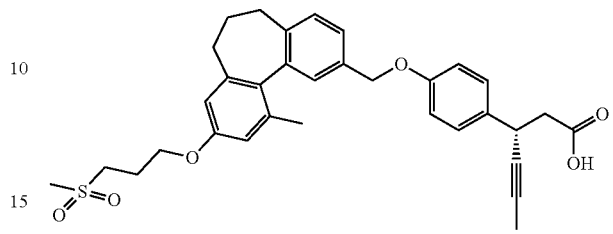

According to the procedures as described in <1-11>, the compound obtained in <128-2> was used to prepare the title compound (white foam, 50.0 mg, 85% yield).

MS m/z 583 [M+Na]+.

$^1$H NMR (600 MHz, CDCl$_3$) δ 7.32-7.26 (m, 4H), 7.23 (d, 1H), 6.92 (m, 2H), 6.71 (d, 1H), 6.62 (d, 1H), 5.06 (s, 2H), 4.13 (t, 2H), 4.03 (m, 1H), 3.27 (m, 2H), 2.96 (s, 3H), 2.78 (dd, 1H), 2.69 (dd, 1H), 2.50 (m, 1H), 2.41 (m, 1H), 2.38-2.19 (m, 7H), 2.05-1.97 (m, 2H), 1.82 (d, 3H).

Example 129

Preparation of (S)-3-(4-((9-(3-(methylsulfonyl)propoxy)dibenzo[d,f][1,3]dioxepin-2-yl)methoxy)phenyl)hex-4-ynoic acid <129-1> Preparation of 2-(bromomethyl)-9-(3-(methylsulfonyl)propoxy)dibenzo[d,f][1,3]dioxepin

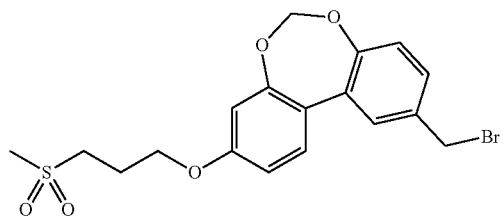 [SMILES: CS(=O)(=O)CCCOc1ccc2c(c1)OCOc1ccc(CBr)cc1-2]

According to the procedures as described in <110-1>, the compound obtained in <80-6> was used to prepare the title compound (white solid, 57 mg, 47% yield).

$^1$H NMR (600 MHz, CDCl$_3$) δ 7.66 (d, 1H), 7.62 (d, 1H), 7.25 (dd, 1H), 7.06 (d, 1H), 6.75 (dd, 1H), 6.64 (d, 1H), 5.54 (s, 2H), 4.53 (s, 2H), 4.13 (t, 2H), 3.29-3.23 (m, 2H), 2.96 (s, 3H), 2.41-2.32 (m, 2H).

<129-2> Preparation of (S)-methyl 3-(4-((9-(3-(methylsulfonyl)propoxy)dibenzo[d,f][1,3]dioxepin-2-yl)methoxy)phenyl)hex-4-ynoate

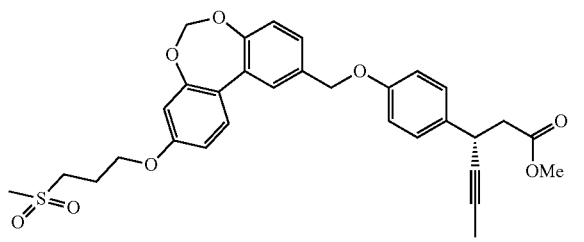 [SMILES: CC#C[C@@H](CC(=O)OC)c1ccc(OCc2ccc3c(c2)-c2ccc(OCCCS(C)(=O)=O)cc2OCO3)cc1]

According to the procedures as described in <110-2>, the compound obtained in <129-1> was used to prepare the title compound (white solid, 66 mg, 89% yield).

$^1$H NMR (600 MHz, CDCl$_3$) δ 7.69 (d, 1H), 7.61 (d, 1H), 7.31-7.27 (m, 3H), 7.11 (d, 1H), 6.95-6.91 (m, 2H), 6.74 (dd, 1H), 6.64 (d, 1H), 5.56 (s, 2H), 5.04 (s, 2H), 4.13 (t, 2H), 4.06 (m, 1H), 3.65 (s, 3H), 3.29-3.22 (m, 2H), 2.95 (s, 3H), 2.75 (dd, 1H), 2.65 (dd, 1H), 2.40-2.32 (m, 2H), 1.82 (d, 3H).

<129-3> Preparation of (S)-3-(4-((9-(3-(methylsulfonyl)propoxy)dibenzo[d,f][1,3]dioxepin-2-yl)methoxy)phenyl)hex-4-ynoic acid

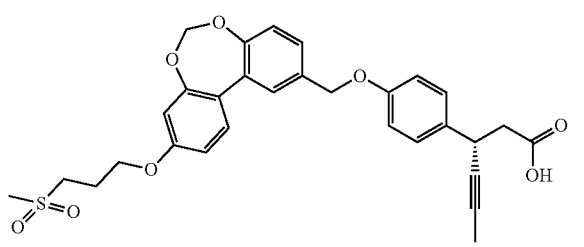 [SMILES: CC#C[C@@H](CC(=O)O)c1ccc(OCc2ccc3c(c2)-c2ccc(OCCCS(C)(=O)=O)cc2OCO3)cc1]

According to the procedures as described in <1-11>, the compound obtained in <129-2> was used to prepare the title compound (white foam, 47 mg, 73% yield).

MS m/z 573 [M+Na]$^+$.

$^1$H NMR (600 MHz, CDCl$_3$) δ 7.68 (d, 1H), 7.61 (d, 1H), 7.32-7.29 (m, 2H), 7.28 (dd, 1H), 7.11 (d, 1H), 6.95-6.92 (m, 2H), 6.74 (dd, 1H), 6.64 (d, 1H), 5.56 (s, 2H), 5.04 (s, 2H), 4.13 (t, 2H), 4.05 (m, 1H), 3.25 (m, 2H), 2.95 (s, 3H), 2.81 (dd, 1H), 2.70 (dd, 1H), 2.36 (m, 2H), 1.82 (d, 3H).

Example 130

Preparation of (S)-3-(4-((6,6-dimethyl-9-(3-(methylsulfonyl)propoxy)-6,7-dihydrodibenzo[b,d]oxepin-2-yl)methoxy)phenyl)hex-4-ynoic acid

<130-1> Preparation of 2-(bromomethyl)-6,6-dimethyl-9-(3-(methylsulfonyl)propoxy)-6,7-dihydrodibenzo[b,d]oxepin

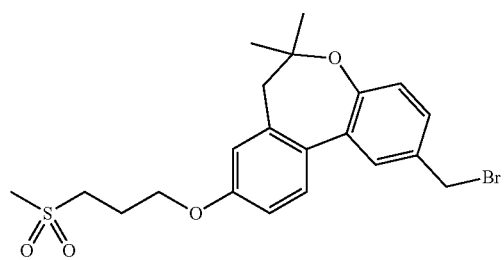 [SMILES: CC1(C)Cc2cc(OCCCS(C)(=O)=O)ccc2-c2cc(CBr)ccc2O1]

According to the procedures as described in <110-1>, the compound obtained in <43-7> was used to prepare the title compound (white foam, 112 mg, 91% yield).

$^1$H NMR (300 MHz, CDCl$_3$) δ 7.4 (d, 1H), 7.39 (d, 1H), 7.31 (dd, 1H), 7.00 (d, 1H), 6.90 (dd, 1H), 6.78 (d, 1H), 4.56 (s, 2H), 4.17 (t, 2H), 3.29 (m, 2H), 2.97 (s, 3H), 2.57 (s, 2H), 2.46-2.30 (m, 2H), 1.40 (s, 6H).

<130-2> Preparation of (S)-methyl 3-(4-((6,6-dimethyl-9-(3-(methylsulfonyl)propoxy)-6,7-dihydrodibenzo[b,d]oxepin-2-yl)methoxy)phenyl)hex-4-ynoate

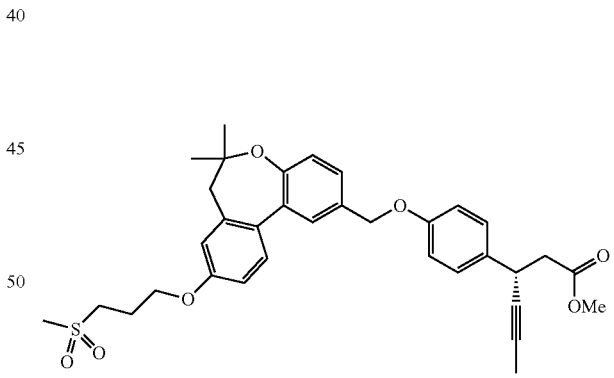

According to the procedures as described in <110-2>, the compound obtained in <130-1> was used to prepare the title compound (white foam, 125 mg, 88% yield).

$^1$H NMR (600 MHz, CDCl$_3$) δ 7.44 (d, 1H), 7.38 (d, 1H), 7.33 (dd, 1H), 7.31-7.27 (m, 2H), 7.04 (d, 1H), 6.96-6.92 (m, 2H), 6.89 (dd, 1H), 6.77 (d, 1H), 5.04 (s, 2H), 4.16 (t, 2H), 4.09-4.03 (m, 1H), 3.65 (s, 3H), 3.33-3.23 (m, 2H), 2.96 (s, 3H), 2.75 (dd, 1H), 2.65 (dd, 1H), 2.56 (s, 2H), 2.42-2.33 (m, 2H), 1.82 (d, 3H), 1.40 (s, 6H).

<130-3> Preparation of (S)-3-(4-((6,6-dimethyl-9-(3-(methylsulfonyl)propoxy)-6,7-dihydrodibenzo[b,d]oxepin-2-yl)methoxy)phenyl)hex-4-ynoic acid

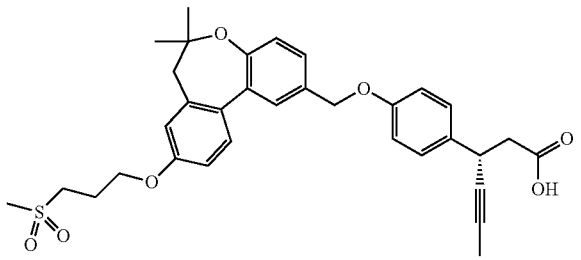 [SMILES: CC#C[C@@H](CC(=O)O)c1ccc(OCc2ccc3c(c2)-c2ccc(OCCCS(C)(=O)=O)cc2CC(C)(C)O3)cc1]

According to the procedures as described in <1-11>, the compound obtained in <130-2> was used to prepare the title compound (white foam, 109 mg, 89% yield).

MS m/z 599 [M+Na]$^+$.

$^1$H NMR (600 MHz, CDCl$_3$) δ 7.44 (d, 1H), 7.37 (d, 1H), 7.33 (dd, 1H), 7.31-7.28 (m, 2H), 7.04 (d, 1H), 6.96-6.93 (m, 2H), 6.88 (dd, 1H), 6.77 (d, 1H), 5.04 (s, 2H), 4.15 (t, 2H), 4.05 (m, 1H), 3.32-3.23 (m, 2H), 2.96 (s, 3H), 2.80 (dd, 1H), 2.70 (dd, 1H), 2.56 (s, 2H), 2.43-2.28 (m, 2H), 1.82 (d, 3H), 1.40 (s, 6H).

Example 131

Preparation of (S)-3-(4-((1-methyl-3-(3-(methylsulfonyl)propoxy)-6,7-dihydro-5H-benzo[3,4]cyclohepta[1,2-d]pyrimidin-10-yl)methoxy)phenyl)hex-4-ynoic acid

<131-1> Preparation of 10-(bromomethyl)-1-methyl-3-(3-(methylsulfonyl)propoxy)-6,7-dihydro-5H-benzo[3,4]cyclohepta[1,2-d]pyrimidine

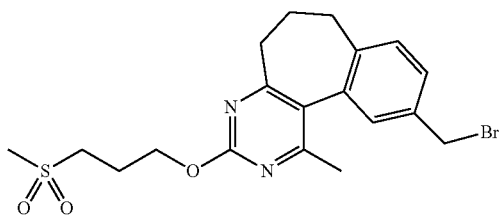 [SMILES: Cc1nc(OCCCS(C)(=O)=O)nc2c1-c1cc(CBr)ccc1CCC2]

According to the procedures as described in <110-1>, the compound obtained in <90-10> was used to prepare the title compound (white foam, 47 mg, 84% yield).

$^1$H NMR (300 MHz, CDCl$_3$) δ 7.36-7.20 (m, 3H), 4.65-4.45 (m, 4H), 3.37-3.26 (m, 2H), 2.96 (s, 5H), 2.64 (m, 2H), 2.48 (s, 3H), 2.44-2.31 (m, 8H), 2.31-2.08 (m, 2H).

<131-2> Preparation of (S)-methyl 3-(4-((1-methyl-3-(3-(methylsulfonyl)propoxy)-6,7-dihydro-5H-benzo[3,4]cyclohepta[1,2-d]pyrimidin-10-yl)methoxy)phenyl)hex-4-ynoate

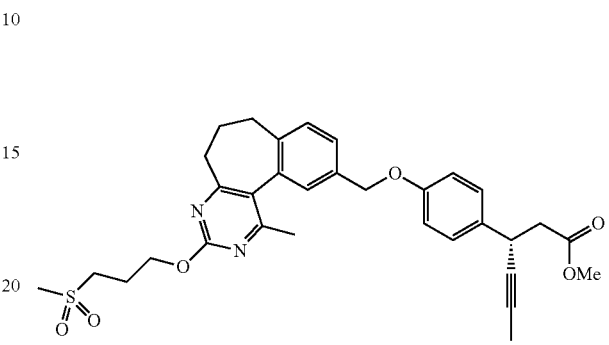

According to the procedures as described in <110-2>, the compound obtained in <131-1> was used to prepare the title compound (colorless oil, 38 mg, 62% yield).

$^1$H NMR (600 MHz, CDCl$_3$) δ 7.34 (dd, 1H), 7.30-7.26 (m, 4H), 6.93-6.89 (m, 2H), 5.07 (s, 2H), 4.53 (h, 2H), 4.05 (m, 1H), 3.65 (s, 3H), 3.35-3.27 (m, 2H), 2.94 (s, 3H), 2.74 (dd, 1H), 2.67-2.57 (m, 3H), 2.45 (m, 1H), 2.42-2.34 (m, 6H), 2.22 (m, 1H), 2.18-2.09 (m, 1H), 1.81 (d, 3H).

<131-3> Preparation of (S)-3-(4-((1-methyl-3-(3-(methylsulfonyl)propoxy)-6,7-dihydro-5H-benzo[3,4]cyclohepta[1,2-d]pyrimidin-10-yl)methoxy)phenyl)hex-4-ynoic acid

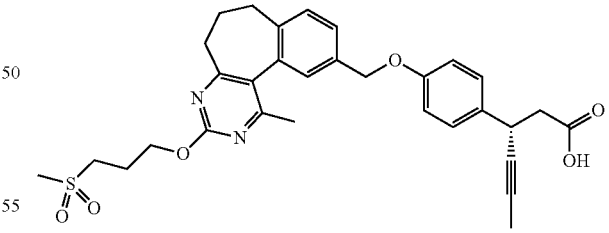

According to the procedures as described in <1-11>, the compound obtained in <131-2> was used to prepare the title compound (white foam, 28 mg, 76% yield).

MS m/z 585 [M+Na]$^+$.

$^1$H NMR (600 MHz, CDCl$_3$) δ 7.36-7.32 (d, 1H), 7.31-7.26 (m, 4H), 6.91 (d, 2H), 5.08 (s, 2H), 4.54 (h, 2H), 4.04 (m, 1H), 3.34-3.25 (m, 2H), 2.94 (s, 3H), 2.79 (dd, 1H), 2.69 (dd, 1H), 2.62 (m, 2H), 2.45 (m, 1H), 2.41-2.32 (m, 6H), 2.22 (m, 1H), 2.13 (m, 1H), 1.82 (d, 3H).

Example 132

Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid <132-1> Preparation of (S)-methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoate

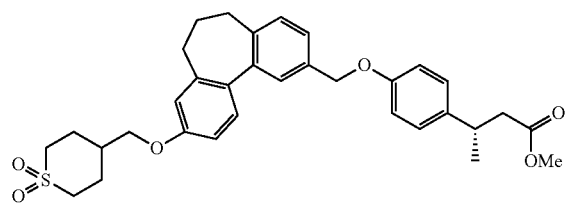 [SMILES: COC(=O)C[C@H](C)c1ccc(OCc2ccc3c(c2)-c2ccc(OCC4CCS(=O)(=O)CC4)cc2CCC3)cc1]

According to the procedures as described in <110-2>, the compound obtained in <109-3> and (S)-methyl 3-(4-hydroxyphenyl)butanoate (prepared in accordance with the reference [WO2008/130514 A1, 2008]; 31 mg, 0.16 mmol) were used to prepare the title compound (white foam, 69 mg, 92% yield).

$^1$H NMR (600 MHz, CDCl$_3$) δ 7.39 (d, 1H), 7.33-7.30 (m, 2H), 7.24 (d, 1H), 7.16-7.13 (m, 2H), 6.95-6.92 (m, 2H), 6.84 (dd, 1H), 6.79 (d, 1H), 5.06 (s, 2H), 3.91 (d, 2H), 3.62 (s, 3H), 3.26-3.22 (m, 1H), 3.17-3.13 (m, 2H), 3.07-3.02 (m, 2H), 2.61-2.57 (m, 1H), 2.54-2.46 (m, 5H), 2.34-2.30 (m, 2H), 2.20-2.15 (m, 2H), 2.09-2.05 (m, 3H), 1.27 (d, 3H).

<132-2> Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid

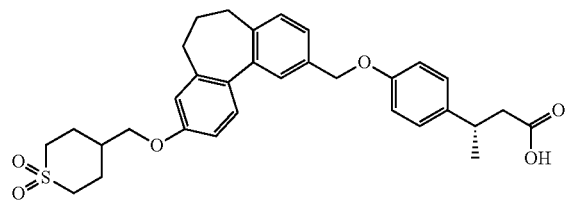 [SMILES: C[C@@H](CC(=O)O)c1ccc(OCc2ccc3c(c2)-c2ccc(OCC4CCS(=O)(=O)CC4)cc2CCC3)cc1]

According to the procedures as described in <1-11>, the compound obtained in <132-1> was used to prepare the title compound (white foam, 55 mg, 79% yield).

MS m/z 547 [M–H]$^-$.

$^1$H NMR (600 MHz, CDCl$_3$) δ 7.39 (d, 1H), 7.33-7.30 (m, 2H), 7.24 (d, 1H), 7.17-7.14 (m, 2H), 6.95-6.93 (m, 2H), 6.84 (dd, 1H), 6.79 (d, 1H), 5.06 (s, 2H), 3.91 (d, 2H), 3.26-3.22 (m, 1H), 3.17-3.13 (m, 2H), 3.07-3.02 (m, 2H), 2.66-2.62 (m, 1H), 2.58-2.54 (m, 1H), 2.51-2.46 (m, 4H), 2.34-2.30 (m, 2H), 2.20-2.17 (m, 2H), 2.09-2.04 (m, 3H), 1.30 (d, 3H).

Example 133

Preparation of (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid <133-1> Preparation of (R)-methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoate

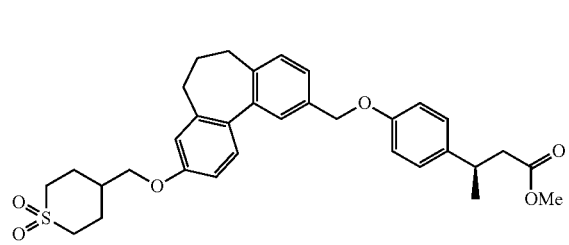 [SMILES: COC(=O)C[C@@H](C)c1ccc(OCc2ccc3c(c2)-c2ccc(OCC4CCS(=O)(=O)CC4)cc2CCC3)cc1]

According to the procedures as described in <110-2>, the compound obtained in <109-3> and (R)-methyl 3-(4-hydroxyphenyl)butanoate (prepared in accordance with the reference [WO2008/130514 A1, 2008]; 31 mg, 0.16 mmol) were used to prepare the title compound (white foam, 68 mg, 90% yield).

$^1$H NMR (600 MHz, CDCl$_3$) δ 7.39 (d, 1H), 7.33-7.30 (m, 2H), 7.24 (d, 1H), 7.16-7.13 (m, 2H), 6.95-6.92 (m, 2H), 6.84 (dd, 1H), 6.79 (d, 1H), 5.06 (s, 2H), 3.91 (d, 2H), 3.62 (s, 3H), 3.26-3.22 (m, 1H), 3.17-3.13 (m, 2H), 3.07-3.02 (m, 2H), 2.61-2.57 (m, 1H), 2.54-2.46 (m, 5H), 2.34-2.30 (m, 2H), 2.20-2.15 (m, 2H), 2.10-2.05 (m, 3H), 1.27 (d, 3H).

<133-2> Preparation of (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid

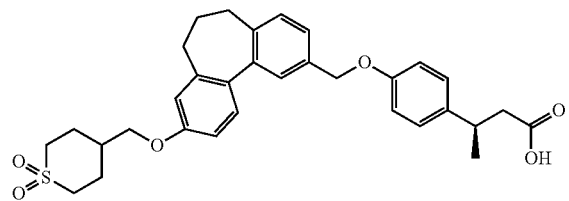 [SMILES: C[C@H](CC(=O)O)c1ccc(OCc2ccc3c(c2)-c2ccc(OCC4CCS(=O)(=O)CC4)cc2CCC3)cc1]

According to the procedures as described in <1-11>, the compound obtained in <133-1> was used to prepare the title compound (white foam, 55 mg, 79% yield).

MS m/z 547 [M–H]$^-$.

$^1$H NMR (600 MHz, CDCl$_3$) δ 7.39 (d, 1H), 7.33-7.30 (m, 2H), 7.24 (d, 1H), 7.17-7.14 (m, 2H), 6.95-6.93 (m, 2H), 6.84 (dd, 1H), 6.79 (d, 1H), 5.06 (s, 2H), 3.91 (d, 2H), 3.26-3.22 (m, 1H), 3.17-3.13 (m, 2H), 3.07-3.02 (m, 2H), 2.65-2.62 (m, 1H), 2.58-2.54 (m, 1H), 2.52-2.46 (m, 4H), 2.34-2.30 (m, 2H), 2.20-2.15 (m, 2H), 2.09-2.02 (m, 3H), 1.30 (d, 3H).

Example 134

Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-4-ethoxybutanoic acid

<134-1> Preparation of (S)-methyl 3-(4-(benzyloxy)phenyl)hex-4-ynoate

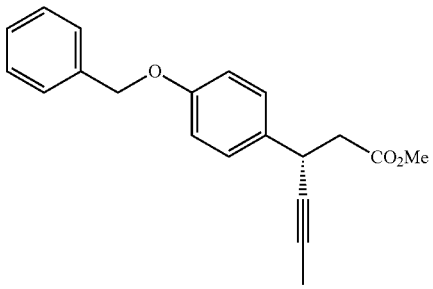 [SMILES: CC#C[C@@H](CC(=O)OC)c1ccc(OCc2ccccc2)cc1]

A solution of (S)-methyl 3-(4-hydroxyphenyl)hex-4-ynoate (prepared in accordance with the reference [Bioorganic & Medicinal Chemistry Letters, 2012, 22, p. 1267-12'70]; 500 mg, 2.29 mmol) in acetone (11 mL) was added with benzyl bromide (0.3 mL, 2.52 mmol) and $Cs_2CO_3$ (896 mg, 2.75 mmol), and the mixture thus obtained was stirred at room temperature for 15 hours. The reaction mixture was filtered and washed with acetone. The filtrate thus obtained was concentrated and purified by silica gel chromatography to obtain the title compound (white solid, 671 mg, 95% yield).

$^1$H NMR (600 MHz, $CDCl_3$) δ 7.43-7.42 (m, 2H), 7.40-7.37 (m, 2H), 7.34-7.32 (m, 1H), 7.31-7.28 (m, 2H), 6.93-6.91 (m, 2H), 5.04 (s, 2H), 4.07-4.04 (m, 1H), 3.66 (s, 3H), 2.77-2.73 (m, 1H), 2.67-2.64 (m, 1H), 1.82 (d, 3H).

<134-2> Preparation of (R,Z)-methyl 3-(4-(benzyloxy)phenyl)hex-4-enoate

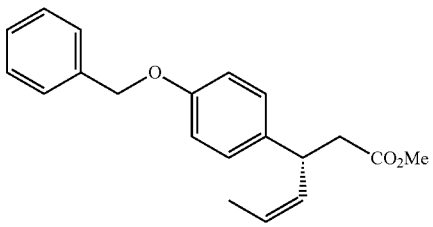 [SMILES: C/C=C\[C@@H](CC(=O)OC)c1ccc(OCc2ccccc2)cc1]

A solution of the compound obtained in <134-1> (671 mg, 2.18 mmol) in ethyl acetate (30 mL) was added with a Lindlar catalyst (100 mg) and stirred under a hydrogen atmosphere for 6 hours. The reaction mixture thus obtained was filtered, and the filtrate was concentrated and purified by silica gel chromatography to obtain the title compound (colorless oil, 620 mg, 92% yield).

$^1$H NMR (600 MHz, $CDCl_3$) δ 7.43-7.41 (m, 2H), 7.39-7.37 (m, 2H), 7.33-7.32 (m, 1H), 7.17-7.13 (m, 2H), 6.92-6.90 (m, 2H), 5.53-5.50 (m, 2H), 5.03 (s, 2H), 4.15-4.13 (m, 1H), 3.62 (s, 3H), 2.72-2.68 (m, 1H), 2.62-2.58 (m, 1H), 1.69-1.68 (m, 3H).

<134-3> Preparation of (S)-methyl 3-(4-(benzyloxy)phenyl)-4-oxobutanoate

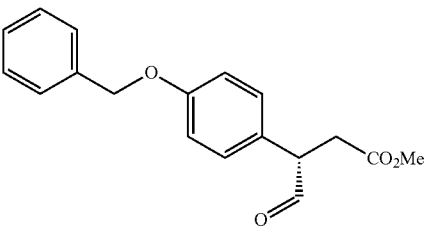 [SMILES: COC(=O)C[C@H](C=O)c1ccc(OCc2ccccc2)cc1]

A solution of the compound obtained in <134-2> (620 mg, 2.00 mmol) in acetone (20 mL) and distilled water (5 mL) was slowly added with 2,6-lutidine (0.46 mL, 3.99 mmol) and $OsO_4$ (4 wt % aqueous solution, 0.24 mL, 0.04 mmol), and then stirred at room temperature for 5 minutes. The reaction mixture thus obtained was slowly added with $NaIO_4$ (1M aqueous solution, 8 mL, 8.00 mmol) and stirred for 4 hours. The mixture was diluted with a saturated $Na_2S_2O_3$ aqueous solution and extracted with EtOAc. The organic layer was washed with 0.5M HCl aqueous solution, dried over sodium sulfate, filtered and concentrated under reduced pressure. The residue thus obtained was purified by silica gel chromatography to obtain the title compound (colorless oil, 417 mg, 70% yield).

$^1$H NMR (600 MHz, $CDCl_3$) δ 9.67 (s, 1H), 7.43-7.41 (m, 2H), 7.40-7.38 (m, 2H), 7.35-7.31 (m, 1H), 7.13-7.09 (m, 2H), 7.00-6.97 (m, 2H), 5.06 (s, 2H), 4.11-4.09 (m, 1H), 3.66 (s, 3H), 3.15-3.11 (m, 1H), 2.60-2.56 (m, 1H).

<134-4> Preparation of (S)-methyl 3-(4-(benzyloxy)phenyl)-4-hydroxybutanoate

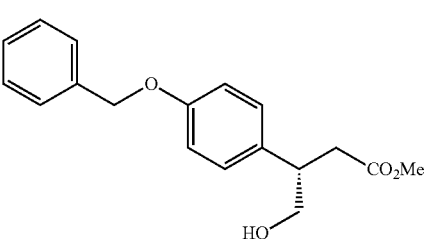 [SMILES: COC(=O)C[C@H](CO)c1ccc(OCc2ccccc2)cc1]

A solution of the compound obtained in <134-3> (417 mg, 1.40 mmol) in EtOAc (6.3 mL) and acetic acid (0.7 mL) was slowly added with sodium cyanoborohydride (88 mg, 1.40 mmol) and then stirred at room temperature for 20 minutes. The mixture thus obtained was added with a saturated $NH_4Cl$ aqueous solution and extracted with EtOAc. The organic layer was washed with brine, dried over sodium sulfate, filtered and concentrated under reduced pressure. The residue thus obtained was purified by silica gel chromatography to obtain the title compound (white solid, 399 mg, 95% yield).

$^1$H NMR (600 MHz, $CDCl_3$) δ 7.43-7.41 (m, 2H), 7.40-7.37 (m, 2H), 7.34-7.31 (m, 1H), 7.17-7.14 (m, 2H), 6.96-6.93 (m, 2H), 5.04 (s, 2H), 3.77-3.72 (m, 1H), 3.63 (s, 3H), 3.33-3.30 (m, 1H), 2.81-2.77 (m, 1H), 2.65-2.61 (m, 1H).

<134-5> Preparation of (S)-methyl 3-(4-(benzyloxy)phenyl)-4-ethoxybutanoate

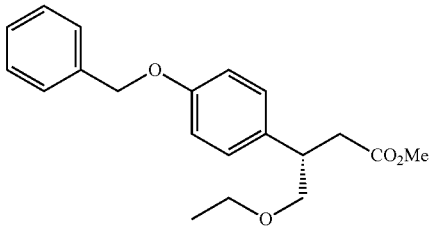 [SMILES: CCOC[C@@H](CC(=O)OC)c1ccc(OCc2ccccc2)cc1]

A solution of the compound obtained in <134-4> (220 mg, 0.73 mmol) in chloroform (3 mL) was cooled to 0° C., and then slowly added with DIPEA (0.38 mL, 2.20 mmol) and triethyloxonium tetrafluoroborate (1M chloroform solution, 1.83 mL, 1.83 mmol). The mixture was stirred at room temperature for 15 hours, washed with brine, dried over sodium sulfate, filtered, and then concentrated under reduced pressure. The residue thus obtained was purified by silica gel chromatography to obtain the title compound (colorless oil, 220 mg, 92% yield).

$^1$H NMR (600 MHz, CDCl$_3$) δ 7.43-7.41 (m, 2H), 7.40-7.37 (m, 2H), 7.34-7.31 (m, 1H), 7.17-7.14 (m, 2H), 6.92-6.90 (m, 2H), 5.03 (s, 2H), 3.59 (s, 3H), 3.57-3.54 (m, 1H), 3.50-3.38 (m, 4H), 2.86-3.83 (m, 1H), 2.59-2.55 (m, 1H), 1.17 (t, 3H).

<134-6> Preparation of (S)-methyl 4-ethoxy-3-(4-hydroxyphenyl)butanoate

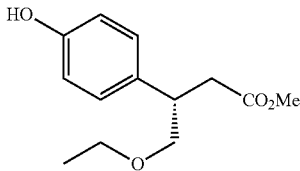 [SMILES: CCOC[C@@H](CC(=O)OC)c1ccc(O)cc1]

A solution of the compound obtained in <134-5> (217 mg, 0.66 mmol) in methanol (6 mL) was added with 10% Pd/C (21 mg, 0.02 mmol) and stirred under a hydrogen atmosphere for 4 hours. The reaction mixture was filtered through Celite, washed EtOAc, and then the filtrate was concentrated under reduced pressure. The residue thus obtained was purified by silica gel chromatography to obtain the title compound (white solid, 156 mg, 99% yield).

$^1$H NMR (600 MHz, CDCl$_3$) δ 7.07-7.04 (m, 2H), 6.69-6.67 (m, 2H), 3.61 (s, 3H), 3.57-3.55 (m, 1H), 3.52-3.44 (m, 3H), 3.40-3.36 (m, 1H), 2.86-3.83 (m, 1H), 2.59-2.55 (m, 1H), 1.17 (t, 3H).

<134-7> Preparation of (S)-methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)-4-ethoxybutanoate

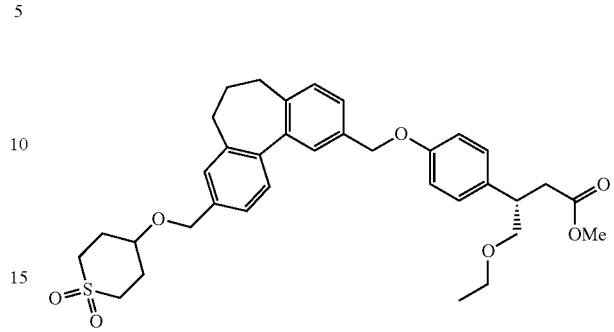

According to the procedures as described in <110-2>, the compounds obtained in <109-3> and <134-6> were used to prepare the title compound (white foam, 90 mg, 95% yield).

$^1$H NMR (600 MHz, CDCl$_3$) δ 7.39 (d, 1H), 7.33-7.30 (m, 2H), 7.24 (d, 1H), 7.16-7.14 (m, 2H), 6.95-6.92 (m, 2H), 6.84 (dd, 1H), 6.79 (d, 1H), 5.05 (s, 2H), 3.91 (d, 2H), 3.60 (s, 3H), 3.57-3.55 (m, 1H), 3.51-3.43 (m, 3H), 3.41-3.38 (m, 1H), 3.18-3.14 (m, 2H), 3.07-3.03 (m, 2H), 2.87-2.83 (m, 1H), 2.59-2.55 (m, 1H), 2.51-2.47 (m, 4H), 2.34-2.30 (m, 2H), 2.20-2.16 (m, 2H), 2.10-2.05 (m, 3H), 1.17 (t, 3H).

<134-8> Preparation of (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-4-ethoxybutanoic acid

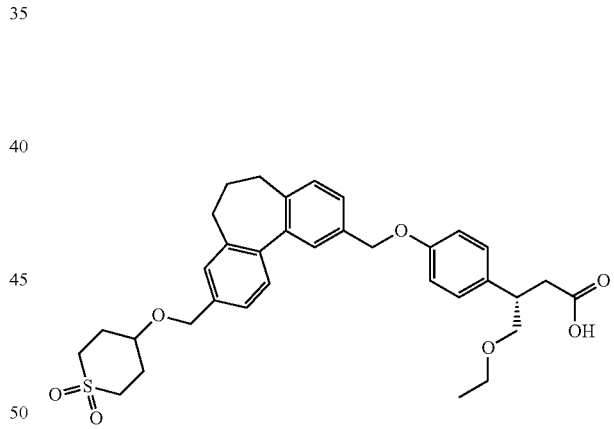

According to the procedures as described in <1-11>, the compound obtained in <134-7> was used to prepare the title compound (white foam, 82 mg, 93% yield).

MS m/z 591 [M−H]$^-$.

$^1$H NMR (600 MHz, CDCl$_3$) δ 7.38 (d, 1H), 7.32-7.30 (m, 2H), 7.24 (d, 1H), 7.16-7.14 (m, 2H), 6.95-6.92 (m, 2H), 6.84 (dd, 1H), 6.79 (d, 1H), 5.05 (s, 2H), 3.91 (d, 2H), 3.59-3.57 (m, 1H), 3.51-3.46 (m, 3H), 3.38-3.36 (m, 1H), 3.16-3.13 (m, 2H), 3.07-3.03 (m, 2H), 2.92-2.89 (m, 1H), 2.65-2.61 (m, 1H), 2.52-2.46 (m, 4H), 2.34-2.30 (m, 2H), 2.20-2.16 (m, 2H), 2.09-2.05 (m, 3H), 1.17 (t, 3H).

Example 135

Preparation of (S)-3-(4-(((9-(3-(methylsulfonyl)propoxy)-6,7-dihydro-5H-dibenzo[a,c][7]annulen-2-yl)methyl)amino)phenyl)hex-4-ynoic acid <135-1> Preparation of (S)-methyl 3-(4-(((trifluoromethyl)sulfonyl)oxy)phenyl)hex-4-ynoate

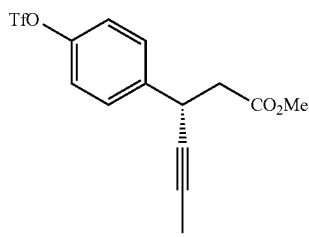 [SMILES: CC#C[C@@H](CC(=O)OC)c1ccc(OS(=O)(=O)C(F)(F)F)cc1]

A solution of (S)-methyl 3-(4-hydroxyphenyl)hex-4-ynoate (prepared in accordance with the reference [Bioorganic & Medicinal Chemistry Letters, 2012, 22, p. 1267-1270]; 395 mg, 1.81 mmol) in pyridine (10 mL) at 0° C. was added with triflic acid anhydride (0.37 mL, 2.17 mmol), heated to room temperature, and then stirred for 15 hours. The reaction mixture thus obtained was diluted with EtOAc and 1M HCl aqueous solution. The aqueous layer was extracted with EtOAc one more time, and the organic layer was washed with brine, dried over MgSO₄, concentrated, and then purified by silica gel chromatography to obtain the title compound (colorless oil, 415 mg, 65% yield).

$^1$H NMR (600 MHz, CDCl$_3$) δ 7.49-7.44 (m, 2H), 7.23-7.19 (m, 2H), 4.14 (m, 1H), 3.66 (s, 2H), 2.78 (dd, 1H), 2.66 (dd, 1H), 1.83 (d, 2H).

<135-2> Preparation of (S)-methyl 3-(4-aminophenyl)hex-4-ynoate

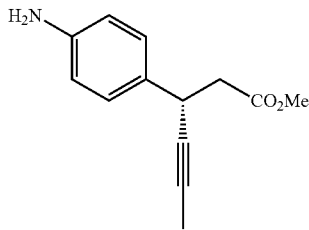 [SMILES: CC#C[C@@H](CC(=O)OC)c1ccc(N)cc1]

A solution of the compound obtained in <135-1> (415 mg, 1.185 mmol), benzophenone-imine (0.28 mL, 1.659 mmol) and Cs₂CO₃ (1.16 g, 3.554 mmol) in THF (5 mL) was substituted with nitrogen, added with Xantphos (41 mg, 0.0711 mmol) and Pd₂(dba)₃ (33 mg, 0.0355 mmol), and refluxed for 12 hours. The reaction mixture thus obtained was cooled room temperature, filtered through Celite, and then washed with CH₂Cl₂. The concentrated filtrate was dissolved in THF (4 mL), and the solution thus formed was added with 3M HCl aqueous solution (1.2 mL, 3.554 mmol) and stirred for 30 minutes. The reaction mixture was diluted with EtOAc, added with a saturated NaHCO₃ aqueous solution, and the layers were separated. The aqueous layer was extracted with CH₂Cl₂, and the organic layer was dried over Na₂SO₄, concentrated and purified by silica gel chromatography to obtain the title compound (yellow oil, 134 mg, 52% yield).

$^1$H NMR (600 MHz, CDCl$_3$) δ 7.17-7.11 (m, 2H), 6.66-6.59 (m, 2H), 3.99 (m, 1H), 3.65 (s, 3H), 3.60 (br s, 2H), 2.72 (dd, 1H), 2.62 (dd, 1H), 1.81 (d, 3H).

<135-3> Preparation of (S)-methyl 3-(4-(((9-(3-(methylsulfonyl)propoxy)-6,7-dihydro-5H-dibenzo[a,c][7]annulen-2-yl)methyl)amino)phenyl)hex-4-ynoate

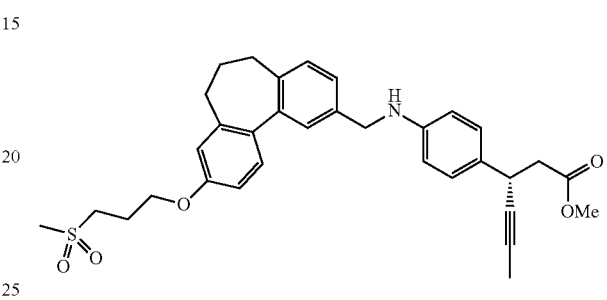

According to the procedures as described in <3-4>, the compounds obtained in <6-1> and <135-2> were used to prepare the title compound (yellow foam, 138 mg, 97% yield).

$^1$H NMR (600 MHz, CDCl$_3$) δ 7.32 (d, 1H), 7.27 (d, 1H), 7.26-7.22 (m, 1H), 7.18 (d, 1H), 7.17-7.14 (m, 2H), 6.83 (dd, 1H), 6.78 (d, 1H), 6.63-6.58 (m, 2H), 4.32 (s, 2H), 4.15 (t, 2H), 4.06-3.96 (m, 2H), 3.65 (s, 3H), 3.31-3.24 (m, 2H), 2.96 (s, 3H), 2.72 (dd, 1H), 2.63 (dd, 1H), 2.51-2.42 (m, 4H), 2.39-2.31 (m, 2H), 2.17 (m, 2H), 1.81 (d, 3H).

<135-4> Preparation of (S)-3-(4-(((9-(3-(methylsulfonyl)propoxy)-6,7-dihydro-5H-dibenzo[a,c][7]annulen-2-yl)methyl)amino)phenyl)hex-4-ynoic acid

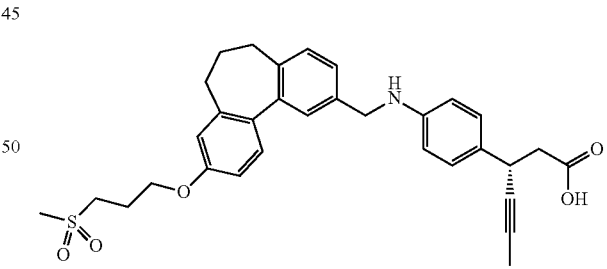

According to the procedures as described in <1-11>, the compound obtained in <135-3> was used to prepare the title compound (yellow foam, 96 mg, 71% yield).

MS m/z 544 [M−H]⁻.

$^1$H NMR (600 MHz, CDCl$_3$) δ 7.31 (d, 1H), 7.27 (d, 1H), 7.25-7.22 (m, 1H), 7.18 (m, 3H), 6.83 (dd, 1H), 6.78 (d, 1H), 6.64-6.58 (m, 2H), 4.32 (s, 2H), 4.14 (t, 2H), 3.99 (m, 1H), 3.31-3.23 (m, 2H), 2.96 (s, 3H), 2.76 (dd, 1H), 2.68 (dd, 1H), 2.53-2.40 (m, 4H), 2.40-2.30 (m, 2H), 2.16 (m, 2H), 1.81 (d, 3H).

Example 136

Preparation of (S)-3-(4-(((9-((1,1-dioxidotetrahydro-2H-thiopyran-4-yl)methoxy)-6,7-dihydro-5H-dibenzo[a,c][7]annulen-2-yl)methyl)amino)phenyl)hex-4-ynoic acid <136-1> Preparation of (S)-methyl 3-(4-(((9-((1,1-dioxidotetrahydro-2H-thiopyran-4-yl)methoxy)-6,7-dihydro-5H-dibenzo[a,c][7]annulen-2-yl)methyl)amino)phenyl)hex-4-ynoate

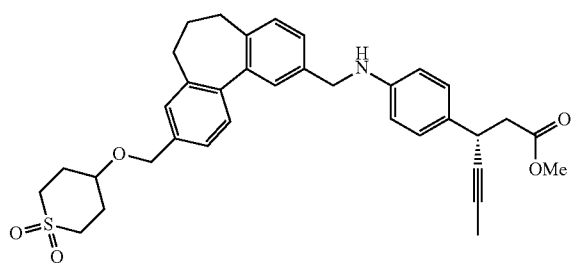 [SMILES: CC#C[C@@H](CC(=O)OC)c1ccc(NCc2ccc3c(c2)-c2ccc(COC4CCS(=O)(=O)CC4)cc2CCC3)cc1]

According to the procedures as described in <3-4>, the compounds obtained in <78-3> and <135-2> were used to prepare the title compound (yellow oil, 136 mg, 100% yield).

$^1$H NMR (600 MHz, CDCl$_3$) δ 7.31 (d, 1H), 7.27 (d, 1H), 7.24 (dd, 1H), 7.18 (d, 1H), 7.17-7.14 (m, 2H), 6.82 (dd, 1H), 6.77 (d, 1H), 6.63-6.57 (m, 2H), 4.32 (s, 2H), 4.03 (br s, 1H), 3.99 (m, 1H), 3.90 (d, 2H), 3.65 (s, 3H), 3.18-3.10 (m, 2H), 3.03 (m, 2H), 2.72 (dd, 1H), 2.63 (dd, 1H), 2.52-2.41 (m, 4H), 2.31 (m, 2H), 2.17 (m, 2H), 2.10-1.99 (m, 3H), 1.80 (d, 3H).

<136-2> Preparation of (S)-3-(4-(((9-((1,1-dioxidotetrahydro-2H-thiopyran-4-yl)methoxy)-6,7-dihydro-5H-dibenzo[a,c][7]annulen-2-yl)methyl)amino)phenyl)hex-4-ynoic acid

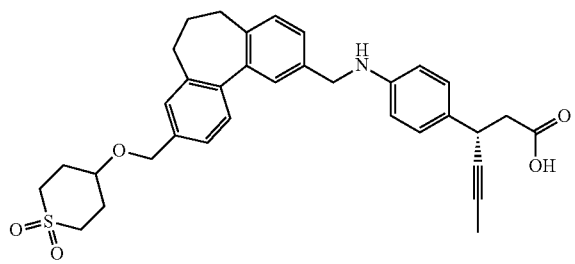 [SMILES: CC#C[C@@H](CC(=O)O)c1ccc(NCc2ccc3c(c2)-c2ccc(COC4CCS(=O)(=O)CC4)cc2CCC3)cc1]

According to the procedures as described in <1-11>, the compound obtained in <136-1> was used to prepare the title compound (yellow foam, 75 mg, 56% yield).

MS m/z 570 [M–H]$^-$.

$^1$H NMR (600 MHz, CDCl$_3$) δ 7.31 (d, 1H), 7.27 (d, 1H), 7.24 (dd, 1H), 7.20-7.15 (m, 3H), 6.82 (dd, 1H), 6.77 (d, 1H), 6.63-6.58 (m, 2H), 4.32 (s, 2H), 3.99 (m, 1H), 3.90 (d, 2H), 3.19-3.09 (m, 2H), 3.08-2.96 (m, 2H), 2.77 (dd, 1H), 2.68 (dd, 1H), 2.52-2.39 (m, 4H), 2.35-2.24 (m, 2H), 2.16 (m, 2H), 2.11-1.98 (m, 3H), 1.81 (d, 3H).

Example 137

Preparation of 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(4-fluorophenyl)propanoic acid <137-1> Preparation of methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(4-fluorophenyl)propanoate

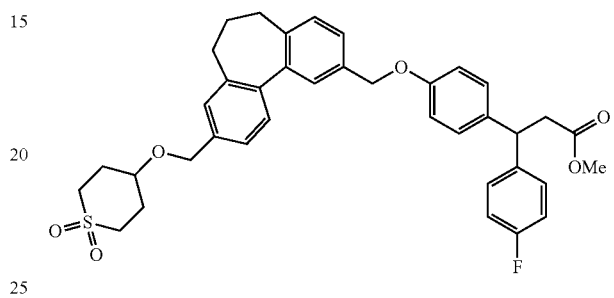

According to the procedures as described in <110-2>, the compound obtained in <109-3> and methyl 3-(4-fluorophenyl)-3-(4-hydroxyphenyl)propanoate (prepared in accordance with the reference [Bioorganic & Medicinal Chemistry Letters, 2012, 22, p. 1267-1270]) were used to prepare the title compound (colorless oil, 85 mg, 99% yield).

$^1$H NMR (600 MHz, CDCl$_3$) δ 7.36 (d, 1H), 7.31-7.27 (m, 2H), 7.22 (d, 1H), 7.19-7.14 (m, 2H), 7.13-7.09 (m, 2H), 6.98-6.93 (m, 2H), 6.93-6.89 (m, 2H), 6.82 (dd, 1H), 6.77 (d, 1H), 5.03 (s, 2H), 4.48 (t, 1H), 3.90 (d, 2H), 3.57 (s, 3H), 3.21-3.11 (m, 2H), 3.04 (m, 2H), 2.99 (dd, 2H), 2.47 (m, 4H), 2.31 (m, 2H), 2.16 (m, 2H), 2.11-2.00 (m, 3H).

<137-2> Preparation of 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(4-fluorophenyl)propanoic acid

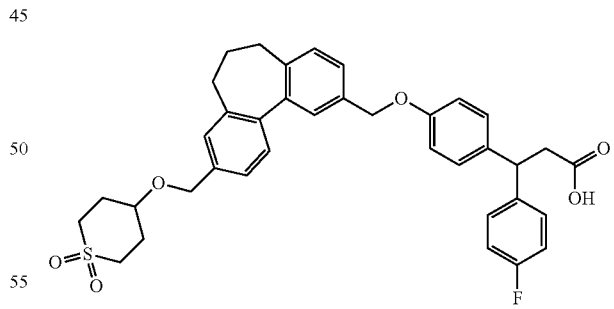

According to the procedures as described in <1-11>, the compound obtained in <137-1> was used to prepare the title compound (white foam, 63 mg, 79% yield).

MS m/z 627 [M–H]$^-$.

$^1$H NMR (600 MHz, CDCl$_3$) δ 7.36 (d, 1H), 7.29 (m, 2H), 7.22 (d, 1H), 7.19-7.14 (m, 2H), 7.11 (m, 2H), 6.98-6.93 (m, 2H), 6.93-6.88 (m, 2H), 6.82 (dd, 1H), 6.77 (d, 1H), 5.03 (s, 2H), 4.46 (t, 1H), 3.90 (d, 2H), 3.19-3.09 (m, 2H), 3.03 (m, 4H), 2.47 (m, 4H), 2.38-2.23 (m, 2H), 2.17 (m, 2H), 2.12-1.97 (m, 3H).

Example 138

Preparation of (S)-3-(4-((11-methyl-9-(((R)-tetrahydrofuran-3-yl)oxy)-6,7-dihydro-5H-dibenzo[a,c][7]annulen-2-yl)methoxy)phenyl)hex-4-ynoic acid <138-1> Preparation of methyl 11-methyl-9-(((R)-tetrahydrofuran-3-yl)oxy)-6,7-dihydro-5H-dibenzo[a,c][7]annulene-2-carboxylate

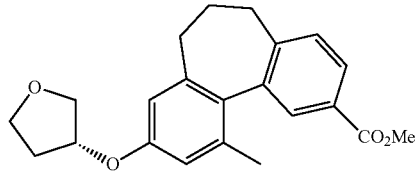 [SMILES: COC(=O)c1ccc2c(c1)-c1c(C)cc(O[C@@H]3CCOC3)cc1CCC2]

According to the procedures as described in <106-1>, the compound obtained in <7-6> was used to prepare the title compound (white foam, 71 mg, 93% yield).

$^1$H NMR (600 MHz, CDCl$_3$) δ 7.94 (d, 1H), 7.91 (dd, 1H), 7.30 (d, 1H), 6.72-6.70 (m, 1H), 6.60 (d, 1H), 4.99-4.96 (m, 1H), 4.05-3.99 (m, 3H), 3.95-3.92 (m, 1H), 3.91 (s, 3H), 2.58-2.55 (m, 1H), 2.45-2.37 (m, 2H), 2.30 (s, 3H), 2.25-2.17 (m, 3H), 2.09-2.01 (m, 2H).

<138-2> Preparation of (11-methyl-9-(((R)-tetrahydrofuran-3-yl)oxy)-6,7-dihydro-5H-dibenzo[a,c][7]annulen-2-yl)methanol

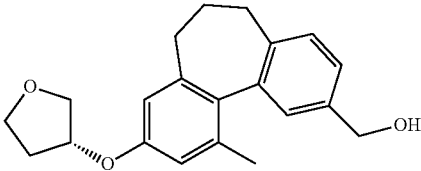 [SMILES: Cc1cc(O[C@@H]2CCOC2)cc2c1-c1cc(CO)ccc1CCC2]

According to the procedures as described in <1-9>, the compound obtained in <138-1> was used to prepare the title compound (white foam, 60 mg, 92% yield).

$^1$H NMR (600 MHz, CDCl$_3$) δ 7.26-7.22 (m, 3H), 6.70 (d, 1H), 7.60 (d, 1H), 6.98-6.96 (m, 1H), 4.05-3.99 (m, 3H), 3.94-3.91 (m, 1H), 2.52-2.49 (m, 1H), 2.44-2.40 (m, 1H), 2.38-2.33 (m, 1H), 2.30 (s, 3H), 2.26-2.19 (m, 3H), 2.05-1.99 (m, 2H), 1.61 (t, 1H).

<138-3> Preparation of (R)-3-((10-(bromomethyl)-1-methyl-6,7-dihydro-5H-dibenzo[a,c][7]annulen-3-yl)oxy)tetrahydrofuran

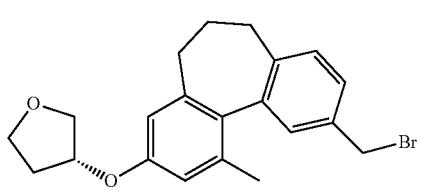 [SMILES: Cc1cc(O[C@@H]2CCOC2)cc2c1-c1cc(CBr)ccc1CCC2]

According to the procedures as described in <110-1>, the compound obtained in <138-2> was used to prepare the title compound (white foam, 58 mg, 82% yield).

$^1$H NMR (600 MHz, CDCl$_3$) δ 7.29 (d, 1H), 7.25 (dd, 1H), 7.20 (d, 1H), 6.70 (d, 1H), 6.60 (d, 1H), 4.98-4.96 (m, 1H), 4.56-4.52 (m, 2H), 4.04-3.99 (m, 3H), 3.94-3.91 (m, 1H), 2.52-2.48 (m, 1H), 2.44-2.41 (m, 1H), 2.37-2.32 (m, 1H), 2.30 (s, 3H), 2.28-2.19 (m, 3H), 2.05-1.99 (m, 2H).

<138-4> Preparation of (S)-methyl 3-(4-((11-methyl-9-(((R)-tetrahydrofuran-3-yl)oxy)-6,7-dihydro-5H-dibenzo[a,c][7]annulen-2-yl)methoxy)phenyl)hex-4-ynoate

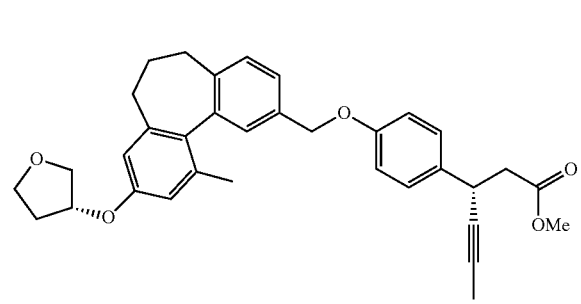 [SMILES: CC#C[C@@H](CC(=O)OC)c1ccc(OCc2ccc3c(c2)-c2c(C)cc(O[C@@H]4CCOC4)cc2CCC3)cc1]

According to the procedures as described in <110-2>, the compound obtained in <138-3> was used to prepare the title compound (white foam, 75 mg, 95% yield).

$^1$H NMR (600 MHz, CDCl$_3$) δ 7.30-7.27 (m, 4H), 7.24-7.23 (m, 1H), 6.94-6.91 (m, 2H), 6.68 (d, 1H), 6.60 (d, 1H), 5.07 (s, 2H), 4.98-4.96 (m, 1H), 4.05-4.00 (m, 4H), 3.94-3.92 (m, 1H), 3.66 (s, 3H), 2.52-2.48 (m, 1H), 2.77-2.73 (m, 1H), 2.67-2.63 (m, 1H), 2.52-2.49 (m, 1H), 2.44-2.41 (m, 1H), 2.38-2.33 (m, 1H), 2.28-2.19 (m, 6H), 2.05-2.00 (m, 2H), 1.83-1.82 (m, 3H).

<138-5> Preparation of (S)-3-(4-((11-methyl-9-(((R)-tetrahydrofuran-3-yl)oxy)-6,7-dihydro-5H-dibenzo[a,c][7]annulen-2-yl)methoxy)phenyl)hex-4-ynoic acid

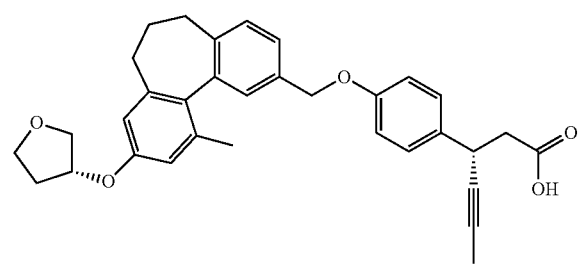 [SMILES: CC#C[C@@H](CC(=O)O)c1ccc(OCc2ccc3c(c2)-c2c(C)cc(O[C@@H]4CCOC4)cc2CCC3)cc1]

According to the procedures as described in <1-11>, the compound obtained in <138-4> was used to prepare the title compound (white foam, 54 mg, 74% yield).

MS m/z 509 [M−H]$^-$.

$^1$H NMR (600 MHz, CDCl$_3$) δ 7.30-7.28 (m, 4H), 7.24-7.23 (m, 1H), 6.94-6.92 (m, 2H), 6.68 (d, 1H), 6.60 (d, 1H), 5.07 (s, 2H), 4.98-4.95 (m, 1H), 4.06-3.99 (m, 4H), 3.94-3.92 (m, 1H), 2.52-2.48 (m, 1H), 2.82-2.78 (m, 1H), 2.72-2.69 (m, 1H), 2.52-2.49 (m, 1H), 2.43-2.40 (m, 1H), 2.38-2.32 (m, 1H), 2.28-2.19 (m, 6H), 2.05-1.99 (m, 2H), 1.83-1.82 (m, 3H).

Example 139

Preparation of (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)pent-4-ynoic acid <139-1> Preparation of (R)-methyl 3-(4-((9-((1,1-dioxidotetrahydro-2H-thiopyran-4-yl)methoxy)-6,7-dihydro-5H-dibenzo[a,c][7]annulen-2-yl)methoxy)phenyl)pent-4-ynoate

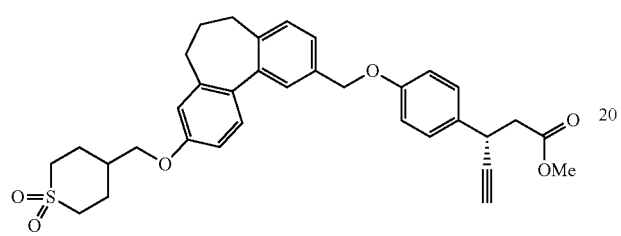

According to the procedures as described in <110-2>, the compound obtained in <109-3> was used to prepare the title compound (white foam, 75.2 mg, 75% yield).

$^1$H NMR (300 MHz, CDCl$_3$) δ 7.39 (d, 1H), 7.33-7.30 (m, 4H), 7.24 (d, 1H), 6.96 (d, 2H), 6.85 (dd, 1H), 6.79 (d, 1H), 5.08 (s, 2H), 4.14 (t, 1H), 3.92 (d, 2H), 3.68 (s, 3H), 3.18-3.02 (m, 4H), 2.83 (dd, 1H), 2.71 (dd, 1H), 2.48 (m, 4H), 2.33 (m, 2H), 2.29 (d, 1H), 2.18 (m, 2H), 2.07 (m, 3H).

<139-2> Preparation of (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)pent-4-ynoic acid

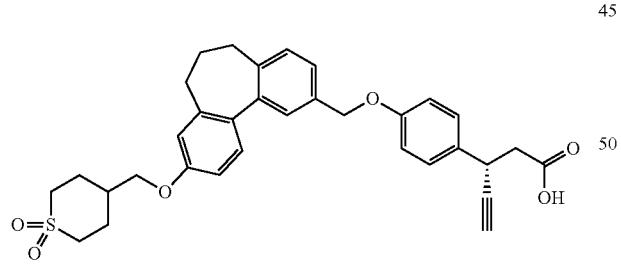

According to the procedures as described in <1-11>, the compound obtained in <139-1> was used to prepare the title compound (white foam, 65.4 mg, 90% yield).

MS m/z 580 [M+Na]$^+$.

$^1$H NMR (300 MHz, CDCl$_3$) δ 7.39 (d, 1H), 7.34-7.30 (m, 4H), 7.24 (d, 1H), 6.96 (d, 2H), 6.84 (dd, 1H), 6.79 (d, 1H), 5.08 (s, 2H), 4.12 (t, 1H), 3.92 (d, 2H), 3.18-3.01 (m, 4H), 2.88 (dd, 1H), 2.76 (dd, 1H), 2.49 (m, 4H), 2.33 (m, 2H), 2.30 (d, 1H), 2.18 (m, 2H), 2.07 (m, 3H).

Example 140

Preparation of (S)-3-(4-((5-ethyl-9-(((R)-tetrahydrofuran-3-yl)oxy)-6,7-dihydro-5H-dibenzo[b,d]azepin-2-yl)methoxy)phenyl)hex-4-ynoic acid <140-1> Preparation of (R)-ethyl 5-ethyl-9-((tetrahydrofuran-3-yl)oxy)-6,7-dihydro-5H-dibenzo[b,d]azepin-2-carboxylate

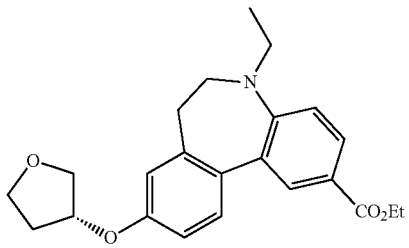 [SMILES: CCOC(=O)c1ccc2c(c1)-c1ccc(O[C@@H]3CCOC3)cc1CCN2CC]

According to the procedures as described in <106-1>, the compound obtained in <44-6> was used to prepare the title compound (white foam, 110 mg, 85% yield).

$^1$H NMR (600 MHz, CDCl$_3$) δ 7.96-7.93 (m, 2H), 7.33 (d, 1H), 7.02 (d, 1H), 6.84 (dd, 1H), 6.75 (d, 1H), 4.99-4.97 (m, 1H), 4.36 (q, 2H), 4.05-3.99 (m, 3H), 3.95-3.90 (m, 1H), 3.53 (t, 2H), 3.17 (q, 2H), 2.71 (t, 2H), 2.27-2.19 (m, 2H), 1.38 (t, 3H), 1.09 (t, 3H).

<140-2> Preparation of (R)-(5-ethyl-9-((tetrahydrofuran-3-yl)oxy)-6,7-dihydro-5H-dibenzo[b,d]azepin-2-yl)methanol

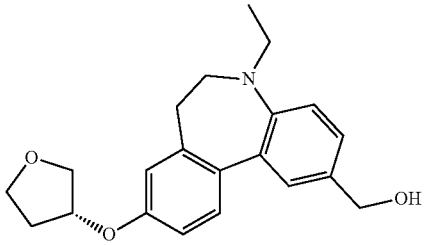 [SMILES: CCN1CCc2cc(O[C@@H]3CCOC3)ccc2-c2cc(CO)ccc21]

According to the procedures as described in <1-9>, the compound obtained in <140-1> was used to prepare the title compound (white foam, 91 mg, 90% yield).

$^1$H NMR (600 MHz, CDCl$_3$) δ 7.31-7.29 (m, 3H), 7.03-7.02 (m, 1H), 6.82 (dd, 1H), 6.76 (d, 1H), 4.99-4.96 (m, 1H), 4.68 (d, 2H), 4.05-3.99 (m, 3H), 3.94-3.91 (m, 1H), 3.42 (t, 2H), 3.10 (q, 2H), 2.65 (t, 2H), 2.24-2.20 (m, 2H), 1.60 (t, 1H), 1.04 (t, 3H).

<140-3> Preparation of (S)-methyl 3-(4-((5-ethyl-9-(((R)-tetrahydrofuran-3-yl)oxy)-6,7-dihydro-5H-dibenzo[b,d]azepin-2-yl) methoxy)phenyl)hex-4-ynoate

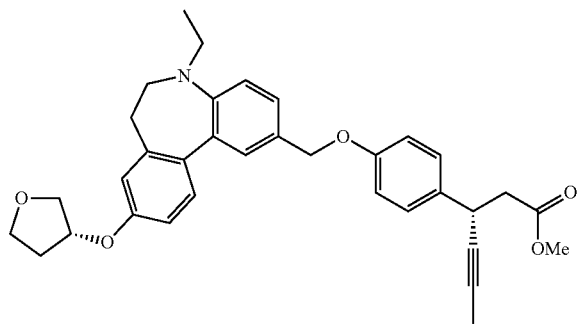 [SMILES: CC#C[C@@H](CC(=O)OC)c1ccc(OCc2ccc3c(c2)-c2ccc(O[C@@H]4CCOC4)cc2CCN3CC)cc1]

According to the procedures as described in <108-3>, <140-2> was used to prepare the title compound (white foam, 55 mg, 38% yield).

$^1$H NMR (600 MHz, CDCl$_3$) δ 7.35-7.33 (m, 2H), 7.31-7.28 (m, 3H), 7.05-7.03 (m, 1H), 6.96-6.94 (m, 2H), 6.82 (dd, 1H), 6.76 (d, 1H), 5.02 (s, 2H), 4.99-4.96 (m, 1H), 4.08-3.99 (m, 4H), 3.94-3.91 (m, 1H), 3.66 (s, 3H), 3.43 (t, 2H), 3.10 (q, 2H), 2.78-2.74 (m, 1H), 2.68-2.64 (m, 3H), 2.24-2.20 (m, 2H), 1.83 (d, 3H), 1.05 (t, 3H).

<140-4> Preparation of (S)-3-(4-((5-ethyl-9-(((R)-tetrahydrofuran-3-yl)oxy)-6,7-dihydro-5H-dibenzo[b,d]azepin-2-yl)methoxy)phenyl)hex-4-ynoic acid

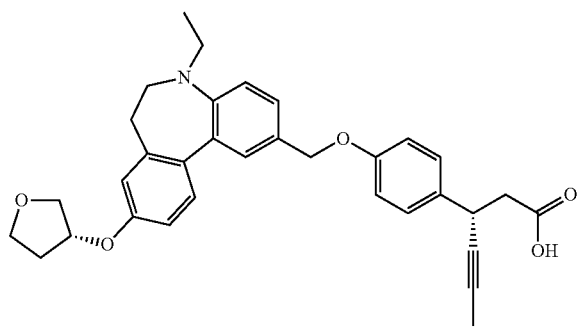 [SMILES: CC#C[C@@H](CC(=O)O)c1ccc(OCc2ccc3c(c2)-c2ccc(O[C@@H]4CCOC4)cc2CCN3CC)cc1]

According to the procedures as described in <1-11>, the compound obtained in <140-3> was used to prepare the title compound (white foam, 45 mg, 90% yield).

MS m/z 524 [M−H]$^-$.

$^1$H NMR (600 MHz, CDCl$_3$) δ 7.35-7.33 (m, 2H), 7.32-7.28 (m, 3H), 7.05-7.03 (m, 1H), 6.97-6.95 (m, 2H), 6.82 (dd, 1H), 6.77 (d, 1H), 5.02 (s, 2H), 4.98-4.96 (m, 1H), 4.06-3.99 (m, 4H), 3.94-3.91 (m, 1H), 3.43 (t, 2H), 3.10 (q, 2H), 2.82-2.78 (m, 1H), 2.73-2.69 (m, 1H), 2.66 (t, 2H), 2.24-2.20 (m, 2H), 1.84 (d, 3H), 1.05 (t, 3H).

Example 141

Preparation of sodium (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylate

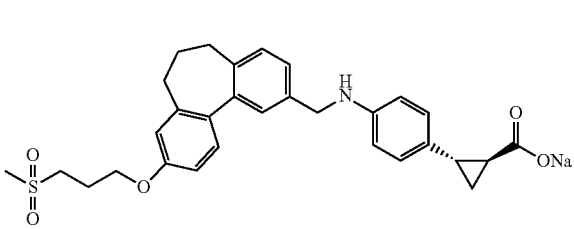

The compound obtained in <6-3> (90.5 mg, 0.174 mmol) was suspended in water (1.9 mL), which was then added with 1N NaOH (183 μL, 0.183 mmol) and stirred. The mixture was diluted with acetonitrile, stirred until the solid was completely dissolved, and then concentrated under reduced pressure to obtain the title compound (white solid, 89.5 mg, 95% yield).

$^1$H NMR (300 MHz, DMSO-d$_6$) δ 7.27 (s, 1H), 7.23-7.7.14 (m, 3H), 6.91-6.86 (m, 2H), 6.70 (d, 2H), 6.47 (d, 2H), 4.19 (s, 2H), 4.10 (t, 2H), 2.47 (m, 5H), 2.35 (m, 4H), 2.14-2.04 (m, 4H), 1.85 (m, 1H), 1.25 (m, 1H), 1.01 (m, 1H), 0.63 (m, 1H).

Example 142

Preparation of sodium 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-yl)acetate

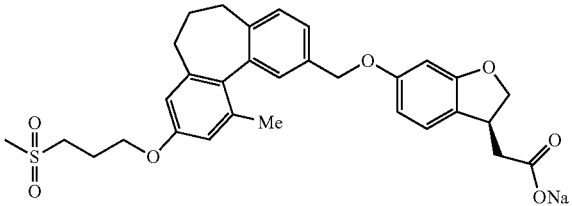

The compound obtained in <7-10> (56.8 mg, 0.103 mmol) was suspended in water (1.2 mL), added with 1N NaOH (108 μL, 0.108 mmol), and then stirred until the solid was completely dissolved. The mixture was diluted with acetonitrile and concentrated under reduced pressure to obtain the title compound (white solid, 56.6 mg, 96% yield).

$^1$H NMR (300 MHz, DMSO-d$_6$) δ 7.26 (m, 3H), 7.04 (d, 1H), 6.76 (d, 1H), 6.69 (d, 1H), 6.41-6.36 (m, 2H), 5.04 (s, 2H), 4.63 (t, 2H), 4.12-4.07 (m, 3H), 3.55 (m, 1H), 3.26 (m, 3H), 3.01 (s, 3H), 2.29 (dd, 2H), 2.15 (m, 6H), 2.05-1.93 (m, 4H).

Example 143

Preparation of sodium (1S,2S)-2-(4-((11-methyl-9-(3-(methylsulfonyl)propoxy)-6,7-dihydrodibenzo[b,d]oxepin-2-yl)methoxy)phenyl)cyclopropanecarboxylate

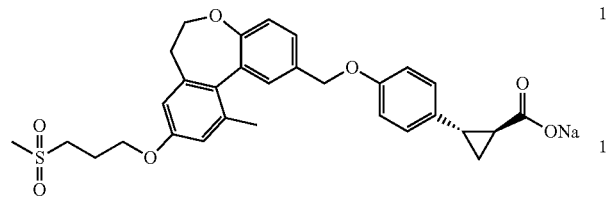

According to the procedures as described in <142>, the compound obtained in <39-2> was used to prepare the title compound (white solid, 55.1 mg, 94% yield).

$^1$H NMR (300 MHz, DMSO-d$_6$) δ 7.34 (m, 2H), 7.08 (d, 1H), 6.90 (d, 2H), 6.84 (d, 2H), 6.79 (m, 2H), 5.05 (s, 2H), 4.29 (m, 2H), 4.10 (t, 2H), 3.26 (m, 2H), 3.01 (s, 3H), 2.58 (m, 2H), 2.22 (s, 3H), 2.13 (m, 2H), 1.95 (m, 1H), 1.33 (m, 1H), 1.07 (m, 1H), 0.07 (m, 1H).

Example 144

Preparation of sodium (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylate

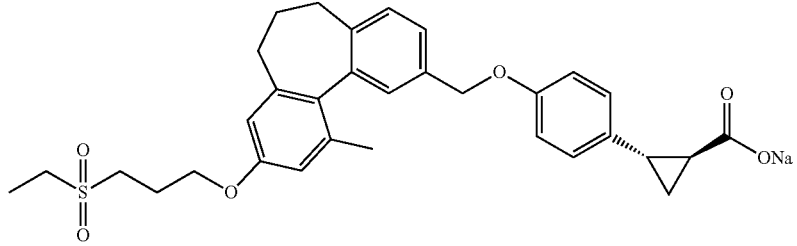

According to the procedures as described in <142>, the compound obtained in <58-2> was used to prepare the title compound (white solid, 72.6 mg, 95% yield).

$^1$H NMR (300 MHz, DMSO-d$_6$) δ 7.31-7.24 (m, 3H), 6.92 (d, 2H), 6.85 (d, 2H), 6.78 (d, 1H), 6.71 (d, 1H), 5.08 (s, 2H), 4.11 (t, 2H), 3.25 (m, 2H), 3.15 (q, 2H), 2.45 (m, 2H), 2.17 (s, 3H), 2.15 (m, 3H), 1.97 (m, 4H), 1.34 (m, 1H), 1.24 (t, 3H), 1.09 (m, 1H), 1.72 (m, 1H).

Example 145

Sodium (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-yl)acetate

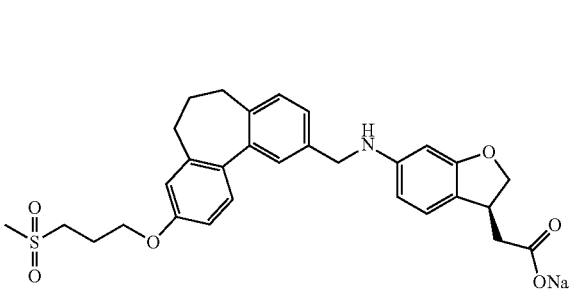

According to the procedures as described in <142>, the compound obtained in <82-2> was used to prepare the title compound (white solid, 65.3 mg, 96% yield).

$^1$H NMR (300 MHz, DMSO-d$_6$) δ 7.27 (s, 1H), 7.24-7.15 (m, 3H), 6.92-6.86 (m, 2H), 6.82 (d, 1H), 6.06-6.00 (m, 2H), 5.96 (s, 1H), 4.53 (t, 1H), 4.19 (d, 2H), 4.10 (t, 2H), 4.00 (t, 1H), 3.45 (m, 1H), 3.27 (m, 2H), 3.01 (s, 3H), 2.35 (m, 4H), 2.25 (dd, 1H), 2.18-2.02 (m, 4H), 1.91 (dd, 1H).

Example 146

Preparation of sodium (S)-3-(4-((9-(3-(methylsulfonyl)propoxy)-6,7-dihydro-5H-dibenzo[a,c][7]annulen-2-yl) methoxy)phenyl)hex-4-ynoate

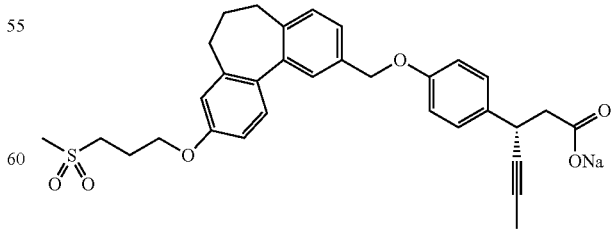

According to the procedures as described in <142>, the compound obtained in <108-10> was used to prepare the title compound (white solid, 45.8 mg, 92% yield).

¹H NMR (300 MHz, DMSO-d₆) δ 7.35-7.20 (m, 6H), 6.92-6.87 (m, 4H), 5.06 (s, 2H), 4.10 (t, 2H), 3.95 (m, 1H), 3.27 (t, 2H), 3.01 (s, 3H), 2.37 (m, 4H), 2.25 (dd, 1H), 2.16-2.06 (m, 5H), 1.71 (d, 3H).

Example 147

Preparation of sodium (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl) hex-4-ynoate

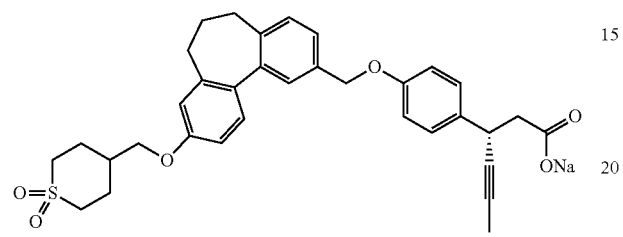

According to the procedures as described in <142>, the compound obtained in <109-4> was used to prepare the title compound (white solid, 18.6 mg, 99% yield).

¹H NMR (300 MHz, DMSO-d₆) δ 7.34-7.20 (m, 6H), 6.91-6.87 (m, 4H), 5.06 (s, 2H), 3.95 (m, 1H), 3.90 (d, 2H), 3.18 (m, 2H), 3.05 (m, 2H), 2.36 (m, 4H), 2.25 (dd, 1H), 2.16-2.04 (m, 6H), 1.79 (m, 2H), 1.74 (d, 3H).

The chemical structures of the compounds prepared in the above Examples 1 to 147 are shown in Table 1 below.

TABLE 1

| No. | Chemical name | Structure |
| --- | --- | --- |
| 1 | 2-((3S)-6-((11-methyl-9-(3-(methylsulfonyl)propoxy)-6,7-dihydro-5H-dibenzo[a,c][7]annulen-4-yl)methoxy)-2,3-dihydrobenzofuran-3-yl)acetic acid | 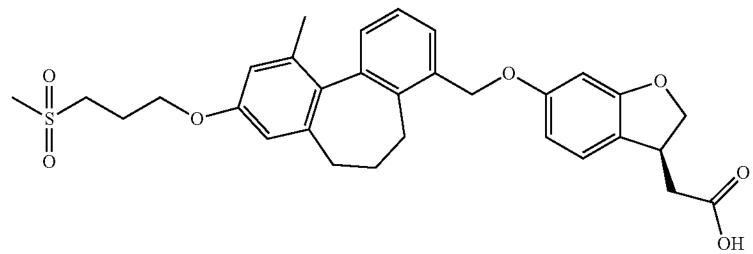 |
| 2 | (1S,2S)-2-(4-((9-(3-(methylsulfonyl)propoxy)-6,7-dihydrodibenzo[b,d]oxepin-2-yl)methoxy)phenyl)cyclopropanecarboxylic acid | 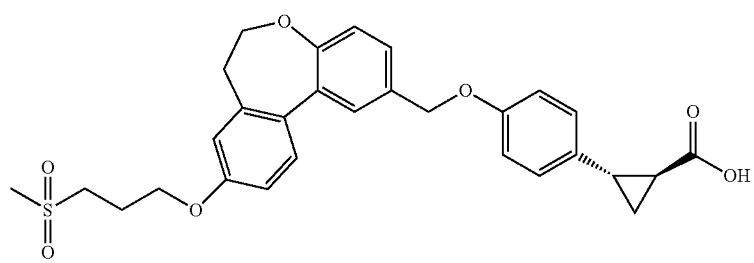 [SMILES: CS(=O)(=O)CCCOc1ccc2c(c1)CCOc1ccc(COc3ccc([C@H]4C[C@@H]4C(=O)O)cc3)cc1-2] |
| 3 | (1S,2S)-2-(4-(((9-(2-ethoxyethoxy)-6,7-dihydrodibenzo[b,d]oxepin-2-yl)methyl)amino)phenyl)cyclopropanecarboxylic acid | 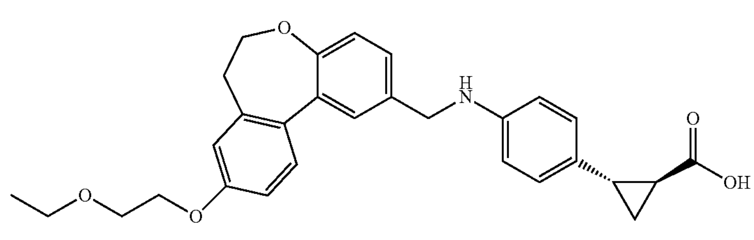 [SMILES: CCOCCOc1ccc2c(c1)CCOc1ccc(CNc3ccc([C@H]4C[C@@H]4C(=O)O)cc3)cc1-2] |

TABLE 1-continued

| No. | Chemical name | Structure |
|---|---|---|
| 4 | (1S,2S)-2-(4-(((9-(3-(methylsulfonyl)propoxy)-6,7-dihydrodibenzo[b,d]oxepin-2-yl)methyl)amino)phenyl)cyclopropanecarboxylic acid | 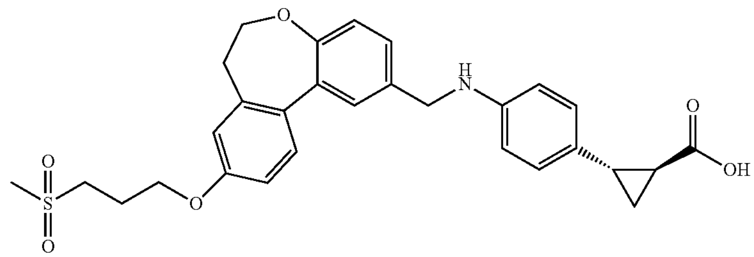 [SMILES: CS(=O)(=O)CCCOc1ccc2c(c1)CCOc1ccc(CNc3ccc([C@H]4C[C@@H]4C(=O)O)cc3)cc1-2] |
| 5 | (S)-2-(6-((9-(3-(methylsulfonyl)propoxy)-6,7-dihydro-5H-dibenzo[a,c][7]annulen-2-yl)methoxy)-2,3-dihydrobenzofuran-3-yl)acetic acid | 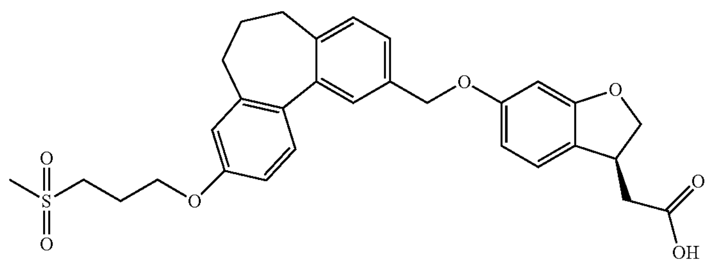 [SMILES: CS(=O)(=O)CCCOc1ccc2c(c1)CCCc1ccc(COc3ccc4c(c3)OC[C@H]4CC(=O)O)cc1-2] |
| 6 | (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylic acid | 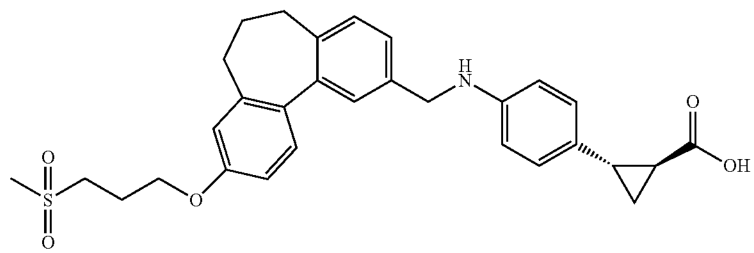 [SMILES: CS(=O)(=O)CCCOc1ccc2c(c1)CCCc1ccc(CNc3ccc([C@H]4C[C@@H]4C(=O)O)cc3)cc1-2] |
| 7 | 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-yl)acetic acid | 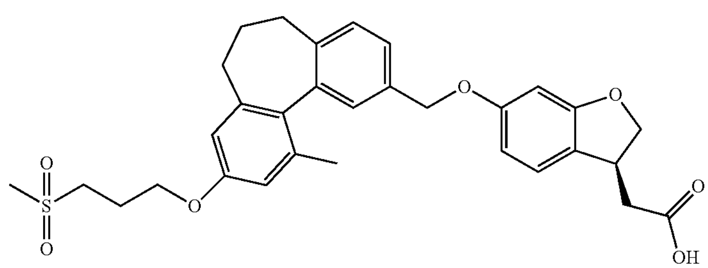 [SMILES: Cc1cc(OCCCS(C)(=O)=O)cc2c1-c1cc(COc3ccc4c(c3)OC[C@H]4CC(=O)O)ccc1CCC2] |
| 8 | (1R,2R)-2-(4-(((10-methyl-8-(3-(methylsulfonyl)propoxy)-6H-benzo[c]chromen-4-yl)methyl)amino)phenyl)cyclopropanecarboxylic acid | 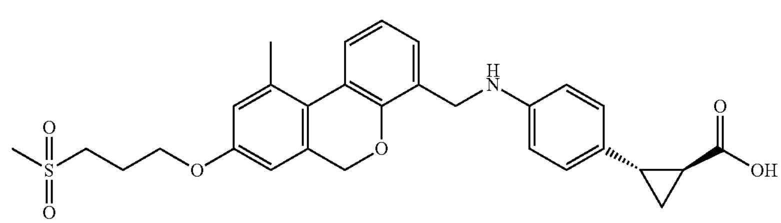 [SMILES: Cc1cc(OCCCS(C)(=O)=O)cc2c1-c1cccc(CNc3ccc([C@H]4C[C@@H]4C(=O)O)cc3)c1OC2] |
| 9 | (1S,2S)-2-(4-(((10-methyl-8-(3-(methylsulfonyl)propoxy)-6H-benzo[c]chromen-2-yl)methyl)amino)phenyl)cyclopropanecarboxylic acid | 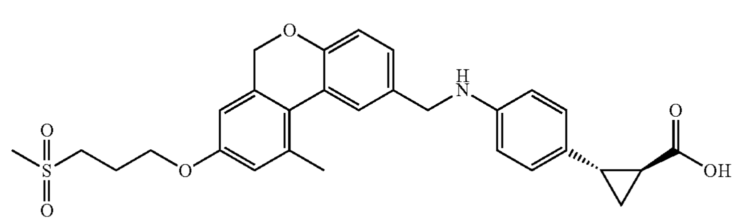 [SMILES: Cc1cc(OCCCS(C)(=O)=O)cc2c1-c1cc(CNc3ccc([C@H]4C[C@@H]4C(=O)O)cc3)ccc1OC2] |

TABLE 1-continued

| No. | Chemical name |
|---|---|
| 10 | (S)-2-(6-((5-methyl-7-(3-(methylsulfonyl)propoxy)-9,10-dihydrophenanthren-1-yl)methoxy)-2,3-dihydrobenzofuran-3-yl) acetic acid |
| 11 | (S)-2-(6-((5-methyl-7-(3-(methylsulfonyl)propoxy)-9,10-dihydrophenanthren-3-yl)methoxy)-2,3-dihydrobenzofuran-3-yl) acetic acid |
| 12 | (S)-2-(6-((7-(2-ethoxyethoxy)-5-methyl-9,10-dihydrophenanthren-3-yl)methoxy)-2,3-dihydrobenzofuran-3-yl) acetic acid |
| 13 | 2-((3S)-6-((11-methyl-9-(3-(methylsulfonyl)propoxy)-6,7-dihydrodibenzo[b,d]oxepin-4-yl)methoxy)-2,3-dihydrobenzofuran-3-yl) acetic acid |
| 14 | 2-((3S)-6-((11-methyl-9-(3-(methylsulfonyl)propoxy)-6,7-dihydrodibenzo[b,d]oxepin-2-yl)methoxy)-2,3-dihydrobenzofuran-3-yl)acetic acid |
| 15 | (1S,2S)-2-(4-(((11-methyl-9-(3-(methylsulfonyl)propoxy)-6,7-dihydrodibenzo[b,d]oxepin-2-yl)methyl) amino)phenyl) cyclopropanecarboxylic acid |

TABLE 1-continued

| No. | Chemical name | Structure |
| --- | --- | --- |
| 16 | (1S,2S)-2-(4-(((8-(2-ethoxyethoxy)-10-methyl-6H-benzo[c]chromen-2-yl)methyl)amino)phenyl)cyclopropanecarboxylic acid | 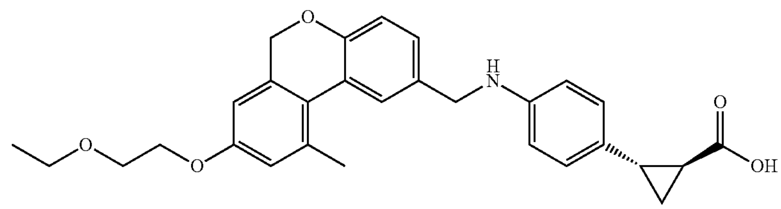 [SMILES: CCOCCOc1cc(C)c2c(c1)COc1ccc(CNc3ccc([C@H]4C[C@@H]4C(=O)O)cc3)cc1-2] |
| 17 | (S)-2-(6-((8-(2-ethoxyethoxy)-10-methyl-6H-benzo[c]chromen-2-yl)methoxy)-2,3-dihydrobenzofuran-3-yl)acetic acid | 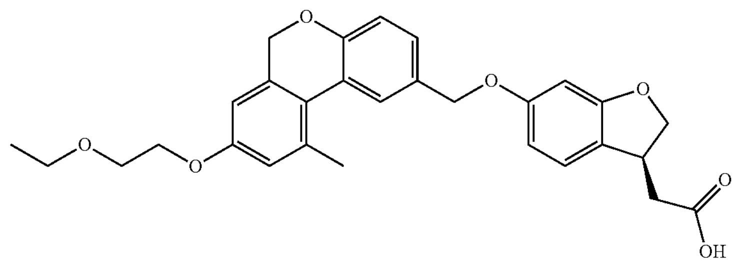 [SMILES: CCOCCOc1cc(C)c2c(c1)COc1ccc(COc3ccc4c(c3)OC[C@H]4CC(=O)O)cc1-2] |
| 18 | (1S,2S)-2-(4-(((9-(3-(methylsulfonyl)propoxy)-5,7-dihydrodibenzo[c,e]oxepin-2-yl)methyl)amino)phenyl)cyclopropanecarboxylic acid | 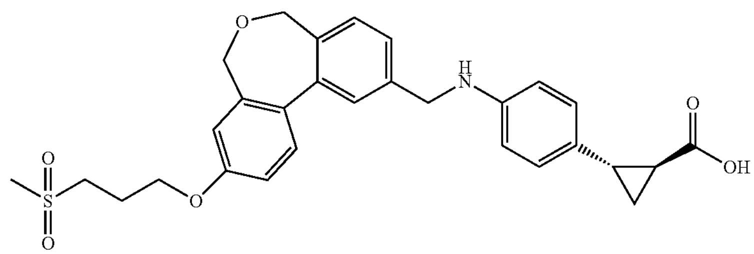 |
| 19 | (1S,2S)-2-(4-(((11-methyl-9-(3-(methylsulfonyl)propoxy)-5,7-dihydrodibenzo[c,e]oxepin-4-yl)methyl)amino)phenyl)cyclopropanecarboxylic acid | 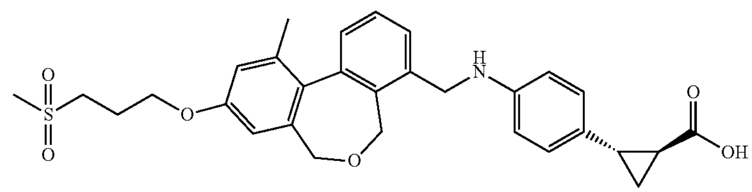 [SMILES: Cc1cc(OCCCS(C)(=O)=O)cc2c1-c1cccc(CNc3ccc([C@H]4C[C@@H]4C(=O)O)cc3)c1COC2] |
| 20 | (S)-2-(6-((9-(3-(methylsulfonyl)propoxy)-5,7-dihydrodibenzo[c,e]oxepin-2-yl)methoxy)-2,3-dihydrobenzofuran-3-yl)acetic acid | 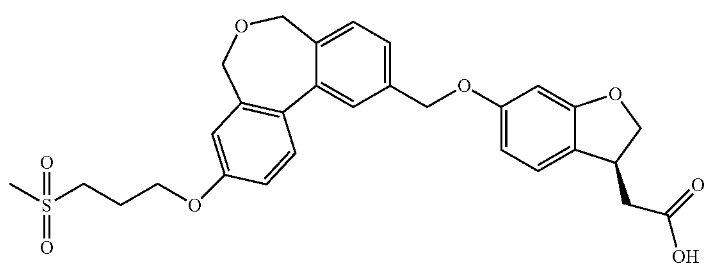 [SMILES: CS(=O)(=O)CCCOc1ccc2c(c1)COCc1ccc(COc3ccc4c(c3)OC[C@H]4CC(=O)O)cc1-2] |
| 21 | (1S,2S)-2-(4-(((3-(3-(methylsulfonyl)propoxy)-6,7-dihydrodibenzo[b,d]oxepin-10-yl)methyl)amino)phenyl)cyclopropanecarboxylic acid | 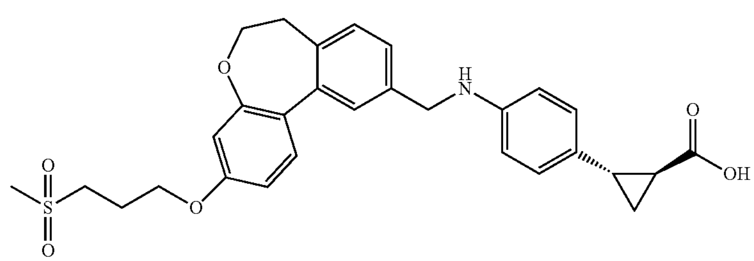 |

TABLE 1-continued

| No. | Chemical name |
|---|---|
| 22 | (1S,2S)-2-(4-(((9-(2-ethoxyethoxy)-5,7-dihydrodibenzo[c,e]oxepin-2-yl)methyl)amino)phenyl)cyclopropanecarboxylic acid |
| 23 | (S)-2-(6-((9-(2-ethoxyethoxy)-5,7-dihydrodibenzo[c,e]oxepin-2-yl)methoxy)-2,3-dihydrobenzofuran-3-yl)acetic acid |
| 24 | (1S,2S)-2-(4-((9-(3-(methylsulfonyl)propoxy)-5,7-dihydrodibenzo[c,e]oxepin-2-yl)methoxy)phenyl)cyclopropanecarboxylic acid |
| 25 | (1S,2S)-2-(4-((9-(3-(methylsulfonyl)propoxy)-6,7-dihydro-5H-dibenzo[a,c][7]annulen-2-yl)methoxy)phenyl)cyclopropanecarboxylic acid |
| 26 | (S)-2-(6-((10-methyl-8-(3-(methylsulfonyl)propoxy)-6H-benzo[c]chromen-2-yl)methoxy)-2,3-dihydrobenzofuran-3-yl)acetic acid |
| 27 | (S)-2-(6-((9-(2-ethoxyethoxy)-6,7-dihydro-5H-dibenzo[a,c][7]annulen-2-yl)methoxy)-2,3-dihydrobenzofuran-3-yl)acetic acid |

TABLE 1-continued

| No. | Chemical name |
|---|---|
| 28 | (1S,2S)-2-(4-(((9-(2-ethoxyethoxy)-6,7-dihydro-5H-dibenzo[a,c][7]annulen-2-yl)methyl)amino)phenyl)cyclopropanecarboxylic acid |
| 29 | (1S,2S)-2-(4-(((11-methyl-9-(3-(methylsulfonyl)propoxy)-6,7-dihydro-5H-dibenzo[a,c][7]annulen-2-yl)methyl)amino)phenyl)cyclopropanecarboxylic acid |
| 30 | (1S,2S)-2-(4-((10-methyl-8-(3-(methylsulfonyl)propoxy)-6H-benzo[c]chromen-2-yl)methoxy)phenyl)cyclopropanecarboxylic acid |
| 31 | (1S,2S)-2-(4-((5-methyl-7-(3-(methylsulfonyl)propoxy)-9,10-dihydrophenanthren-3-yl)methoxy)phenyl)cyclopropanecarboxylic acid |
| 32 | (S)-2-(6-((9-(3-(methylsulfonyl)propoxy)-6,7-dihydrodibenzo[b,d]oxepin-2-yl)methoxy)-2,3-dihydrobenzofuran-3-yl)acetic acid |
| 33 | 2-((3S)-6-((11-methyl-9-(3-(methylsulfonyl)propoxy)-5,7-dihydrodibenzo[c,e]oxepin-2-yl)methoxy)-2,3-dihydrobenzofuran-3-yl)acetic acid |

TABLE 1-continued

| No. | Chemical name |
|---|---|
| 34 | (1S,2S)-2-(4-(((11-methyl-9-(3-(methylsulfonyl)propoxy)-5,7-dihydrodibenzo[c,e]oxepin-2-yl)methyl)amino)phenyl)cyclopropanecarboxylic acid |
| 35 | 2-((3S)-6-((9-(2-ethoxyethoxy)-11-methyl-6,7-dihydro-5H-dibenzo[a,c][7]annulen-2-yl)methoxy)-2,3-dihydrobenzofuran-3-yl)acetic acid |
| 36 | 2-((3S)-6-((9-((1,1-dioxidotetrahydro-2H-thiopyran-4-yl)oxy)-11-methyl-6,7-dihydrodibenzo[b,d]oxepin-2-yl)methoxy)-2,3-dihydrobenzofuran-3-yl)acetic acid |
| 37 | 2-((3S)-6-((9-(2-(1,1-dioxidothiomorpholino)ethoxy)-11-methyl-6,7-dihydrodibenzo[b,d]oxepin-2-yl)methoxy)-2,3-dihydrobenzofuran-3-yl)acetic acid |
| 38 | 2-((3S)-6-((9-(3-(ethylsulfonyl)propoxy)-11-methyl-6,7-dihydrodibenzo[b,d]oxepin-2-yl)methoxy)-2,3-dihydrobenzofuran-3-yl)acetic acid |
| 39 | (1S,2S)-2-(4-((11-methyl-9-(3-(methylsulfonyl)propoxy)-6,7-dihydrodibenzo[b,d]oxepin-2-yl)methoxy)phenyl)cyclopropanecarboxylic acid |

TABLE 1-continued

| No. | Chemical name | Structure |
|-----|---------------|-----------|
| 40 | (1S,2S)-2-(2-fluoro-4-((11-methyl-9-(3-(methylsulfonyl)propoxy)-6,7-dihydrodibenzo[b,d]oxepin-2-yl)methoxy)phenyl)cyclopropanecarboxylic acid | 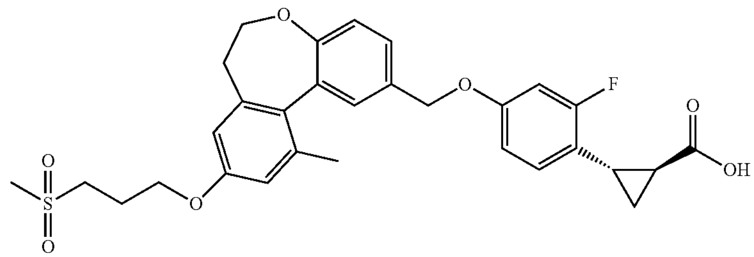 [SMILES: Cc1cc(OCCCS(C)(=O)=O)cc2c1-c1cc(COc3ccc([C@H]4C[C@@H]4C(=O)O)c(F)c3)ccc1OCC2] |
| 41 | (1S,2S)-2-(4-((9-(3-(ethylsulfonyl)propoxy)-11-methyl-6,7-dihydrodibenzo[b,d]oxepin-2-yl)methoxy)-2-fluorophenyl)cyclopropanecarboxylic acid | 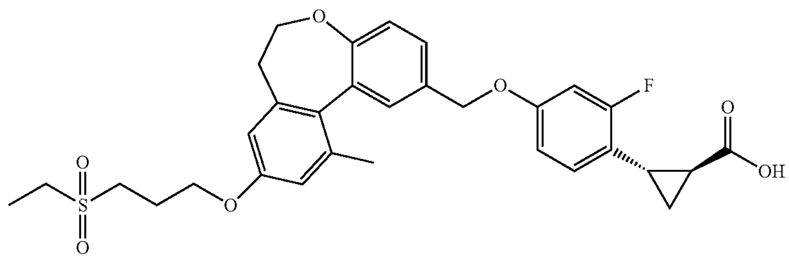 [SMILES: CCS(=O)(=O)CCCOc1cc(C)c2c(c1)CCOc1ccc(COc3ccc([C@H]4C[C@@H]4C(=O)O)c(F)c3)cc1-2] |
| 42 | (S)-2-(6-((3-(3-(methylsulfonyl)propoxy)-6,7-dihydrodibenzo[b,d]oxepin-10-yl)methoxy)-2,3-dihydrobenzofuran-3-yl)acetic acid | 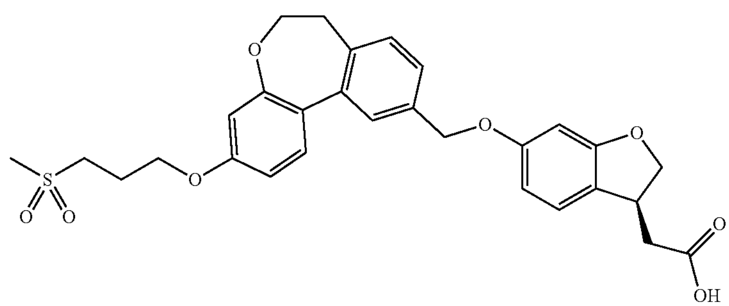 [SMILES: CS(=O)(=O)CCCOc1ccc2c(c1)OCCc1ccc(COc3ccc4c(c3)OC[C@H]4CC(=O)O)cc1-2] |
| 43 | (S)-2-(6-((6,6-dimethyl-9-(3-(methylsulfonyl)propoxy)-6,7-dihydrodibenzo[b,d]oxepin-2-yl)methoxy)-2,3-dihydrobenzofuran-3-yl)acetic acid | 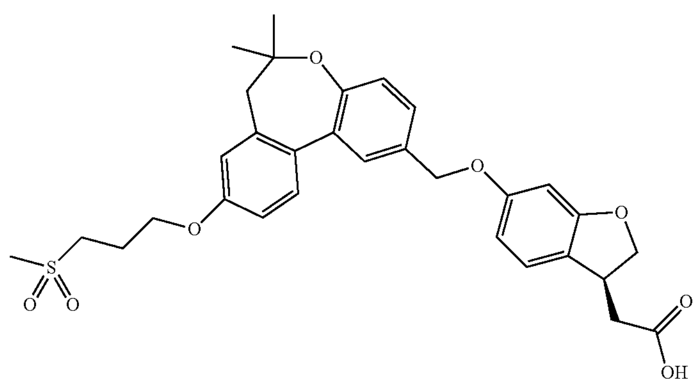 [SMILES: CC1(C)Cc2cc(OCCCS(C)(=O)=O)ccc2-c2cc(COc3ccc4c(c3)OC[C@H]4CC(=O)O)ccc2O1] |
| 44 | (S)-2-(6-((5-ethyl-9-(3-(methylsulfonyl)propoxy)-6,7-dihydro-5H-dibenzo[b,d]azepin-2-yl)methoxy)-2,3-dihydrobenzofuran-3-yl)acetic acid | 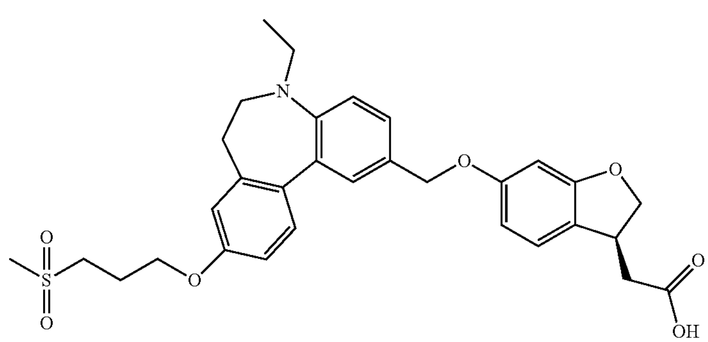 [SMILES: CCN1CCc2cc(OCCCS(C)(=O)=O)ccc2-c2cc(COc3ccc4c(c3)OC[C@H]4CC(=O)O)ccc21] |

TABLE 1-continued

| No. | Chemical name |
|---|---|
| 45 | (1S,2S)-2-(4-((5-ethyl-9-(3-(methylsulfonyl)propoxy)-6,7-dihydro-5H-dibenzo[b,d]azepin-2-yl)methoxy)phenyl)cyclopropanecarboxylic acid |
| 46 | 2-((3S)-6-((9-((4-hydroxy-1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid |
| 47 | 2-((3S)-6-((9-((1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid |
| 48 | (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)phenyl)cyclopropanecarboxylic acid |
| 49 | (1S,2S)-2-(4-((9-(3-(ethylsulfonyl)propoxy)-11-methyl-6,7-dihydrodibenzo[b,d]oxepin-2-yl)methoxy)phenyl)cyclopropanecarboxylic acid |

TABLE 1-continued

| No. | Chemical name |
|---|---|
| 50 | (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)-2-fluorophenyl)cyclopropanecarboxylic acid |
| 51 | (1S,2S)-2-{2-fluoro-4-[9-(4-hydroxy-1,1-dioxido-hexahydro-thiopyran-4-ylmethoxy)-11-methyl-6,7-dihydro-5-oxa-dibenzo[a,c]cyclohepten-2-ylmethoxy]-phenyl}-cyclopropanecarboxylic acid |
| 52 | (1S,2S)-2-(4-(((9-((1,1-dioxidotetrahydro-2H-thiopyran-4-yl)oxy)-11-methyl-6,7-dihydrodibenzo[b,d]oxepin-2-yl)methyl)amino)-2-fluorophenyl)cyclopropanecarboxylic acid |
| 53 | (1S,2S)-2-(4-(((9-(3-(ethylsulfonyl)propoxy)-11-methyl-6,7-dihydrodibenzo[b,d]oxepin-2-yl)methyl)amino)-2-fluorophenyl)cyclopropanecarboxylic acid |
| 54 | 2-((3S)-6-((6,6,11-trimethyl-9-(3-(methylsulfonyl)propoxy)-6,7-dihydrodibenzo[b,d]oxepin-2-yl)methoxy)-2,3-dihydrobenzofuran-3-yl)acetic acid |

TABLE 1-continued

| No. | Chemical name | Structure |
|---|---|---|
| 55 | 2-((3S)-6-((9-((1,1-dioxidotetrahydro-2H-thiopyran-4-yl)oxy)-11-methyl-6,7-dihydro-5H-dibenzo[a,c][7]annulen-2-yl)methoxy)-2,3-dihydrobenzofuran-3-yl)acetic acid | 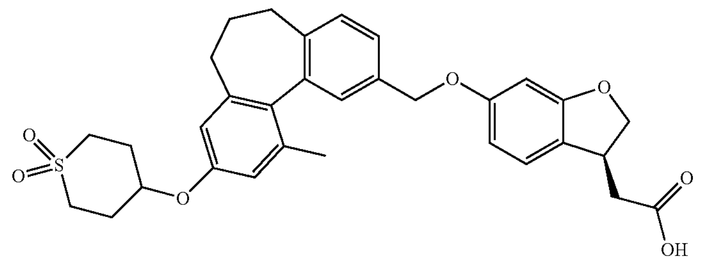 [SMILES: Cc1cc(OC2CCS(=O)(=O)CC2)cc2c1-c1cc(COc3ccc4c(c3)OC[C@H]4CC(=O)O)ccc1CCC2] |
| 56 | 2-((3S)-6-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)-2,3-dihydro-benzofuran-3-yl)acetic acid | 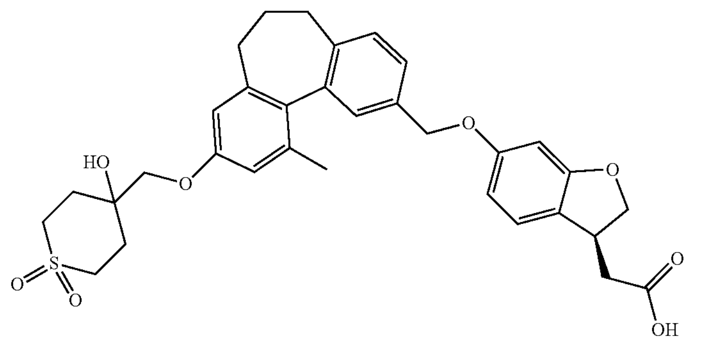 [SMILES: Cc1cc(OCC2(O)CCS(=O)(=O)CC2)cc2c1-c1cc(COc3ccc4c(c3)OC[C@H]4CC(=O)O)ccc1CCC2] |
| 57 | 2-((3S)-6-((9-(3-(ethylsulfonyl)propoxy)-11-methyl-6,7-dihydro-5H-dibenzo[a,c][7]annulen-2-yl)methoxy)-2,3-dihydrobenzofuran-3-yl)acetic acid | 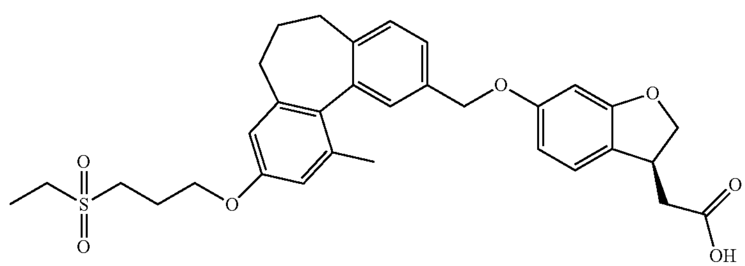 [SMILES: CCS(=O)(=O)CCCOc1cc(C)c2c(c1)CCCc1ccc(COc3ccc4c(c3)OC[C@H]4CC(=O)O)cc1-2] |
| 58 | (1S,2S)-2-(4-((11-methyl-9-(3-(methylsulfonyl)propoxy)-6,7-dihydro-5H-dibenzo[a,c][7]annulen-2-yl)methoxy)phenyl)cyclopropanecarboxylic acid | 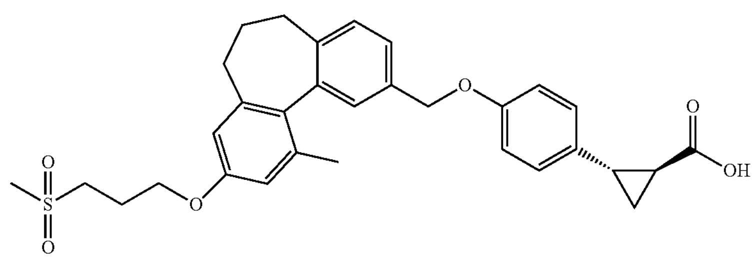 [SMILES: Cc1cc(OCCCS(C)(=O)=O)cc2c1-c1cc(COc3ccc([C@H]4C[C@@H]4C(=O)O)cc3)ccc1CCC2] |
| 59 | (1S,2S)-2-(4-((9-((1,1-dioxidotetrahydro-2H-thiopyran-4-yl)oxy)-11-methyl-6,7-dihydro-5H-dibenzo[a,c][7]annulen-2-yl)methoxy)phenyl)cyclopropanecarboxylic acid | 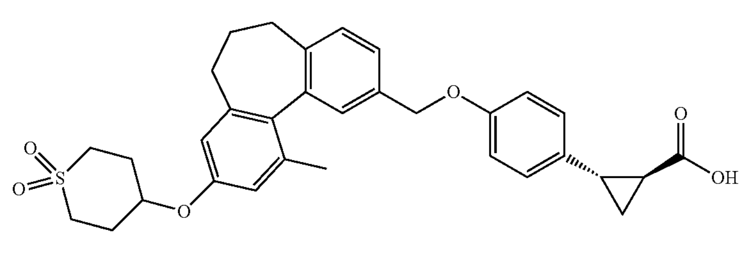 [SMILES: Cc1cc(OC2CCS(=O)(=O)CC2)cc2c1-c1cc(COc3ccc([C@H]4C[C@@H]4C(=O)O)cc3)ccc1CCC2] |

TABLE 1-continued

| No. | Chemical name | Structure |
|---|---|---|
| 60 | (1S,2S)-2-(4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid | 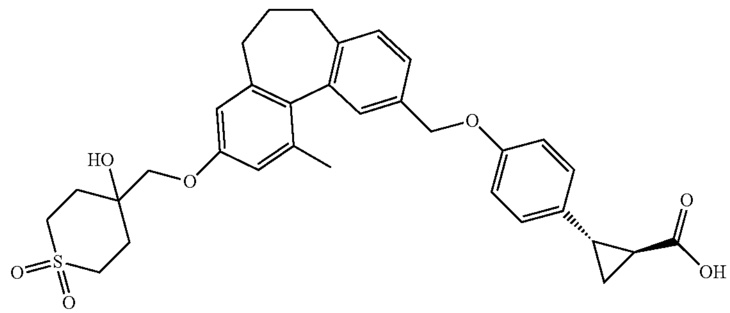 [SMILES: Cc1cc(OCC2(O)CCS(=O)(=O)CC2)cc2c1-c1cc(COc3ccc([C@H]4C[C@@H]4C(=O)O)cc3)ccc1CCC2] |
| 61 | (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylic acid | 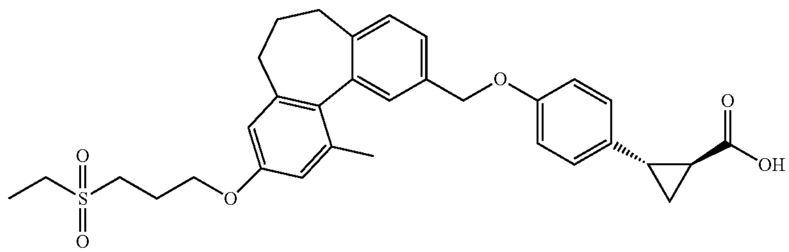 [SMILES: CCS(=O)(=O)CCCOc1cc(C)c2c(c1)CCCc1ccc(COc3ccc([C@H]4C[C@@H]4C(=O)O)cc3)cc1-2] |
| 62 | (1S,2S)-2-(2-fluoro-4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid | 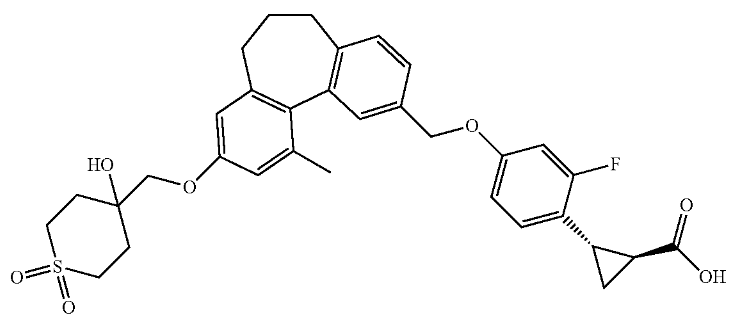 [SMILES: Cc1cc(OCC2(O)CCS(=O)(=O)CC2)cc2c1-c1cc(COc3ccc([C@H]4C[C@@H]4C(=O)O)c(F)c3)ccc1CCC2] |
| 63 | (1S,2S)-2-(2-fluoro-4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid | 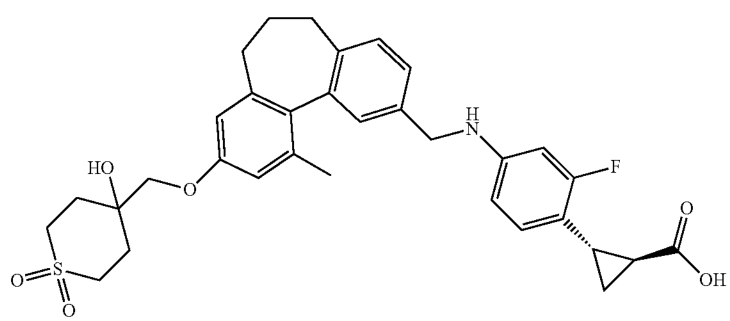 [SMILES: Cc1cc(OCC2(O)CCS(=O)(=O)CC2)cc2c1-c1cc(CNc3ccc([C@H]4C[C@@H]4C(=O)O)c(F)c3)ccc1CCC2] |
| 64 | (S)-2-(6-((9-((1,1-dioxidotetrahydro-2H-thiopyran-4-yl)oxy)-6,7-dihydro-5H-dibenzo[a,c][7]annulen-2-yl)methoxy)-2,3-dihydrobenzofuran-3-yl)acetic acid | 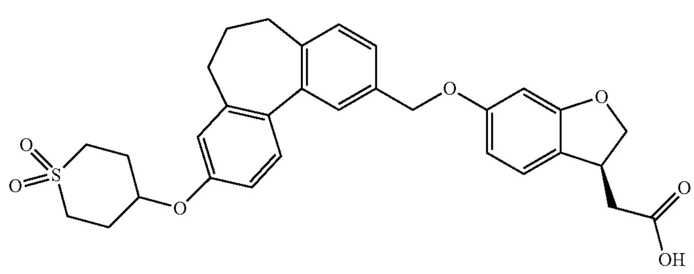 [SMILES: O=C(O)C[C@@H]1COc2cc(OCc3ccc4c(c3)-c3ccc(OC5CCS(=O)(=O)CC5)cc3CCC4)ccc21] |

TABLE 1-continued

| No. | Chemical name | Structure |
|---|---|---|
| 65 | (S)-2-(6-((9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid | 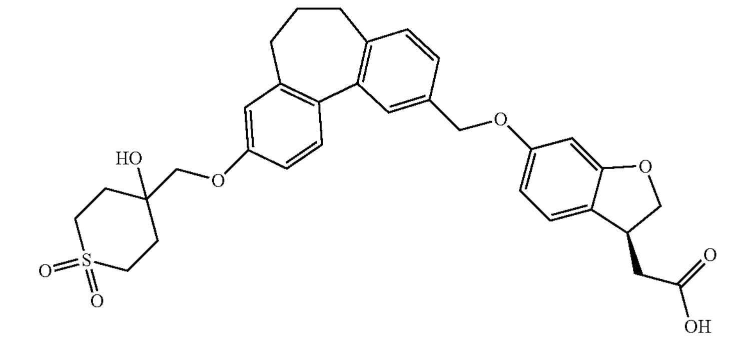 [SMILES: O=C(O)C[C@@H]1COc2cc(OCc3ccc4c(c3)-c3ccc(OCC5(O)CCS(=O)(=O)CC5)cc3CCC4)ccc21] |
| 66 | (S)-2-(6-((9-(3-(ethylsulfonyl)propoxy)-6,7-dihydro-5H-dibenzo[a,c][7]annulen-2-yl)methoxy)-2,3-dihydrobenzofuran-3-yl)acetic acid | 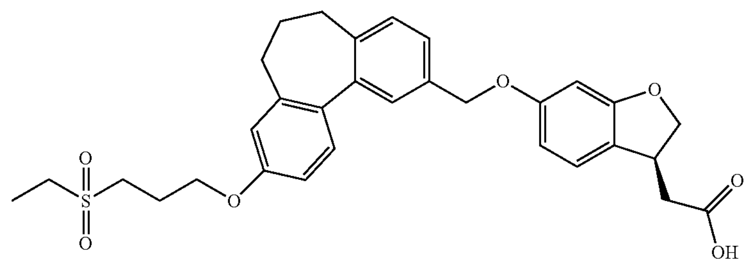 [SMILES: CCS(=O)(=O)CCCOc1ccc2c(c1)CCCc1ccc(COc3ccc4c(c3)OC[C@H]4CC(=O)O)cc1-2] |
| 67 | (1S,2S)-2-(4-((9-((1,1-dioxidotetrahydro-2H-thiopyran-4-yl)oxy)-6,7-dihydro-5H-dibenzo[a,c][7]annulen-2-yl)methoxy)phenyl)cyclopropanecarboxylic acid | 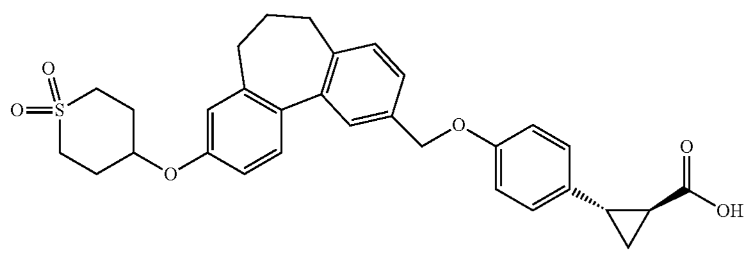 [SMILES: O=C(O)[C@H]1C[C@@H]1c1ccc(OCc2ccc3c(c2)-c2ccc(OC4CCS(=O)(=O)CC4)cc2CCC3)cc1] |
| 68 | (1S,2S)-2-(4-((9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid | 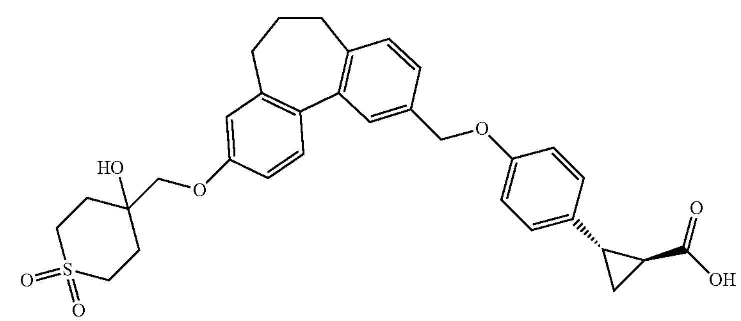 [SMILES: O=C(O)[C@H]1C[C@@H]1c1ccc(OCc2ccc3c(c2)-c2ccc(OCC4(O)CCS(=O)(=O)CC4)cc2CCC3)cc1] |
| 69 | (1S,2S)-2-(4-((9-(3-(ethylsulfonyl)propoxy)-6,7-dihydro-5H-dibenzo[a,c][7]annulen-2-yl)methoxy)phenyl)cyclopropanecarboxylic acid | 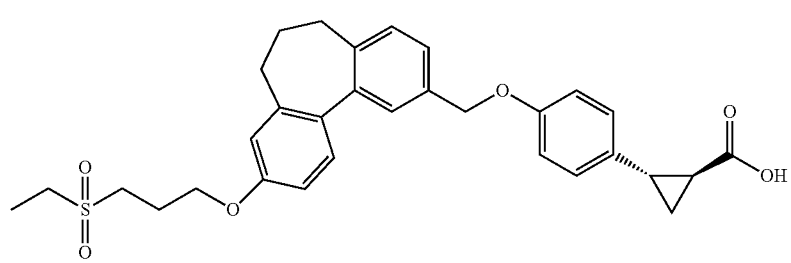 [SMILES: CCS(=O)(=O)CCCOc1ccc2c(c1)CCCc1ccc(COc3ccc([C@H]4C[C@@H]4C(=O)O)cc3)cc1-2] |

TABLE 1-continued

| No. | Chemical name | Structure |
|---|---|---|
| 70 | (1S,2S)-2-(4-(((9-((1,1-dioxidotetrahydro-2H-thiopyran-4-yl)oxy)-6,7-dihydro-5H-dibenzo[a,c][7]annulen-2-yl)methyl)amino)phenyl)cyclopropanecarboxylic acid | 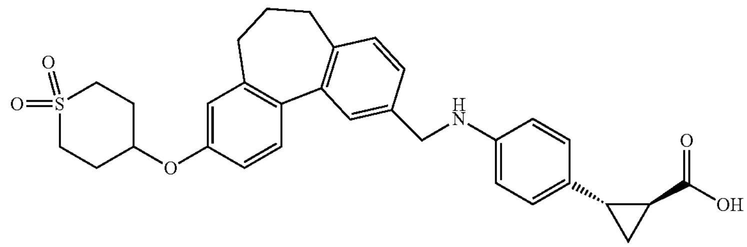 [SMILES: O=C(O)[C@H]1C[C@@H]1c1ccc(NCc2ccc3c(c2)-c2ccc(OC4CCS(=O)(=O)CC4)cc2CCC3)cc1] |
| 71 | (1S,2S)-2-(4-(((9-((4-hydroxy-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid | 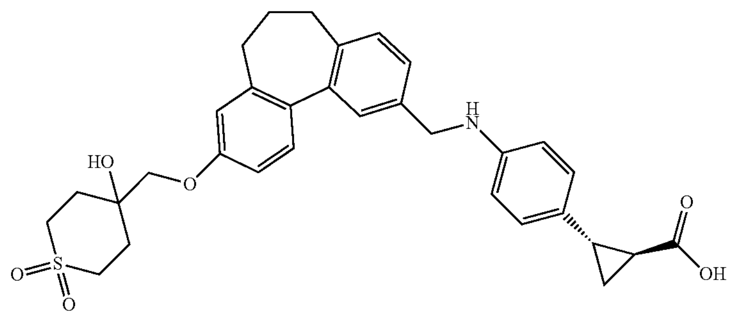 [SMILES: O=C(O)[C@H]1C[C@@H]1c1ccc(NCc2ccc3c(c2)-c2ccc(OCC4(O)CCS(=O)(=O)CC4)cc2CCC3)cc1] |
| 72 | (1S,2S)-2-(4-(((9-(3-(ethylsulfonyl)propoxy)-6,7-dihydro-5H-dibenzo[a,c][7]annulen-2-yl)methyl)amino)phenyl)cyclopropanecarboxylic acid | 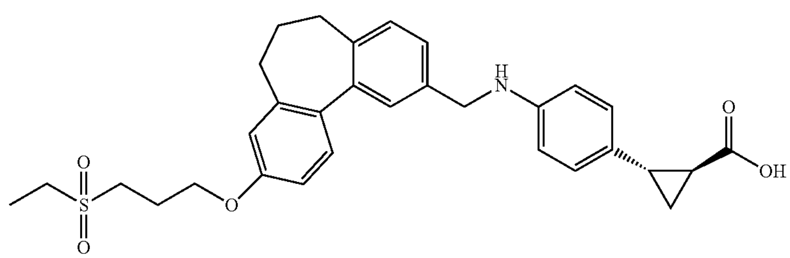 [SMILES: CCS(=O)(=O)CCCOc1ccc2c(c1)CCCc1ccc(CNc3ccc([C@H]4C[C@@H]4C(=O)O)cc3)cc1-2] |
| 73 | (1S,2S)-2-(4-(((9-((1,1-dioxidotetrahydro-2H-thiopyran-4-yl)oxy)-11-methyl-6,7-dihydrodibenzo[b,d]oxepin-2-yl)methyl)amino)phenyl)cyclopropanecarboxylic acid | 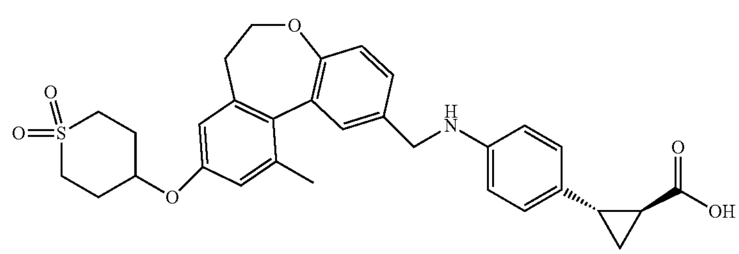 [SMILES: Cc1cc(OC2CCS(=O)(=O)CC2)cc2c1-c1cc(CNc3ccc([C@H]4C[C@@H]4C(=O)O)cc3)ccc1OCC2] |
| 74 | (1S,2S)-2-(4-(((9-(3-(ethylsulfonyl)propoxy)-11-methyl-6,7-dihydro-5H-dibenzo[a,c][7]annulen-2-yl)methyl)amino)phenyl)cyclopropanecarboxylic acid | 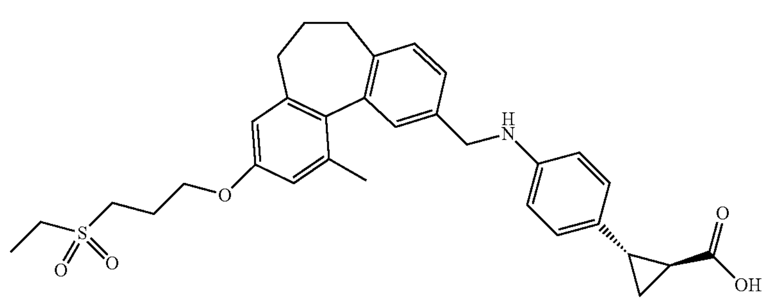 [SMILES: CCS(=O)(=O)CCCOc1cc(C)c2c(c1)CCCc1ccc(CNc3ccc([C@H]4C[C@@H]4C(=O)O)cc3)cc1-2] |

TABLE 1-continued

| No. | Chemical name | Structure |
|---|---|---|
| 75 | (1S,2S)-2-(4-(((9-((1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid | 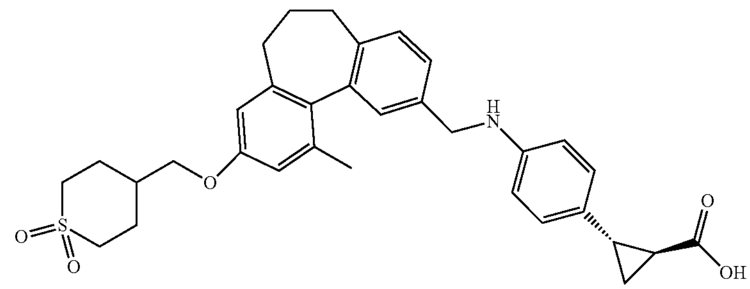 [SMILES: Cc1cc(OCC2CCS(=O)(=O)CC2)cc2c1-c1cc(CNc3ccc([C@H]4C[C@@H]4C(=O)O)cc3)ccc1CCC2] |
| 76 | (1S,2S)-2-(4-(((9-((1,1-dioxidotetrahydro-2H-thiopyran-4-yl)oxy)-11-methyl-6,7-dihydro-5H-dibenzo[a,c][7]annulen-2-yl)methyl)amino)phenyl)cyclopropanecarboxylic acid | 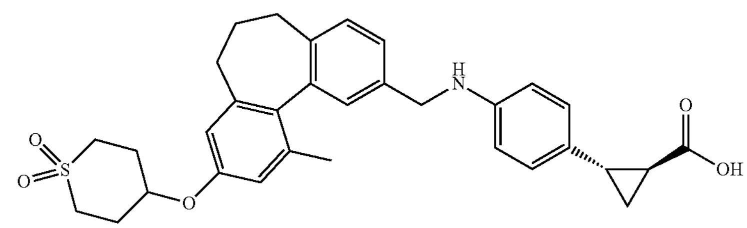 [SMILES: Cc1cc(OC2CCS(=O)(=O)CC2)cc2c1-c1cc(CNc3ccc([C@H]4C[C@@H]4C(=O)O)cc3)ccc1CCC2] |
| 77 | (1S,2S)-2-(4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid | 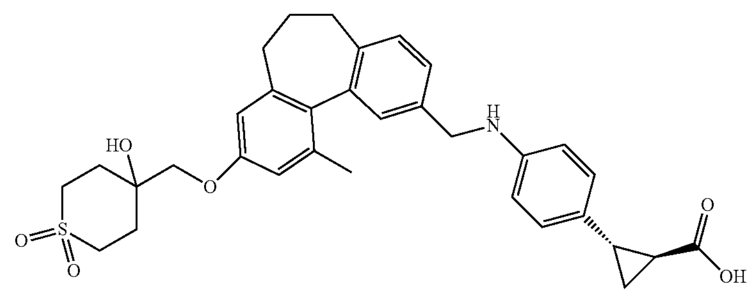 [SMILES: Cc1cc(OCC2(O)CCS(=O)(=O)CC2)cc2c1-c1cc(CNc3ccc([C@H]4C[C@@H]4C(=O)O)cc3)ccc1CCC2] |
| 78 | (1S,2S)-2-(4-(((9-((1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid | 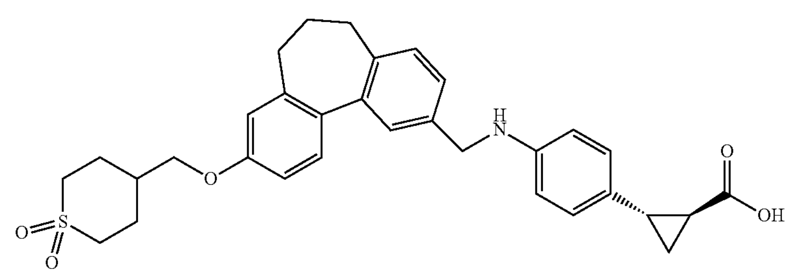 [SMILES: O=C(O)[C@H]1C[C@@H]1c1ccc(NCc2ccc3c(c2)-c2ccc(OCC4CCS(=O)(=O)CC4)cc2CCC3)cc1] |
| 79 | 2-((S)-6-(((R)-6-methyl-9-(3-(methylsulfonyl)propoxy)-6,7-dihydrodibenzo[b,d]oxepin-2-yl)methoxy)-2,3-dihydrobenzofuran-3-yl)acetic acid | 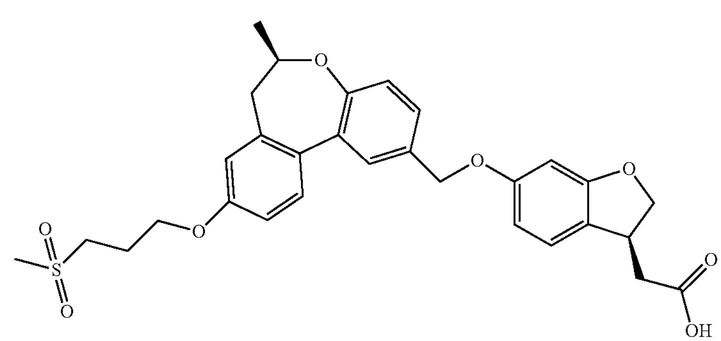 [SMILES: C[C@@H]1Cc2cc(OCCCS(C)(=O)=O)ccc2-c2cc(COc3ccc4c(c3)OC[C@H]4CC(=O)O)ccc2O1] |

TABLE 1-continued

| No. | Chemical name |
|---|---|
| 80 | (S)-2-(6-((9-(3-(methylsulfonyl)propoxy)dibenzo[d,f][1,3]dioxepin-2-yl)methoxy)-2,3-dihydrobenzofuran-3-yl)acetic acid |
| 81 | 2-((3S)-6-((1-methyl-3-morpholino-6,7-dihydro-5H-benzo[3,4]cyclohepta[1,2-d]pyrimidin-10-yl)methoxy)-2,3-dihydrobenzofuran-3-yl)acetic acid |
| 82 | (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-yl)acetic acid |
| 83 | (S)-2-(6-(((9-((1,1-dioxidotetrahydro-2H-thiopyran-4-yl)methoxy)-6,7-dihydro-5H-dibenzo[a,c][7]annulen-2-yl)methyl)amino)-2,3-dihydrobenzofuran-3-yl)acetic acid |
| 84 | (S)-2-(6-((9-((1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid |

TABLE 1-continued

| No. | Chemical name | Structure |
|---|---|---|
| 85 | (S)-2-(6-((9-((1,1-dioxidotetrahydro-2H-thiopyran-4-yl)methoxy)-3-fluoro-6,7-dihydro-5H-dibenzo[a,c][7]annulen-2-yl)methoxy)-2,3-dihydro-benzofuran-3-yl)acetic acid | 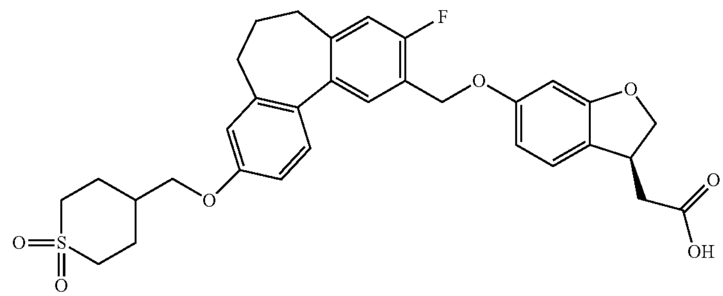 [SMILES: O=C(O)C[C@@H]1COc2cc(OCc3cc4c(cc3F)CCCc3cc(OCC5CCS(=O)(=O)CC5)ccc3-4)ccc21] |
| 86 | (1S,2S)-2-(4-(((9-((1,1-dioxidotetrahydro-2H-thiopyran-4-yl)methoxy)-3-fluoro-6,7-dihydro-5H-dibenzo[a,c][7]annulen-2-yl)methyl)amino)phenyl)cyclopropanecarboxylic acid | 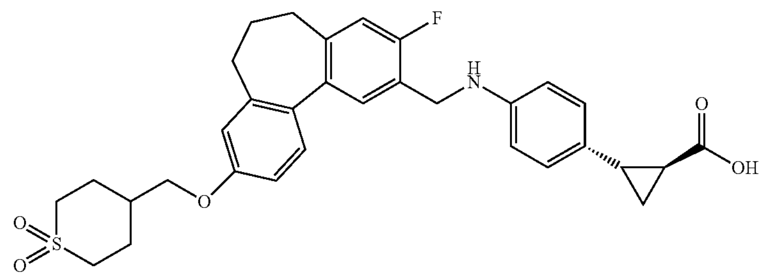 |
| 87 | (1S,2S)-2-(4-(((9-(3-(ethylsulfonyl)propoxy)-11-methyl-6,7-dihydrodibenzo[b,d]oxepin-2-yl)methyl)amino)phenyl)cyclopropanecarboxylic acid | 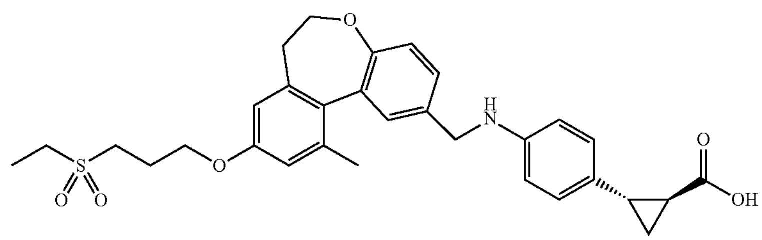 [SMILES: CCS(=O)(=O)CCCOc1cc(C)c2c(c1)CCOc1ccc(CNc3ccc([C@H]4C[C@@H]4C(=O)O)cc3)cc1-2] |
| 88 | 2-((3S)-6-((9-(2-ethoxyethoxy)-11-methyl-6,7-dihydrodibenzo[b,d]oxepin-2-yl)methoxy)-2,3-dihydrobenzofuran-3-yl)acetic acid | 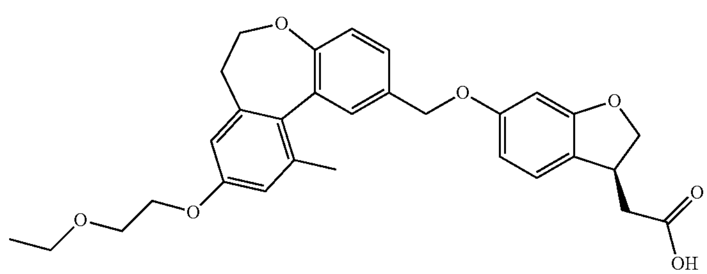 [SMILES: CCOCCOc1cc(C)c2c(c1)CCOc1ccc(COc3ccc4c(c3)OC[C@H]4CC(=O)O)cc1-2] |
| 89 | (1S,2S)-2-(4-((1-methyl-3-morpholino-6,7-dihydro-5H-benzo[3,4]cyclohepta[1,2-d]pyrimidin-10-yl)methoxy)phenyl)cyclopropanecarboxylic acid | 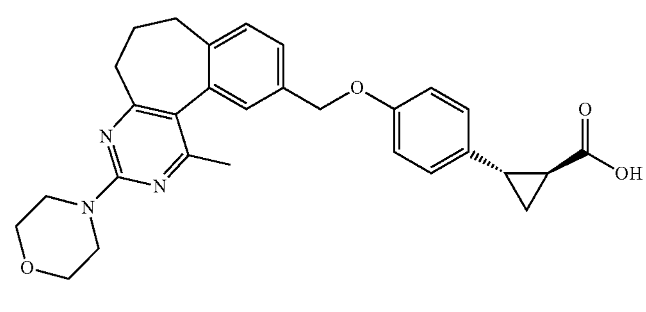 [SMILES: Cc1nc(N2CCOCC2)nc2c1-c1cc(COc3ccc([C@H]4C[C@@H]4C(=O)O)cc3)ccc1CCC2] |

TABLE 1-continued

| No. | Chemical name | Structure |
|---|---|---|
| 90 | 2-((3S)-6-((1-methyl-3-(3-(methylsulfonyl)propoxy)-6,7-dihydro-5H-benzo[3,4]cyclohepta[1,2-d]pyrimidin-10-yl)methoxy)-2,3-dihydrobenzofuran-3-yl)acetic acid | 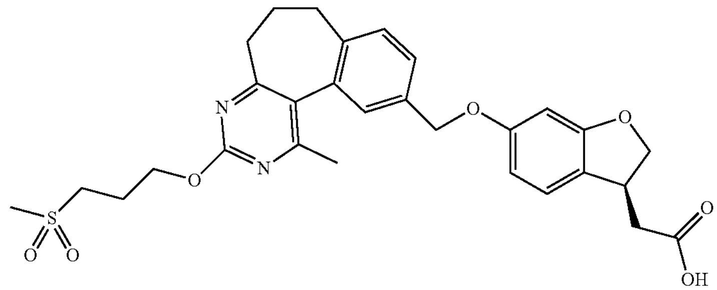 [SMILES: Cc1nc(OCCCS(C)(=O)=O)nc2c1-c1cc(COc3ccc4c(c3)OC[C@H]4CC(=O)O)ccc1CCC2] |
| 91 | (S)-2-(6-(((9-(2-ethoxyethoxy)-6,7-dihydro-5H-dibenzo[a,c][7]annulen-2-yl)methyl)amino)-2,3-dihydrobenzofuran-3-yl)acetic acid | 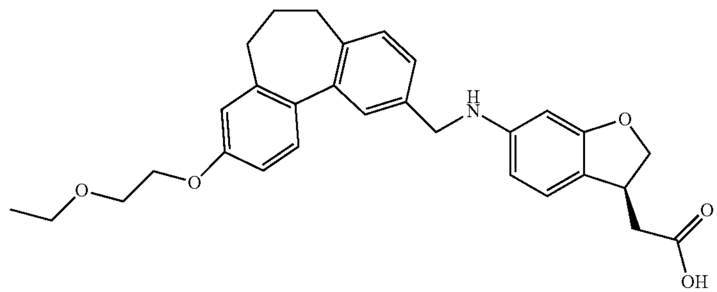 [SMILES: CCOCCOc1ccc2c(c1)CCCc1ccc(CNc3ccc4c(c3)OC[C@H]4CC(=O)O)cc1-2] |
| 92 | (S)-2-(6-(((9-(3-(ethylsulfonyl)propoxy)-6,7-dihydro-5H-dibenzo[a,c][7]annulen-2-yl)methyl)amino)-2,3-dihydrobenzofuran-3-yl)acetic acid | 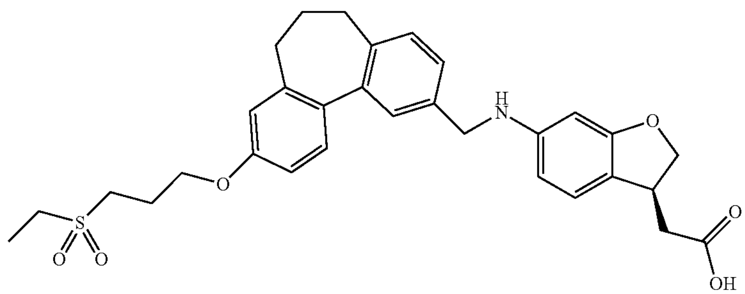 [SMILES: CCS(=O)(=O)CCCOc1ccc2c(c1)CCCc1ccc(CNc3ccc4c(c3)OC[C@H]4CC(=O)O)cc1-2] |
| 93 | (S)-2-(6-((9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid | 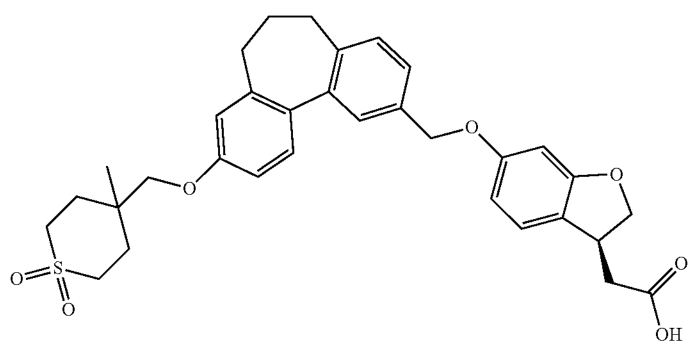 [SMILES: CC1(COc2ccc3c(c2)CCCc2ccc(COc4ccc5c(c4)OC[C@H]5CC(=O)O)cc2-3)CCS(=O)(=O)CC1] |
| 94 | (1S,2S)-2-(4-(((9-((4-methyl-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid | 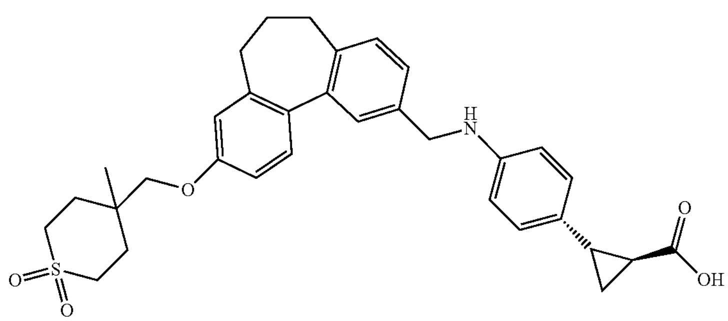 |

TABLE 1-continued

| No. | Chemical name |
|---|---|
| 95 | (S)-2-(6-((3-fluoro-9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid |
| 96 | (S)-2-(6-((3-fluoro-9-(3-(methylsulfonyl)propoxy)-6,7-dihydro-5H-dibenzo[a,c][7]annulen-2-yl)methoxy)-2,3-dihydrobenzofuran-3-yl)acetic acid |
| 97 | (S)-2-(6-((9-(3-(ethylsulfonyl)propoxy)-3-fluoro-6,7-dihydro-5H-dibenzo[a,c][7]annulen-2-yl)methoxy)-2,3-dihydrobenzofuran-3-yl)acetic acid |
| 98 | (S)-2-(6-((9-((1,1-dioxidotetrahydro-2H-thiopyran-4-yl)oxy)-3-fluoro-6,7-dihydro-5H-dibenzo[a,c][7]annulen-2-yl)methoxy)-2,3-dihydrobenzofuran-3-yl)acetic acid |
| 99 | (S)-2-(6-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid |

TABLE 1-continued

| No. | Chemical name |
|---|---|
| 100 | (1S,2S)-2-(4-((9-((1,1-dioxidotetrahydro-2H-thiopyran-4-yl)oxy)-3-fluoro-6,7-dihydro-5H-dibenzo[a,c][7]annulen-2-yl)methoxy)phenyl)cyclopropanecarboxylic acid |
| 101 | (1S,2S)-2-(4-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid |
| 102 | (1S,2S)-2-(4-((3-fluoro-9-(3-(methylsulfonyl)propoxy)-6,7-dihydro-5H-dibenzo[a,c][7]annulen-2-yl)methoxy)phenyl)cyclopropanecarboxylic acid |
| 103 | (1S,2S)-2-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)cyclopropanecarboxylic acid |
| 104 | (1S,2S)-2-(4-(((3-fluoro-9-(3-(methylsulfonyl)propoxy)-6,7-dihydro-5H-dibenzo[a,c][7]annulen-2-yl)methyl)amino)phenyl)cyclopropanecarboxylic acid |
| 105 | (1S,2S)-2-(4-(((9-(3-(ethylsulfonyl)propoxy)-3-fluoro-6,7-dihydro-5H-dibenzo[a,c][7]annulen-2-yl)methyl)amino)phenyl)cyclopropanecarboxylic acid |

TABLE 1-continued

| No. | Chemical name |
|---|---|
| 106 | 2-((S)-6-((3-fluoro-9-(((R)-tetrahydrofuran-3-yl)oxy)-6,7-dihydro-5H-dibenzo[a,c][7]annulen-2-yl)methoxy)-2,3-dihydrobenzofuran-3-yl) acetic acid |
| 107 | (S)-2-(6-((3-fluoro-9-(2-morpholinoethoxy)-6,7-dihydro-5H-dibenzo[a,c][7]annulen-2-yl)methoxy)-2,3-dihydrobenzofuran-3-yl)acetic acid |
| 108 | (S)-3-(4-((9-(3-(methylsulfonyl)propoxy)-6,7-dihydro-5H-dibenzo[a,c][7]annulen-2-yl)methoxy)phenyl)hex-4-ynoic acid |
| 109 | (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoic acid |
| 110 | (S)-3-(4-((9-((1,1-dioxidotetrahydro-2H-thiopyran-4-yl)oxy)-6,7-dihydro-5H-dibenzo[a,c][7]annulen-2-yl)methoxy)phenyl)hex-4-ynoic acid |

TABLE 1-continued

| No. | Chemical name |
|---|---|
| 111 | (S)-3-(4-((9-(3-(ethylsulfonyl)propoxy)-6,7-dihydro-5H-dibenzo[a,c][7]annulen-2-yl)methoxy)phenyl)hex-4-ynoic acid |
| 112 | (S)-3-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)hex-4-ynoic acid |
| 113 | (S)-3-(4-((9-((1,1-dioxidotetrahydro-2H-thiopyran-4-yl)methoxy)-6,7-dihydrodibenzo[b,d]oxepin-2-yl)methoxy)phenyl)hex-4-ynoic acid |
| 114 | (S)-3-(4-((3-((1,1-dioxidotetrahydro-2H-thiopyran-4-yl)methoxy)-6,7-dihydro-5H-benzo[3,4]cyclohepta[1,2-b]pyridin-10-yl)methoxy)phenyl)hex-4-ynoic acid |
| 115 | (R)-3-cyclopropyl-3-(3-((9-((1,1-dioxidotetrahydro-2H-thiopyran-4-yl)methoxy)-6,7-dihydro-5H-dibenzo[a,c][7]annulen-2-yl)methoxy)phenyl)propanoic acid |

| No. | Chemical name | Structure |
| --- | --- | --- |
| 116 | 3-cyclopropyl-3-(4-((9-((1,1-dioxidotetrahydro-2H-thiopyran-4-yl)methoxy)-6,7-dihydro-5H-dibenzo[a,c][7]annulen-2-yl)methoxy)phenyl) propanoic acid | 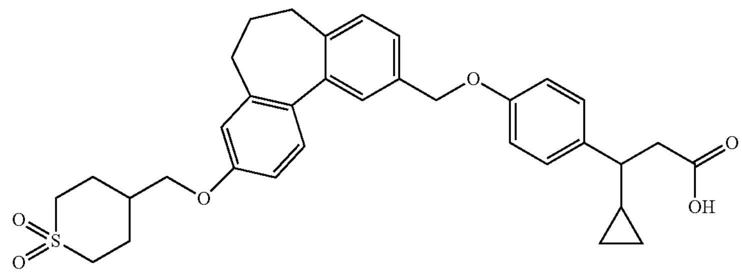 [SMILES: O=C(O)CC(c1ccc(OCc2ccc3c(c2)-c2ccc(OCC4CCS(=O)(=O)CC4)cc2CCC3)cc1)C1CC1] |
| 117 | (S)-3-(4-((9-((1,1-dioxidotetrahydro-2H-thiopyran-4-yl) methoxy)-6,7-dihydro-5H-dibenzo[a,c][7]annulen-2-yl)methoxy)phenyl) hexanoic acid | 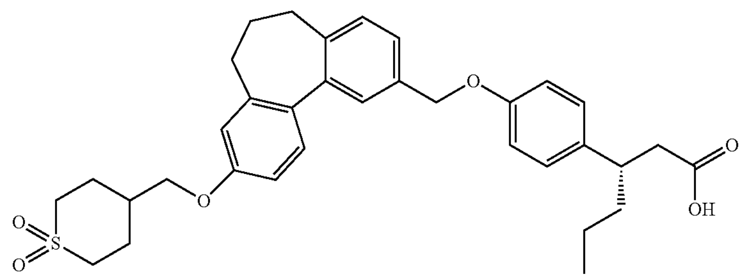 [SMILES: CCC[C@@H](CC(=O)O)c1ccc(OCc2ccc3c(c2)-c2ccc(OCC4CCS(=O)(=O)CC4)cc2CCC3)cc1] |
| 118 | (R,Z)-3-(4-((9-((1,1-dioxidotetrahydro-2H-thiopyran-4-yl) methoxy)-6,7-dihydro-5H-dibenzo[a,c][7]annulen-2-yl)methoxy)phenyl)hex-4-enoic acid | 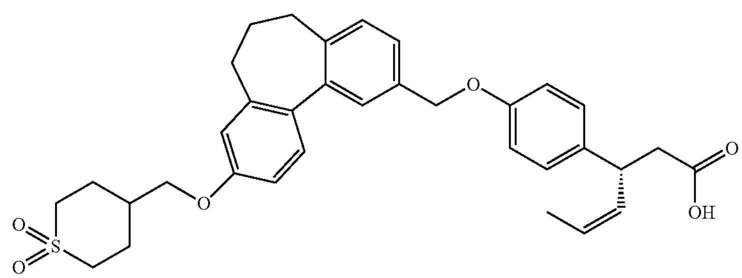 [SMILES: C/C=C\[C@@H](CC(=O)O)c1ccc(OCc2ccc3c(c2)-c2ccc(OCC4CCS(=O)(=O)CC4)cc2CCC3)cc1] |
| 119 | (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(5-methylisoxazol-3-yl) propanoic acid | 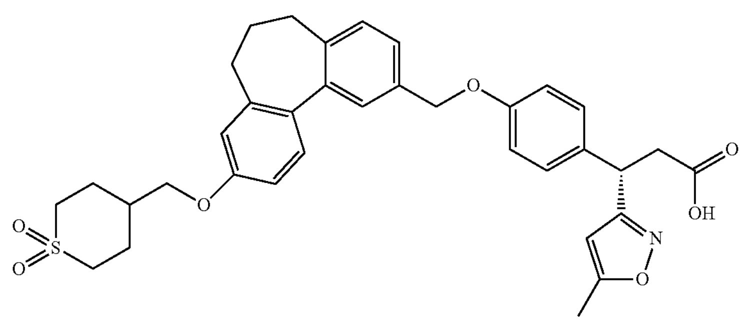 [SMILES: Cc1cc([C@@H](CC(=O)O)c2ccc(OCc3ccc4c(c3)-c3ccc(OCC5CCS(=O)(=O)CC5)cc3CCC4)cc2)no1] |
| 120 | (S)-3-(4-((9-((1,1-dioxidotetrahydro-2H-thiopyran-4-yl)methoxy)-6,7-dihydro-5H-dibenzo[a,c][7]annulen-2-yl)methoxy)phenyrol)-3-(isoxazol-3-yl)propanoic acid | 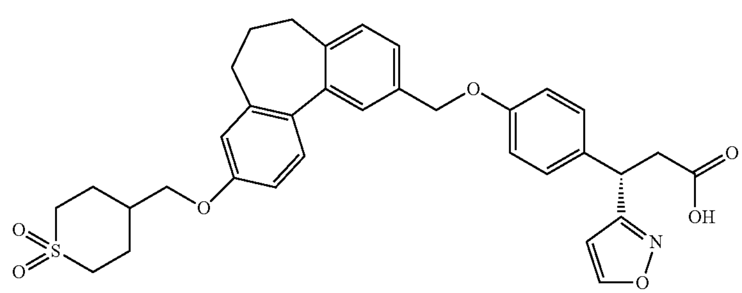 [SMILES: O=C(O)C[C@@H](c1ccc(OCc2ccc3c(c2)-c2ccc(OCC4CCS(=O)(=O)CC4)cc2CCC3)cc1)c1ccon1] |

| No. | Chemical name | Structure |
|---|---|---|
| 121 | 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(3-methylisoxazol-5-yl)propanoic acid | 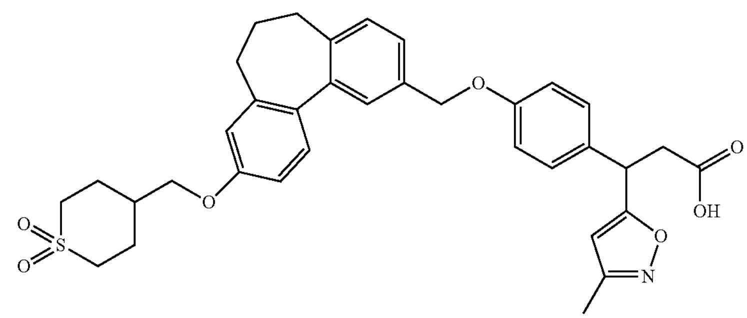 [SMILES: Cc1cc(C(CC(=O)O)c2ccc(OCc3ccc4c(c3)-c3ccc(OCC5CCS(=O)(=O)CC5)cc3CCC4)cc2)on1] |
| 122 | (S)-3-(4-((3-(3-(methylsulfonyl)propoxy)-6,7-dihydro-5H-benzo[3,4]cyclohepta[1,2-b]pyridin-10-yl)methoxy)phenyl)hex-4-ynoic acid | 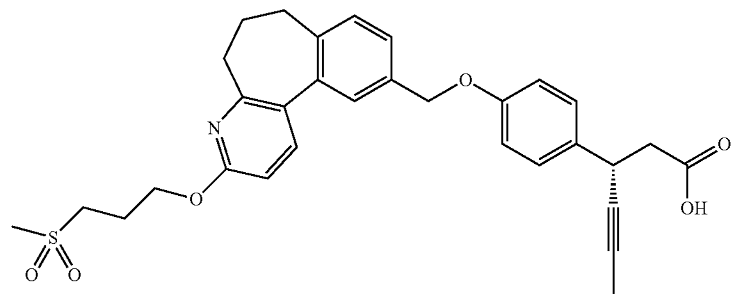 [SMILES: CC#C[C@@H](CC(=O)O)c1ccc(OCc2ccc3c(c2)-c2ccc(OCCCS(C)(=O)=O)nc2CCC3)cc1] |
| 123 | (S)-3-(4-((3-(3-(ethylsulfonyl)propoxy)-6,7-dihydro-5H-benzo[3,4]cyclohepta[1,2-b]pyridin-10-yl)methoxy)phenyl)hex-4-ynoic acid | 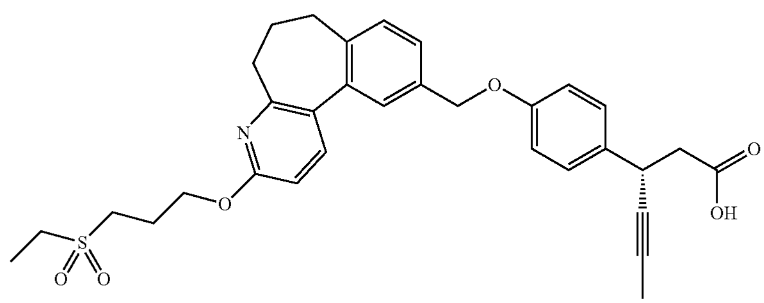 [SMILES: CC#C[C@@H](CC(=O)O)c1ccc(OCc2ccc3c(c2)-c2ccc(OCCCS(=O)(=O)CC)nc2CCC3)cc1] |
| 124 | (S)-3-(4-((3-((1,1-dioxidotetrahydro-2H-thiopyran-4-yl)oxy)-6,7-dihydro-5H-benzo[3,4]cyclohepta[1,2-b]pyridin-10-yl)methoxy)phenyl)hex-4-ynoic acid | 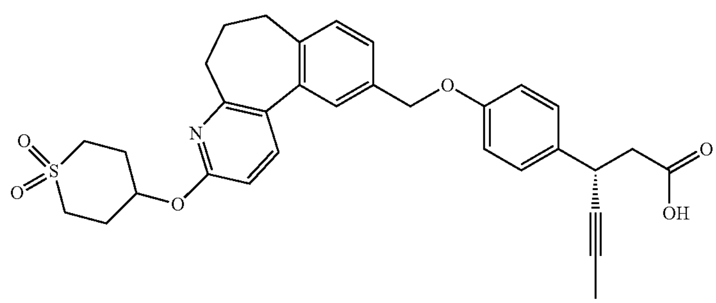 [SMILES: CC#C[C@@H](CC(=O)O)c1ccc(OCc2ccc3c(c2)-c2ccc(OC4CCS(=O)(=O)CC4)nc2CCC3)cc1] |
| 125 | (S)-3-(4-((5-methyl-7-(3-(methylsulfonyl)propoxy)-9,10-dihydrophenanthren-3-yl)methoxy)phenyl)hex-4-ynoic acid | 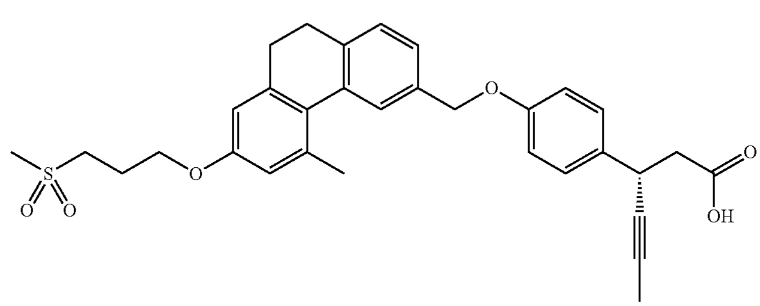 [SMILES: CC#C[C@@H](CC(=O)O)c1ccc(OCc2ccc3c(c2)-c2c(C)cc(OCCCS(C)(=O)=O)cc2CC3)cc1] |

TABLE 1-continued

| No. | Chemical name |
|---|---|
| 126 | (S)-3-(4-((7-(2-ethoxyethoxy)-5-methyl-9,10-dihydrophenanthren-3-yl)methoxy)phenyl)hex-4-ynoic acid |
| 127 | (S)-3-(4-((5-methyl-7-(3-(methylsulfonyl)propoxy)-9,10-dihydrophenanthren-1-yl)methoxy)phenyl)hex-4-ynoic acid |
| 128 | (S)-3-(4-((11-methyl-9-(3-(methylsulfonyl)propoxy)-6,7-dihydro-5H-dibenzo[a,c][7]annulen-2-yl)methoxy)phenyl)hex-4-ynoic acid |
| 129 | (S)-3-(4-((9-(3-(methylsulfonyl)propoxy)dibenzo[d,f][1,3]dioxepin-2-yl)methoxy)phenyl)hex-4-ynoic acid |
| 130 | (S)-3-(4-((6,6-dimethyl-9-(3-(methylsulfonyl)propoxy)-6,7-dihydrodibenzo[b,d]oxepin-2-yl)methoxy)phenyl)hex-4-ynoic acid |

TABLE 1-continued

| No. | Chemical name |
|---|---|
| 131 | (S)-3-(4-((1-methyl-3-(3-(methylsulfonyl)propoxy)-6,7-dihydro-5H-benzo[3,4]cyclohepta[1,2-d]pyrimidin-10-yl)methoxy)phenyl)hex-4-ynoic acid |
| 132 | (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid |
| 133 | (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid |
| 134 | (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-4-ethoxybutanoic acid |
| 135 | (S)-3-(4-(((9-(3-(methylsulfonyl)propoxy)-6,7-dihydro-5H-dibenzo[a,c][7]annulen-2-yl)methyl)amino)phenyl)hex-4-ynoic acid |

TABLE 1-continued

| No. | Chemical name |
|---|---|
| 136 | (S)-3-(4-(((9-((1,1-dioxidotetrahydro-2H-thiopyran-4-yl)methoxy)-6,7-dihydro-5H-dibenzo[a,c][7]annulen-2-yl)methyl)amino)phenyl)hex-4-ynoic acid |
| 137 | 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(4-fluorophenyl)propanoic acid |
| 138 | (S)-3-(4-((11-methyl-9-(((R)-tetrahydrofuran-3-yl)oxy)-6,7-dihydro-5H-dibenzo[a,c][7]annulen-2-yl)methoxy)phenyl)hex-4-ynoic acid |
| 139 | (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)pent-4-ynoic acid |

TABLE 1-continued

| No. | Chemical name | Structure |
|---|---|---|
| 140 | (S)-3-(4-((5-ethyl-9-(((R)-tetrahydrofuran-3-yl)oxy)-6,7-dihydro-5H-dibenzo[b,d]azepin-2-yl)methoxy)phenyl)hex-4-ynoic acid | 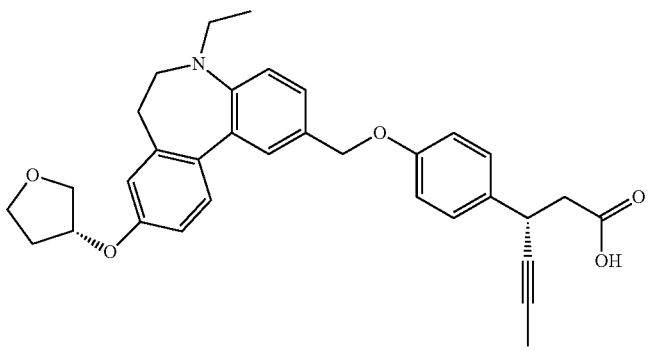 [SMILES: CC#C[C@@H](CC(=O)O)c1ccc(OCc2ccc3c(c2)-c2ccc(O[C@@H]4CCOC4)cc2CCN3CC)cc1] |
| 141 | Sodium (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylate | 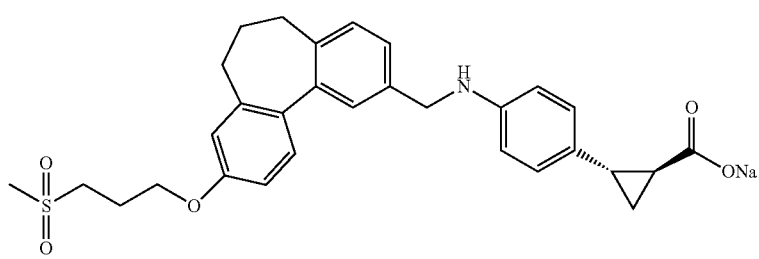 |
| 142 | Sodium 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-yl)acetate | 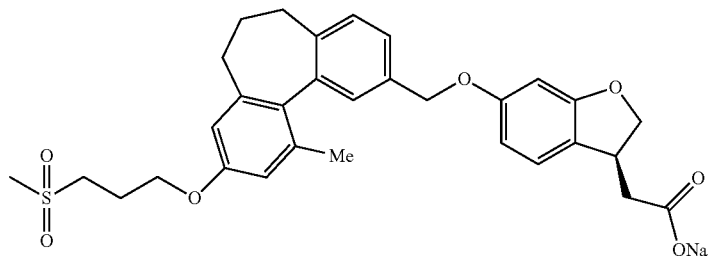 |
| 143 | Sodium (1S,2S)-2-(4-((11-methyl-9-(3-(methylsulfonyl)propoxy)-6,7-dihydrodibenzo[b,d]oxepin-2-yl)methoxy)phenyl)cyclopropanecarboxylate | 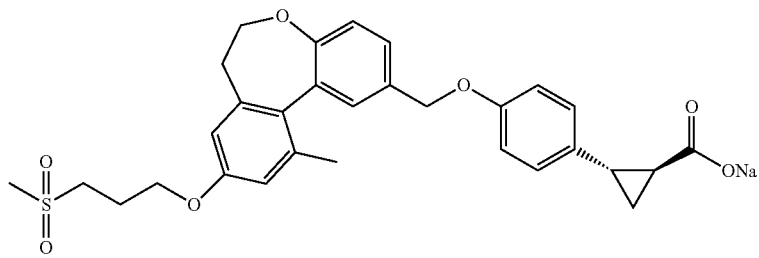 |
| 144 | Sodium (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylate | 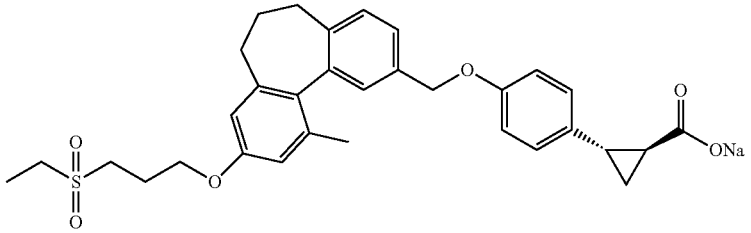 |

TABLE 1-continued

| No. | Chemical name |
|-----|---------------|
| 145 | Sodium (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-yl)acetate |
| 146 | Sodium (S)-3-(4-((9-(3-(methylsulfonyl)propoxy)-6,7-dihydro-5H-dibenzo[a,c][7]annulen-2-yl)methoxy)phenyl)hex-4-ynoate |
| 147 | Sodium (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoate |

Test Example 1

Measurement of 50% Inhibitory Concentration (ID$_{50}$) for GPR40 Agonist Binding To examine the efficacy of the compounds according to one exemplary embodiment of the present invention in modulating GPR40, the half maximal inhibitory concentrations (IC$_{50}$) of the compounds according to one exemplary embodiment of the present invention were measured by Microbeta2™ (PerkinElmer Inc.) using a change in radiation dose emitted from $^3$H-labeled propanoic acid (i.e., 3-(4-((2,6'-dimethyl-6-((4-($^3$H))-phenylmethoxy)biphenyl-3-yl)methoxy)phenyl)propanoic acid), which is a radioactive isotope which binds to a human GPR40 protein, as an indicator.

Specifically, a test compound was prepared by serial dilution with DMSO, and 100 µL of a binding buffer (including 25 mM HEPES (pH 7.5), 5 mM MgCl$_2$, 100 mM NaCl, and 0.1% free fatty acid BSA; Sigma-Aldrich Corp.) was put into each well of a 96-well transparent plate. Thereafter, each of the diluted compound, propanoic acid which was prepared by dissolving propanoic acid in DMSO to a concentration of 500 mM and not labeled with a radioactive isotope, and DMSO was dispensed at 5 µL per well. $^3$H-labeled propanoic acid was dissolved in a binding buffer at a concentration of 1 nM and dispensed at 50 µL into the corresponding wells, and a membrane protein including a human GPR40 protein was dissolved in a binding buffer at a concentration of 20 µg/well and dispensed at 100 µL, into the corresponding wells.

After the dispensation was completed, the plate was incubated at a temperature of 25° C. and a rotary speed of 230 rpm for 2 hours while shaking. A human GPR40 complex was transferred to Filtermat A (PerkinElmer Inc.) using a cell harvester (PerkinElmer Inc.), washed 10 times with 50 mM tris-HCl, dried, and then scintillated using Meltilex (PerkinElmer Inc.). Thereafter, an emitted radiation dose was measured using Microbeta2™. The radiation doses emitted from the complex in the well containing 10 mM unlabeled propanoic acid and the complex in the well containing DMSO alone were set as 0% and 100%, respectively. Thus, a change curve for each of the radiation doses was plotted to calculate the half maximal inhibitory concentration of the test compound. The test results are listed in Table 2.

TABLE 2

| Compound | Half maximal inhibitory concentration (nM) |
|----------|---------------------------------------------|
| Example 1 | 157.8 |
| Example 6 | 116.2 |
| Example 14 | 17.7 |
| Example 18 | 752.1 |

TABLE 2-continued

| Compound | Half maximal inhibitory concentration (nM) |
|---|---|
| Example 25 | 102.8 |
| Example 31 | 45.7 |
| Example 38 | 39.1 |
| Example 41 | 125.0 |
| Example 44 | 75.7 |
| Example 47 | 53.1 |
| Example 59 | 71.0 |
| Example 61 | 26.6 |
| Example 65 | 159.8 |
| Example 76 | 14.7 |
| Example 79 | 84.4 |
| Example 81 | 180.7 |
| Example 93 | 50.5 |
| Example 105 | 16.2 |
| Example 108 | 9.6 |
| Example 109 | 5.6 |

As listed in Table 2, it was revealed that the compounds according to one exemplary embodiment of the present invention inhibited the binding of propanoic acid to GRP40 at a low concentration.

Test Example 2

Measurement of Hypoglycemic Rate in Rats

An effect of the compound according to one exemplary embodiment of the present invention on blood glucose inhibition after glucose loading was examined in male ZFDM rats (Japan SLC, Inc.).

Specifically, male ZFDM rats (7 week-old) pre-fed for a week were fasted overnight, and used as an animal to be tested. A test compound was prepared into a 0.5% methylcellulose suspension, which was orally administered to rats at a dose of 0.1 to 30 mg/kg before an hour of glucose loading (1.5 g/kg). As the control, 0.5% methylcellulose was administered. After the glucose administration, blood was drawn from the rats' tails after 0, 15, 30, 60 and 120 minutes to measure a blood glucose level. The area under the curve (AUC) for compound treatment was calculated using a blood glucose change profile from t=0 to 120 minutes, and a hypoglycemic rate (%) for the control was calculated. The results are listed in the following Table 3.

TABLE 3

| Compound | Hypoglycemic rate (%) |
|---|---|
| Example 6 | 18.0 |
| Example 26 | 31.0 |
| Example 57 | 21.7 |
| Example 78 | 27.4 |
| Example 108 | 37.5 |

As listed in Table 3, it can be seen that the compounds according to one exemplary embodiment of the present invention had a hypoglycemic effect.

What is claimed is:

1. A compound selected from the group consisting of a tricyclic compound of Formula I, and a pharmaceutically acceptable salt, isomer, and solvate thereof:

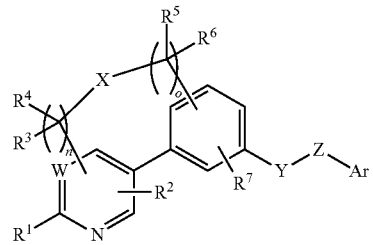

<Formula I>

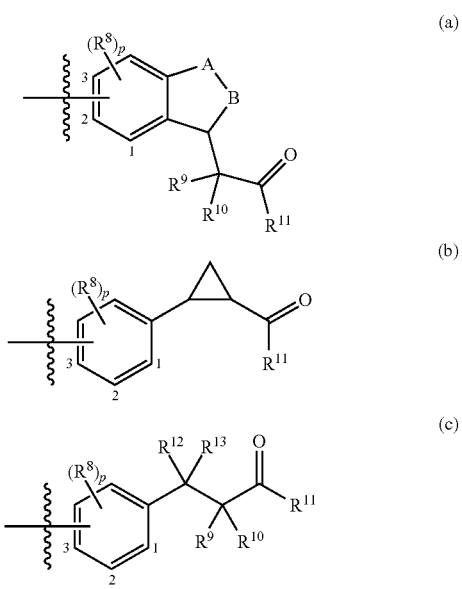

wherein
V and W are each independently $=C(R^{14})-$, or $=N-$;
X is $-CH_2-$, $-O-$, $-O-CH_2-O-$, $-S-$, $-C(=O)-$, $-S(=O)-$, $-S(=O)_2-$, or $-NR^{15}-$;
Y is a $C_{1-6}$ alkylene;
Z is $-O-$, $-S-$, $-C(=O)-$, $-S(=O)-$, $-S(=O)_2-$, or $-NR^{15}-$;
Ar is one of the following substituents (a) to (c), wherein A is $-CH_2-$, $-CF_2-$, $-O-$, $-NR^{15}-$, $-S-$, $-S(=O)-$, $-S(=O)_2-$, $-C(=O)-$, or $-CH(OR^{15})-$;
B is a $C_{1-3}$ alkylene;
$R^1$ is hydrogen, a halogen, hydroxy, amino, nitro, cyano, a $C_{1-6}$ alkyl, a $C_{1-10}$ alkoxy, a $C_{1-6}$ alkylthio, acyl, a $C_{1-6}$ alkylsulfonyloxy, a $C_{3-12}$ carbocyclyl, a $C_{3-12}$ carbocyclyloxy, a $C_{3-12}$ carbocyclylsulfonyloxy, a 5- to 14-membered heterocyclyl, a 5- to 14-membered heterocyclyloxy, or a 5- to 14-membered heterocyclylsulfonyloxy;
$R^2$, $R^3$, $R^4$, $R^5$, $R^6$, and $R^7$ are each independently hydrogen, a halogen, amino, cyano, a $C_{1-6}$ alkyl, a $C_{1-6}$ alkoxy, a $C_{1-6}$ alkylthio, acyl, a $C_{3-12}$ carbocyclyl, or a 5- to 14-membered heterocyclyl;
$R^8$ is hydrogen, a halogen, hydroxy, amino, nitro, cyano, a $C_{1-6}$ alkyl, a $C_{1-6}$ alkoxy, or a $C_{1-6}$ alkylthio;
$R^9$ and $R^{10}$ are each independently hydrogen, a halogen, hydroxy, a $C_{1-6}$ alkyl, or a $C_{1-6}$ alkoxy;

$R^{11}$ is hydroxy, amino, or a $C_{1-6}$ alkoxy;

$R^{12}$ is hydrogen, a $C_{1-6}$ alkyl, a $C_{2-6}$ akenyl, a $C_{2-6}$ alkynyl, a $C_{1-6}$ alkoxy, a $C_{1-6}$ alkoxy-$C_{1-6}$ alkyl, a $C_{3-12}$ carbocyclyl, or a 5- to 14-membered heterocyclyl;

$R^{13}$ is hydrogen, or a $C_{1-6}$ alkyl;

$R^{14}$ is hydrogen, a halogen, amino, —$CF_3$, nitro, cyano, a $C_{1-6}$ alkyl, a $C_{1-6}$ alkoxy, a $C_{1-6}$ alkylthio, acyl, a $C_{3-12}$ carbocyclyl, or a 5- to 14-membered heterocyclyl;

$R^{15}$ is hydrogen, or a $C_{1-6}$ alkyl; and n, o, and p are each independently 0, 1, 2, or 3;

provided that the alkylene, the alkyl, the akenyl, the alkynyl, the alkoxy, the alkylthio, the amino, the acyl, the alkylsulfonyloxy, the carbocyclyl, the carbocyclyloxy, the carbocyclylsulfonyloxy, the heterocyclyl, the heterocyclyloxy, and the heterocyclylsulfonyloxy may each independently be substituted with at least one substituent selected from the group consisting of a 4- to 7-membered heterocyclyl (unsubstituted or substituted with 1 to 3 substituents selected from the group consisting of hydroxy, a halogenated $C_{1-6}$ alkyl, and a $C_{1-6}$ alkoxy-carbonyl), a $C_{3-8}$ cycloalkyl, hydroxy, a $C_{1-6}$ alkoxy, a halogenated $C_{1-6}$ alkoxy, amino, a mono- or di-$C_{1-6}$ alkyl-amino, an N—$C_{1-6}$ alkyl-N—$C_{1-6}$ alkyl-carbonyl-amino, a $C_{7-16}$ aralkyloxy, a $C_{1-6}$ alkylthio, a $C_{1-6}$ alkylsulfinyl, a $C_{1-6}$ alkylsulfonyl, and a mono- or di-$C_{1-6}$ alkyl-phosphono; and the heterocyclyl contains 1 to 4 heteroelements selected from the group consisting of N, O, S, S(=O), and S(=O)$_2$.

2. The compound of claim 1, wherein

V and W are each independently =C($R^{14}$)—, or =N—;

X is —$CH_2$—, —O—, —O—$CH_2$—O—, —S—, or —$NR^{15}$—;

Y is a $C_{1-3}$ alkylene;

Z is —O—, —S—, or —$NR^{15}$—, provided that Z is substituted at the $2^{nd}$ or $3^{rd}$ carbon atom of Ar;

Ar is one of the substituents (a) to (c);

A is —$CH_2$—, —$CF_2$—, —O—, or —$NR^{15}$—;

B is a $C_{1-2}$ alkylene;

$R^1$ is hydrogen, a halogen, hydroxy, amino, nitro, cyano, a $C_{1-6}$ alkyl, a $C_{1-10}$ alkoxy, a $C_{1-6}$ alkylthio, acyl, a $C_{1-6}$ alkylsulfonyloxy, a $C_{3-12}$ carbocyclyl, a $C_{3-12}$ carbocyclyloxy, a $C_{3-12}$ carbocyclylsulfonyloxy, a 5- to 14-membered heterocyclyl, a 5- to 14-membered heterocyclyloxy, or a 5- to 14-membered heterocyclylsulfonyloxy;

$R^2$ is hydrogen, a halogen, amino, cyano, a $C_{1-6}$ alkyl, a $C_{1-6}$ alkoxy, a $C_{1-6}$ alkylthio, a $C_{3-12}$ carbocyclyl, or a 5- to 14-membered heterocyclyl;

$R^3$, $R^4$, $R^5$, and $R^6$ are each independently hydrogen, a halogen, amino, a $C_{1-6}$ alkyl, or a $C_{1-6}$ alkoxy;

$R^7$ is hydrogen, a halogen, amino, cyano, a $C_{1-6}$ alkyl, a $C_{1-6}$ alkoxy, a $C_{1-6}$ alkylthio, a $C_{3-12}$ carbocyclyl, or a 5- to 14-membered heterocyclyl;

$R^8$ is hydrogen, a halogen, amino, a $C_{1-6}$ alkyl, or a $C_{1-6}$ alkoxy;

$R^9$ and $R^{10}$ are each independently hydrogen, a halogen, hydroxy, a $C_{1-6}$ alkyl, or a $C_{1-6}$ alkoxy;

$R^{11}$ is hydroxy, or a $C_{1-6}$ alkoxy;

$R^{12}$ is hydrogen, a $C_{1-6}$ alkyl, a $C_{2-6}$ akenyl, a $C_{2-6}$ alkynyl, a $C_{1-6}$ alkoxy, a $C_{1-6}$ alkoxy-$C_{1-6}$ alkyl, a $C_{3-12}$ carbocyclyl, or a 5- to 14-membered heterocyclyl;

$R^{13}$ is hydrogen, or a $C_{1-6}$ alkyl;

$R^{14}$ is hydrogen, a halogen, amino, —$CF_3$, a $C_{1-6}$ alkyl, a $C_{1-6}$ alkoxy, acyl, a $C_{3-12}$ carbocyclyl, or a 5- to 14-membered heterocyclyl;

$R^{15}$ is hydrogen, or a $C_{1-6}$ alkyl; and n, o, and p are each independently 0, 1, or 2;

provided that the alkylene, the alkyl, the alkynyl, the alkoxy, the alkylthio, the amino, the acyl, the alkylsulfonyloxy, the carbocyclyl, the carbocyclyloxy, the carbocyclylsulfonyloxy, the heterocyclyl, and the heterocyclyloxy may each independently substituted with at least one substituent selected from the group consisting of a 4- to 7-membered heterocyclyl (unsubstituted or substituted with 1 to 3 substituents selected from the group consisting of hydroxy, a halogenated $C_{1-6}$ alkyl, and a $C_{1-6}$ alkoxy-carbonyl), a $C_{3-8}$ cycloalkyl, hydroxy, a $C_{1-6}$ alkoxy, a halogenated $C_{1-6}$ alkoxy, amino, a mono- or di-$C_{1-6}$ alkyl-amino, an N—$C_{1-6}$ alkyl-N—$C_{1-6}$ alkyl-carbonyl-amino, a $C_{7-16}$ aralkyloxy, a $C_{1-6}$ alkylthio, a $C_{1-6}$ alkylsulfinyl, a $C_{1-6}$ alkylsulfonyl, and a mono- or di-$C_{1-6}$ alkyl-phosphono; and the heterocyclyl contains 1 to 4 heteroelements selected from the group consisting of N, O, S, S(=O), and S(=O)$_2$.

3. The compound of claim 1, wherein

V and W are each independently =C($R^{14}$)—, or =N—;

X is —$CH_2$—, —O—$CH_2$—O—, —O—, —S—, or —$NR^{15}$—;

Y is a $C_{1-3}$ alkylene;

Z is —O—, —S—, or —$NR^{15}$—, provided that Z is substituted at the $2^{nd}$ or $3^{rd}$ carbon atom of Ar;

Ar is one of the substituents (a) to (c);

A is —$CH_2$—, —$CF_2$—, —O—, or —$NR^{15}$—;

B is a $C_{1-2}$ alkylene;

$R^1$ is hydrogen, a halogen, hydroxy, amino, a $C_{1-6}$ alkyl, a $C_{1-10}$ alkoxy, acyl, a $C_{1-6}$ alkylsulfonyloxy, a $C_{3-12}$ carbocyclyloxy, a 5- to 14-membered heterocyclyl, or a 5- to 14-membered heterocyclyloxy;

$R^2$, $R^3$, $R^4$, $R^5$, $R^6$, $R^7$, and $R^8$ are each independently hydrogen, a halogen, amino, a $C_{1-6}$ alkyl, or a $C_{1-6}$ alkoxy;

$R^9$ and $R^{10}$ are each independently hydrogen, or a halogen;

$R^{11}$ is hydroxy, or a $C_{1-6}$ alkoxy;

$R^{12}$ is hydrogen, a $C_{1-6}$ alkyl, a $C_{2-6}$ akenyl, a $C_{2-6}$ alkynyl, a $C_{1-6}$ alkoxy, a $C_{1-6}$ alkoxy-$C_{1-6}$ alkyl, a $C_{3-12}$ carbocyclyl, or a 5- to 14-membered heterocyclyl;

$R^{13}$ is hydrogen;

$R^{14}$ is hydrogen, a halogen, amino, a $C_{1-6}$ alkyl, a $C_{1-6}$ alkoxy, or acyl;

$R^{15}$ is hydrogen, methyl, ethyl, or isopropyl; and n, o, and p are each independently 0, 1, or 2;

provided that the alkylene, the alkyl, the alkynyl, the alkoxy, the amino, the acyl, the alkylsulfonyloxy, the carbocyclyloxy, the heterocyclyl, and the heterocyclyloxy may each independently be substituted with at least one substituent selected from the group consisting of a 4- to 7-membered heterocyclyl (unsubstituted or substituted with 1 to 3 substituents selected from the group consisting of hydroxy, a halogenated $C_{1-6}$ alkyl, and a $C_{1-6}$ alkoxy-carbonyl), a $C_{3-8}$ cycloalkyl, hydroxy, a $C_{1-6}$ alkoxy, a halogenated $C_{1-6}$ alkoxy, amino, a mono- or di-$C_{1-6}$ alkyl-amino, an N—$C_{1-6}$ alkyl-N—$C_{1-6}$ alkyl-carbonyl-amino, a $C_{7-16}$ aralkyloxy, a $C_{1-6}$ alkylthio, a $C_{1-6}$ alkylsulfinyl, a $C_{1-6}$ alkylsulfonyl, and a mono- or di-$C_{1-6}$ alkyl-phosphono; and the heterocyclyl contains 1 to 4 heteroelements selected from the group consisting of N, O, S, S(=O), and S(=O)$_2$.

4. The compound of claim 1, wherein

V and W are each independently =CH—, or =N—;
X is —CH$_2$—, —O—, —O—CH$_2$—O—, or —N(CH$_2$CH$_3$)—;
Y is methylene;
Z is —O— or —NH—, provided that Z is substituted at the 2$^{nd}$ or 3$^{rd}$ carbon atom of Ar;
Ar is one of the substituents (a) to (c);
A is —O—;
B is methylene;
R$^1$ is methylsulfonylpropoxy, ethylsulfonylpropoxy, ethoxyethoxy, morpholino, morpholinoethoxy, tetrahydrofuranyloxy,

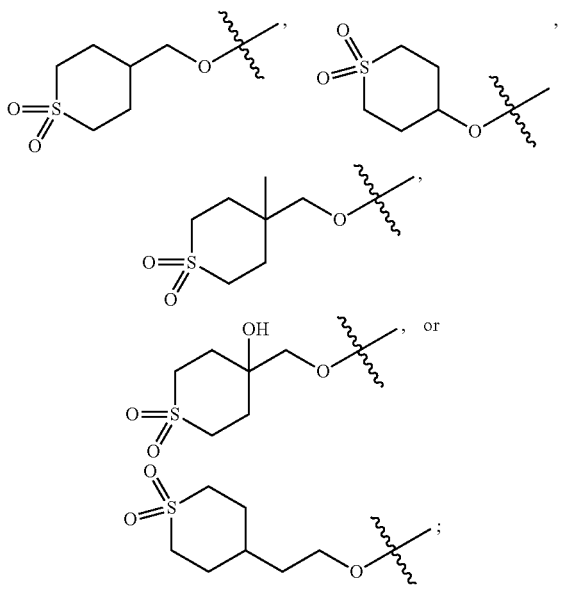

R$^2$ is hydrogen, or methyl;
R$^3$, R$^4$, R$^5$, and R$^6$ are each independently hydrogen, or methyl;
R$^7$ and R$^8$ are each independently hydrogen, or fluoro;
R$^9$ and R$^{10}$ are hydrogen;
R$^{11}$ is hydroxy;
R$^{12}$ is hydrogen, methyl, propyl, cyclopropyl, ethoxymethyl, ethynyl, —CH=CH—CH$_3$, —C≡C—CH$_3$, fluorophenyl, or methyloxazolyl;
R$^{13}$ is hydrogen;
n and o are each independently 0, 1, or 2; and
p may be 0 or 1.

5. The compound of claim 1, which is selected from the group consisting of:

(1) 2-((3S)-6-((11-methyl-9-(3-(methylsulfonyl)propoxy)-6,7-dihydro-5H-dibenzo[a,c][7]annulen-4-yl)methoxy)-2,3-dihydrobenzofuran-3-yl)acetic acid;
(2) (1S,2S)-2-(4-((9-(3-(methylsulfonyl)propoxy)-6,7-dihydrodibenzo[b,d]oxepin-2-yl)methoxy)phenyl)cyclopropanecarboxylic acid;
(3) (1S,2S)-2-(4-(((9-(2-ethoxyethoxy)-6,7-dihydrodibenzo[b,d]oxepin-2-yl)methyl)amino)phenyl)cyclopropanecarboxylic acid;
(4) (1S,2S)-2-(4-(((9-(3-(methylsulfonyl)propoxy)-6,7-dihydrodibenzo[b,d]oxepin-2-yl)methyl)amino)phenyl)cyclopropanecarboxylic acid;
(5) (S)-2-(6-((9-(3-(methylsulfonyl)propoxy)-6,7-dihydro-5H-dibenzo[a,c][7]annulen-2-yl)methoxy)-2,3-dihydrobenzofuran-3-yl)acetic acid;
(6) (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylic acid;
(7) 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-yl)acetic acid;
(8) (1R,2R)-2-(4-(((10-methyl-8-(3-(methylsulfonyl)propoxy)-6H-benzo[c]chromen-4-yl)methyl)amino)phenyl)cyclopropanecarboxylic acid;
(9) (1S,2S)-2-(4-(((10-methyl-8-(3-(methylsulfonyl)propoxy)-6H-benzo[c]chromen-2-yl)methyl)amino)phenyl)cyclopropanecarboxylic acid;
(10) (S)-2-(6-((5-methyl-7-(3-(methylsulfonyl)propoxy)-9,10-dihydrophenanthren-1-yl)methoxy)-2,3-dihydrobenzofuran-3-yl)acetic acid;
(11) (S)-2-(6-((5-methyl-7-(3-(methylsulfonyl)propoxy)-9,10-dihydrophenanthren-3-yl)methoxy)-2,3-dihydrobenzofuran-3-yl)acetic acid;
(12) (S)-2-(6-((7-(2-ethoxyethoxy)-5-methyl-9,10-dihydrophenanthren-3-yl)methoxy)-2,3-dihydrobenzofuran-3-yl)acetic acid;
(13) 2-((3S)-6-((11-methyl-9-(3-(methylsulfonyl)propoxy)-6,7-dihydrodibenzo[b,d]oxepin-4-yl)methoxy)-2,3-dihydrobenzofuran-3-yl)acetic acid;
(14) 2-((3S)-6-((11-methyl-9-(3-(methylsulfonyl)propoxy)-6,7-dihydrodibenzo[b,d]oxepin-2-yl)methoxy)-2,3-dihydrobenzofuran-3-yl)acetic acid;
(15) (1S,2S)-2-(4-(((11-methyl-9-(3-(methylsulfonyl)propoxy)-6,7-dihydrodibenzo[b,d]oxepin-2-yl)methyl)amino)phenyl)cyclopropanecarboxylic acid;
(16) (1S,2S)-2-(4-(((8-(2-ethoxyethoxy)-10-methyl-6H-benzo[c]chromen-2-yl)methyl)amino)phenyl)cyclopropanecarboxylic acid;
(17) (S)-2-(6-((8-(2-ethoxyethoxy)-10-methyl-6H-benzo[c]chromen-2-yl)methoxy)-2,3-dihydrobenzofuran-3-yl)acetic acid;
(18) (1S,2S)-2-(4-(((9-(3-(methylsulfonyl)propoxy)-5,7-dihydrodibenzo[c,e]oxepin-2-yl)methyl)amino)phenyl)cyclopropanecarboxylic acid;
(19) (1S,2S)-2-(4-(((11-methyl-9-(3-(methylsulfonyl)propoxy)-5,7-dihydrodibenzo[c,e]oxepin-4-yl)methyl)amino)phenyl)cyclopropanecarboxylic acid;
(20) (S)-2-(6-((9-(3-(methylsulfonyl)propoxy)-5,7-dihydrodibenzo[c,e]oxepin-2-yl)methoxy)-2,3-dihydrobenzofuran-3-yl)acetic acid;
(21) (1S,2S)-2-(4-(((3-(3-(methylsulfonyl)propoxy)-6,7-dihydrodibenzo[b,d]oxepin-10-yl)methyl)amino)phenyl)cyclopropanecarboxylic acid;
(22) (1S,2S)-2-(4-(((9-(2-ethoxyethoxy)-5,7-dihydrodibenzo[c,e]oxepin-2-yl)methyl)amino)phenyl)cyclopropanecarboxylic acid;
(23) (S)-2-(6-((9-(2-ethoxyethoxy)-5,7-dihydrodibenzo[c,e]oxepin-2-yl)methoxy)-2,3-dihydrobenzofuran-3-yl)acetic acid;
(24) (1S,2S)-2-(4-((9-(3-(methylsulfonyl)propoxy)-5,7-dihydrodibenzo[c,e]oxepin-2-yl)methoxy)phenyl)cyclopropanecarboxylic acid;
(25) (1S,2S)-2-(4-((9-(3-(methylsulfonyl)propoxy)-6,7-dihydro-5H-dibenzo[a,c][7]annulen-2-yl)methoxy)phenyl)cyclopropanecarboxylic acid;
(26) (S)-2-(6-((10-methyl-8-(3-(methylsulfonyl)propoxy)-6H-benzo[c]chromen-2-yl)methoxy)-2,3-dihydrobenzofuran-3-yl)acetic acid;

(27) (S)-2-(6-((9-(2-ethoxyethoxy)-6,7-dihydro-5H-dibenzo[a,c][7]annulen-2-yl)methoxy)-2,3-dihydrobenzofuran-3-yl)acetic acid;
(28) (1S,2S)-2-(4-(((9-(2-ethoxyethoxy)-6,7-dihydro-5H-dibenzo[a,c][7]annulen-2-yl)methyl)amino)phenyl)cyclopropanecarboxylic acid;
(29) (1S,2S)-2-(4-(((11-methyl-9-(3-(methylsulfonyl)propoxy)-6,7-dihydro-5H-dibenzo[a,c][7]annulen-2-yl)methyl)amino)phenyl)cyclopropanecarboxylic acid;
(30) (1S,2S)-2-(4-((10-methyl-8-(3-(methylsulfonyl)propoxy)-6H-benzo[c]chromen-2-yl)methoxy)phenyl)cyclopropanecarboxylic acid;
(31) (1S,2S)-2-(4-((5-methyl-7-(3-(methylsulfonyl)propoxy)-9,10-dihydrophenanthren-3-yl)methoxy)phenyl)cyclopropanecarboxylic acid;
(32) (S)-2-(6-((9-(3-(methylsulfonyl)propoxy)-6,7-dihydrodibenzo[b,d]oxepin-2-yl)methoxy)-2,3-dihydrobenzofuran-3-yl)acetic acid;
(33) 2-((3S)-6-((11-methyl-9-(3-(methylsulfonyl)propoxy)-5,7-dihydrodibenzo[c,e]oxepin-2-yl)methoxy)-2,3-dihydrobenzofuran-3-yl)acetic acid;
(34) (1S,2S)-2-(4-(((11-methyl-9-(3-(methylsulfonyl)propoxy)-5,7-dihydrodibenzo[c,e]oxepin-2-yl)methyl)amino)phenyl)cyclopropanecarboxylic acid;
(35) 2-((3S)-6-((9-(2-ethoxyethoxy)-11-methyl-6,7-dihydro-5H-dibenzo[a,c][7]annulen-2-yl)methoxy)-2,3-dihydrobenzofuran-3-yl)acetic acid;
(36) 2-((3S)-6-((9-((1,1-dioxidotetrahydro-2H-thiopyran-4-yl)oxy)-11-methyl-6,7-dihydrodibenzo[b,d]oxepin-2-yl)methoxy)-2,3-dihydrobenzofuran-3-yl)acetic acid;
(37) 2-((3S)-6-((9-(2-(1,1-dioxidothiomorpholino)ethoxy)-11-methyl-6,7-dihydrodibenzo[b,d]oxepin-2-yl)methoxy)-2,3-dihydrobenzofuran-3-yl)acetic acid;
(38) 2-((3S)-6-((9-(3-(ethylsulfonyl)propoxy)-11-methyl-6,7-dihydrodibenzo[b,d]oxepin-2-yl)methoxy)-2,3-dihydrobenzofuran-3-yl)acetic acid;
(39) (1S,2S)-2-(4-((11-methyl-9-(3-(methylsulfonyl)propoxy)-6,7-dihydrodibenzo[b,d]oxepin-2-yl)methoxy)phenyl)cyclopropanecarboxylic acid;
(40) (1S,2S)-2-(2-fluoro-4-((11-methyl-9-(3-(methylsulfonyl)propoxy)-6,7-dihydrodibenzo[b,d]oxepin-2-yl)methoxy)phenyl)cyclopropanecarboxylic acid;
(41) (1S,2S)-2-(4-((9-(3-(ethylsulfonyl)propoxy)-11-methyl-6,7-dihydrodibenzo[b,d]oxepin-2-yl)methoxy)-2-fluorophenyl)cyclopropanecarboxylic acid;
(42) (S)-2-(6-((3-(3-(methylsulfonyl)propoxy)-6,7-dihydrodibenzo[b,d]oxepin-10-yl)methoxy)-2,3-dihydrobenzofuran-3-yl)acetic acid;
(43) (S)-2-(6-((6,6-dimethyl-9-(3-(methylsulfonyl)propoxy)-6,7-dihydrodibenzo[b,d]oxepin-2-yl)methoxy)-2,3-dihydrobenzofuran-3-yl)acetic acid;
(44) (S)-2-(6-((5-ethyl-9-(3-(methylsulfonyl)propoxy)-6,7-dihydro-5H-dibenzo[b,d]azepin-2-yl)methoxy)-2,3-dihydrobenzofuran-3-yl)acetic acid;
(45) (1S,2S)-2-(4-((5-ethyl-9-(3-(methylsulfonyl)propoxy)-6,7-dihydro-5H-dibenzo[b,d]azepin-2-yl)methoxy)phenyl)cyclopropanecarboxylic acid;
(46) 2-((3S)-6-((9-((4-hydroxy-1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid;
(47) 2-((3S)-6-((9-((1,1-dioxidotetrahydro-2H-thiopyran-4-yl)methoxy)-11-methyl-6,7-dihydrodibenzo[b,d]oxepin-2-yl)methoxy)-2,3-dihydrobenzofuran-3-yl)acetic acid;
(48) (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)phenyl)cyclopropanecarboxylic acid;
(49) (1S,2S)-2-(4-((9-(3-(ethylsulfonyl)propoxy)-11-methyl-6,7-dihydrodibenzo[b,d]oxepin-2-yl)methoxy)phenyl)cyclopropanecarboxylic acid;
(50) (1S,2S)-2-(4-((9-((1,1-dioxidotetrahydro-2H-thiopyran-4-yl)oxy)-11-methyl-6,7-dihydrodibenzo[b,d]oxepin-2-yl)methoxy)-2-fluorophenyl)cyclopropanecarboxylic acid;
(51) (1S,2S)-2-{2-fluoro-4-[9-(4-hydroxy-1,1-dioxido-hexahydro-thiopyran-4-ylmethoxy)-11-methyl-6,7-dihydro-5-oxa-dibenzo[a,c]cyclohepten-2-ylmethoxy]phenyl}-cyclopropanecarboxylic acid;
(52) (1S,2S)-2-(4-(((9-((1,1-dioxidotetrahydro-2H-thiopyran-4-yl)oxy)-11-methyl-6,7-dihydrodibenzo[b,d]oxepin-2-yl)methyl)amino)-2-fluorophenyl)cyclopropanecarboxylic acid;
(53) (i1S,2S)-2-(4-(((9-(3-(ethylsulfonyl)propoxy)-11-methyl-6,7-dihydrodibenzo[b,d]oxepin-2-yl)methyl)amino)-2-fluorophenyl)cyclopropanecarboxylic acid;
(54) 2-((3S)-6-((6,6,11-trimethyl-9-(3-(methylsulfonyl)propoxy)-6,7-dihydrodibenzo[b,d]oxepin-2-yl)methoxy)-2,3-dihydrobenzofuran-3-yl)acetic acid;
(55) 2-((3S)-6-((9-((1,1-dioxidotetrahydro-2H-thiopyran-4-yl)oxy)-11-methyl-6,7-dihydro-5H-dibenzo[a,c][7]annulen-2-yl)methoxy)-2,3-dihydrobenzofuran-3-yl)acetic acid;
(56) 2-((3S)-6-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)-2,3-dihydrobenzofuran-3-yl)acetic acid;
(57) 2-((3S)-6-((9-(3-(ethylsulfonyl)propoxy)-11-methyl-6,7-dihydro-5H-dibenzo[a,c][7]annulen-2-yl)methoxy)-2,3-dihydrobenzofuran-3-yl)acetic acid;
(58) (1S,2S)-2-(4-((11-methyl-9-(3-(methylsulfonyl)propoxy)-6,7-dihydro-5H-dibenzo[a,c][7]annulen-2-yl)methoxy)phenyl)cyclopropanecarboxylic acid;
(59) (1S,2S)-2-(4-((9-((1,1-dioxidotetrahydro-2H-thiopyran-4-yl)oxy)-11-methyl-6,7-dihydro-5H-dibenzo[a,c][7]annulen-2-yl)methoxy)phenyl)cyclopropanecarboxylic acid;
(60) (1S,2S)-2-(4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid;
(61) (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylic acid;
(62) (1S,2S)-2-(2-fluoro-4-((9-((4-hydroxy-1,1-dioxidotetrahydro-2H-thiopyran-4-yl)methoxy)-11-methyl-6,7-dihydro-5H-dibenzo[a,c][7]annulen-2-yl)methoxy)phenyl)cyclopropanecarboxylic acid;
(63) (1S,2S)-2-(2-fluoro-4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid;
(64) (S)-2-(6-((9-((1,1-dioxidotetrahydro-2H-thiopyran-4-yl)oxy)-6,7-dihydro-5H-dibenzo[a,c][7]annulen-2-yl)methoxy)-2,3-dihydrobenzofuran-3-yl)acetic acid;
(65) (S)-2-(6-((9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;

(66) (S)-2-(6-((9-(3-(ethylsulfonyl)propoxy)-6,7-dihydro-5H-dibenzo[a,c][7]annulen-2-yl)methoxy)-2,3-dihydrobenzofuran-3-yl)acetic acid;
(67) (1S,2S)-2-(4-((9-((1,1-dioxidotetrahydro-2H-thiopyran-4-yl)oxy)-6,7-dihydro-5H-dibenzo[a,c][7]annulen-2-yl)methoxy)phenyl)cyclopropanecarboxylic acid;
(68) (1S,2S)-2-(4-((9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid;
(69) (1S,2S)-2-(4-((9-(3-(ethylsulfonyl)propoxy)-6,7-dihydro-5H-dibenzo[a,c][7]annulen-2-yl)methoxy)phenyl)cyclopropanecarboxylic acid;
(70) (1S,2S)-2-(4-(((9-((1,1-dioxidotetrahydro-2H-thiopyran-4-yl)oxy)-6,7-dihydro-5H-dibenzo[a,c][7]annulen-2-yl)methyl)amino)phenyl)cyclopropanecarboxylic acid;
(71) (1S,2S)-2-(4-(((9-((4-hydroxy-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid;
(72) (1S,2S)-2-(4-(((9-(3-(ethylsulfonyl)propoxy)-6,7-dihydro-5H-dibenzo[a,c][7]annulen-2-yl)methyl)amino)phenyl)cyclopropanecarboxylic acid;
(73) (1S,2S)-2-(4-(((9-((1,1-dioxidotetrahydro-2H-thiopyran-4-yl)oxy)-11-methyl-6,7-dihydrodibenzo[b,d]oxepin-2-yl)methyl)amino)phenyl)cyclopropanecarboxylic acid;
(74) (i1S,2S)-2-(4-(((9-(3-(ethylsulfonyl)propoxy)-11-methyl-6,7-dihydro-5H-dibenzo[a,c][7]annulen-2-yl)methyl)amino)phenyl)cyclopropanecarboxylic acid;
(75) (1S,2S)-2-(4-(((9-((1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid;
(76) (1S,2S)-2-(4-(((9-((1,1-dioxidotetrahydro-2H-thiopyran-4-yl)oxy)-11-methyl-6,7-dihydro-5H-dibenzo[a,c][7]annulen-2-yl)methyl)amino)phenyl)cyclopropanecarboxylic acid;
(77) (1S,2S)-2-(4-(((9-((4-hydroxy-1,1-dioxidotetrahydro-2H-thiopyran-4-yl)methoxy)-11-methyl-6,7-dihydro-5H-dibenzo[a,c][7]annulen-2-yl)methyl)amino)phenyl)cyclopropanecarboxylic acid;
(78) (1S,2S)-2-(4-(((9-((1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid;
(79) 2-((S)-6-(((R)-6-methyl-9-(3-(methylsulfonyl)propoxy)-6,7-dihydrodibenzo[b,d]oxepin-2-yl)methoxy)-2,3-dihydrobenzofuran-3-yl)acetic acid;
(80) (S)-2-(6-((9-(3-(methylsulfonyl)propoxy)dibenzo[d,f][1,3]dioxepin-2-yl)methoxy)-2,3-dihydrobenzofuran-3-yl)acetic acid;
(81) 2-((3S)-6-((1-methyl-3-morpholino-6,7-dihydro-5H-benzo[3,4]cyclohepta[1,2-d]pyrimidin-10-yl)methoxy)-2,3-dihydrobenzofuran-3-yl)acetic acid;
(82) (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-yl)acetic acid;
(83) (S)-2-(6-(((9-((1,1-dioxidotetrahydro-2H-thiopyran-4-yl)methoxy)-6,7-dihydro-5H-dibenzo[a,c][7]annulen-2-yl)methyl)amino)-2,3-dihydrobenzofuran-3-yl)acetic acid;
(84) (S)-2-(6-((9-((1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;
(85) (S)-2-(6-((9-((1,1-dioxidotetrahydro-2H-thiopyran-4-yl)methoxy)-3-fluoro-6,7-dihydro-5H-dibenzo[a,c][7]annulen-2-yl)methoxy)-2,3-dihydrobenzofuran-3-yl)acetic acid;
(86) (1S,2S)-2-(4-(((9-((1,1-dioxidotetrahydro-2H-thiopyran-4-yl)methoxy)-3-fluoro-6,7-dihydro-5H-dibenzo[a,c][7]annulen-2-yl)methyl)amino)phenyl)cyclopropanecarboxylic acid;
(87) (1S,2S)-2-(4-(((9-(3-(ethylsulfonyl)propoxy)-11-methyl-6,7-dihydrodibenzo[b,d]oxepin-2-yl)methyl)amino)phenyl)cyclopropanecarboxylic acid;
(88) 2-((3S)-6-((9-(2-ethoxyethoxy)-11-methyl-6,7-dihydrodibenzo[b,d]oxepin-2-yl)methoxy)-2,3-dihydrobenzofuran-3-yl)acetic acid;
(89) (1S,2S)-2-(4-((1-methyl-3-morpholino-6,7-dihydro-5H-benzo[3,4]cyclohepta[1,2-d]pyrimidin-10-yl)methoxy)phenyl)cyclopropanecarboxylic acid;
(90) 2-((3S)-6-((1-methyl-3-(3-(methylsulfonyl)propoxy)-6,7-dihydro-5H-benzo[3,4]cyclohepta[1,2-d]pyrimidin-10-yl)methoxy)-2,3-dihydrobenzofuran-3-yl)acetic acid;
(91) (S)-2-(6-(((9-(2-ethoxyethoxy)-6,7-dihydro-5H-dibenzo[a,c][7]annulen-2-yl)methyl)amino)-2,3-dihydrobenzofuran-3-yl)acetic acid;
(92) (S)-2-(6-(((9-(3-(ethylsulfonyl)propoxy)-6,7-dihydro-5H-dibenzo[a,c][7]annulen-2-yl)methyl)amino)-2,3-dihydrobenzofuran-3-yl)acetic acid;
(93) (S)-2-(6-((9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;
(94) (1S,2S)-2-(4-(((9-((4-methyl-1,1-dioxidotetrahydro-2H-thiopyran-4-yl)methoxy)-6,7-dihydro-5H-dibenzo[a,c][7]annulen-2-yl)methyl)amino)phenyl)cyclopropanecarboxylic acid;
(95) (S)-2-(6-((3-fluoro-9-((4-methyl-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;
(96) (S)-2-(6-((3-fluoro-9-(3-(methylsulfonyl)propoxy)-6,7-dihydro-5H-dibenzo[a,c][7]annulen-2-yl)methoxy)-2,3-dihydrobenzofuran-3-yl)acetic acid;
(97) (S)-2-(6-((9-(3-(ethylsulfonyl)propoxy)-3-fluoro-6,7-dihydro-5H-dibenzo[a,c][7]annulen-2-yl)methoxy)-2,3-dihydrobenzofuran-3-yl)acetic acid;
(98) (S)-2-(6-((9-((1,1-dioxidotetrahydro-2H-thiopyran-4-yl)oxy)-3-fluoro-6,7-dihydro-5H-dibenzo[a,c][7]annulen-2-yl)methoxy)-2,3-dihydrobenzofuran-3-yl)acetic acid;
(99) (S)-2-(6-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)-2,3-dihydrobenzofuran-3-yl)acetic acid;
(100) (1S,2S)-2-(4-((9-((1,1-dioxidotetrahydro-2H-thiopyran-4-yl)oxy)-3-fluoro-6,7-dihydro-5H-dibenzo[a,c][7]annulen-2-yl)methoxy)phenyl)cyclopropanecarboxylic acid;
(101) (1S,2S)-2-(4-((3-fluoro-9-((4-hydroxy-1,1-dioxidotetrahydro-2H-thiopyran-4-yl)methoxy)-6,7-dihydro-5H-dibenzo[a,c][7]annulen-2-yl)methoxy)phenyl)cyclopropanecarboxylic acid;
(102) (1S,2S)-2-(4-((3-fluoro-9-(3-(methylsulfonyl)propoxy)-6,7-dihydro-5H-dibenzo[a,c][7]annulen-2-yl)methoxy)phenyl)cyclopropanecarboxylic acid;

(103) (1S,2S)-2-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)cyclopropanecarboxylic acid;

(104) (1S,2S)-2-(4-(((3-fluoro-9-(3-(methylsulfonyl)propoxy)-6,7-dihydro-5H-dibenzo[a,c][7]annulen-2-yl)methyl)amino)phenyl)cyclopropanecarboxylic acid;

(105) (1S,2S)-2-(4-(((9-(3-(ethylsulfonyl)propoxy)-3-fluoro-6,7-dihydro-5H-dibenzo[a,c][7]annulen-2-yl)methyl)amino)phenyl)cyclopropanecarboxylic acid;

(106) 2-((S)-6-((3-fluoro-9-(((R)-tetrahydrofuran-3-yl)oxy)-6,7-dihydro-5H-dibenzo[a,c][7]annulen-2-yl)methoxy)-2,3-dihydrobenzofuran-3-yl)acetic acid;

(107) (S)-2-(6-((3-fluoro-9-(2-morpholinoethoxy)-6,7-dihydro-5H-dibenzo[a,c][7]annulen-2-yl)methoxy)-2,3-dihydrobenzofuran-3-yl)acetic acid;

(108) (S)-3-(4-((9-(3-(methylsulfonyl)propoxy)-6,7-dihydro-5H-dibenzo[a,c][7]annulen-2-yl)methoxy)phenyl)hex-4-ynoic acid;

(109) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoic acid;

(110) (S)-3-(4-((9-((1,1-dioxidotetrahydro-2H-thiopyran-4-yl)oxy)-6,7-dihydro-5H-dibenzo[a,c][7]annulen-2-yl)methoxy)phenyl)hex-4-ynoic acid;

(111) (S)-3-(4-((9-(3-(ethylsulfonyl)propoxy)-6,7-dihydro-5H-dibenzo[a,c][7]annulen-2-yl)methoxy)phenyl)hex-4-ynoic acid;

(112) (S)-3-(4-((9-((1,1-dioxidotetrahydro-2H-thiopyran-4-yl)methoxy)-3-fluoro-6,7-dihydro-5H-dibenzo[a,c][7]annulen-2-yl)methoxy)phenyl)hex-4-ynoic acid;

(113) (S)-3-(4-((9-((1,1-dioxidotetrahydro-2H-thiopyran-4-yl)methoxy)-6,7-dihydrodibenzo[b,d]oxepin-2-yl)methoxy)phenyl)hex-4-ynoic acid;

(114) (S)-3-(4-((3-((1,1-dioxidotetrahydro-2H-thiopyran-4-yl)methoxy)-6,7-dihydro-5H-benzo[3,4]cyclohepta[1,2-b]pyridin-10-yl)methoxy)phenyl)hex-4-ynoic acid;

(115) (R)-3-cyclopropyl-3-(3-((9-((1,1-dioxidotetrahydro-2H-thiopyran-4-yl)methoxy)-6,7-dihydro-5H-dibenzo[a,c][7]annulen-2-yl)methoxy)phenyl)propanoic acid;

(116) 3-cyclopropyl-3-(4-((9-((1,1-dioxidotetrahydro-2H-thiopyran-4-yl)methoxy)-6,7-dihydro-5H-dibenzo[a,c][7]annulen-2-yl)methoxy)phenyl)propanoic acid;

(117) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hexanoic acid;

(118) (R,Z)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-enoic acid;

(119) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(5-methylisoxazol-3-yl)propanoic acid;

(120) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(isoxazol-3-yl)propanoic acid;

(121) 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(3-methylisoxazol-5-yl)propanoic acid;

(122) (S)-3-(4-((3-(3-(methylsulfonyl)propoxy)-6,7-dihydro-5H-benzo[3,4]cyclohepta[1,2-b]pyridin-10-yl)methoxy)phenyl)hex-4-ynoic acid;

(123) (S)-3-(4-((3-(3-(ethylsulfonyl)propoxy)-6,7-dihydro-5H-benzo[3,4]cyclohepta[1,2-b]pyridin-10-yl)methoxy)phenyl)hex-4-ynoic acid;

(124) (S)-3-(4-((3-((1,1-dioxidotetrahydro-2H-thiopyran-4-yl)oxy)-6,7-dihydro-5H-benzo[3,4]cyclohepta[1,2-b]pyridin-10-yl)methoxy)phenyl)hex-4-ynoic acid;

(125) (S)-3-(4-((5-methyl-7-(3-(methylsulfonyl)propoxy)-9,10-dihydrophenanthren-3-yl)methoxy)phenyl)hex-4-ynoic acid;

(126) (S)-3-(4-((7-(2-ethoxyethoxy)-5-methyl-9,10-dihydrophenanthren-3-yl)methoxy)phenyl)hex-4-ynoic acid;

(127) (S)-3-(4-((5-methyl-7-(3-(methylsulfonyl)propoxy)-9,10-dihydrophenanthren-1-yl)methoxy)phenyl)hex-4-ynoic acid;

(128) (S)-3-(4-((11-methyl-9-(3-(methylsulfonyl)propoxy)-6,7-dihydro-5H-dibenzo[a,c][7]annulen-2-yl)methoxy)phenyl)hex-4-ynoic acid;

(129) (S)-3-(4-((9-(3-(methylsulfonyl)propoxy)dibenzo[d,f][1,3]dioxepin-2-yl)methoxy)phenyl)hex-4-ynoic acid;

(130) (S)-3-(4-((6,6-dimethyl-9-(3-(methylsulfonyl)propoxy)-6,7-dihydrodibenzo[b,d]oxepin-2-yl)methoxy)phenyl)hex-4-ynoic acid;

(131) (S)-3-(4-((1-methyl-3-(3-(methylsulfonyl)propoxy)-6,7-dihydro-5H-benzo[3,4]cyclohepta[1,2-d]pyrimidin-10-yl)methoxy)phenyl)hex-4-ynoic acid;

(132) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid;

(133) (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)butanoic acid;

(134) (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)-4-ethoxybutanoic acid;

(135) (S)-3-(4-(((9-(3-(methylsulfonyl)propoxy)-6,7-dihydro-5H-dibenzo[a,c][7]annulen-2-yl)methyl)amino)phenyl)hex-4-ynoic acid;

(136) (S)-3-(4-(((9-((1,1-dioxidotetrahydro-2H-thiopyran-4-yl)methoxy)-6,7-dihydro-5H-dibenzo[a,c][7]annulen-2-yl)methyl)amino)phenyl)hex-4-ynoic acid;

(137) 3-(4-((9-((1,1-dioxidotetrahydro-2H-thiopyran-4-yl)methoxy)-6,7-dihydro-5H-dibenzo[a,c][7]annulen-2-yl)methoxy)phenyl)-3-(4-fluorophenyl)propanoic acid;

(138) (S)-3-(4-((11-methyl-9-(((R)-tetrahydrofuran-3-yl)oxy)-6,7-dihydro-5H-dibenzo[a,c][7]annulen-2-yl)methoxy)phenyl)hex-4-ynoic acid;

(139) (R)-3-(4-((9-((1,1-dioxidotetrahydro-2H-thiopyran-4-yl)methoxy)-6,7-dihydro-5H-dibenzo[a,c][7]annulen-2-yl)methoxy)phenyl)pent-4-ynoic acid;

(140) (S)-3-(4-((5-ethyl-9-(((R)-tetrahydrofuran-3-yl)oxy)-6,7-dihydro-5H-dibenzo[b,d]azepin-2-yl)methoxy)phenyl)hex-4-ynoic acid;

(141) sodium (1S,2S)-2-(4-(((9-(3-(methylsulfonyl)propoxy)-6,7-dihydro-5H-dibenzo[a,c][7]annulen-2-yl)methyl)amino)phenyl)cyclopropanecarboxylate;

(142) sodium 2-((3S)-6-((11-methyl-9-(3-(methylsulfonyl)propoxy)-6,7-dihydro-5H-dibenzo[a,c][7]annulen-2-yl)methoxy)-2,3-dihydrobenzofuran-3-ylacetate;

(143) sodium (1S,2S)-2-(4-((11-methyl-9-(3-(methylsulfonyl)propoxy)-6,7-dihydrodibenzo[b,d]oxepin-2-yl)methoxy)phenyl)cyclopropanecarboxylate;

(144) sodium (1S,2S)-2-(4-((9-(3-(ethylsulfonyl)propoxy)-11-methyl-6,7-dihydro-5H-dibenzo[a,c][7]annulen-2-yl)methoxy)phenyl)cyclopropanecarboxylate;

(145) sodium (S)-2-(6-(((9-(3-(methylsulfonyl)propoxy)-6,7-dihydro-5H-dibenzo[a,c][7]annulen-2-yl)methyl)amino)-2,3-dihydrobenzofuran-3-yl)acetate;

(146) sodium (S)-3-(4-((9-(3-(methylsulfonyl)propoxy)-6,7-dihydro-5H-dibenzo[a,c][7]annulen-2-yl)methoxy)phenyl)hex-4-ynoate; and (147) sodium (S)-3-(4-((9-((1,1-dioxidotetrahydro-2H-thiopyran-4-yl)methoxy)-6,7-dihydro-5H-dibenzo[a,c][7]annulen-2-yl)methoxy)phenyl)hex-4-ynoate.

6. A pharmaceutical composition comprising the compound of claim 1 and a pharmaceutically acceptable carrier.

7. A method of treating type II diabetes mellitus in a mammal in need thereof said method comprising administering the compound of claim 1 to the mammal.

8. A method of inhibiting GPR40 in a mammal having a disease selected from the group consisting of diabetes, impaired glucose tolerance, ketosis, acidosis, diabetic neuropathy, diabetic nephropathy, diabetic retinopathy, macular edema, hyperlipidemia, genital disorders, skin diseases, arthropathia, osteopenia, arteriosclerosis, thrombotic diseases, dyspepsia, memory and learning difficulties, depression, manic depression, schizophrenia, attention-deficit hyperactivity disorder, visual impairments, appetite dysregulation, obesity, hypoglycemia, hypertension, edemas, insulin resistance, labile diabetes, lipoatrophia, insulin allergies, insulinoma, lipotoxicity, pancreatic fatigue, hyperinsulinemia, cancers, metabolic syndromes, immune diseases, inflammatory diseases, multiple sclerosis and acute renal failure, said method comprising administering the compound of claim 1 to the mammal.

* * * * *